(12) United States Patent
Park et al.

(10) Patent No.: US 12,168,060 B2
(45) Date of Patent: Dec. 17, 2024

(54) ANTIBODY-DRUG CONJUGATES COMPRISING ANTI-B7-H3 ANTIBODIES

(71) Applicants: IntoCell, Inc., Daejeon (KR);
Y-Biologics Inc., Daejeon (KR)

(72) Inventors: Taekyo Park, Daejeon (KR);
Sunyoung Kim, Daejeon (KR); Suho Park, Daejeon (KR); Doohwan Jung, Daejeon (KR); Donghoon Seo, Daejeon (KR); Sangkwang Lee, Daejeon (KR); Sanghyeon Yun, Daejeon (KR); Jihyeon Ha, Daejeon (KR); Hyang Sook Lee, Daejeon (KR); Okku Park, Daejeon (KR); Beomseok Seo, Daejeon (KR); Sena Kim, Daejeon (KR); Minah Seol, Daejeon (KR); Jina Song, Daejeon (KR); Sung Ho Woo, Daejeon (KR); Jongun Cho, Daejeon (KR); Jaeho Lee, Sejong-Si (KR); Hyun Mi Lee, Daejeon (KR); Jae Eun Park, Daejeon (KR); Youngja Song, Daejeon (KR); Eunjin Lee, Daejeon (KR); Hyun Ju Lee, Daejeon (KR); Eun-Young Shim, Daejeon (KR); Yunjung Ko, Daejeon (KR); Minju Lee, Daejeon (KR); Young woo Park, Daejeon (KR); Yosup Rew, Daejeon (KR)

(73) Assignees: IntoCell, Inc., Daejeon (KR);
Y-Biologics Inc., Daejeon (KR)

(*) Notice: Subject to any disclaimer, the term of this patent is extended or adjusted under 35 U.S.C. 154(b) by 342 days.

(21) Appl. No.: 17/358,306

(22) Filed: Jun. 25, 2021

(65) Prior Publication Data
US 2022/0047717 A1 Feb. 17, 2022

Related U.S. Application Data

(60) Provisional application No. 63/044,764, filed on Jun. 26, 2020.

(51) Int. Cl.
*A61K 47/68* (2017.01)
*C07K 16/28* (2006.01)

(52) U.S. Cl.
CPC ...... *A61K 47/6849* (2017.08); *A61K 47/6813* (2017.08); *A61K 47/6817* (2017.08); *A61K 47/6851* (2017.08); *C07K 16/2827* (2013.01)

(58) Field of Classification Search
None
See application file for complete search history.

(56) References Cited

U.S. PATENT DOCUMENTS

| 10,604,582 B2 | 3/2020 | Dimitrov et al. |
| 2019/0127471 A1 | 5/2019 | Loo et al. |

(Continued)

FOREIGN PATENT DOCUMENTS

| WO | WO-2017/214335 A1 | 12/2017 |
| WO | WO-2021/260438 A1 | 12/2021 |

OTHER PUBLICATIONS

Carey, FA. Organic Chemistry 6th Ed. McGraw Hill. 2006, chapter 1, p. 9. (Year: 2006).*
Park et al., Bioconjugate Chemistry 2019 30 (7), 1969-1978 (Year: 2019).*
Park et al., "Aryl Sulfate is a Useful Motif for Conjugating and Releasing Phenolic Molecules: Sulfur Fluorine Exchange Click Chemistry Enables Discovery of Ortho-Hydroxy-Protected Aryl Sulfate Linker," Bioconjugate Chem., 30:1957-1968 (2019).

(Continued)

*Primary Examiner* — Karl J Puttlitz
(74) *Attorney, Agent, or Firm* — Foley Hoag LLP; David P. Halstead; Lucas Watkins

(57) ABSTRACT

The present disclosure relates to antibody-drug conjugates (ADCs) wherein one or more active agents are conjugated to an anti-B7-H3 antibody through a linker. The linker may comprise a unit that covalently links active agents to the antibody. The disclosure further relates to monoclonal anti- (Continued)

bodies and antigen binding fragments, variants, multimeric versions, or bispecifics thereof that specifically bind B7-H3, as well as methods of making and using these anti-B7-H3 antibodies and antigen-binding fragments thereof in a variety of therapeutic, diagnostic and prophylactic indications.

22 Claims, 9 Drawing Sheets

Specification includes a Sequence Listing.

(56) References Cited

U.S. PATENT DOCUMENTS

2020/0031934 A1    1/2020   Gu et al.
2022/0348663 A1*   11/2022   Lee ......................... A61P 35/00

OTHER PUBLICATIONS

Park et al., "Introduction of Para-Hydroxy Benzyl Spacer Greatly Expands the Utility of Ortho-Hydroxy-Protected Aryl Sulfate System: Application to Nonphenolic Payloads," Bioconjugate Chem., 30:1969-1978 (2019).
Park et al., "Sulfonate Version of OHPAS Linker has Two Distinct Pathways of Breakdown: Elimination Route Allows Para-Hydroxy-Protected Benzylsulfonate (PHP-BS) to Serve as an Alternative Self-Immolative Group," Bioconjugate Chem., Manuscript (2020).
International Search Report and Written Opinion for International Application No. PCT/IB2021/000445 dated Dec. 9, 2021.
Loo et al., "Anti-B7-H3 antibody-drug conjugates as potential therapeutics for solid cancer," Presented at the 2016 American Associate for Cancer Research Annual Meeting: Abstract 1201 (2016).

* cited by examiner

ANTIBODY-DRUG CONJUGATES COMPRISING ANTI-B7-H3 ANTIBODIES

RELATED APPLICATIONS

This application claims the benefit of priority to U.S. Provisional Patent Application Ser. No. 63/044,764 filed Jun. 26, 2020. This application is incorporated herein by reference in its entirety.

STATEMENT OF JOINT RESEARCH AGREEMENT

The inventions disclosed herein were made as a result of activities undertaken within the scope of a joint research agreement between IntoCell, Inc., and Y-Biologics, Inc., which agreement was in effect on or before the effective filing date of the claimed invention.

SEQUENCE LISTING

The instant application contains a Sequence Listing which has been submitted electronically in ASCII format and is hereby incorporated by reference in its entirety. Said ASCII copy, created on Sep. 20, 2021, is named ICH-00701_SL.txt and is 99,977 bytes in size.

BACKGROUND

Antibody-drug conjugates (ADCs) combine the binding specificity of antibodies with the potency of chemotherapeutic agents. Since ADC technology allows a drug to be accurately delivered to a target cancer cell and released under specific conditions, while minimizing collateral damage to healthy cells, ADC technology increases the efficacy of a therapeutic antibody and decreases the risk of an adverse reaction.

B7-H3 (CD276) is a novel member of the B7 family and shares approximately up to 30% sequence homology. B7-H3 was initially introduced as co-stimulatory molecule for T cells, but has been proved as co-inhibitory checkpoint ligand, which can regulate helper T cells, cytotoxic T cells as well as Natural killer cells in human immunity. The expression of B7-H3 protein is very limited in normal tissues, but induced on the cell surface of antigen presenting cells and pervasive in a variety of solid tumors with primary and metastatic cancers. Also B7-H3 expression is detected on multiple cancer cell types including cancer stem cells and tumor vasculature. B7-H3 overexpression looks to be deeply correlated with disease severity and poor clinical outcomes in tumors.

Accordingly, there exists a need for improved antibody-drug conjugates that target B7-H3.

SUMMARY OF THE DISCLOSURE

In some aspects, the disclosure relates to antibody-drug conjugates (ADCs). In some embodiments, the disclosure relates to an antibody-drug conjugate, comprising an antibody, a linker, and an active agent (e.g., a drug). The antibody-drug conjugate may comprise a self-immolative group, e.g., for use in releasing an active agent from the antibody and linker.

The disclosure provides monoclonal antibodies and antigen binding fragments or any fragments, variants, multimeric versions, or bispecifics thereof that bind B7-H3. These antibodies and antigen binding fragments or any fragments, variants, multimeric versions, or bispecifics thereof are collectively referred to herein as anti-B7-H3 monoclonal antibodies or anti-B7-H3 mAbs or antigen binding fragments or any fragments, variants, multimeric versions, or bispecifics thereof. Preferably, the monoclonal antibodies and antigen-binding fragments or any fragments, variants, multimeric versions, or bispecifics thereof are specific for at least human B7-H3. In some embodiments, the monoclonal antibodies and antigen-binding fragments or any fragments, variants, multimeric versions, or bispecifics thereof that recognize human B7-H3 are also cross-reactive for at least one other non-human B7-H3 protein, such as, by way of non-limiting example, non-human primate B7-H3, e.g., cynomolgus monkey B7-H3, and/or rodent B7-H3.

In some aspects, the disclosure relates to antibody-drug conjugates (ADCs) comprising an antibody, at least one branched linker covalently coupled to the antibody, and at least one or two active agents covalently coupled to the branched linker. A branched linker may comprise a branching unit, with at least one drug coupled to the branching unit through a secondary linker; the branching unit is coupled to the antibody by a primary linker. The primary and/or secondary linker may comprise at least one polyethylene glycol unit.

In some aspects, the disclosure relates to an antibody conjugate represented by Formula I, or a pharmaceutically acceptable salt or solvate thereof:

$$Ab\text{-}(G)_n \qquad \text{Formula I}$$

wherein:

Ab is an anti-B7-H3 antibody or antigen-binding fragment thereof, comprising a variable heavy chain complimentarity determining region 1 (CDRH1), a variable heavy chain complimentarity determining region 2 (CDRH2), a variable heavy chain complimentarity determining region 3 (CDRH3), a variable light chain complimentarity determining region 1 (CDRL1), a variable light chain complimentarity determining region 2 (CDRL2), and a variable light chain complimentarity determining region 3 (CDRL3); wherein, CDRH1 comprises an amino acid sequence of SEQ ID NO: 1, 7, 13, 19, 25, 31, 37, or 43;
CDRH2 comprises an amino acid sequence of SEQ ID NO: 2, 8, 14, 20, 26, 32, 38, or 44;
CDRH3 comprises an amino acid sequence of SEQ ID NO: 3, 9, 15, 21, 27, 33, 39, or 45;
CDRL1 comprises an amino acid sequence of SEQ ID NO: 4, 10, 16, 22, 28, 34, 40, or 46,
CDRL2 comprises an amino acid sequence of SEQ ID NO: 5, 11, 17, 23, 29, 35, 41, or 47;
CDRL3 comprises an amino acid sequence of SEQ ID NO: 6, 12, 18, 24, 30, 36, 42, or 48;
each G is, independently, a chemical moiety comprising an active agent and a linker, wherein the linker links Ab to the active agent; and
n is an integer between 1 to 20.

DETAILED DESCRIPTION OF THE DISCLOSURE

Figure 1:
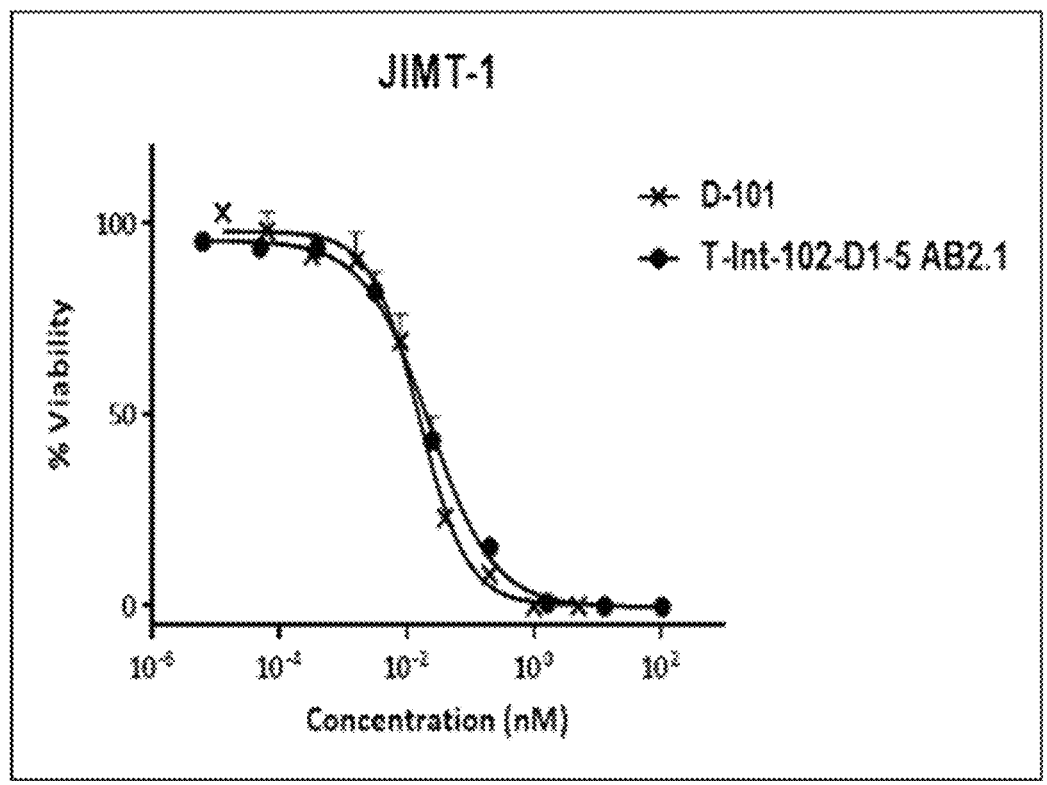
FIG. 1 shows $IC_{50}$ generated using a sigmoidal dose-response nonlinear regression curve fit (GraphPad software Inc.) for T-Int-102-D1-5 AB2.1 in JIMT-1.
Figure 2:
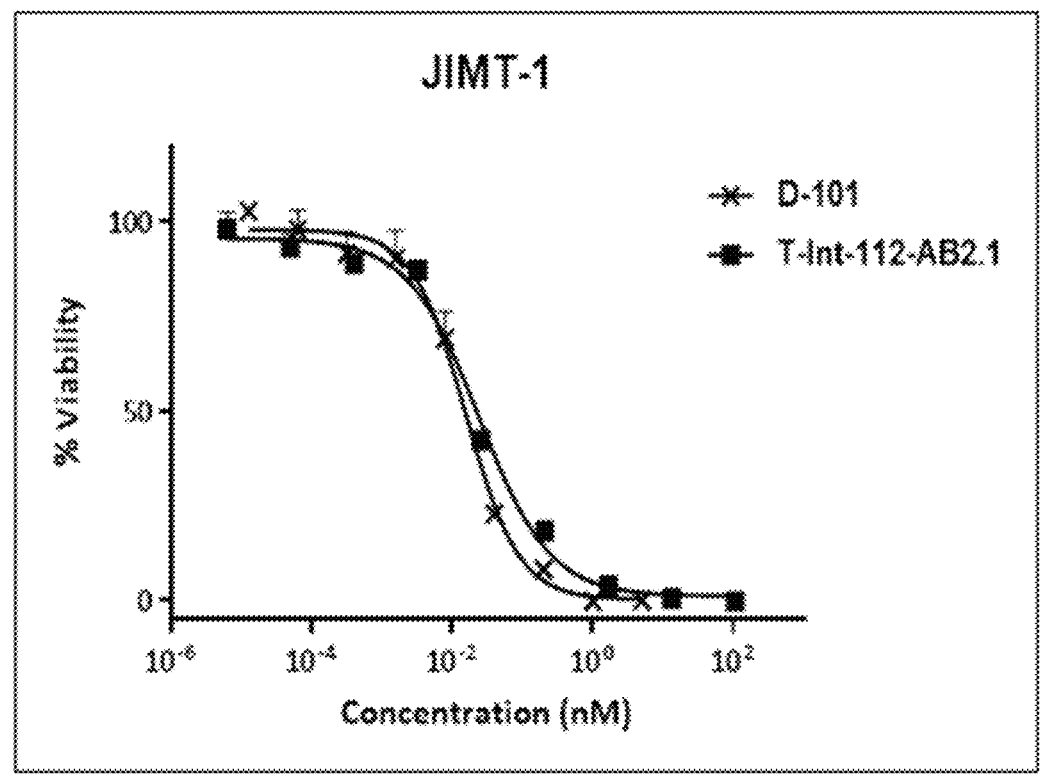
FIG. 2 shows $IC_{50}$ generated using a sigmoidal dose-response nonlinear regression curve fit (GraphPad software Inc.) for T-Int-112-AB2.1 in JIMT-1.
Figure 3:
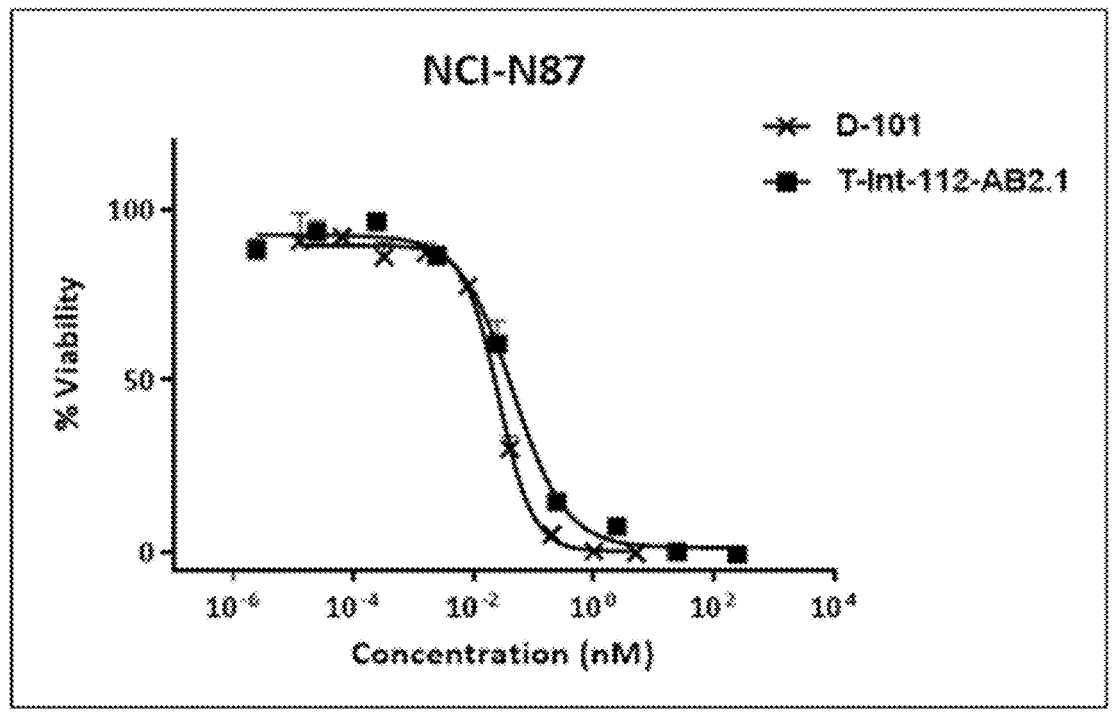
FIG. 3 shows $IC_{50}$ generated using a sigmoidal dose-response nonlinear regression curve fit (GraphPad software Inc.) for T-Int-112-AB2.1 in NCI-N87.
Figure 4:
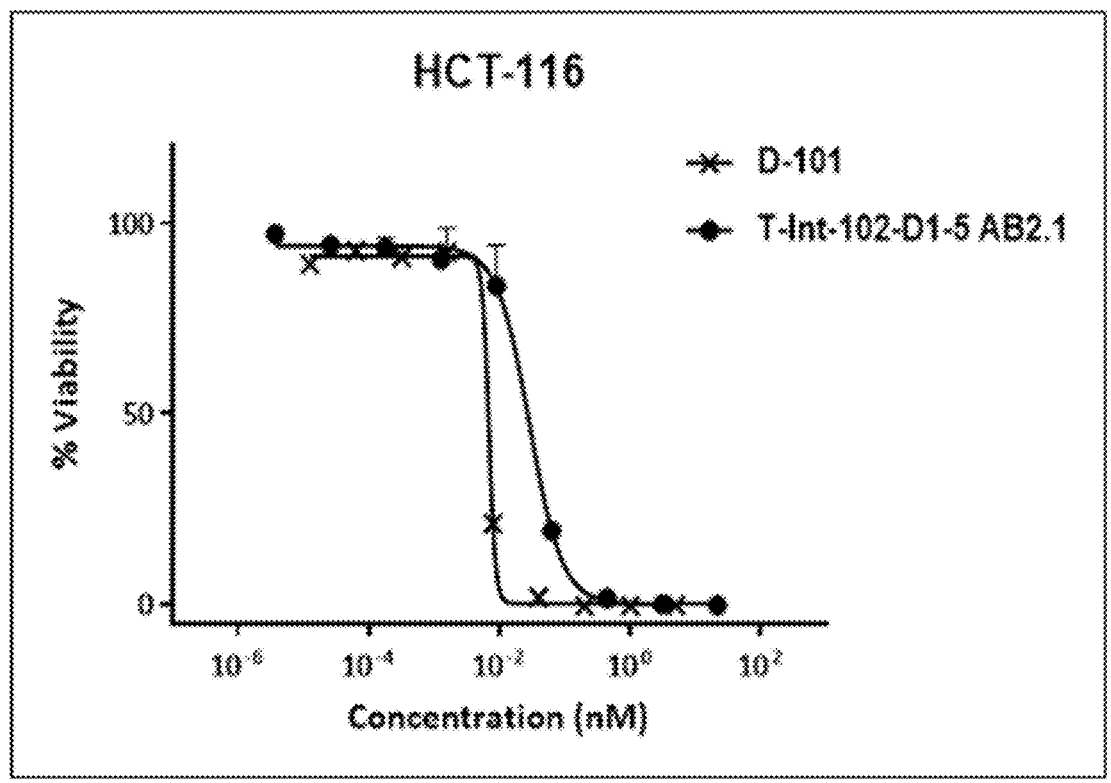
FIG. 4 shows $IC_{50}$ generated using a sigmoidal dose-response nonlinear regression curve fit (GraphPad software Inc.) for T-Int-102-D1-5 AB2.1 in HCT-116.
Figure 5:
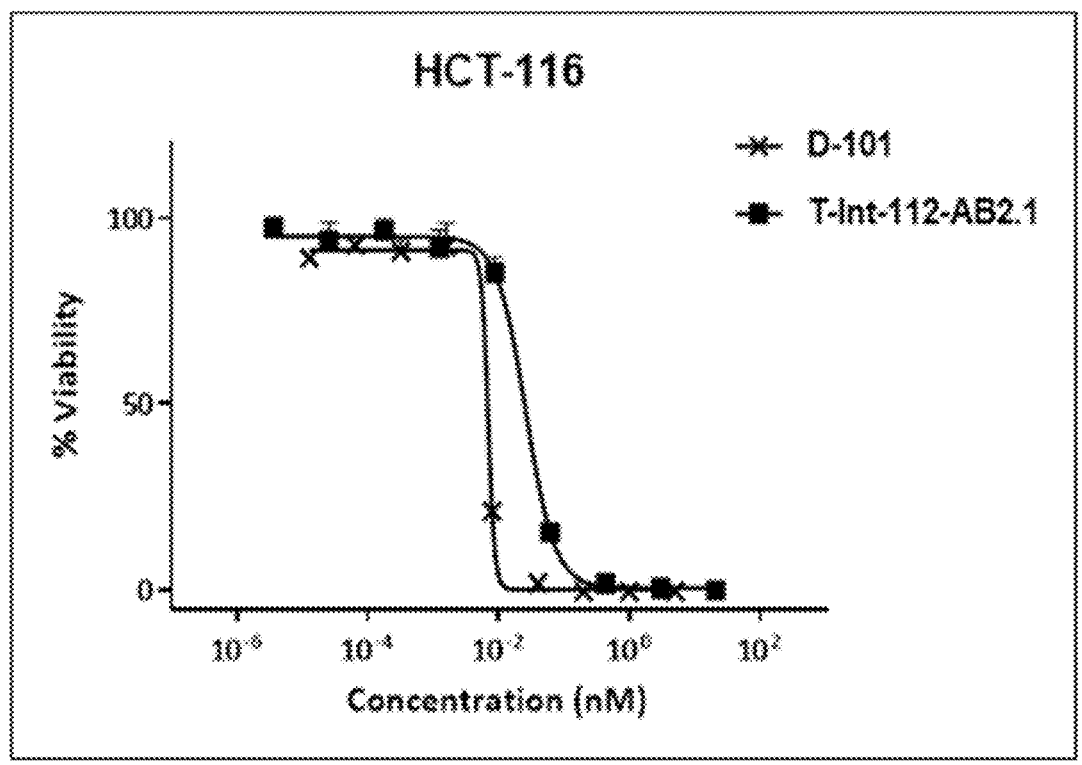
FIG. 5 shows $IC_{50}$ generated using a sigmoidal dose-response nonlinear regression curve fit (GraphPad software Inc.) for T-Int-112-AB2.1 in HCT-116.
Figure 6:
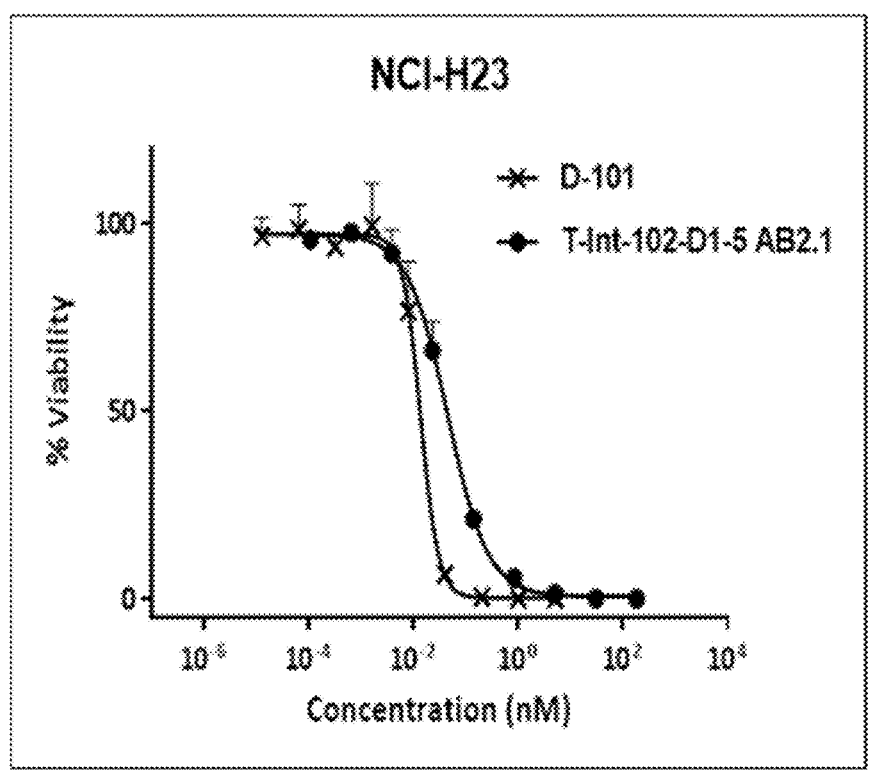
FIG. 6 shows $IC_{50}$ generated using a sigmoidal dose-response nonlinear regression curve fit (GraphPad software Inc.) for T-Int-102-D1-5 AB2.1 in NCI-H23.
Figure 7:
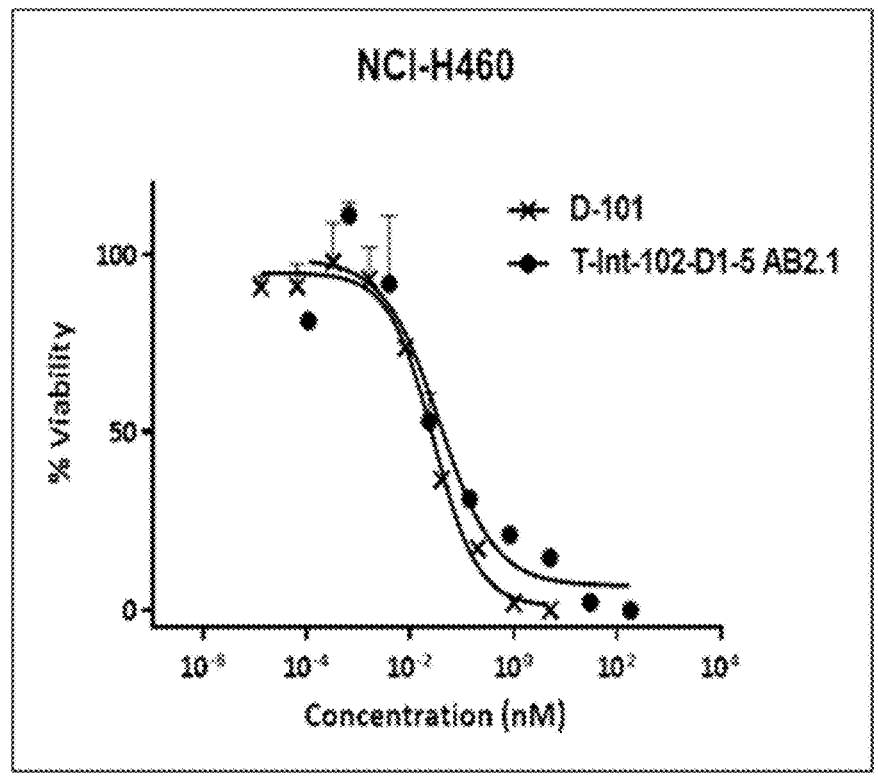
FIG. 7 shows $IC_{50}$ generated using a sigmoidal dose-response nonlinear regression curve fit (GraphPad software Inc.) for T-Int-102-D1-5 AB2.1 in NCI-H460.
Figure 8:
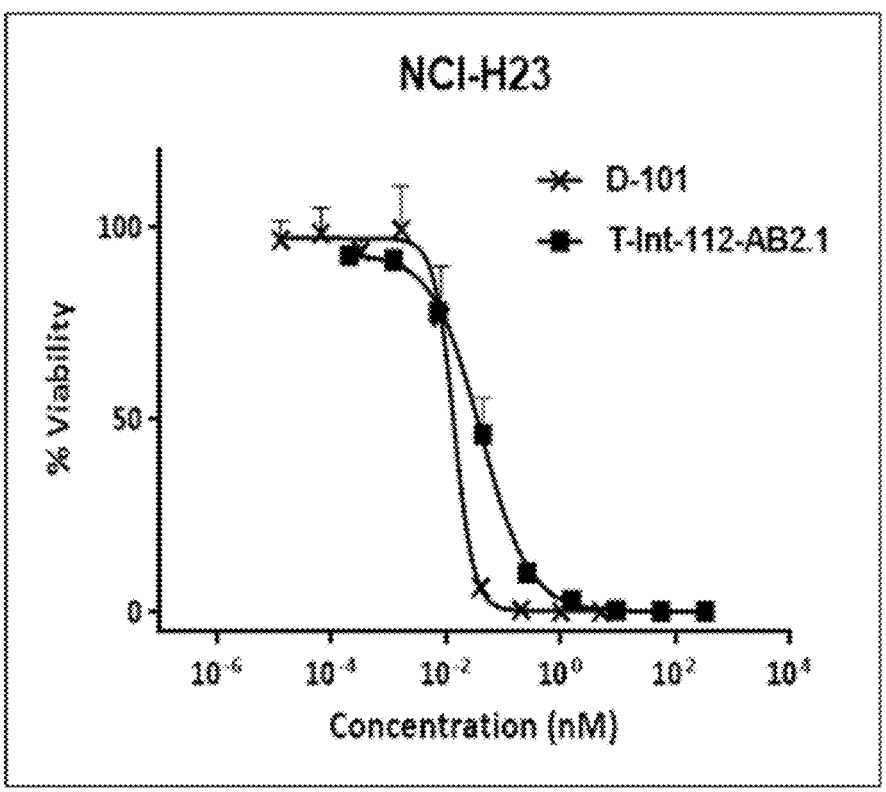
FIG. 8 shows $IC_{50}$ generated using a sigmoidal dose-response nonlinear regression curve fit (GraphPad software Inc.) for T-Int-112-AB2.1 in NCI-H23.
Figure 9:
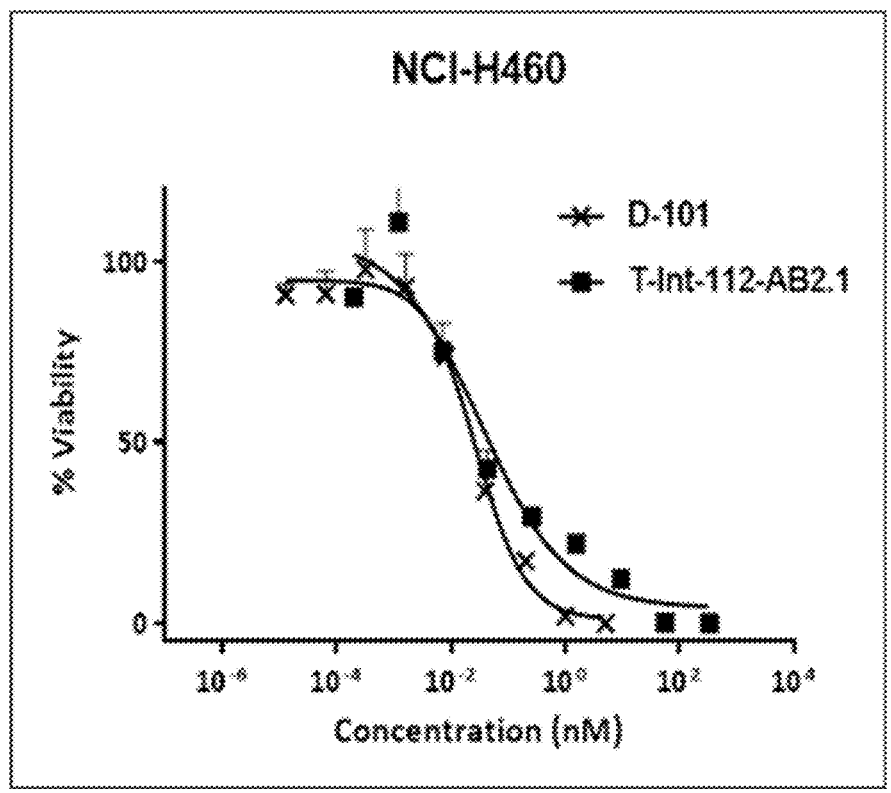
FIG. 9 shows $IC_{50}$ generated using a sigmoidal dose-response nonlinear regression curve fit (GraphPad software Inc.) for T-Int-112-AB2.1 in NCI-H460.

A basic structure of an antibody-drug conjugate is as follows: antibody-linker-low molecular weight drug or toxin. The linker ideally allows the drug to exhibit an effect on a target cancer cell, e.g., after separating from the antibody after the drug reaches a target cell. The linker also plays a functional role, by connecting the antibody and the drug.

B7-H3 (CD276) is a member of the B7 family and shows high sequence homology [up to ~30%] with the family. The expression of B7-H3 is very limited in normal tissues, but it is pervasive in a variety of solid cancers, including breast, lung, pancreatic, prostate, kidney, and colon cancer, as well as melanoma and glioblastoma. B7-H3 has been observed in tumor epithelium as well as tumor associated vasculature and stroma. Furthermore, overexpression of B7-H3 has been correlated with poor outcome in many cancer diseases. High B7-H3 expression, common (about 85%) in NSCLC, is associated with metastasis and advanced stage. Higher incidences and expression levels of B7-H3 were observed in cancers resistant to anti-PD-1 therapy. Thus, targeting of B7-H3 is warranted for relapsed or refractory NSCLC. A series of anti-B7-H3 ADCs were prepared and tested. Key components of the ADCs are OHPAS linker and benzodiazepines equipped with OHPAS compatible functional groups. With proved stability in plasma, the ADCs release toxins efficiently in target tumor cells, implying potential amplification of therapeutic window. The ADCs showed excellent efficacy with minimal body weight change in vivo, offering a new option for NSCLC patients' refractory to anti-PD-1 therapy.

A series of tight binding anti-B7-H3 mAbs and their thiomab versions were generated (Kd~1.7~5.4×10$^{-11}$ M). Exploiting newly discovered OHPAS linker and OHPAS-compatible benzodiazepine payloads, a series of anti-B7-H3 ADCs were prepared and tested. Exemplary OHPAS linkers are further described herein and are also disclosed, for example, in International Application Publication WO 2019/008441, which is incorporated herein by reference in its entirety. Exemplary OHPAS-compatible benzodiazepine payloads are further described herein and are also disclosed, for example, in U.S. Patent Application Publication US2019/0367488, which is incorporated herein by reference in its entirety. The ADCs were highly potent against B7-H3-positive tumor cell lines in vitro. The ADCs were effective when tested in mouse xenograft models of NSCLC.

The ADCs disclosed herein can target specific tumors expressing B7-H3 (e.g., breast, lung, pancreatic, prostate, kidney, and colon cancer, as well as melanoma and Glioblastoma) (*Cancer Cell.* 2017 Apr. 10; 31(4): 501-515.e8). Overexpression of B7-H3 shows good correlation with disease severity and poor outcome. B7-H3 is strongly expressed at a high frequency across a broad range of tumors. B7-H3 targeting for cancer therapy is beneficial because of its expression on cancer stem cell population and on tumor vasculature and stroma (*Journal of Clinical Oncology* 35, no. 15 suppl). Both tumor cells and tumor vasculature are B7-H3 (CD276) positive (*Cancer Cell.* 2017 Apr. 10; 31(4): 501-515.e8). The disclosed B7-H3 antibodies have improved internalization capability confirmed by Fab-Assay. Accordingly, the improved antibody-drug conjugates, disclosed herein, that target B7-H3 are expected to be useful in methods to to treat or alleviate symptoms associated with cancer.

Examples of B7-H3 antibodies and their use are listed in Table 1.

Table 1 shows development state of B7-H3 ADC.

| Name | Payload | Status | Indication | Linker | $K_D$ |
| --- | --- | --- | --- | --- | --- |
| Enoblituzumab (MGA271) | Enhanced Fc function | Phase II | *Solid (multiple indication) | — | $K_D$ = 7 nM |
| Omburtamab (8H9) | I$^{131}$- I$^{124}$- | Phase II/III | Brain & CNS Neuroblastoma Sarcoma | — | — |
| B7-H3-DUBA ADC (*MGC018) | DUBA (~2.7) DNA alkylating (A-T) | Phase I | Solid | VC | $K_D$ = 20 nM |

-continued

| Name | Payload | Status | Indication | Linker | K$_D$ |
|---|---|---|---|---|---|
| DS-7300 | Dxd (~8.0) Topo inhibitor | Phase I | Solid | GGPG (SEQ ID NO: 109) | — |
| BVD CD276-ADC (m276-ADC) | PBD(~2.0) DNA alkylating (G-C) | Preclinical (IgG1) | Solid | VA | Glycan based site specific KD = 24~33 nM |
| huB7H3 | TBD | Preclinical | Solid | — | — |

*Indication: B7-H3 expressed children cancer (Neuroblastoma, Rhabdomyosarcoma, Osteosarcoma, Ewing Sarcoma, Wilms Tumor, Desmoplastic Small Round Cell Tumor), Refractory cancer (Prostate, Melanoma, RCC, TNBC, Head & Neck Bladder, NSCLC), Intermediate and high-risk Prostate cancer.

B7-H3 expression contributes to tumor invasion and metastasis. Different patterns of B7-H3 fucosylation or different isoform expression in cancer cells show conflicting costimulatory and coinhibitory functions (*Immunological Reviews* 2017; 276: 52-65). B7-H3 is expressed highly in tumor tissues (FIGS. 26A-26B). B7-H3 expression is significantly associated with poor outcome in patients with RCC, lung cancer, prostate cancer, colorectal carcinoma, gallbladder cancer, esophageal squamous cancer, cervical cancer, osteosarcoma, breast cancer, head and neck, pancreatic cancer, and ovarian cancer (*Clin Cancer Res* 2008; 14:5150-7; *J. Cell. Mol. Med.* Vol 21, No 9, 2017 pp. 2199-2210; *OncoTargets and Therapy* 2014:7 1465-1472; *Cell Research* volume 27, pages 1034-1045(2017); *Am J Transl Res* 2015; 7(12):2646-2660; *Clin Cancer Res,* 2012, 18(14): 3834-3845).

B7-H3 is not expressed in many hematological cell lines (*Tissue Antigens* 2005: 66: 83-92). 44.8% of acute myeloid leukemia (AML) and acute lymphocytic leukemia (ALL) show B7-H3 expression and 65% of mantle cell lymphoma (MCL) cases show B7-H3 expression. There is no expression of B7-H3 in B cells, T cells, and monocytes (*CMI* 2005 2(4) 307-311). B7-H3 is inducibly expressed in macrophages, DCsm and tumors. B7-H3 is constitutively expressed in dendritic cells derived from monocytes (Mo-DCs). B7-H3 is weakly expressed in monocytes derived DCs (*Clin Cancer Res* 18(14); 3834-45, 2012).

The disclosure also provides monovalent antibodies and/or bispecific antibodies that include at least a first arm that is specific for B7-H3. Preferably, the monovalent antibodies and/or bispecific antibodies are specific for at least human B7-H3. In some embodiments, the monovalent antibodies and/or bispecific antibodies that recognize human B7-H3 are also cross-reactive for at least one other non-human B7-H3 protein, such as, by way of non-limiting example, non-human primate B7-H3, e.g., cynomolgus monkey B7-H3, and/or rodent B7-H3. The disclosure also provides antibodies that bind to the same epitope as an anti-B7-H3 monovalent and/or an anti-B7-H3 bispecific antibody disclosed herein.

Exemplary anti-B7-H3 monoclonal antibodies of the disclosure and antigen binding fragments thereof include, for example, antibodies listed in Tables 19-24.

In some embodiments, exemplary anti-B7-H3 monoclonal antibodies of the disclosure and antigen binding fragments thereof include a combination of heavy chain complementarity determining regions (CDRs) selected from the CDR sequences shown in Table 19 and light chain CDRs selected from the CDR sequences shown in Table 19. In some embodiments, exemplary anti-B7-H3 monoclonal antibodies of the disclosure and antigen binding fragments thereof include a combination of variable sequences of the heavy domain and the light domain shown in Tables 20-24. In some embodiments, exemplary anti-B7-H3 monoclonal antibodies of the disclosure include a combination of constant sequences of the heavy domain and the light domain shown in Table 21-24.

Antibody-Drug Conjugates

In certain aspects, the antibody-drug conjugates disclosed herein are represented by Formula I or a pharmaceutically acceptable salt or solvate thereof:

$$Ab\text{-}(G)_n \quad \text{Formula I}$$

wherein:

Ab is an anti-B7-H3 antibody or antigen-binding fragment thereof comprising a variable heavy chain complimentarity determining region 1 (CDRH1), a variable heavy chain complimentarity determining region 2 (CDRH2), a variable heavy chain complimentarity determining region 3 (CDRH3), a variable light chain complimentarity determining region 1 (CDRL1), a variable light chain complimentarity determining region 2 (CDRL2), and a variable light chain complimentarity determining region 3 (CDRL3); wherein CDRH1 comprises an amino acid sequence of SEQ ID NO: 1, 7, 13, 19, 25, 31, 37, or 43;

CDRH2 comprises an amino acid sequence of SEQ ID NO: 2, 8, 14, 20, 26, 32, 38, or 44;

CDRH3 comprises an amino acid sequence of SEQ ID NO: 3, 9, 15, 21, 27, 33, 39, or 45;

CDRL1 comprises an amino acid sequence of SEQ ID NO: 4, 10, 16, 22, 28, 34, 40, or 46, CDRL2 comprises an amino acid sequence of SEQ ID NO: 5, 11, 17, 23, 29, 35, 41, or 47;

CDRL3 comprises an amino acid sequence of SEQ ID NO: 6, 12, 18, 24, 30, 36, 42, or 48;

each G is, independently, a chemical moiety comprising one or more active agents and a linker, wherein the linker covalently links Ab to the active agent(s); and n is an integer between 1 to 20.

In some embodiments, Ab is a monoclonal antibody, a domain antibody (dAb), a single chain antibody (scAb), a Fab fragment, a F(ab')2 fragment, a single chain variable fragment (scFv), a scFv-Fc fragment, a single domain heavy chain antibody, a single domain light chain antibody, a variant antibody, a multimeric antibody, or a bispecific antibody. Ab may be a rabbit, mouse, chimeric, humanized or fully human monoclonal antibody. In some embodiments, Ab is an IgG isotype, such as an IgG1 isotype.

In some embodiments, Ab comprises a combination of a variable heavy chain comprising the amino acid sequence of SEQ ID NO: 49, 51, 53, 55, 57, 59, 61, 63, 65, 67, 69, 71, 73, 75, 77, 79, or 81 and a variable light chain comprising the amino acid sequence of SEQ ID NO: 50, 52, 54, 56, 58, 60, 62, 64, 83, 85, 87, 89, 91, 93, 95, or 97.

In some embodiments, Ab comprises a combination of a variable heavy chain sequence and a variable light chain sequence selected from:
(a) a variable heavy chain comprising the amino acid sequence of SEQ ID NO: 49 and a variable light chain comprising the amino acid sequence of SEQ ID NO: 50;
(b) a variable heavy chain comprising the amino acid sequence of SEQ ID NO: 51, and a variable light chain comprising the amino acid sequence of SEQ ID NO: 52;
(c) a variable heavy chain comprising the amino acid sequence of SEQ ID NO: 53 and a variable light chain comprising the amino acid sequence of SEQ ID NO: 54;
(d) a variable heavy chain comprising the amino acid sequence of SEQ ID NO: 55 and a variable light chain comprising the amino acid sequence of SEQ ID NO: 56;
(e) a variable heavy chain comprising the amino acid sequence of SEQ ID NO: 57 and a variable light chain comprising the amino acid sequence of SEQ ID NO: 58; and
(f) a variable heavy chain comprising the amino acid sequence of SEQ ID NO: 59 and a variable light chain comprising the amino acid sequence of SEQ ID NO: 60;
(g) a variable heavy chain comprising the amino acid sequence of SEQ ID NO: 61 and a variable light chain comprising the amino acid sequence of SEQ ID NO: 62; and
(h) a variable heavy chain comprising the amino acid sequence of SEQ ID NO: 63 and a variable light chain comprising the amino acid sequence of SEQ ID NO: 64.

In some embodiments, the B7-H3 is human B7-H3.

In some embodiments, the cleavage group is capable of cleaving within a target cell. In some embodiments, the cleavage group is capable of releasing one or more active agents. In some embodiments, the antibody conjugate comprises Ab; at least one branched linker covalently coupled to Ab; and at least two active agents covalently coupled to the branched linker. In some embodiments, at least two branched linkers are coupled to Ab, and each branched linker is coupled to at least two active agents. In some embodiments, three branched linkers are coupled to Ab. In other embodiments, four branched linkers are coupled to Ab. In yet other embodiments, exactly one branched linker is coupled to Ab. In yet other embodiments, each branched linker is coupled to exactly two active agents. In some embodiments, the conjugate comprises at least two different active agents. In some embodiments, at least one branched linker is coupled to two different active agents.

In some embodiments, each active agent is coupled to a branched linker by a cleavable (e.g., hydrolysable) bond. In some embodiments, each branched linker comprises a branching unit, and each active agent is coupled to the branching unit through a secondary linker and the branching unit is coupled to the anti-B7-H3 antibody by a primary linker. In some embodiments, the branching unit is a nitrogen atom, e.g., of an amine or an amide. In some embodiments, the branching unit is an amide and the primary linker comprises the carbonyl of the amide. In some embodiments, the branching unit is an amide and the secondary linker comprises the carbonyl of the amide. In some preferred embodiments, the branching unit is a lysine unit.

Linkers and Conjugation Partners

In some preferred embodiments, each G independently is a group having the structure of Formula (II):

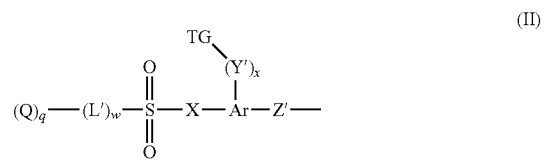

each Q is, independently, an active agent linked to L' via a heteroatom, preferably O or N;
Z' is a linking group;
L' is a spacer moiety attached to the $SO_2$ via a heteroatom selected from O, S, and N, preferably O or N, and is selected such that cleavage of the bond between L' and $SO_2$ promotes cleavage of the bond between L' and Q to release the active agent;
X is —O—, —$C(R^b)_2$—, or —$N(R^c)$—, preferably —O—;
Ar represents a ring, such as aryl, heteroaryl, cycloalkyl, or heterocycloalkyl, preferably aryl or heteroaryl;
Y' is —$(CR^b{}_2)_yN(R^a)$—, —$(CR^b{}_2)_yO$—, or —$(CR^b{}_2)_yS$—, positioned such that the N, O, or S atom is attached to TG if y is 1;
X and Y' are positioned on adjacent atoms of Ar;
TG is a triggering group that, when activated, generates an N, O, or S atom capable of reacting with the $SO_2$ to displace $(Q)_q$-$(L')_w$ and form a 5-6-membered ring including X—$SO^2$ and the intervening atoms of Ar;
q is an integer having a value from 1 to about 20, preferably from 1 to about 10;
w, x, and y are each independently an integer having a value of 0 or 1;
each $R^a$ and $R^c$ is independently hydrogen or lower alkyl; and
each $R^b$ is independently hydrogen or lower alkyl; or two $R^b$, together with the atom to which they are attached, form a 3-5-membered ring, preferably a 3-4-membered ring,
provided that when w is 0, q is 1.

Each active agent can be any suitable active agent, as described in greater detail below. While many traditional conjugation methods require the presence of functional groups such as amines or hydroxyl groups to form a stable linkage, the disclosure herein provides strategies for forming connections using functional groups heretofore unavailable for this purpose, such as phenols and tertiary amines. These functional groups form stable linkages in the conjugates disclosed herein, while still permitting release under the predetermined conditions that activate the triggering group.

Many suitable triggering groups are known in the art, and exemplary triggering groups and the conditions that activate them are discussed below, such as moieties described for Y below. Some triggering groups include the N, O, or S atom, but in a non-nucleophilic form. For example, an $NO_2$ group is a triggering group that, under reductive conditions, is reduced to an $NH_2$ or NHOH group that can react with the $SO_2$, and an acetate group is a triggering group that, under hydrolytic conditions, is hydrolyzed to a hydroxyl group that can react with the $SO_2$. Other triggering groups do not include the N, O, or S atom, but when activated are converted to a nucleophilic N, O, or S atom. For example, a boronate group is a triggering group that, under oxidative conditions (such as peroxide), is converted to a hydroxyl group that can react with the SO$_2$. Preferably, the triggering group is selected such that the conditions that activate it do so selectively, without cleaving or degrading other portions of the conjugate, such as the targeting moiety. Once the nucleophilic N, O, or S atom is generated, that atom intramolecularly attacks the SO$_2$ moiety to form a ring, expelling the moiety (Q)$_q$-(L')$_w$—H, where the H is bonded to the heteroatom of Q or L' that was formerly attached to the SO$_2$ moiety.

In embodiments where w is 0, q is 1 and Q is directly attached to the SO$_2$ via a heteroatom. Accordingly, activating the triggering group generates a nucleophilic heteroatom that intramolecularly attacks the SO$_2$ moiety to form a ring, expelling the active agent Q-H, where the H is bonded to the heteroatom formerly attached to SO$_2$.

In embodiments where w is 1, L' may be selected to permit attachment of multiple occurrences of Q, which may be the same or different. Accordingly, each instance of Q is indirectly attached to the SO$_2$ via a spacer moiety. In such embodiments, activating the triggering group generates a nucleophilic heteroatom that intramolecularly attacks the SO$_2$ moiety to form a ring, expelling the moiety (Q)$_q$-L'-H, where the H is bonded to the heteroatom in L' that was formerly attached to SO$_2$. In such embodiments, the released heteroatom triggers an intramolecular reaction that expels the active agent(s) Q (such as if Q has a tertiary amine that was attached to L' as a quarternary ammonium) or Q-H. For example, the heteroatom may undergo an intramolecular cyclization reaction with an ester moiety formed with a hydroxyl of Q-H, forming a ring and ejecting the active agent Q-H. Alternatively, the heteroatom may undergo an intramolecular tautomerization that expels the active agent Q or Q-H.

Ar can be any suitable ring, including a ring of a bicycle or other polycycle, so that the moieties that undergo intramolecular cyclization are held in close proximity to facilitate that reaction after activation of the triggering group. The planar character of aromatic and heteroaromatic rings is preferred, as the rigid geometry of substituents on such rings ensures favorable placement of the reactive moieties, although other types of rings, such as cycloalkenyl or heterocycloalkenyl, can enforce similar geometries. A five- or six-membered ring, and/or the number or identities of heteroatoms in the ring, and/or substituents (e.g., electron-donating or electron-withdrawing substituents) on other the ring, may be selected to modulate the rate of cyclization based on the resulting bond angles of the ring. Similarly, the more flexible conformations of cycloalkyl and heterocyclyl rings can be useful when it is desired to slow the rate of intramolecular cyclization.

Z' can be any suitable linking group that connects Ar to one or more Ab groups. Typically, the linking group should be sufficiently hydrophilic to promote water-solubility and discourage aggregation of the conjugate, such as by including moieties such as polyethylene glycol moieties, peptide sequences, charge-bearing moieties (such as carboxylates, amines, nitrogen-containing rings, etc.), etc. to balance the hydrophobic character of any alkyl chains that may be included. Because it is often advantageous to prepare conjugates in a modular fashion, Z' may contain a linking unit, a functional group that results from the conjugation of one reactive moiety to another. Representative linking units are discussed in greater detail below (e.g., in connection with the variable Z), and common linking groups include amides, triazoles, oximes, carbamates, etc. Representative Z' groups include L'-Z groups as discussed in greater detail below. In some embodiments, all of the G groups attached to each Ab are identical, while in other embodiments, each Ab may be attached to two or more distinct G groups. For example, some G groups may have a triggering group that is activated under a first condition, while other G groups may have a triggering group that is activated under a second condition, so that, for example, one active agent can be selectively released under the first condition, but a second active agent can be selectively released under the second condition.

In certain embodiments of Formula (II), —Y' is —(CH$_2$)$_y$NR''—, —(CH$_2$)$_y$O— or —(CH$_2$)$_y$S—, positioned such that the N, O, or S atom is attached to TG if y is 1; R'' is hydrogen or C$_1$-C$_6$-alkyl; and y is an integer having a value of 0 or 1. In some such embodiments, TG is a β-galactoside, β-glucuronide, or a combination of β-galactoside and β-glucuronide.

In some embodiments of Formula (II), (L')w links each Q to the —SO$_2$—; and each Q is an active agent linked to one of the the L' groups through a heteroatom, preferably O or N, and forming an —O—, an —OC(O)—, an —OC(O)O— or an —OC(O)NH— linkage including the heteroatom of Q. In other embodiments, (Q)$_q$-(L')$_w$— is selected from:

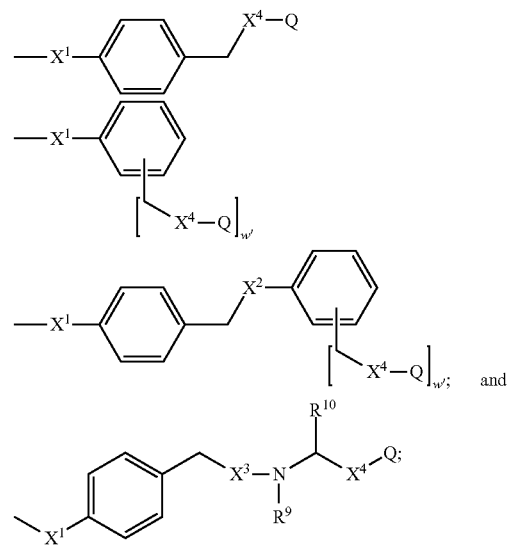

wherein:

Q is an active agent linked to L' through a heteroatom, preferably O or N,

X$^4$ is absent or forms an —O—, an —OC(O)—, an —OC(O)O— or an —OC(O)NH— linkage including the heteroatom of Q;

X$^1$ is —O— or —NR$^a$—;

X$^2$ is —O—, —OC(O)—, —OC(O)O— or —OC(O)NH—;

X$^3$ is —OC(=O)—;

w' is an integer having a value of 1, 2, 3, 4, or 5;

R$^9$ and R$^{10}$ are each independently hydrogen, alkyl, aryl, or heteroaryl, wherein alkyl, aryl, and heteroaryl are unsubstituted or substituted with one or more substituents, e.g., selected from alkyl, —(CH$_2$)$_u$NH$_2$, —(CH$_2$)$_u$NR$^{u1}$R$^{u2}$, and —(CH$_2$)$_u$SO$_2$R$^{u3}$;

R$^{u1}$, R$^{u2}$, and R$^{u3}$ are each independently hydrogen, alkyl, aryl, or heteroaryl; and u is an integer having a value of 1 to about 10.

In some such embodiments, $(Q)_q$-$(L')_w$- is selected from:

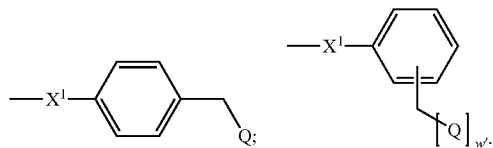

In certain embodiments, Z' includes a reactive group (e.g., a precursor group, as discussed in greater detail below with respect to Z) that can be used to attach the compound to a triggering agent, to a solid surface (e.g., to form a solid-supported array, or sensor particles), or to any other molecule or support of interest.

In certain embodiments, Z' is a linking group having a structure of Formula (IIa), (IIb), (IIc), (IId), (IIe), (IIf), (IIg), or (IIh):

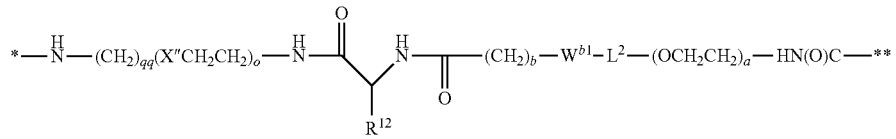

(IIa)

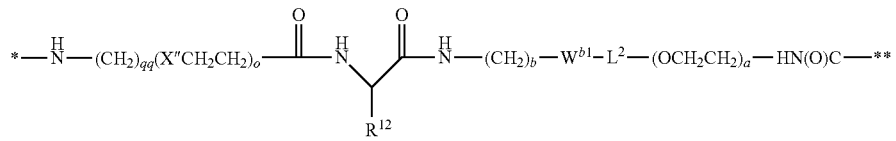

(IIb)

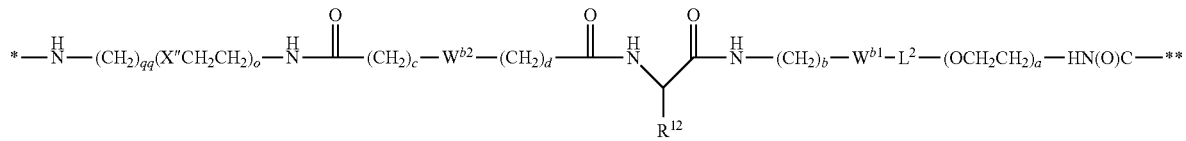

(IIc)

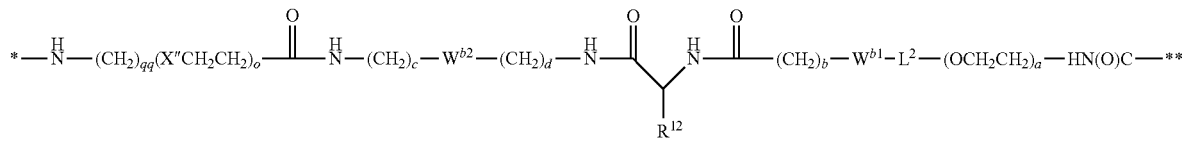

(IId)

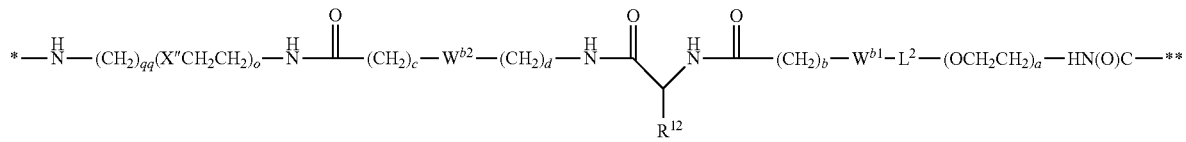

(IIe)

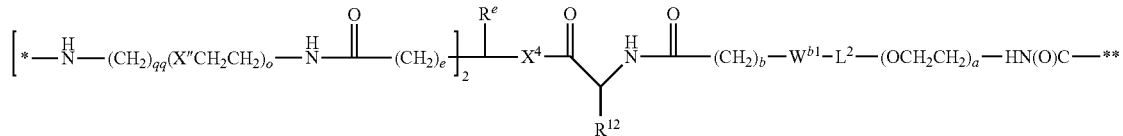

(IIf)

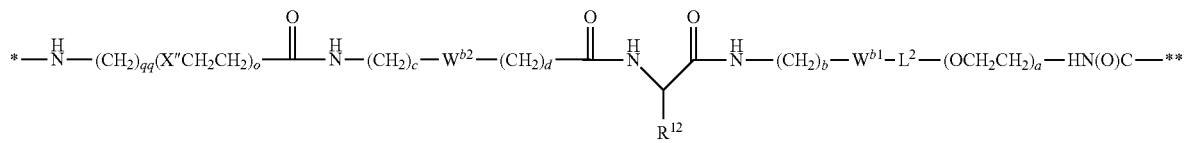

(IIg)

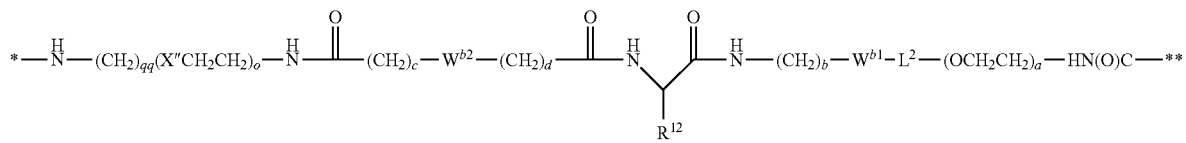

(IIh)

wherein:
* is the point of attachment to Ab;
** is point of attachment to Ar;
$R^e$ is alkyl;
X" is —O—, —S—, —NH—, or —CH$_2$—;
$X^4$ is —NHC(O)—(CH$_2$)$_g$—NH— or —C(O)NH—(CH$_2$)$_h$—NH—;
$W^{b1}$ and $W^{b2}$ are each independently —C(O)NH—, —NHC(O)—,

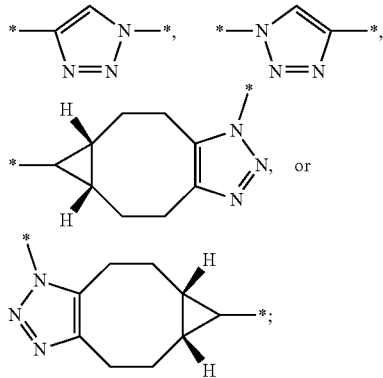

$L^2$ is an optionally present spacer moiety, and may be further substituted with one or more substituents, such as $C_1$-$C_6$ alkyl, $C_5$-$C_{14}$ aryl, and $C_3$-$C_8$ heteroaryl, wherein the alkyl, aryl and heteroaryl may be further substituted, e.g., with one or more substituents selected from the group consisting of $C_1$-$C_{10}$ alkyl, —(CH$_2$)$_u$NH$_2$, —(CH$_2$)$_u$NR$^{u1}$R$^{u2}$, —(CH$_2$)$_u$CO$_2$H, —(CH$_2$)$_u$CO$_2$R$^{u1}$, and —(CH$_2$)$_u$SO$_2$R$^{u3}$, wherein R$^{u1}$, R$^{u2}$, and R$^{u3}$ are each independently hydrogen, $C_1$-$C_{15}$ alkyl, $C_6$-$C_{20}$ aryl or $C_3$-$C_{10}$ heteroaryl; and u is an integer having a value of 1 to about 10;

$R^{12}$ is hydrogen, $C_1$-$C_8$ alkyl, or an amino acid moiety, such as a natural amino acid moiety;

a, b, c, d, e, g, h, o, and qq are each independently an integer having a value of 1 to about 10; and s' is an integer having a value of 1 to about 10.

In preferred embodiments, $W^{b1}$ and $W^{b2}$ are each independently

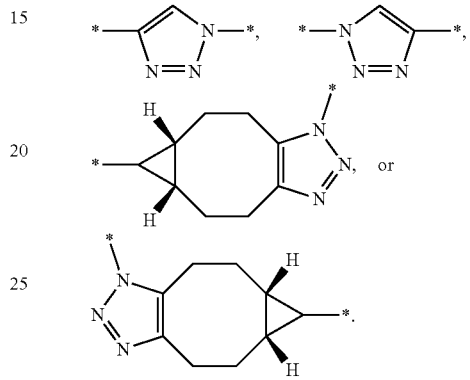

In other embodiments, Z' is a linking group having a structure of Formula (IIa'), (IIb'), (IIc'), (IId'), (IIe'), (IIf'), (IIg'), or (IIh'):

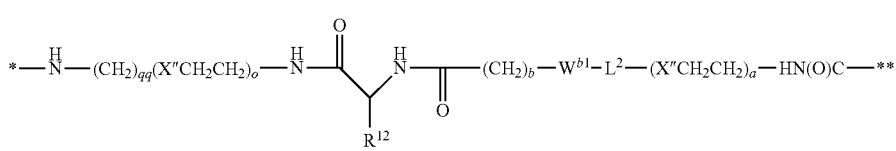

(IIa')

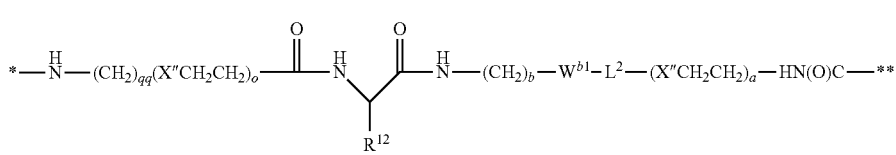

(IIb')

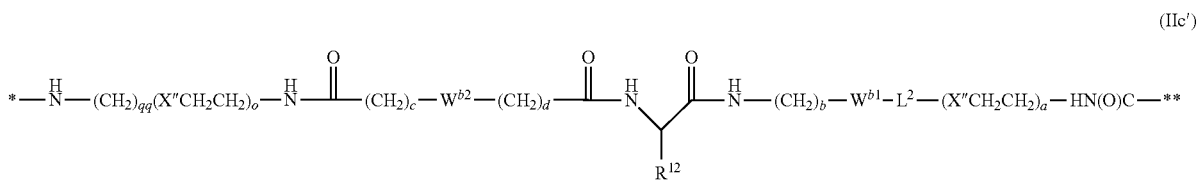

(IIc')

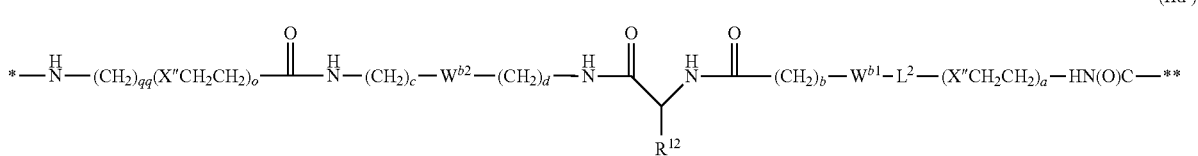

(IId')

-continued
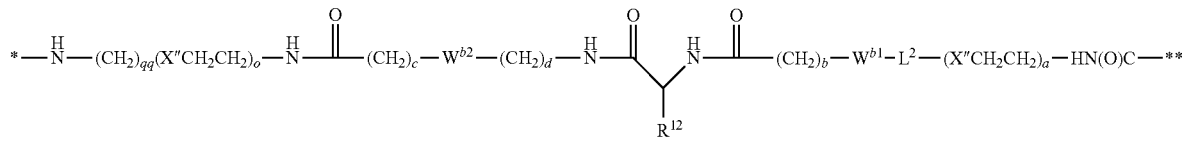
(IIe′)
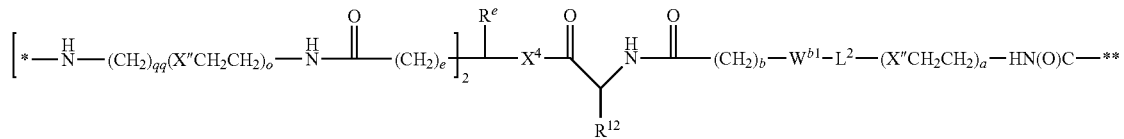
(IIf′)
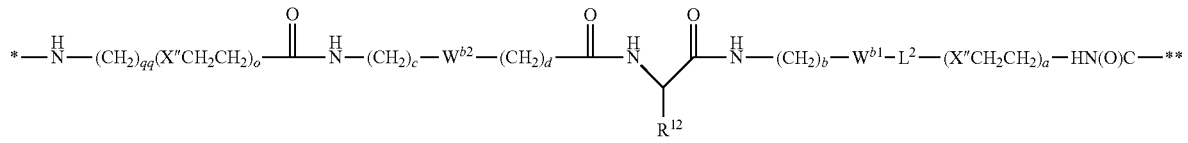
(IIg′)
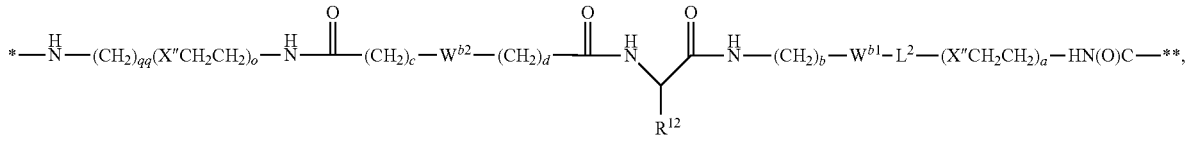
(IIh′)
wherein:
* is the point of attachment to Ab;
** is point of attachment to Ar.
In some preferred embodiments, Z′ is a linking group selected from
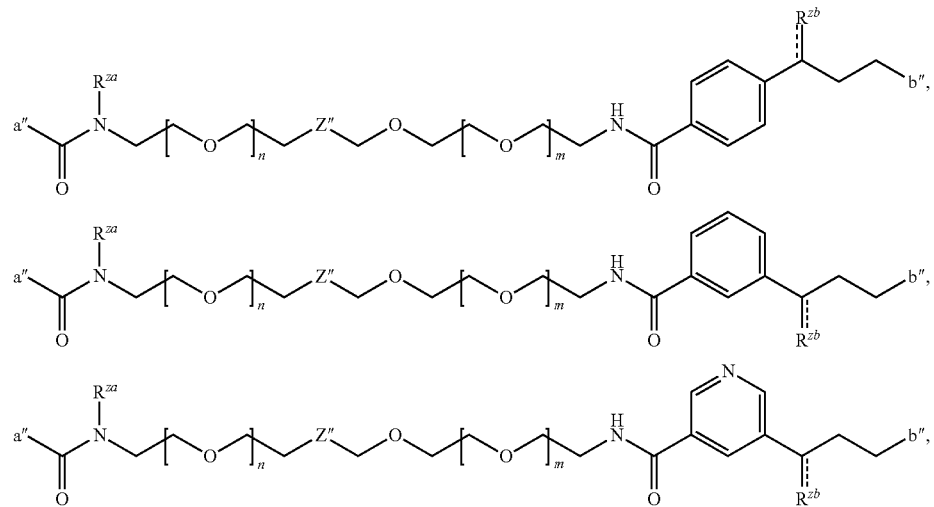

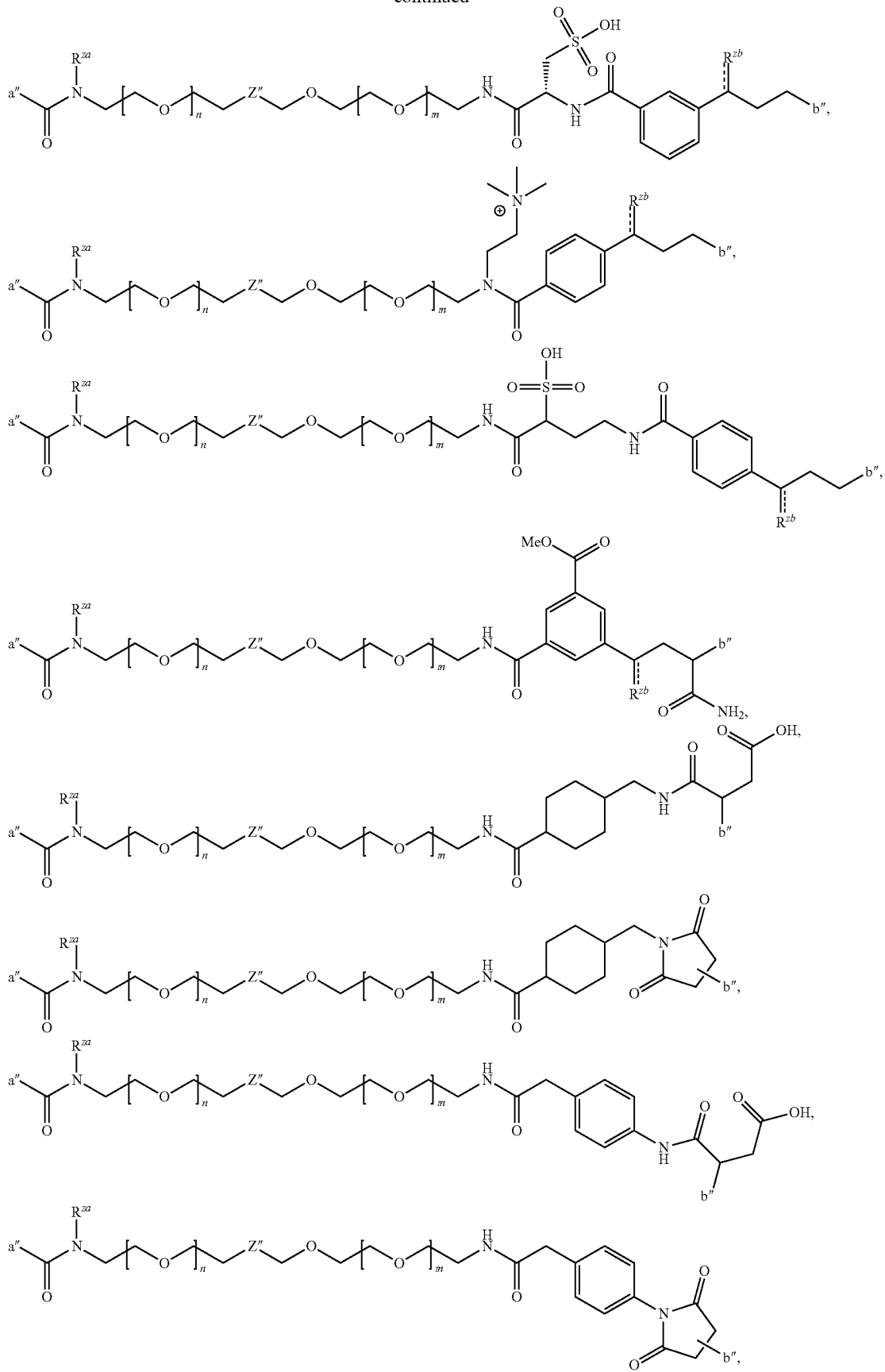

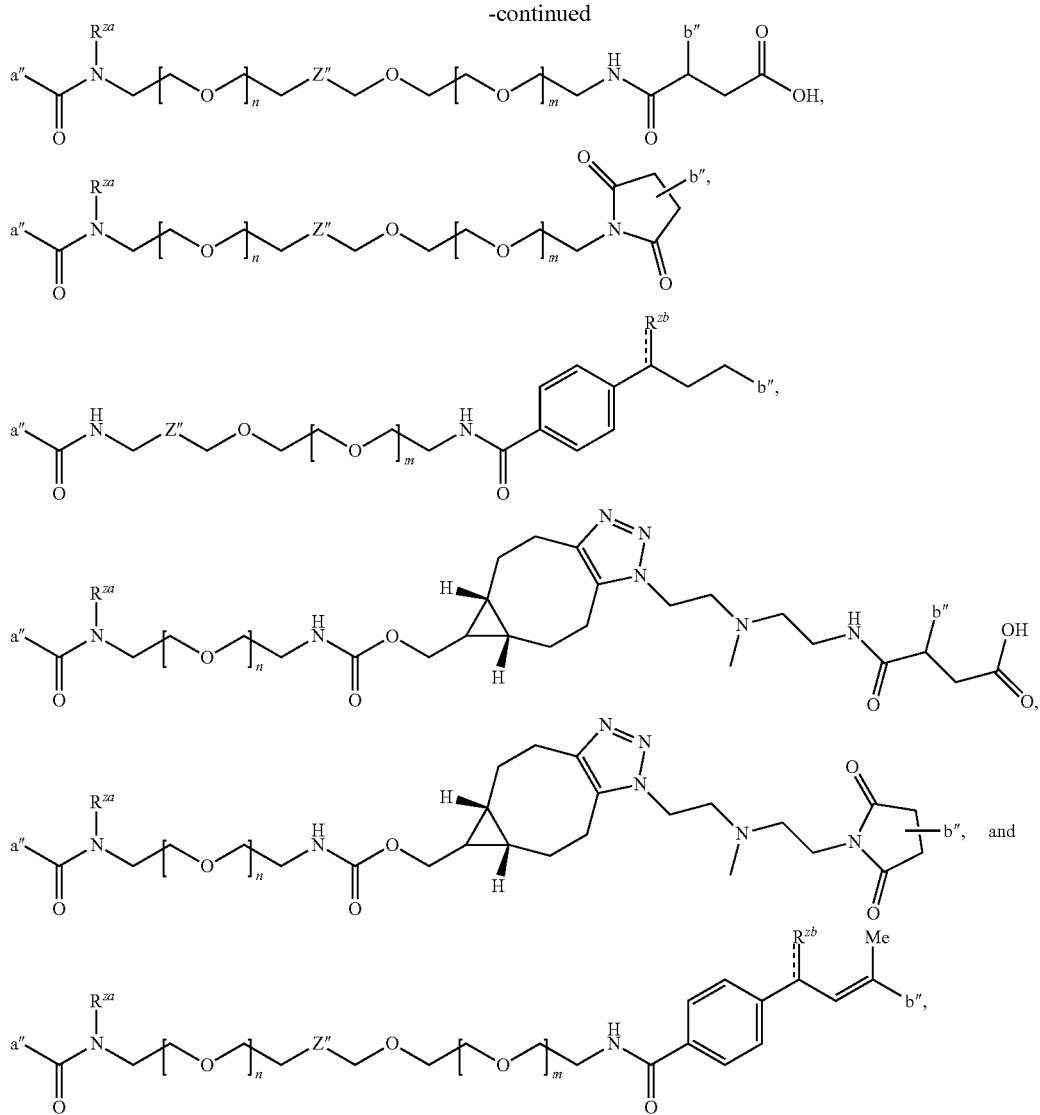
wherein
$R^{za}$ is H or methyl;
$R^{zb}$ is —OH, =O, or =NHOH;
------ a single bond or a double bond;
a" represents the bond between Z' and Ar of Formula (II);
b" represents the bond between Z' and Ab; and
Z" is selected from
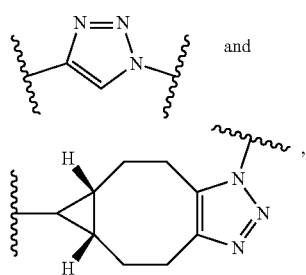
and
positioned in either direction.
In some embodiments, G comprises a moiety selected from the following:
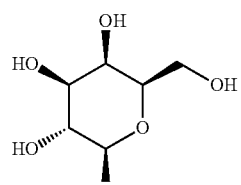
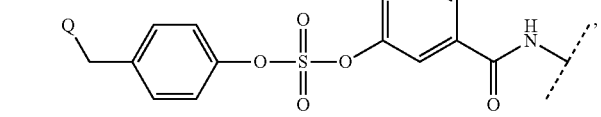

-continued

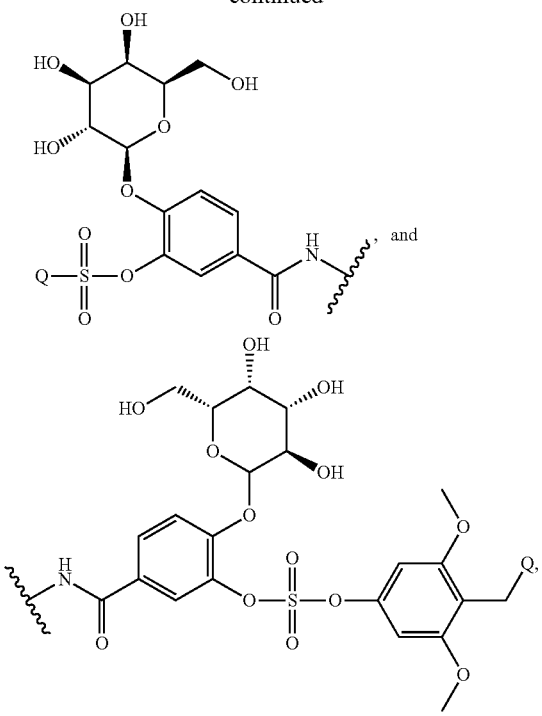
, and wherein Q is an active agent and

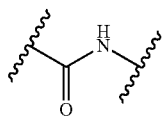 [SMILES: *NC(*)=O]

is the fragment of the linking group Z' that connects Z' to the substituted phenyl group (represented as Ar in formula (II)).

In certain embodiments, Ab-(G)$_n$ is represented by a compound of formula (III):

or a salt thereof, wherein:

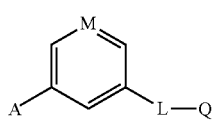
(III)

A is

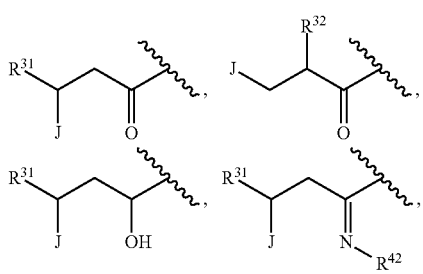

-continued

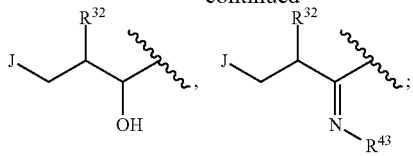

M is N, CR$^{30}$, or C(-L-Q);
each L is independently selected from a spacer moiety;
each Q is an active agent;
J is a B7-H3 antibody, as described herein;
R$^{30}$ and R$^{31}$ are each independently selected from an electron-withdrawing group, hydrogen, alkyl, alkenyl, alkynyl, aryl, heteroaryl, carbocyclyl, heterocyclyl, and haloalkyl;
R$^{42}$ and R$^{43}$ are each independently selected from —OH, alkoxy, —NR$^{44}$R$^{45}$, alkyl, alkenyl, alkynyl, aryl, heteroaryl, carbocyclyl, and heterocyclyl, wherein R$^{44}$ and R$^{45}$ together with the nitrogen atom to which they are attached can form a 5-8-membered cycle, optionally fused with an aryl or a heteroaryl ring;
R$^{32}$, R$^{44}$, and R$^{45}$ are each independently selected from hydrogen, alkyl, alkenyl, alkynyl, aryl, heteroaryl, carbocyclyl, heterocyclyl, and haloalkyl; and
n is 1 to 4.

In some embodiments, M is N.

In certain embodiments, M is CR$^{30}$, and R$^{30}$ is an electron-withdrawing group.

In some embodiments, A is selected from

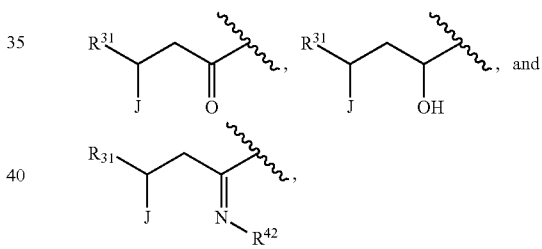

wherein R$^{31}$ is an electron-withdrawing group, preferably wherein L is coupled to C by an electron-withdrawing group selected from an amide or an ester.

In some embodiments, M is C(-L-Q), and wherein L is coupled to C by an electron-withdrawing group.

In some embodiments, R$^{30}$ is —CO$_2$NR$^{33}$R$^{34}$ or —CO$_2$R$^{35}$, and R$^{33}$, R$^{34}$, and R$^{35}$ are each independently selected from hydrogen, alkyl, alkenyl, alkynyl, aryl, heteroaryl, carbocyclyl, heterocyclyl, and haloalkyl.

In some embodiments, each electron-withdrawing group is independently selected from —NO$_2$, —CN, -haloalkyl, —CO$_2$NR$^{33}$R$^{34}$, —CO$_2$R$^{35}$, —C(=O)R$^{36}$, —S(=O)R$^{37}$, —S(=O)$_2$OR$^{38}$, and —NR$^{39}$R$^{40}$R$^{41}$; and R$^{36}$, R$^{37}$, R$^{38}$, R$^{39}$, R$^{40}$, and R$^{41}$ are each independently selected from hydrogen, alkyl, alkenyl, alkynyl, aryl, heteroaryl, carbocyclyl, heterocyclyl, and haloalkyl.

In certain embodiments, each electron-withdrawing group is independently selected from —CN, —CONR$^{33}$R$^{34}$, and —CO$_2$R$^{35}$.

In some embodiments, each electron withdrawing group is independently selected from —CN, —CONH$_2$, and —CO$_2$Me.

In certain embodiments, Q is an agent.

In some embodiments, Q comprises L' and Q', wherein L' is a linker and Q' is an active agent.

In certain embodiments, L' comprises a coupling group, wherein the coupling group is coupled to L.

In some embodiments, the coupling group is selected from —C(=O)NR$^{32}$—, —C(=O)O—, —C(=NR$^{32}$)—, —C=NO—, —NR$^{32}$—C(=O)—NR$^{32}$—, —OC(=O)O—, —S—S—, —NR$^{32}$S(=O)$_2$O—, and —OS(=O)$_2$O—.

In certain preferred embodiments, the coupling group is selected from

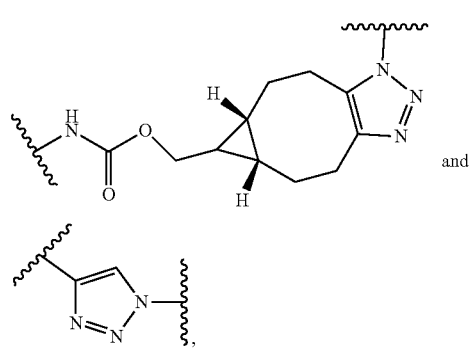

and

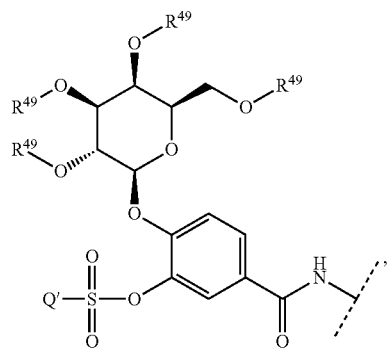

oriented in either direction.

In some embodiments, L' further comprises a cleavable group, wherein the cleavable group is coupled to Q'.

In certain embodiments, the cleavable group-Q' moiety is selected from

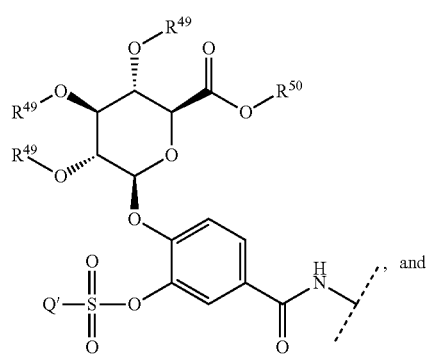

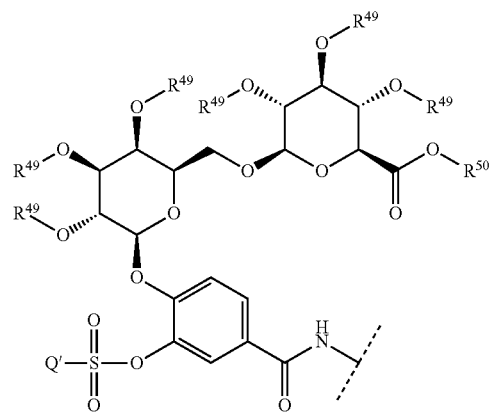

wherein

R$^{49}$ is hydrogen or —C(=O)R$^{50}$; and

R$^{50}$ is lower alkyl.

In some embodiments, L' further comprises a C$_6$-C$_{100}$ alkylene comprising at least one group selected from —NH—, —C(=O)—, —O—, —S—, —S(O)—, and —S(=O)$_2$—.

In certain embodiments, L comprises a C$_6$-C$_{100}$ alkylene comprising at least one group selected from —NH—, —C(=O)—, —O—, —S—, —S(O)—, and —S(=O)$_2$—. For example, L comprises

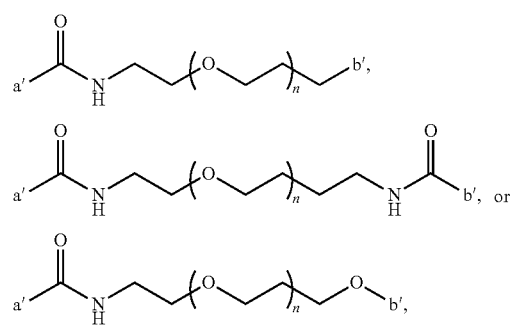

wherein a' is the bond to the M-containing aromatic ring, and b' is the bond to L'; and n is 2-20.

In some embodiments, A is

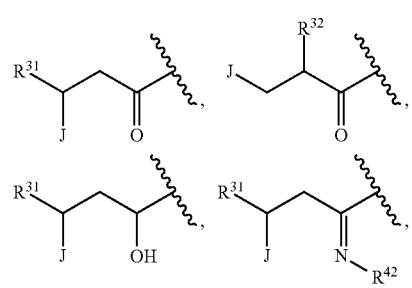

-continued

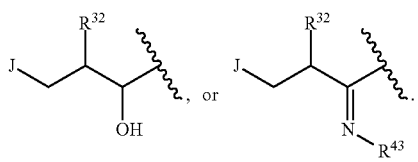, or

For example, A may be

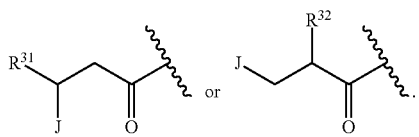 or

Alternatively, A may be

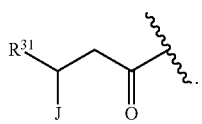.

In other embodiments, A may be

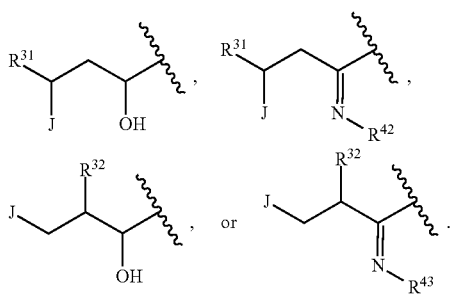

In some embodiments, A is

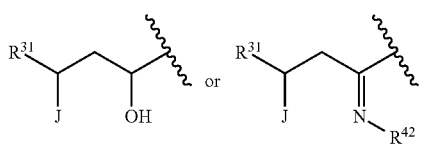

In certain embodiments, $R^{42}$ is —OH or —NR$^{44}$R$^{45}$.

In some embodiments, the present disclosure relates to methods of making ADCs as disclosed here comprising reacting an antibody as disclosed herein with compounds of Formula (IV) or Formula (V):

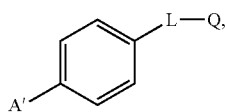 (IV)

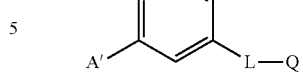 (V)

wherein A' is

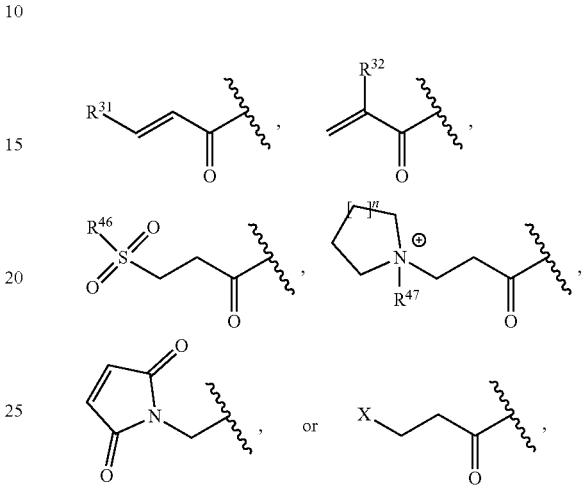

M is N, CR$^{30}$, or C(-L-Q);

each L is independently selected from a spacer moiety;

each Q is independently selected from an active agent or a reactive group;

X is selected from —Cl, —Br, and —I;

R$^{30}$ and R$^{31}$ are each independently selected from an electron-withdrawing group, hydrogen, alkyl, alkenyl, alkynyl, aryl, heteroaryl, carbocyclyl, heterocyclyl, and haloalkyl;

R$^{46}$ is selected from selected from alkyl, alkenyl, alkynyl, aryl, heteroaryl, carbocyclyl, heterocyclyl, and haloalkyl;

R$^{32}$ is selected from hydrogen, alkyl, alkenyl, alkynyl, aryl, heteroaryl, carbocyclyl, heterocyclyl, and haloalkyl;

R$^{47}$ is O$^-$, alkyl, alkenyl, alkynyl, aryl, heteroaryl, carbocyclyl, heterocyclyl; and n is 1 to 4.

In some embodiments, M is N.

In certain embodiments, M is CR$^{30}$, and R$^{30}$ is an electron-withdrawing group.

In some embodiments, A' is selected from

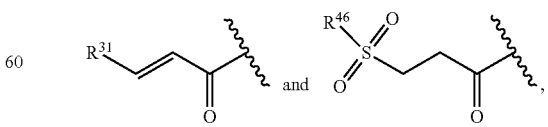

wherein R$^{31}$ is an electron-withdrawing group, preferably wherein L is coupled to C by an electron-withdrawing group selected from an amide or an ester.

In some embodiments, A' is

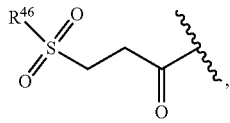

wherein $R^{46}$ is an aryl group substituted with a $C_{1-3}$ alkyl.

In some embodiments, A' is

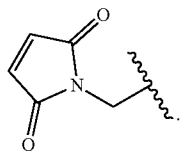 [SMILES: *CN1C(=O)C=CC1=O]

In some embodiments, A' is

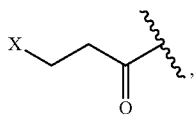

wherein X is —C(O)NH$_2$.

In some embodiments, M is C(-L-Q), and wherein L is coupled to C by an electron-withdrawing group.

In some embodiments, $R^{30}$ is —CO$_2$NR$^{33}$R$^{34}$ or —CO$_2$R$^{35}$, and $R^{33}$, $R^{34}$, and $R^{35}$ are each independently selected from hydrogen, alkyl, alkenyl, alkynyl, aryl, heteroaryl, carbocyclyl, heterocyclyl, and haloalkyl.

In some embodiments, each electron-withdrawing group is independently selected from —NO$_2$, —CN, -haloalkyl, —CO$_2$NR$^{33}$R$^{34}$, —CO$_2$R$^{35}$, —C(=O)R$^{36}$, —S(=O)R$^{37}$, —S(=O)$_2$OR$^{38}$, and —NR$^{39}$R$^{40}$R$^{41}$; and $R^{36}$, $R^{37}$, $R^{38}$, $R^{39}$, $R^{40}$, and $R^{41}$ are each independently selected from hydrogen, alkyl, alkenyl, alkynyl, aryl, heteroaryl, carbocyclyl, heterocyclyl, and haloalkyl.

In certain embodiments, each electron-withdrawing group is independently selected from —CN, —CONR$^{33}$R$^{34}$, and —CO$_2$R$^{35}$.

In some embodiments, each electron withdrawing group is independently selected from —CN, —CONH$_2$, and —CO$_2$Me.

In certain embodiments, Q is an active agent.

In some embodiments, Q comprises L' and Q', wherein L' is a linker and Q' is an active agent.

In certain embodiments, L' comprises a coupling group, wherein the coupling group is coupled to L.

In some embodiments, the coupling group is selected from —C(=O)NR$^{32}$—, —C(=O)O—, —C(=NR$^{32}$)—, —C=NO—, —NR$^{32}$—C(=O)—NR$^{32}$—, —OC(=O)O—, —S—S—, —NR$^{32}$S(=O)$_2$O—, and —OS(=O)$_2$O—.

In certain embodiments, the coupling group is selected from

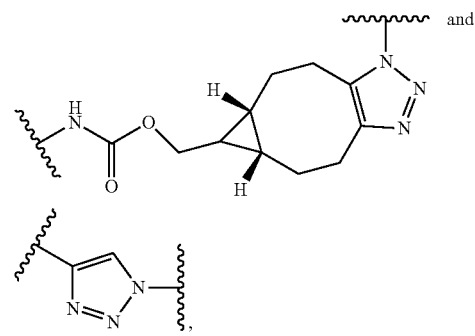

oriented in either direction.

In some embodiments, L' further comprises a cleavable group, wherein the cleavable group is coupled to Q'.

In certain embodiments, the cleavable group coupled to Q' is selected from

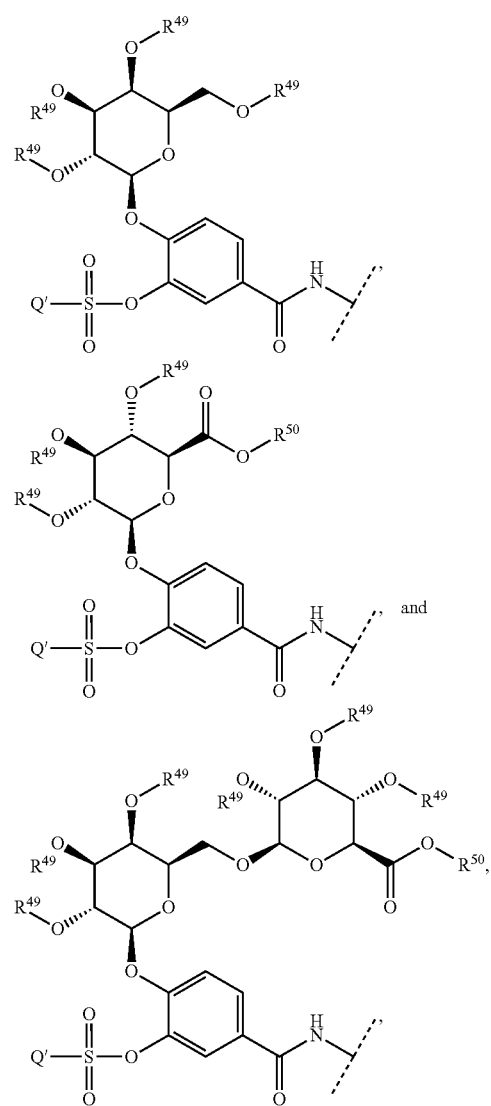

wherein

R$^{49}$ is hydrogen or —C(=O)R$^{50}$; and

R$^{50}$ is lower alkyl.

In some embodiments, L' further comprises a C$_6$-C$_{100}$ alkylene comprising at least one group selected from —NH—, —C(=O)—, —O—, —S—, —S(O)—, and —S(=O)$_2$—.

In certain embodiments, L comprises a C$_6$-C$_{100}$ alkylene comprising at least one group selected from —NH—, —C(=O)—, —O—, —S—, —S(O)—, and —S(=O)$_2$—. For example, L comprises

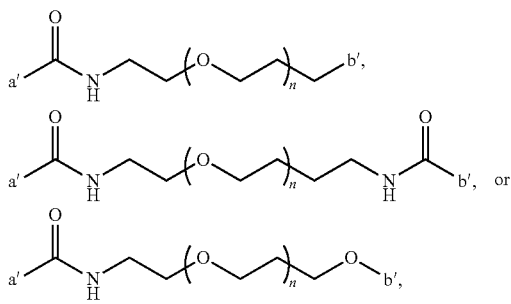

wherein a is the bond to the M-containing aromatic ring, and b is the bond to L'; and n is 2-20.

In some embodiments, Q' is a hormone, an oligonucleotide, a toxin, an affinity ligand, a probe for detection, or a combination thereof.

In certain embodiments, Q' is selected from a cytokine, an immunomodulatory compound, an anti-cancer agent, an anti-viral agent, an anti-bacterial agent, an anti-fungal agent, an anthelmintic agent, or a combination thereof.

In certain embodiments, Q is a reactive group.

In some embodiments, the reactive group is selected from —N$_3$, —C≡CH,

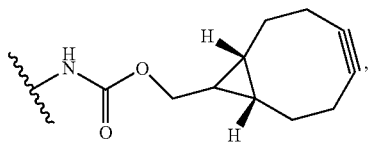 [SMILES: *NC(=O)OCC1[C@H]2CCC#CCC[C@@H]12]

—S(O)$_2$Hal, —NH$_2$, —CO$_2$Hal, —OH, —C(O)H, —SH, —N=C=O, and —N=S=C, wherein Hal is —Cl, —Br, or —I.

In some embodiments, A is

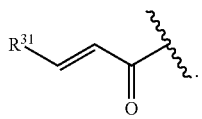

In certain embodiments, R$^{31}$ is —CN, —CO$_2$NR$^{33}$R$^{34}$, or —CO$_2$R$^{35}$.

In certain embodiments, A is

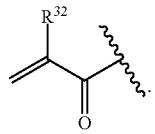

In some embodiments, R$^{32}$ is hydrogen or C$_{1-3}$ alkyl.

In some embodiments, A is

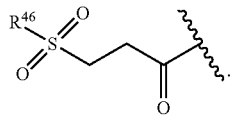

In certain embodiments, R$^{46}$ is optionally substituted C$_{1-3}$ alkyl, optionally substituted C$_6$-C$_{12}$ aryl, or optionally substituted heteroaryl.

In some embodiments, A is

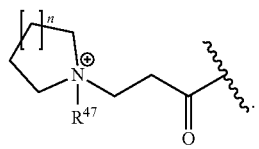

In certain embodiments, R$^{47}$ is O$^-$ or C$_{1-3}$ alkyl.

In certain embodiments, A is

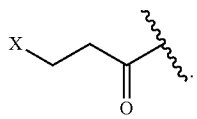

Active Agents

As described above, in preferred embodiments of the disclosure, Q is an active agent that forms a part of the ADCs disclosed herein. In some embodiments, the active agent is independently selected from chemotherapeutic agents and toxins. In some embodiments, the active agent is an immunomodulatory compound, an anticancer agent, an antiviral agent, an antibacterial agent, an antifungal agent, an antiparasitic agent, or a combination thereof.

Exemplary Drugs for Conjugation

The ADCs of the invention provide a targeted therapy that may, for example, reduce the side effects often seen with anti-cancer therapies, as the one or more active agent(s) is delivered to a specific cell.

For example, the active agent may be selected from the group consisting of erlotinib (TARCEVA; Genentech/OSI Pharm.); bortezomib (VELCADE; MilleniumPharm.); fulvestrant (FASLODEX; AstraZeneca); sutent (SU11248; Pfizer); letrozole (FEMARA; Novartis); imatinib mesylate (GLEEVEC; Novartis); PTK787/ZK 222584 (Novartis); oxaliplatin (Eloxatin; Sanofi); 5-fluorouracil (5-FU); leucovorin; rapamycin (Sirolimus, RAPAMUNE; Wyeth); lapatinib (TYKERB, GSK572016; GlaxoSmithKline); lonafarnib (SCH 66336); sorafenib (BAY43-9006; Bayer Labs.); gefitinib (IRESSA; Astrazeneca); AG1478, AG1571 (SU 5271; Sugen); alkylating agent (e.g., thiotepa or CYTOXAN® cyclophosphamide); alkyl sulfonate (e.g., busulfan, improsulfan or piposulfan); aziridine (e.g., benzodopa, carboquone, meturedopa or uredopa); ethylenimine, methylmelamine, altretamine, triethylenemelamine, triethylenephosphoramide, triethylenethiophosphoramide, trimethylolmelamine; acetogenins (e.g., bullatacin or bullatacinone); camptothecin including synthetic analogue topotecan; bryostatin; callystatin; CC-1065 (including adozelesin, carzelesin or bizelesin synthetic analogues thereof); cryptophycins (e.g., cryptophycin 1 or cryptophycin 8); dolastatin; duocarmycin (including a synthetic analogue, KW-2189, and CB1-TM1); eleutherobin; pancratistatin; sarcodictyin; spongistatin; nitrogen mustard (e.g., chlorambucil, chlornaphazine, cholophosphamide, estramustine, ifosfamide, mechlorethamine, mechlorethamine oxide hydrochloride, melphalan, novembichin, phenesterine, prednimustine, trofosfamide or uracil mustard); nitrousurea (e.g., carmustine, chlorozotocin, fotemustine, lomustine, nimustine or ranimnustine); antibiotics (e.g., calicheamicin selected from calicheamycin gammal I and calicheamycin omega I 1 or dynemicin including dynemicin A as enediyne antibiotics); bisphosphonate (e.g., clodronate); esperamicin, neocarzinostatin chromophore or related chromoprotein enediyne antibiotic chromophores, aclacinomycin, actinomycin, antramycin, azaserine, bleomycin, cactinomycin, carabicin, carninomycin, carzinophilin, chromomycin, dactinomycin, daunorubicin, detorubicin, 6-diazo-5-oxo-L-norleucine, ADRLIMYCIN® doxorubicin (e.g., morpholino-doxorubicin, cyanomorpholino-doxorubicin, 2-pyrrolino-doxorubicin, liposomal doxorubicin or deoxydoxorubicin), epirubicin, esorubicin, marcellomycin, mitomycin (e.g., mitomycin C, mycophenolic acid, nogalamycin, olivomycin, peplomycin, potfiromycin, puromycin, quelamycin, rodorubicin, streptomigrin, streptozocin, tubercidin, ubenimex, zinostatin or zorubicin); anti-metabolites (e.g., 5-fluorouracil (5-FU)); folic acid analogues (e.g., denopterin, methotrexate, pteropterin or trimetrexate); purine analogs (e.g., fludarabine, 6-mercaptopurine, thiamiprine or thiguanine); pyrimidine analogs (e.g., ancitabine, azacitidine, 6-azauridine, carmofur, cytarabine, dideoxyuridine, doxifluridine, enocitabine or floxuridine); androgen (e.g., calusterone, dromostanolone propionate, epitiostanol, mepitiostane or testolactone); anti-adrenal (e.g., aminoglutethimide, mitotane or trilostane); folic acid replenisher (e.g., folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoid (e.g., maytansine or ansamitocin; trichothecene (e.g., T-2 toxin, verracurin A, roridin A or anguidine); mitoguazone; mitoxantrone; mopidanmol; nitraerine; pentostatin; phenamet; pirarubicin; losoxantrone; 2-ethylhydrazide; procarbazine; PSK® polysaccharide; razoxane; rhizoxin; sizofiran; spirogermanium; tenuazonic acid; triaziquone; 2,2',2"-trichlorotriethylamine; trichothecene (particularly, T-2 toxin, verracurin A, roridin A or anguidine); urethane; vindesine; dacarbazine; mannomustine; mitobronitol; mitolactol; pipobroman; gacytosine; arabinoside ('Ara-C'); cyclophosphamide; thiotepa; taxoids (e.g., TAXOL® paclitaxel (Bristol-Myers Squibb Oncology, Princeton, N.J.), ABRAXANE™ cremophor-free, albumin-engineered nanoparticle formulation of paclitaxel, American Pharmaceutical Partners, Schaumber, Ill. or TAXOTERE® doxetaxel ((Rhone-Poulenc Rorer, Antony, France))); chloranbucil; gemcitabine; 6-thioguanine; mercaptopurine; platinum analog (e.g., cisplatin or carboplatin); vinblastine; platinum; etoposide, ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethlylornithine (DFMO); retinoid (e.g., retinoic acid); capecitabine; and a pharmaceutically acceptable salt thereof, a solvate thereof, an acid thereof or a derivative thereof.

Mitotic Inhibitors

In some embodiments, linkers of the disclosure may be used to conjugate an antibody to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by affecting microtubule polymerization or microtubule depolymerization. Thus, in certain embodiments, an antibody is conjugated to one or more mitotic inhibitor(s) that disrupts microtubule formation by inhibiting tubulin polymerization. In certain embodiments, the mitotic inhibitor used in the ADCs of the disclosure is Taxol® (paclitaxel), Taxotere® (docetaxel), or Ixempra® (ixabepilone). Examples of mitotic inhibitors that may be used in the ADCs disclosed herein are provided below. Included in the genus of mitotic inhibitors are auristatins, described above.

Auristatins

The linkers of the disclosure may be used to conjugate an antibody to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein.

Dolastatins

In certain embodiments, the active agent in the ADCs described herein is a dolastatin. Dolastatins are short peptidic compounds isolated from the Indian Ocean sea hare Dolabella auricularia (see Pettit et al., *J. Am. Chem. Soc.,* 1976, 98, 4677). Examples of dolastatins include dolastatin 10 and dolatstin 15. Dolastatin 15, a seven-subunit depsipeptide derived from Dolabella auricularia, and is a potent antimitotic agent structurally related to the antitubulin agent dolastatin 10, a five-subunit peptide obtained from the same organism. Thus, in certain embodiments, the ADC of the disclosure comprises an antibody, a linker as described herein, and at least one dolastatin. Auristatins, described above, are synthetic derivatives of dolastatin 10.

Maytansinoids

The linkers of the disclosure may be used to conjugate an antibody to at least one maytansinoid to form an ADC. Maytansinoids are potent antitumor agents that were originally isolated from members of the higher plant families Celastraceae, Rhamnaceae and Euphorbiaceae, as well as some species of mosses (Kupchan et al, J. Am. Chem. Soc. 94:1354-1356 [1972]; Wani et al, J. Chem. Soc. Chem. Commun 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the disclosure can be isolated from natural sources, synthetically produced, or semi-synthetically produced. Moreover, the maytansinoid can be modified in any suitable manner, so long as sufficient cytotoxicity is preserved in the ultimate conjugate molecule. The structure of an exemplary maytansinoid, mertansine (DM1), is provided below.

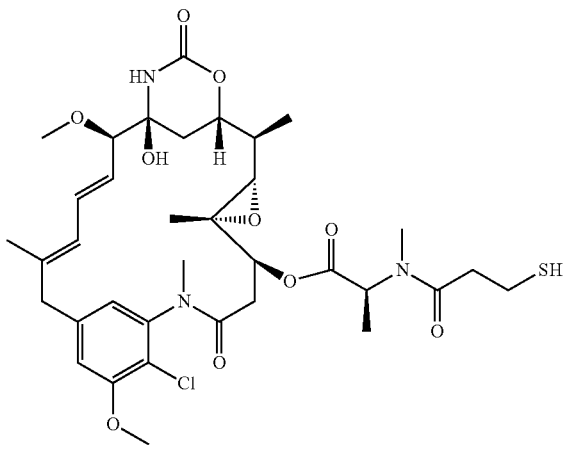

Mertansine (DM1)

Representative examples of maytansinoids include, but are not limited, to DM1 (N2'-deacetyl-N2'-(3-mercapto-1-oxopropyl)-maytansine; also referred to as mertansine, drug maytansinoid 1; ImmunoGen, Inc.; see also Chari et al. (1992) Cancer Res 52:127), DM2, DM3 (N2' -deacetyl-N2'-(4-mercapto-1-oxopentyl)-maytansine), DM4 (4-methyl-4-mercapto-1-oxopentyl)-maytansine) and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

Plant Alkaloids

The linkers of the disclosure may be used to conjugate an antibody to at least one plant alkaloid, e.g., a taxane or vinca alkaloid. Plant alkaloids are chemotherapy treatments derived made from certain types of plants. The vinca alkaloids are made from the periwinkle plant catharanthus rosea), whereas the taxanes are made from the bark of the Pacific Yew tree taxus). Both the vinca alkaloids and taxanes are also known as antimicrotubule agents, and are described in more detail below.

Taxanes

The linkers of the disclosure may be used to conjugate an antibody to at least one taxane. The term "taxane" as used herein refers to the class of antineoplastic agents having a mechanism of microtubule action and having a structure that includes the taxane ring structure and a stereospecific side chain that is required for cytostatic activity. Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869, each of which is incorporated by reference herein. Taxane compounds have also previously been described in U.S. Pat. Nos. 5,641,803, 5,665,671, 5,380,751, 5,728,687, 5,415,869, 5,407,683, 5,399,363, 5,424,073, 5,157,049, 5,773,464, 5,821,263, 5,840,929, 4,814,470, 5,438,072, 5,403,858, 4,960,790, 5,433,364, 4,942,184, 5,362,831, 5,705,503, and 5,278,324, all of which are expressly incorporated by reference. Further examples of taxanes include, but are not limited to, docetaxel (Taxotere®; Sanofi Aventis), paclitaxel (Abraxane® or Taxol®; Abraxis Oncology), and nanoparticle paclitaxel (ABI-007/Abraxene®; Abraxis Bioscience).

In certain embodiments, the linkers of the disclosure may be used to conjugate an antibody to at least one docetaxel. In certain embodiments, the linkers of the disclosure may be used to conjugate an antibody to at least one paclitaxel.

Vinca Alkaloids

In certain embodiments, the linkers of the disclosure may be used to conjugate an antibody to at least one vinca alkaloid. Vinca alkaloids are a class of cell-cycle-specific drugs that work by inhibiting the ability of cancer cells to divide by acting upon tubulin and preventing the formation of microtubules. Examples of vinca alkaloids that may be used in the ADCs of the disclosure include, but are not limited to, vindesine sulfate, vincristine, vinblastine and vinorelbine.

Antitumor Antibiotics

The linkers of the disclosure may be used to conjugate an antibody to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the ADCs disclosed herein include, but are not limited to, actinomycines (e.g., pyrrolo[2,1-c][1,4]benzodiazepines), anthracyclines, calicheamicins, and duocarmycins, described in more detail below.

Actinomycines

The linkers of the disclosure may be used to conjugate an antibody to at least one actinomycine. Actinomycines are a subclass of antitumor antibiotics isolated from bacteria of the genus *Streptomyces*. Representative examples actinomycines include, but are not limited to, actinomycin D (Cosmegen [also known as actinomycin, dactinomycin, actinomycin IV, actinomycin C1], Lundbeck, Inc.), anthramycin, chicamycin A, DC-81, mazethramycin, neothramycin A, neothramycin B, porothramycin, prothracarcin B, SG2285, sibanomicin, sibiromycin and tomaymycin. In certain embodiments, D is pyrrolobenzodiazepine (PBD). Examples of PBDs include, but are not limited to, anthramycin, chicamycin A, DC-81, mazethramycin, neothramycin A, neothramycin B, porothramycin, prothracarcin B, SG2000 (SJG-136), SG2202 (ZC-207), SG2285 (ZC-423), sibanomicin, sibiromycin and tomaymycin. Thus, in certain embodiments, D is actinomycine, e.g., actinomycin D, or PBD, e.g., a pyrrolobenzodiazepine (PBD) dimer.

The structures of PBDs can be found, for example, in U.S. Patent Application Pub. Nos. 2013/0028917 and 2013/0028919, and in WO 2011/130598 A1, each of which are incorporated herein by reference in their entirety. The generic structure of a PBD is provided below.

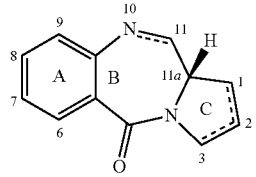

PBDs differ in the number, type and position of substituents, in both their aromatic A rings and pyrrolo C rings, and in the degree of saturation of the C ring. In the B-ring, there is generally an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11α position which provides them with a right-handed twist when viewed from the C ring towards the A ring. Further examples of PBDs which may be conjugated to antibodies via the linkers disclosed herein can be found, for example, in U.S. Patent Application Publication Nos. 2013/0028917 A1 and 2013/0028919 A1, in U.S. Pat. No. 7,741,319 B2, and in WO 2011/130598 A1 and WO 2006/111759 A1, each of which are incorporated herein by reference in their entirety.

Anthracyclines

The linkers of the disclosure may be used to conjugate an antibody to at least one anthracycline. Anthracyclines are a subclass of antitumor antibiotics isolated from bacteria of the genus *Streptomyces*. Representative examples include, but are not limited to daunorubicin (Cerubidine, Bedford Laboratories), doxorubicin (Adriamycin, Bedford Laboratories; also referred to as doxorubicin hydrochloride, hydroxydaunorubicin, and Rubex), epirubicin (Ellence, Pfizer), and idarubicin (Idamycin; Pfizer Inc.). Thus, in certain embodiments, D is anthracycline, e.g., doxorubicin.

Calicheamicins

The linkers of the disclosure may be used to conjugate an antibody to at least one calicheamicin. Calicheamicins are a family of enediyne antibiotics derived from the soil organism Micromonospora echinospora. Calicheamicins bind the minor groove of DNA and induce double-stranded DNA breaks, resulting in cell death with a 100 folds increase over other chemotherapeutics (Damle et al. (2003) Curr Opin Pharmacol 3:386). Preparation of calicheamicins that may be used as drug conjugates in the disclosure have been described, see U.S. Pat. Nos. 5,712,374; 5,714,586; 5,739,116; 5,767,285; 5,770,701; 5,770,710; 5,773,001; and 5,877,296. Structural analogues of calicheamicin which may be used include, but are not limited to, γ1 I, α2 I, α3 I, N-acetyl-γ1 I, PSAG and θI 1 (Hinman et al., Cancer Research 53:3336-3342 (1993), Lode et al., Cancer Research 58:2925-2928 (1998) and the aforementioned U.S. Pat. Nos. 5,712,374; 5,714,586; 5,739,116; 5,767,285; 5,770,701; 5,770,710; 5,773,001; and 5,877,296). Thus, in certain embodiments, D is calicheamicin.

Duocarmycins

The linkers of the disclosure may be used to conjugate an antibody to at least one duocarmycin. Duocarmycins are a subclass of antitumor antibiotics isolated from bacteria of the genus *Streptomyces*. (see Nagamura and Saito (1998) Chemistry of Heterocyclic Compounds, Vol. 34, No. 12). Duocarmycins bind to the minor groove of DNA and alkylate the nucleobase adenine at the N3 position (Boger (1993) Pure and Appl Chem 65(6):1123; and Boger and Johnson (1995) PNAS USA 92:3642). Synthetic analogs of duocarmycins include, but are not limited to, adozelesin, bizelesin, and carzelesin. Thus, in certain embodiments, the D is duocarmycin.

Other Antitumor Antibiotics

In addition to the foregoing, additional antitumor antibiotics that may be used in the ADCs of the disclosure include bleomycin (Blenoxane, Bristol-Myers Squibb), mitomycin, and plicamycin (also known as mithramycin).

Immunomodulating Agents

In some embodiments, the linkers of the disclosure may be used to conjugate an antibody to at least one immunomodulating agent. As used herein, the term "immunomodulating agent" refers to an agent that can stimulate or modify an immune response. In certain embodiments, an immunomodulating agent is an immunostimuator which enhances a subject's immune response. In some embodiments, an immunomodulating agent is an immunosuppressant, which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, bacillus calmette-guerin (BCG) and levamisole (Ergamisol). Other examples of immunomodulating agents that may be used in the ADCs of the disclosure include, but are not limited to, cancer vaccines, cytokines, and immunomodulating gene therapy.

Cancer Vaccines

The linkers of the disclosure may be used to conjugate an antibody to a cancer vaccine. As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the ADCs disclosed herein include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in certain embodiments, D is a cancer vaccine that is either an immunostimulator or is an immunosuppressant.

Cytokines

The linkers of the disclosure may be used to conjugate an antibody at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) Cancers 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs of the disclosure include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in certain embodiments, D is a cytokine.

Colony-Stimulating Factors (CSFs)

The linkers of the disclosure may be used to conjugate an antibody to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in ADCs disclosed herein include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in certain embodiments, D is a CSF.

Gene Therapy

The linkers of the disclosure may be used to conjugate an antibody to at least one nucleic acid (directly or indirectly via a carrier) for gene therapy. Gene therapy generally refers to the introduction of genetic material into a cell whereby the genetic material is designed to treat a disease. As it pertains to immunomoduatory agents, gene therapy is used to stimulate a subject's natural ability to inhibit cancer cell proliferation or kill cancer cells. In certain embodiments, the ADC of the disclosure comprises a nucleic acid encoding a functional, therapeutic gene that is used to replace a mutated or otherwise dysfunctional (e.g., truncated) gene associated with cancer. In other embodiments, the ADC of the disclosure comprises a nucleic acid that encodes for or otherwise provides for the production of a therapeutic protein to treat cancer. The nucleic acid that encodes the therapeutic gene may be directly conjugated to the antibody, or alternatively, may be conjugated to the antibody through a carrier. Examples of carriers that may be used to deliver a nucleic acid for gene therapy include, but are not limited to, viral vectors or liposomes.

Alkylating Agents

The linkers of the disclosure may be used to conjugate an antibody to one or more alkylating agent(s). Alkylating agents are a class of antineoplastic compounds that attaches an alkyl group to DNA. Examples of alkylating agents that may be used in the ADCs of the disclosure include, but are not limited to, alkyl sulfonates, ethylenimimes, methylamine derivatives, epoxides, nitrogen mustards, nitrosoureas, triazines and hydrazines.

Alkyl Sulfonates

The linkers of the disclosure may be used to conjugate an antibody to at least one alkyl sulfonate. Alkyl sulfonates are a subclass of alkylating agents with a general formula: $R—SO_2—O—R^1$, wherein R and $R^1$ are typically alkyl or aryl groups. A representative example of an alkyl sulfonate is busulfan (Myleran®, GlaxoSmithKline; Busulfex IV®, PDL BioPharma, Inc.).

Nitrogen Mustards

The linkers of the disclosure may be used to conjugate an antibody to at least one nitrogen mustard. Representative examples of this subclass of anti-cancer compounds include, but are not limited to chlorambucil (Leukeran®, GlaxoSmithKline), cyclophosphamide (Cytoxan®, Bristol-Myers Squibb; Neosar, Pfizer, Inc.), estramustine (estramustine phosphate sodium or Estracyt®), Pfizer, Inc.), ifosfamide (Ifex®, Bristol-Myers Squibb), mechlorethamine (Mustargen®, Lundbeck Inc.), and melphalan (Alkeran® or L-Pam® or phenylalanine mustard; GlaxoSmithKline).

Nitrosoureas

The linkers of the disclosure may be used to conjugate an antibody to at least one nitrosourea. Nitrosoureas are a subclass of alkylating agents that are lipid soluble. Representative examples include, but are not limited to, carmustine (BCNU [also known as BiCNU, N,N-bis(2-chloroethyl)-N-nitrosourea, or 1,3-bis(2-chloroethyl)-1-nitrosourea], Bristol-Myers Squibb), fotemustine (also known as Muphoran®), lomustine (CCNU or 1-(2-chloroethyl)-3-cyclohexyl-1-nitrosourea, Bristol-Myers Squibb), nimustine (also known as ACNU), and streptozocin (Zanosar®, Teva Pharmaceuticals).

Triazines and Hydrazines

The linkers of the disclosure may be used to conjugate an antibody to at least one triazine or hydrazine. Triazines and hydrazines are a subclass of nitrogen-containing alkylating agents. In some embodiments, these compounds spontaneously decompose or can be metabolized to produce alkyl diazonium intermediates that facilitate the transfer of an alkyl group to nucleic acids, peptides, and/or polypeptides, thereby causing mutagenic, carcinogenic, or cytotoxic effects. Representative examples include, but are not limited to dacarbazine (DTIC-Dome, Bayer Healthcare Pharmaceuticals Inc.), procarbazine (Mutalane®, Sigma-Tau Pharmaceuticals, Inc.), and temozolomide (Temodar®, Schering Plough).

Other Alkylating Agents

The linkers of the disclosure may be used to conjugate an antibody to at least one ethylenimine, methylamine derivative, or epoxide. Ethylenimines are a subclass of alkylating agents that typically containing at least one aziridine ring. Epoxides represent a subclass of alkylating agents that are characterized as cyclic ethers with only three ring atoms.

Representatives examples of ethylenimines include, but are not limited to thiopeta (Thioplex, Amgen), diaziquone (also known as aziridinyl benzoquinone (AZQ)), and mitomycin C. Mitomycin C is a natural product that contains an aziridine ring and appears to induce cytoxicity through cross-linking DNA (Dorr R T, et al. Cancer Res. 1985; 45:3510; Kennedy K A, et al Cancer Res. 1985; 45:3541). Representative examples of methylamine derivatives and their analogs include, but are not limited to, altretamine (Hexalen, MGI Pharma, Inc.), which is also known as hexamethylamine and hexastat. Representative examples of epoxides of this class of anti-cancer compound include, but are not limited to dianhydrogalactitol. Dianhydrogalactitol (1,2:5,6-dianhydrodulcitol) is chemically related to the aziridines and generally facilitate the transfer of an alkyl group through a similar mechanism as described above. Dibromodulcitol is hydrolyzed to dianhydrogalactitol and thus is a pro-drug to an epoxide (Sellei C, et al. Cancer Chemother Rep. 1969; 53:377).

Antiangiogenic Agents

In some embodiments, the linkers of the disclosure may be used to conjugate an antibody to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs of the disclosure include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

Antimetabolites

The linkers of the disclosure may be used to conjugate an antibody to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolies that may be used in the ADCs of the disclosure include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

Antifolates

The linkers of the disclosure may be used to conjugate an antibody to at least one antifolate. Antifolates are a subclass of antimetabolites that are structurally similar to folate. Representative examples include, but are not limited to, methotrexate, 4-amino-folic acid (also known as aminopterin and 4-aminopteroic acid), lometrexol (LMTX), pemetrexed (Alimpta, Eli Lilly and Company), and trimetrexate (Neutrexin, Ben Venue Laboratories, Inc.)

Purine Antagonists

The linkers of the disclosure may be used to conjugate an antibody to at least one purine antagonist. Purine analogs are a subclass of antimetabolites that are structurally similar to the group of compounds known as purines. Representative examples of purine antagonists include, but are not limited to, azathioprine (Azasan, Salix; Imuran, GlaxoSmithKline), cladribine (Leustatin [also known as 2-CdA], Janssen Biotech, Inc.), mercaptopurine (Purinethol [also known as 6-mercaptoethanol], GlaxoSmithKline), fludarabine (Fludara, Genzyme Corporation), pentostatin (Nipent, also known as 2'-deoxycoformycin (DCF)), 6-thioguanine (Lanvis [also known as thioguanine], GlaxoSmithKline).

Pyrimidine Antagonists

The linkers of the disclosure may be used to conjugate an antibody to at least one pyrimidine antagonist. Pyrimidine antagonists are a subclass of antimetabolites that are structurally similar to the group of compounds known as purines. Representative examples of pyrimidine antagonists include, but are not limited to azacitidine (Vidaza, Celgene Corporation), capecitabine (Xeloda, Roche Laboratories), Cytarabine (also known as cytosine arabinoside and arabinosylcytosine, Bedford Laboratories), decitabine (Dacogen, Eisai Pharmaceuticals), 5-fluorouracil (Adrucil, Teva Pharmaceuticals; Efudex, Valeant Pharmaceuticals, Inc), 5-fluoro-2'-deoxyuridine 5'-phosphate (FdUMP), 5-fluorouridine triphosphate, and gemcitabine (Gemzar, Eli Lilly and Company).

Boron-Containing Agents

The linkers of the disclosure may be used to conjugate an antibody to at least one boron containing agent. Boron-containing agents comprise a class of cancer therapeutic compounds which interfere with cell proliferation. Representative examples of boron containing agents include, but are not limited, to borophycin and bortezomib (Velcade, Millenium Pharmaceuticals).

Chemoprotective Agents

The linkers of the disclosure may be used to conjugate an antibody to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

Hormone Agents

The linkers of the disclosure may be used to conjugate an antibody to at least one hormone agent. A hormone agent (including synthetic hormones) is a compound that interferes with the production or activity of endogenously produced hormones of the endocrine system. In some embodiments, these compounds interfere with cell growth or produce a cytotoxic effect. Non-limiting examples include androgens, estrogens, medroxyprogesterone acetate (Provera, Pfizer, Inc.), and progestins.

Antihormone Agents

The linkers of the disclosure may be used to conjugate an antibody to at least one antihormone agent. An "antihormone" agent is an agent that suppresses the production of and/or prevents the function of certain endogenous hormones. In certain embodiments, the antihormone agent interferes with the activity of a hormone selected from androgens, estrogens, progesterone, and goanadotropin-releasing hormone, thereby interfering with the growth of various cancer cells. Representative examples of antihormone agents include, but are not limited to, aminoglutethimide, anastrozole (Arimidex, AstraZeneca Pharmaceuticals), bicalutamide (Casodex, AstraZeneca Pharmaceuticals), cyproterone acetate (Cyprostat, Bayer PLC), degarelix (Firmagon, Ferring Pharmaceuticals), exemestane (Aromasin, Pfizer Inc.), flutamide (Drogenil, Schering-Plough Ltd), fulvestrant (Faslodex, AstraZeneca Pharmaceuticals), goserelin (Zolodex, AstraZeneca Pharmaceuticals), letrozole (Femara, Novartis Pharmaceuticals Corporation), leuprolide (Prostap), lupron, medroxyprogesterone acetate (Provera, Pfizer Inc.), Megestrol acetate (Megace, Bristol-Myers Squibb Company), tamoxifen (Nolvadex, AstraZeneca Pharmaceuticals), and triptorelin (Decapetyl, Ferring).

Corticosteroids

The linkers of the disclosure may be used to conjugate an antibody to at least one corticosteroid. Corticosteroids may be used in the ADCs of the disclosure to decrease inflammation. An example of a corticosteroid includes, but is not limited to, a glucocorticoid, for example, prednisone (Deltasone, Pharmacia & Upjohn Company, a division of Pfizer, Inc.).

Photoactive Therapeutic Agents

The linkers of the disclosure may be used to conjugate an antibody to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

Oligonucleotides

The linkers of the disclosure may be used to conjugate an antibody to at least one oligonucleotide. Oligonucleotides are made of short nucleic acid chains that work by interfering with the processing of genetic information. In some embodiments, the oligonucleotides for use in ADCs are unmodified single-stranded and/or double-stranded DNA or RNA molecules, while in other embodiments, these therapeutic oligonucleotides are chemically-modified single-stranded and/or double-stranded DNA or RNA molecules. In certain embodiments, the oligonucleotides used in the ADCs are relatively short (19-25 nucleotides) and hybridize to a unique nucleic acid sequence in the total pool of nucleic acid targets present in cells. Some of the important oligonucleotide technologies include the antisense oligonucleotides (including RNA interference (RNAi)), aptamers, CpG oligonucleotides, and ribozymes.

Antisense Oligonucleotides

The linkers of the disclosure may be used to conjugate an antibody to at least one antisense oligonucleotide. Antisense oligonucleotides are designed to bind to RNA through Watson-Crick hybridization. In some embodiments the antisense oligonucleotide is complementary to a nucleotide encoding a region, domain, portion, or segment of the conjugated antibody. In some embodiments, the antisense oligonucleotide comprises from about 5 to about 100 nucleotides, from about 10 to about 50 nucleotides, from about 12 to about 35, and from about 18 to about 25 nucleotides There are multiple mechanisms that can be exploited to inhibit the function of the RNA once the oligonucleotide binds to the target RNA (Crooke ST. (1999). *Biochim. Biophys. Acta,* 1489, 30-42). The best-characterized antisense mechanism results in cleavage of the targeted RNA by endogenous cellular nucleases, such as RNase H or the nuclease associated with the RNA interference mechanism. However, oligonucleotides that inhibit expression of the target gene by non-catalytic mechanisms, such as modulation of splicing or translation arrest, can also be potent and selective modulators of gene function.

Another RNase-dependent antisense mechanism that has recently received much attention is RNAi (Fire et al. (1998). Nature, 391, 806-811; Zamore P D. (2002). Science, 296, 1265-1269.). RNA interference (RNAi) is a post-transcriptional process where a double stranded RNA inhibits gene expression in a sequence specific fashion. In some embodiments, the RNAi effect is achieved through the introduction of relatively longer double-stranded RNA (dsRNA), while in preferred embodiments, this RNAi effect is achieved by the introduction of shorter double-stranded RNAs, e g small interfering RNA (siRNA) and/or microRNA (miRNA). In yet another embodiment, RNAi can also be achieved by introducing of plasmid that generate dsRNA complementary to target gene. In each of the foregoing embodiments, the double-stranded RNA is designed to interfere with the gene expression of a particular the target sequence within cells. Generally, the mechanism involves conversion of dsRNA into short RNAs that direct ribonucleases to homologous mRNA targets (summarized, Ruvkun, Science 2294:797 (2001)), which then degrades the corresponding endogenous mRNA, thereby resulting in the modulation of gene expression. Notably, dsRNA has been reported to have antiproliferative properties, which makes it possible also to envisage therapeutic applications (Aubel et al., Proc. Natl. Acad. Sci., USA 88:906 (1991)). For example, synthetic dsRNA has been shown to inhibit tumor growth in mice (Levy et al. Proc. Nat. Acad. Sci. USA, 62:357-361 (1969)), is active in the treatment of leukemic mice (Zeleznick et al., Proc. Soc. Exp. Biol. Med. 130:126-128 (1969)), and inhibits chemically induced tumorigenesis in mouse skin (Gelboin et al., Science 167:205-207 (1970)). Thus, in preferred embodiments, the disclosure provides for the use of antisense oligonucleotides in ADCs for the treatment of breast cancer. In other embodiments, the disclosure provides compositions and methods for initiating antisense oligonucleotide treatment, wherein dsRNA interferes with target cell expression of EGFR at the mRNA level. dsRNA, as used above, refers to naturally-occurring RNA, partially purified RNA, recombinantly produced RNA, synthetic RNA, as well as altered RNA that differs from naturally-occurring RNA by the inclusion of non-standard nucleotides, non-nucleotide material, nucleotide analogs (e.g. locked nucleic acid (LNA)), deoxyribonucleotides, and any combination thereof. RNA of the disclosure need only be sufficiently similar to natural RNA that it has the ability to mediate the antisense oligonucleotide-based modulation described herein.

Aptamers

The linkers of the disclosure may be used to conjugate an antibody to at least one aptamer. An aptamer is a nucleic acid molecule that has been selected from random pools based on its ability to bind other molecules. Like antibodies, aptamers can bind target molecules with extraordinary affinity and specificity. In many embodiments, aptamers assume complex, sequence-dependent, three-dimensional shapes that allow them to interact with a target protein, resulting in a tightly bound complex analogous to an antibody-antigen interaction, thereby interfering with the function of said protein. The particular capacity of aptamers to bind tightly and specifically to their target protein underlines their potential as targeted molecular therapies.

CpG Oligonucleotides

The linkers of the disclosure may be used to conjugate an antibody to at least one CpG oligonucleotide. Bacterial and viral DNA are known to be strong activators of both the innate and specific immunity in humans. These immunologic characteristics have been associated with unmethylated CpG dinucleotide motifs found in bacterial DNA. Owing to the fact that these motifs are rare in humans, the human immune system has evolved the ability to recognize these motifs as an early indication of infection and subsequently initiate immune responses. Therefore, oligonucleotides containing this CpG motif can be exploited to initiate an antitumor immune response.

Ribozymes

The linkers of the disclosure may be used to conjugate an antibody to at least one ribozyme. Ribozymes are catalytic RNA molecules ranging from about 40 to 155 nucleotides in length. The ability of ribozymes to recognize and cut specific RNA molecules makes them potential candidates for therapeutics. A representative example includes angiozyme.

Radionuclide Agents (Radioactive Isotopes)

The linkers of the disclosure may be used to conjugate an antibody to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of 111In, 177Lu, 212Bi, 213Bi, 211At, 62Cu, 64Cu, 67Cu, 90Y, 125I, 131I, 32P, 33P, 47Sc, 111Ag, 67Ga, 142Pr, 153Sm, 161Tb, 166Dy, 166Ho, 186Re, 188Re, 189Re, 212Pb, 223Ra, 225Ac, 59Fe, 75Se, 77As, 89Sr, 99Mo, 105Rh, 109Pd, 143Pr, 149Pm, 169Er, 194Ir, 198Au, 199Au, and 211Pb. Also preferred are radionuclides that substantially decay with Auger-emitting particles. For example, Co-58, Ga-67, Br-80m, Tc-99m, Rh-103m, Pt-109, In-111 1, Sb-119, 1-125, Ho-161, Os-189m and Ir-192. Decay energies of useful beta-particle-emitting nuclides are preferably Dy-152, At-211, Bi-212, Ra-223, Rn-219, Po-215, Bi-21 1, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include 11C, 13N, 150, 75Br, 198Au, 95Ru, 97Ru, 103Ru, 105Ru, 107Hg, 203Hg, 121mTe, 122mTe, 125mTe, 165Tm, 167Tm, 168Tm, 197Pt, 109Pd, 105Rh, 142Pr, 143Pr, 161Tb, 166Ho, 199Au, 57Co, 58Co, 51Cr, 59Fe, 75Se, 201Tl, 225Ac, 76Br, 169Yb, and the like.

Radiosensitizers

The linkers of the disclosure may be used to conjugate an antibody to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

Topoisomerase Inhibitors

The linkers of the disclosure may be used to conjugate an antibody to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

Tyrosine Kinase Inhibitors

The linkers of the disclosure may be used to conjugate an antibody to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs of the disclosure include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

Other Agents

Examples of other agents that may be used in the ADCs of the disclosure include, but are not limited to, abrin (e.g. abrin A chain), alpha toxin, Aleurites fordii proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas endotoxin, Pseudomonas exotoxin* (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the ADCs of the disclosure are not exclusive, in that certain examples of drugs may be found in more than one category, e.g., ansamitocins are both mitotic inhibitors and antitumor antibiotics.

All stereoisomers of the above drug moieties are contemplated for the compounds of the disclosure, i.e. any combination of R and S configurations at the chiral carbons of D.

A "detectable moiety" or a "marker" refers to a composition that is detectable by spectroscopic, photochemical, biochemical, immunochemical, radioactive or chemical means. For example, a useful label includes $^{32}$P, $^{35}$S, fluorescent dyes, electron-dense reagents, enzymes (e.g., enzymes that are generally used in ELISA), biotin-streptavidin, dioxigenin, hapten, and proteins for which antisera or monoclonal antibodies are available, or nucleic acid molecules with a sequence complementary to a target. The detectable moiety often generates a measurable signal, e.g., a radioactive signal, a color signal or a fluorescent signal, which is usable to quantify an amount of the detectable moiety that binds in the sample. Quantification of the signal may be accomplished by, for example, scintillation counting, density gauge, flow cell analysis, ELISA, or direct analysis by mass spectroscopy of circular or subsequently digested peptides (one or more peptides may be assayed). Those skilled in the art are familiar with techniques and detection means for a label compound of interest. These techniques and methods are conventional and well known in the art.

The probe for detection refers to (i) a material capable of providing a detectable signal, (ii) a material capable of interacting with a first probe or a second probe to change a detectable signal provided by the first probe or the second probe, such as fluorescence resonance energy transfer (FRET), (iii) a material capable of stabilizing an interaction with an antigen or a ligand or increasing binding affinity, (iv) a material capable of affecting electric mobility or cell-invasive action by physical parameters such as charge, hydrophobicity, etc., or (v) a material capable of adjusting ligand affinity, antigen-antibody binding or ion complex formation.

In some embodiments, each active agent is independently selected from:

(a) erlotinib, bortezomib, fulvestrant, sutent, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, trietylenephosphormide, triethiylenethiophosphoramide, trimethylolomelamine, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, antrmycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubucin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2"-trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;

(b) monokine, a lymphokine, a traditional polypeptide hormone, parathyroid hormone, thyroxine, relaxin, prorelaxin, a glycoprotein hormone, follicle stimulating hormone, thyroid stimulating hormone, luteinizing hormone, hepatic growth factor fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-α, interferon-β, interferon-γ, a colony stimulating factor ("CSF"), macrophage-CSF, granulocyte-macrophage-CSF, granulocyte-CSF, an interleukin ("IL"), IL-1, IL-1α, IL-2, IL-3, IL-4, IL-5, IL-6, IL-7, IL-8, IL-9, IL-10, IL-11, IL-12, a tumor necrosis factor, TNF-α, TNF-β, a polypeptide factor, LIF, kit ligand, or a combination of any of the foregoing;

(c) diphtheria toxin, botulium toxin, tetanus toxin, dysentery toxin, cholera toxin, amanitin, amanitin derivatives, α-amanitin, pyrrolobenzodiazepine, pyrrolobenzodiazepine derivatives, tetrodotoxin, brevetoxin, ciguatoxin, ricin, AM toxin, auristatin, tubulysin, geldanamycin, maytansinoid, calicheamicin, daunomycin, doxorubicin, methotrexate, vindesine, SG2285, dolastatin, a dolastatin analog, cryptophycin, camptothecin, camptothecin derivatives and metabolites, rhizoxin, a rhizoxin derivative, CC-1065, a CC-1065 analogue or derivative, duocarmycin, an enediyne antibiotic, esperamicin, epothilone, azonafide, aplidine, a toxoid, or a combination of any of the foregoing;

(d) an affinity ligand, wherein the affinity ligand is a substrate, an inhibitor, a stimulating agent, a neurotransmitter, a radioisotope, or a combination of any of the foregoing;

(e) a radioactive label, $^{32}P$, $^{35}S$, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;

(f) an immunomodulatory compound, an anti-cancer agent, an anti-viral agent, an anti-bacterial agent, an anti-fungal agent, and an anti-parasitic agent, or a combination of any of the foregoing;

(g) tamoxifen, raloxifene, droloxifene, 4-hydroxytamoxifen, trioxifene, keoxifene, LY117018, onapristone, or toremifene;

(h) 4(5)-imidazoles, aminoglutethimide, megestrol acetate, exemestane, letrozole, or anastrozole;

(i) flutamide, nilutamide, bicalutamide, leuprolide, goserelin, or troxacitabine;

(j) an aromatase inhibitor;

(k) a protein kinase inhibitor;

(l) a lipid kinase inhibitor;

(m) an antisense oligonucleotide;

(n) a ribozyme;

(o) a vaccine; and (p) an anti-angiogenic agent.

In some preferred embodiments, G comprises a moiety selected from the following:

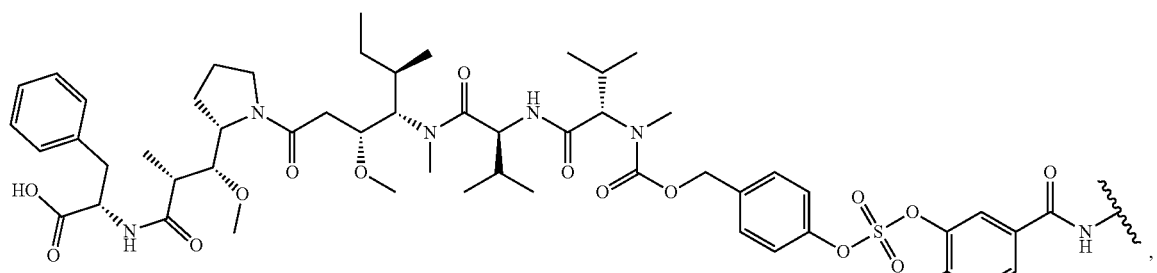
(OHPAS-MMAF)
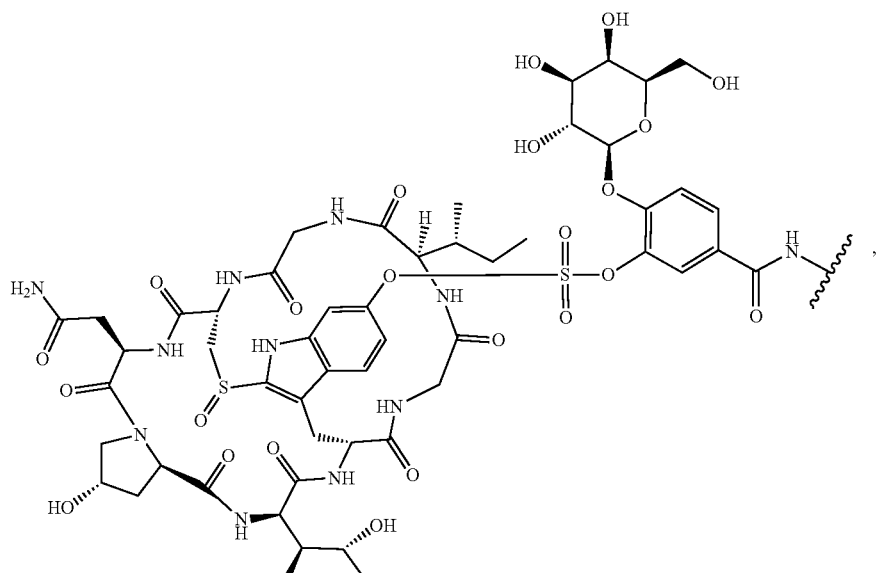
(OHPAS-α-Amantin)
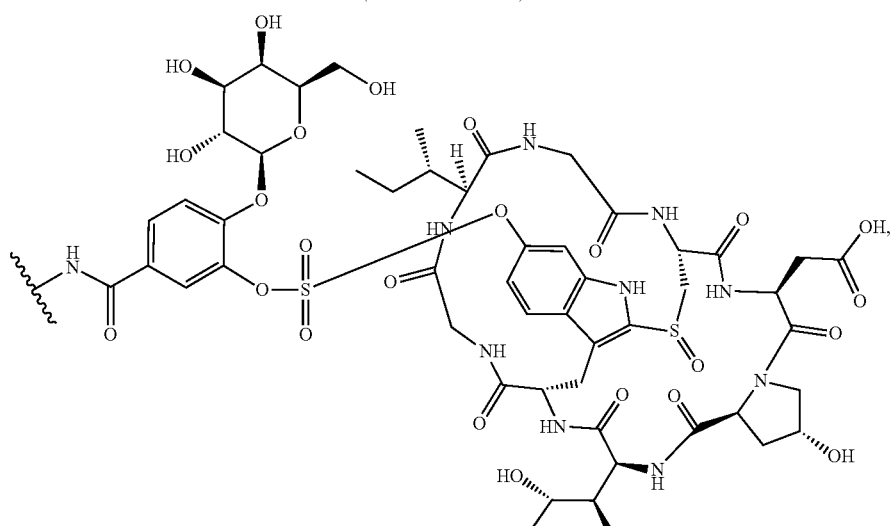
(OHPAS-β-Amantin)

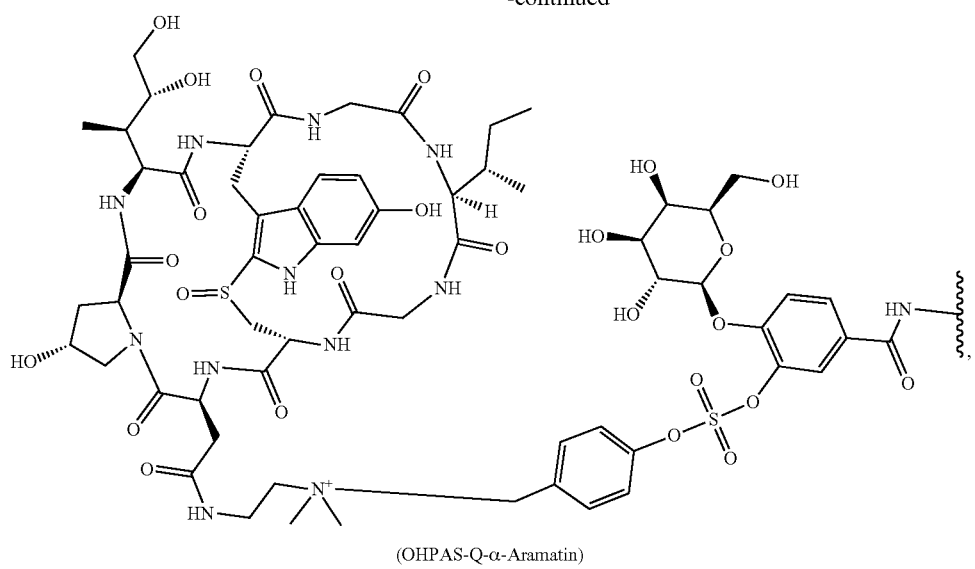
(OHPAS-Q-α-Aramatin)
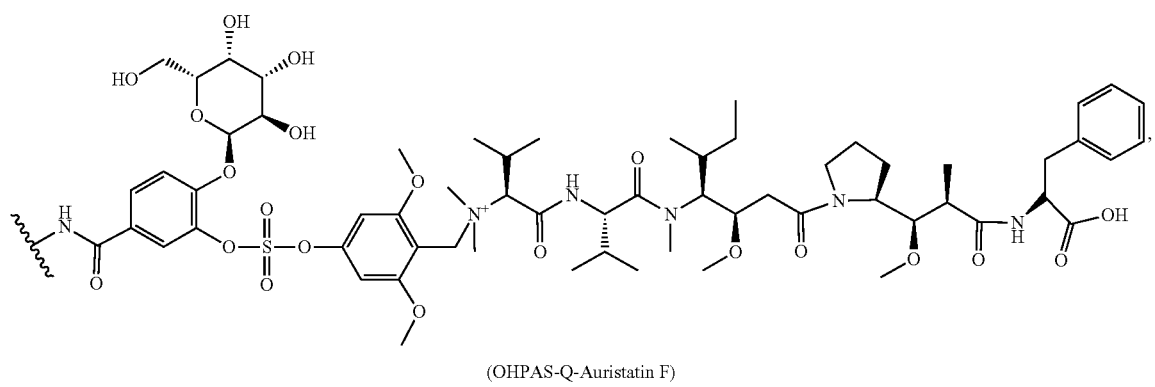
(OHPAS-Q-Auristatin F)
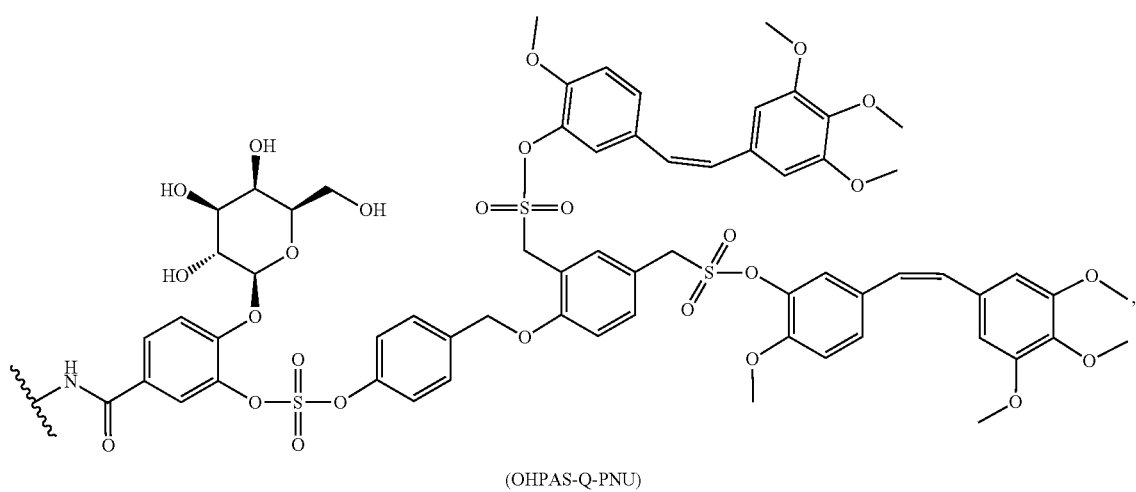
(OHPAS-Q-PNU)

-continued
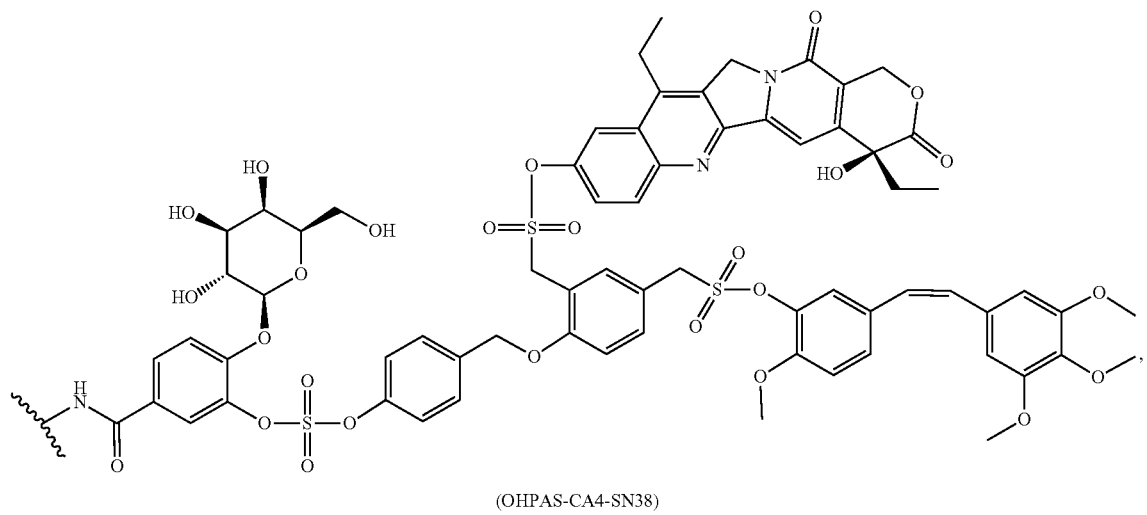
(OHPAS-CA4-SN38)
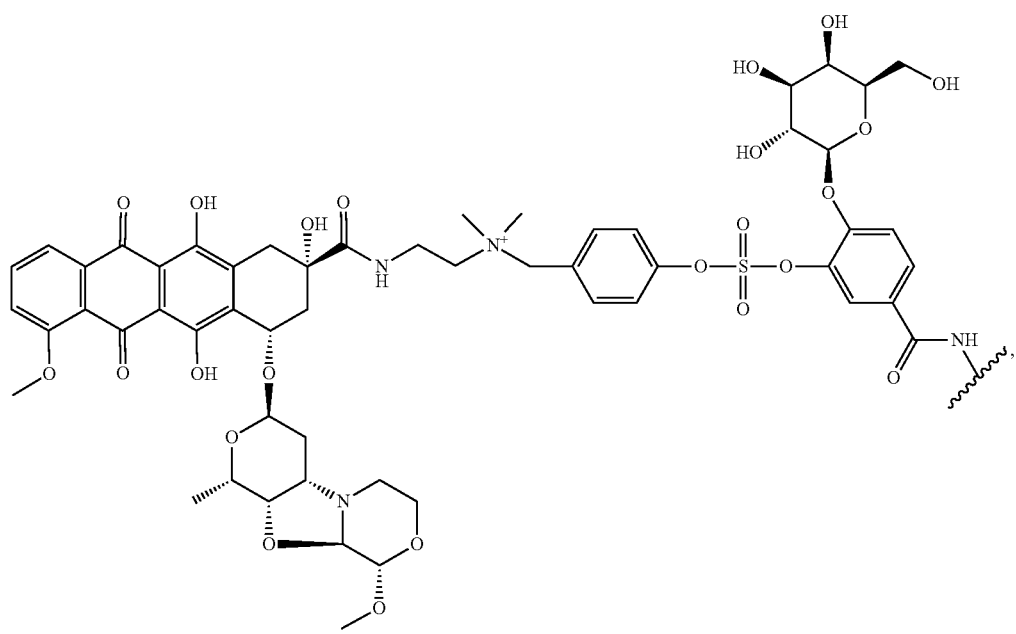
(OHPAS-Q-PNU)

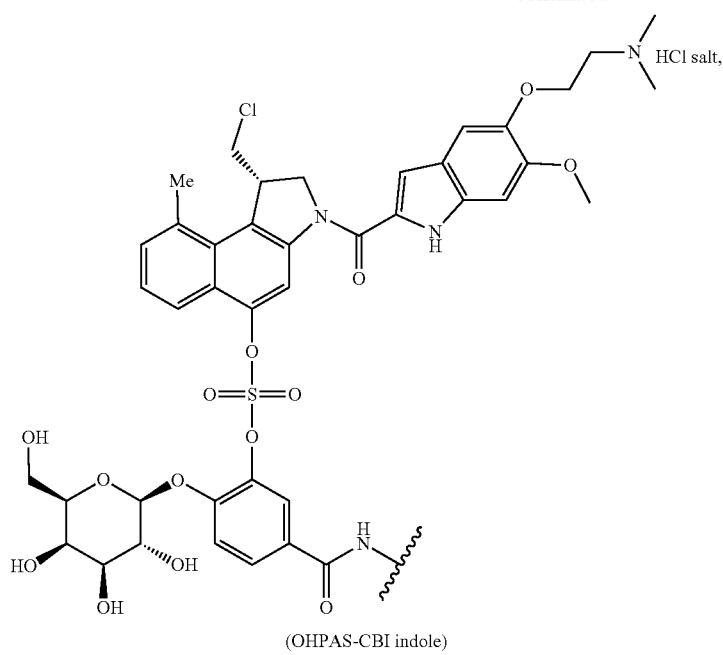
(OHPAS-CBI indole)
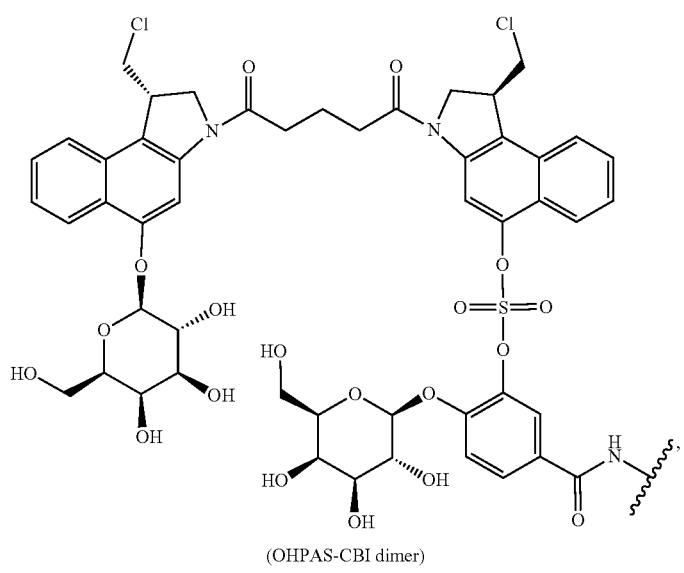
(OHPAS-CBI dimer)
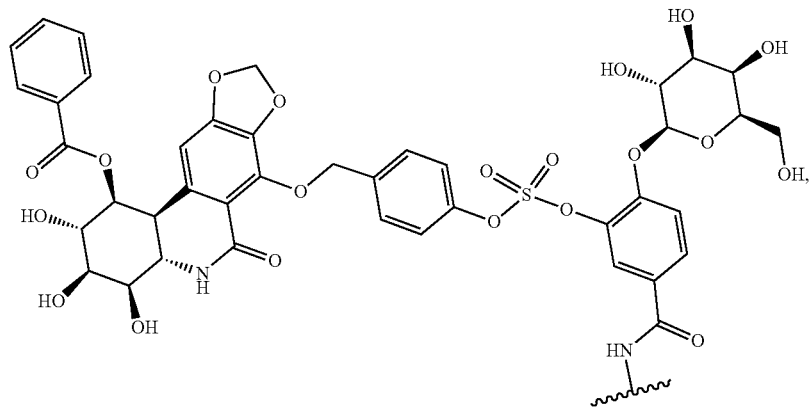
(OHPAS-Phenpanstatin)

-continued
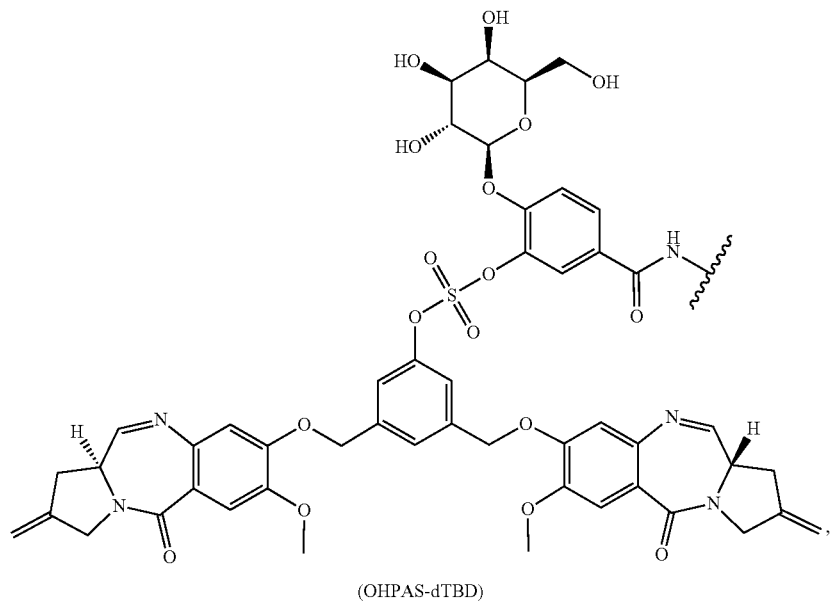
(OHPAS-dTBD)
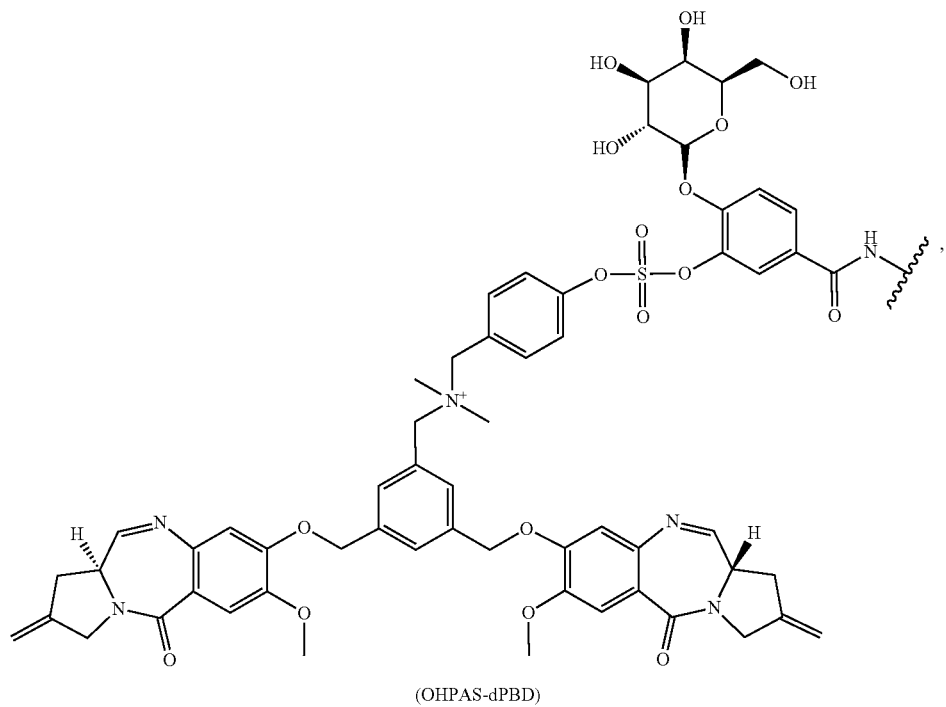
(OHPAS-dPBD)

-continued
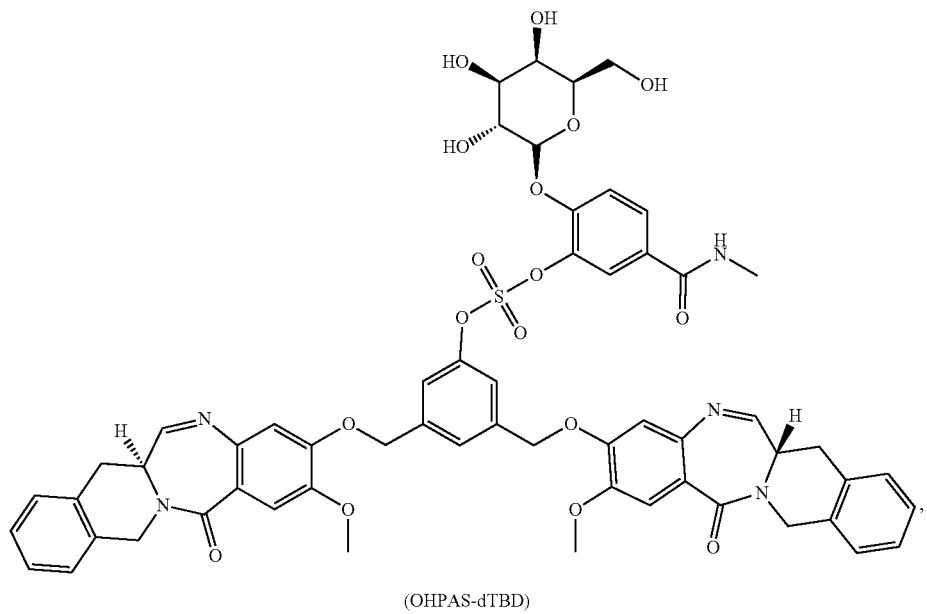
(OHPAS-dTBD)
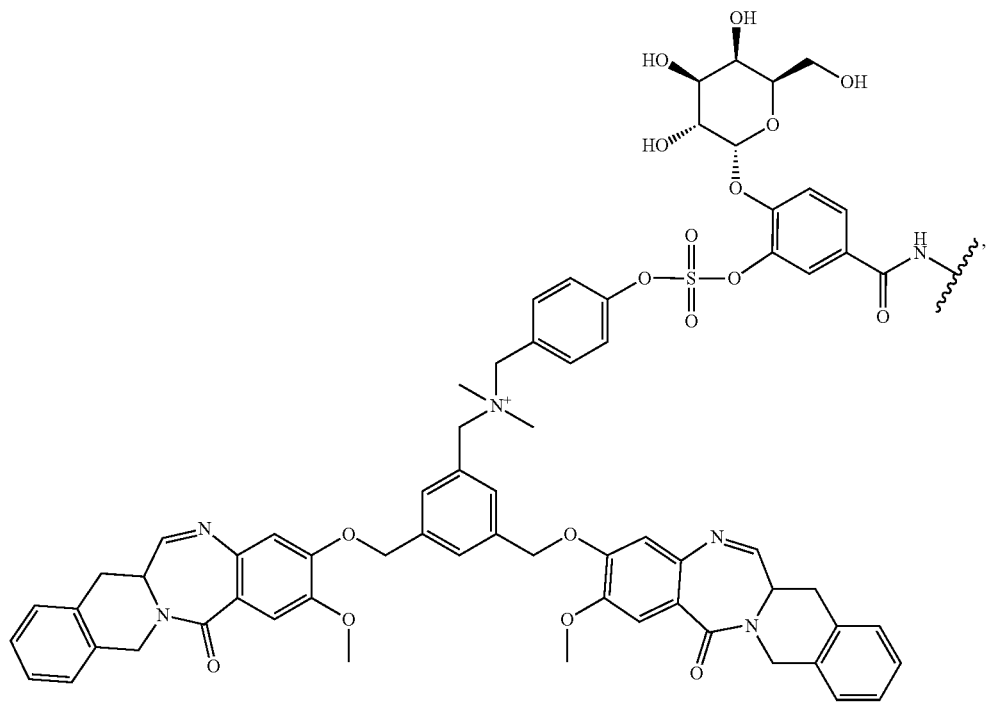
(OHPAS-Q-dTBD)
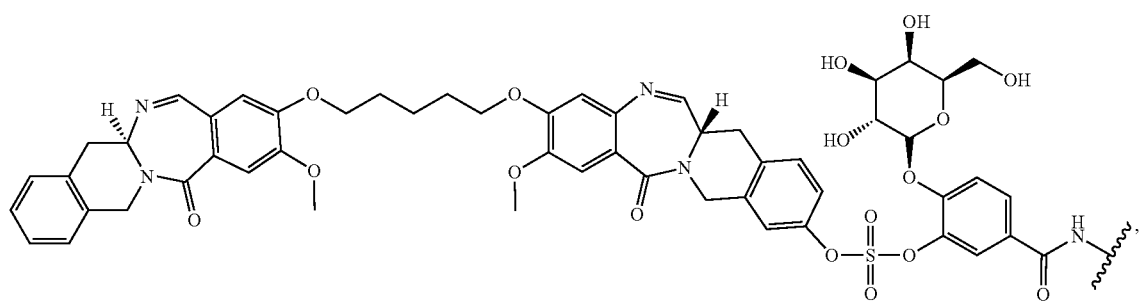
(OHPAS-adTBD, asymmetric dTBD)

-continued
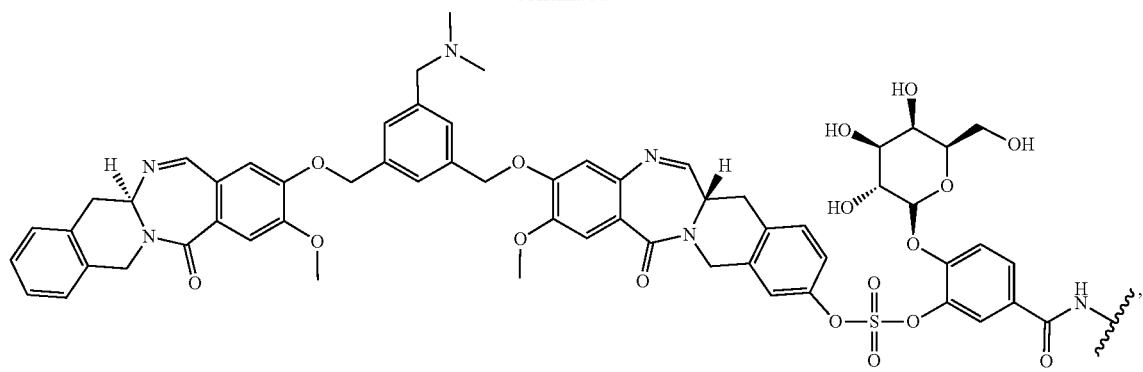
(OHPAS-adTBD DMBA)
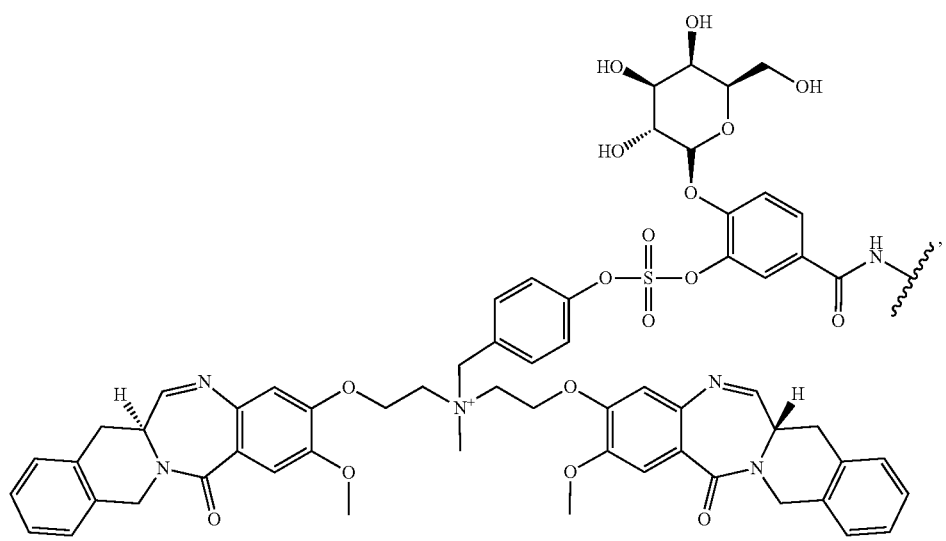
(OHPAS-dTBD alkyl amine)
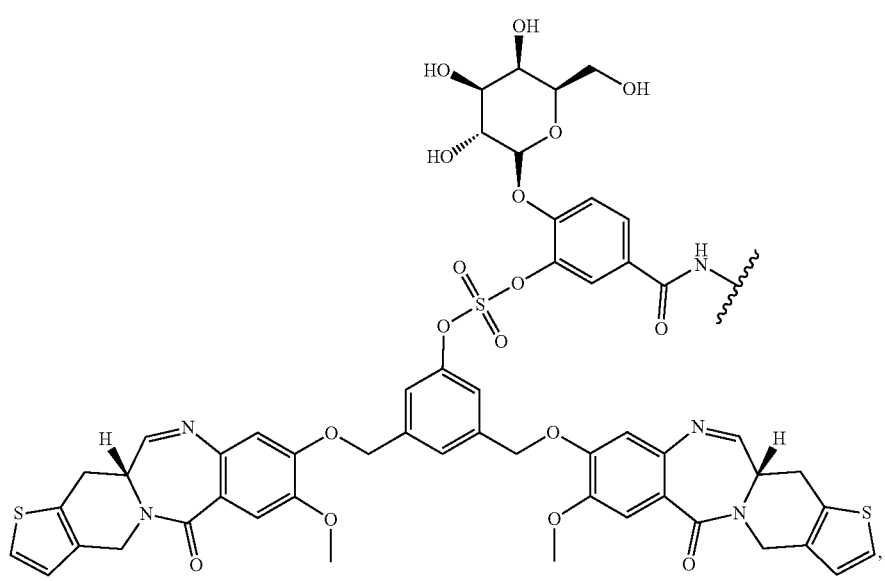
(OHPAS-dThBD)

-continued
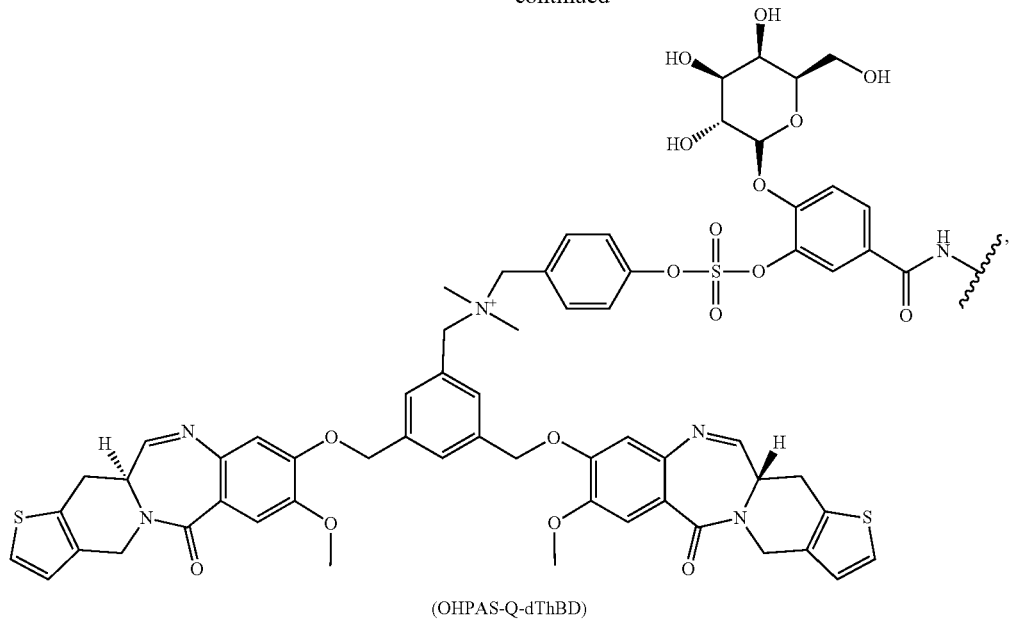
(OHPAS-Q-dThBD)
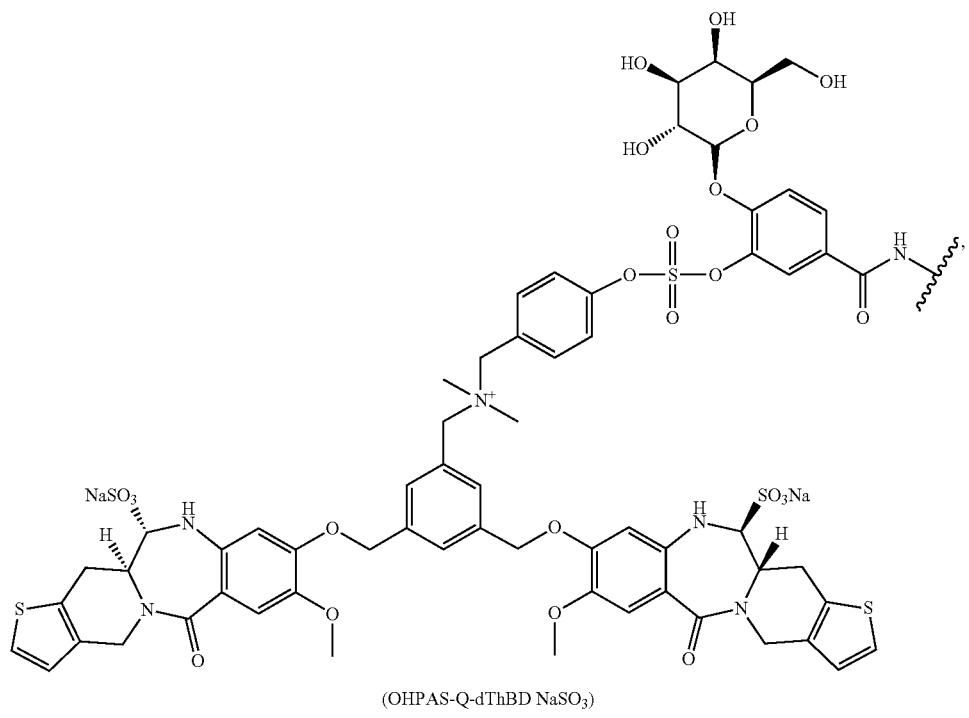
(OHPAS-Q-dThBD NaSO₃)

-continued
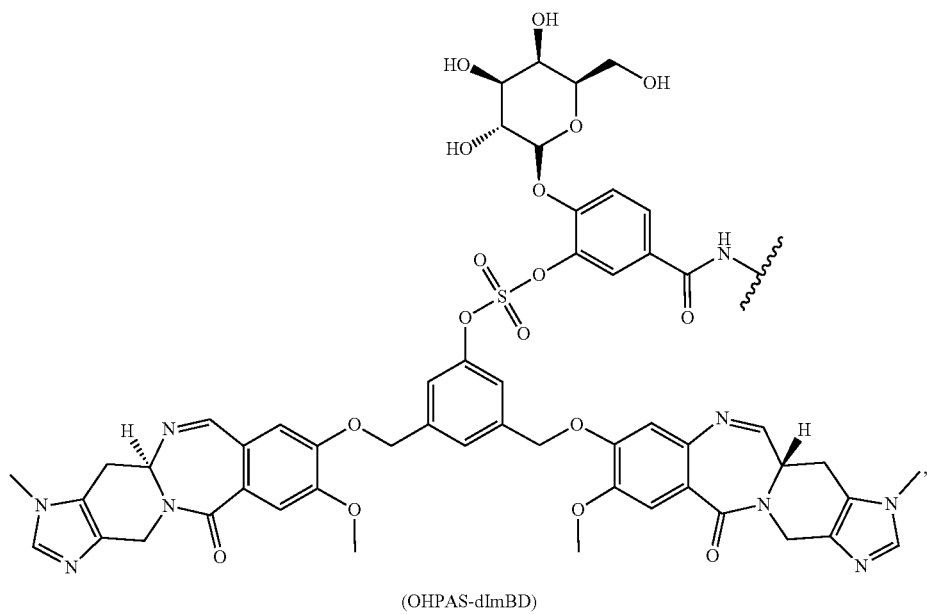
(OHPAS-dImBD)
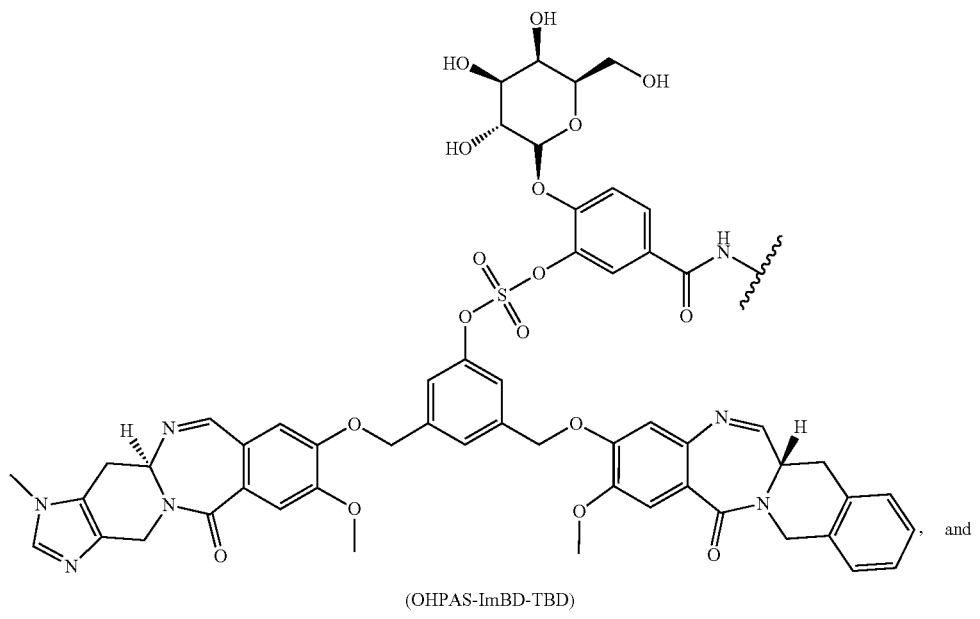
(OHPAS-ImBD-TBD), and

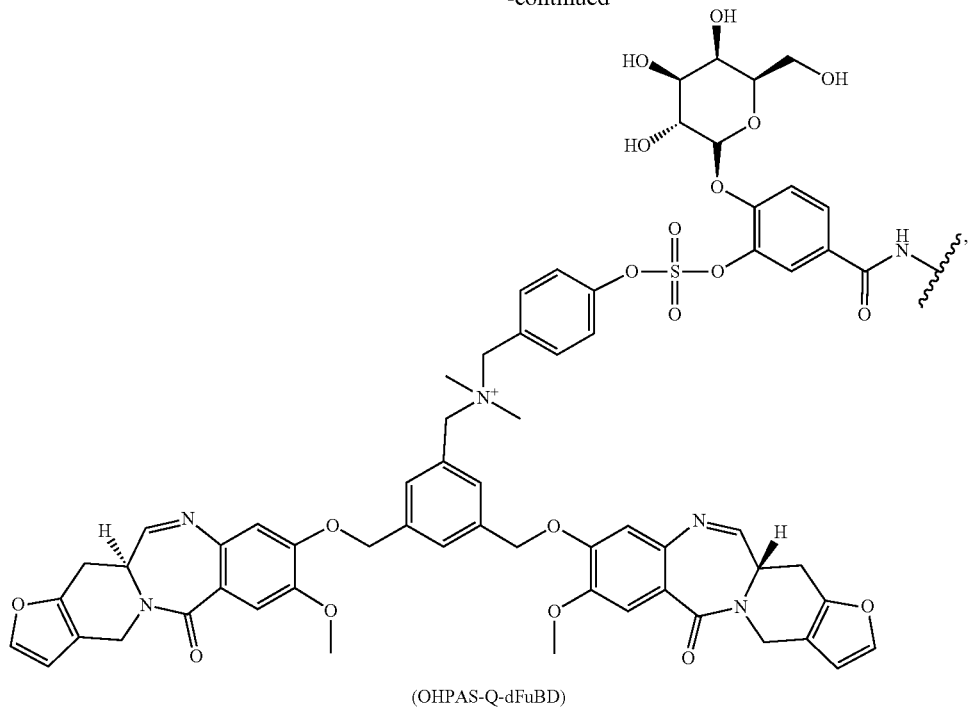

(OHPAS-Q-dFuBD)

wherein

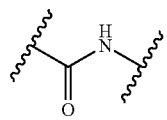 [SMILES: *NC(*)=O]

is the fragment of the linking group Z' that connects Z' to Ar, in this case the substituted Ph group.

Conjugation Strategies

Compounds of Formula I can be prepared in a one or two step conjugation procedure.

One-Step Conjugation

In some embodiments, the present disclosure relates to methods of preparation of compounds of Formula I that involve one-step conjugation between the antibody and the linker. Compounds of Formulas (II) and (III) described above are suitable for one-step conjugation with antibodies.

For example, precursors containing methyl phenyl sulfone moiety (MPS) can undergo conjugation according to the sequence of steps indicated in Scheme 1. Step A involves in situ elimination of p-methylphenyl sulfonyl group, resulting in the formation of a reactive intermediate; in Step B the intermediate undergoes conjugation with a thiol residue of an antibody.

Scheme 1.

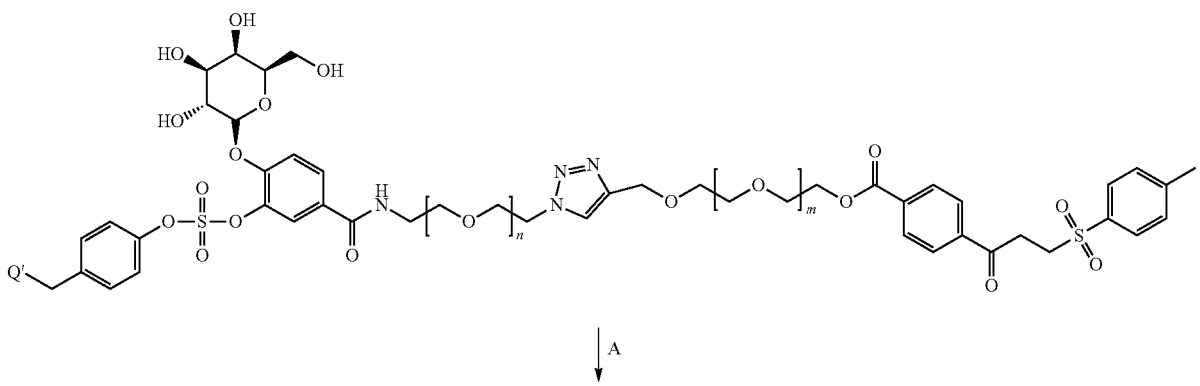

↓ A

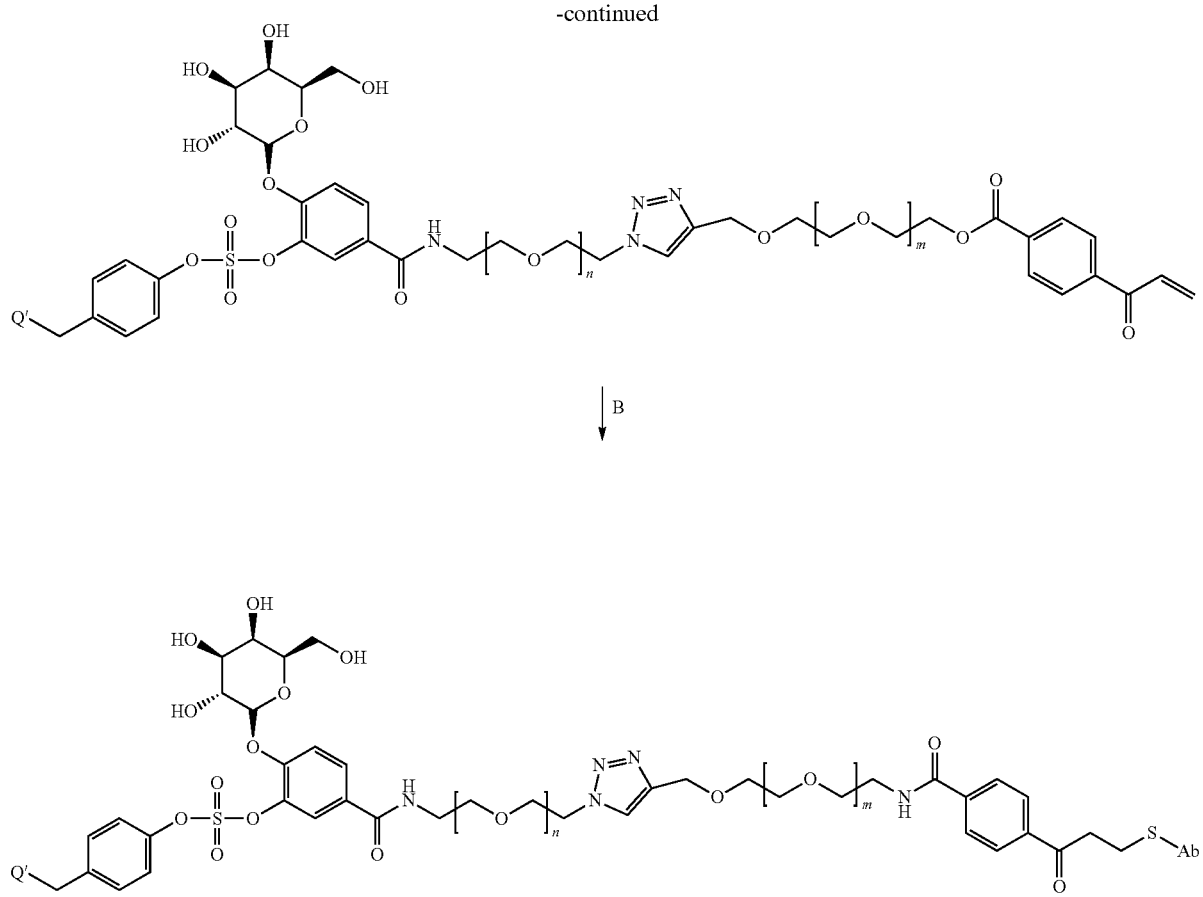

The resulting ADC can be further stabilized by treatment with hydroxylamine or a reducing agent, as shown in Scheme 2:

In some embodiments, the MPS-containing presursors are comprise moieties that generate activated Michael acceptors upon elimination of sulfinic acid. Examples of such precursors are shown in Scheme 3.

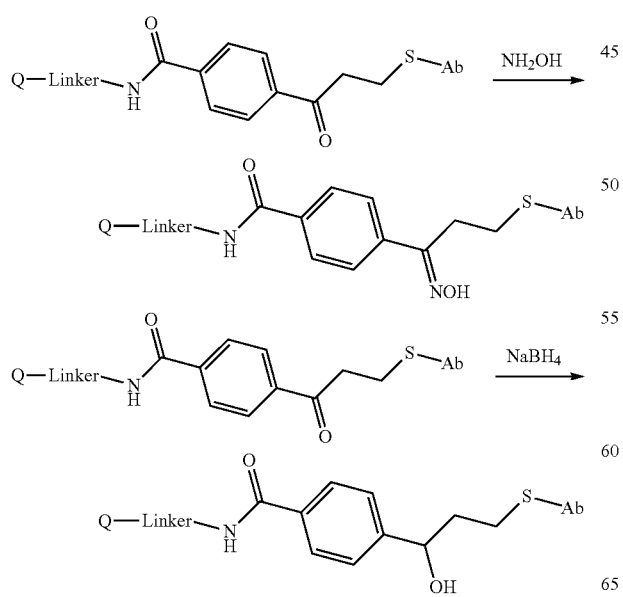

Scheme 2.

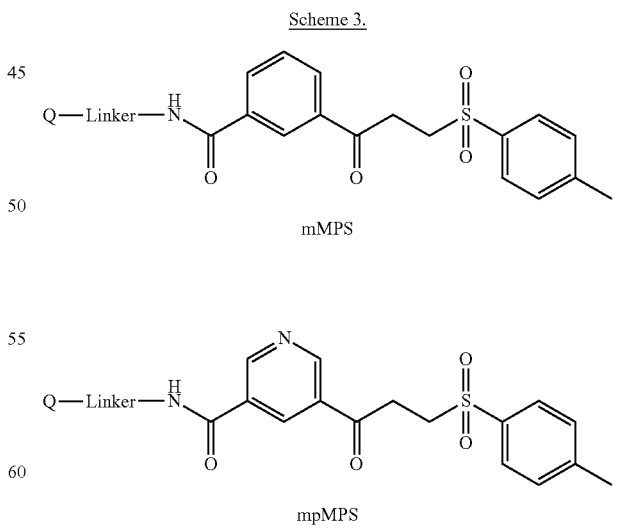

Scheme 3.

In some embodiments, the precursors comprise moieties that act as activated Michael acceptors in the conjugation reaction. An example of a conjugation reaction with an activated Michael acceptor is shown in Scheme 4.

Scheme 4.

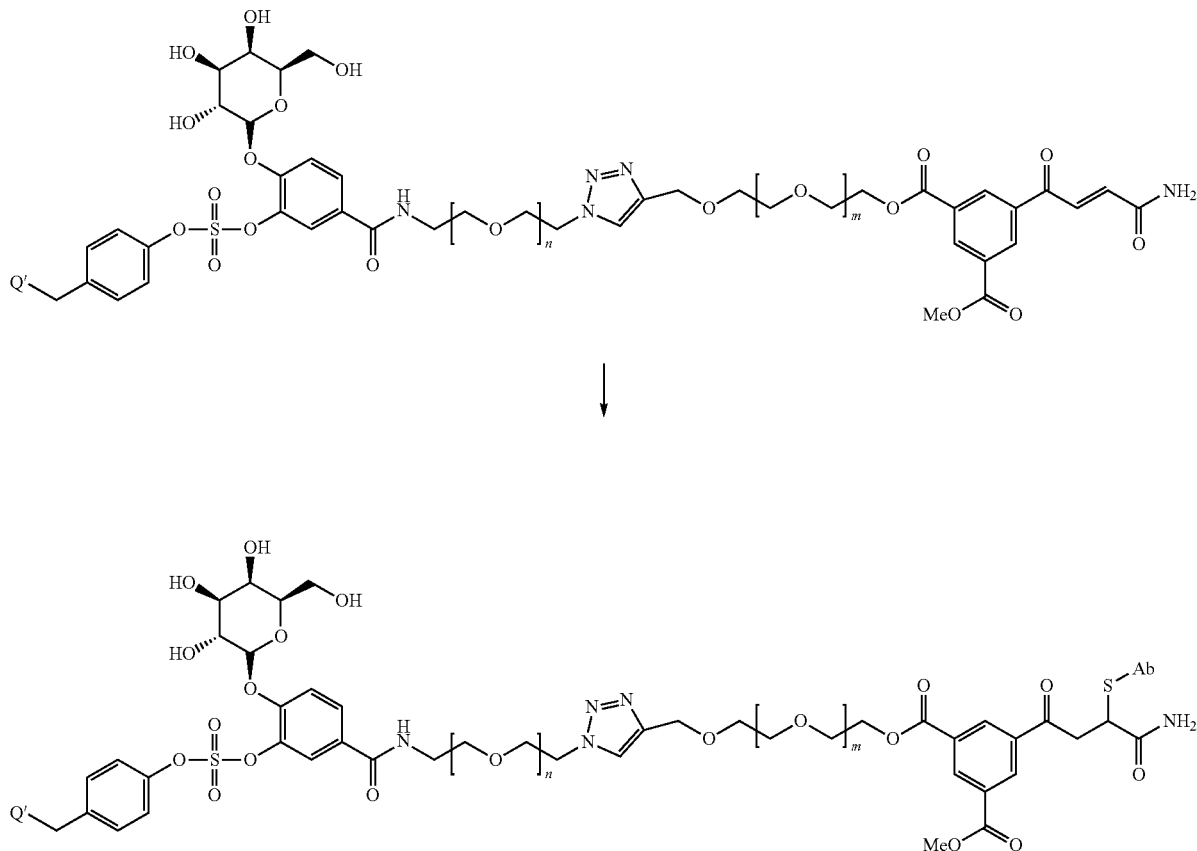

In some embodiments, precursors for one step conjugation contain maleimide. Examples of conjugation of thiol-containing antibodies with maleimide-containing presursors are shown in Scheme 5. A precursor containing an maleimidomethyl cyclohexane-1-carboxylate (Mal-mcc) linker is shown in part A; a precursor with a melimide moiety bound directly to the PEG spacer is shown in part B.

Scheme 5.

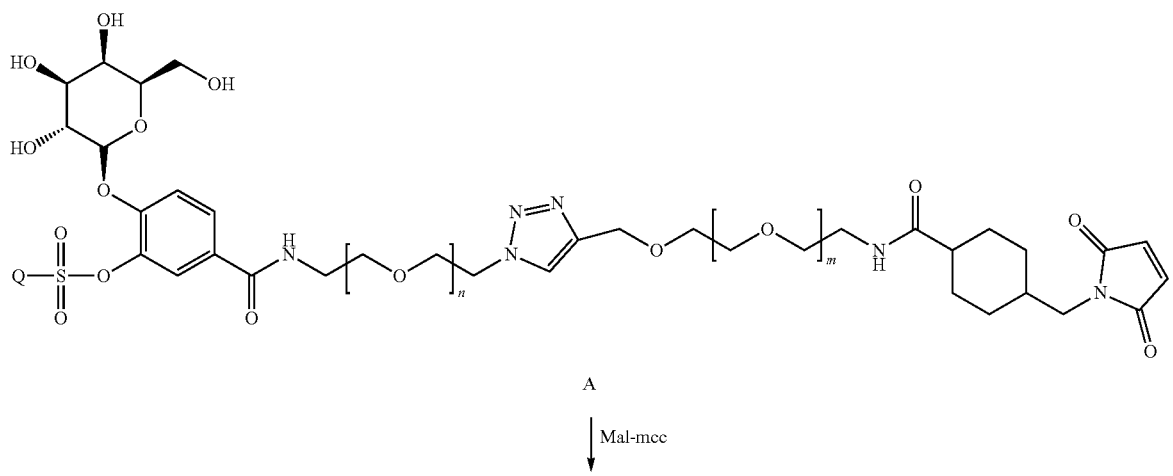

A

Mal-mcc

-continued

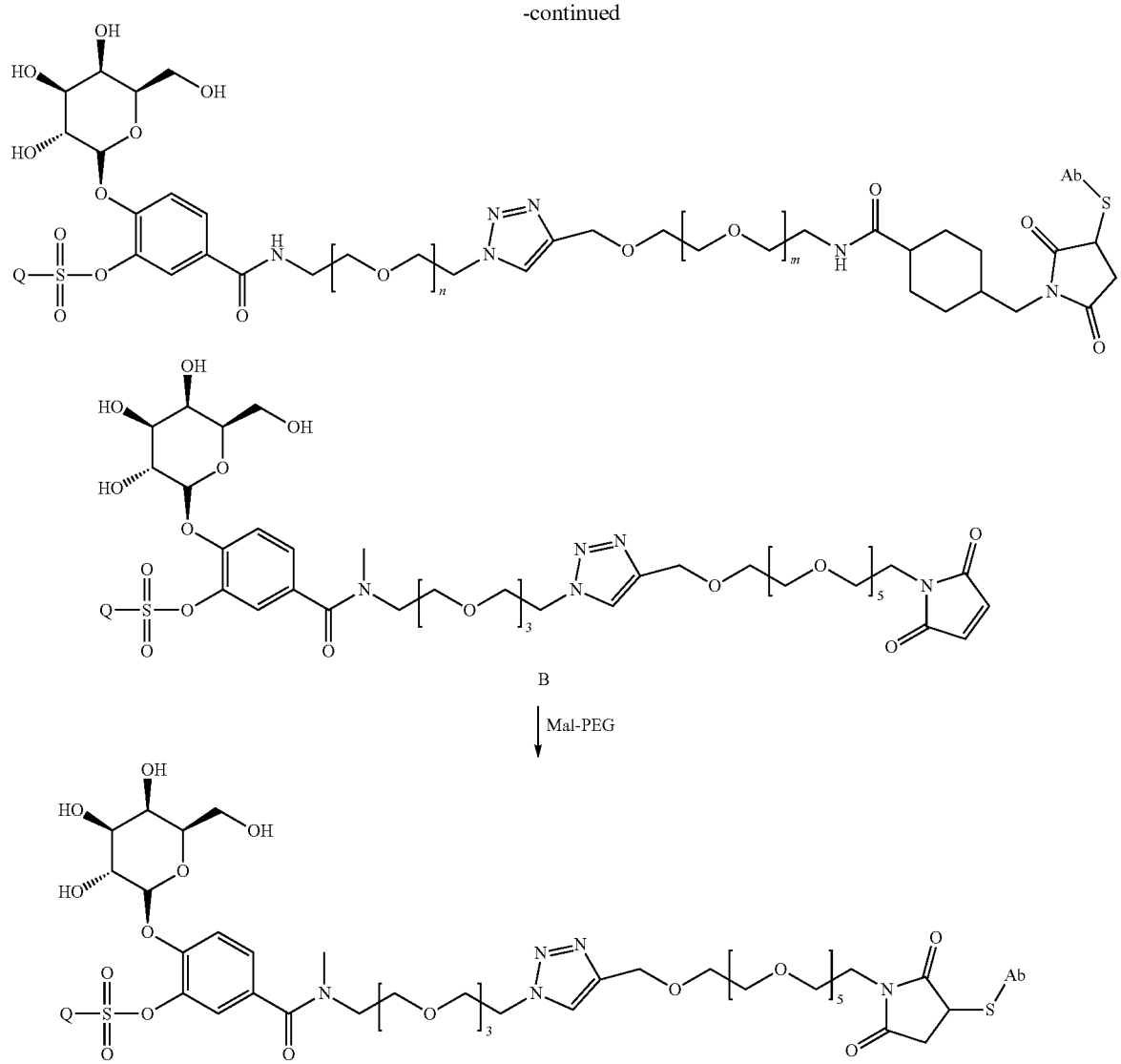

B

↓ Mal-PEG

Two-Step Conjugation

In some embodiments, the present disclosure relates to methods of preparation of compounds of Formula I that involve two-step conjugation. The first step involves conjugation of the the antibody and the linker, where the linker is terminated with a reactive group, such as an azide or an alkyne. In the second step the antibody-containing precursor undergoes a reaction with a precursor containing the active agent, generating the final ADC.

In some embodiments, the first step of the two-step procedure involves conjugation of an antibody with a precursor containing any of the reactive groups disclosed above in the section "One-Step Conjugation". Exemplary precursors for the first conjugation step are shown in Scheme 6.

Scheme 6.

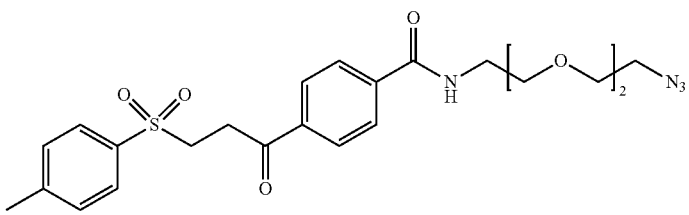

MPS-N₃(2)

-continued

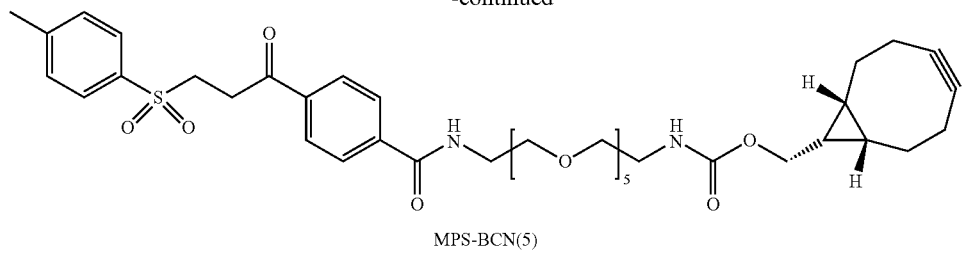

MPS-BCN(5)

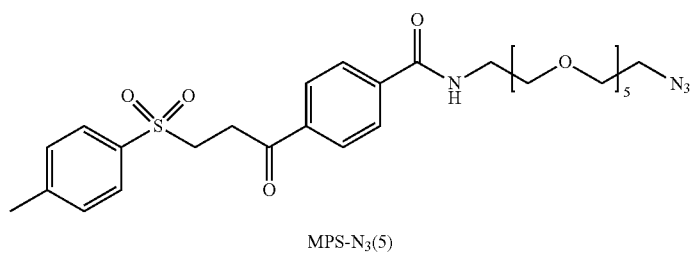

MPS-N₃(5)

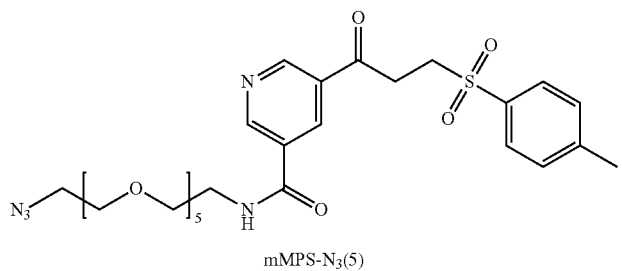

mMPS-N₃(5)

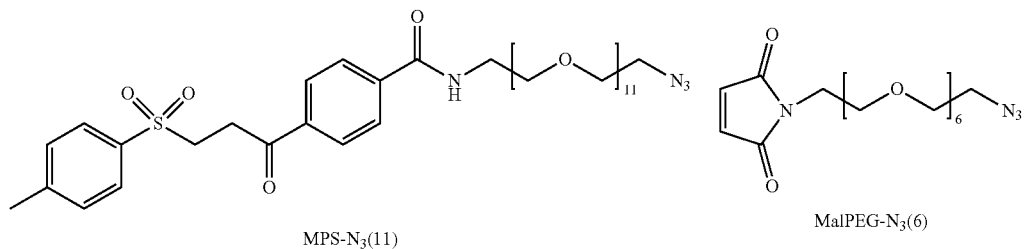

MPS-N₃(11)

MalPEG-N₃(6)

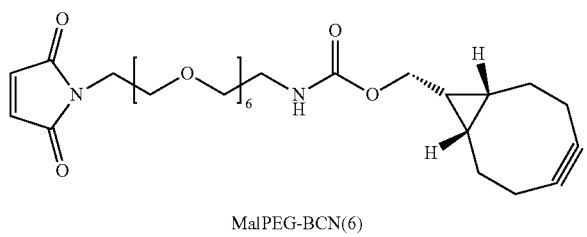

MalPEG-BCN(6)

In some embodiments, the second step of the conjugation process involves reacting the antibody-containing precursor obtained in the first step with an active agent-containg precursor. The active agent-containg precursors comprise a reactive group complementary to the reactive group of the precursor obtained in the first step. For example, the antibody-containg precursor is terminated with an azide, and the active agent-containing precursor is terminated with an alkyne, or vice versa. Examples of active agent-containing precursors are shown in Scheme 7.

Scheme 7
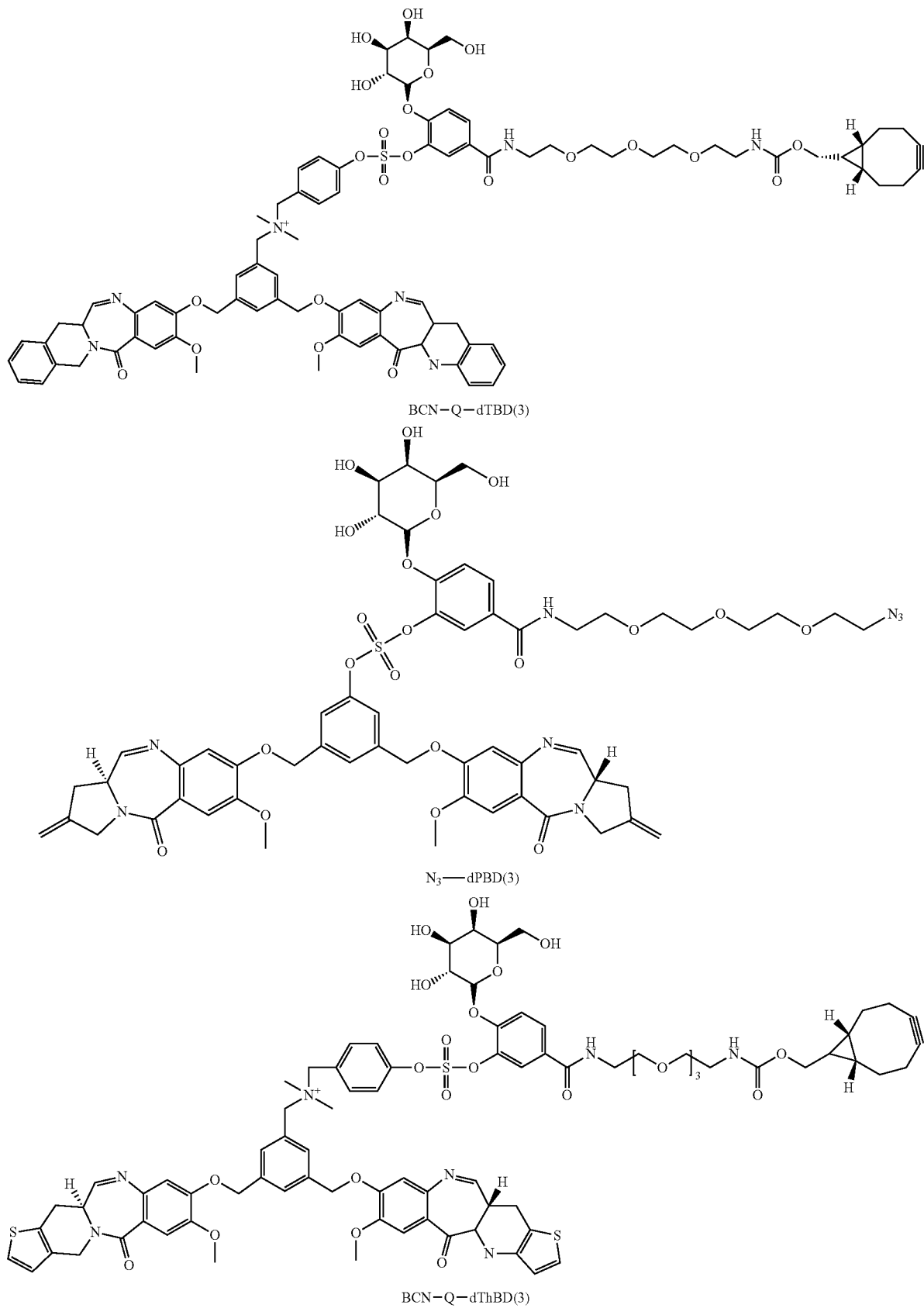

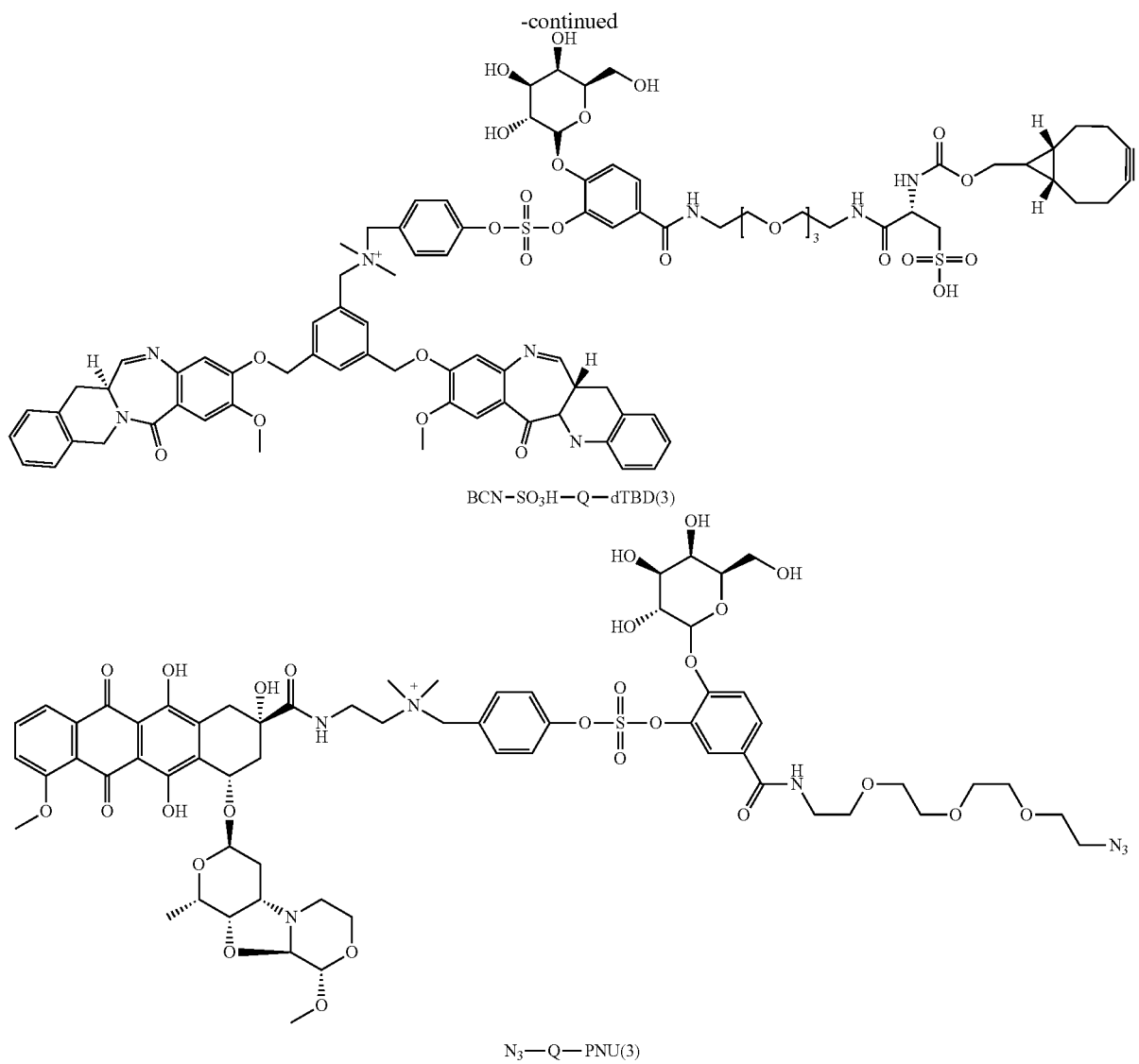

Anti-B7-H3 Antibodies

Exemplary anti-B7-H3 antibodies include the antibodies referred to herein in Tables 19-24, or any fragments, variants, multimeric versions, or bispecifics thereof. Similarly, the anti-B7-H3 antibody may be an antibody or any fragment, variant, multimeric version, or bispecific variant thereof that binds to the same epitope as the antibodies listed in Tables 19-24. Suitable anti-B7-H3 antibodies of the disclosure include fully human monoclonal antibodies, as well as humanized monoclonal antibodies and chimeric antibodies, or any fragments, variants, multimeric versions, or bispecifics thereof. These antibodies show specificity for human B7-H3, and they have been shown to modulate, e.g., block, inhibit, reduce, antagonize, neutralize or otherwise interfere with at least one biological function or activity of B7-H3.

The antibodies are considered to completely modulate, block, inhibit, reduce, antagonize, neutralize or otherwise interfere with at least one functional activity of B7-H3 when the level of functional activity of B7-H3 in the presence of the antibody is decreased by at least 95%, e.g., by 96%, 97%, 98%, 99% or 100% as compared to the level of functional activity of B7-H3 in the absence of binding with an antibody described herein. The antibodies are considered to partially modulate, block, inhibit, reduce, antagonize, neutralize or otherwise interfere with at least one functional activity of B7-H3 when the level of functional activity of B7-H3 in the presence of the antibody is decreased by less than 95%, e.g., 10%, 20%, 25%, 30%, 40%, 50%, 60%, 75%, 80%, 85% or 90% as compared to the level of functional activity of B7-H3 in the absence of binding with an antibody described herein.

Each of the anti-B7-H3 monoclonal antibodies or any fragment, variant, multimeric version, or bispecific variant thereof described herein includes a heavy chain variable region (VH) and a light chain variable region (VL), as shown in the amino acid and corresponding nucleic acid sequences listed in Tables 20-24.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen atoms in a given structure with a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen atoms in a given structure with the substituents mentioned above. More preferably, one to three hydrogen substituents are replaced by the substituents as mentioned above. It is understood that the substituent can be further substituted.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O) NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

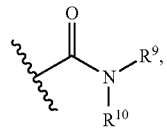

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

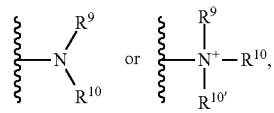

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

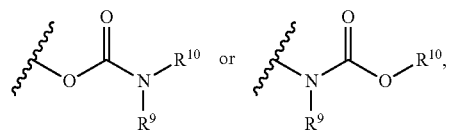

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group —$OCO_2$—.

The term "carboxy", as used herein, refers to a group represented by the formula —$CO_2H$.

The term "ester", as used herein, refers to a group —$C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —$OSO_3H$, or a pharmaceutically acceptable salt thereof.

The term "sulfonamide" is art-recognized and refers to the group represented by the general formulae

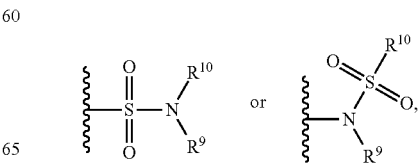

wherein $R^9$ and $R^{10}$ independently represents hydrogen or hydrocarbyl.

The term "sulfoxide" is art-recognized and refers to the group —S(O)—.

The term "sulfonate" is art-recognized and refers to the group SO$_3$H, or a pharmaceutically acceptable salt thereof.

The term "sulfone" is art-recognized and refers to the group —S(O)$_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)SR$^9$ or —SC(O)R$^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

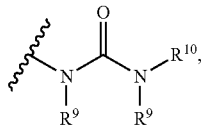

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

In certain embodiments, compounds of the disclosure may be racemic. In certain embodiments, compounds of the disclosure may be enriched in one enantiomer. For example, a compound of the disclosure may have greater than about 30% ee, 40% ee, 50% ee, 60% ee, 70% ee, 80% ee, 90% ee, 95%, 96% ee, 97% ee, 98% ee, 99% ee, or greater ee.

As is generally understood in the art, single bonds drawn without stereochemistry do not indicate the stereochemistry of the compound. The compound of formula I provides an example of a compound for which no stereochemistry is indicated.

In certain embodiments, a composition or compound of the disclosure may be enriched to provide predominantly one enantiomer of a compound. An enantiomerically enriched composition or compound may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound contains 98 grams of a first enantiomer and 2 grams of a second enantiomer, it would be said to contain 98 mol percent of the first enantiomer and only 2 mol % of the second enantiomer.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The term "Log of solubility", "Log S" or "log S" as used herein is used in the art to quantify the aqueous solubility of a compound. The aqueous solubility of a compound significantly affects its absorption and distribution characteristics. A low solubility often goes along with a poor absorption. Log S value is a unit stripped logarithm (base 10) of the solubility measured in mol/liter.

General Method for Preparing Antibodies

Various procedures known within the art may be used for the production of polyclonal or monoclonal antibodies directed against a given target, such as, for example, B7-H3, a tumor associated antigen or other target, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

In some embodiments, the antibodies of the disclosure are monoclonal antibodies. Monoclonal antibodies are generated, for example, by using the procedures set forth in the Examples provided herein. Antibodies are also generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (MA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the disclosure can be readily isolated and sequenced using conventional procedures (e.g., by using oligonucleotide probes that are capable of binding specifically to genes encoding the heavy and light chains of murine antibodies). The hybridoma cells of the disclosure serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the disclosure, or can be substituted for the variable domains of one antigen-combining site of an antibody of the disclosure to create a chimeric bivalent antibody.

Monoclonal antibodies of the disclosure include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs arise from human genes. Such antibodies are termed "human antibodies" or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds specifically to the relevant epitope with high affinity are disclosed in U.S. publication U.S. 2003/009212.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in U.S. Pat. No. 7,186,697 which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short-term expression of the nucleic acid. Adenovirus vectors, adeno-associated virus vectors and herpes simplex virus (HSV) vectors are preferred for introducing the nucleic acid into neural cells. The adenovirus vector results in a shorter-term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other suitable routes of administration.

Bispecific antibodies are antibodies that have binding specificities for at least two different antigens. In the present case, one of the binding specificities is for a target such as B7-H3 or any fragment thereof. The second binding target is any other antigen, and advantageously is a cell-surface protein or receptor or receptor subunit.

Many methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Bispecific and/or monovalent antibodies of the disclosure can be made using any of a variety of art-recognized techniques, including those disclosed in application WO 2012/023053, filed Aug. 16, 2011, the contents of which are hereby incorporated by reference in their entirety. The methods described in WO 2012/023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain. Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions. However it is also possible to obtain bispecific antibodies of the disclosure by fusing a Kappa light chain variable domain to a constant Lambda domain for a first specificity and fusing a Lambda light chain variable domain to a constant Kappa domain for the second specificity. The bispecific antibodies described in WO 2012/023053 are referred to as IgGκλ antibodies or "κλ bodies," a new fully human bispecific IgG format. This κλ-body format allows the affinity purification of a bispecific antibody that is undistinguishable from a standard IgG molecule with characteristics that are undistinguishable from a standard monoclonal antibody and, therefore, favorable as compared to previous formats.

An essential step of the method is the identification of two antibody Fv regions (each composed by a variable light chain and variable heavy chain domain) having different antigen specificities that share the same heavy chain variable domain. Numerous methods have been described for the generation of monoclonal antibodies and fragments thereof (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies" herein. Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of suitable techniques for producing xenogenic non-human animals are well-known in the art. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular the CDR3 on the heavy chain is the most diverse CDR in sequence, length and structure. Thus, two antibodies specific for different antigens will almost invariably carry different heavy chain variable domains.

The methods disclosed in application U.S. Pat. No. 9,926, 382 overcomes this limitation and greatly facilitates the isolation of antibodies having the same heavy chain variable domain by the use of antibody libraries in which the heavy chain variable domain is the same for all the library members and thus the diversity is confined to the light chain variable domain. Such libraries are described, for example, in U.S. Pat. No. 8,921,281 and Application WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the disclosure. The bispecific antibodies of the disclosure can be of different Isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the disclosure. (see for example Strohl, W R Curr Opin Biotechnol 2009 (6):685-91; U.S. Pat. No. 6,528,624; PCT/US2009/0191199 filed Jan. 9, 2009). The methods of the disclosure can also be used to generate bispecific antibodies and antibody mixtures in a F(ab')2 format that lacks the Fc portion.

The common heavy chain and two different light chains are co-expressed into a single cell to allow for the assembly of a bispecific antibody of the disclosure. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Therefore, a means to modulate the relative expression of the different polypeptides is used to compensate for their intrinsic expression characteristics or different propensities to assemble with the common heavy chain. This modulation can be achieved via promoter strength, the use of internal ribosome entry sites (IRES) featuring different efficiencies or other types of regulatory elements that can act at transcriptional or translational levels as well as acting on mRNA stability. Different promoters of different strength could include CMV (Immediate-early Cytomegalovirus virus promoter); EF1-1α (Human elongation factor 1α-subunit promoter); Ubc (Human ubiquitin C promoter); SV40 (Simian virus 40 promoter). Different IRES have also been described from mammalian and viral origin. (See e.g., Hellen C U and Sarnow P. Genes Dev 2001 15: 1593-612). These IRES can greatly differ in their length and ribosome recruiting efficiency. Furthermore, it is possible to further tune the activity by introducing multiple copies of an IRES (Stephen et al. 2000 Proc Natl Acad Sci USA 97: 1536-1541). The modulation of the expression can also be achieved by multiple sequential transfections of cells to increase the copy number of individual genes expressing one or the other light chain and thus modify their relative expressions. The Examples provided herein demonstrate that controlling the relative expression of the different chains is critical for maximizing the assembly and overall yield of the bispecific antibody.

The co-expression of the heavy chain and two light chains generates a mixture of three different antibodies into the cell culture supernatant: two monospecific bivalent antibodies and one bispecific bivalent antibody. The latter has to be purified from the mixture to obtain the molecule of interest. The method described herein greatly facilitates this purification procedure by the use of affinity chromatography media that specifically interact with the Kappa or Lambda light chain constant domains such as the CaptureSelect Fab Kappa and CaptureSelect Fab Lambda affinity matrices (BAC BV, Holland). This multi-step affinity chromatography purification approach is efficient and generally applicable to antibodies of the disclosure. This is in sharp contrast to specific purification methods that have to be developed and optimized for each bispecific antibodies derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

Other suitable purification methods include those disclosed in US2013/0317200, the contents of which are hereby incorporated by reference in their entirety.

In other embodiments of producing bispecific antibodies, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, $CH_2$, and $CH_3$ regions. It is preferred to have the first heavy-chain constant region ($CH_1$) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the disclosure. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present disclosure. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the disclosure with respect to effector function, so as to enhance, e.g., the effectiveness of the antibody in treating cancer and/or other diseases and disorders associated with aberrant B7-H3 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

Conjugated Antibodies

The disclosure also pertains to conjugated antibodies, also referred to herein as immunoconjugates, comprising an antibody or antigen-binding fragment thereof conjugated to a cytotoxic agent such as a toxin (e.g., an enzymatically active toxin of bacterial, fungal, plant, or animal origin, or fragments thereof), or a radioactive isotope (i.e., a radioconjugate).

In some embodiments, the toxin is a microtubule inhibitor or a derivative thereof. In some embodiments, the toxin is a dolastatin or a derivative thereof. In some embodiments, the toxin is auristatin E, auristatin F, AFP, MMAF, MMAE, MMAD, DMAF, or DMAE. In some embodiments, the toxin is a maytansinoid or maytansinoid derivative. In some embodiments, the toxin is DM1 or DM4. In some embodiments, the toxin is a nucleic acid damaging toxin. In some embodiments, the toxin is a duocarmycin or derivative thereof. In some embodiments, the toxin is a calicheamicin or a derivative thereof. In some embodiments, the agent is a pyrrolobenzodiazepine or a derivative thereof. In some embodiments, the agent is an exatecane or a derivative thereof.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NETS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody can be prepared by any suitable methods, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Use of Anti-B7-H3 Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a conjugate of the disclosure, are used to treat or alleviate a symptom associated with a cancer, such as, by way of non-limiting example, leukemias, lymphomas, breast cancer, colon cancer, ovarian cancer, bladder cancer, prostate cancer, glioma, lung & bronchial cancer, colorectal cancer, pancreatic cancer, esophageal cancer, liver cancer, urinary bladder cancer, kidney and renal pelvis cancer, oral cavity & pharynx cancer, uterine corpus cancer, and/or melanoma The present disclosure also provides methods of treating or alleviating a symptom associated with a cancer. A therapeutic regimen can include identifying a subject, e.g., a human patient suffering from (or at risk of developing) a cancer, e.g., using standard methods.

Therapeutic formulations of the disclosure, which include a conjugate of the disclosure that recognizes B7-H3 and, optionally, a second target can be used to treat or alleviate a symptom associated with an autoimmune disease and/or inflammatory disease, such as, for example, B-cell mediated autoimmune diseases and/or inflammatory diseases, including by way of non-limiting example, systemic lupus erythematosus (SLE), rheumatoid arthritis (RA), idiopathic thrombocytopenic purpura (ITP), Waldenstrom's hypergammaglobulinaemia, Sjogren's syndrome, multiple sclerosis (MS), and/or lupus nephritis.

Efficaciousness of treatment can be determined in association with any suitable method for diagnosing or treating the particular immune-related disorder. Alleviation of one or more symptoms of the immune-related disorder indicates that the conjugate confers a clinical benefit.

Conjugates directed against a target such as B7-H3, a tumor associated antigen or other antigen may be used in methods relating to the localization and/or quantitation of these targets, e.g., for use in measuring levels of these targets within appropriate physiological samples, for use in diagnostic methods, for use in imaging the protein, and the like). For example, conjugates specific for any of these targets, or derivative, fragment, analog or homolog thereof, that contain the antibody derived antigen-binding domain, can be utilized as pharmacologically active compounds (referred to hereinafter as "Therapeutics").

A conjugate of the disclosure can be used to isolate a particular target using standard techniques, such as immunoaffinity, chromatography or immunoprecipitation. Conjugates of the disclosure can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Conjugates of the disclosure may be used as therapeutic agents. Such agents will generally be employed to treat or prevent a disease or pathology associated with aberrant expression or activation of a given target in a subject. A conjugate preparation, preferably one having high specificity and high affinity for its target antigen, is administered to the subject and will generally have an effect due to its binding with the target. Administration of the conjugate may abrogate or inhibit or interfere with the signaling function of the target. Administration of the conjugate may abrogate or inhibit or interfere with the binding of the target with an endogenous ligand to which it naturally binds.

A therapeutically effective amount of a conjugate of the disclosure relates generally to the amount needed to achieve a therapeutic objective. As noted above, this may be a binding interaction between the antibody and its target antigen that, in certain cases, interferes with the functioning of the target and/or the effect of an active agent conjugated to the antibody. The amount required to be administered will furthermore depend on the binding affinity of the antibody for its specific antigen and/or the potency of the active agent, and will also depend on the rate at which an administered antibody is depleted from the free volume other subject to which it is administered. Common ranges for therapeutically effective dosing of a conjugate of the disclosure may be, by way of nonlimiting example, from about 0.1 mg/kg body weight to about 50 mg/kg body weight. Common dosing frequencies may range, for example, from twice daily to once a week.

Conjugates of the disclosure can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration are preferably sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

A conjugate according to the disclosure can be used as an agent for detecting the presence of a given target (or a protein fragment thereof) in a sample. In some embodiments, the conjugate contains a detectable label. Antibodies can be polyclonal, or more preferably, monoclonal. An intact antibody, or a fragment thereof (e.g., $F_{ab}$, scFv, or $F_{(ab)2}$) can be used. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte conjugate. For example, the antibody can be labeled with a radioactive marker whose presence and location in a subject can be detected by standard imaging techniques.

Pharmaceutical Compositions

The antibody-drug conjugate may be used to transfer the active agent to a target cell of a subject to treat the subject using any suitable method of preparing a composition. In some aspects, the disclosure relates to a composition (e.g., a pharmaceutical composition) comprising an antibody-drug conjugate as described herein.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as lyophile for reconstitution, powder, solution, injection or the like.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A pharmaceutical composition (preparation) can be administered to a subject by any of a number of routes of administration. For example, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any suitable method in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Many methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

The patient receiving this treatment may be any animal in need, including primates, in particular humans; and other mammals such as equines, cattle, swine, sheep, cats, and dogs; poultry; and pets in general.

In certain embodiments, compounds of the disclosure may be used alone or conjointly administered with another type of therapeutic agent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Compositions may be prepared in an injectable form, either as a liquid solution or as a suspension. Solid forms suitable for injection may also be prepared, e.g., as emulsions, or with the antibody-drug conjugate encapsulated in liposomes. Antibody-drug conjugates may be combined with a pharmaceutically acceptable carrier, which includes any carrier that does not induce the production of antibodies harmful to the subject receiving the carrier. Suitable carriers typically comprise large macromolecules that are slowly metabolized, for example, proteins, polysaccharides, polylactic acids, polyglycolic acids, polymeric amino acids, amino acid copolymers, lipid aggregates, and the like.

The compositions may also contain diluents, for example, water, saline, glycerol, and ethanol. Auxiliary substances, for example, wetting or emulsifying agents, pH buffering substances, and the like may also be present therein. The compositions may be parenterally administered by injection, wherein such injection may be either subcutaneous or intramuscular injection. In some embodiments, a composition may be administered into a tumor. The composition may be inserted (e.g., injected) into a tumor. Additional formulations are suitable for other forms of administration, such as suppository or oral administration. Oral compositions may be administered as a solution, suspension, tablet, pill, capsule, or sustained release formulation.

The compositions may be administered in a manner compatible with a dose and a formulation. The composition preferably comprises a therapeutically effective amount of the antibody-drug conjugate. A dose may vary, depending on the subject to be treated, the subject's health and physical conditions, a degree of protection to be desired, and other relevant factors. The exact amount of an active ingredient (e.g., the antibody-drug conjugate) may depend on the judgment of a doctor. For example, a therapeutically effective amount of the antibody-drug conjugate or composition containing the same may be administered to a patient suffering from a cancer or tumor to treat the cancer or tumor.

The antibody-drug conjugate according to the present disclosure or the composition containing the same may be administered in the form of a pharmaceutically acceptable salt thereof. In some embodiments, the antibody-drug conjugate according to the present disclosure or the composition containing the same may be administered with a pharmaceutically acceptable carrier, a pharmaceutically acceptable excipient, and/or a pharmaceutically acceptable additive. The effective amount and the type of the pharmaceutically acceptable salt, excipient and additive may be measured using standard methods (see, e.g., Remington's Pharmaceutical Sciences, Mack Publishing Co., Easton, Pa., 18th Edition, 1990).

In some embodiments, the disclosure relates to a method of treating cancer in a subject, comprising administering a pharmaceutical composition comprising an antibody-drug conjugate as described herein to the subject. In preferred embodiments, the subject is a mammal. For example, the subject may be selected from rodents, lagomorphs, felines, canines, porcines, ovines, bovines, equines, and primates. In certain preferred embodiments, the subject is a human.

The conjugates of the disclosure (also referred to herein as "active compounds"), and derivatives, fragments, analogs and homologs thereof, can be incorporated into pharmaceutical compositions suitable for administration. Such compositions typically comprise the conjugate and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, and subcutaneous administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

In certain embodiments, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to suitable methods, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

In some aspects, the present disclosure provides pharmaceutical compositions comprising an antibody drug conjugate as described herein, optionally further comprising a therapeutically effective amount of a chemotherapeutic agent.

In some aspects, the present disclosure provides methods of treating cancer, comprising administering an antibody-drug conjugate of the disclosure or a pharmaceutical composition thereof. In some such embodiments, the cancer is selected from leukemia, lymphoma, breast cancer, colon cancer, ovarian cancer, bladder cancer, prostate cancer, glioma, lung cancer, bronchial cancer, colorectal cancer, pancreatic cancer, esophageal cancer, liver cancer, urinary bladder cancer, kidney cancer, renal pelvis cancer, oral cavity cancer, pharynx cancer, uterine corpus cancer, or melanoma.

In some aspects, the present disclosure provides methods of treating autoimmune diseases or inflammatory diseases, comprising administering an antibody drug conjugate of the disclosure or a pharmaceutical composition thereof. In some embodiments, the autoimmune diseases or the inflammatory disease is selected from B-cell mediated autoimmune diseases or inflammatory diseases, for example, systemic lupus erythematosus (SLE), rheumatoid arthritis (RA), idiopathic thrombocytopenic purpura (ITP), Waldenstrom's hypergammaglobulinaemia, Sjogren's syndrome, multiple sclerosis (MS), or lupus nephritis.

Hereinafter, configurations of the present disclosure will be described in detail through Examples, but the following Examples are only to assist in understanding of the present disclosure. The scope of the present disclosure is not limited thereto. Further, unless specifically described otherwise, the reagent, solvent, and starting material described in the specification can be easily obtained from a commercial supplier.

EXEMPLIFICATION

The table below lists the abbreviations used throughout the following Examples:

| Abbreviation | Reference |
| --- | --- |
| Ac | acetyl |
| AcOH | acetic acid |
| aq. | aqueous |
| Bn | benzyl |
| brine | saturated aqueous sodium chloride solution |
| Boc | t-butoxycarbonyl |
| Cbz | benzyloxycarbonyl |
| DBU | 1,8-diazabicyclo[5.4.0]undec-7-ene |
| DCM | dichloromethane |
| DIC | N,N'-diisopropylcarbodiimide |
| DIPEA | N,N-diisopropylethylamine |
| DMAP | 4-(dimethylamino)pyridine |
| DMF | N,N-dimethylformamide |
| DMSO | dimethyl sulfoxide |
| EDC | N-(3-dimethylaminopropyl)-N'-ethylcarbodiimide |
| Et | ethyl |
| Et2O | diethyl ether |
| EtOAc | ethyl acetate |
| EtOH | ethanol |
| HBTU | O-(benzotriazol-1-yl)-N,N,N',N'-tetramethyluronium hexafluorophosphate |
| Hex | n-hexane |
| HOBt | 1-hydroxybenzotriazole |
| HPLC | high performance liquid chromatography |
| Me | Methyl |
| MeCN | acetonitrile |
| MeOH | methanol |
| MMAE | monomethyl auristatin E |
| MMAF | monomethyl auristatin F |
| MMAF-OMe | monomethyl auristatin F methyl ester |

-continued

| Abbreviation | Reference |
|---|---|
| i-PrOH | isopropanol |
| PyBOP | (benzotriazol-1-yloxy)tripyrrolidinophosphonium hexafluorophosphate |
| TBAF | tetrabutylammonium fluoride |
| TBS | t-butyldimethylsilyl |
| THF | tetrahydrofuran |
| TFA | trifluoroacetic acid |
| Ts | p-toluenesulfonyl |
| wt | weight |

EXAMPLES

Example 1

Synthesis of MPS Derivatives

Example 1.1

Preparation of MPS-D1

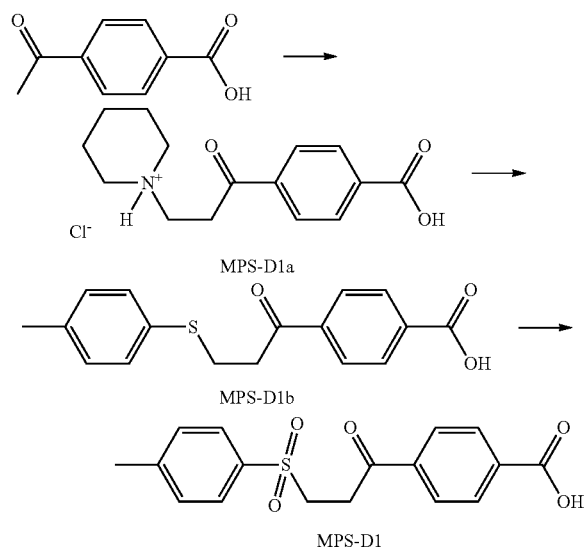

Preparation of Compound MPS-D1a

To a solution of 4-acetylbenzoic acid (9 g, 54.82 mmol) in EtOH (50 mL) was added piperidine hydrochloride (6.66 g, 54.82 mmol), paraformaldehyde (4.95 g, 164.5 mmol), and conc. HCl (0.6 mL) at room temperature under $N_2$ atmosphere. The mixture was stirred at 100° C. for 16 hours and cooled to room temperature, acetone (90 mL) was added dropwise thereto. The mixture was stirred at 0° C. for 1 hour. The solid was filtered and washed with diethyl ether (30 mL×2) to obtain compound MPS-D1a (6.11 g, 38%).

$^1$H NMR (400 Hz, DMSO-$d_6$) δ 8.08 (s, 4H), 5.73 (s, 1H), 3.65 (t, J=7.2 Hz, 2H), 3.35 (t, J=7.2 Hz, 2H), 3.31 (m, 6H), 1.74 (s, 4H).

Preparation of Compound MPS-D1b

To a solution of MPS-D1a (6.11 g, 20.52 mmol) in EtOH (40 mL) and MeOH (26 mL) was added 4-methoxybenzenethiol (2.55 g, 20.52 mmol) and piperidine (0.3 mL, 3.08 mmol) at room temperature. The mixture was stirred at 100° C. for 16 hours and cooled to 0° C. and additionally stirred for 1 hour. The solid was filtered and washed with ether (30 mL×2) to obtain compound MPS-D1b (5.56 g, 90%).

$^1$H NMR (400 Hz, CDCl$_3$) δ 8.04-7.99 (m, 4H), 7.27 (d, J=8.4 Hz, 2H), 7.15 (d, J=7.6 Hz, 2H), 3.39-3.36 (m, 2H), 3.25-3.21 (m, 2H), 2.27 (s, 3H).

Preparation of Compound MPS-D1

To a solution of MPS-D1b (5.56 g, 18.51 mmol) in MeOH (90 mL) and distilled water (90 mL) was added oxone (25.03 g, 40.72 mmol) at 0° C. under $N_2$ atmosphere. After stirring at room temperature for 14 hours, the mixture was quenched with distilled water (100 mL) and chloroform (150 mL×3). The organic layer was washed with brine (200 mL), dried over anhydrous Na$_2$SO$_4$, filtered and concentrated under reduced pressure to obtain compound MPS-D1 (5.29 g, 86%).

$^1$H NMR (400 Hz, CDCl$_3$) δ 8.04-7.99 (m, 4H), 7.81 (d, J=8.4 Hz, 2H), 7.46 (d, J=8.4 Hz, 2H), 3.63 (t, J=7.2 Hz, 2H), 3.41 (t, J=7.2 Hz, 2H), 2.44 (s, 3H). ESI-MS m/z: 333 (M$^+$).

Example 1.2

Preparation of BCN-PNP

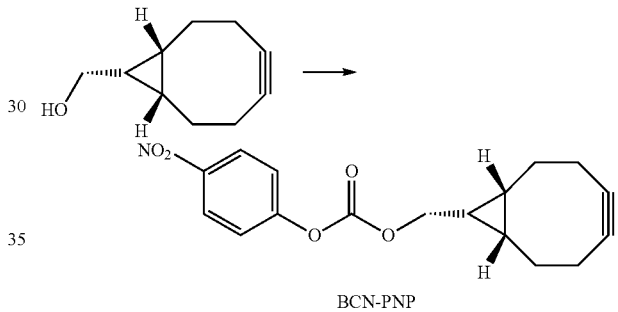

(1R,8S,9S)-Bicyclo[6.1.0]non-4-yn-9-yl methanol (800 mg, 5.3 mmol) was dissolved in DCM (125 mL) at room temperature under $N_2$ atmosphere. Pyridine (1.22 mL, 15.9 mmol) and 4-nitrophenyl chloroformate (1.75 g, 8.74 mmol) were added thereto. After the mixture was stirred for 4 hours at the same temperature, the reaction was quenched by the addition of saturated NH$_4$Cl solution (100 mL) and extracted with EA (100 mL×4). The organic layer was dried over Na$_2$SO$_4$, filtered and concentrated in vacuo. The residue was purified by column chromatography (Hex:EA=10:1) to obtain compound BCN-PNP (1.34 g, 84%) as white solid.

$^1$H NMR (600 MHz, CDCl$_3$) δ 8.29 (d, J=9 Hz, 2H), 7.39 (d, J=9 Hz, 2H), 4.41 (d, J=8.4 Hz, 2H), 2.36-2.24 (m, 6H), 1.62-1.55 (m, 2H), 1.53-1.49 (m, 1H), 1.07 (t, J=10.2 Hz, 2H).

Example 1.3

Preparation of MPS-D1-1

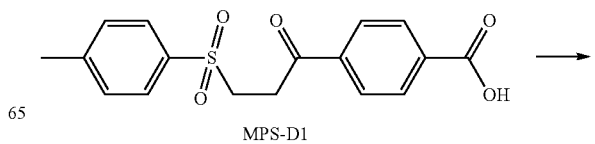

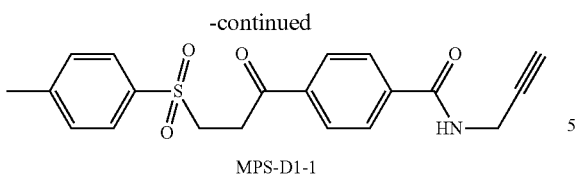

MPS-D1-1

To a solution of compound MPS-D1 (500 mg, 1.50 mmol) in DMF (8 mL) was added propargyl amine (106 µL, 1.65 mmol) at room temperature under $N_2$ atmosphere. The reaction was cooled to 0° C. and PyBop (1.17 g, 2.26 mmol) and DIPEA (524 µL, 3.01 mmol) were added thereto. The mixture was stirred at room temperature for 2 hours and diluted with EA (30 mL×2) and distilled water (20 mL). The organic layer was extracted and washed with brine (50 mL), dried over anhydrous $Na_2SO_4$, filtered, and concentrated under reduced pressure. The residue was purified by column chromatography to obtain compound MPS-D1-1 (510 mg, 92%).

$^1$H NMR (400 Hz, $CDCl_3$) δ 9.11 (t, J=5.2 Hz, 1H), 7.98-7.89 (m, 4H), 7.79 (d, J=8.0 Hz, 2H), 7.43 (d, J=8.4 Hz, 2H), 4.05-4.03 (m, 2H), 3.60 (t, J=7.6 Hz, 2H), 3.39 (t, J=7.2 Hz, 2H), 3.12 (s, 1H), 2.38 (s, 3H).

Example 1.4

Preparation of L-2 and L-2a

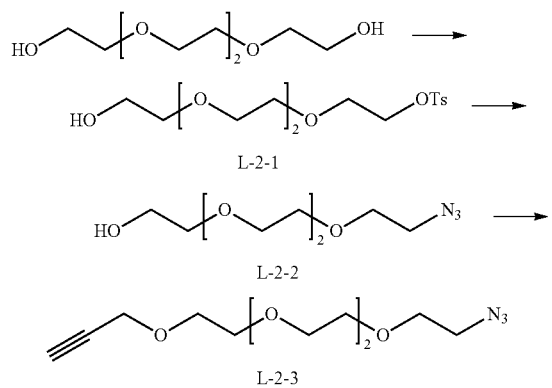

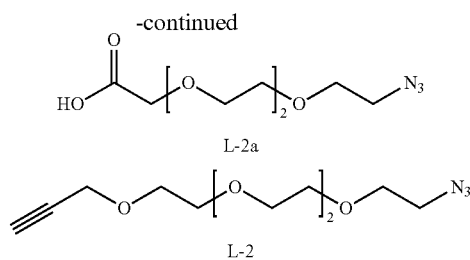

Compound L-2 was synthesized by a similar synthetic route as described in Journal of Polymer Science, Part A: Polymer Chemistry, 2012, 50(19), 3986-3995, incorporated herein by reference.

Preparation of Compound L-2-1
Yield 30%
$^1$H NMR (400 Hz, CDCl3) δ 7.80 (d, J=8.4 Hz, 2H), 7.34 (d, J=8.4 Hz, 2H), 4.16 (t, J=4.8 Hz, 2H), 3.74-3.58 (m, 14H), 2.45 (s, 3H).

Preparation of Compound L-2-2
Yield 68%
$^1$H NMR (400 Hz, CDCl3) δ 3.74-3.61 (m, 14H), 3.40 (t, J=4.8 Hz, 2H), 2.45 (t, J=6.0 Hz, 2H).

Preparation of Compound L-2-3
Yield 63%
$^1$H NMR (400 Hz, CDCl3) δ 4.21 (d, J=2.4 Hz, 2H), 3.72-3.67 (m, 14H), 3.39 (t, J=5.2 Hz, 2H), 2.43 (t, J=2.4 Hz, 1H).

Preparation of Compound L-2
Yield 76%
$^1$H NMR (400 Hz, CDCl3) δ 4.20 (d, J=2.4 Hz, 2H), 3.71-3.61 (m, 12H), 3.51 (t, J=4.8 Hz, 2H), 2.87 (t, J=5.6 Hz, 2H), 2.43 (t, J=2.4 Hz, 1H).

Preparation of Compound L-2a
To a solution of compound L-2-2 (3.0 g, 13.7 mmol) in Acetone (100 mL) at 0° C. N2 atmosphere was treated with Jones reagent (20 mL) and stirred for 4 hours. The reaction mixture was filtered and concentrated under reduced pressure. The residue was extracted with DCM (50 mL×2) and distilled water (15 mL). The organic layer was washed with brine (50 mL), dried over anhydrous Na2SO4, filtered, and concentrated under reduced pressure. The residue was purified by column chromatography to obtain compound L-2a (2.8 g, 88%).

1H NMR (400 Hz, $CDCl_3$) δ 4.22-4.14 (m, 2H), 3.80-3.64 (m, 10H), 3.42 (t, J=4.4 Hz, 2H).

Example 1.5

Preparation of L-3

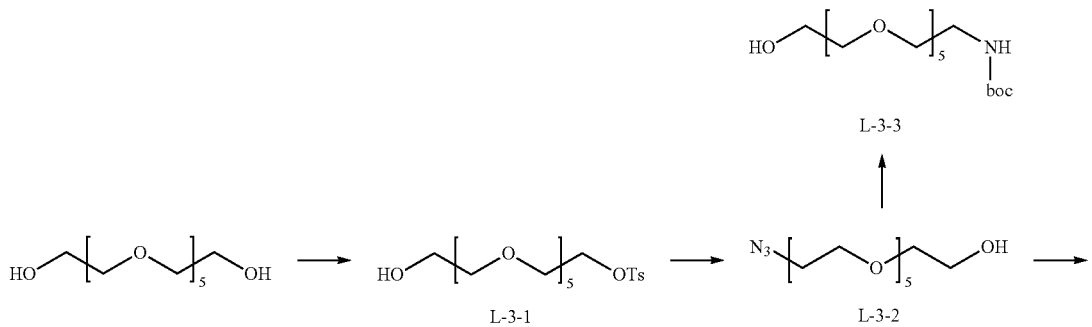

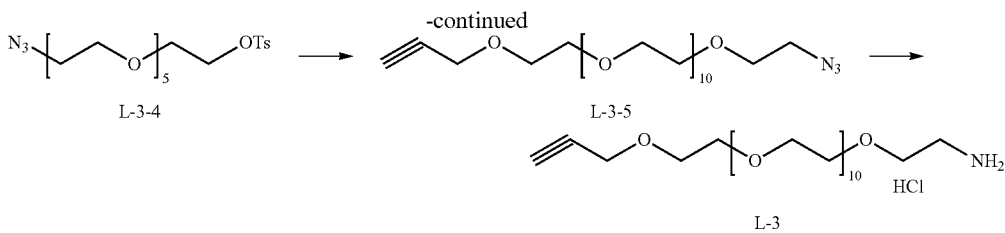

L-3

Preparation of Compound L-3-1

To a solution of hexaethylene glycol (5.0 g, 17.71 mmol) in anhydrous DCM (178 mL) were added KI (294 mg, 1.77 mmol) and Ag$_2$O (4.92 g, 19.48 mmol) under N$_2$ atmosphere. The mixture was stirred overnight at room temperature. After the reaction was completed, the mixture was filtered through Celite® and washed with DCM (100 mL). The filtrate was concentrated under reduced pressure. The residue was purified by column chromatography to obtain compound L-3-1 (5.98 g, 73%).

1H NMR (400 Hz, CDCl$_3$) δ 7.80 (d, J=8.4 Hz, 2H), 7.35 (d, J=8.4 Hz, 2H), 4.16 (t, J=4.8 Hz, 2H), 3.71-3.58 (m, 22H), 2.88 (br, 1H), 2.45 (s, 3H).

Preparation of Compound L-3-2

To a solution of compound L-3-1 (5.98 g, 13.7 mmol) in DMF (30 mL) was added NaN$_3$ (1.34 g, 20.55 mmol) under N$_2$ atmosphere. The mixture was stirred at 110° C. for 1 h and concentrated under reduced pressure. The residue was purified by column chromatography to obtain compound L-3-2 (4.1 g, 97%).

$^1$H NMR (400 Hz, CDCl$_3$) δ 3.72-3.60 (m, 22H), 3.39 (t, J=4.8 Hz, 2H), 2.78 (br, 1H).

Preparation of Compound L-3-3

5% Pd/C (1.04 g, 0.49 mmol) was added to a stirred solution of L-3-2 (1.0 g, 3.25 mmol) in EtOH (5 mL) at room temperature. Hydrogen gas was bubbled through the reaction mixture for 4 h. The mixture was filtered through Celite® to remove Pd/C, and concentrated under reduced pressure. After the residue was dissolved in DCM (25 mL), BOC$_2$O (852.1 mg, 3.9 mmol) was added thereto. The mixture was stirred at room temperature for 3 hours. The mixture was concentrated under reduced pressure. The residue was purified by column chromatography to produce compound L-3-3 (330 mg, 28%).

$^1$H NMR (400 Hz, CDCl$_3$) δ 5.19 (brs, 1H), 3.73 (t, J=4.8 Hz, 2H), 3.67 (s, 12H), 3.63-3.60 (m, 6H), 3.54 (t, J=5.2 Hz, 2H), 3.34-3.27 (m, 1H), 1.44 (s, 9H).

ESI-MS m/z: 382 (M$^+$+1).

Preparation of Compound L-3-4

Compound L-3-2 (1.9 g, 6.18 mmol) was dissolved in DCM (20 mL) under N$_2$ atmosphere. Triethylamine (2.0 mL, 14.22 mmol) and p-TsCl (2.4 g, 12.36 mmol) were added thereto, and the mixture was stirred overnight at room temperature. After the reaction was completed, the mixture was concentrated under reduced pressure. The residue was purified by column chromatography to obtain compound L-3-4 (2.58 g, 91%).

$^1$H NMR (400 Hz, CDCl$_3$) δ 7.80 (d, J=8.4 Hz, 2H), 7.35 (d, J=8.4 Hz, 2H), 4.16 (t, J=4.8 Hz, 2H), 3.70-3.61 (m, 16H), 3.56 (s, 1H), 3.39 (t, J=4.8 Hz, 2H), 2.45 (s, 3H).

ESI-MS m/z: 462 (M$^+$+1).

Preparation of Compound L-3-5

A homogeneous solution of L-2 (1.1 g, 3.4 mmol) in anhydrous THF (30 mL) under N$_2$ atmosphere was treated with NaH (60% dispersion in mineral oil, 135 mg, 3.4 mmol) and cooled to 0° C. After the mixture was stirred at 0° C. for 20 min, L-3-4 (1.56 g, 3.4 mmol) was added thereto. The reaction was allowed to warm up to room temperature and stirred overnight. The reaction was allowed to cool, quenched with MeOH (5 mL) and concentrated under reduced pressure. The residue was purified by column chromatography to obtain compound L-3-5 (1.91 g, 93%).

ESI-MS m/z: 610 (M$^+$+1).

Preparation of Compound L-3

At 0° C., to a solution of compound L-3-5 (906.7 mg, 1.49 mmol) in EA (4 mL) and ether (4 mL) under N$_2$ atmosphere was slowly added 5% HCl solution (8 mL) and triphenylphosphine (390 mg, 1.49 mmol). The mixture was stirred at 0° C. overnight. The mixture was diluted with DCM (10 mL). The aqueous layer was extracted with DCM (10 mL×3). The aqueous phase was concentrated under high vacuum to obtain compound L-3 (495 mg, 54%).

ESI-MS m/z: 584 (M$^+$+1).

Example 1.6

Preparation of L-4

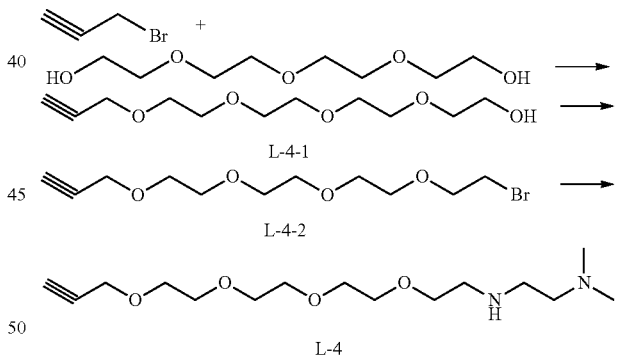

Preparation of Compound L-4-1

At −20° C. under N$_2$ atmosphere, to a solution of KOtBu (943 mg, 8.41 mmol) in dry THF (50 mL) was added tetraethylene glycol (4.35 mL, 25.22 mmol) followed by propargyl bromide (1.0 g, 8.41 mL) The reaction was allowed to warm up to room temperature and stirred for 17 hours. The reaction was quenched by the addition of MeOH (1 mL) and H$_2$O (50 mL) with cooling in an ice bath and extracted with EA (100 mL). The organic layer was dried over anhydrous Na$_2$SO$_4$, filtered and concentrated under reduced pressure. The residue was purified by column chromatography to obtain compound L-4-1 (1.46 g, 75%).

$^1$H NMR (400 MHz, CDCl$_3$) δ 4.26-4.20 (m, 2H), 3.78-3.60 (m, 16H), 2.42-2.40 (m, 1H).

Preparation of Compound L-4-2

To a solution of CBr$_4$ (1.43 g, 4.31 mmol) in dry DCM (20 mL) cooled in an ice bath was added triphenylphosphine (1.13 g, 4.31 mmol) followed by L-4-1 (500 mg, 2.15 mmol). The mixture was allowed to warm up to room temperature and stirred for 18 hours. The reaction was diluted with water (50 mL) and extracted with DCM (100 mL). The organic layer was dried over anhydrous Na$_2$SO$_4$, filtered and concentrated under reduced pressure. The residue was purified by column chromatography to obtain compound L-4-2 (410 mg, 65%).

$^1$H NMR (400 Hz, CDCl$_3$) δ 4.21 (s, 2H), 3.82 (t, J=6.4 Hz, 2H), 3.74-3.64 (m, 12H), 3.45 (t, J=6.4 Hz, 2H), 2.45-2.42 (m, 1H).

Preparation of Compound L-4

To a solution of compound L-4-2 (300 mg, 1.02 mmol) in DMF (10 mL) was added N, N-dimethylethylenediamine (555 µL, 5.08 mmol) at room temperature under N$_2$ atmosphere. The mixture was stirred at room temperature for 5 hours. After the reaction was completed, the mixture was concentrated under reduced pressure. The residue was purified by column chromatography to obtain compound L-4 (218 mg, 71%).

ESI-MS m/z: 303 (M$^{+1}$).

Example 1.7

Preparation of L-5

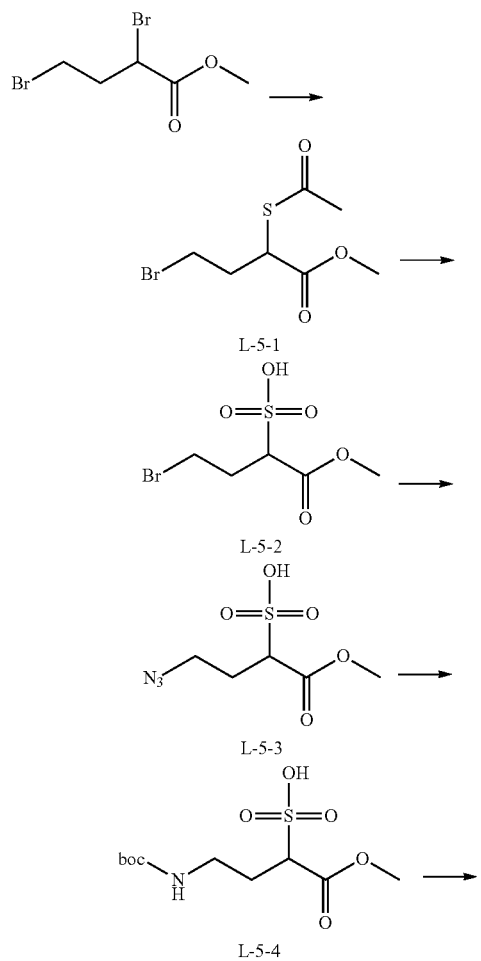

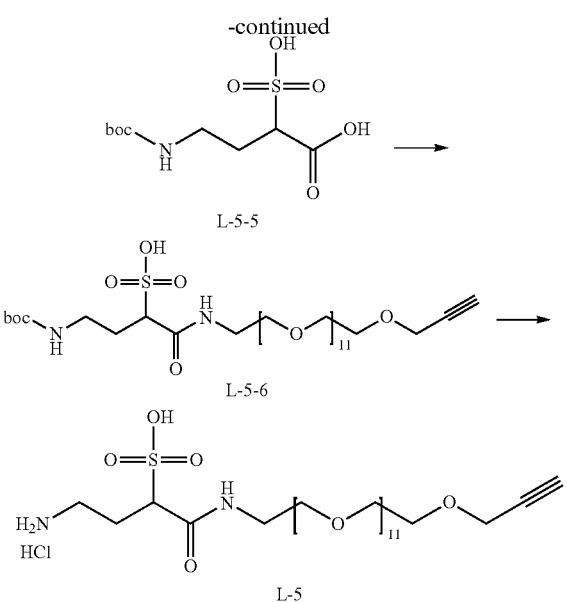

Preparation of Compound L-5-1

A homogeneous solution of methyl 2,4-dibromobutyrate (10 g, 38.47 mmol) in dry THF (100 mL) at room temperature under N$_2$ atmosphere was added dropwise the mixture of thioacetic acid (2.75 mL, 38.47 mmol, 1.0 eq.) and DIPEA (8.5 mL, 48.9 mmol, 1.3 eq.) in dry THF (50 mL) for 1.5 hour. After stirring for 4 hours at −20° C. under N$_2$ atmosphere, the mixture was concentrated, diluted with water (100 mL) and extract with EA (200 mL×3). The organic layer was dried over anhydrous Na$_2$SO$_4$, filtered, and concentrated under reduced pressure. The residue was purified by column chromatography (Hex:EA=12:1) to obtain compound L-5-1 (9.67 g, 98%) as white solid.

$^1$H NMR (600 MHz, CDCl$_3$) δ 4.38 (t, J=7.6 Hz, 1H), 3.46-3.39 (m, 2H), 2.56-2.47 (m, 1H), 2.36 (s, 3H), 2.32-2.23 (m, 1H).

Preparation of Compound L-5-2

L-5-1 (9.67 g, 37.90 mmol) in AcOH (80 mL) at room temperature under N$_2$ atmosphere was added 35% hydrogen peroxide (40 mL). The mixture was stirred overnight, then concentrated, diluted with water (20 mL), neutralized with NaHCO$_3$ and washed with EA/Hex (1/1, 30 mL×2). The aqueous layer was concentrated under reduced pressure. The residue was purified by column chromatography (DCM:MeOH:AcOH=8:1:0.01 to 5:1:0.01) to obtain compound L-5-2 (7.0 g, 71%) as white solid.

$^1$H NMR (600 MHz, D$_2$O) δ 4.11 (dd, J=5.4, 4.8 Hz, 1H), 3.82 (s, 3H), 3.65-3.62 (m, 1H), 3.52-3.47(m, 1H), 2.62-2.48 (m, 2H).

Preparation of Compound L-5-3

To a solution of L-5-2 (7.0 g, 26.81 mmol) in DMF (20 mL) was added NaN$_3$ (4.5 g, 69.71 mmol, 2.6 eq) under N$_2$ atmosphere, and the mixture was stirred overnight at room temperature. After the reaction was completed, the mixture was concentrated under reduced pressure. The residue was purified by column chromatography (DCM:MeOH:AcOH=7:1:0.01 to 5:1:0.01) to obtain compound L-5-3 (5.4 g, 90%) as white solid.

$^1$H NMR (600 MHz, D$_2$O) δ 3.82 (dd, J=4.2, 6.0 Hz, 1H), 3.63 (s, 3H), 3.36-3.26 (m, 2H), 2.29-2.02 (m, 2H).

Preparation of Compound L-5-4

In a 50 mL round-bottled flask was added L-5-3 (500 mg, 2.24 mmol), 10 mL of MeOH, 5% Pd/C (715 mg, 0.34 mmol, 0.15 eq.) and Boc₂O (538 mg, 2.46 mmol, 1.1 eq). After sucked out air, the mixture was stirred at room temperature under H₂ for 15 hours. The catalyst was filtered through Celite®, and the Celite® was washed with MeOH (20 mL×2). The solvent was removed by rotary evaporator and the residue was purified by column chromatography (DCM:MeOH:AcOH=7:1:0.01 to 5:1:0.01) to obtain compound L-5-4 (450.2 mg, 68%) as white solid.

¹H NMR (600 MHz, DMSO-d6) δ 6.79 (s, 1H), 4.13 (brs, 1H), 3.55 (s, 3H), 2.88-2.80 (m, 2H), 1.96-1.88 (m, 2H), 1.36(s, 9H).

Preparation of Compound L-5-5

A homogeneous solution of L-5-4 (100 mg, 0.34 mmol) in THF/water (4 mL/8 mL) at room temperature under N₂ was treated with LiOH (21.2 mg, 0.50 mmol, 1.5 eq.) and stirred for 8 hours. The reaction mixture was neutralized with 2N HCl solution and concentrated under reduced pressure. The compound L-5-5 was used directly in the next step without further purification.

ESI-MS m/z: 284 (M⁺+1).

Preparation of Compound L-5-6

A homogeneous solution of L-5-5 (0.34 mmol), N-hydroxysuccinimide (77.4 mg, 0.67 mmol, 2.0 eq.) and EDCI-HCl (260.7 mg, 1.36 mmol, 4.0 eq.) in DMF (2 mL) at room temperature under N₂ atmosphere was stirred overnight. The mixture was treated with L-3 (210.8 mg, 0.34 mmol, 1.0 eq.), DIPEA (177.6 uL, 1.02 mmol, 3.0 eq.) and stirred overnight. The reaction was concentrated under reduced pressure. The residue was purified by column chromatography (DCM:MeOH:AcOH=12:1:0.01 to 5:1:0.01) to obtain compound L-5-6 (159.1 mg, 55%) as yellow oil.

ESI-MS m/z: 850 (M⁺+1).

Preparation of Compound L-5

A homogeneous solution of L-5-6 (100 mg 0.12 mmol) in 1,4-dioxane (2 mL) at room temperature under N₂ atmosphere was treated with c-HCl (500 uL) and stirred for 30 minutes. The reaction mixture was concentrated under reduced pressure to obtain compound L-5 (92 mg, 99%) as yellow oil.

ESI-MS m/z: 749 (M⁺+1).

Example 1.8

Preparation of L-6

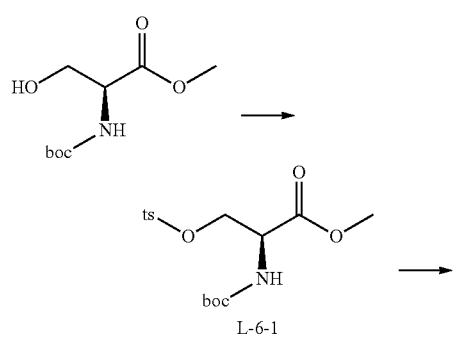

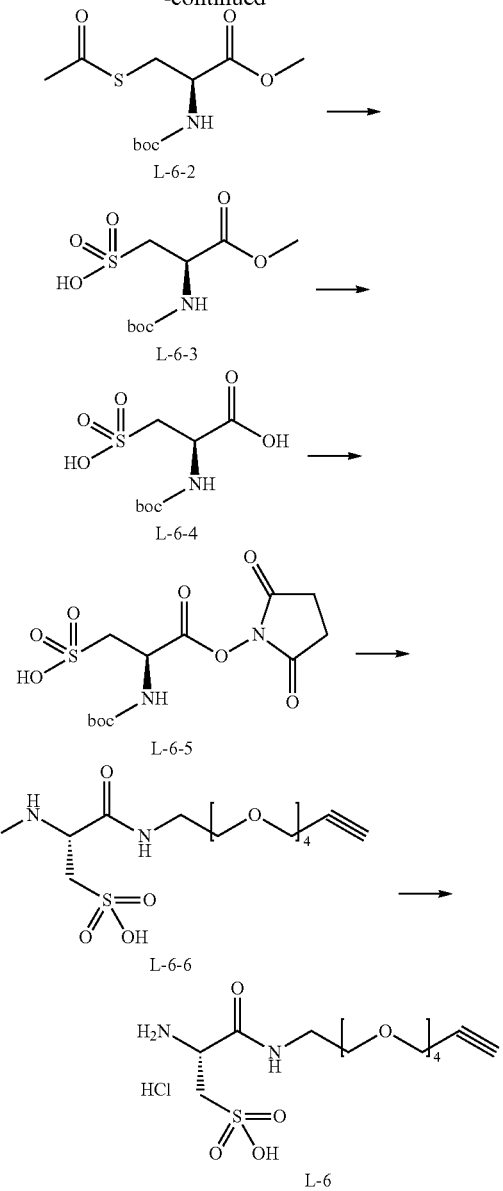

Preparation of Compound L-6-1

A homogeneous solution of Boc-L-serine methyl ester (5.0 g, 22.8 mmol) in DCM (30 mL) at room temperature under N₂ atmosphere was treated with pyridine (8 mL), P-toluene sulfonyl chloride (5.22 g, 27.4 mmol, 1.2 eq.) and stirred overnight. The reaction was quenched by addition of water (50 mL) and extract with EA (100 mL×3). The combined organic layer was dried over anhydrous Na₂SO₄, filtered, and concentrated under reduced pressure. The residue was purified by column chromatography (Hex:EA=9:1 to 2:1) to obtain compound L-6-1 (7.0 g, 82%) as white solid.

¹H NMR (600 MHz, CDCl₃) δ 7.76 (d, J=8.4 Hz, 2H), 7.35 (d, J=7.8 Hz, 2H), 5.29 (S, 1H), 4.53-4.47 (m, 1H), 4.39 (dd, J=2.4, 7.8 Hz, 1H), 4.29 (d, J=7.2, 2.4 Hz, 1H), 3.69 (s, 3H), 2.45 (s, 3H).

Preparation of Compound L-6-2

A suspension of CsCO₃ (1.05 g, 3.21 mmol, 0.6 eq.) in DMF (12 mL) at room temperature under N₂ atmosphere was treated with thioacetic acid (498 uL, 6.96 mmol, 1.3 eq.) and L-6-1 (2.0 g, 5.36 mmol) in DMF (8 mL) and stirred overnight. The mixture was quenched by addition of water (50 mL) and extracted of with EA (100 mL×3). The organic layer was dried over anhydrous $Na_2SO_4$, filtered, and concentrated under reduced pressure. The residue was purified by column chromatography (Hex:EA=5:1) to obtain compound L-6-2 (1.4 g, 95%) as white solid.

$^1$H NMR (600 MHz, $CDCl_3$) δ 5.24 (s, 1H), 4.53-4.49 (m, 1H), 3.75 (s, 3H), 2.45 (s, 3H), 4.41-4.31 (m, 2H).

Preparation of Compound L-6-3

L-6-2 (1.2 g, 4.33 mmol) in AcOH (10 mL) at room temperature under $N_2$ atmosphere was added 35% hydrogen peroxide (4 mL). The mixture was stirred for 7 hours, then concentrated under reduced pressure. The residue was diluted with water (5 mL) and basified using saturated aqueous solution of $NaHCO_3$ at 0° C. to a pH of 9. $Boc_2O$ (1.4 g, 6.49 mmol, 1.5 eq.) was added and the resultant mixture was stirred overnight. The mixture was neutralized with 2N HCl at 0° C. and concentrated under reduced pressure. The residue was purified by column chromatography (DCM:MeOH:AcOH=8:1:0.01 to 5:1:0.01) to obtain compound L-6-3 (521.5 mg, 42%) as white solid.

$^1$H NMR (400 MHz, DMSO-d6) δ 6.96 (d, J=7.2 Hz, 1H), 4.20 (q, J=6.8, 4.8 Hz, 1H), 3.58 (s, 3H), 2.84 (dd, J=14, 6.4 Hz, 1H), 2.76 (dd, J=9.2, 4.4 Hz, 1H), 1.37 (s, 9H).

Preparation of Compound L-6-4

A homogeneous solution of L-6-3 (71 mg, 0.25 mmol) in THF/$H_2O$ (2.0 mL/4.0 mL) at room temperature under $N_2$ atmosphere was treated with LiOH (17.3 mg, 0.41, 1.5 eq.) and stirred for 3 hours. The mixture was neutralized with 2N HCl at 0° C. and concentrated under reduced pressure to obtain compound L-6-4 (67 mg, 99%) as white solid.

$^1$H NMR (400 MHz, DMSO-d6) δ 6.40 (d, J=7.2 Hz, 1H), 3.96 (q, J=6.4, 5.6 Hz, 1H), 2.88-2.78 (n, 2H), 1.36 (s, 9H).

Preparation of Compound L-6-5

L-6-4 (35 mg, 0.13 mmol), N-hydroxysuccinimide (22.4 mg, 0.19 mmol, 1.5 eq.) and EDCI-HCl (50 mg, 0.26 mmol, 2.0 eq.) were dissolved in DMF (2 mL) at room temperature under $N_2$ atmosphere. After the mixture was stirred overnight, the compound L-6-5 was used directly in the next step without further purification.

ESI-MS m/z: 367 ($M^+$+1).

Preparation of Compound L-6-6

To a stirred solution of L-6-5 (0.13 mmol) in DMF (2 mL) at room temperature under $N_2$ atmosphere was added L-2 (0.19 mmol, 1.5 eq.) and EDCI-HCl (50 mg, 0.26 mmol, 2.0 eq.). The mixture was stirred overnight at room temperature. After the resulting mixture was concentrated under reduced pressure, the residue was purified by column chromatography (DCM:MeOH:AcOH=12:1:0.01 to 5:1:0.01) to obtain compound L-6-6 (34.8 mg, 64%) as yellow oil.

ESI-MS m/z: 483 ($M^+$+1).

Preparation of Compound L-6 c-HCl (300 uL) was added to a stirred solution of L-6-6 (29.6 mg 0.061 mmol in 1,4-dioxane (1.2 mL) at room temperature under $N_2$ atmosphere and the mixture stirred for 30 minutes. The mixture was concentrated under reduced pressure to obtain compound L-6 (25.4 mg, 99%) as yellow oil.

ESI-MS m/z: 382 ($M^+$+1).

Example 1.9

Preparation of MPS-D1-10

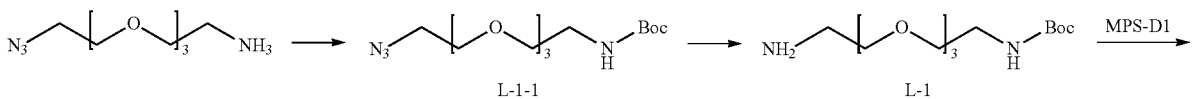

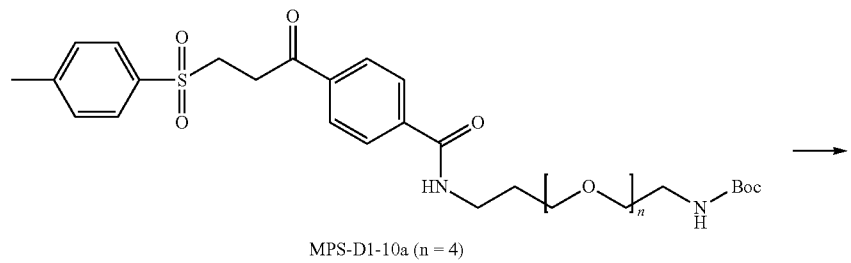

MPS-D1-10a (n = 4)

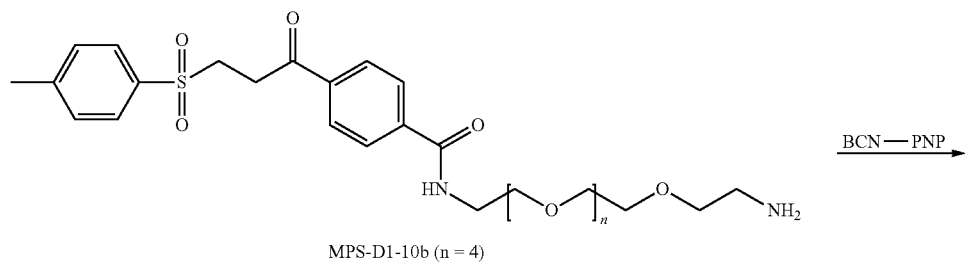

MPS-D1-10b (n = 4)

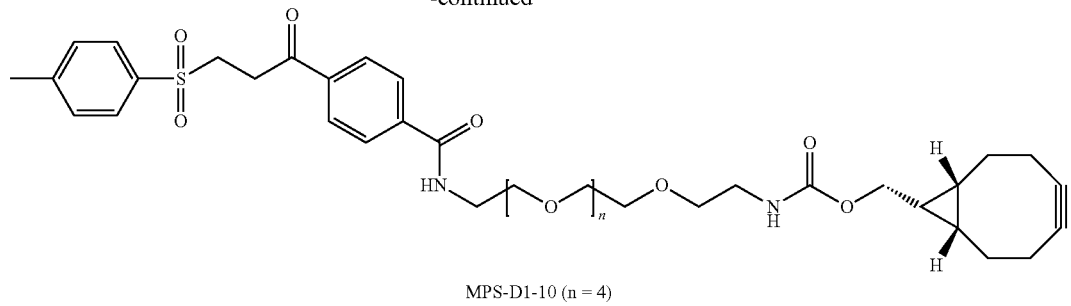

MPS-D1-10 (n = 4)

Preparation of Compound L-1-1

A clear solution of 11-azido-3,6,9-trioxaundecan-1-amine (Aldrich, CAS 134179-38-7, 5.0 g, 22.9 mmol) in 1,4-dioxane (100 mL) and H$_2$O (25 mL) at room temperature under N$_2$ atmosphere was treated with NaHCO$_3$ (3.8 g, 45.8 mmol, 2.0 eq.) and BOC$_2$O (6.0 g, 27.5 mmol, 1.2 eq.) and then stirred for 6 hours. The reaction was quenched with water (50 mL) and extracted with DCM (100 mL×3). The organic layer was dried over anhydrous Na$_2$SO$_4$, filtered, and concentrated under reduced pressure. The residue was purified by column chromatography (1% to 3% MeOH in DCM) to obtain compound L-1-1 (7.2 g, 99%) as a colorless oil.

$^1$H NMR (400 MHz, CDCl$_3$) δ 5.03 (brs, 1H), 3.72-3.60 (m, 10H), 3.98-3.52 (m, 1H), 3.43-3.36 (m, 1H), 3.35-3.24 (m, 1H), 1.26 (s, 9H).

ESI-MS m/z: 319 (M$^+$+1).

Preparation of Compound L-1

A clear solution of L-1-1 (7.2 g, 22.6 mmol) in THF (30 mL), Ether (15 mL) and H$_2$O (15 mL) at room temperature under N$_2$ atmosphere was treated with triphenylphosphine (6.5 g, 24.9 mmol, 1.1 eq.) and then stirred overnight. The reaction mixture was diluted with water (10 mL) and extract with DCM (60 mL×3). The water layer was concentrated under reduced pressure to obtain compound L-1-1 (6.3 g, 95%) as a colorless oil.

ESI-MS m/z: 293 (M$^+$+1)

Compound MPS-D1-10a was synthesized via a similar manner to the preparation method of the compound MPS-D1-1 of Example 2.

Preparation of Compound MPS-D1-10a

Yield 71%, light yellow oil $^1$H NMR (400 MHz, CDCl$_3$) δ 7.99-7.93 (m, 4H), 7.83 (d, J=8.0 Hz, 2H), 7.39 (d, J=8.0 Hz, 2H), 7.30 (brs, 1H), 5.01 (brs, 1H), 3.74-3.46 (m, 26H), 3.34-3.26 (m, 2H), 2.46 (s, 3H), 1.43 (s, 9H); ESI-MS m/z: 695 (M$^+$+1).

Compound MPS-D1-10b was synthesized via a similar manner to the preparation method of the compound L-6 in Example 1.8.

Preparation of Compound MPS-D1-10b

Yield 99%, light yellow oil.

$^1$H NMR (400 MHz, DMSO-D6) δ 8.74 (t, J=8.0 Hz, 1H), 7.98 (dd, J=12, 8.4 Hz, 2H), 7.82 (d, J=8.4 Hz, 2H), 7.46 (d, J=8.0 Hz, 2H), 3.68-3.36 (m, 24H), 3.01-2.94 (m, 2H), 2.22 (s, 3H); ESI-MS m/z: 595 (M$^+$+1).

Preparation of Compound MPS-D1-10

A homogeneous solution of MPS-D1-10b (63 mg, 0.10 mmol) and BCN-PNP (31.5 mg, 0.10 mmol, 1.0 eq.) in anhydrous DMF (2.0 mL) at room temperature under N$_2$ atmosphere was treated with DIPEA (52 uL, 0.3 mmol, 3 eq.) and HBTU (57 mg, 0.15 mmol, 1.5 eq.) and stirred for 2 hours. The reaction was quenched with H$_2$O (20 mL) and extracted with EA (30 mL×3). The combined organic layer was washed with brine (10 mL), dried over anhydrous Na$_2$SO$_4$, filtered and concentrated under reduced pressure. The residue was purified by preparative TLC to obtain compound MPS-D1-10 (57 mg, 74%). ESI-MS m/z: 771 (M$^+$+1).

Example 1.10

Preparation of L-11

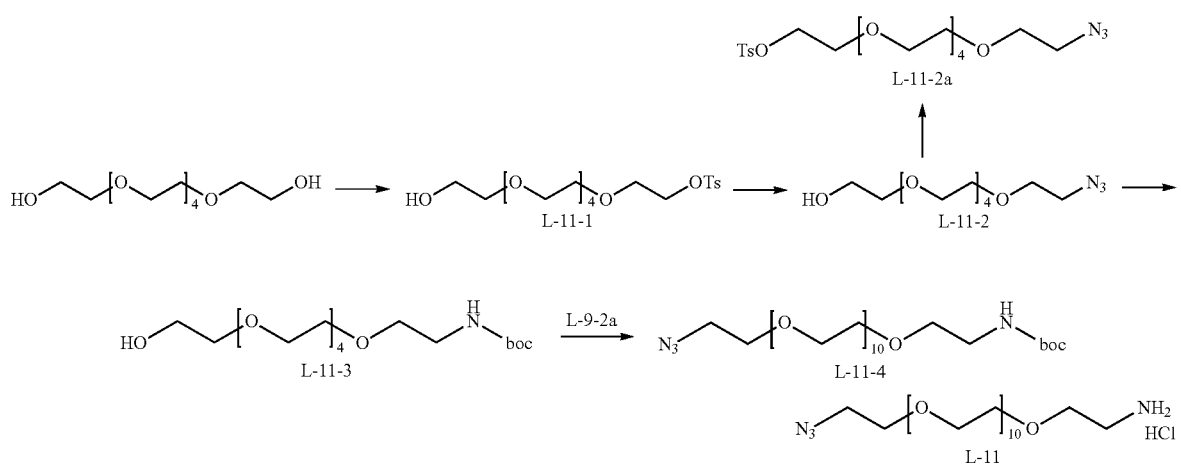

Preparation of Compound L-11-1

To a solution of hexaethylene glycol (5.0 g, 17.71 mmol) in anhydrous DCM (178 mL) was added KI (294 mg, 1.77 mmol), Ag$_2$O (4.92 g, 19.48 mmol), and p-TsCl (3.7 g, 19.48 mmol) under N$_2$ atmosphere. The mixture was stirred overnight at room temperature. After the reaction was completed, the mixture was filtered through Celite®, the Celite® plug was washed with DCM (100 mL). The filtrate was concentrated under reduced pressure. The residue was purified by column chromatography to obtain compound L-11-1 (5.98 g, 73%).

$^1$H NMR (400 Hz, CDCl$_3$) δ 7.80 (d, J=8.4 Hz, 2H), 7.35 (d, J=8.4 Hz, 2H), 4.16 (t, J=4.8 Hz, 2H), 3.71-3.58 (m, 22H), 2.88 (br, 1H), 2.45 (s, 3H).

Preparation of Compound L-11-2

To a solution of compound L-11-1 (5.98 g, 13.7 mmol) DMF (30 mL) was added NaN$_3$ (1.34 g, 20.55 mmol) under N$_2$ atmosphere. The mixture was stirred at 110° C. for 1 hour and concentrated under reduced pressure. The residue was purified by column chromatography to obtain compound L-11-2 (4.1 g, 97%).

$^1$H NMR (400 Hz, CDCl$_3$) δ 3.72-3.60 (m, 22H), 3.39 (t, J=4.8 Hz, 2H), 2.78 (br, 1H).

Preparation of Compound L-11-2a

Compound L-11-2 (1.9 g, 6.18 mmol) was dissolved in DCM (20 mL) under N$_2$ atmosphere, and triethyamine (2.0 mL, 14.22 mmol) and p-TsCl (2.4 g, 12.36 mmol) were added thereto, and the mixture was stirred overnight at room temperature. After the reaction was completed, the mixture was concentrated under reduced pressure. The residue was purified by column chromatography to obtain compound L-11-2a (2.58 g, 91%).

$^1$H NMR (400 Hz, CDCl$_3$) δ 7.80 (d, J=8.4 Hz, 2H), 7.35 (d, J=8.4 Hz, 2H), 4.16 (t, J=4.8 Hz, 2H), 3.70-3.61 (m, 16H), 3.56 (s, 1H), 3.39 (t, J=4.8 Hz, 2H), 2.45 (s, 3H).

ESI-MS m/z: 462 (M$^+$+1).

Preparation of Compound L-11-3

To a solution of compound L-11-2 (1.0 g, 3.25 mmol) in EtOH (5 mL) was added 5% Pd/C (1.04 g, 0.49 mmol) under H$_2$ atmosphere. The mixture was stirred at room temperature for 4 hours. The mixture was filtered through Celite® to remove Pd/C, and concentrated under reduced pressure. The residue was dissolved in DCM (25 mL). BOC$_2$O (852.1 mg, 3.9 mmol) was added and the resultant mixture was stirred at room temperature for 3 hours. The mixture was concentrated under reduced pressure. The residue was purified by column chromatography to produce compound L-11-3 (330 mg, 28%).

$^1$H NMR (400 Hz, CDCl$_3$) δ 5.19 (brs, 1H), 3.73 (t, J=4.8 Hz, 2H), 3.67 (s, 12H), 3.63-3.60 (m, 6H), 3.54 (t, J=5.2 Hz, 2H), 3.34-3.27 (m, 1H), 1.44 (s, 9H).

ESI-MS m/z: 382 (M$^+$+1).

Preparation of Compound L-11-4

A homogeneous solution of compound L-11-3 (450 mg, 1.18 mmol) in anhydrous THF (10 mL) under N$_2$ atmosphere at 0° C. was treated with NaH (60% dispersion in mineral oil, 47.2 mg, 1.18 mmol) After the mixture was stirred at 0° C. for 20 minutes, L-11-2a (544.5 mg, 1.18 mmol) was added thereto. The reaction was allowed to warm up to room temperature and stirred overnight. The reaction was allowed to cool, quenched with MeOH (5 mL) and concentrated under reduced pressure. The residue was purified by column chromatography to obtain compound L-11-4 (582.9 mg, 74%).

Preparation of Compound L-11

To a solution of compound L-11-4 (582.9 mg, 0.87 mmol) in DCM (3 mL) was added 4M-HCl (in 1,4-dioxane, 1 mL) at 0° C. under N$_2$ atmosphere. The mixture was stirred at room temperature for 2 hour. The mixture was concentrated to obtain compound L-11 (527.6 mg, quant).

ESI-MS m/z: 571 (M$^+$+1).

Table 2 below lists the compounds that were synthesized via a similar synthetic route as described in Example 2.

TABLE 2

R$_{101}$ in compound

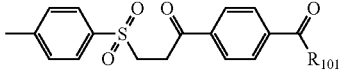

| | | Characterization Data |
|---|---|---|
| MPS-D1-2 | 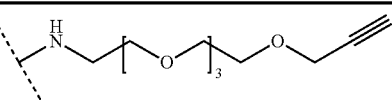 | Yield 80%; $^1$H NMR (400 Hz, CDCl$_3$) δ 8.11-7.94 (m, 4H), 7.83 (d, J = 7.6 Hz, 2H), 7.44 (brs, 1H), 7.38 (d, J = 8.0 Hz, 2H), 4.15 (s, 2H), 3.69-3.65 (m, 14H), 3.58-3.48 (m, 4H), 2.80 (s, 1H), 2.46 (s, 3H). ESI-MS m/z: 546 (M$^+$ + 1). |
| MPS-D1-3 | 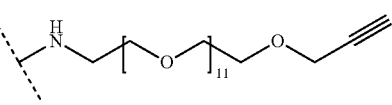 | Yield 72% ESI-MS m/z: 899 (M$^+$) |
| MPS-D1-4 | 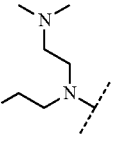 MPS-D1-4 | Yield 48% ESI-MS m/z: 617 (M$^+$) |
| MPS-D1-5 | 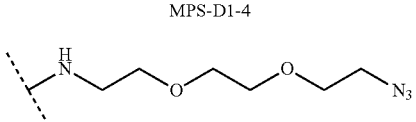 | Yield 53%, light yellow solid $^1$H NMR (400 MHz, CDCl$_3$) δ 7.98 (d, J = 8.4 Hz, 2H), 7.88 (d, J = 8.4 Hz, 2H), 7.83 (d, J = 8.0 Hz, 2H), 7.38 (d, J = 8.0 Hz, 2H), 6.75 (brs, 1H), 3.74-3.66 (m, 10H), 3.58-3.48 (m, |

TABLE 2-continued

| | | |
|---|---|---|
| | | 4H), 3.37 (t, J = 5.2 Hz, 2H), 2.46 (s, 3H); ESI-MS m/z: 489 (M⁺ + 1). |
| MPS-D1-6 | ⋰N(H)-CH₂CH₂-O-(CH₂CH₂O)₂-CH₂CH₂-N₃ | Yield 52%, yellow solid<br>¹H NMR (400 MHz, CDCl₃) δ 7.98 (d, J = 8.4 Hz, 2H), 7.90 (d, J = 8.4 Hz, 2H), 7.83 (d, J = 8.0 Hz, 2H), 7.38 (d, J = 8.0 Hz, 2H), 6.93 (brs, 1H), 3.74-3.62 (m, 14H), 3.58-3.47 (m, 4H), 3.34 (t, J = 5.2 Hz, 2H), 2.46 (s, 3H); ESI-MS m/z: 533 (M⁺ + 1). |
| MPS-D1-7 | ⋰N(H)-CH₂CH₂-O-(CH₂CH₂O)₄-CH₂CH₂-N₃ | Yield 84%, light yellow oil<br>ESI-MS m/z: 621 (M⁺ + 1). |
| MPS-D1-8 | ⋰N(H)-CH₂CH₂-O-(CH₂CH₂O)₇-CH₂CH₂-N₃ | Yield 53%, yellow oil<br>ESI-MS m/z: 753 (M⁺ + 1). |
| MPS-D1-9 | ⋰N(H)-CH₂CH₂-O-(CH₂CH₂O)₂-NHC(O)O-BCN | Yield 82%, light yellow oil.<br>ESI-MS m/z: 639 (M⁺ + 1). |
| MPS-D1-11 | ⋰N(H)-CH₂CH₂-O-(CH₂CH₂O)₁₀-CH₂CH₂-N₃ | Yield 67%.<br>ESI-MS m/z: 886 (M⁺ + 1). |
| MPS-D1-12 | ⋰N(H)-CH₂CH₂-O-(CH₂CH₂O)₅-NHC(O)O-BCN | Yield 74%,<br>ESI-MS m/z: 771 (M⁺ + 1). |

R₁₀₂ in compound

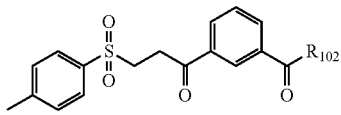

| | | Characterization Data |
|---|---|---|
| MPS-D2-1 | ⋰N(H)-CH₂CH₂-(O-CH₂CH₂)₁₁-O-CH₂-C≡CH | Yield 36%, white solid.<br>ESI-MS m/z: 898 (M⁺) |
| MPS-D2-2 | ⋰N(H)-CH₂CH₂-(O-CH₂CH₂)₃-O-CH₂-C≡CH | Yield 60%, white solid.<br>ESI-MS m/z: 546 (M⁺ + 1). |
| MPS-D2-3 | ⋰N(H)-CH(CH₂SO₃H)-C(O)NH-CH₂CH₂-(O-CH₂CH₂)₄-C≡CH | Yield 20% as yellow oil;<br>ESI-MS m/z: 1064 (M⁺) |
| MPS-D2-4 | ⋰N(H)-CH₂CH₂-(O-CH₂CH₂)₅-NHC(O)O-BCN | Yield 383%;<br>ESI-MS m/z: 771 (M⁺) |

TABLE 2-continued

R₁₀₃ in compound

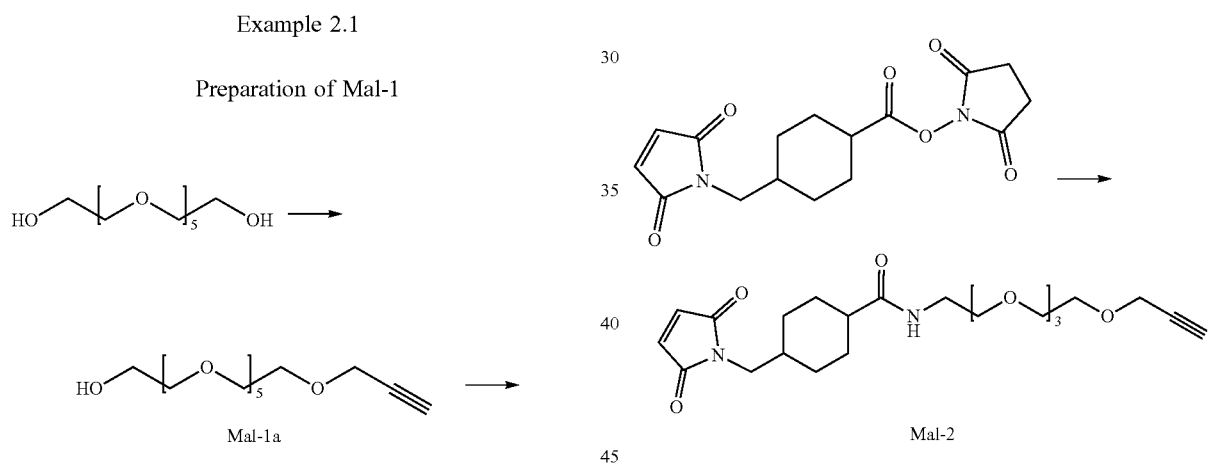

| | R₁₀₃ | Characterization Data |
|---|---|---|
| MPS-D3-1 | –NH-CH₂CH₂-(O-CH₂CH₂)₄-O-CH₂CH₂-N₃ | Yield 13%, yellowish oil. ESI-MS m/z: 622 (M⁺ + 1). |
| MPS-D3-2 | –NH-CH₂CH₂-(O-CH₂CH₂)₃-O-CH₂-C≡CH | Yield 22%. ESI-MS m/z: 547 (M⁺). |
| MPS-D3-3 | –NH-CH₂CH₂-(O-CH₂CH₂)₁₁-O-CH₂-C≡CH | Yield 26%. ESI-MS m/z: 900 (M⁺). |

Example 2

Synthesis of Maleimide- and POS-Derivatives

Example 2.1

Preparation of Mal-1

HO-CH₂CH₂-(O-CH₂CH₂)₅-OH →

HO-CH₂CH₂-(O-CH₂CH₂)₅-O-CH₂-C≡CH

Mal-1a

↓

Mal-1 (maleimide-PEG-alkyne structure)

Compound L-4 was synthesized by a similar synthetic route as described in Journal of Medicinal Chemistry, 52(19), 5816-5825; 2009, incorporated herein by reference.

Preparation of Compound Mal-1a

Yield 55%

¹H NMR (400 Hz, CDCl₃) δ 4.21 (d, J=2.0 Hz, 2H), 3.72-3.60 (m, 24H), 2.79 (brs, 1H), 2.43 (t, J=2.4 Hz, 1H).

Preparation of Compound Mal-1

ESI-MS m/z: 400 (M⁺)

Example 2.2

Preparation of Mal-2

(N-succinimidyl 4-(N-maleimidomethyl)cyclohexane-carboxylate structure)

↓

Mal-2 (maleimide-cyclohexane-amide-PEG-alkyne structure)

A homogeneous solution of N-succinimidyl 4-(N-maleimidomethyl)cyclohexane-carboxylate (85.5 mg, 0.26 mmol) and L-2 (75.3 mg, 0.28 mmol) in dry DCM at room temperature under N₂ atmosphere was treated with DIPEA (44.5 uL, 0.26 mmol, 1 eq) and stirred to room temperature for 45 minutes. The reaction was diluted with DCM (32 mL) and washed with 1N HCl (30 mL), brine (30 mL), dried over anhydrous Na₂SO₄, filtered and concentrated in vacuo. The residue was purified by prep-HPLC to give the titled compound L-5 (70.8 mg, 61%, mixture 9 mg) as a white gum.

ESI-MS m/z: 451 (M⁺¹)

Example 2.3

Preparation of Mal-3

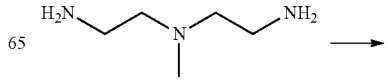

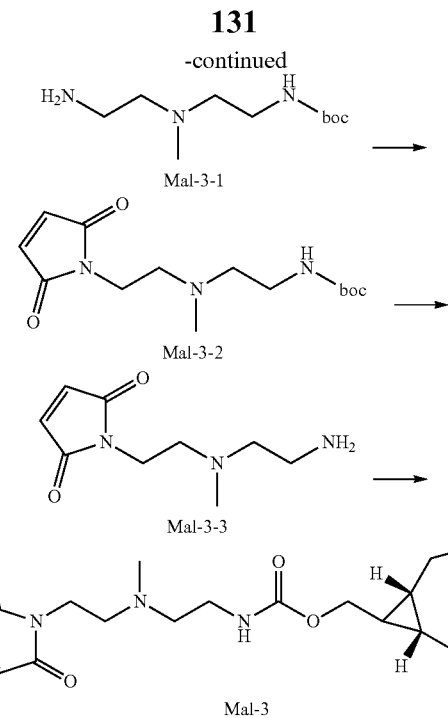

Mal-3-1

Mal-3-2

Mal-3-3

Mal-3

Preparation of Compound Mal-3-1

To a solution of BOC$_2$O (9.6 g, 44.0 mmol) in THF (50 mL) at 0° C. was added 2,2'-Diamino-N-methyldiethylamine (10.3 g, 88.0 mmol) under N$_2$ atmosphere. The mixture was stirred for 2 hours at room temperature. The mixture was quenched with H$_2$O (100 mL) and DCM (150 mL×2). The organic layer was dried over anhydrous Na$_2$SO$_4$, filtered and concentrated under reduced pressure. The residue was purified by column to obtain compound Mal-3-1 (3.3 g, 35%).

$^1$H NMR (400 Hz, CDCl$_3$) δ 5.04 (brs, 1H), 3.26-3.16 (m, 2H), 2.78 (t, J=6.0 Hz, 2H), 2.47 (t, J=6.0 Hz, 2H), 2.43 (t, J=6.0 Hz, 2H), 2.22 (s, 3H), 1.45 (s, 9H).

Preparation of Compound Mal-3-2

To a solution of Mal-3-1 (500 mg, 2.3 mmol) in AcOH (3.0 mL) at room temperature was added maleic anhydride (248 mg, 2.53 mmol) under N$_2$ atmosphere. The mixture was stirred for 3 hours at room temperature. The mixture was concentrated under reduced pressure, the residue was dissolved in Acetic anhydride (5.0 mL) at room temperature. NaOAc (95.7 mg, 1.17 mmol) was added in reaction mixture and stirred for 5 hours at 75° C. The mixture was concentrated under reduced pressure. The residue was purified by column to obtain compound Mal-3-2 (415 mg, 60%).

$^1$H NMR (400 Hz, CDCl$_3$) δ 6.70 (s, 2H), 3.63 (t, J=6.4 Hz, 2H), 3.18-3.10 (m, 2H), 2.57 (t, J=6.4 Hz, 2H), 2.48 (t, J=6.0 Hz, 2H), 2.24 (s, 3H), 1.44 (s, 9H).

ESI-MS m/z: 298 (M$^+$).

Preparation of Compound Mal-3-3

To a solution of compound Mal-3-2 (370 mg, 1.24 mmol) in DCM (4.0 mL) was added TFA (3.0 mL) at 0° C. The reaction was allowed to warm to room temperature and stirred for 2.5 hours. The mixture was concentrated under reduced pressure and used directly in the next step without further purification (387 mg, quant).

ESI-MS m/z: 198 (M$^+$).

Preparation of Compound Mal-3

To a solution of compound Mal-3-3 (50 mg, 0.16 mmol) and BCN-PNP (50.6 mg, 0.16 mmol) in DMF (3.0 mL) was added DIPEA (57 uL, 0.32 mmol) at room temperature under N$_2$ atmosphere. The mixture was stirred for 2.5 hours and EA (50 mL×2) and H$_2$O (30 mL) were added. The organic layer was dried over anhydrous Na$_2$SO$_4$, filtered and concentrated under reduced pressure. The residue was purified by column chromatography to obtain compound Mal-3 (13.2 mg, 22%).

$^1$H NMR (400 Hz, CDCl$_3$) δ 6.70 (s, 2H), 5.12 (brs, 1H), 4.14 (d, J=8.0 Hz, 2H), 3.63 (t, J=6.0 Hz, 2H), 3.24-3.18 (m, 2H), 2.58 (t, J=6.4 Hz, 2H), 2.50 (t, J=6.0 Hz, 2H), 2.30-2.20 (m, 9H), 1.28-1.22 (m, 3H), 0.98-0.94 (m, 1H).

ESI-MS m/z: 374 (M$^+$).

Example 2.4

Preparation of POS-1

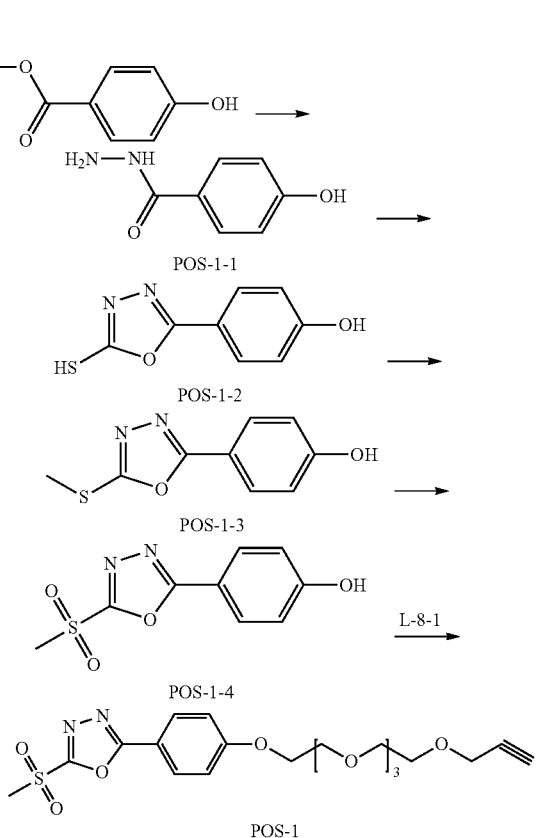

POS-1-1

POS-1-2

POS-1-3

POS-1-4

POS-1

Preparation of Compound POS-1-1

To a solution of ethyl 4-hydrobenzoate (20 g, 120.35 mmol) in EtOH (60 mL) was added NH$_2$NH$_2$.H$_2$O (88 mL, 1805.4 mmol) under N$_2$ atmosphere. The mixture was stirred overnight at reflux. The mixture was cooled to room temperature, and concentrated under reduced pressure, followed by EtOH trituration, thereby obtaining compound POS-1-1 (17.54 g, 9 6%).

$^1$H NMR (400 Hz, DMSO-d$_6$) δ 9.50 (s, 1H), 7.68 (d, J=8.4 Hz, 2H), 6.78 (d, J=8.8 Hz, 2H), 4.37 (s, 2H). ESI-MS m/z: 431 (M$^+$+1).

Preparation of Compound POS-1-2

To a solution of compound POS-1-1 (17.54 g, 115.28 mmol) in EtOH (200 mL) and DMF (100 mL) was added CS$_2$ (45 mL, 749.32 mmol) and KOH (6.5 g, 115.28 mmol)

under N₂ atmosphere. After stirring at 85° C. for 18 hours, the reaction mixture was adjusted to pH 4 by addition of 1M HCl solution and diluted with distilled water (500 mL) and EA (500 mL2). The organic layer was washed with H₂O (500 mL), and brine (500 mL), dried over anhydrous Na₂SO₄, filtered and concentrated under reduced pressure. The residue was subjected to ether/Hex trituration to obtain compound POS-1-2 (20.7 g, 93%).

¹H NMR (400 Hz, DMSO-d₆) δ 10.44 (s, 1H), 7.72 (d, J=8.4 Hz, 2H), 6.94 (d, J=8.0 Hz, 2H). ESI-MS m/z: 195 (M⁺+1).

Preparation of Compound POS-1-3

To a solution of compound POS-1-2 (5 g, 25.75 mmol) in THF (100 mL) was added dropwise Et₃N (4.3 mL, 30.9 mmol) and MeI (1.76 mL, 28.33 mmol) at 0° C. After stirring at 0° C. for 10 minutes, the mixture was allowed to warm up to room temperature stirred for 2 hours. The mixture was diluted with H₂O (150 mL) and extracted with EA (100 mL×2). The organic layer was dried over anhydrous Na₂SO₄, filtered and concentrated under reduced pressure. The residue was subjected to ether trituration to obtain compound POS-1-3 (5.15 g, 96%).

¹H NMR (400 Hz, DMSO-d₆) δ 7.80 (d, J=8.4 Hz, 2H), 6.94 (d, J=8.4 Hz, 2H), 2.74 (s, 3H). ESI-MS m/z: 209 (M⁺+1).

Preparation of Compound POS-1-4

To a solution of compound POS-1-3 (3.2 g, 15.37 mmol) in EtOH (150 mL) was added 70% m-CPBA (11.4 g, 46.11 mmol) at 0° C. under N₂ atmosphere. After stirring at room temperature for 5 hours, 70% m-CPBA (11.4 g, 46.11 mmol) was further added. Then the mixture was stirred overnight at room temperature and quenched with H₂O (500 mL), saturated NaHCO₃ (300 mL) and extracted with EA (500 mL×2). The organic layer was washed with brine (300 mL), dried over anhydrous Na₂SO₄, filtered and concentrated under reduced pressure. The residue was subjected to Hex/EA=1:1 (100 mL) trituration to obtain compound POS-1-4 (3.2 g, 89%).

¹H NMR (400 Hz, DMSO-d₆) δ 7.95 (d, J=8.8 Hz, 2H), 7.01 (d, J=8.8 Hz, 2H), 3.69 (4s, 3H). ESI-MS m/z: 241 (M⁺+1).

Preparation of Compound POS-1

To a solution of POS-1-4 (310 mg, 1.29 mmol) and L-8-1 (660 mg, 2.84 mmol) in THF (8 mL) and DMF (0.8 mL) was added PPh₃ (667 mg, 2.58 mmol). The mixture was cooled to 0° C. and DEAD (1.17 mL, 2.58 mmol) was added thereto, and the mixture was stirred at 0° C. for 3 hours. The mixture was diluted with water (15 mL) and extracted with EA (15 mL×2). The obtained organic layer was dried over anhydrous Na₂SO₄, filtered and concentrated under reduced pressure to obtain compound POS-1 (205 mg, 30%).

ESI-MS m/z: 455 (M⁺+1).

Example 2.5

Preparation of Int-3

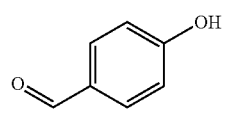

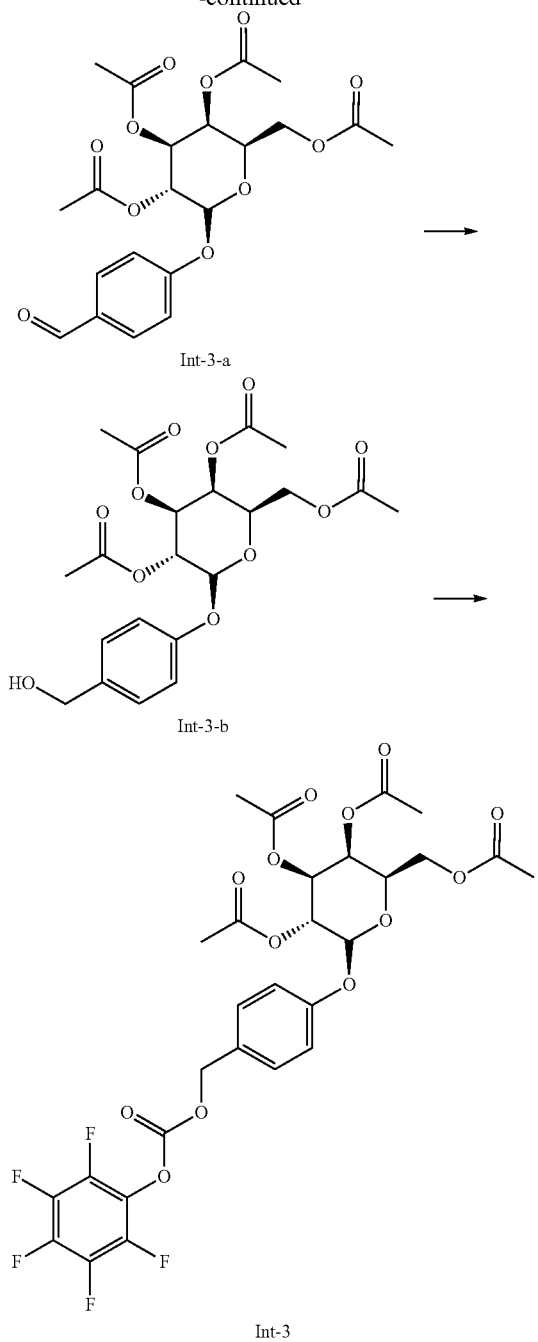

Preparation of Compound Int-3-a

To a solution of Int-TG (18.5 g, 45.0 mmol), 4-hydroxybenzaldyhyde (5.0 g, 40.9 mmol) molecular sieve (10.0 g) in ACN (150 mL) at room temperature under N₂ atmosphere was treated with Ag₂O (38.0 g, 0.164 mol) and stirred for 3 hours. The reaction mixture was filtered through a pad of celite and the filtrate was concentrated under reduced pressure. The residue was purified by column chromatography to obtain compound Int-3-a (16.0 g, 86%)

¹H NMR (400 MHz, CDCl₃) δ 9.93 (s, 1H), 7.86 (d, J=6.8 Hz, 2H). 7.11 (d, J=6.8 Hz, 2H), 5.52-5.47 (m, 2H), 5.18-5.14 (m, 2H), 4.24-4.11 (m, 3H), 2.19 (s, 3H), 2.07(s, 6H), 2.02 (s, 3H).

Preparation of Compound Int-3-b

To a solution of Int-3-a (540 mg, 1.19 mmol) in anhydrous THF (15 mL) at 0° C. under $N_2$ atmosphere was treated with $NaBH_4$ (113 mg, 2.98 mmol) and stirred for 10 minutes at 0° C. After stirring for 4 hours at room temperature, the reaction was diluted with $H_2O$ and EA. The organic layer was dried over $Na_2SO_4$, filtered and concentrated under reduced pressure. The residue was purified by column chromatography (EA:HEX=1:1) to obtain compound Int-3-b (430 mg, 79%).

$^1$H NMR (400 MHz, $CDCl_3$) δ 7.30 (d, J=8.8 Hz, 2H), 6.99 (d, J=8.8 Hz, 2H). 5.51-5.54 (m, 2H), 5.11 (dd, J=10.8 Hz, 1H), 5.03 (d, J=8.0 Hz, 1H), 4.65 (d, J=5.6 2H) 4.25-4.04 (m, 3H), 2.19 (s, 3H), 2.07 (s, 3H), 2.06 (s, 3H), 2.01 (s, 3H).

Preparation of Compound Int-3

To a solution of Int-3-b (1.0 g, 2.2 mmol) in dry. DMF (6.0 ml) at room temperature under $N_2$ atmosphere was treated with bis(pentafluorophenylcarbonate) (1.3 g, 3.3 mmol) and stirred for 3 hours. The reaction mixture was extracted with EA (20 mL×2), $H_2O$ (30 mL). The organic layer was dried over anhydrous $Na_2SO_4$, filtered, concentrated under reduced pressure. The reaction mixture was purified by column chromatography to obtain Int-3 (1.4 g, 98%). $^1$H NMR (400 MHz, $CDCl_3$): δ 7.384 (d, J=8.8 Hz, 2H), 7.039 (d, J=8.4 Hz, 2H), 5.529-5.465 (m, 2H), 5.280 (s, 2H), 5.141-5.068 (m, 2H), 4.262-4.070 (m, 4H), 2.195 (s, 3H), 2.078 (s, 3H), 2.073 (s, 3H), 2.025 (s, 3H).

Example 2.6

Preparation of Int-4

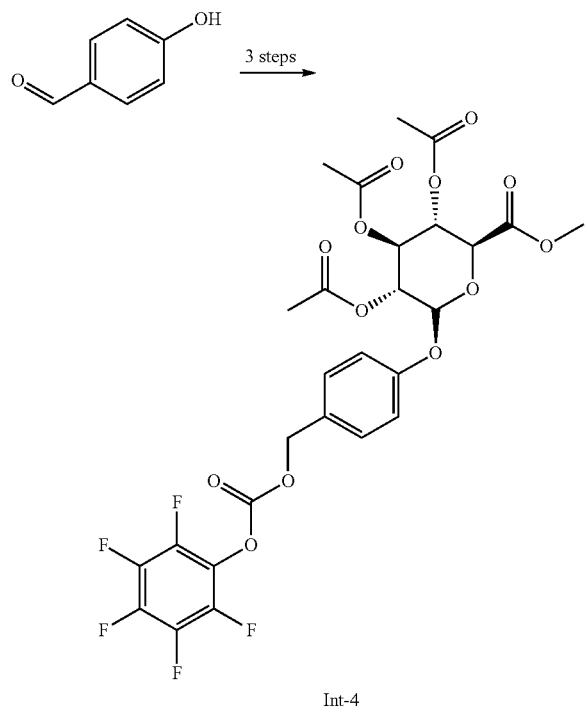

Int-4

Compound Int-4 was synthesized via a similar method as described in Example 2.5 Yield 72%.

$^1$H NMR (400 MHz, $CDCl_3$) δ 9.93 (s, 1H), 7.86 (d, J=6.8 Hz, 2H). 7.11 (d, J=6.8 Hz, 2H), 5.52-5.47 (m, 2H), 5.18-5.14 (m, 2H), 4.24-4.11 (m, 3H), 2.19 (s, 3H), 2.07(s, 6H), 2.02 (s, 3H).

Example 2.7

Preparation of Int-5

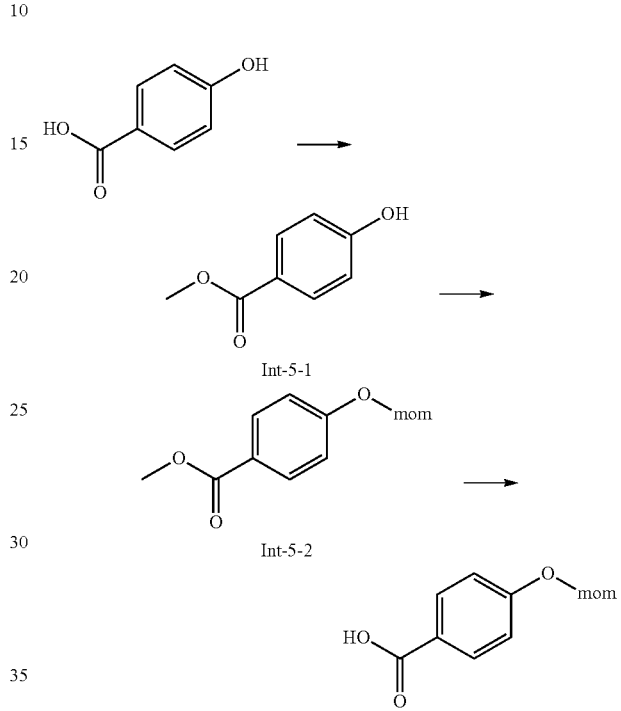

Int-5

Preparation of Compound Int-5-1

To a solution of 4-hydroxybenzoic acid (5.0 g, 36.2 mmol) in methanol (150 mL) was added thionyl chloride (26.3 mL, 362 mmol) at 0° C. under $N_2$ atmosphere. The reaction mixture was stirred at room temperature for 4 h. The reaction was quenched with aqueous $NaHCO_3$ and extracted with EtOAc. The organic layer was dried over anhydrous $Na_2SO_4$, filtered and concentrated under reduced pressure. The residue was purified by column chromatography to obtain compound Int-5-1 (4.87 g, 89%).

$^1$H NMR (400 Hz, $CDCl_3$) δ 7.87 (d, J=8.8 Hz, 2H), 6.82 (d, J=9.2 Hz, 2H), 3.85 (s, 3H) ESI-MS m/z: 153 ($M^+$+1).

Preparation of Compound Int-5-2

To a solution of compound Int-5-1 (1.0 g, 6.57 mmol) in DCM (22.0 mL) was added DIPEA (2.3 mL, 13.4 mmol) and MOM-Cl (0.55 mL, 7.23 mmol) at 0° C. under $N_2$ atmosphere. The reaction mixture was stirred at room temperature for 6 h. The reaction was quenched with water and extracted with EtOAc. The organic layer was dried over anhydrous $Na_2SO_4$, filtered and concentrated under reduced pressure. The residue was purified by column chromatography to obtain compound Int-5-2 (1.14 g, 88%).

$^1$H NMR (400 Hz, $CDCl_3$) δ 8.01-7.97 (m, 2H), 7.07-7.04 (m, 2H), 5.23 (s, 2H), 3.89 (s, 3H), 3.48 (s, 3H)

Preparation of Compound Int-5

To a solution of compound Int-5-2 (1.14 g, 5.81 mmol) in methanol/$H_2O$/1,4-dioxane (16.0 mL/8.0 mL/16.0 mL) was added lithium hydroxide monohydrate (975 mg, 23.2 mmol)

at 0° C. under N₂ atmosphere. The reaction mixture was stirred at room temperature for 5 h. The reaction was quenched with 2N HCl and extracted with EtOAc. The organic layer was dried over anhydrous Na$_2$SO$_4$, filtered and concentrated under reduced pressure. The compound Int-5 was used in the next step without further purification. (995 mg, 94%)

¹H NMR (400 Hz, MeOH-D$_4$) δ 7.96 (d, J=8.8 Hz, 2H), 7.08 (d, J=8.8 Hz, 2H), 5.25 (s, 2H), 3.55 (s, 3H)

Example 3

Synthesis of OHPAS-Linker Derivatives

Example 3.1

Preparation of Int-TG

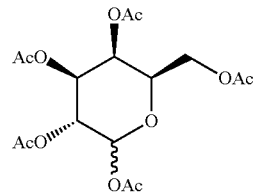

→

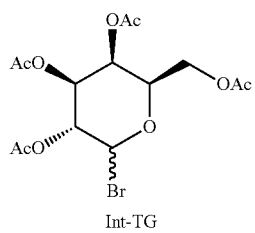

Int-TG

β-D-galactose pentaacetate (Alfa, CAS 4163-60-4, 5.0 g, 12.81 mmol) was dissolved in 33% HBr in AcOH (20 mL) at 0° C. under N₂ atmosphere. The mixture was warmed to room temperature. After stirring at room temperature for 4 hours, the mixture was concentrated under reduced pressure, and then EA (1000 mL) and saturated sodium bicarbonate (1000 mL) were added. The organic layer was dried over anhydrous Na$_2$SO$_4$, filtered, and concentrated under reduced pressure. The residue was purified by column chromatography to provide compound Int-TG (5.2 g, 99%).

Example 3.1.2

Preparation of Int-TG2

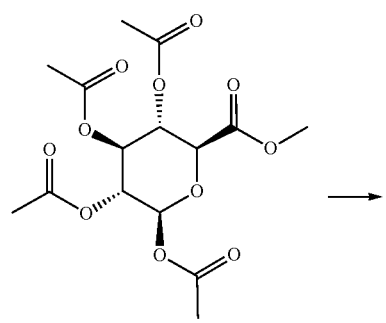

→

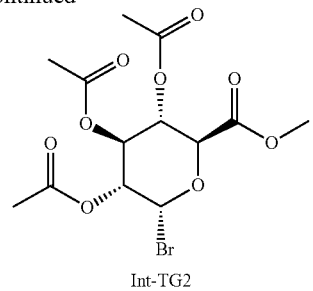

Int-TG2

Compound Int-TG2 was synthesized via a similar method as described in Example 3.1.1.

Yield 80%

¹H NMR (400 MHz, CDCl$_3$) δ 6.654 (d, J=4.0 Hz, 1H), 5.627 (t, J=10.0 Hz, 1H), 5.252 (dd, J=10.4 Hz, 9.6 Hz, 1H), 4.865 (dd, J=10.0 Hz, 4.0 Hz, 1H), 4.593 (d, J=10.4 Hz, 1H), 3.777 (s, 3H), 2.113 (s, 3H), 2.071 (s, 3H), 2.065 (s, 3H)

Example 3.1.3

Preparation of Int-TG3

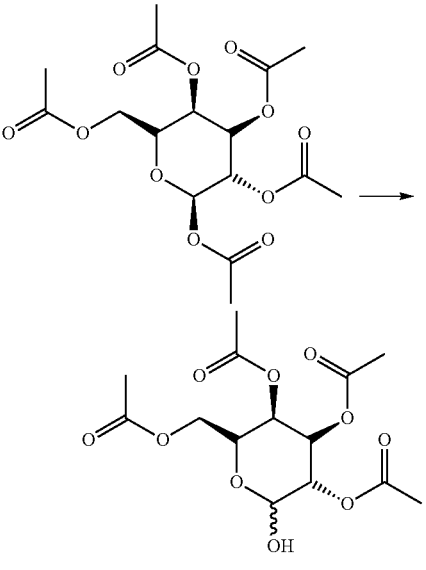

Int-TG3-1

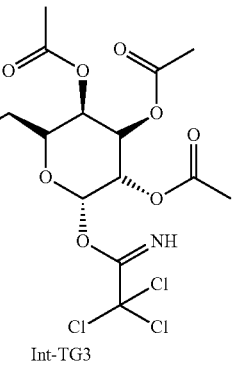

Int-TG3

Preparation of Compound Int-TG3-1

To a solution of beta-D-galactose pentaacetate (1 g, 2.56 mmol) in THF (10 mL) was added 3-(dimethylamino)1-propylamine (1.61 mL, 12.8 mmol) at room temperature under $N_2$ atmosphere. After stirring at same temperature for 3 hours, the reaction was extracted with EA (250 ml×3), $H_2O$ (200 ml). The organic layer was dried over anhydrous $Na_2SO_4$, filtered and concentrated under reduced pressure. Producing compound Int-TG3-1 (891 mg, 100%), which was used without further purification.

ESI-MS m/z: 371 ($M^+$+Na).

Preparation of Compound Int-TG3

To a solution of Int-TG3-1 (891 mg, 2.56 mmol) in DCM (10 mL) was added trichloroacetonitrile (2.57 mL, 25.6 mmol) and DBU (0.3 mL, 2.05 mmol) at 0° C. under $N_2$ atmosphere. After stirring at room temperature for 30 minutes, the reaction was extracted with DCM (250 ml×3), $H_2O$ (200 ml). The organic layer was dried over anhydrous $Na_2SO_4$, filtered and concentrated under reduced pressure. The residue was purified by column chromatography to obtain a compound Int-TG3 (880 mg, 70%).

$^1$H NMR (400 MHz, $CDCl_3$) δ 8.70 (s, 1H), 6.61 (d, J=3.6 Hz, 1H), 5.57 (dd, J=2.8, 0.8 Hz, 1H), 5.55-5.35 (m, 2H), 4.44 (t, J=7.6 Hz, 1H), 4.19-4.06 (m, 2H), 2.17 (s, 3H), 2.04 (s, 3H), 2.03 (s, 3H), 2.02 (s, 3H).

ESI-MS m/z: 515 ($M^+$+Na).

Example 3.1.3

Preparation of Int-TG4

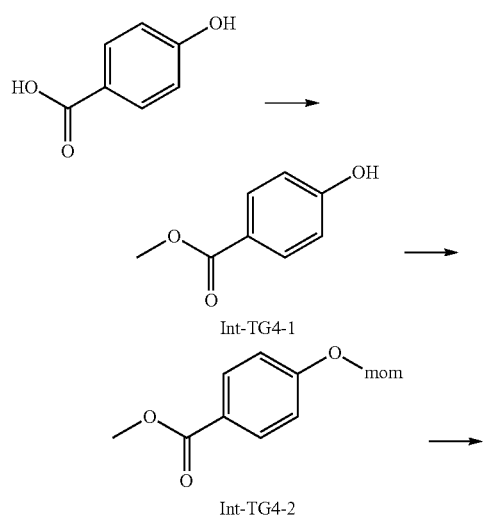

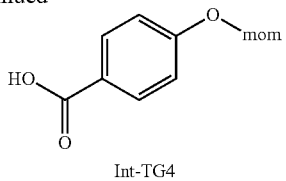

Int-TG4

Preparation of Compound Int-TG4-1

To a solution of 4-hydroxybenzoic acid (5.0 g, 36.2 mmol) in methanol (150 mL) was added thionyl chloride (26.3 mL, 362 mmol) at 0° C. under $N_2$ atmosphere. The reaction mixture was stirred at room temperature for 4 h. The reaction was quenched with aqueous $NaHCO_3$ and extracted with EtOAc. The organic layer was dried over anhydrous $Na_2SO_4$, filtered and concentrated under reduced pressure. The residue was purified by column chromatography to obtain compound Int-TG4-1 (4.87 g, 89%).

$^1$H NMR (400 Hz, $CDCl_3$) δ 7.87 (d, J=8.8 Hz, 2H), 6.82 (d, J=9.2 Hz, 2H), 3.85 (s, 3H)

EI-MS m/z: 153 ($M^+$+1).

Preparation of Compound Int-TG4-2

To a solution of compound Int-TG4-1 (1.0 g, 6.57 mmol) in DCM (22.0 mL) was added DIPEA (2.3 mL, 13.4 mmol) and MOM-Cl (0.55 mL, 7.23 mmol) at 0° C. under $N_2$ atmosphere. The reaction mixture was stirred at room temperature for 6 h. The reaction was quenched with water and extracted with EtOAc. The organic layer was dried over anhydrous $Na_2SO_4$, filtered and concentrated under reduced pressure. The residue was purified by column chromatography to obtain compound Int-TG4-2 (1.14 g, 88%).

$^1$H NMR (400 Hz, $CDCl_3$) δ 8.01-7.97 (m, 2H), 7.07-7.04 (m, 2H), 5.23 (s, 2H), 3.89 (s, 3H), 3.48 (s, 3H)

Preparation of Compound Int-TG4

To a solution of compound Int-TG4-2 (1.14 g, 5.81 mmol) in methanol/$H_2O$/1,4-dioxane (16.0 mL/8.0 mL/16.0 mL) was added lithium hydroxide monohydrate (975 mg, 23.2 mmol) at 0° C. under $N_2$ atmosphere. The reaction mixture was stirred at room temperature for 5 h. The reaction was quenched with 2N HCl and extracted with EtOAc. The organic layer was dried over anhydrous $Na_2SO_4$, filtered and concentrated under reduced pressure. The compound Int-TG4 was used in the next step without further purification. (995 mg, 94%)

$^1$H NMR (400 Hz, MeOH-$D_4$) δ 7.96 (d, J=8.8 Hz, 2H), 7.08 (d, J=8.8 Hz, 2H), 5.25 (s, 2H), 3.55 (s, 3H)

Example 3.2

Preparation of OHPAS-D1, OHPAS-D1a, and OHPAS-D2

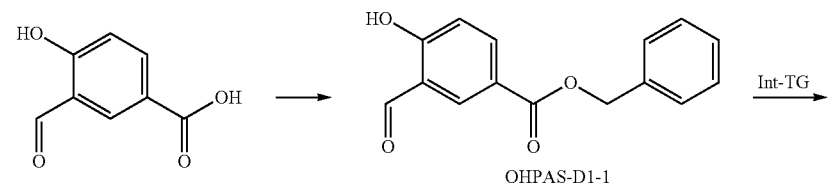

-continued

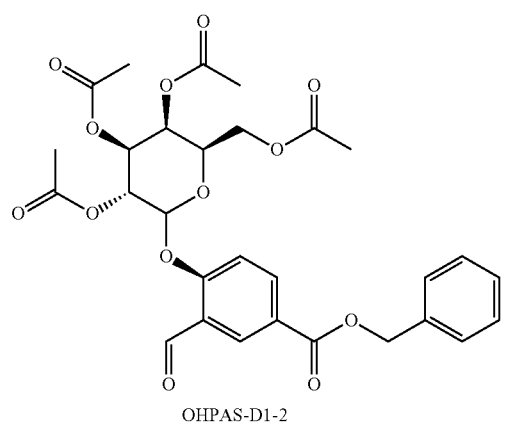
OHPAS-D1-2

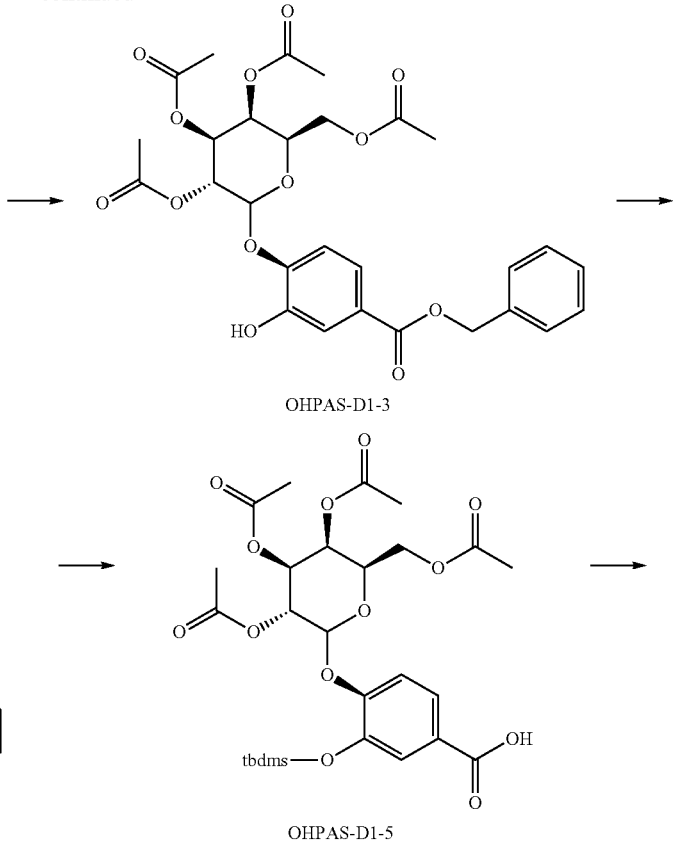
OHPAS-D1-3

OHPAS-D1-4

OHPAS-D1-5

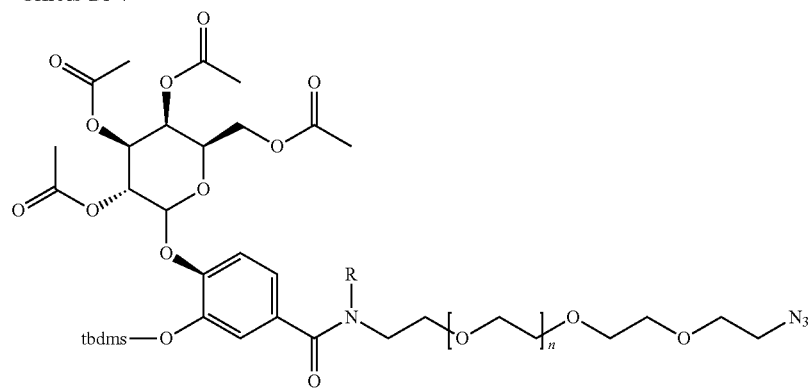

OHPAS-D1 (n = 1, R = H)
OHPAS-D1a (n = 1, R = Me)
OHPAS-D2 (n = 9, R = H)

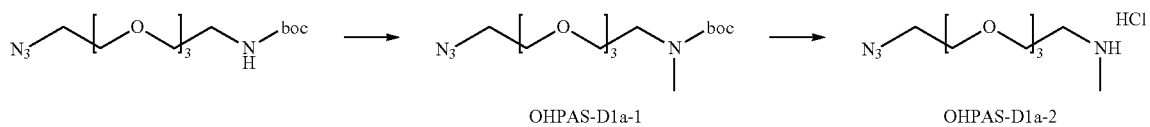

OHPAS-D1a-1

OHPAS-D1a-2

Preparation of Compound OHPAS-D 1 a-1

To a solution of L-1-1 (2 g, 6.282 mmol) in DMF (25 mL) was added sodium hydride (301 mg, 12.56 mmol, 60%) at 0° C. under $N_2$ atmosphere. After 10 minutes, iodomethane (3.9 mL, 62.82 mmol) was added at same temperature under $N_2$ atmosphere. The reaction was stirred at room temperature for 3 hours under $N_2$ atmosphere. After the reaction was completed, the reaction mixture was quenched 2N HCl (10 mL) and extracted with EA (500 mL×3). The organic layer was dried over $Na_2SO_4$, filtered and concentrated under reduced pressure. The compound OHPAS-D1a-1 (yellow oil) was used directly in the next step without further purification.

¹H NMR (400 MHz, CDCl₃) δ 3.70-3.62 (m, 12H), 3.4 (t, J=5.2 Hz, 4H), 2.91(s, 3H), 1.46 (s, 9H). ESI-MS m/z: 333 (M⁺1)

Preparation of Compound OHPAS-D1a-2

To a solution of compound OHPAS-D1a-1 (3.3 g, 6.282 mmol) in DCM (70 mL) was added 4N HCl in dioxane (25 ml) at 0° C. under N₂ atmosphere. The reaction was stirred at 0° C. for 1 hour under N₂ atmosphere. After the reaction was completed, the reaction mixture concentrated under reduced pressure. The compound OHPAS-D1a-2 was used directly in the next step without further purification.

¹H NMR (400 MHz, CDCl₃) δ 3.92 (t, J=4.8 Hz, 2H), 3.73-3.69 (m, 10H), 3.45 (t, J=5.2 Hz, 2H), 3.22-3.16 (m, 2H), 2.77 (t, J=5.6 Hz, 3H), 2.35 (brs, 1H). ESI-MS m/z: 233 (M⁺1)

Preparation of Compound OHPAS-D1-1

To a solution of the 3-formyl-4-hydroxybenzoic acid (5 g, 43.06 mmol) in DMF (100 mL) was added benzyl bromide (5.1 mL, 43.06 mmol) and NaHCO₃ (2.53 g, 43.06 mmol) at room temperature under N₂ atmosphere. The mixture was stirred overnight at room temperature under N₂ atmosphere. The reaction was extract with EA (200 mL×2) and distilled water (100 mL). The obtained organic layer was dried over anhydrous Na₂SO₄, filtered, and concentrated under reduced pressure. The residue was purified by column chromatography to obtain compound OHPAS-D1-1 (2.56 g, 39%).

¹H NMR (400 Hz, CDCl₃) δ 11.41 (s, 1H), 9.95 (s, 1H), 8.34 (d, J=2.0 Hz, 1H), 8.23 (dd, J=6.4 Hz, 2.4 Hz, 1H), 7.46-7.35 (m, 5H), 7.04 (d, J=9.2 Hz, 1H), 5.37 (s, 2H).

Preparation of Compound OHPAS-D1-2

To a solution of compound Int-TG-1 (1.0 g, 3.90 mmol) and compound Int-TG (1.6 g, 3.90 mmol) in anhydrous ACN (30 mL) was added molecular sieve (8 g) and Ag₂O (3.62 g, 15.61 mmol) at room temperature under N₂ atmosphere. The mixture was stirred at room temperature for 1 hours, then filtered by Celite®. The organic layer was dried over Na₂SO₄, filtered and concentrated under reduced pressure. The residue was purified by column chromatography to obtain compound OHPAS-D1-2 (2.1 g, 92%).

¹H NMR (400 Hz, CDCl₃) δ 10.34 (s, 1H), 8.55 (d, J=2.0 Hz, 1H), 8.26 (dd, J=6.8, 2.0 Hz, 1H), 7.45-7.35 (m, 5H), 7.17 (d, J=8.8 Hz, 1H), 5.63-5.60 (m, 1H), 5.50 (d, J=3.6 Hz, 1H), 5.37 (s, 2H), 5.23 (d, J=8.0 Hz, 1H), 5.16 (dd, J=7.2, 3.6 Hz, 1H) 4.24-4.10 (m, 4H), 2.20 (s, 3H), 2.10-2.03 (m, 9H).

Preparation of Compound OHPAS-D1-3

To a solution of compound OHPAS-D1-2 (2.1 g, 3.58 mmol) in DCM (30 mL) was added m-CPBA (2.65 g, 10.74 mmol) at 0° C. under N₂ atmosphere. After stirring for 7 hours at 0° C., the mixture was quenched by addition of saturated sodium bicarbonate (40 mL×2). The mixture was separated and the organic layers were washed with brine, dried over Na₂SO₄, filtered, and concentrated under reduced pressure. The residue was dissolved in DCM (5 mL) was added hydrazine-hydrate (261 µL, 5.37 mmol) at 0° C. under N₂ atmosphere. After stirring at 0° C. for 1 hours, EA (30 mL×2) and 1M HCl aqueous solution (10 mL) were added. The obtained organic layer was dried over anhydrous Na₂SO₄, filtered and concentrated under reduced pressure to obtain compound OHPAS-D1-3 (1.1 g, 55%).

ESI-MS m/z: 574 (M⁺+Na)

Preparation of Compound OHPAS-D1-4

To a solution of compound OHPAS-D1-3 (280 mg, 0.49 mmol) in DCM (5 mL) was added TBDMS-OTf (224 µL, 0.97 mmol) and Et₃N (207 µL, 1.46 mmol) at 0° C. under N₂ atmosphere. The mixture was stirred for 1.5 hours at room temperature, and then quenched by addition of citric acid (20 ml). The organic layer was washed with brine (20 mL), dried over Na₂SO₄, filtered, and concentrated under reduced pressure. The residue was purified by column chromatography to obtain compound OHPAS-D1-4 (246.3 mg, 68%).

¹H NMR (400 Hz, CDCl₃) δ 7.67 (d, J=8.4 Hz, 1H), 7.57 (s, 1H), 7.44-7.34 (m, 5H), 7.02 (d, J=8.4 Hz, 1H), 5.49-5.44 (m, 2H), 5.30 (s, 2H), 5.19 (d, J=7.6 Hz, 1H), 5.10 (dd, J=6.8, 3.2 Hz, 1H) 4.20-4.11 (m, 2H), 4.05 (t, J=6.8 Hz, 2H), 2.19 (s, 3H), 2.04(s, 3H), 2.01 (d, J=6.0 Hz, 6H), 1.02 (s, 9H), 0.20 (d, J=15.6 Hz, 6H).

Preparation of Compound OHPAS-D1-5

To a solution of compound OHPAS-D1-4 (283.2 mg, 0.41 mmol) in EA (5 mL) was added Pd/C (5%, 87.5 mg, 0.04 mmol) at room temperature under H₂. The mixture was stirred for 1 hours and filtered by Celite®, and then concentrated under reduced pressure. The compound OHPAS-D1-5 was used directly in the next step without further purification (246 mg, quant).

¹H NMR (400 Hz, CDCl₃) δ 7.67 (d, J=8.8 Hz, 1H), 7.57 (s, 1H), 7.05 (d, J=8.4 Hz, 1H), 5.49-5.45 (m, 2H), 5.22 (d, J=7.6 Hz, 1H), 5.12 (dd, J=7.2, 3.6 Hz, 1H) 4.20-4.06 (m, 4H), 2.19 (s, 3H), 2.05(s, 3H), 2.02 (d, J=7.6 Hz, 6H), 1.01 (s, 9H), 0.21 (d, J=15.2 Hz, 6H).

Preparation of Compound OHPAS-D1

To a solution of compound OHPAS-D1-5 (243.2 mg, 0.41 mmol) and 11-azido-3,6,9-trioxaundecan-1-amine (Aldrich, CAS 134179-38-7, 89.5 mg, 0.41 mmol) in DMF (5 mL) were added PyBOP (275 mg, 0.53 mmol) and DIPEA (176 uL, 1.02 mmol) at room temperature under N₂ atmosphere. The mixture was stirred for 2 hours at room temperature under N₂ atmosphere. The reaction was extracted with EA (30 mL×2) and distilled water (10 mL). The obtained organic layer was dried over anhydrous Na₂SO₄, filtered, and concentrated under reduced pressure. The residue was purified by column chromatography to obtain compound OHPAS-D1 (272.8 mg, 84%).

¹H NMR (400 Hz, CDCl₃) δ 7.34(s, 1H), 7.31 (d, J=9.2 Hz, 1H), 7.02 (d, J=8.0 Hz, 1H), 6.73(s, 1H), 5.48-5.44 (m, 2H), 5.19 (d, J=7.6 Hz, 1H), 5.10 (dd, J=6.4, 3.6 Hz, 1H), 4.20-4.10 (m, 2H), 4.06 (t, J=6.4 Hz, 2H), 3.66 (s, 14H), 3.38 (t, J=4.4 Hz, 2H), 2.19 (s, 3H), 2.02 (t, J=8.4 Hz, 9H), 1.00 (s, 9H), 0.20 (d, J=14.4 Hz, 6H).

ESI-MS m/z: 799 (M⁺+1).

Compound OHPAS-D1a and OHPAS-D2 were synthesized via a similar manner to the preparation method of the compound OHPAS-D1.

Preparation of Compound OHPAS-D1a

Yield: 83%;

¹H NMR (400 MHz, CDCl₃) δ 7.00-6.96 (m, 2H), 6.90 (s, 1H), 5.48-5.43 (m, 2H), 5.16 (d, J=8.0 Hz, 1H), 5.10 (dd, J=3.2, 10.4 Hz, 1H), 4.20-4.11 (m, 2H), 4.05 (t, J=7.2 Hz, 1H), 3.76-3.49 (m, 14H), 3.46-3.39 (m, 2H), 3.10-3.04 (m, 3H), 2.19 (s, 3H), 2.04 (s, 3H), 2.03 (s, 3H), 2.01 (s, 3H), 0.99 (s, 9H), 0.21 (s, 3H), 0.17 (s, 3H). ESI-MS m/z: 813 (M⁺1)

Preparation of Compound OHPAS-D2

Yield: 81%, ESI-MS m/z: 1152 (M⁺¹).

Example 3.3
Preparation of OHPAS-D3, OHPAS-D3a, and OHPAS-D4
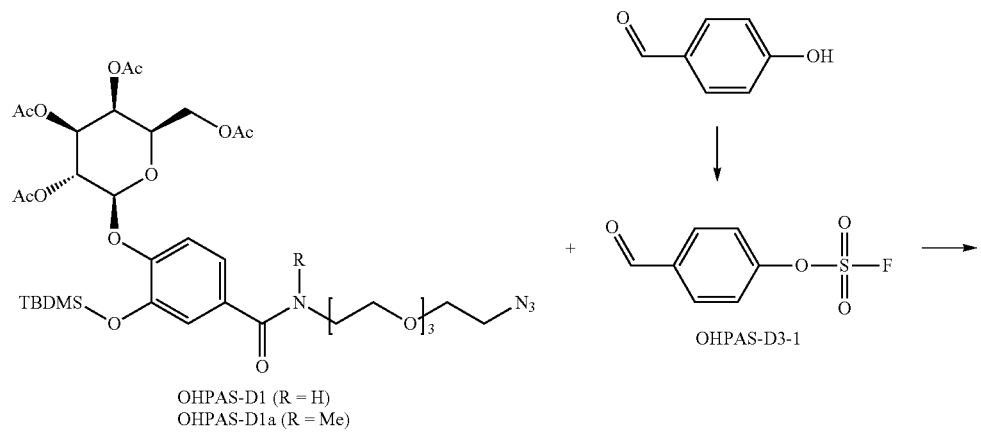
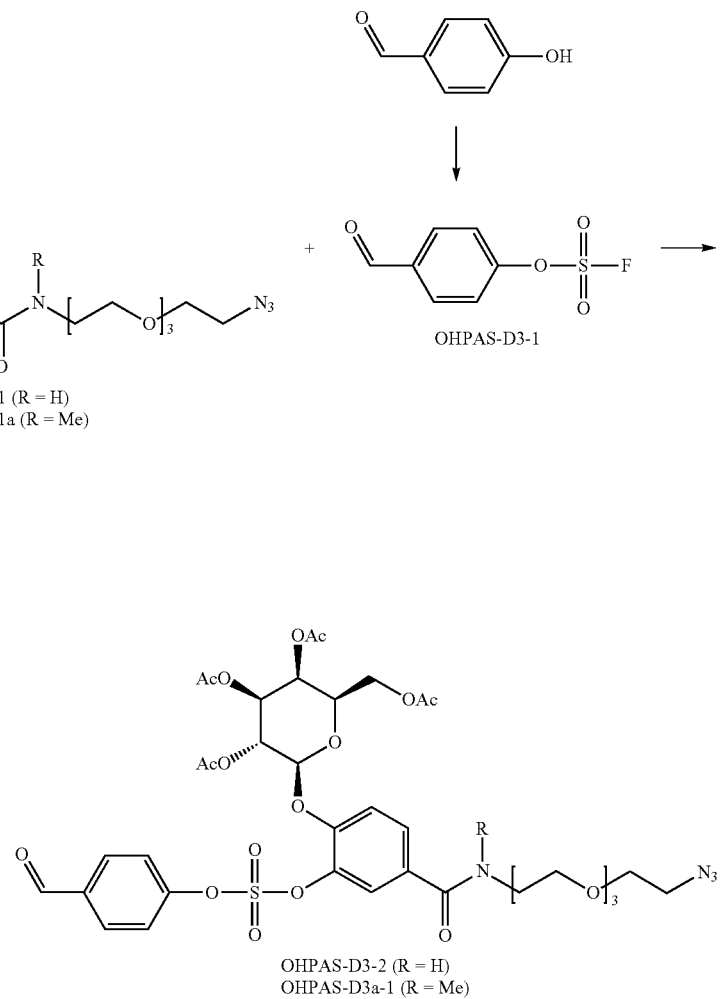
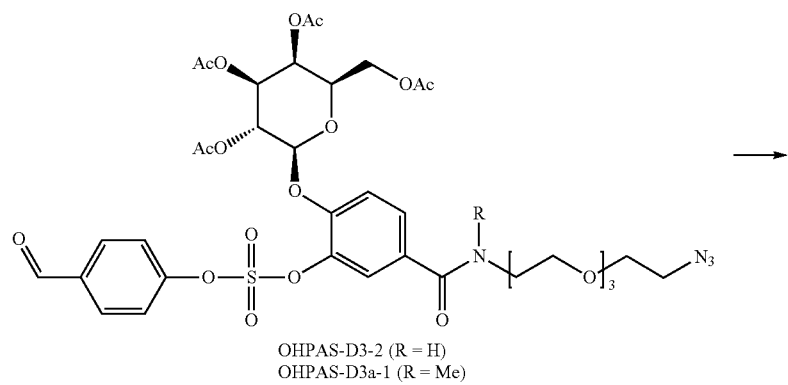

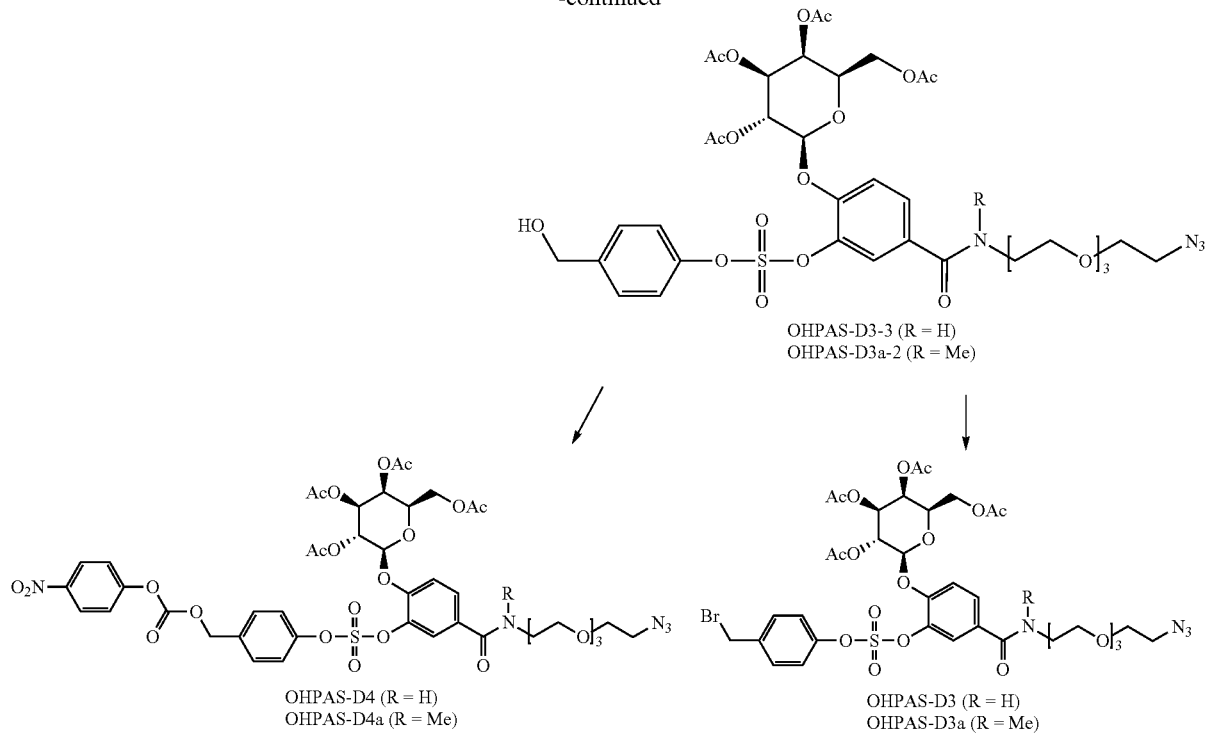

OHPAS-D3-3 (R = H)
OHPAS-D3a-2 (R = Me)

OHPAS-D4 (R = H)
OHPAS-D4a (R = Me)

OHPAS-D3 (R = H)
OHPAS-D3a (R = Me)

Preparation of Compound OHPAS-D3-1

To a solution of 4-hydroxybenzaldehyde (1 g, 8.19 mmol) in DCM (3 mL) was added Et$_3$N (2.28 mL, 16.38 mmol) at room temperature under N$_2$ atmosphere. SO$_2$F$_2$ gas was introduced via balloon, and the mixture was stirred at room temperature for 2 hours. Then the mixture was washed with DCM (30 mL×3) and brine (30 mL), the organic layer was dried over anhydrous Na$_2$SO$_4$, filtered and concentrated under reduced pressure. The residue was purified by column chromatography to obtain compound OHPAS-D3-1 (790 mg, 63%).

$^1$H NMR (400 Hz, CDCl$_3$) δ 10.06 (s, 1H), 8.05 (d, J=8.0 Hz, 2H), 7.55 (d, J=8.8 Hz, 2H).

Preparation of Compound OHPAS-D3-2

To a solution of compound OHPAS-D1 (100 mg, 0.13 mmol) and compound OHPAS-D3-1 (26 mg, 0.13 mmol) in anhydrous ACN (3 mL) were added DBU (4 μL, 25 μmol). The mixture was stirred at room temperature for 1 hour and was washed with distilled water (10 mL) and EA (10 mL×2). The organic layer was dried over anhydrous Na$_2$SO$_4$, filtered and concentrated under reduced pressure. The residue was purified by column chromatography to obtain compound OHPAS-D3-2 (103 mg, 94%).

ESI-MS m/z: 869 (M$^+$).

Preparation of Compound OHPAS-D3-3

To a solution of compound OHPAS-D3-2 (103 mg, 0.12 mmol) in THF (8 mL) was added NaBH$_4$ (9 mg, 0.24 mmol) at 0° C. under N$_2$ atmosphere. After stirring at room temperature for 2 hours, distilled water (10 mL) and EA (10 mL×2) were added. The organic layer was dried over anhydrous Na$_2$SO$_4$, filtered and concentrated under reduced pressure to obtain compound OHPAS-D3-3 (101 mg, 98%).

ESI-MS m/z: 871 (M$^+$).

Preparation of Compound OHPAS-D3

To a solution of compound OHPAS-D3-3 (320.5 mg, 0.0.37 mmol) in DCM (3 ml) was added 1M PBr$_3$ in DCM (165 ul, 0.19 mmol) at 0° C. under N$_2$ atmosphere. After stirring for 2 hours, the mixture was quenched by addition of saturated sodium bicarbonate (8 mL×2).The organic layers were washed with brine, dried over Na$_2$SO$_4$, filtered, and concentrated under reduced pressure. The residue was purified by column chromatography to produce compound OHPAS-D3 (202.6 mg, 59%).

ESI-MS m/z: 934 (M+).

Preparation of Compound OHPAS-D4

To a solution of compound OHPAS-D3-3 (47 mg, 54 μmol) in DMF (2 mL) was added bis(4-nitrophenyl) carbonate (25 mg, 81 μmol) and DIPEA (14 μL, 81 μmol) at room temperature under a nitrogen atmosphere. The mixture was stirred overnight at room temperature. Then distilled water (10 mL) and EA (10 mL×2) were added, the organic layer was dried over anhydrous Na$_2$SO$_4$, filtered and concentrated under reduced pressure. The residue was purified by column chromatography to obtain compound OHPAS-D3-4 (53 mg, 94%).

ESI-MS m/z: 1036 (M$^+$).

Compound OHPAS-D3a and OHPAS-D4a were prepared by a similar synthetic route of preparing compound OHPAS-D3 or OHPAS-D4.

Preparation of Compound OHPAS-D3a-1

Yield 80%; $^1$H NMR (400 MHz, CDCl$_3$) δ 10.04 (s, 1H), 8.00 (d, J=8.8 Hz, 2H), 7.57 (d, J=8.4 Hz, 2H), 7.44-7.27 (m, 3H), 5.57-5.51 (m, 1H), 5.47 (d, J=3.2 Hz, 1H), 5.14-5.10 (m, 2H), 4.27-4.09 (m, 3H), 3.76-3.53 (m, 14H), 3.42-3.36 (m, 2H), 3.12-3.04 (m, 3H), 2.19 (s, 3H), 2.07 (s, 3H), 2.06 (s, 3H), 2.02 (s, 3H). ESI-MS m/z: 883 (M$^{+1}$)

Preparation of Compound OHPAS-D3a-2

Yield 81%; $^1$H NMR (400 MHz, CDCl$_3$) δ 7.47-7.42 (m, 2H), 7.40-7.31 (m, 3H), 7.24-7.21 (m, 2H), 5.54-5.45 (m, 2H), 5.11-5.07 (m, 2H), 4.74-4.70 (m, 2H), 4.25-4.21 (m, 1H), 4.17-4.12 (m, 1H), 4.06 (t, J=7.2 Hz, 1H), 3.74-3.44

(m, 12H), 3.37 (t, J=4.8 Hz, 2H), 3.07-3.04 (s, 3H), 2.20 (s, 3H), 2.06 (s, 6H), 2.02 (s, 3H). ESI-MS m/z: 885 (M$^{+1}$).

Preparation of Compound OHPAS-D3a

Yield 90%; $^1$H NMR (400 MHz, CDCl$_3$) δ 7.48-7.41 (m, 2H), 7.35 (d, J=8.4 Hz, 2H), 7.29-7.21 (m, 2H), 5.59-5.55 (m, 1H), 5.47 (d, J=3.2 Hz, 1H), 5.13-5.09 (m, 2H), 4.26-4.22 (m, 1H), 4.18-4.08 (m, 2H), 3.80-3.48 (m, 12H), 3.37 (t, J=5.2 Hz, 2H), 3.12-3.06 (s, 3H), 2.19 (s, 3H), 2.07 (s, 3H), 2.06 (s, 3H), 2.02 (s, 3H). ESI-MS m/z: 948 (M$^{+1}$)

Preparation of Compound OHPAS-D4a

Yield 94%; ESI-MS m/z: 1036 (M$^+$1)

Example 3.4

Preparation of OHPAS-D5

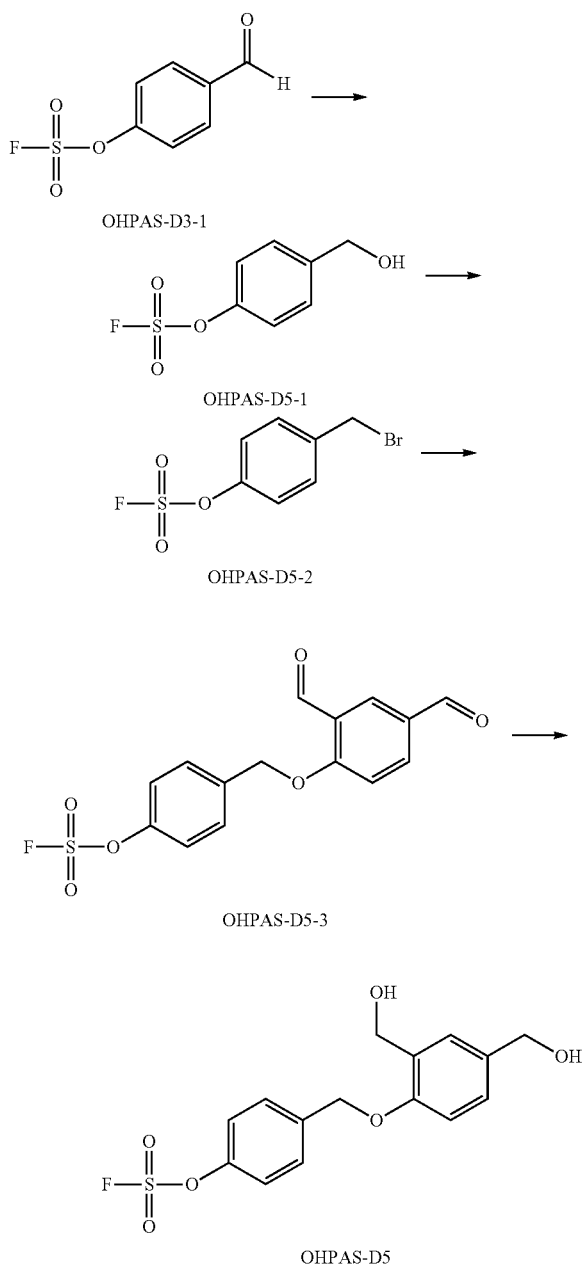

Preparation of Compound OHPAS-D5-1

To a solution of compound OHPAS-D3-1 (5 g, 24.49 mmol) in MeOH (40 mL) and THF (245 mL) was added NaBH$_4$ (1.85 g, 48.98 mmol) at −78° C. under N$_2$ atmosphere. After stirring at 0° C. for 1 hour, the reaction mixture was quenched by addition of 2N HCl (5 mL) and extracted with H$_2$O (250 mL) and EA (250 mL×3). The organic layer was dried over Na$_2$SO$_4$, filtered, and concentrated under reduced pressure. The residue was purified by column chromatography to provide compound OHPAS-D5-1 (5.01 g, 99%).

$^1$H NMR (400 MHz, CDCl$_3$) δ 7.50-7.46 (m, 2H), 7.34-7.31 (m, 2H), 4.75 (d, J=5.6 Hz, 2H), 1.90 (t, J=5.6 Hz, 1H).

Preparation of Compound OHPAS-D5-2

To a solution of compound OHPAS-D5-1 (2 g, 9.7 mmol) in ether (32 mL) was added 1.0 M PBr$_3$ in DCM (3.88 mL, 3.88 mmol) at 0° C. under N$_2$ atmosphere. After stirring for 2 hours ether (100 mL) and NaHCO$_3$ (100 mL×3) were added to perform extraction. The organic layer was dried over Na$_2$SO$_4$, filtered, and concentrated under reduced pressure. The residue was purified by column chromatography to provide compound OHPAS-D5-2 (2.35 g, 90%).

$^1$H NMR (400 MHz, CDCl$_3$) δ 7.52-7.49 (m, 2H), 7.34-7.31 (m, 2H), 4.49 (s, 2H).

Preparation of Compound OHPAS-D5-3

To a solution of 4-hydroxyisophathalaldehyde (112 mg, 0.746 mmol, CAS No: 3328-70-9) and sodium hydride (45 mg, 1.12 mmol, 60%) in DMF (5 mL) was added OHPAS-D5-2 (280 mg, 0.97 mmol) in DMF (2 mL) at 0° C. under N$_2$ atmosphere. After stirring at room temperature for 4 hours under N$_2$ atmosphere, the reaction mixture was quenched by the addition of H$_2$O (10 mL) and extracted with H$_2$O (100 mL) and EA (100 mL×2). The organic layer was dried over Na$_2$SO$_4$, filtered, and concentrated under reduced pressure. The residue was purified by column chromatography to provide compound OHPAS-D5-3 (180 mg, 71%) as a white solid.

$^1$H NMR (400 MHz, CDCl$_3$) δ 10.54 (s, 1H), 9.98 (s, 1H), 8.38 (d, J=2.4 Hz, 1H), 8.14 (dd, J=2.0, 8.8 Hz, 1H), 7.60 (d, J=9.2 Hz, 2H), 7.43 (d, J=8.8 Hz, 2H), 7.19 (d, J=8.8 Hz, 1H), 5.33 (s, 2H).

Preparation of Compound OHPAS-D5

To a solution of compound OHPAS-D5-3 (1 g, 2.96 mmol) in THF (8 mL) was added sodium borohydride (391 mg, 10.35 mmol) in MeOH (1.5 mL) and THF (1 mL) at −78° C. under N$_2$ atmosphere. The reaction mixture was stirred at 0° C. for 1 hour under N$_2$ atmosphere. After the reaction was completed, the mixture was quenched with 2N HCl (2 mL) and extracted with H$_2$O (100 mL) and EA (100 mL×3). The organic layer was dried over Na$_2$SO$_4$, filtered, and concentrated under reduced pressure. The residue was purified by column chromatography to provide compound OHPAS-D5 (850 mg, 85%) as a white solid.

$^1$H NMR (400 MHz, CDCl$_3$) δ 7.55 (d, J=8.8 Hz, 2H), 7.39-7.37 (m, 3H), 7.30-7.28 (m, 1H), 6.89 (d, J=8.4 Hz, 1H), 5.16 (s, 2H), 4.76 (d, J=6.0 Hz, 2H), 4.65 (d, J=5.6 Hz, 2H).

Example 3.5
Preparation of OHPAS-D6
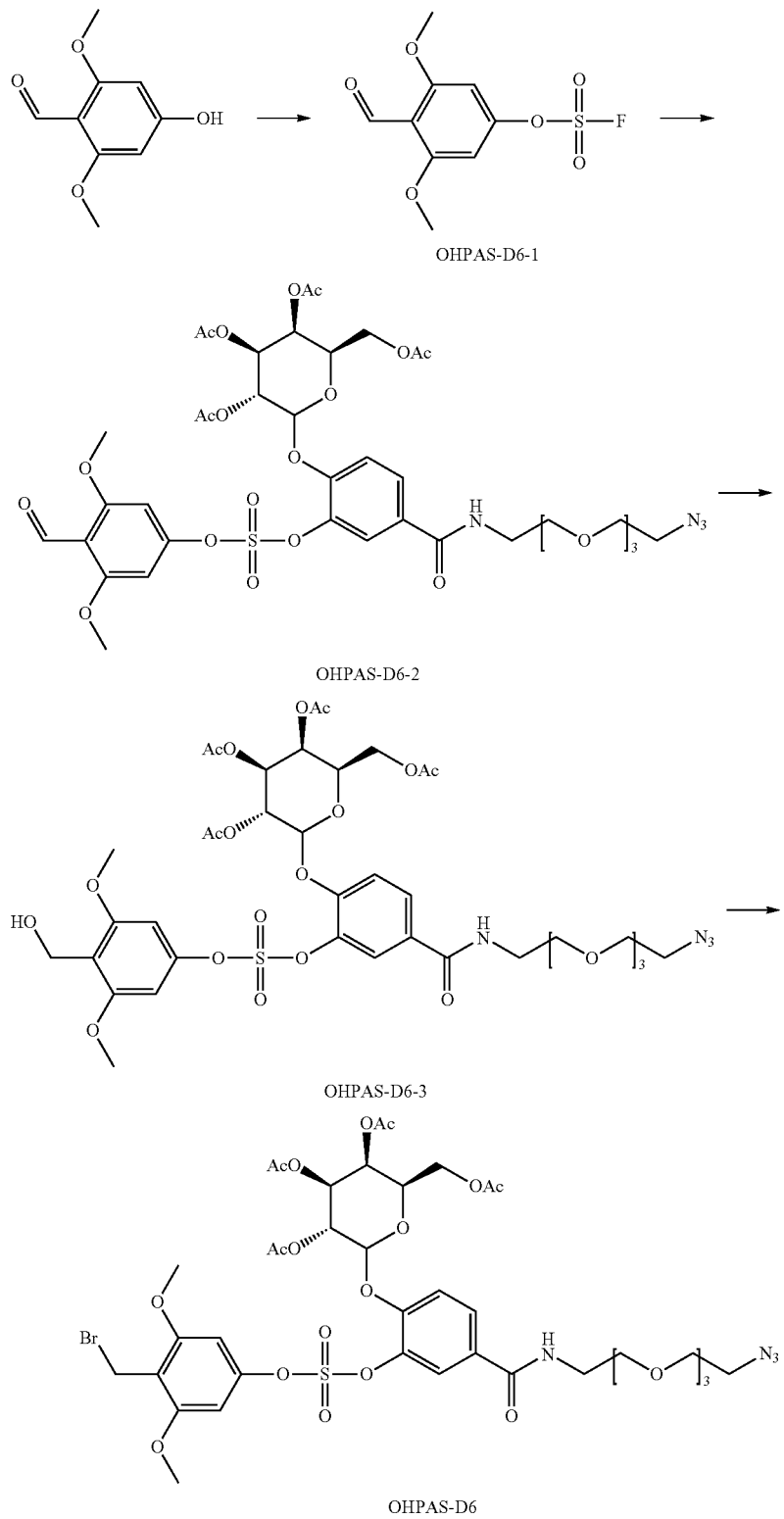

Preparation of Compound OHPAS-D6-1

To a solution of 2,6-dimethoxy-4-hydroxybenzaldehyde (0.5 g, 2.74 mmol) in DCM (8 mL) was added Et$_3$N (3.8 mL, 27.4 mmol) at room temperature under N$_2$ atmosphere. SO$_2$F$_2$ gas was introduced via balloon, and the mixture was stirred at room temperature for 2 hours. Then the mixture was washed with DCM (30 mL×3) and brine (30 mL), the organic layer was dried over anhydrous Na$_2$SO$_4$, filtered and concentrated under reduced pressure. The residue was purified by column chromatography to obtain compound OHPAS-D6-1 (728 mg, 99%).

Yield 99%

ESI-MS m/z: 265 (M+). 1H-NMR (400 MHz, CDCl$_3$) δ 10.41 (s, 1H), 6.54 (s, 2H), 3.91 (s, 6H).

Preparation of Compound OHPAS-D6-2

To a solution of compound OHPAS-D6-1 (101 mg, 0.38 mmol) and compound OHPAS-D1 (254 mg, 0.32 mmol,) in acetonitrile (6 mL) were added BEMP (19 μl, 0.064 mmol) at room temperature. After 2 hours, the reaction mixture was diluted with aqueous citric acid (8 mL), and extracted with EtOAc (2×8 mL). The combined organic layers were dried over anhydrous Na$_2$SO$_4$, filtered and concentrated under reduced pressure. The residue was purified by column chromatography to produce the compound OHPAS-D6-2 (295 mg, 99%). ESI-MS m/z: 929 (M$^+$).

Compound OHPAS-D6 was synthesized via a similar synthetic route as described in Example 3.3.

Preparation of Compound OHPAS-D6-3

Yield 96%; ESI-MS m/z: 931 (M+).

Preparation of Compound OHPAS-D6

Yield 75%; ESI-MS m/z: 750 (M+).

Example 3.6

Preparation of OHPAS-D7

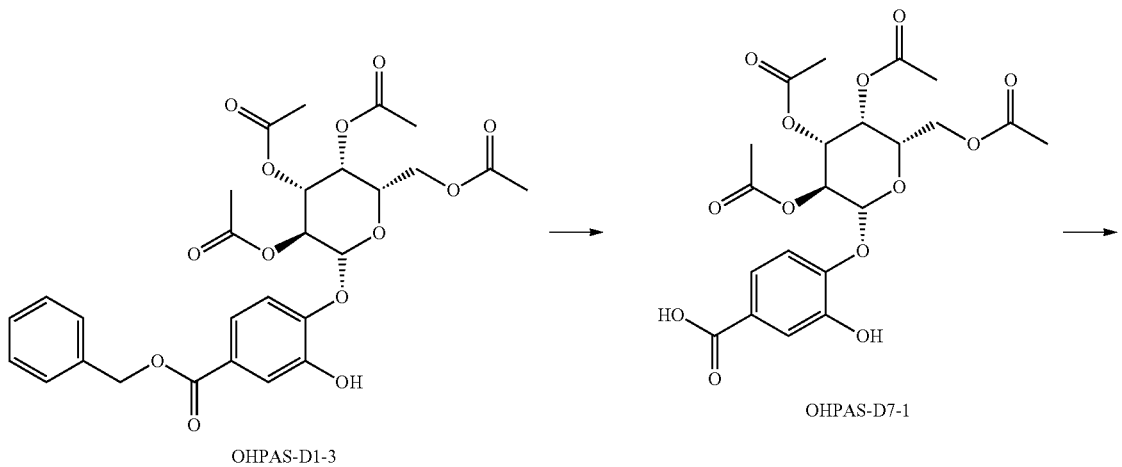

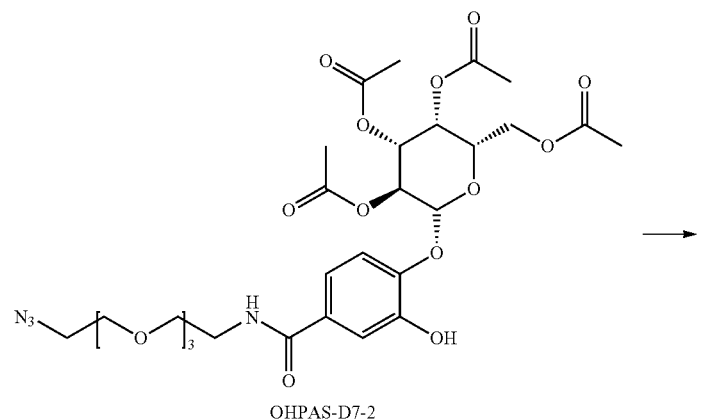

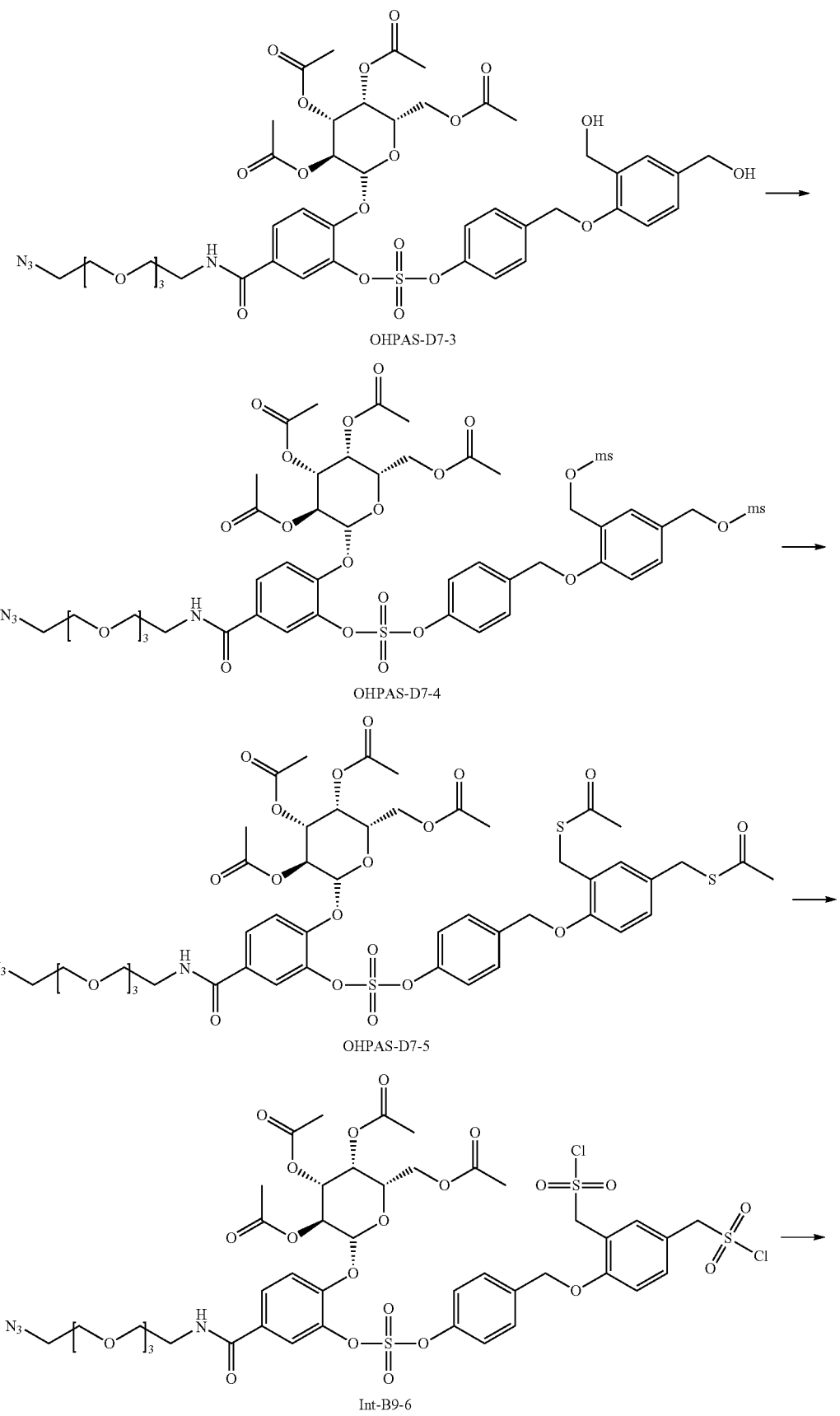

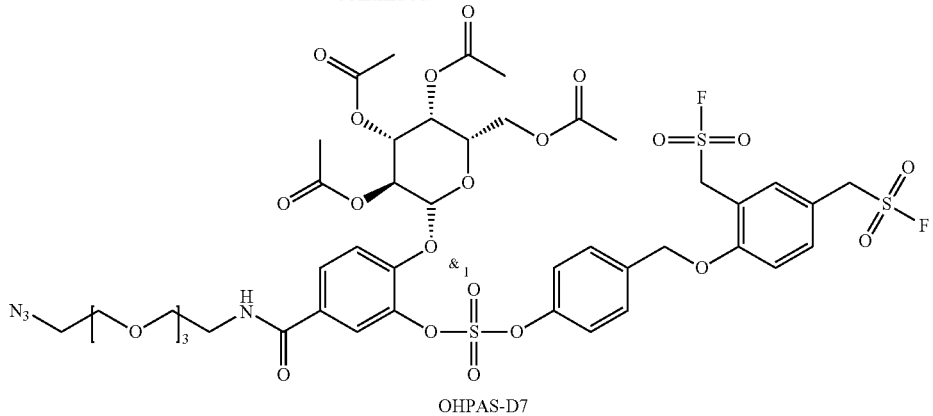

OHPAS-D7

Preparation of Compound OHPAS-D7-1

To a solution of compound OHPAS-D1-3 (3 g, 5.22 mmol) in EA (240 mL) was added Pd/C (300 mg, 10 wt %) at 0° C., and the mixture was stirred at the room temperature for 3 hours while injecting H$_2$ gas. After the reaction was completed, the mixture was filtered through Celite®, and then concentrated under reduced pressure. Compound OHPAS-D7-1 was used directly in the next reaction without further purification (2.84 g, 100%, beige foam)

ET-MS m/z: 507.2 (M$^{+1}$+Na)

OHPAS-D7-2 was prepared by a similar method of preparing compound OHPAS-D1 in Example 3.2.

Preparation of Compound OHPAS-D7-2

Yield 84%, a white solid; $^1$H NMR (400 MHz, CDCl$_3$) δ 7.38-7.34 (m, 2H), 7.00 (d, J=8.0 Hz, 1H), 6.82 (d, J=5.2 Hz, 1H), 6.10 (brs, 1H), 5.49-5.45 (m, 2H), 5.14 (dd, J=3.6, 10.4 Hz, 1H), 4.99 (d, J=7.6 Hz, 1H), 4.27-4.08 (m, 3H), 3.74-3.63 (m, 14H), 3.37 (t, J=5.2 Hz, 2H), 2.20 (s, 3H), 2.12 (s, 3H), 2.08 (s, 3H), 2.03 (s, 3H). ET-MS m/z: 685.3 (M$^{+1}$).

OHPAS-D7-3 was prepared by a similar method of preparing compound OHPAS-D3-2 in Example 3.3.

Preparation of Compound OHPAS-D7-3

Yield 81%, a white solid; $^1$H NMR (400 MHz, CDCl$_3$) δ 7.80 (d, J=2.0 Hz, 1H), 7.76 (dd, J=2.4, 8.8 Hz, 1H), 7.50 (d, J=8.4 Hz, 2H) 7.43-7.40 (m, 2H), 7.37 (d, J=2.0 Hz, 1H), 7.29-7.25 (m, 2H), 7.08 (d, J=4.8 Hz, 1H), 6.90 (d, J=8.4 Hz, 1H), 5.60-5.56 (m, 1H), 5.47 (d, J=3.2 Hz, 1H), 5.17-5.10 (m, 4H), 4.74 (d, J=6.4 Hz, 2H), 4.64 (d, J=6.0 Hz, 2H), 4.26-4.08 (m, 3H), 3.71-3.58 (m, 14H), 3.34 (t, J=4.8 Hz, 2H), 2.41 (t, J=6.4 Hz, 1H), 2.18 (s, 3H), 2.08 (s, 3H), 2.07 (s, 3H), 2.01 (s, 3H), 1.77 (t, J=6.0 Hz, 1H). ET-MS m/z: 1007.2 (M$^{+1}$).

Preparation of Compound OHPAS-D7-4

To a solution of compound OHPAS-D7-3 (150 mg, 0.15 mmol) in CH$_2$Cl$_2$ (3 mL) was added methanesulfonyl chloride (150 mg, 0.15 mmol) at 0° C. under N$_2$ atmosphere. The reaction mixture was stirred at room temperature for 24 hours under N$_2$ atmosphere. After the reaction was completed, the mixture was quenched with H$_2$O (50 mL) and extracted with CH$_2$Cl$_2$ (50 mL×3). The organic layer was dried over Na$_2$SO$_4$, filtered, and concentrated under reduced pressure, producing compound OHPAS-D7-4 (214 mg, 100%) as a beige foam, which was used directly in the next step without further purification.

Preparation of Compound OHPAS-D7-5

To a solution of compound OHPAS-D7-4 (214 mg, 0.15 mmol) in ACN (3 mL) was added potassium thioacetate (43 mg, 0.37 mmol) at room temperature under N$_2$ atmosphere. After stirring at room temperature for 3 hours under N$_2$ atmosphere, the mixture was quenched with H$_2$O (50 mL) and extracted with EA (50 mL×3). The organic layer was dried over Na$_2$SO$_4$, filtered, and concentrated under reduced pressure. The residue was purified by column chromatography to provide compound OHPAS-D7 (147 mg, 88%) as a pale yellow foam.

$^1$H NMR (400 MHz, CDCl$_3$) δ 7.87 (d, J=2.0 Hz, 1H), 7.78 (dd, J=2.0, 8.4 Hz, 1H), 7.51 (d, J=8.4 Hz, 2H), 7.43-7.41 (m, 2H), 7.31-7.27 (m, 2H), 7.15 (dd, J=2.0, 8.0 Hz, 1H), 7.07-7.06 (m, 1H), 6.79 (d, J=8.4 Hz, 1H), 5.61-5.56 (m, 1H), 5.47 (d, J=3.2 Hz, 1H), 5.17 (d, J=8.0 Hz, 1H), 5.14-5.10 (m, 3H), 4.26-4.09 (m, 5H), 4.05 (s, 2H), 3.66-3.59 (m, 14H), 3.34 (t, J=5.6 Hz, 2H), 2.34 (s, 3H), 2.32 (s, 3H), 2.18 (s, 3H), 2.08 (s, 3H), 2.07 (s, 3H), 2.01 (s, 3H). ET-MS m/z: 1123.2 (M$^{+1}$).

Preparation of Compound OHPAS-D7-6

To a solution of compound OHPAS-D7-5 (100 mg, 0.089 mmol) in ACN (2 mL) was added N-chlorosuccinimide (90 mg, 0.676 mmol) and 2N HCl (356 uL, 0.712 mmol) at 0° C. under N$_2$ atmosphere. After stirring at 0° C. for 1 hour under N$_2$ atmosphere, dimethylsulfide (19.6 uL, 0.267 mmol) was added thereto at room temperature. The reaction mixture was further stirred at the same temperature for 5 minutes. H$_2$O (20 mL) and EA (20 mL×3) were added to perform extraction, and the obtained organic layers were dried over Na$_2$SO$_4$, filtered, and concentrated under reduced pressure, producing compound OHPAS-D7 (140 mg, 100%) as a white foam, which was used directly in the next step without further purification.

ET-MS m/z: 1173.9 (M$^{+1}$).

Preparation of Compound OHPAS-D7

To a solution of compound OHPAS-D7-6 (140 mg, 0.089 mmol) in ACN (2 mL) was added potassium hydrogen fluoride (41.7 mg, 0.534 mmol) in H$_2$O (0.2 mL) at room temperature under N$_2$ atmosphere. After stirring for 2 hours at room temperature, the mixture was purified by prep-HPLC to provide compound OHPAS-D7 (42 mg, 41%) as a white foam.

$^1$H NMR (400 MHz, CDCl$_3$) δ 7.86 (d, J=2.0 Hz, 1H), 7.78 (dd, J=2.0, 8.4 Hz, 1H), 7.53-7.43 (m, 6H), 7.29 (d, J=8.8 Hz, 1H), 7.13-7.11 (m, 1H), 7.05 (d, J=9.2 Hz, 1H), 5.61-5.56 (m, 1H), 5.48 (d, J=2.4 Hz, 1H), 5.20 (s, 2H), 5.17 (d, J=8.0 Hz, 1H), 5.12 (dd, J=3.2, 10.4 Hz, 1H), 4.78 (d, J=3.6 Hz, 2H), 4.26-4.09 (m, 3H), 3.70-3.60 (m, 14H), 3.5 (t, J=5.2 Hz, 2H), 2.18 (s, 3H), 2.08 (s, 3H), 2.07 (s, 3H), 2.01 (s, 3H). ET-MS m/z: 1139.1 (M$^{+1}$).

Example 3.7
Preparation of OHPAS-D9 and OHPAS-D10
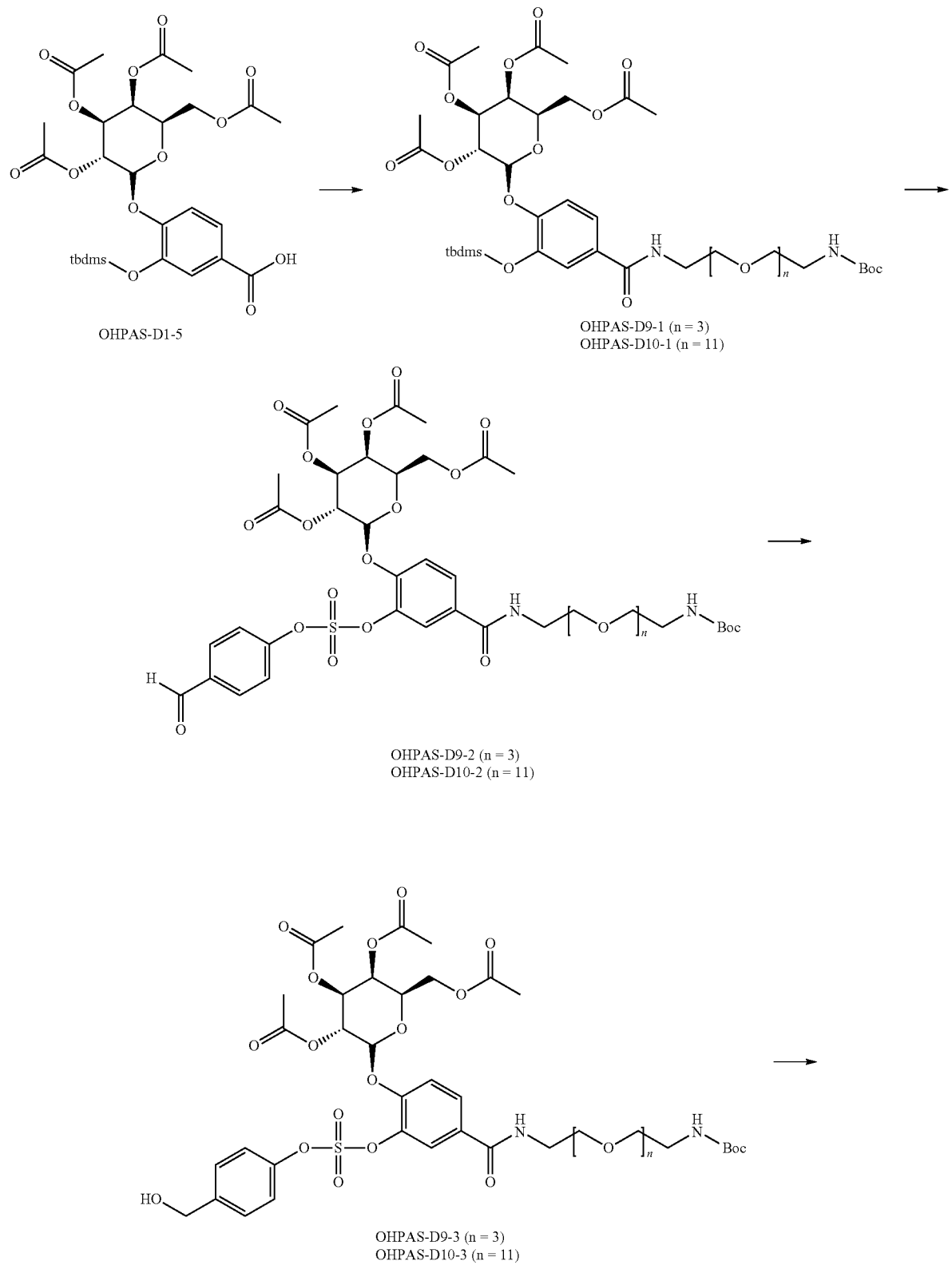

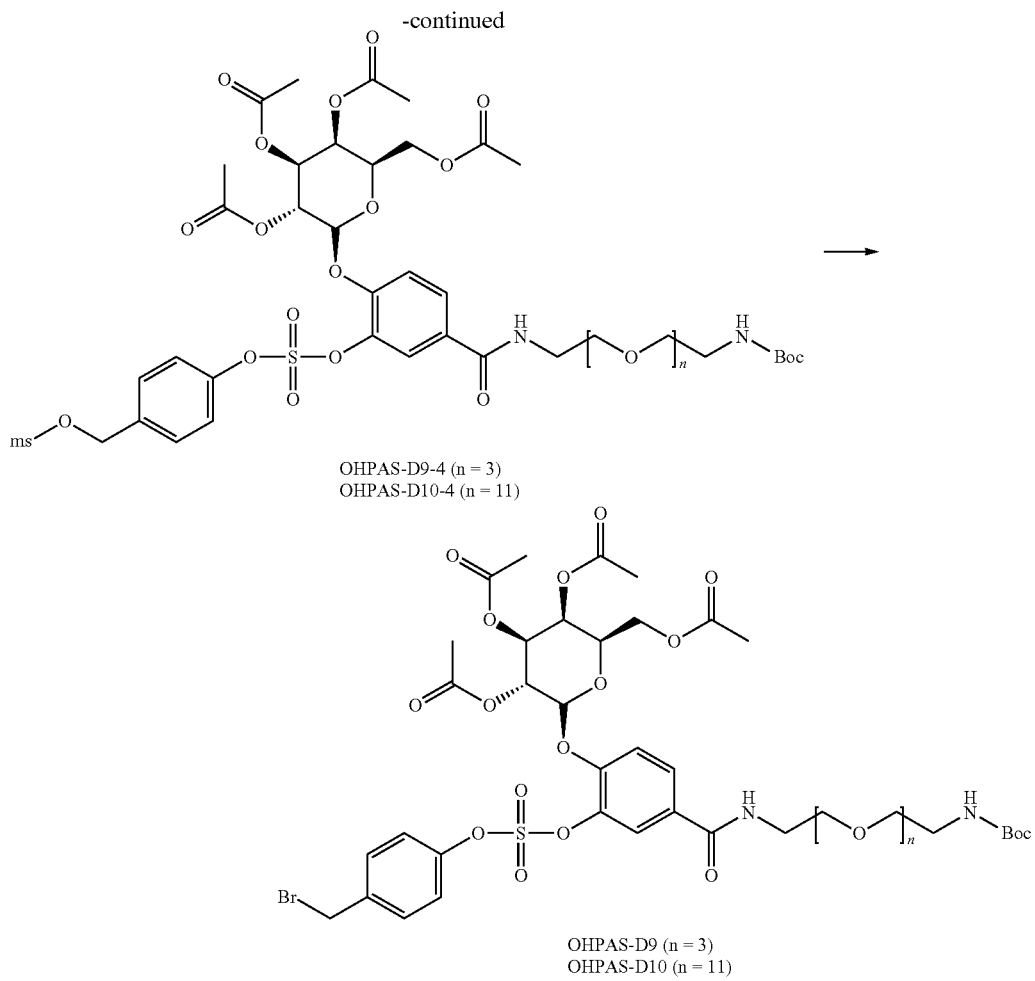

OHPAS-D9-4 (n = 3)
OHPAS-D10-4 (n = 11)

OHPAS-D9 (n = 3)
OHPAS-D10 (n = 11)

Preparation of Compound OHPAS-D9-1

A homogeneous solution of compound OHPAS-D1-5 (1.0 g, 0.26 mmol) and L-1 (586 mg, 2.0 mmol, 1.2 eq.) in DMF (10 mL) at room temperature under $N_2$ atmosphere was treated with PyBOP (1.13 g, 2.17 mmol, 1.3 eq.), DIPEA (873 uL, 5.01 mmol, 3.0 eq.) and stirred for 4 hours. The reaction was quenched with water (20 mL) and extracted with EA (30 mL×2). The organic layer was dried over anhydrous $Na_2SO_4$, filtered and concentrated under reduced pressure. The residue was purified by column chromatography (Hex:EA=1:1 to 1:3) to obtain compound OHPAS-D9-1 (1.05 g, 72%) as white foam solid.

ESI-MS m/z: 874 ($M^+$+1).

Preparation of Compound OHPAS-D9-2

A homogeneous solution of compound OHPAS-D9-1 (500 mg, 0.57 mmol) and compound OHPAS-D3-1 (140 mg, 0.69 mmol, 1.2 eq.) in anhydrous ACN (10 mL) at room temperature under $N_2$ atmosphere was treated with BEMP (66.3 µL, 0.23 mmol, 0.4 eq.) and stirred for 4 hours. The reaction was quenched with water (20 mL) and extracted with EA (30 mL×2). The organic layer was dried over anhydrous $Na_2SO_4$, filtered, and concentrated under reduced pressure. The residue was purified by column chromatography (4% MeOH in DCM) to obtain compound OHPAS-D9-2 (495 mg, 85%) as white foam solid.

ESI-MS m/z: 869 ($M^+$+1).

Preparation of Compound OHPAS-D9-3

To a solution of compound OHPAS-D9-2 (495 mg, 0.52 mmol) in anhydrous THF (5.0 mL) at 0° C. under $N_2$ atmosphere was treated with NaBH4 (39.7 mg, 1.05 mmol, 2.0 eq.) and stirred for 2 hours. The reaction was quenched with water (20 mL) and extracted with EA (30 mL×2). The organic layer was dried over anhydrous $Na_2SO_4$, filtered, and concentrated under reduced pressure. The residue was purified by column chromatography (2% to 3% MeOH in DCM) to obtain compound OHPAS-D9-3 (418 mg, 91%) as white foam solid.

ESI-MS m/z: 945 ($M^+$+1).

Preparation of Compound OHPAS-D9-4

To a solution of compound OHPAS-D9-3 (214.2 mg, 0.23 mmol) in anhydrous THF (5.0 mL) at 0° C. under $N_2$ atmosphere was treated with methane sulfonyl chloride (24.6 uL, 0.32 mmol, 1.4 eq.) and TEA (79.2 uL, 0.57 mmol, 1.5 eq.) and stirred overnight at room temperature. The reaction was quenched with water (10 mL) and extracted with DCM (20 mL×2). The organic layer was dried over anhydrous $Na_2SO_4$, filtered, and concentrated under reduced pressure. The residue was purified by column chromatography (100% DCM to 5% MeOH in DCM) to obtain compound OHPAS-D9-4 (164 mg, 70%) as white foam solid.

ESI-MS m/z: 1024 ($M^+$+1).

Preparation of Compound OHPAS-D9

To a solution of compound OHPAS-D9-4 (164 mg, 0.16 mmol) in anhydrous THF (10 mL) at room temperature under $N_2$ atmosphere was treated with LiBr (69.6 mg, 0.80 mmol, 5.0 eq.) and stirred for 3 hours. The reaction was diluted with water (10 mL) and extracted with DCM (20 mL×2). The organic layer was dried over anhydrous Na$_2$SO$_4$, filtered, and concentrated under reduced pressure. The residue was purified by column chromatography (3% to 5% MeOH in DCM) to obtain compound OHPAS-D9 (161 mg, 99%) as white foam solid.

ESI-MS m/z: 1008 (M$^+$+1).

Compound OHPAS-D10 was synthesized via a similar manner to the preparation method of the compound OHPAS-D9.

Preparation of Compound OHPAS-D10-1
Yield 72%, a colorless oil
ESI-MS m/z: 1226 (M$^+$+1).

Preparation of Compound OHPAS-D10-2
Yield 82%, a colorless oil
ESI-MS m/z: 1296 (M$^+$+1).

Preparation of Compound OHPAS-D10-3
Yield 75%, a colorless oil
ESI-MS m/z: 1298 (M$^+$+1).

Preparation of Compound OHPAS-D10-4
Yield 82%, a colorless oil
ESI-MS m/z: 1376 (M$^+$+1).

Preparation of Compound OHPAS-D10
Yield 82%, a colorless oil
ESI-MS m/z: 1361 (M$^+$+1).

Example 3.8

Preparation of OHPAS-D11

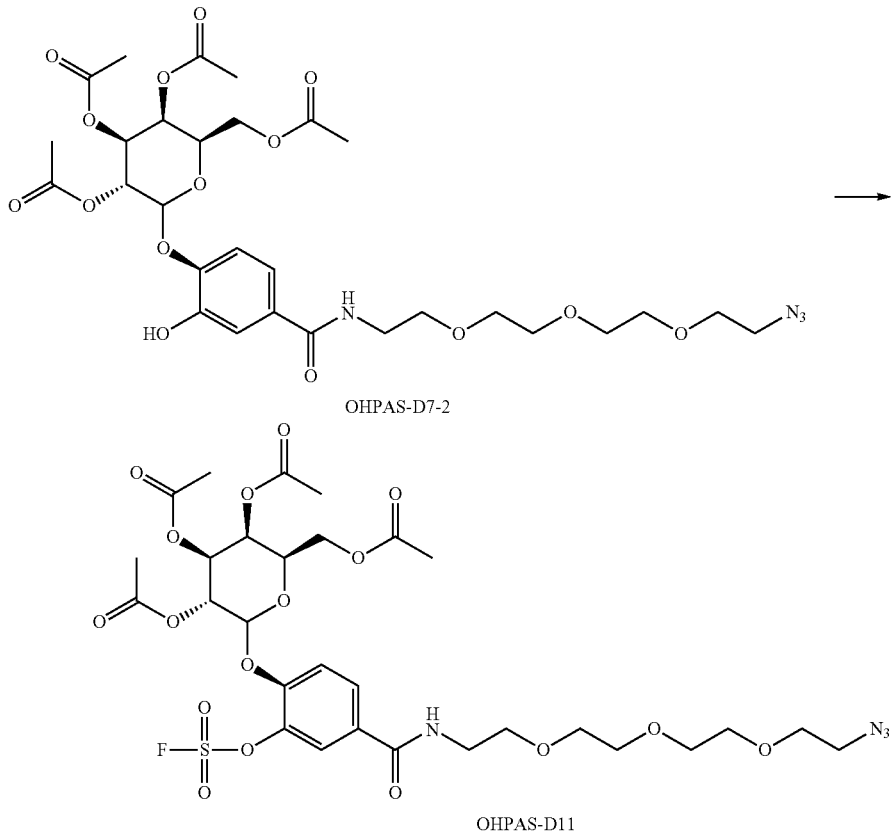

Compound OHPAS-D11 was synthesized via a similar manner to the preparation method of the compound OHPAS-D3-1 in Example 3.3.

Preparation of Compound OHPAS-D11
Yield 81%, white foam solid
$^1$H NMR (400 Hz, CDCl$_3$) δ 7.88 (s, 1H), 7.68 (d, J=8.8 Hz, 1H), 7.30 (d, J=8.8 Hz, 1H), 7.05 (brs, 1H), 5.62-5.56 (m, 1H), 5.48 (d, J=2.8 Hz 1H), 5.17 (d, J=8.0 Hz, 1H), 5.12 (dd, J=7.2, 3.2 Hz, 1H), 4.26-4.08 (m, 3H), 3.72-3.60 (m, 14H), 3.36 (t, J=4.8 Hz, 2H), 2.20 (s, 3H), 2.08 (s, 6H), 2.02 (s, 3H); ESI-MS m/z: 767 (M$^+$+1).

Example 3.9

Preparation of OHPAS-D12 and OHPAS-D13

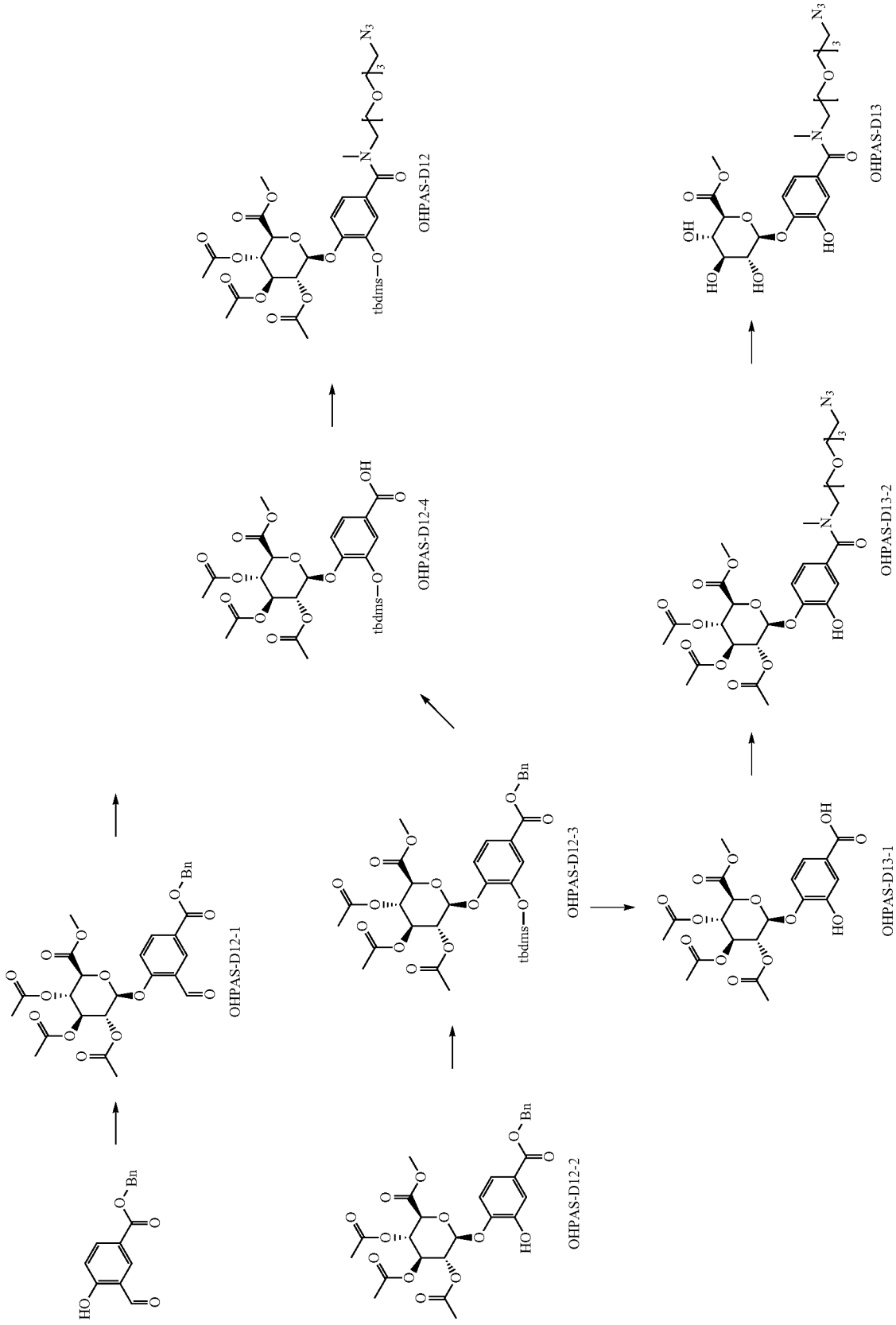

Compound OHPAS-D12 was synthesized via a similar method as described in Example3.2.

Compound OHPAS-D12-1
 Yield 65%
 $^1$H NMR (400 MHz, CDCl$_3$) δ 10.32 (s, 1H), 8.54 (d, J=2.4 Hz, 1H), 8.28 (dd, J=8.8 Hz, 1H), 7.45-7.35 (m, 5H), 7.16 (d, J=8.8 Hz, 1H), 5.39-5.34 (m, 6H), 4.28-4.26 (m, 1H), 3.72 (s, 3H), 2.11-2.06 (m, 9H).

Compound OHPAS-D12-2
 Yield 63%
 $^1$H NMR (400 MHz, CDCl$_3$) δ 7.66 (d, J=2 Hz, 1H), 7.60 (dd, J=8.4 Hz, 1H), 7.43-7.31 (m, 5H), 7.00 (d, J=8.4 Hz, 1H), 6.13 (s, 1H), 5.41-5.28 (m, 5H), 5.12 (d, J=7.2 Hz, 1H), 4.23 (d, J=9.2 Hz, 1H), 3.76 (s, 3H), 2.09 (s, 3H), 2.06 (d, J=3.6 Hz, 6H).

Compound OHPAS-D12-3
 Yield 70%
 $^1$H NMR (400 MHz, CDCl$_3$) δ 7.60 (dd, J=2.0, 2.0 Hz, 1H), 7.43 (d, J=0.8 Hz, 1H), 7.48-7.32 (m, 5H), 7.01 (d, J=8.4 Hz, 1H), 5.40-5.26 (m, 6H), 4.18 (d, J=9.2 Hz, 1H), 3.72 (s, 3H), 2.09-2.04 (m, 9H). 0.99 (s, 9H), 0.18 (d, J=12.8 Hz, 1H).

Compound OHPAS-D12-4
 Yield quant
 ESI-MS m/z: 607 (M$^+$+Na)

Compound OHPAS-D13-1
 Yield 96%
 $^1$H NMR (400 Hz, DMSO-d6) δ 9.73 (brs, 1H), 7.44 (d, J=2.0 Hz, 1H), 7.37 (dd, J=2.4, 6.4 Hz, 1H), 7.08 (d, J=8.4 Hz, 1H), 5.61 (d, J=7.6 Hz, 2H), 5.45 (t, J=9.6 Hz, 1H), 5.15-5.02 (m, 2H), 4.67 (d, J=10 Hz, 1H) 3.63 (s, 3H), 2.04-1.98 (m, 9H).
 ESI-MS m/z: 785 (M$^+$+1)

Compound OHPAS-D13-2
 Yield 78%
 ESI-MS m/z: 685 (M$^+$+1)

Compound OHPAS-D12
 Yield 85%
 ESI-MS m/z: 785 (M$^+$+1)

Compound OHPAS-D12a
 Yield 70%
 ESI-MS m/z: 559 (M$^+$+1)

Example 4

Synthesis of Drug Derivatives

Example 4.1.1

Preparation of Q-1 and Q-2

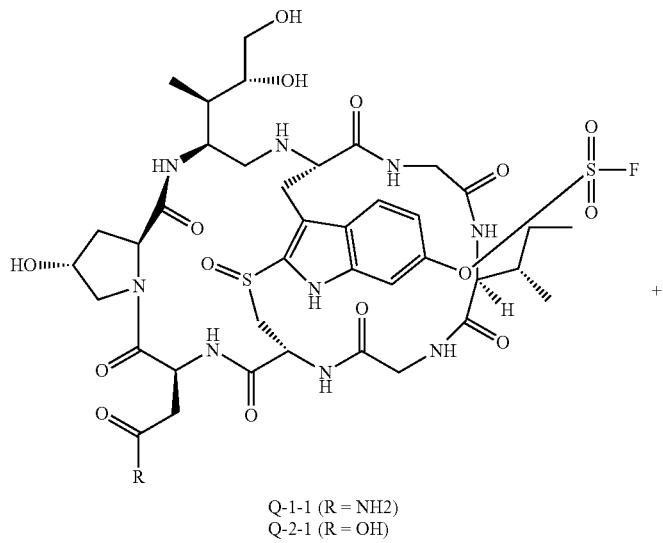

Q-1-1 (R = NH2)
Q-2-1 (R = OH)

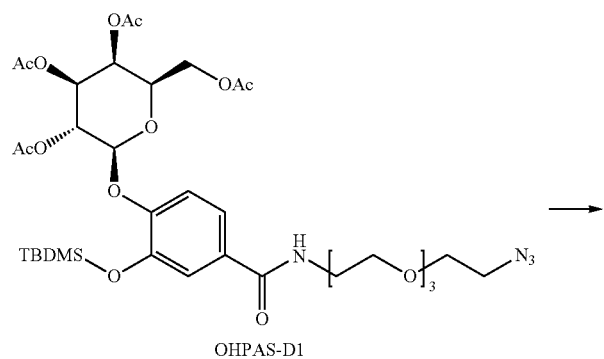

OHPAS-D1

-continued

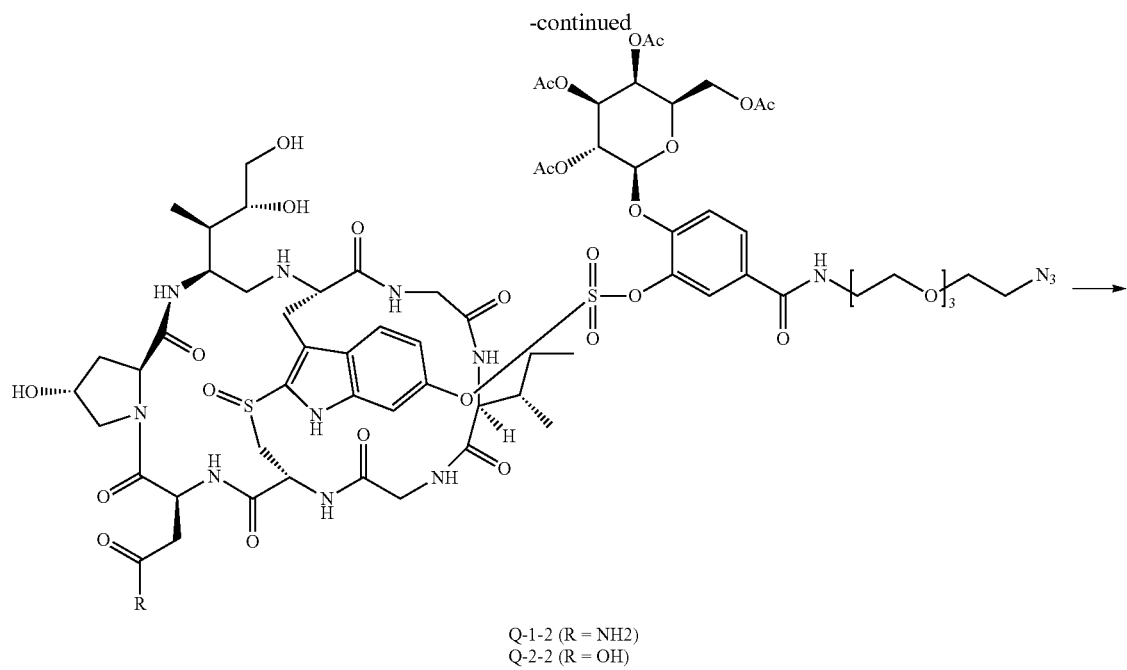

Q-1-2 (R = NH2)
Q-2-2 (R = OH)

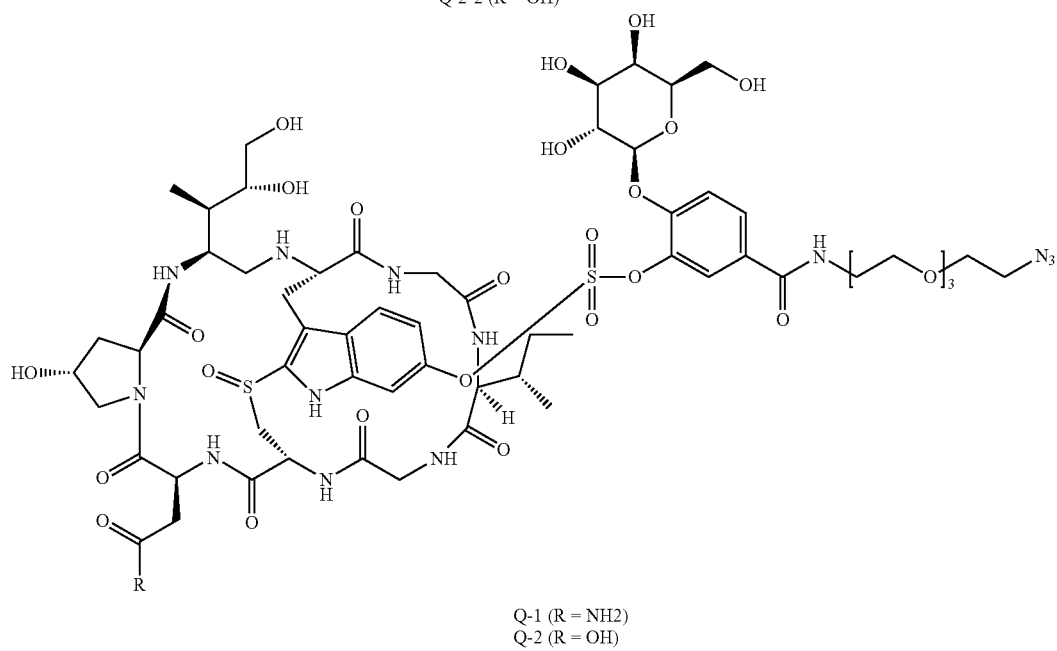

Q-1 (R = NH2)
Q-2 (R = OH)

Q-1-1 and Q-2-1 were prepared from β- & α-amanitin by a similar method of preparing compound OHPAS-D3-1 in Example 3.3.

Preparation of Compound Q-1-1
Yield 89%; ESI-MS m/z: 1002 (M+1).

Preparation of Compound Q-2-1
Yield 88%; ESI-MS m/z: 1003 (M+1).

Q-1-2 and Q-2-2 were prepared by a similar method of preparing compound OHPAS-D3-2 in Example 3.3.

Preparation of Compound Q-1-2
Yield 62%; ESI-MS m/z: 1666 (M$^{+1}$).

Preparation of Compound Q-2-2
Yield 41%; ESI-MS m/z: 1667 (M$^{+1}$).

Preparation of Compound Q-1
To a solution of compound Q-1-2 (50 mg, 0.30 μmol) in MeOH (4 mL) was added K$_2$CO$_3$ (21 mg, 1.5 μmol) at 0° C. under N$_2$ atmosphere. After stirring for 0.5 hr, the resulting residue was diluted with DMSO (0.5 mL) and purified by Prep-HPLC to obtain compound Q-1 (10.5 mg, 19%) as pale yellow solid.

ESI-MS m/z: 1498 (M$^{+1}$).

Preparation of Compound Q-2
Yield 61% over 2 steps; ESI-MS m/z: 1499 (M$^{+1}$).

Example 4.1.2

Preparation of Q-1a

Compound Q-1a was synthesized via a similar synthetic route as described in Example 4.1.1.

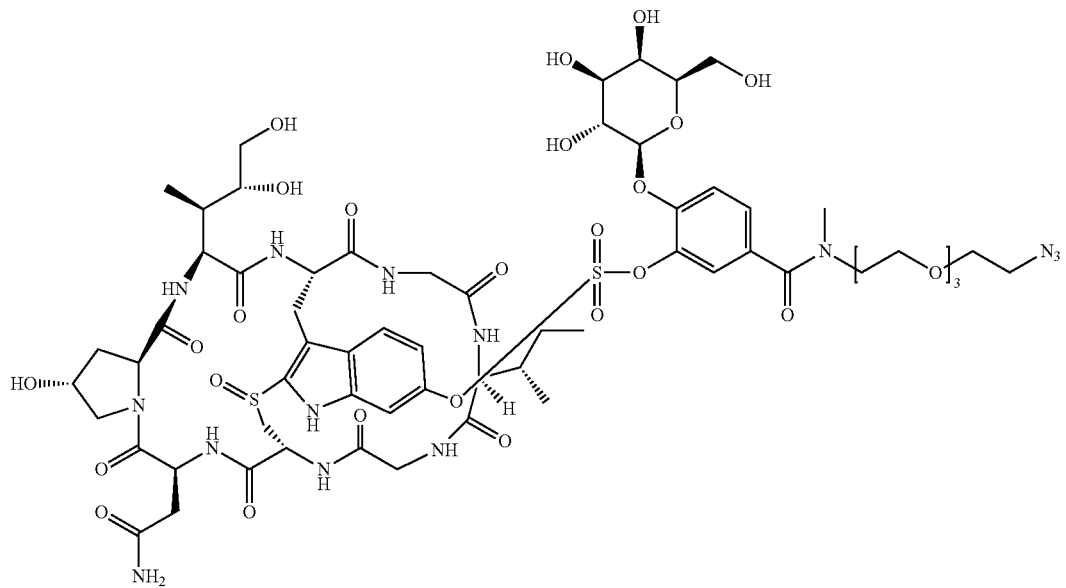
Preparation of Compound Q-1a
Yield 83%; ESI-MS m/z: 756 (M/2$^{+1}$).
Example 4.2
Preparation of Q-3
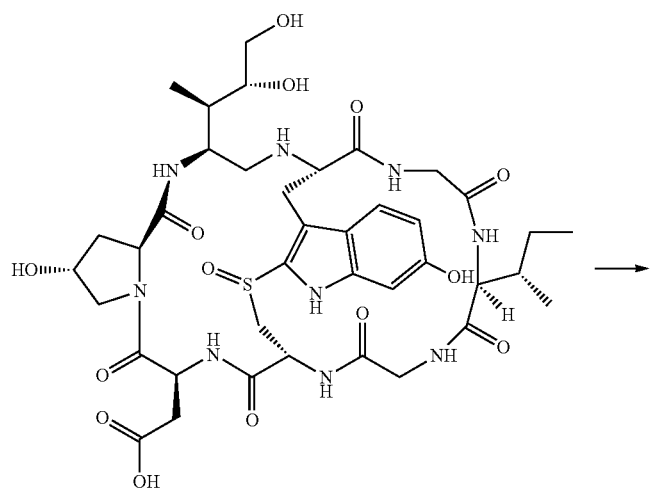

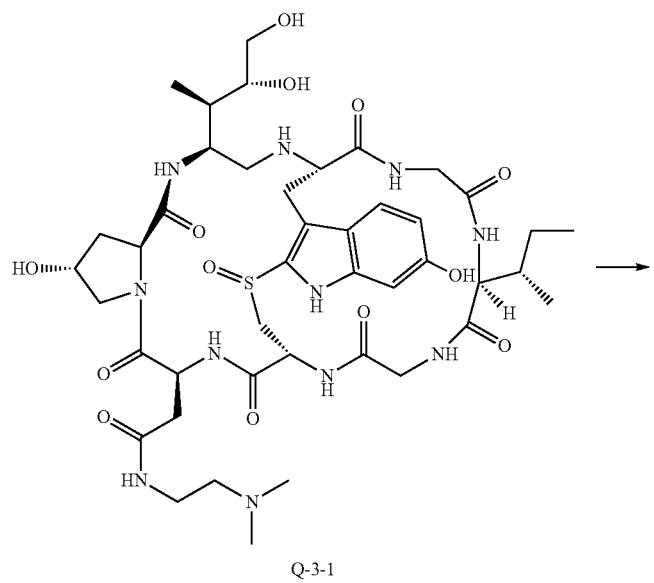
Q-3-1
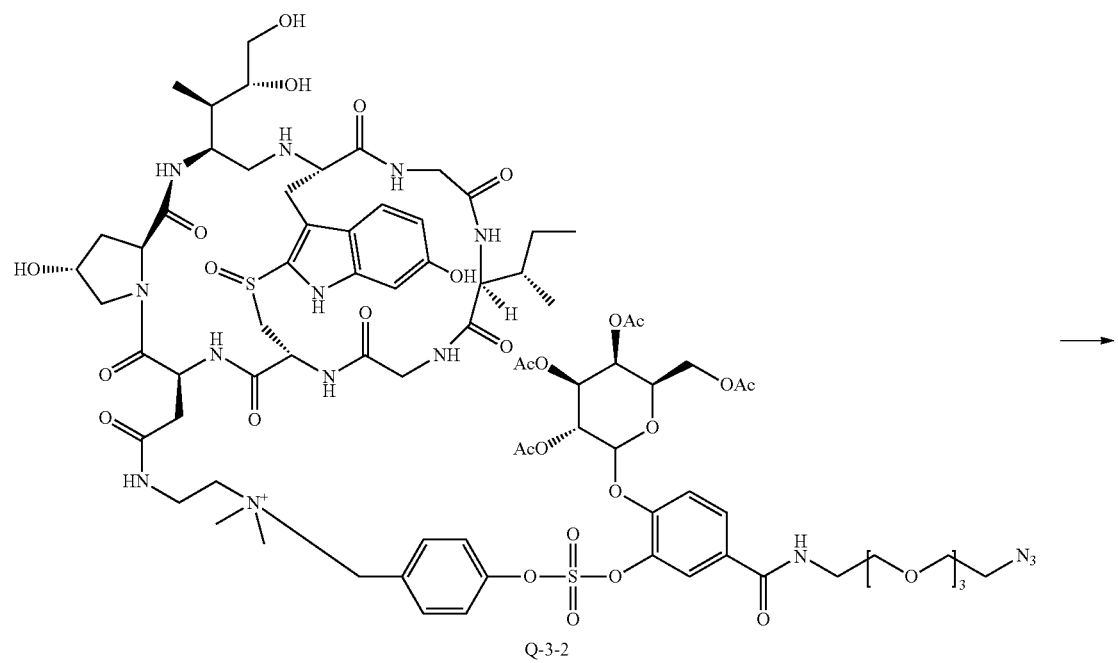
Q-3-2

-continued

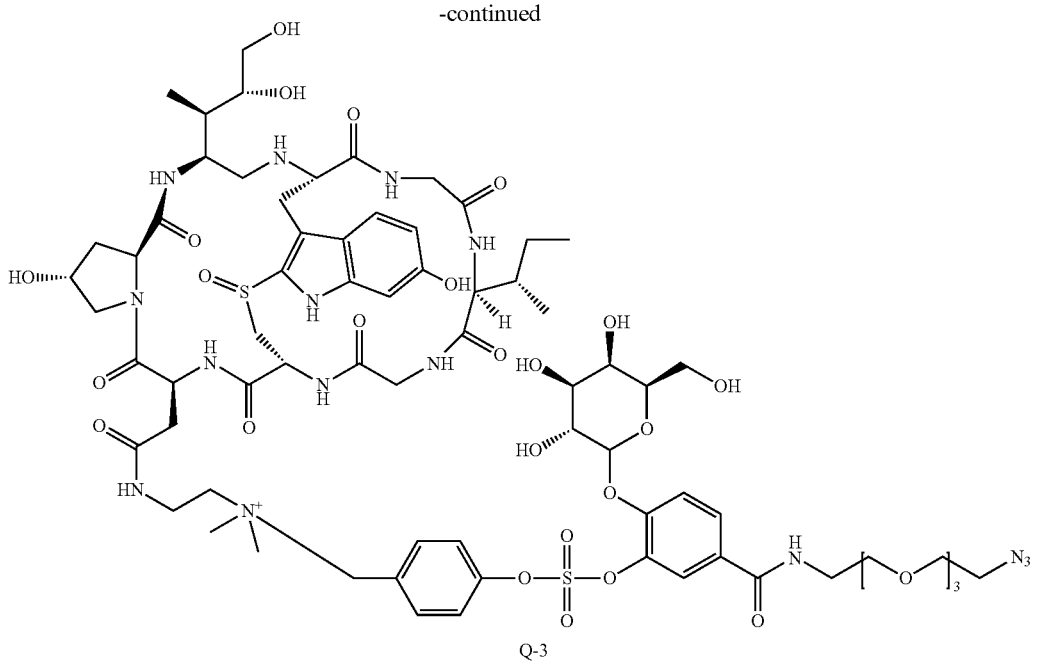

Q-3

Preparation of Compound Q-3-1

To a solution of β-Amanitin (40 mg, 43.5 μmol) in DMF (3 mL) was added N,N-dimethylethylenediamine (10 μl, 47.83 μmol) and TBTU (46 mg, 0.11 mmol) and TEA (18 μl, 0.13 mmol) at room temperature. After stirring overnight at 40° C. heat, the mixture was separated and purified by Prep-HPLC to obtain compound Q-3-1 (28 mg, 65%).

ESI-MS m/z: 991 (M+1)

Preparation of Compound Q-3-2

To a solution of compound Q-3-1 (20 mg, 20.2 μmol) and OHPAS-D3 (30 mg, 24.2 μmol) in DMF (2 mL) was added dropwise DIPEA (11 μL, 60.6 mmol) under $N_2$ atmosphere. After stirring overnight at room temperature, the mixture was separated and purified by Prep-HPLC to obtain compound Q-3-2 (34 mg, Yield 65%), ESI-MS m/z: 992 (M/2$^+$$_1$).

Compound Q-3 was synthesized via a similar synthetic route as described in Example 4.1.1.

Preparation of Compound Q-3

Yield 71%; ESI-MS m/z: 838 (M/2$^{+1}$)

Example 4.3

Preparation of Q-4 and Q-4a

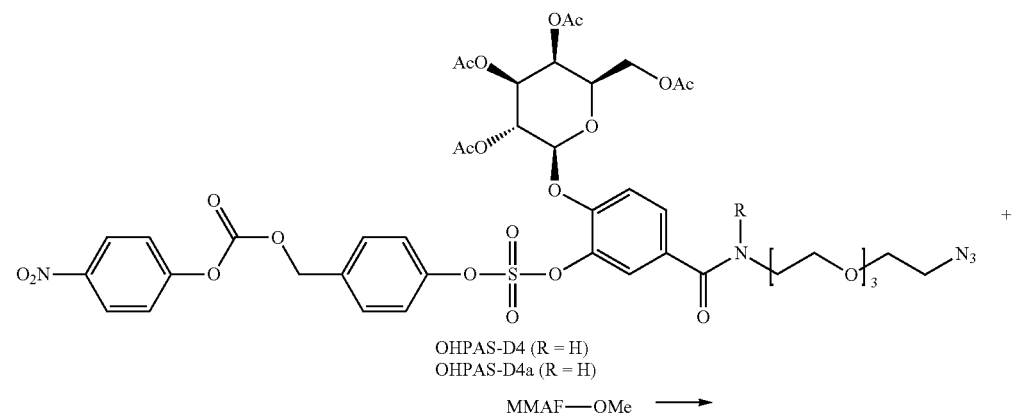

OHPAS-D4 (R = H)
OHPAS-D4a (R = H)

MMAF—OMe ⟶

-continued
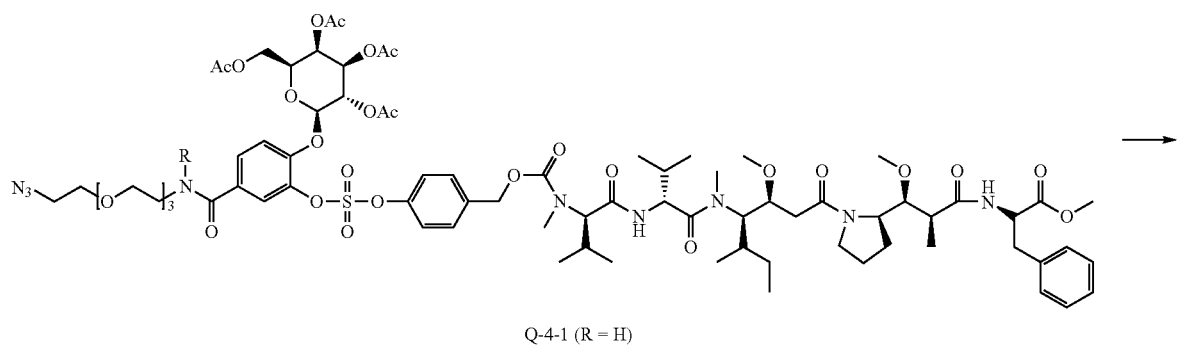
Q-4-1 (R = H)
Q-4-1a (R = Me)
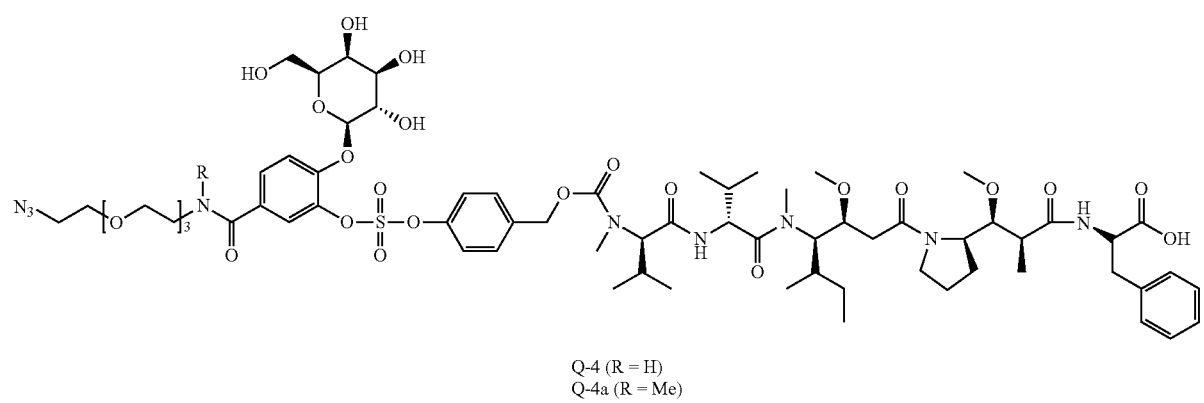
Q-4 (R = H)
Q-4a (R = Me)
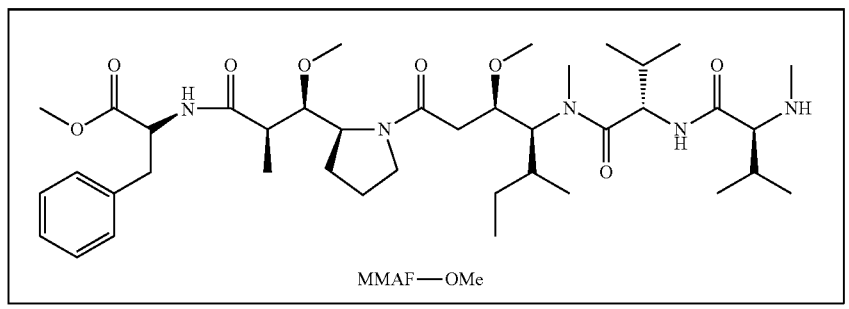
MMAF—OMe

Preparation of Compound Q-4-1

To a solution of compound OHPAS-D4 (65 mg, 0.063 mmol) and MMAF-OMe (52 mg, 0.069 mmol) in DMF (1 mL) was added HOBt (2 mg, 0.013 mmol), DIPEA (12 μL, 0.069 mmol), and pyridine (330 μL) at room temperature under $N_2$ atmosphere. After stirring overnight, the mixture was adjusted to have pH of 2 to 3 with 1N HCl, extracted with EA (8 mL×2). The organic layer was washed distilled water (8 mL) and brine (12 mL), dried over anhydrous $Na_2SO_4$, filtered and concentrated under reduced pressure. The residue was subjected to column chromatography to obtain compound Q-4-1 (73 mg, 71%).

ESI-MS m/z: 1644 ($M^{+1}$).

Compound Q-4 was synthesized via a similar synthetic route as described in Example 4.2.

Preparation of Compound Q-4

Yield 69%; ESI-MS m/z: 1462 ($M^{+1}$).

Compound Q-4a was synthesized via a similar synthetic route as described above.

Preparation of Compound Q-4-1a

Yield 99%; ESI-MS m/z: 828 ($M/2^{+1}$).

Preparation of Compound Q-4a

Yield 46%; ESI-MS m/z: 738 ($M/2^{+1}$).

Example 4.4

Preparation of Q-5

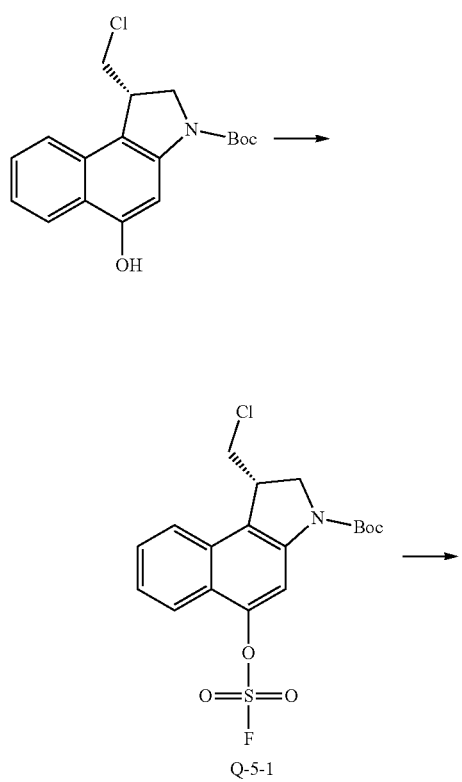

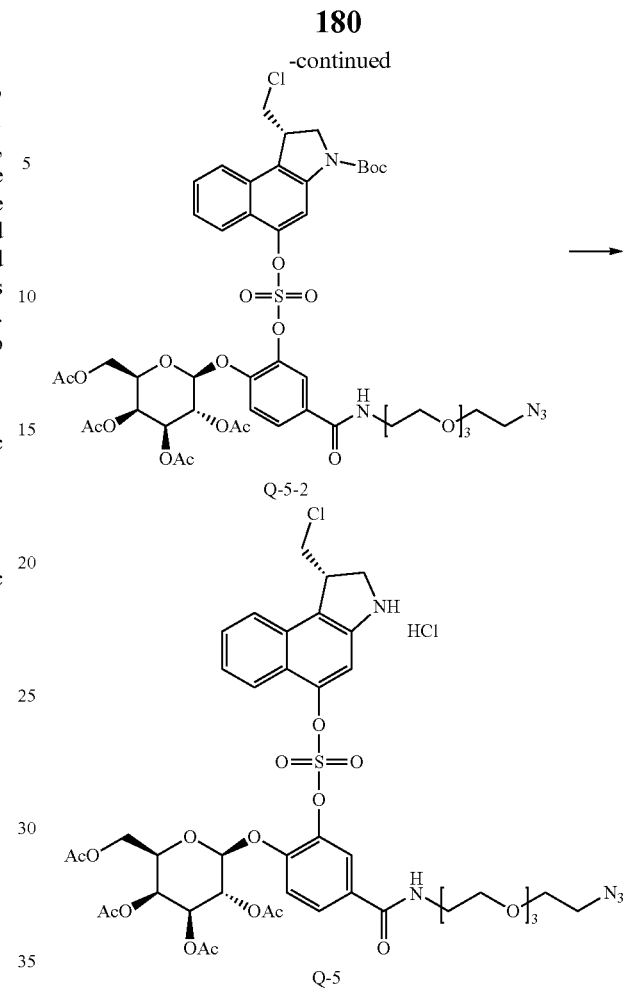

Q-5-1 and Q-5-2 were synthesized via a similar synthetic route as described in Example 3.5.

Preparation of Compound Q-5-1

Yield 98%

1H NMR (400 MHz, $CDCl_3$) δ 8.37 (brs, 1H) 8.02 (d, J=8.8 Hz, 1H), 7.75 (d, J=8.4 Hz, 1H), 7.61 (t, J=7.2, 1H), 7.51 (t, J=8.0 Hz, 1H), 4.32 (brs, 1H), 4.18 (t, J=8.8, 1H), 4.05 (m, 1H), 3.93 (dd, J=11.2, 2.8 Hz, 1H), 3.52 (t, J=10.8 Hz, 1H), 1.61 (s, 9H). ESI-MS m/z: 438.2 ($M^{+1}$+Na).

Preparation of Compound Q-5-2

Yield 79%

$^1$H NMR (400 MHz, $CDCl_3$) δ 8.09 (brs, 1H) 7.77 (m, 3H), 7.57 (t, J=7.2 Hz, 1H), 7.46 (t, J=7.6 Hz, 1H), 7.32 (m, 1H), 6.78 (m, 1H), 5.56 (m, 1H), 5.46 (d, J=2.8 Hz, 1H), 5.22 (d, J=7.6 Hz, 1H), 5.12 (dd, J=10.4, 3.2 Hz, 1H), 4.30 (brs, 1H), 4.25-4.02 (m, 5H), 3.93 (m, 1H), 3.60 (m, 15H), 3.31 (m, 2H), 2.17 (s, 3H), 2.04 (s, 3H), 1.95 (s, 6H), 1.56 (s, 9H). ESI-MS m/z: 1080.6 ($M^{+1}$).

Preparation of Compound Q-5

Compound Q-5-2 (50 mg, 0.046 mmol) was dissolved in 4N HCl in 1,4-dioxane (1 mL) at 0° C. under $N_2$ atmosphere. After stirring at room temperature for 4 hours, the mixture was diluted with DCM (5 mL) and concentrated. The compound Q-5 was used directly in the next step without further purification (47 mg, 99%).

ESI-MS m/z: 980.5 ($M^{+1}$).

Example 4.5
Preparation of Q-6
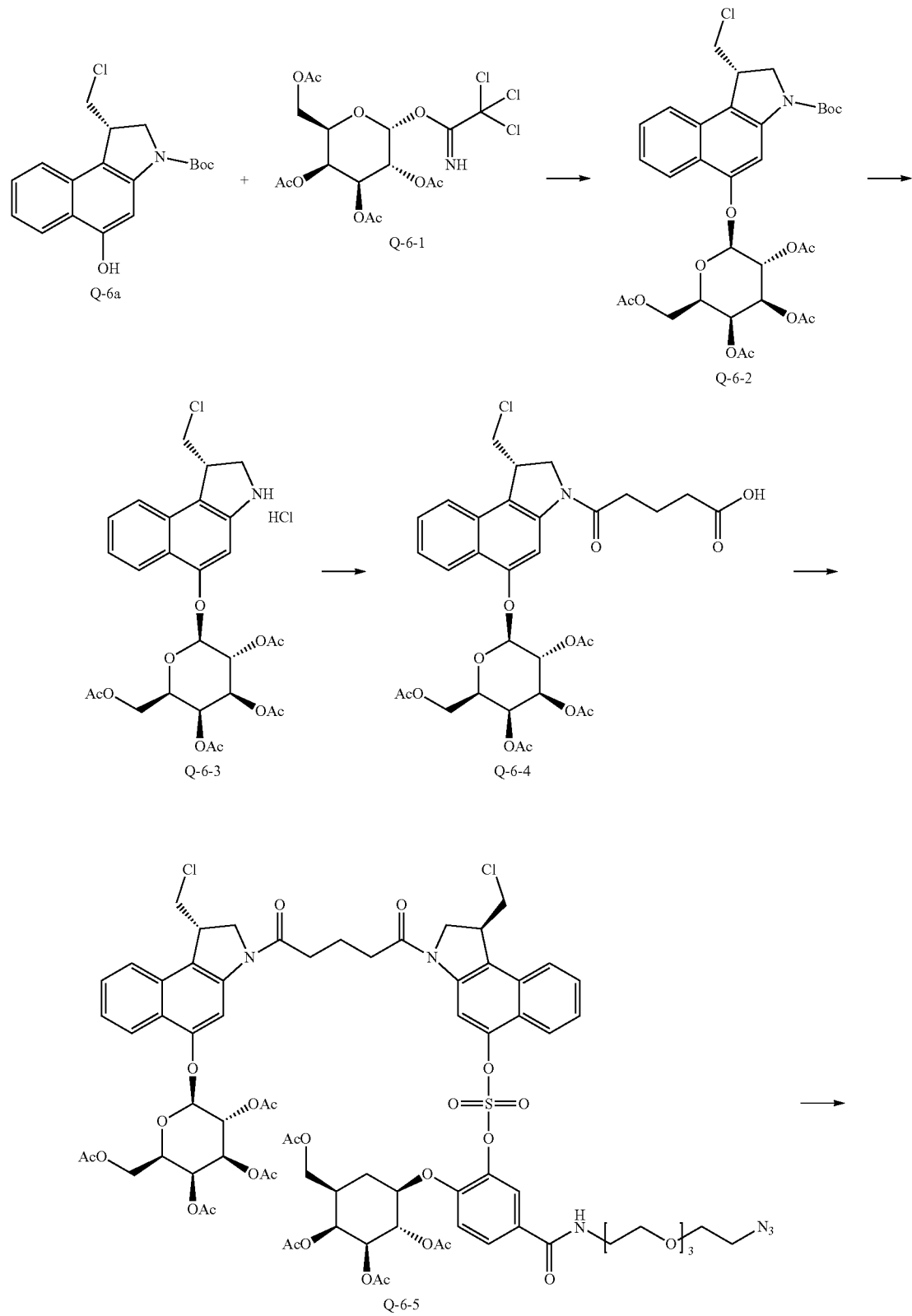

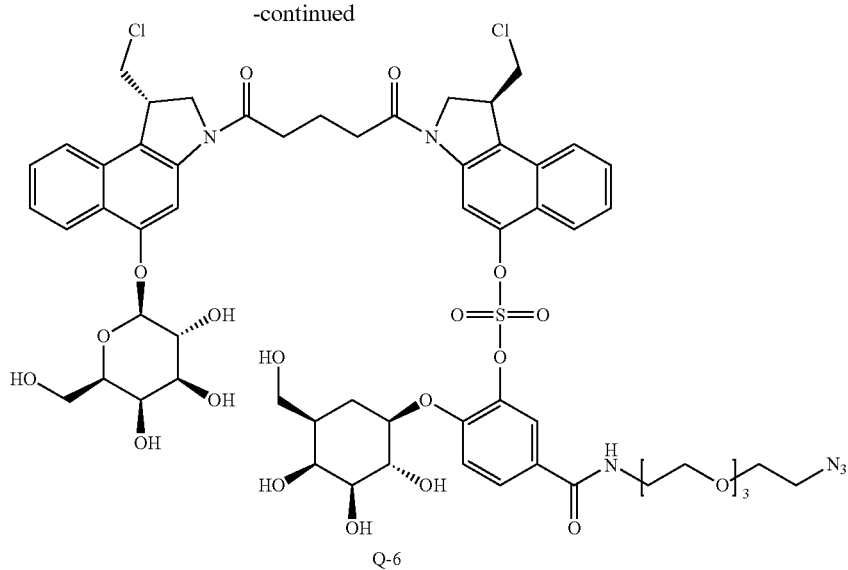

Q-6

Preparation of Compound Q-6a

Compound Q-6a was synthesized by a similar synthetic route as described in document [see Mol. Pharmaceutics 2015, 12, 1813-1835]

Preparation of Compound Q-6-1

Compound Q-6-1 was synthesized by a similar synthetic route as described in document [see Angew. Chem. Int. Ed. 2010, 49, 7336-7339 and WO2015110935A1]

Preparation of Compound Q-6-2

To a solution of compound Q-6a (80 mg, 0.239 mmol) and compound Q-6-1 (118 mg, 0.239 mmol) in DCM (10 mL) was added molecular sieve and $BF_3.OEt_2$ (14.8 µL, 0.12 mmol) at 0° C. under $N_2$ atmosphere. After stirring for 2 hours, the mixture was filtered through Celite® and washed with DCM (50 mL) and concentrated under reduced pressure. The residue was purified by column chromatography to obtain compound Q-6-2 (105 mg, 66%) as white foam.

$^1$H NMR (400 MHz, $CDCl_3$) δ 8.12 (d, J=8.0 Hz, 1H), 7.89 (brs, 1H), 7.63 (d, J=8.0 Hz, 1H), 7.50 (m, 1H), 7.35 (m, 1H), 5.70 (m, 1H), 5.51 (s, 1H), 5.33 (m, 1H), 5.20 (m, 1H), 4.23 (m, 3H), 4.11 (m, 2H), 3.93 (m, 2H), 3.42 (t, J=10.8 Hz, 1H), 2.18 (s, 3H), 2.08 (s, 3H), 2.04 (s, 3H), 2.00 (s, 3H), 1.55 (s, 9H). ESI-MS m/z: 564.4 ($M^{+1}$).

Preparation of Compound Q-6-3

Compound Q-6-2 (100 mg, 0.15 mmol) was dissolved in DCM (2 mL) and then 4N HCl in 1,4-dioxane (1 mL) was added at 0° C. under $N_2$ atmosphere. After stirring for 4 hours, the reaction was concentrated under reduced pressure. The reaction mixture was stirred at room temperature for 4 hours under $N_2$. The compound Q-6-2 was used directly in the next step without further purification (90 mg, 99%).

ESI-MS m/z: 564.2 ($M^{+1}$).

Preparation of Compound Q-6-4

To a solution of compound Q-6-3 (90 mg, 0.149 mmol) in THF (5 mL) was added glutaric anhydride (18.8 µL, 0.164 mmol), $Et_3N$ (52 µL, 0.373 mmol) and 4-DMAP (2 mg, 0.015 mmol) at room temperature under $N_2$ atmosphere. The reaction mixture was stirred at room temperature for 2 hours and purified by Prep-HPLC, which obtained compound Q-6-4 (30 mg, 30%) as white solid.

Preparation of Compound Q-6-5

To a solution of compound Q-6-4 (30 mg, 0.043 mmol) and compound Q-5 (51 mg, 0.05 mmol) in DMF (3 mL) was added EDC.HCl (27.2 mg, 0.142 mmol) at 0° C. under $N_2$ Atmosphere. After stirring for 11 hours, the mixture was purified by Prep-HPLC to obtained compound Q-6-5 (20 mg, 28%) as light brown solid.

ESI-MS m/z: 821.7 ($M^{+1}/2$).

Preparation of Compound Q-6

To a solution of compound Q-6-5 (10 mg, 0.006 mmol) in MeOH (1.5 mL) was added NaOMe 25% in MeOH (11 µL, 0.048 mmol) at 0° C. under $N_2$ atmosphere. The reaction mixture was stirred at room temperature for 1 hours under $N_2$ atmosphere and adjusted to pH 7 by addition of 5% TFA in ACN solution. The mixture was purified by Prep-HPLC to obtain compound Q-6 (5 mg, 63%) as pale yellow solid.

ESI-MS m/z: 1305.3 ($M^{+1}$).

Example 4.6
Preparation of Q-7
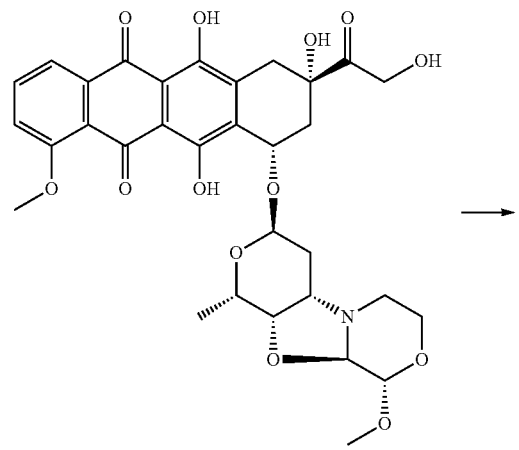
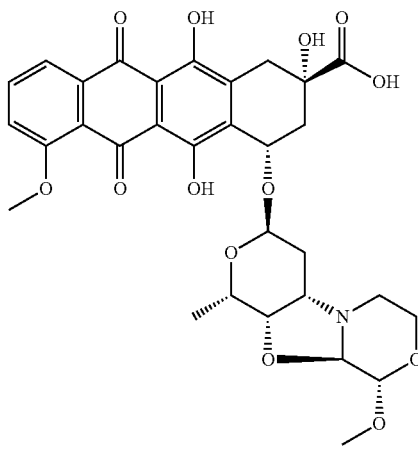
Q-7a
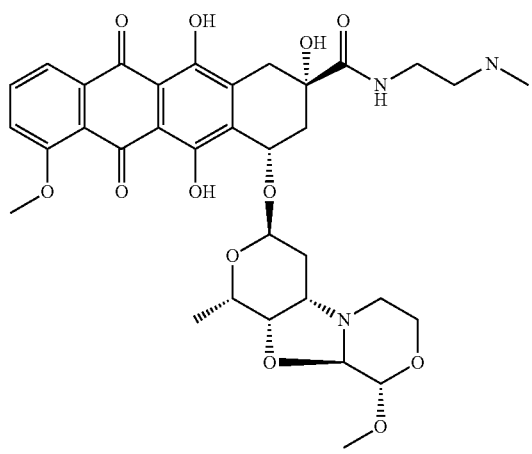
Q-7b
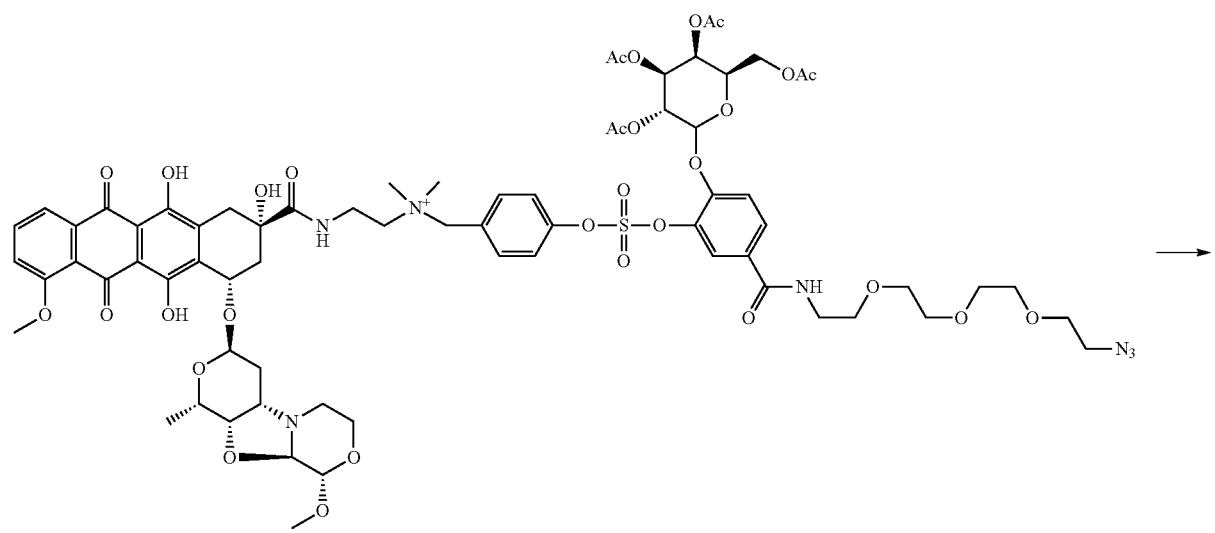
Q-7-1

-continued

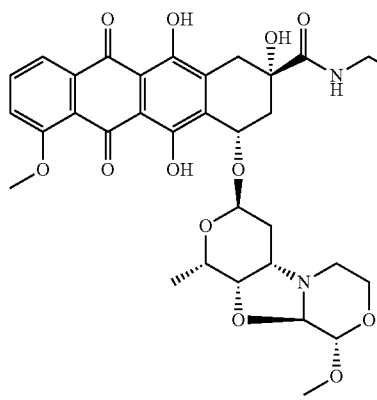
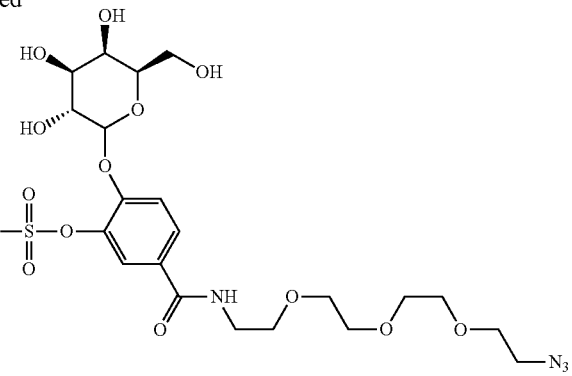

Q-7

Preparation of Compound Q-7a

To a solution of PNU-159682 (52 mg, 0.081 mmol) in MeOH (5 ml)/distilled water (3 mL) was added NaIO$_4$ (18 mg, 0.081 mmol) at room temperature. After stirring 2 hours, the mixture was concentrated under reduced pressure, which produced the crude compound Q-7a (51 mg, 99%). ESI-MS m/z: 628 (M$^{+1}$).

Preparation of Compound Q-7b

To a solution of compound Q-7a (51 mg, 0.081 mmol) in dry DCM (5 mL) was added 2-(dimethylamino)ethyl amine (6.1 μl, 0.089 mmol) and TEA (34 μl, 0.243 mmol), TBTU (52 mg, 0.162 mmol) at room temperature. After stirring 1 hours, the mixture was diluted with DCM (2×8 mL). The organic layer was washed with H$_2$O (8 mL), died over anhydrous Na$_2$SO$_4$, filtered and concentrated under reduced pressure. The residue was purified by column chromatography to produce compound Q-7b (38 mg, 67%).

ESI-MS m/z: 698 (M$^{+1}$).

Q-7 was prepared by a similar method of preparing compound Q-3-2 in Example 4.2.

Preparation of Compound Q-7-1

Yield 38%; ESI-MS m/z: 1551 (M$^{+1}$).

Preparation of Compound Q-7

Yield 54%; ESI-MS m/z: 1383 (M$^+$).

Example 4.7

Preparation of Q-8

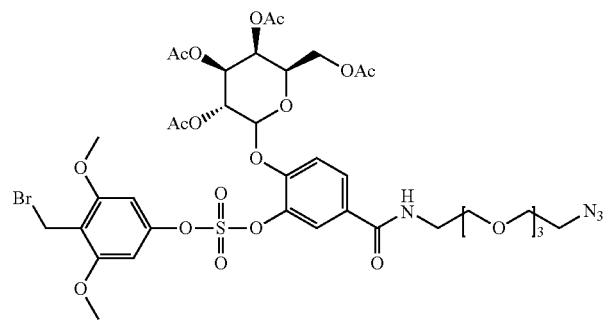

OHPAS-D6

+ N,N-Dimethyl-MMAF—OMe

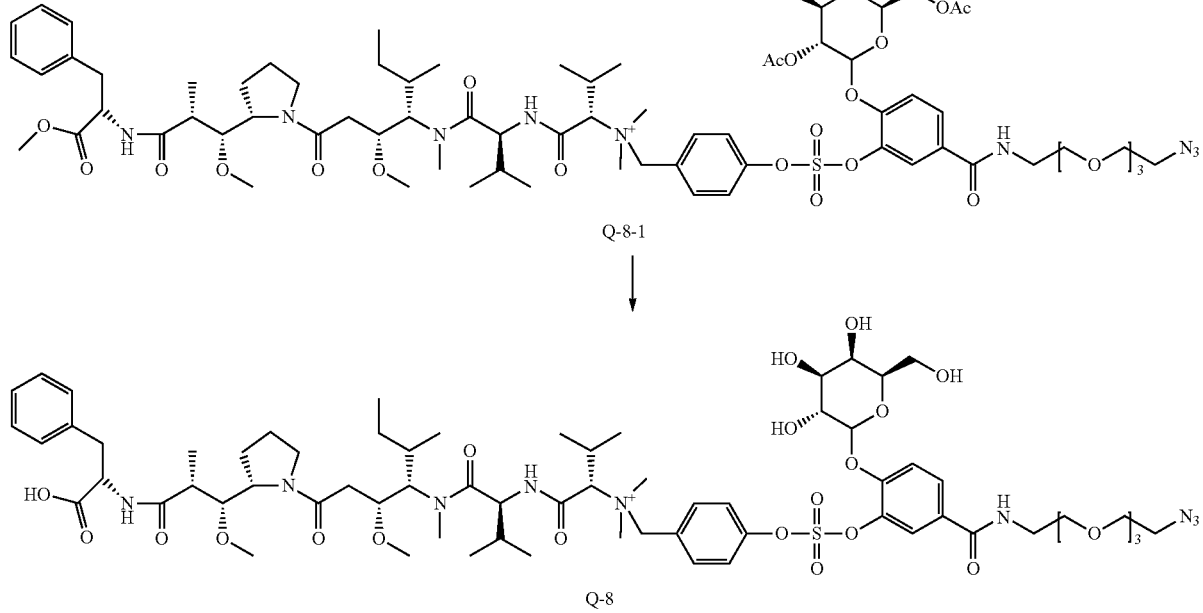

Q-8-1

Q-8

Compound Q-8 was synthesized via a similar synthetic route as described in Example 4.6.

Preparation of Compound Q-8-1

Yield 42%; ESI-MS m/z: 837 (M/2$^{+1}$).

Preparation of Compound Q-8

Yield 81%; ESI-MS m/z: 746 (M/2$^{+1}$).

Example 4.8

Preparation of Benzodiazepine Monomer Derivatives

Example 4.8.1

Preparation of Pyrrolo-Benzodiazepine Monomer (Hereinafter "PBD-Monomer")

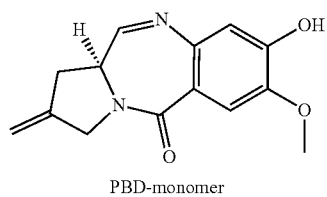

PBD-monomer

PBD monomer was obtained by performing a reaction in a similar method described in EP20071813614.

Example 4.8.2

Preparation of Indolino-Benzodiazepine Monomer (Hereinafter "IBD-Monomer")

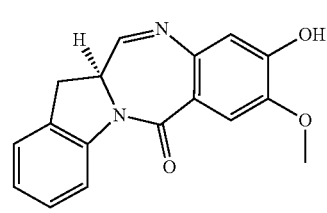

IBD-monomer

IBD monomer was obtained by performing a reaction in a similar synthetic method described in WO2010091150.

Example 4.8.3

Preparation of MCBI-Monomer

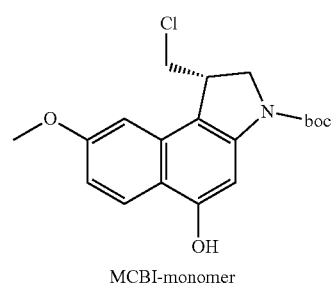

MCBI-monomer

IBD monomer was obtained by performing a reaction in a similar synthetic method described in U.S. Pat. No. 5,985,908.

Example 4.8.4

Preparation of Tetrahydroisoquinolino-Benzodiazepine Monomer (Hereinafter "TBD-Monomer")

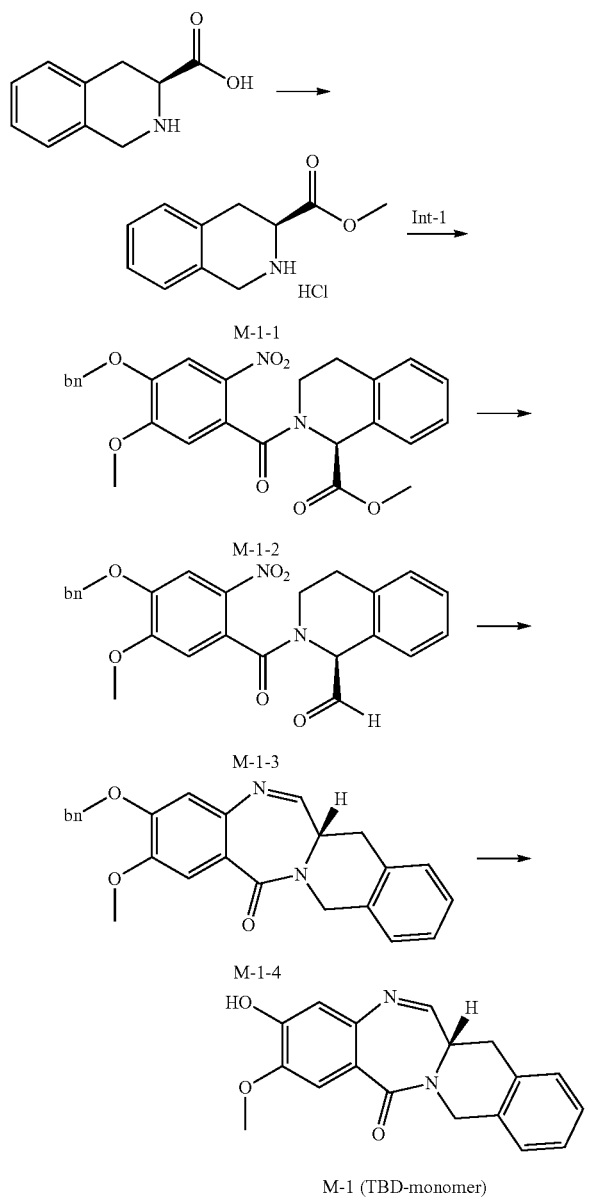

Preparation of Compound M-1-1

To a solution of (s)-(−)-1,2,3,4,-tetrahydroisoquinoline-3-carboxylic acid (5.0 g, 28.22 mmol) in MeOH (140 mL) was added dropwise $SOCl_2$ (2.30 mL, 31.04 mmol) to 0° C. under $N_2$ atmosphere. After stirring for 21 hours at 40° C., the mixture was concentrated under reduced pressure. Diethyl ether (50 mL) was added to give a precipitate, which was filtered with diethyl ether to obtain compound M-1-1 (6.42 g, yield 99%).

$^1$H NMR (400 MHz, DMSO-d6) δ 10.02 (s, 2H), 7.27 (s, 4H), 4.60-4.56 (m, 1H), 4.39-4.29 (m, 2H), 3.82 (s, 3H), 3.19-3.12 (m, 2H); ESI-MS m/z: 192 (M$^+$+1).

Preparation of Compound M-1-2

To a solution of compound Int-1 (9.07 g, 28.22 mmol) in anhydrous THF (50 ml) was added compound M-1-1 (6.42 g, 28.22 mmol) in THF (100 mL) and TEA (7.9 mL, 56.43 mmol) at 0° C. After stirring for 2 hours at room temperature, the reaction was diluted with distilled water (500 mL) and extracted with EA (800 mL). The organic layer was dried over anhydrous $Na_2SO_4$, filtered and concentrated under reduced pressure. The residue was purified by column chromatography to obtain compound M-1-2 (12.01 g, 90%). ESI-MS m/z: 477 (M$^+$+1).

Preparation of Compound M-1-3

To a solution of compound M-1-2 (4 g, 8.39 mmol) in anhydrous DCM (18 mL) and toluene (52 mL) was added dropwise DIBAL (16.8 mL, 16.79 mmol, 1.0M in toluene) at −78° C. under $N_2$ atmosphere. After stirring for 4 hours at −78° C., the reaction was quenched with MeOH (0.4 mL) and 2N HCl (25 mL) at −78° C. The mixture was diluted with water (100 mL) and extracted with EA (500 mL). The organic layer was dried over anhydrous $Na_2SO_4$, filtered and concentrated under reduced pressure. The residue was purified by column chromatography to obtain compound M-1-3 (3.07 g, 82%). ESI-MS m/z: 447 (M$^+$+1).

Preparation of Compound M-1-4

To a solution of compound M-1-3 (3 g, 6.72 mmol) in THF (130 mL) and distilled water (86 mL) was added $Na_2S_2O_4 \cdot 2H_2O$ (11.3 g, 53.76 mmol) at room temperature. After stirring for 5 h, the reaction was concentrated under reduced pressure four times by using toluene as a co-solvent, thereby removing water. Then, the obtained yellow solid was dissolved in anhydrous MeOH (220 mL) and acetyl chloride (4.8 mL, 67.19 mmol) was added thereto. After stirring 15 minutes, the reaction mixture was adjusted to pH 7 by addition of saturated $NaHCO_3$ solution and diluted with distilled water (100 mL) and extracted with EA (250 mL×2). The organic layer was dried over anhydrous $Na_2SO_4$, filtered and concentrated under reduced pressure. The residue was purified by column chromatography to obtain compound M-1-4 (2.48 g, 93%).

$^1$H NMR (400 MHz, CDCl$_3$) δ 7.55 (s, 1H), 7.45-7.27 (m, 10H), 6.84 (s, 1H), 5.24-5.15 (m, 2H), 5.00 (d, J=15.2, 1H), 4.56 (d, J=15.6, 1H), 3.97 (s, 3H), 3.93-3.92 (m, 1H), 3.31-3.12 (m, 2H). ESI-MS m/z: 399 (M$^+$+1).

Preparation of Compound M-1

To a solution of compound M-1-4 (1 g, 2.51 mmol) in anhydrous DCM (10 mL) was added the methane sulfonic acid (5 mL) in DCM (10 mL) at 0° C. After stirring for 3 h at 0° C., the mixture was quenched with $NaHCO_3$ solution, water (100 mL) and extracted with EA (400 mL). The organic layer was dried over anhydrous $Na_2SO_4$, filtered and concentrated under reduced pressure. The residue was purified by column chromatography to obtain compound M-1 (703 mg, 91%).

$^1$H NMR (400 MHz, CDCl$_3$) δ 7.54 (s, 1H), 7.48 (d, J=4.8 Hz, 1H), 7.37-7.26 (m, 4H), 6.88 (s, 1H), 6.03 (s, 1H), 5.00 (d, J=15.6 Hz, 1H), 4.56 (d, J=15.6 Hz, 1H), 3.98 (s, 3H), 3.95-3.90 (m, 1H), 3.30-3.13 (m, 2H). ESI-MS m/z: 309 (M$^+$+1).

Example 4.8.5
Preparation of PBD Compound Bearing C2-Aryl Substituents
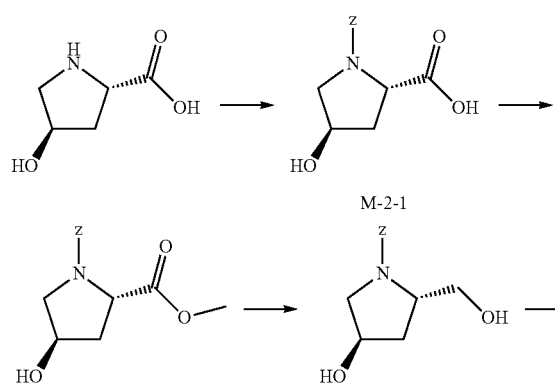
M-2-1
M-2-2  M-2-3
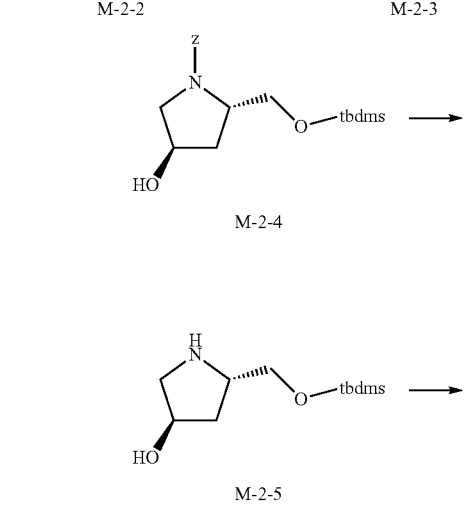
M-2-4
M-2-5
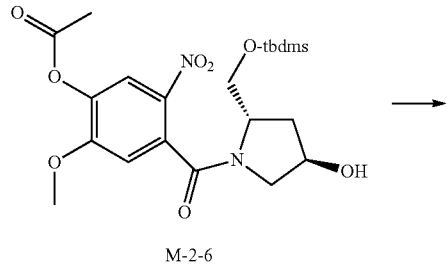
M-2-6
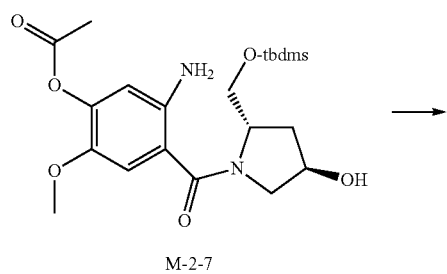
M-2-7
-continued
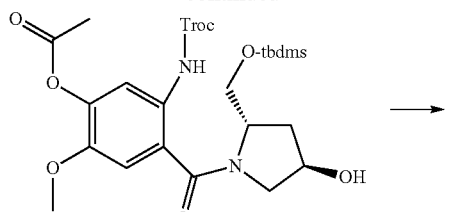
M-2-8
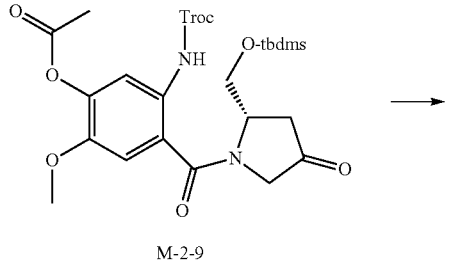
M-2-9
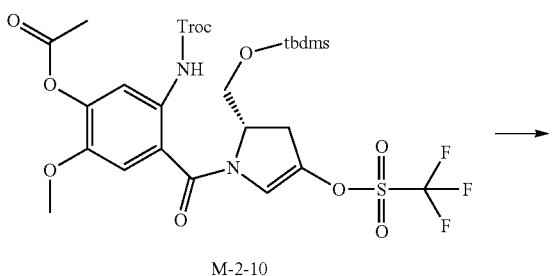
M-2-10
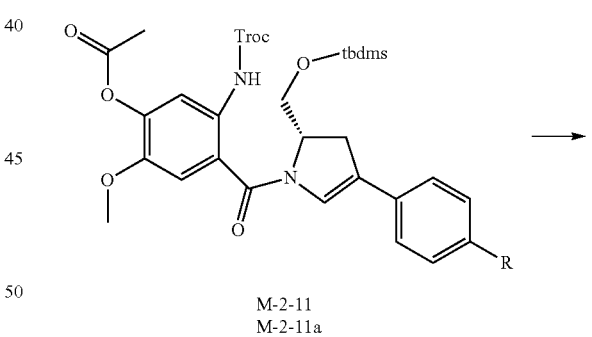
M-2-11
M-2-11a
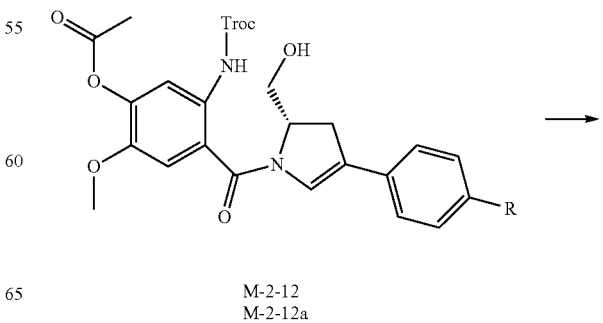
M-2-12
M-2-12a

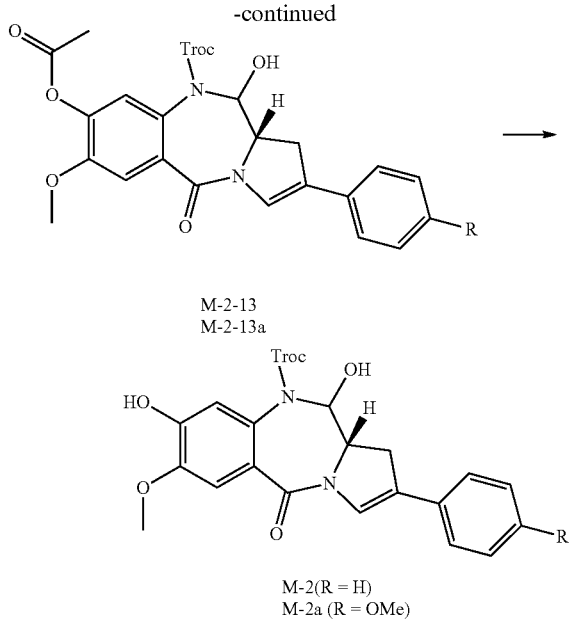

M-2-13
M-2-13a

M-2(R = H)
M-2a (R = OMe)

Preparation of Compound M-2-1

To a stirred solution of trans-4-hydroxy-L-proline (30 g, 230 mmol) and NaHCO$_3$ (43 g, 570 mmol, 2.5 eq.) in H$_2$O/toluene (500 mL/120 mL) at room temperature under N$_2$ atmosphere was added Cbz-Cl (37.4 mL, 260 mmol, 1.15 eq.) After addition, the mixture was stirred at this temperature overnight. The mixture was extracted with EA (500 mL×3). The organic layer was washed with water (500 mL×2) and dried over anhydrous Na$_2$SO$_4$, filtered and concentrated under reduced pressure to obtain compound M-2-1 (57.5 g, 95%) as light brown oil.

$^1$H NMR (400 MHz, DMSO-d6) δ 12.7 (brs, 1H), 7.40-7.28 (m, 5H), 5.18-5.02 (m, 2H), 4.31-4.24 (m, 2H), 3.51-3.35 (m, 2H), 2.23-2.10 (m, 1H), 2.00-1.87 (m, 1H); ESI-MS m/z: 266 (M$^+$+1).

Preparation of Compound M-2-2

A brown solution of compound M-2-1 (57.5 g, 220 mmol) in MeOH (400 mL) at 0° C. under N$_2$ atmosphere was treated with thionyl chloride (45.3 mL, 610 mmol, 2.8 eq.). The reaction mixture was allowed to warm up to room temperature and stirred overnight. The mixture was concentrated under reduced pressure to obtain compound M-2-2 (60.5 g, quant.) as light brown oil.

$^1$H NMR (400 MHz, CDCl$_3$) δ 7.38-7.28 (m, 5H), 5.23-5.09 (m, 2H), 4.56-4.47 (m, 2H), 3.80 (s, 1H), 3.76-3.66 (m, 2H), 3.58-3.52 (m, 1H) 2.38-2.26 (m, 1H), 2.16-2.08 (m, 1H); ESI-MS m/z: 270 (M$^+$+1).

Preparation of Compound M-2-3

A brown solution of compound M-2-2 (60.5 g, 220 mmol) in anhydrous THF (500 mL) at 0° C. under N$_2$ atmosphere was treated with LiBH$_4$ (3.9 g, 180 mmol, 0.8 eq) and stirred for 30 minutes. And then the mixture was stirred at room temperature for further 2 days. The mixture was quenched with water (200 mL) and 2N HCl (100 mL). The organic solvent was removed by rotary evaporator. The residue was extract with EA (500 mL×3) and then the organic layer was dried over anhydrous Na$_2$SO$_4$, filtered and concentrated under reduced pressure to obtain compound M-2-3 (54.6 g, 98%) as light brown oil.

1H NMR (400 MHz, CDCl$_3$) δ 7.39-7.30 (m, 5H), 5.21-5.12 (m, 2H), 4.66 (d, J=7.2 Hz, 1H), 4.39 (s, 1H), 4.21 (q, J=7.6, 7.2 Hz, 1H), 3.76 (t, J=9.6 Hz, 2H), 3.66-3.58 (m, 1H), 3.50 (dd, J=8.0, 4.0 Hz, 1H), 2.10-2.23 (m, 1H), 1.78-1.64 (m, 1H); ESI-MS m/z: 252 (M$^+$+1).

Preparation of Compound M-2-4

A brown solution of M-2-3 (53 g, 210 mmol) in anhydrous DCM (500 mL) at room temperature under N$_2$ atmosphere was treated with t-butyldimethylsilyl chloride (25.4 g, 170 mmol, 0.8 eq.), TEA (30 mL, 210 mmol, 1.0 eq.) and DBU (6.3 mL, 42.2 mmol, 0.2 eq). After addition, the mixture was stirred overnight. The reaction mixture was washed with NH$_4$Cl (300 mL) followed by brine (300 mL), and then the organic layer was dried over anhydrous Na$_2$SO$_4$, filtered and concentrated under reduced pressure. The residue was purified by column chromatography (Hex:EA=1:1) to obtain compound M-2-4 (48.2 g, 63%) as light brown oil.

$^1$H NMR (400 MHz, CDCl$_3$) δ 7.38-7.28 (m, 5H), 5.20-5.08 (m, 2H), 4.50 (s, 1H), 4.12-4.00 (m, 1H), 3.97 (dd, J=6.4, 4.0 Hz, 1H), 3.71 (dd, J=5.6, 4.8 Hz, 1H), 3.66-3.58 (m, 1H), 3.52-3.48 (m, 1H), 2.28-2.18 (m, 1H), 2.02-1.92 (m, 1H), 0.10-0.08 (m, 6H); ESI-MS m/z: 366 (M$^+$1).

Preparation of Compound M-2-5

Palladium on carbon, 5% Pd/C (1.3 g, 1.23 mmol, 0.03 eq.) was added to a stirred solution of M-2-4 (15 g, 41.0 mmol) in EA (50 mL) under N$_2$ atmosphere. The flask was flushed by bubbling hydrogen gas through the solution at room temperature. The mixture was stirred at the same temperature for 5 hours. The mixture was diluted with EA (30 mL), filtered through Celite®, the Celite® plug washed with EA (50 mL×2). The filtrate was concentrated under reduced pressure to obtain compound M-2-5 (9.5 g, quant.) as a light brown oil.

$^1$H NMR 400 MHz, CDCl$_3$) δ 4.41 (brs, 1H), 3.60-3.44 (m, 3H), 3.12 (dd, J=7.2 Hz, 4.8 Hz, 1H), 2.89 (d, J=12 Hz, 1H), 1.84-1.79 (m, 1H), 1.74-1.67 (m, 1H), 0.89 (s, 9H), 0.06 (s, 6H); ESI-MS m/z: 232 (M$^+$1).

Preparation of Compound M-2-6

A brown solution of compound M-2-5 (11.9 g, 51.42 mmol) and Int-2 (14.4 g, 56.6 mmol, 1.1 eq.) in anhydrous THF (400 ml) at 0° C. under N$_2$ atmosphere was treated with DIPEA (26.9 mL, 154.3 mmol, 3.0 eq.) and stirred for 5 hours. The reaction mixture was diluted with distilled water (50 mL) and extracted with EA (150 mL×2). The organic layer was dried over anhydrous Na$_2$SO$_4$, filtered and concentrated under reduced pressure. The residue was purified by column chromatography (Hex:EA=2:1 to 2:1) to obtain compound M-2-6 (20 g, 8 3%) as yellow form solid.

$^1$H NMR (400 MHz, CDCl$_3$) δ 7.95 (s, 1H), 6.87 (s, 1H), 4.60-4.51(m, 1H), 4.49-4.41 (m, 1H), 4.24-4.08 (m, 1H), 3.91 (s, 3H), 3.80-3.68 (m, 1H), 3.37 (dd, J=7.6 Hz, 4.0 Hz, 1H), 3.14 (d, J=10.4 Hz, 1H), 2.35 (s, 3H), 2.18-2.08 (m, 1H), 0.91 (s, 9H), 0.1 (s 6H); ESI-MS m/z: 469 (M$^+$1).

Preparation of Compound M-2-7

Palladium on carbon, 5% Pd/C (9.1 g, 4.27 mmol, 0.1 eq.) was added to a stirred solution of M-2-6 (20 g, 42.68 mmol) in EA (213 mL) under N$_2$ atmosphere. The flask was flushed by bubbling hydrogen gas through the solution at room temperature. After stirring for 8 hours, the mixture was diluted with EA (50 mL), filtered through Celite®, the Celite® plug washed with EA (50 mL×2). The filtrate was concentrated under reduced pressure to obtain compound M-2-7 (18.5 g, 99%) as yellow form solid.

$^1$H NMR (400 MHz, CDCl$_3$) δ 6.81 (s, 1H), 6.44 (s, 1H), 5.79 (brs, 1H), 4.58-4.50 (m, 1H), 4.42-4.36 (m, 1H), 4.10 (brs, 1H), 3.79 (s, 3H), 3.59 (dd, J=8.4 Hz, 2.8 Hz, 1H), 3.50

(d, J=11.2 Hz, 1H), 2.30-2.24 (m, 1H), 2.06-2.01 (m, 1H), 0.89 (s, 9H), 0.05 (d, J=1.6 Hz, 6H); ESI-MS m/z: 439 (M$^+$+1).

Preparation of Compound M-2-8

A yellow solution of M-2-7 (18.5 g, 42.18 mmol) in anhydrous DCM (210 mL) at 0° C. under N$_2$ atmosphere was treated with 2,2,2-trichloroethyl chloroformate (6.4 mL, 46.4 mmol, 1.1 eq.) and pyridine (6.9 mL, 87.4 mmol, 2.0 eq.) and then stirred for 3 hours. The mixture was washed with CuSO$_4$ solution (50 mL) and brine (100 mL×2). The organic layer was dried over anhydrous Na$_2$SO$_4$, filtered and concentrated under reduced pressure. The residue was purified by column chromatography (Hex:EA=2:1) to obtain compound M-2-8 (21.2 g, 82%) as brown form solid.

$^1$H NMR (400 MHz, CDCl$_3$) δ 8.87 (brs, 1H), 7.86 (s, 1H), 6.89 (s, 1H), 4.84 (d, J=12.8 Hz, 1H), 4.71 (d, J=10.8 Hz, 1H), 4.61 (brs, 1H), 4.45 (s, 1H), 4.20 (brs, 1H), 3.78 (s, 3H), 3.70-3.62 (m, 1H), 3.57 (s, 2H), 2.32 (s, 4H), 2.11-2.02 (m, 1H), 1.80 (s, 1H), 0.90 (s, 9H), 0.05 (s, 6H); ESI-MS m/z: 615 (M$^+$+1).

Preparation of Compound M-2-9

A homogeneous solution of oxalyl chloride (21 mL, 24.4 mmol, 1.5 eq) in anhydrous DCM (50 mL) at −78° C. under of N$_2$ atmosphere was treated with DMSO (3.5 mL, 48.9 mmol, 3.0 eq) in anhydrous DCM (20 mL) and stirred for 1 hour. A solution of M-2-8 (10 g, 0.33 mmol) in anhydrous DCM (100 mL) was added dropwise to the reaction mixture and stirred for 2 hours. The reaction mixture was treated with TEA (22.7 mL, 162.9 mmol, 10 eq.) and stirred for 1 hour at room temperature. The mixture was extracted with NH$_4$Cl solution (30 mL) and DCM (100 mL×2). The organic layer was dried over anhydrous Na$_2$SO$_4$, filtered and concentrated under reduced pressure. The residue was purified by column chromatography (Hex:EA=4:1 to 1: 1) to obtain compound M-2-9 (8.2 g, 83%) as brown form solid.

$^1$H NMR (400 MHz, CDCl$_3$) δ 8.68 (brs, 1H), 7.91 (s, 1H), 6.86 (s, 1H), 5.12 (brs, 1H), 4.80 (s, 2H), 4.13 (brs, 1H), 4.04 (d, J=17.2 Hz, 1H), 3.98-3.86 (m, 1H), 3.80 (s, 3H), 3.76-3.62 (m, 1H), 2.84-2.72 (m, 2H), 2.54 (d, J=17.2 Hz, 1H), 2.32 (s, 3H), 2.08-1.98 (m, 1H), 0.88 (s, 9H), 0.21 (s, 6H); ESI-MS m/z: 612 (M$^+$+1).

Preparation of Compound M-2-10

A yellow solution of M-2-9 (2.0 g, 3.27 mmol) and 2,6-lutidine (4.6 mL, 12 eq) in anhydrous DCM (100 mL) at −10° C. under N$_2$ atmosphere was treated with triflic anhydride (5.5 mL, 32.68 mmol, 10 eq.) and stirred for 6 hours. The reaction mixture was allowed to warm up to room temperature and stirred for a further 1 hour. The mixture was diluted with distilled water (50 mL) and extracted with DCM (100 mL×2). The organic layer was dried over anhydrous Na$_2$SO$_4$, filtered and concentrated under reduced pressure. The residue was purified by column chromatography (Hex:EA=4:1) to obtain compound M-2-10 (502 mg, 21%) as yellow oil.

$^1$H NMR (400 MHz, CDCl$_3$) δ 8.78 (brs, 1H), 7.97 (s, 1H), 6.85 (s, 1H), 6.80 (s, 1H), 4.86-4.72 (m, 3H), 4.20-4.32 (m, 1H), 3.80 (s, 3H), 3.76-3.68 (m, 1H), 3.20-3.00 (m, 2H), 2.33 (s, 3H), 0.89 (s, 9H), 0.06 (d, J=10.6 Hz 6H); ESI-MS m/z: 745 (M$^+$+1).

Preparation of Compound M-2-11

A yellow solution of M-2-10 (500 mg, 0.67 mmol) in toluene (4.0 mL), H$_2$O (0.6 mL) and ethanol (4.0 mL) at room temperature under N$_2$ atmosphere was treated with 4,4,5,5-tetramethyl-2-phenyl-1,3,2-dioxaborolane (164.6 mg, 0.81 mmol, 1.2 eq.), Pd(TPP)$_4$ (77.5 mg, 0.067 mmol, 0.1 eq) and TEA (234.2 uL, 1.68 mmol, 2.5 eq.) and then stirred for 3 hours. The mixture was diluted with distilled water (100 mL) and extracted with EA (100 mL). The organic layer was dried over anhydrous Na$_2$SO$_4$, filtered and concentrated under reduced pressure. The residue was purified by column chromatography (Hex:EA=3:1) to obtain compound M-2-11 (343 mg, 76%) as yellow form solid.

$^1$H NMR (400 MHz, CDCl$_3$) δ 8.76 (brs, 1H), 7.96 (s, 1H), 7.38-7.28 (m, 5H), 6.98 (s, 1H), 6.93 (s, 1H), 4.78-4.68 (m, 3H), 4.16-4.04 (m, 2H), 3.92-3.84 (m, 1H), 3.79 (s, 3H), 3.24-3.12 (m, 1H), 3.08-2.90 (m, 1H), 2.34 (s, 3H), 0.85 (s, 9H), 0.05 (s, 6H); ESI-MS m/z: 673 (M$^+$+1).

Preparation of Compound M-2-12

A yellow solution of M-2-11 (340 mg, 0.505 mmol) in THF (4.0 mL) and H$_2$O (2.0 mL) at room temperature under N$_2$ atmosphere was treated with acetic acid (8.0 mL) and stirred for 20 hours. The mixture was diluted with distilled water (10 mL) and extracted with EA (20 mL×2). The organic layer was dried over anhydrous Na$_2$SO$_4$, filtered and concentrated under reduced pressure. The residue was purified by column chromatography (Hex:EA=2:1) to obtain compound M-2-12 (250 mg, 89%) as yellow form solid.

$^1$H NMR (400 MHz, CDCl$_3$) δ 8.86 (brs, 1H), 7.87 (s, 1H), 7.36-7.28 (m, 5H), 7.00 (s, 1H), 6.85 (s, 1H), 4.93 (brs, 1H), 4.75 (s, 2H), 4.16-4.10 (m, 3H), 3.82 (s, 3H), 3.64 (s, 1H), 3.33 (t, J=13.6, 5.6 Hz, 1H), 2.77 (d, J=17.2 Hz, 1H) 2.34 (s, 3H); ESI-MS m/z: 558 (M$^+$+1).

Preparation of Compound M-2-13

A homogeneous solution of oxalyl chloride (58 uL, 0.67 mmol, 1.5 eq.) in anhydrous DCM (1.0 mL) at −78° C. under of N$_2$ atmosphere was treated with DMSO (80 uL, 1.12 mmol, 3.0 eq.) in anhydrous DCM (1.0 mL) and stirred for 15 minutes. A solution of M-2-12 (250 mg, 0.45 mmol) in anhydrous DCM (3.0 mL) was added dropwise to the reaction mixture and stirred for 3 hours followed by TEA (500 uL, 3.58 mmol, 8.0 eq.) and stirred for a further 30 minutes at room temperature. The reaction mixture was diluted with distilled water (5.0 mL) and extracted with EA (15 mL×2). The organic layer was dried over anhydrous Na$_2$SO$_4$, filtered and concentrated under reduced pressure. The residue was purified by column chromatography (Hex:EA=3:1) to obtain compound M-2-13 (202 mg, 81%) as yellow form solid.

$^1$H NMR (400 MHz, CDCl$_3$) δ 7.45 (s, 1H), 7.38 (s, 5H), 7.12 (s, 1H), 5.84 (brs, 1H), 5.18 (d, J=10.6 Hz, 1H), 4.31 (d, J=12.8 Hz, 1H), 4.18-4.06 (m, 3H), 3.84 (s, 3H), 3.72 (s, 1H), 3.43 (t, J=10.0 Hz, 1H), 3.12 (d, J=18.0 Hz, 1H), 2.32 (s, 3H); ESI-MS m/z: 556 (M$^+$+1)

Preparation of Compound M-2

A yellow solution of M-2-13 (175 mg, 0.31 mmol) in MeOH (16 mL) and H$_2$O (3.0 mL) at room temperature under N$_2$ atmosphere was treated with K$_2$CO$_3$ (109 mg, 0.79 mmol, 2.5 eq.) and stirred for 2 hours. The mixture was diluted with water (5 mL) and extracted with EA (10 mL×2). The organic layer was dried over anhydrous Na$_2$SO$_4$, filtered and concentrated under reduced pressure. The residue was purified by column chromatography (Hex:EA=2:1) to obtain compound M-2 (135 mg, 85%) as yellow form solid.

$^1$H NMR (400 MHz, CDCl$_3$) δ 7.49 (s, 1H), 7.37 (s, 5H), 6.94 (s, 1H), 5.93 (brs, 1H), 5.88-5.82 (m, 1H), 5.14 (d, J=11.6 Hz, 1H), 4.32 (d, J=10.8 Hz, 1H), 4.18-4.00 (m, 2H), 3.97 (s, 3H), 3.41 (t, J=9.6 Hz, 1H), 3.10 (d, J=16.0 Hz, 1H); ESI-MS m/z: 514 (M$^+$+1)

M-2a was prepared by a similar method of preparing compound M-2.

Preparation of Compound M-2-11a

Yield 59% as yellow foam solid; $^1$H NMR (400 MHz, CDCl$_3$) δ 8.78 (brs, 1H), 7.95 (s, 1H), 7.22 (d, J=8.4 Hz, 2H), 6.97 (s, 1H), 6.85 (d, J=8.4 Hz, 1H), 6.81 (s, 1H), 4.87-4.69 (m, 3H), 4.09-4.02 (m, 1H), 3.93-3.88 (m, 1H), 3.80 (d, J=8.0 Hz, 6H), 3.20-3.12 (m, 1H), 3.05-2.97 (m, 1H), 2.34 (s, 3H), 0.85 (s, 9H), 0.60 (d, J=8.4 Hz, 6H); ESI-MS m/z: 703 (M⁺+1).

Preparation of Compound M-2-12a

Yield 79% as yellow foam solid.

¹H NMR (400 MHz, CDCl₃) δ 8.85 (brs, 1H), 7.85 (s, 1H), 7.2 (d, J=8.8 Hz, 2H), 7.00 (s, 1H), 6.85 (d, J=7.2 Hz, 1H), 6.72 (s, 1H), 4.95-4.87 (m, 1H), 4.74 (d, J=2.8 Hz, 2H), 4.04-3.84 (m, 3H), 3.81 (d, J=3.6 Hz, 6H), 3.34-3.24 (m, 1H), 2.72 (dd, J=13.2, 3.2 Hz, 1H), 2.34 (s, 3H); ESI-MS m/z: 588 (M⁺+1).

Preparation of Compound M-2-13a

Yield 80% as yellow foam solid.

¹H NMR (400 MHz, CDCl₃) δ 7.37 (s, 2H), 7.32 (d, J=8.0 Hz, 2H), 7.11 (s, 1H), 6.90 (d, J=9.2 Hz, 2H), 5.86-5.81 (m, 1H), 5.18 (d, J=12 Hz, 1H), 4.30 (d, J=11.6 Hz, 1H), 4.10-4.05 (m, 1H), 3.90 (s, 3H), 3.83 (s, 3H), 3.73 (d, J=4.8 Hz, 1H), 3.44-3.35 (m, 1H), 3.12-3.05 (m, 1H), 2.37 (s, 3H); ESI-MS m/z: 586 (M⁺+1)

Preparation of Compound M-2a

Yield 75% as yellow foam solid.

¹H NMR (400 MHz, CDCl₃) δ 7.37 (s, 1H), 7.31 (d, J=8.8 Hz, 2H), 7.30 (s, 1H), 6.94 (s, 1H), 6.89 (d, J=8.8 Hz, 2H), 5.93 (s, 1H), 5.84 (dd, J=5.2, 4.4 Hz, 1H), 5.14 (d, J=11.6 Hz, 1H), 4.32 (d, J=12 Hz, 1H), 4.07-3.99 (m, 1H), 3.97 (s, 3H), 3.83 (s, 1H), 3.64 (d, J=4.4 Hz, 1H), 3.43-3.34 (m, 1H), 3.10-3.03 (m, 1H); ESI-MS m/z: 544 (M⁺+1)

Example 4.8.6

Preparation of Compound M-3

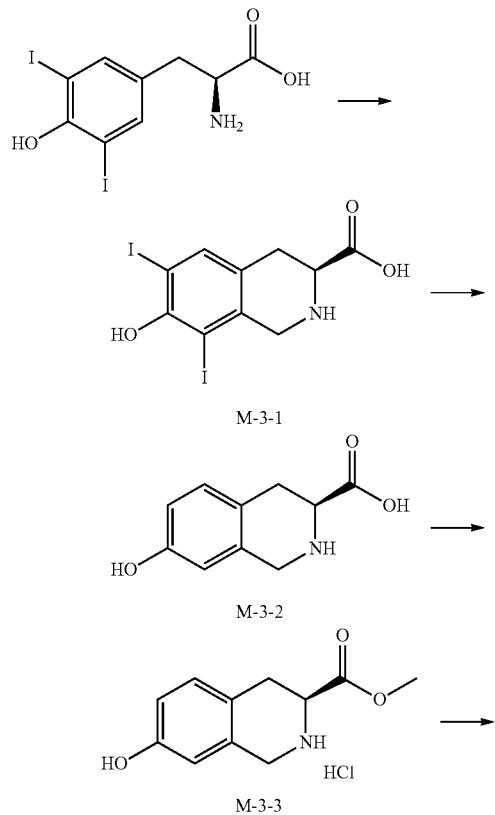

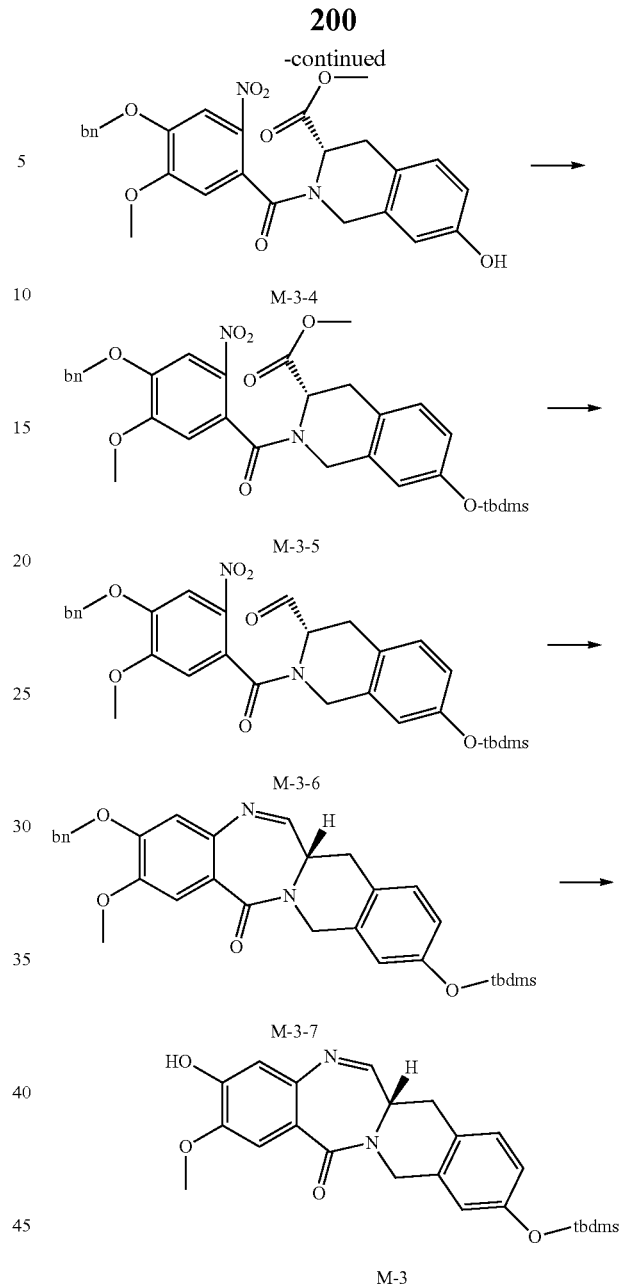

Preparation of Compound M-3-1

To a solution of (S)-2-amino-3-(4-hydroxy-3,5-diiodophenyl)propanoic acid (8.0 g, 18.48 mmol) in concentrated aqueous HCl (90 mL) was added 1,2-dimethoxyethane (7.5 mL) and paraformaldehyde (37% wt. in H₂O, 92.38 mmol). The mixture was stirred vigorously and slowly heated to 72° C. The reaction mixture was stirred overnight at 72° C. The suspension was then cooled in an ice bath and the solids collected by filtration, washed thoroughly with 1,2-dimethoxyethane (3×10 mL) and dried under vacuum to obtain compound M-3-1 (2.49 g, yield 28%).

¹H NMR (400 MHz, DMSO-d6) δ 10.02 (brs, 1H), 9.69 (s, 1H), 7.73 (s, 1H), 4.31 (dd, J=6.8 Hz, 4.4 Hz, 1H), 4.05 (q, J=18.8 Hz, 16 Hz, 2H), 3.21 (dd, J=12 Hz, 4.8 Hz, 1H), 3.12-3.02 (m, 1H); ESI-MS m/z: 446 (M⁺+1).

Preparation of Compound M-3-2

A mixture of M-3-1 (1.4 g, 3.1 mmol), TEA (1.4 mL, 10.38 mmol) and 5% Pd/C (335 mg, 0.16 mmol) in EtOH/

$H_2O$ (40 mL/mL) was stirred at room temperature under $H_2$ atmosphere for 3 hours. The mixture was filtered through Celite® and the filtrate concentrated. The resultant residue was diluted with water and the precipitate was filtered. The solid was washed with cold water and dried under high vacuum to obtain compound M-3-2 (337.3 mg, 60%).

$^1$H NMR (400 MHz, DMSO-d6) δ 9.55 (brs, 1H), 9.69 (s, 1H), 6.98 (d, J=9.0 Hz, 1H), 6.64 (d, J=8.4 Hz, 1H), 6.57 (s, 1H), 4.06 (s, 2H), 3.46 (dd, J=6.0 Hz, 4.8 Hz, 1H), 3.46 (dd, J=11.6 Hz, 5.2 Hz, 1H), 2.82-2.75 (m, 1H); ESI-MS m/z: 194 ($M^+$+1).

Preparation of Compound M-3-3

To a solution M-3-2 (337.3 mg, 1.74 mmol) in MeOH (5.0 mL) was added dropwise $SOCl_2$ (380 uL, 5.24 mmol) to 0° C. under $N_2$ atmosphere. After reflux for 2 hours, the reaction mixture was concentrated under reduced pressure and used directly in the next step without further purification (406 mg, yield 96%).

$^1$H NMR (400 MHz, DMSO-d6) δ 9.83 (brs, 2H), 9.56 (s, 1H), 7.05 (d, J=8.0 Hz, 1H), 6.70 (d, J=8.0 Hz, 1H), 6.63 (s, 1H), 4.53-4.49 (m, 1H), 4.28-4.22 (m, 2H), 3.81 (s, 1H), 3.18 (dd, J=11.6 Hz, 5.2 Hz, 1H), 3.04-2.97 (m, 1H); ESI-MS m/z: 208 ($M^+$+1).

Preparation of Compound M-3-4

To a solution of compound Int-1 (640.9 mg, 1.86 mmol) in anhydrous THF (4.0 mL) was added compound M-3-3 (350 mg, 1.43 mmol) in DMF (5.0 mL) followed by DIPEA (750 uL, 4.3 mmol) at 0° C. After stirring for 2 hours at room temperature, the mixture was diluted with distilled water (10 mL) and EA (2×50 mL). The organic layer was dried over anhydrous $Na_2SO_4$, filtered and concentrated under reduced pressure. The residue was purified by column chromatography to obtain compound M-3-4 (616 mg, 87%); ESI-MS m/z: 493 ($M^+$+1).

Preparation of Compound M-3-5 t-Butyldimethylsilyl chloride (188.5 mg, 1.25 mmol) was added to a solution of M-3-4 (616 mg, 1.25 mmol) and imidazole (102.2 mg, 1.50 mmol) in anhydrous DCM (6.0 mL) at 0° C. The reaction mixture was stirred overnight at room temperature. The reaction was quenched with 2N HCl (5 mL) and brine (10 mL) and extracted with DCM (10 mL×2). The organic layer was dried over anhydrous $Na_2SO_4$, filtered and concentrated under reduced pressure. The residue was purified by column chromatography to obtain compound M-3-5 (655.2 mg, 86%). ESI-MS m/z: 607 ($M^+$+1).

Preparation of Compound M-3-6

To a solution of compound M-3-5 (309 mg, 0.51 mmol) in anhydrous DCM (1.5 mL) and toluene (3.5 mL) at −78° C. under $N_2$ atmosphere was added dropwise DIBAL (990 uL, 0.99 mmol, 1.0M in toluene). After stirring for 1.5 hours, the reaction was quenched with MeOH (0.4 mL) and 2N HCl (15 mL) at −78° C., then extracted with $H_2O$ (20 mL) and EA (30 mL×2). The organic layer was dried over anhydrous $Na_2SO_4$, filtered and concentrated under reduced pressure. The residue was purified by column chromatography to obtain compound M-3-6 (280.4 mg, 95%); ESI-MS m/z: 577 ($M^+$+1).

Preparation of Compound M-3-7

To a solution of compound M-3-6 (280.4 mg, 0.49 mmol) in THF (6.0 mL) and distilled water (86 mL) was added $Na_2S_2O_4$ (677.2 mg, 3.89 mmol) at room temperature. After stirring for 5 h, the mixture was concentrated under reduced pressure four times by using toluene as a co-solvent, thereby removing water. The obtained yellow solid was dissolved in anhydrous MeOH (12 mL). Acetyl chloride (345.6 uL, 4.86 mmol) was added thereto. After stirring 15 minutes, the reaction mixture was filtered and filtrate was stirred for 1 h. The reaction mixture was adjusted to pH 7 by addition of saturated $NaHCO_3$ solution and diluted with distilled water (10 mL) and EA (2×50 mL). The organic layer was dried over anhydrous $Na_2SO_4$, filtered and concentrated under reduced pressure. The residue was purified by column chromatography to obtain compound M-3-7 (107.7 mg, 42%).

$^1$H NMR (400 MHz, $CDCl_3$) δ 7.55 (s, 1H), 7.48-7.31 (m, 6H), 7.16 (d, J=8.4 Hz, 1H), 6.94 (s, 1H), 6.82-6.76 (m, 2H), 5.28-5.15 (m, 2H), 4.93 (d, J=15.6 Hz, 1H), 4.46 (d, J=15.6 Hz, 1H), 3.97 (s, 3H), 3.92-3.86 (m, 1H), 3.18 (dd, J=9.6 Hz, 5.6 Hz, 1H), 3.10-3.02 (m, 1H), 0.99 (s, 9H), 0.21 (s, 6H); ESI-MS m/z: 529 ($M^+$+1).

Preparation of Compound M-3

To a solution of compound M-3-7 (53.4 mg, 0.1 mmol) in EtOH (6.0 mL) was added 5% Pd/C (107.5 mg, 0.05 mmol) under $N_2$ atmosphere. And then 1,4-cyclohexadiene (764.4 uL, 8.08 mmol) was added in reaction mixture. After stirring for 3 hours, the mixture was filtered through Celite® to remove Pd/C, and concentrated under reduced pressure. The residue was purified by column chromatography to obtain compound M-3 (30.3 mg, 68%).

$^1$H NMR (400 MHz, $CDCl_3$) δ 7.54 (s, 1H), 7.47 (d, J=5.2 Hz, 1H), 7.20 (d, J=8.82 Hz, 1H), 6.87 (s, 1H), 6.84-6.75 (m, 2H), 5.98 (s, 1H), 4.93 (d, J=15.6 Hz, 1H), 4.47 (d, J=15.2 Hz, 1H), 3.98 (s, 3H), 3.94-3.85 (m, 1H), 3.19 (dd, J=11.2 Hz, 5.2 Hz, 1H), 3.12-3.02 (m, 1H), 0.99 (s, 9H), 0.21 (s, 6H); ESI-MS m/z: 439 ($M^+$+1).

Example 4.8.7

Preparation of Compound Int-1

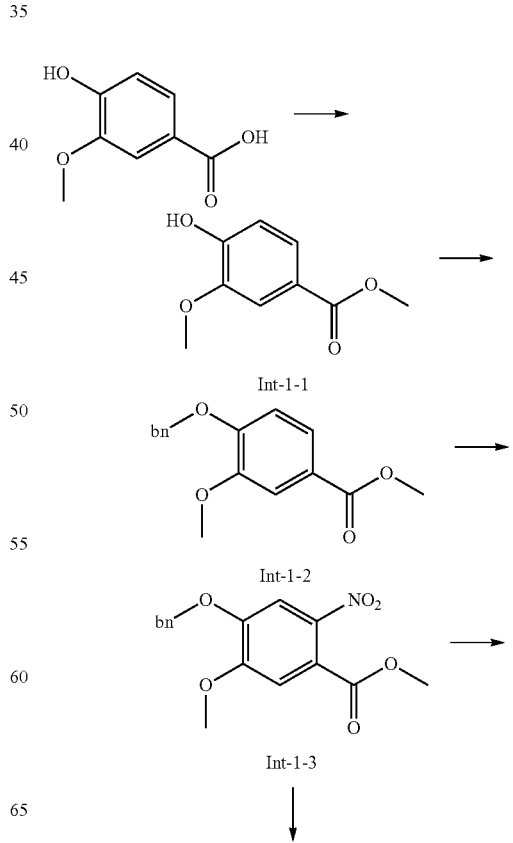

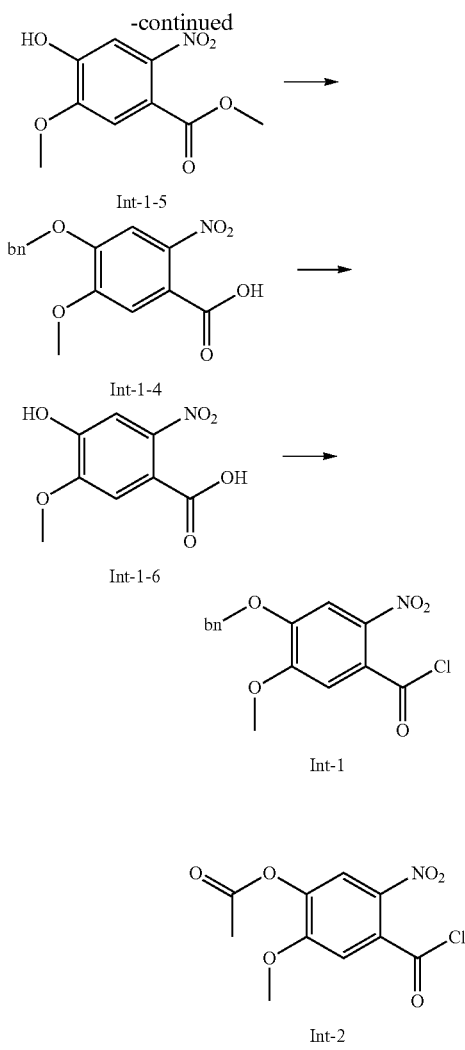

Preparation of Compound Int-1-1

To a solution of vanillic acid (50.0 g, 0.30 mol) in MeOH (700 mL) was added dropwise SOCl$_2$ (207 mL, 2.85 mol) at 0° C. under N$_2$ atmosphere. After stirring for 15 hours at room temperature, the reaction was adjusted to have pH of 7 to 8 with saturated aqueous NaHCO$_3$ solution and then diluted with distilled water (100 mL) and EA (400 mL). The organic layer was dried over anhydrous Na$_2$SO$_4$, filtered and concentrated under reduced pressure. The residue was purified by column chromatography to obtain compound Int-1-1 (54.2 g, quant).

$^1$H NMR (400 MHz, CDCl$_3$) δ 7.64 (dd, J=6.4, 1.6 Hz, 1H), 7.55 (s, 1H), 6.94 (d, J=8.4 Hz, 1H), 6.05 (s, 1H), 3.95 (s, 3H), 3.89 (s, 3H).

Preparation of Compound Int-1-2

To a solution of compound Int-1-1 (54.2 g, 0.30 mol) in DMF (200 mL) was added K$_2$CO$_3$ (61.6 g, 0.45 mol) and benzyl bromide (39.0 mL, 0.33 mol) under N$_2$ atmosphere. After stirring for 6 hours at 100° C., the mixture was cooling to room temperature and diluted with distilled water (100 mL) and EA (400 mL). The organic layer was dried over anhydrous Na$_2$SO$_4$, filtered and concentrated under reduced pressure. The residue was purified by column chromatography to obtain compound Int-1-2 (79.8 g, 98%).

$^1$H NMR (400 MHz, CDCl$_3$) δ 7.60 (dd, J=6.4, 2.0 Hz, 1H), 7.56 (d, J=2.0 Hz, 1H), 7.44-7.31 (m, 5H), 6.89 (d, J=8.4 Hz, 1H), 5.22 (s, 2H), 3.94 (s, 3H), 3.88 (s, 3H).

Preparation of Compound Int-1-3

Compound Int-1-2 (79.8 g, 0.29 mol) was dissolved in acetic anhydride (550 mL) under N$_2$ atmosphere and then cooled to 0° C. Copper (II) nitrate hemi-(pentahydrate) (75.0 g, 0.32 mol) was portion wise added. After stirring for 6 hours at 0° C., the reaction was quenched with ice water (800 mL). The solid was filtered and washed with distilled water (100 mL) and hexane (400 mL) to obtain compound Int-1-3 (85.5 g, 92%).

$^1$H NMR (400 MHz, CDCl$_3$) δ 7.52 (s, 1H), 7.45-7.35 (m, 5H), 7.08 (s, 1H), 5.22 (s, 2H), 3.98 (s, 3H), 3.91 (s, 3H).

Preparation of Compound Int-1-4

To a solution of compound Int-1-3 (85.5 g, 0.27 mol) in THF (800 mL) and MeOH (300 mL) was added 2N NaOH (404 mL, 0.81 mol). After stirring for 5 hr at 65° C., the reaction was cooled to room temperature and adjusted to have pH 2 by addition of 2N HCl solution, and then extracted with distilled water (100 mL) and EA (300 mL×2). The organic layer was dried over anhydrous Na$_2$SO$_4$, filtered and concentrated under reduced pressure. The residue solid was collected and washed with hexane to obtain compound Int-1-4 (79.2 g, 97%).

$^1$H NMR (400 MHz, DMSO-d6) δ 7.69 (s, 1H), 7.47-7.35 (m, 5H), 7.03 (s, 1H), 5.24 (s, 2H), 3.91 (s, 3H).

Preparation of Compound Int-1

To a solution of compound Int-1-4 (100 mg, 0.33 mmol) in anhydrous THF (500 μL) and anhydrous DCM (1.5 mL) were slowly added dropwise oxalyl chloride (42.4 μL) and added 1 drop of DMF at 0° C. under N$_2$ atmosphere. After stirring for 30 min, the reaction mixture was concentrated under reduced pressure. The compound Int-1 was used directly in the next step without further purification.

Preparation of Compound Int-1-5

To a solution of compound Int-1-3 (5.0 g, 15.8 mmol) in DCM (300 mL) at 0° C. under N$_2$ atmosphere was slowly dropwise solution of methane-sulfonic acid (50 mL) in DCM (100 mL) and stirred for 2 hours. The reaction mixture was quench with NaHCO$_3$ solution and extracted with H$_2$O (100 mL). The organic layer was dry over anhydrous Na$_2$SO$_4$, filtered and concentrated under reduced pressure. The residue was purified by column chromatography to obtain compound Int-1-5 (2.54 g, 71%)

$^1$H NMR (400 MHz, CDCl$_3$) δ 7.48 (s, 1H), 7.14 (s, 1H), 6.05 (s, 1H), 4.02 (s, 3H), 3.89 (s, 3H).

Preparation of Compound Int-1-6

To a solution of Int-1-5 (2.0 g, 8.8 mmol) in 1,4-dioxane (28 ml) under N$_2$ atmosphere was treated with 6N NaOH solution (4.4 ml, 26.4 mmol) and stirred for 4 hours at 40° C. The reaction mixture was allowed to cooled to 0° C., and acidified with 2N HCl. The mixture was extracted with EA/H2O. The organic layer was dried over anhydrous Na$_2$SO$_4$, filtered, concentrated under reduced pressure and vacuum dry to obtain a white solid Int-1-6 (2.0 g, quant).

1H NMR (400 MHz, DMSO-d6) δ 10.60 (s, 1H), 7.305 (s, 1H), 7.24 (s, 1H), 3.89 (s, 3H)

Preparation of Compound Int-2

To a solution of Int-1-6 (1.8 7 g, 8.77 mmol) in acetic anhydride (1.0 ml, 10.5 mmol) under N$_2$ atmosphere was treated with TEA (1.8 ml, 13.1 mmol), DMAP (0.2 g, 1.75 mmol) and stirred for 3.5 hours at room temperature. The reaction mixture was extracted with EA/H2O. The organic layer was dried over anhydrous Na$_2$SO$_4$, filtered, concentrated under reduced pressure and vacuum dry to obtain a white solid Int-2 (2.2 g brown solid, 49%).

1H NMR (400 MHz, DMSO-d6): δ 7.981 (s, 1H), 7.451 (s, 1H), 3.933 (s, 3H), 2.294 (s, 3H).

Example 4.8.8

Preparation of Compound M-4

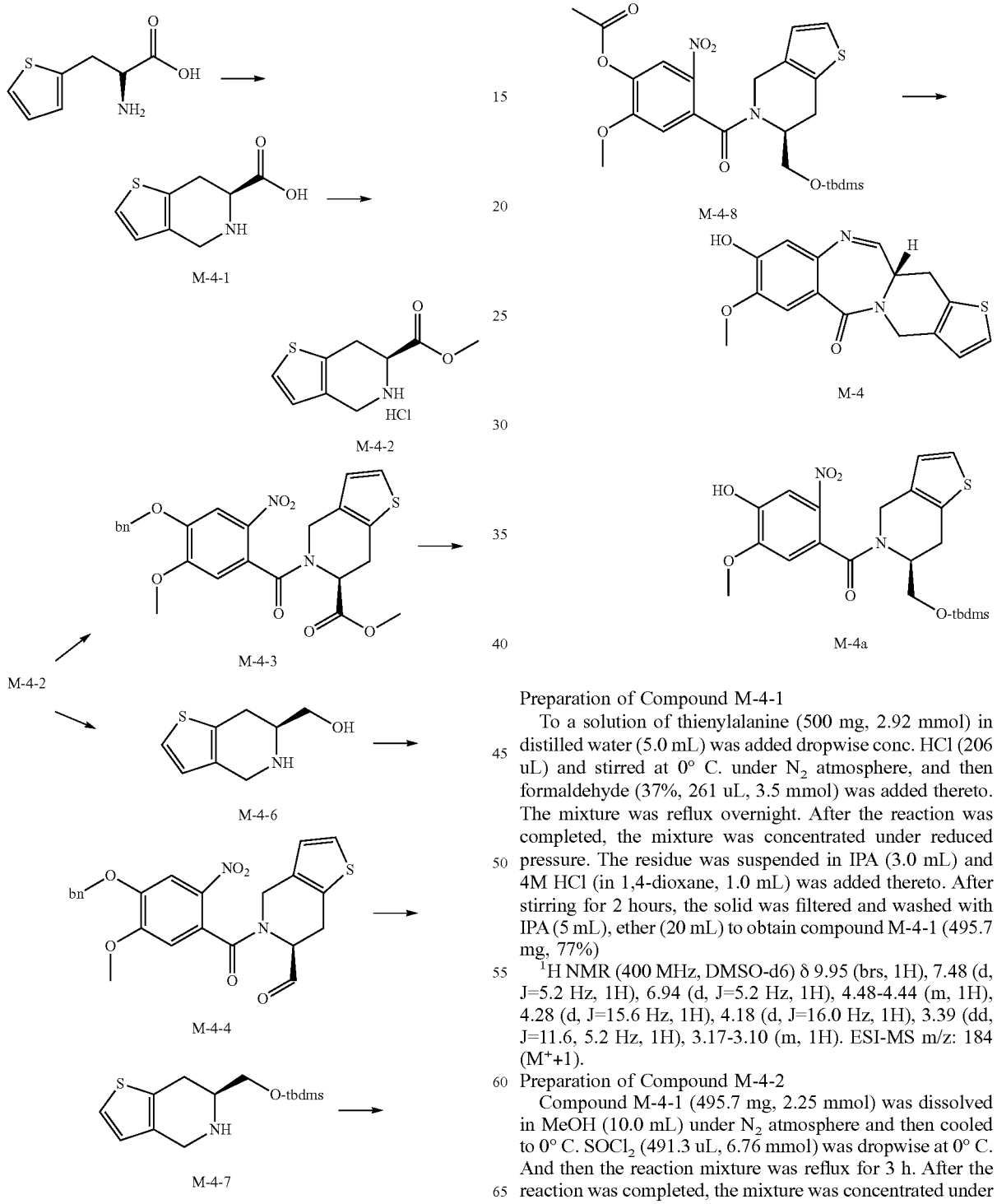

Preparation of Compound M-4-1

To a solution of thienylalanine (500 mg, 2.92 mmol) in distilled water (5.0 mL) was added dropwise conc. HCl (206 uL) and stirred at 0° C. under $N_2$ atmosphere, and then formaldehyde (37%, 261 uL, 3.5 mmol) was added thereto. The mixture was reflux overnight. After the reaction was completed, the mixture was concentrated under reduced pressure. The residue was suspended in IPA (3.0 mL) and 4M HCl (in 1,4-dioxane, 1.0 mL) was added thereto. After stirring for 2 hours, the solid was filtered and washed with IPA (5 mL), ether (20 mL) to obtain compound M-4-1 (495.7 mg, 77%)

$^1$H NMR (400 MHz, DMSO-d6) δ 9.95 (brs, 1H), 7.48 (d, J=5.2 Hz, 1H), 6.94 (d, J=5.2 Hz, 1H), 4.48-4.44 (m, 1H), 4.28 (d, J=15.6 Hz, 1H), 4.18 (d, J=16.0 Hz, 1H), 3.39 (dd, J=11.6, 5.2 Hz, 1H), 3.17-3.10 (m, 1H). ESI-MS m/z: 184 (M$^+$+1).

Preparation of Compound M-4-2

Compound M-4-1 (495.7 mg, 2.25 mmol) was dissolved in MeOH (10.0 mL) under $N_2$ atmosphere and then cooled to 0° C. SOCl$_2$ (491.3 uL, 6.76 mmol) was dropwise at 0° C. And then the reaction mixture was reflux for 3 h. After the reaction was completed, the mixture was concentrated under reduced pressure. The residue was wash with Ether (5 mL×2) to obtain compound M-4-2 (521.5 mg, 99%)

¹H NMR (400 MHz, DMSO-d6) δ 10.22 (brs, 2H), 7.49 (d, J=5.2 Hz, 1H), 6.94 (d, J=5.2 Hz, 1H), 4.65-4.61 (m, 1H), 4.30 (d, J=15.6 Hz, 1H), 4.19 (d, J=15.6 Hz, 1H), 3.80 (s, 3H), 3.60 (dd, J=11.6, 5.2 Hz, 1H), 3.21-3.14, (m, 1H). ESI-MS m/z: 198 (M⁺+1).

Preparation of Compound M-4-3

To a solution of compound Int-1 (856.5 mg, 2.66 mmol) in anhydrous THF (3.0 ml), and addition of compound M-4-2 (518.5 mg, 2.22 mmol) was dissolved in DMF (3.0 mL), DIPEA (772.8 uL, 4.44 mmol) at 0° C. And then the reaction mixture was stirred at room temperature overnight. After the reaction was completed. The distilled water (20 mL) and EA (50 mL×2) were added in reaction mixture. The organic layer was dried over anhydrous $Na_2SO_4$, filtered and concentrated under reduced pressure. The residue was purified by column chromatography to obtain compound M-4-3 (888.5 mg, 89%)

ESI-MS m/z: 483 (M⁺+1).

Preparation of Compound M-4-4

To a solution of Compound M-4-3 (880 mg, 1.82 mmol) in anhydrous DCM (5.0 mL) and toluene (15.0 mL) was added DIBAL (3.6 mL, 3.6 mmol, 1.0M in toluene) dropwise at −78° C. under $N_2$ atmosphere. The reaction mixture was stirred at −78° C. for 3 h. The reaction was quenched with MeOH (5 mL), 2N HCl (20.0 mL) at −78° C. And then the distilled water (20 mL) and EA (50 mL×2) were added in reaction mixture. The organic layer was dried over anhydrous $Na_2SO_4$, filtered and concentrated under reduced pressure. The residue was purified by column chromatography to obtain compound M-4-4 (701.9 mg, 85%).

ESI-MS m/z: 453 (M⁺+1).

Preparation of Compound M-4-5

To a solution of Compound M-4-4 (700 mg, 1.55 mmol) in THF (15.0 mL) and distilled water (3.0 mL) was added $Na_2S_2O_4$ (2.2 g, 12.4 mmol) at room temperature for 4 hours. After the reaction was completed. The reaction was quenched with MeOH (5 mL). And then the reaction mixture was concentrated under reduced pressure. The residue was suspended in toluene (20 mL) and evaporated to help remover any remaining water. The obtained white solid was further completely dried by leaving on a high vacuum overnight. The residue was suspended in anhydrous MeOH (10 mL) followed by addition of acetyl chloride (1.1 mL, 15.5 mmol) was added. After 15 minutes the cloudy solution was filtered and solid wash with anhydrous MeOH (5 mL×2). The filtrate was stir for 2 hours. The reaction was completed. The reaction mixture was quenched with $NaHCO_3$ solution pH~7). After the distilled water (20 mL) and EA (50 mL×2) were added in reaction mixture. The organic layer was dried over anhydrous $Na_2SO_4$, filtered and concentrated under reduced pressure. The residue was purified by column chromatography to obtain compound M-4-5 (701.9 mg, 85%)

¹H NMR (400 MHz, CDCl₃) δ 7.55 (d, J=5.6 Hz, 1H), 7.47 (m, 5H), 7.22 (d, J=5.2 Hz, 1H), 6.95 (d, J=5.2 Hz, 1H), 6.85 (s, 1H), 5.26-5.14 (m, 2H), 4.98 (d, J=16.4 Hz, 1H), 4.44 (d, J=16.8 Hz, 1H), 4.08-4.02 (m, 1H), 3.98 (s, 3H), 3.32-3.26 (m, 1H).

ESI-MS m/z: 453 (M⁺+1).

Preparation of Compound M-4

To a solution of compound M-4-5 (60 mg, 0.15 mmol) in anhydrous DCM (3 mL) and 0° C. cooling. And then methanesulfonic acid (700 uL) in DCM (2.0 mL) was added and stirred for 2 hours at 0° C. After the reaction was completed. The reaction was quenched with $NaHCO_3$ solution (pH~7). And then the distilled water (5 mL) and EA (20 mL×2) were added in reaction mixture. The organic layer was dried over anhydrous $Na_2SO_4$, filtered and concentrated under reduced pressure. The residue was purified by column chromatography to obtain compound M-4 (38.3 mg, 82%).

¹H NMR (400 MHz, CDCl₃) δ 7.58 (d, J=5.6 Hz, 1H), 7.54 (s, 1H), 7.23 (d, J=5.2 Hz, 1H), 6.95 (d, J=5.2 Hz, 1H), 6.89 (s, 1H), 6.06 (s, 1H), 5.30 (s, 1H), 4.99 (d, J=16.4 Hz, 1H), 4.44 (d, J=16.4 Hz, 1H), 4.10-4.04 (m, 1H), 3.99 (s, 3H), 3.32-3.26 (m, 1H).

ESI-MS m/z: 315 (M+1).

Preparation of Compound M-4-6

To a solution of M-4-2 (1 g, 4.28 mmol) in 20 ml of dry THF at 0° C. under $N_2$ atmosphere was treated with 1M LAH solution in THF (5.31 ml, 5.31 mmol) and stirred for 15 hours. The reaction mixture was quenched with water (5.3 ml), 15% NaOH (5.3 ml), $H_2O$ (16.0 mL) and stirred for 30 minutes. The inorganic solid was filtered and washed with EA. The organic layer was dried over $Na_2SO_4$, filtered and concentrated under reduced pressure to obtain compound M-4-6 (652 mg, 3.85 mmol, 90%) as red solid, which was used without further purification.

¹H NMR (400 MHz, CDCl₃) δ 7.08 (d, J=4.8, 1H), 6.73(d, J=5.2 Hz, 1H), 4.01-3.88 (m, 2H), 3.80 (dd, J=11.2 Hz, 1H), 3.55 (dd, J=8.4 Hz, 1H), 3.13-3.07 (m, 1H), 2.78-2.74 (m, 1H), 2.60-2.51 (m, 1H); ET-MS m/z: 170.0 (M⁺¹).

Preparation of Compound M-4-7

To a solution M-4-6 (700 mg, 4.14 mmol) in anhydrous DCM (20 ml) at 0° C. under $N_2$ atmosphere was treated with imidazole (844 mg, 12.41 mmol), TBDMS-Cl (686 mg, 4.55 mmol) and stirred for 4 hours at room temperature. The reaction mixture was extracted with $H_2O$ (100 mL), DCM (100 mL×3). The organic layer was dried over $Na_2SO_4$, filtered and concentrated under reduced pressure. The residue was purified by column chromatography to obtain compound M-4-7 (792 mg, 67%).

¹H NMR (400 MHz, CDCl₃) δ 7.07 (d, J=5.2 Hz, 1H), 6.75 (d, J=5.2 Hz, 1H), 4.04-3.92 (m, 2H), 3.77 (dd, J=9.6 Hz, 1H), 3.65 (dd, J=9.6 Hz, 1H), 3.05-3.00 (m, 1H), 2.75-2.71 (m, 1H), 2.65-2.59 (m, 1H); ET-MS m/z: 284.1 (M⁺¹).

Preparation of Compound M-4-8

To a solution of Int-2 (536 mg, 1.96 mmol) and M-4-7 (666 mg, 2.35 mmol) in anhydrous DMF (1.8 ml) at 0° C. under $N_2$ atmosphere was treated with DIPEA (0.85 ml, 4.89 mmol) and stirred for 3 hours at room temperature. The reaction mixture was extracted with EA/H2O. The organic layer was dried over anhydrous $Na_2SO_4$, filtered, concentrated under reduced pressure. The reaction mixture was purified by column chromatography (EA/HEX: 1/1) to obtain yellow solid M-4-8 (758.5 mg 76%); EI-MS m/z: 521 (M⁺+1).

Preparation of Compound M-4a

To a solution of M-4-8 (200 mg, 0.384 mmol) in MeOH (4.5 ml) at 0° C. under $N_2$ atmosphere was treated with $K_2CO_3$ (63.7 mg, 0.461 mmol) and stirred for 20 minutes. The reaction mixture was extracted with EA/H2O. The organic layer was dried over anhydrous $Na_2SO_4$, filtered, concentrated under reduced pressure and vacuum dry to obtain a yellow solid M-4a (189. 8 mg quant); ELMS m/z: 479 (M⁺+1).

Table 3 below lists the monomer derivatives that were synthesized via a similar synthetic route as described in Example 4.8.7.

TABLE 3

| Monomer | Structure | Characterization Data |
|---|---|---|
| M-5 | 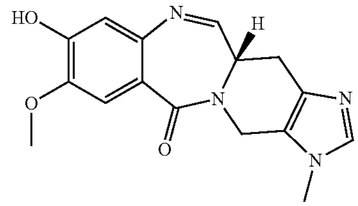 [SMILES: COc1cc2c(cc1O)N=C[C@@H]1Cc3ncn(C)c3CN1C2=O] | Yield 40%; $^1$H NMR (400 MHz, CD$_3$OD) δ 8.34 (brs, 1H), 7.68 (s, 1H), 7.28 (s, 1H), 6.42 (s, 1H), 4.83 (d, J = 16.4 Hz, 1H), 4.63 (d, J = 16.4 Hz, 1H), 4.26 (d, J = 8.4 Hz, 1H), 4.02-3.99 (m, 1H), 3.87 (s, 3H), 3.68 (s, 3H), 2.98-2.86 (m, 2H). ESI-MS m/z: 313 (M$^+$ + 1). |
| M-6 | 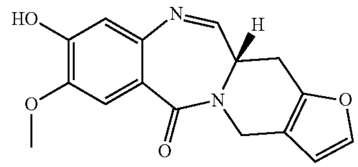 [SMILES: COc1cc2c(cc1O)N=C[C@@H]1Cc3occc3CN1C2=O] | Yield 31%; $^1$H NMR (400 MHz, CDCl$_3$) δ 7.67 (d, J = 6.0 Hz, 1H), 7.50 (s, 1H), 7.41 (s, 1H), 7.37 (d, J = 3.2 Hz, 1H), 6.89 (s, 1H), 6.37 (s, 1H), 4.58 (s, 2H), 4.15 (t, J = 6.8 Hz, 1H), 3.91 (s, 3H), 3.24 (dd, J = 9.6, 6.8 Hz, 1H), 3.12 (d, J = 16.8 Hz, 1H); ESI-MS m/z: 299 (M$^+$ + 1). |
| M-7 | 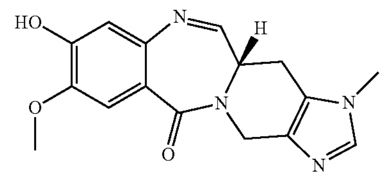 [SMILES: COc1cc2c(cc1O)N=C[C@@H]1Cc3c(ncn3C)CN1C2=O] | Yield 71%; $^1$H NMR (400 MHz, CD$_3$OD) δ 8.34 (brs, 1H), 7.68 (s, 1H), 7.28 (s, 1H), 6.42 (s, 1H), 4.77 (d, J = 16.0 Hz, 1H), 4.56 (d, J = 16.0 Hz, 1H), 4.33 (d, J = 7.6 Hz, 1H), 4.10-4.02 (m, 1H), 3.84 (s, 3H), 3.66 (s, 3H), 3.02-2.82 (m, 2H). ESI-MS m/z: 313 (M$^+$ + 1). |
| M-8 | 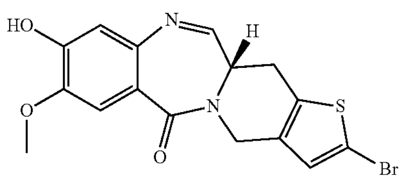 [SMILES: COc1cc2c(cc1O)N=C[C@@H]1Cc3sc(Br)cc3CN1C2=O] | Yield: 84%; $^1$H NMR (400 MHz, CDCl$_3$) δ 7.61 (d, J = 5.6 Hz, 1H), 7.52 (s, 1H), 6.91 (d, J = 12.4 Hz, 1H), 6.02 (s, 1H), 4.87 (d, J = 16.4 Hz, 1H), 4.39 (d, J = 16.8 Hz, 1H), 4.07-4.02 (m, 1H), 3.99 (s, 3H), 3.28-3.16 (m, 2H); ESI-MS m/z: 394 (M$^+$ + 1). |
| M-9 | 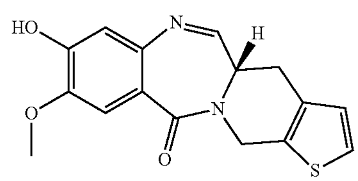 [SMILES: COc1cc2c(cc1O)N=C[C@@H]1Cc3ccsc3CN1C2=O] | Yield: 89%; $^1$H NMR (400 MHz, CDCl$_3$) δ 7.53 (s, 1H), 7.52 (d, J = 5.2 Hz, 1H), 7.02 (d, J = 5.2 Hz, 1H), 6.89 (s, 1H), 6.06 (s, 1H), 5.09 (d, J = 16.4, 1H), 4.57 (d, J = 16.4, 1H), 4.08-3.99 (m, 1H), 3.98 (s, 3H), 3.19-3.14 (m, 2H); ESI-MS m/z: 315 (M$^+$ + 1). |

Example 4.8.9

Preparation of M-10 and M-10a

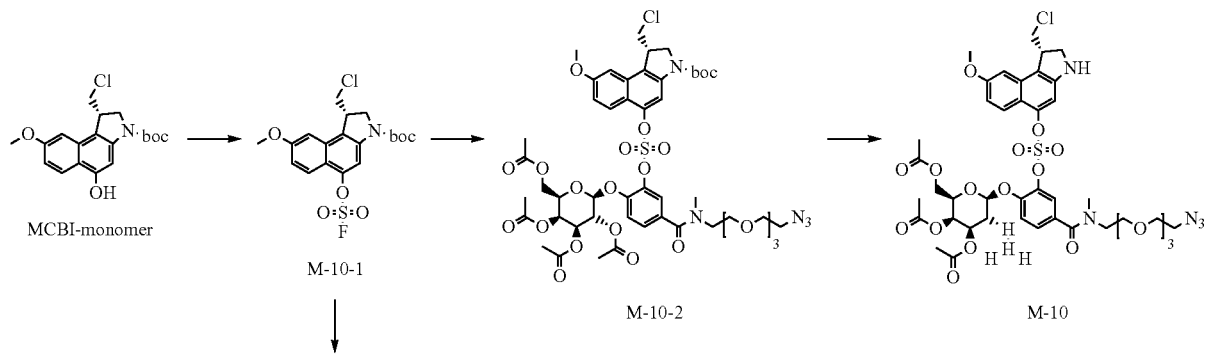

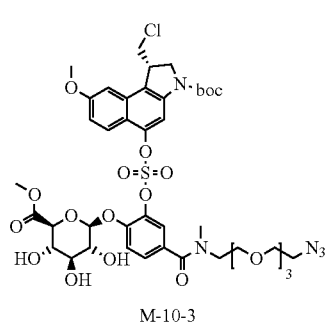
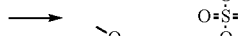
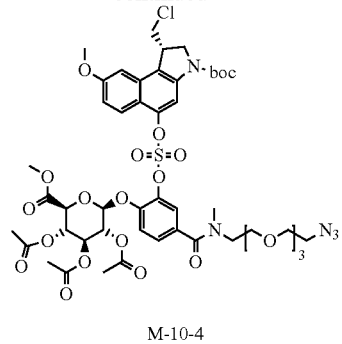
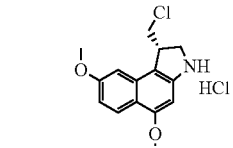

M-10-3

M-10-4

M-10a

Preparation of Compound M-10-1

To a solution of compound MCBI-monomer (330 mg, 0.907 mmol) in DCM (15.0 mL) was added Et$_3$N (0.510 mL, 3.63 mmol) at room temperature under N$_2$ atmosphere. SO$_2$F$_2$ gas was introduced via a balloon, and the mixture was stirred at room temperature for 45 min. The mixture was extracted with DCM. The organic layer was dried over anhydrous Na$_2$SO$_4$, filtered and concentrated under reduced pressure. The residue was purified by column chromatography to obtain compound M-10-1(306 mg, 76%).

$^1$H NMR (400 Hz, CDCl$_3$) δ 8.20-7.82 (m, 1H), 7.93 (d, J=9.6 Hz, 1H), 7.16 (dd, J=9.2, 2.4 Hz, 1H), 6.94 (d, J=2.0 Hz, 1H), 4.31 (brs, 1H), 4.18-4.11 (m, 1H), 4.01-3.89 (m, 2H), 3.95 (s, 3H), 3.50 (t, J=11.2 Hz, 1H), 1.60 (s, 9H)

ESI-MS m/z: 468 (M$^+$+Na).

Preparation of Compound M-10-2

To a solution of compound M-10-1 (150 mg, 0.336 mmol) in DMF (1.50 mL) was added OHPAS-D1a (247 mg, 0.353 mmol) and BEMP (84 µL, 0.302 mmol) at 0° C. under N$_2$ atmosphere. The reaction mixture was stirred at room temperature for 40 min. The reaction was quenched with water and extracted with EtOAc. The organic layer was dried over anhydrous Na$_2$SO$_4$, filtered and concentrated under reduced pressure. The residue was purified by column chromatography to obtain compound M-10-2 (344 mg, 91%).

ESI-MS m/z: 1124 (M$^+$).

Preparation of Compound M-10

To a solution of compound M-10-2(140 mg, 0.124 mmol) in DCM (6.0 mL) was added Hydrogen chloride 4.0 M solution in 1,4-Dioxane (2.0 mL) at room temperature under N$_2$ atmosphere. After stirring for 1.5 hours, the reaction mixture was diluted with DCM and concentrated under reduced pressure. The compound M-10 was used in the next step without further purification. (128 mg, 97%)

ESI-MS m/z: 1024 (M$^+$).

Preparation of Compound M-10-3

To a solution of compound M-10-1 (30.2 mg, 0.068 mmol) in DMF (0.30 mL) was added OHPAS-D13 (37.8 mg, 0.068 mmol), BEMP (23.5 µL, 0.081 mmol) and K$_2$CO$_3$ (9.35 mg, 0.068 mmol) at 0° C. under N$_2$ atmosphere. After stirring for 2 hours at room temperature, the reaction mixture was purified by prep HPLC to obtain compound M-10-3 (10 mg, 15%).

ESI-MS m/z: 984 (M$^+$).

Preparation of Compound M-10-4

To a solution of compound M-10-3 (32.1 mg, 0.033 mmol) in pyridine (0.65 mL) was added acetic anhydride (24.7 µL, 0.261 mmol) and DMAP (0.40 mg, 0.033 mmol) at 0° C. under N$_2$ atmosphere. After stirring for 1 hour at room temperature, the reaction mixture was purified by prep HPLC to obtain compound M-10-4 (35.0 mg, 97%).

ESI-MS m/z: 1110 (M$^+$).

Preparation of Compound M-10a

To a solution of compound M-10-4 (19.8 mg, 0.018 mmol) in DCM (0.50 mL) was added hydrogen chloride 4.0 M solution in 1,4-dioxane (0.20 mL) at 0° C. under N$_2$ atmosphere. After stirring for 1.5 hours at room temperature, the reaction mixture was diluted with DCM and concentrated under reduced pressure. The compound M-10a was used in the next step without further purification. (14.5 mg, 78%)

ESI-MS m/z: 1010 (M$^+$).

Example 4.8.10

Preparation of M-11

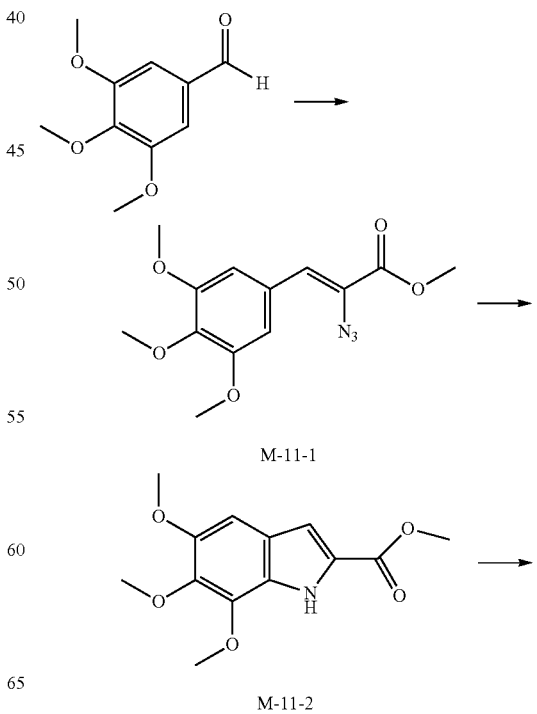

M-11-1

M-11-2

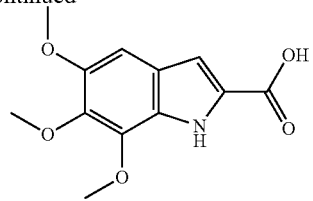

M-11

Preparation of Compound M-11-1

To a solution of sodium methoxide 0.5 M solution in methanol (52.8 mL, 26.4 mmol) was added a solution of 3,4,5-trimethoxybenzaldehyde (650 mg, 3.31 mmol) and methyl azidoacetate (3.81 g, 33.1 mmol, CAS No. 1816-92-8) in MeOH (5.30 mL) at −20° C. under $N_2$ atmosphere. The reaction mixture was stirred at 0° C. for 6 hours. After addition of cold water, the resulting precipitate was collected by filtration. The solid was washed with water and dried in vacuo to obtain compound M-11-1(640 mg, 66%) as yellow solid.

$^1$H NMR (400 Hz, $CDCl_3$) δ 7.10 (s, 2H), 6.85 (s, 1H), 3.92 (s, 3H), 3.90 (s, 6H), 3.89 (s, 3H)

Preparation of Compound M-11-2

To a solution of compound M-11-1 (100 mg, 0.341 mmol) in p-xylene (3.40 mL) at room temperature under $N_2$ atmosphere. The reaction mixture was stirred at 180° C. for 30 min. The reaction mixture was cooled at room temperature and concentrated under reduced pressure. The residue was purified by column chromatography to obtain compound M-11-2 (92.0 mg, quant.).

$^1$H NMR (400 Hz, $CDCl_3$) δ 7.10 (d, J=2.4 Hz, 1H), 6.82 (s, 1H), 4.08 (s, 3H), 3.93 (d, J=1.2 Hz, 6H), 3.90 (s, 3H)

ESI-MS m/z: 266 ($M^+$+1).

Preparation of Compound M-11

To a solution of compound M-11-2 (1.0 g, 3.77 mmol) in methanol/$H_2O$/1,4-dioxane (10.0 mL/5.00 mL/10.0 mL) was added lithium hydroxide monohydrate (316 mg, 7.54 mmol) at 0° C. under $N_2$ atmosphere. The reaction mixture was stirred at room temperature for 5 hrs. After the reaction was quenched with HCl, the resulting precipitate was collected by filtration. The solid washed with water and dried in vacuo to obtain compound M-11 (830 mg, 88%) as white solid.

$^1$H NMR (400 Hz, $CDCl_3$) δ 7.24 (d, J=2.4 Hz, 1H), 6.84 (s, 1H), 4.09 (s, 3H), 3.94 (s, 3H), 3.91 (s, 3H)

ESI-MS m/z: 252 ($M^+$+1).

Example 4.8.11

Preparation of M-12

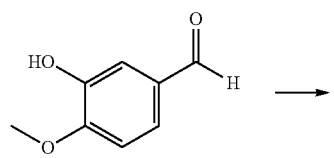

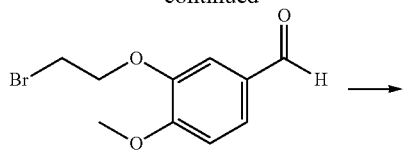

M-12-1

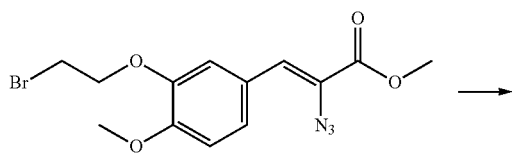

M-12-2

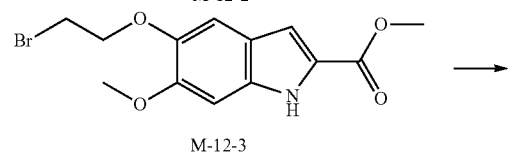

M-12-3

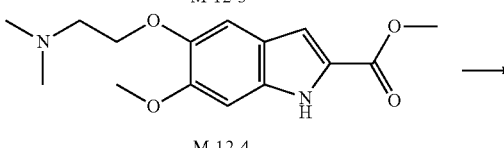

M-12-4

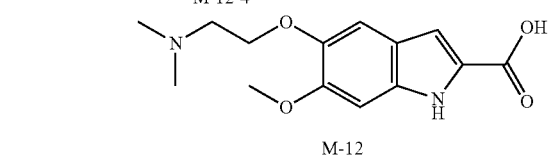

M-12

Preparation of Compound M-12-1

To a solution of isovanilin (5.0 g, 32.9 mmol) in 1.6 N NaOH solution (41.1 mL) was added 1,2-dibromoethane (17.1 mL, 197 mmol) under $N_2$ atmosphere. The mixture was refluxed overnight. After the reaction was completed, the mixture was cooled at room temperature. The reaction mixture was extracted with DCM. The organic layer was dried over anhydrous $Na_2SO_4$, filtered and concentrated under reduced pressure. The residue was purified by column chromatography to obtain compound M-12-1 (5.60 g, 66%).

$^1$H NMR (400 Hz, $CDCl_3$) δ 9.85 (s, 1H), 7.53-7.50 (m, 1H), 7.42 (d, J=1.6 Hz, 1H), 7.01 (d, J=8.0 Hz, 1H), 4.40 (t, J=6.4 Hz, 2H), 3.97 (s, 3H), 3.70 (t, J=6.8 Hz, 2H)

ESI-MS m/z: 260 ($M^+$+1).

Compound M-12-2 and M-12-3 were synthesized in a way similar to the preparation method of compound M-11-1 and M-11-2 in Example 4.8.10.

Compound M-12-2

Yield 18%

$^1$H NMR (400 Hz, $CDCl_3$) δ 7.56 (d, J=2.0 Hz, 1H), 7.39 (dd, J=8.4, 2.0 Hz, 1H), 6.90 (d, J=8.4 Hz, 1H), 6.86 (s, 1H), 4.38 (t, J=7.2 Hz, 2H), 3.91 (s, 3H), 3.90 (s, 3H), 3.69 (t, J=6.8 Hz, 2H)

Compound M-12-3

Yield 73%

$^1$H NMR (400 Hz, $CDCl_3$) δ 7.14 (s, 1H), 7.11-7.10 (m, 1H), 6.86 (s, 1H), 4.35 (t, J=6.8 Hz, 2H), 3.93 (s, 3H), 3.92 (s, 3H), 3.69 (t, J=6.8 Hz, 2H)

ESI-MS m/z: 329 ($M^+$+1).

Preparation of Compound M-12-4

To a solution of compound M-12-3 (100 mg, 0.305 mmol) in DMF (2.50 mL) was added dimethylamine (0.77 mL, 1.53 mmol) and potassium carbonate (42.2 mg, 0.305 mmol)

under N₂ atmosphere. The reaction mixture was stirred at room temperature for 1 hr. The reaction was quenched with water and extracted with EtOAc. The organic layer was dried over anhydrous $Na_2SO_4$, filtered and concentrated under reduced pressure. The residue was purified by column chromatography to obtain compound M-12-4 (90.0 mg, quant.).

ESI-MS m/z: 293 (M⁺+1).

Preparation of Compound M-12

To a solution of compound M-12-4 (45.0 mg, 0.154 mmol) in methanol (1.0 mL) at 0° C. under N₂ atmosphere was treated with 2 N NaOH solution (0.92 mL, 1.85 mmol) was stirred overnight. The mixture was purified by preparative HPLC to obtain compound M-12 (53 mg, quant.).

¹H NMR (400 Hz, CDCl₃) δ 11.6 (s, 1H), 7.24 (s, 1H), 6.97 (d, J=2.0 Hz, 1H), 6.92 (s, 1H), 4.24 (t, J=4.8 Hz, 2H), 3.82 (s, 3H), 3.48-3.44 (m, 2H), 2.86 (s, 6H)

ESI-MS m/z: 279 (M⁺+1).

Table 4 below lists the monomer derivatives that were synthesized via a similar synthetic route as described in Example 4.8.9.

TABLE 4

| Monomer | Structure | Characterization Data |
|---|---|---|
| M-13 | 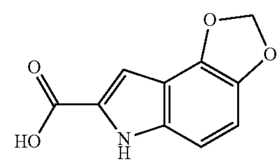 [SMILES: O=C(O)c1cc2c3c(ccc2[nH]1)OCO3] | Yield 27%<br>1H NMR (400 Hz, Methanol-D4) δ 6.91-6.81 (m, 3H), 5.94 (S, 2H); ESI-MS m/z: 206 (M ++ 1). |
| M-14 | 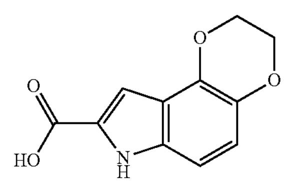 [SMILES: O=C(O)c1cc2c3c(ccc2[nH]1)OCCO3] | Yield 71%<br>¹H NMR (400 Hz, CDCl₃) δ 7.06 (s, 1H), 6.89 (d, J = 8.8 Hz, 1H), 6.80 (d, J = 8.4 Hz, 1H), 4.36-4.34 (m, 2H), 4.26-4.25 (m, 2H) |
| M-15 | 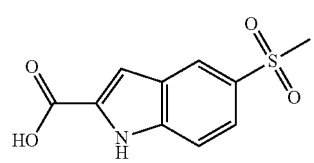 [SMILES: CS(=O)(=O)c1ccc2[nH]c(C(=O)O)cc2c1] | Yield 99%<br>1H NMR (400 Hz, DMSO) δ 12.3 (s, 1H), 8.30 (d, J = 1.6 Hz, 1H), 7.75 (dd, J = 9.2, 2.0 Hz, 1H), 7.64 (d, J = 8.8 Hz, 1H), 7.32 (d, J = 1.2 Hz, 1H), 3.18 (s, 3H); ESI-MS m/z: 239 (M+). |
| M-16 | 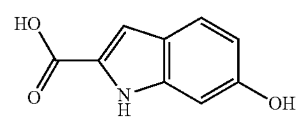 [SMILES: O=C(O)c1cc2ccc(O)cc2[nH]1] | Yield 99%<br>¹H NMR (400 MHz, DMSO-d6) δ 11.32 (s, 1H), 9.32 (s, 1H), 7.41 (dd, J = 8.8, 2.8 Hz, 1H), 6.96 (s, 1H), 6.77 (s, 1H), 6.61-6.58 (m, 1H); ESI-MS m/z: 178 (M⁺ + 1). |
| M-17 | 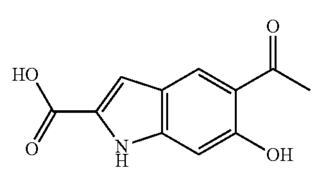 [SMILES: CC(=O)c1cc2cc(C(=O)O)[nH]c2cc1O] | ¹H NMR (400 MHz, MeOH-d4) δ 8.34 (s, 1H), 7.18 (d, J = 0.8 Hz, 1H), 6.80 (s, 1H), 2.70 (s, 3H). ESI-MS m/z: 220 (M⁺ + 1). |
| M-18 | 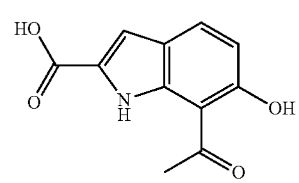 [SMILES: CC(=O)c1c(O)ccc2cc(C(=O)O)[nH]c12] | Yield 99%<br>¹H NMR (400 MHz, MeOH-d4) δ 7.68 (d, J = 8.4 Hz, 1H), 6.97 (s, 1H), 6.72 (d, J = 8.8 Hz, 1H), 2.76 (s, 3H); ESI-MS m/z: 220 (M⁺ + 1). |

Example 4.8.12

Preparation of M-19

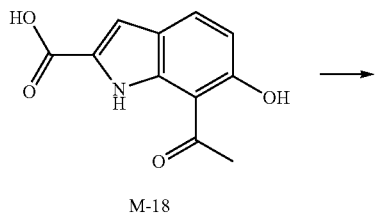

M-18

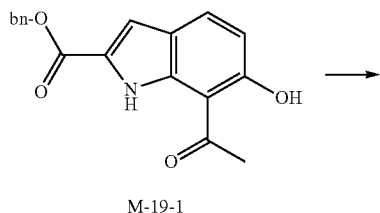

M-19-1

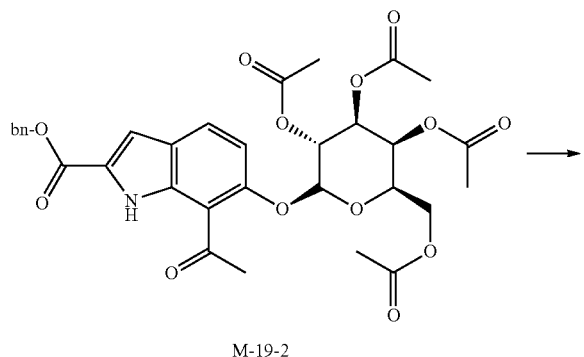

M-19-2

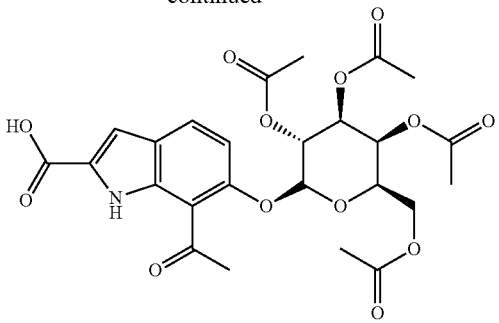

M-19

Preparation of Compound M-19-1

To a solution of compound M-18 (90 mg, 0.411 mmol) in DMF (2 mL) was added DIPEA (0.193 mL, 1.13 mmol) and benzyl bromide (0.079 mL, 0.658 mmol) at room temperature under $N_2$ atmosphere. The reaction was stirred at room temperature for 4 hours under $N_2$ atmosphere. After the reaction was completed, the reaction mixture was extracted with EA (50 mL×3), $H_2O$ (50 mL). The organic layer was dried over anhydrous $Na_2SO_4$, filtered, and concentrated under reduced pressure. The residue was purified by column chromatography to obtain compound M-19-1 (99 mg, 78%).

$^1$H NMR (400 Hz, CDCl$_3$) δ 9.06 (s, 1H), 7.77 (d, J=8.8 Hz, 1H), 7.47-7.36 (m, 5H), 7.27 (s, 1H), 6.84 (d, J=8.8 Hz, 1H), 5.40 (s, 2H), 2.82 (s, 3H).

ESI-MS m/z: 310 (M$^+$+1).

Preparation of Compound M-19-2

To a solution of compound M-19-1 (5 mg, 0.411 mmol) in anhydrous DMF (2 mL) was added Int-TG (66.5 mg, 0.162 mmol), silver oxide (56.3 mg, 0.243 mmol) and molecular sieve (200 mg) at room temperature under $N_2$ atmosphere. After stirring at same temperature for 18 hours, the reaction was filtered through CELITE®, and then concentrated under reduced pressure. The reaction mixture was purified by prep HPLC to obtain compound M-19-2 (3.2 mg, 31%).

$^1$H NMR (400 MHz, CDCl$_3$) δ 10.95 (s, 1H), 7.81 (d, J=8.8 Hz, 1H), 7.47-7.33 (m, 5H), 7.24 (d, J=2.4 Hz, 1H), 6.94 (d, J=8.8 Hz, 1H), 5.61 (dd, J=10.4, 8.0 Hz, 1H), 5.49 (d, J=3.2 Hz, 1H), 5.39 (s, 2H), 5.34 (d, J=8.0 Hz, 1H), 5.17 (dd, J=10.4, 3.6 Hz, 1H), 4.31-4.05 (m, 3H), 2.71 (s, 3H), 2.22 (s, 3H), 2.07 (s, 3H), 2.04 (s, 3H), 2.03 (s, 3H).

ESI-MS m/z: 662 (M$^+$+Na).

Preparation of Compound M-19

To a solution of compound M-19-2 (3.2 mg, 0.005 mmol) in MeOH (1 mL) was added Pd/C (5%, 1 mg, 0.0005 mmol) at room temperature under $H_2$. The mixture was stirred for 1 hour and filtered through CELITE®, and then concentrated under reduced pressure. The compound M-19 was used directly in the next step without further purification (2.7 mg, 100%).

ESI-MS m/z: 572 (M$^+$+Na).

Table 5 below lists the monomer derivatives that were synthesized via a similar synthetic route as described in Example 4.8.12.

TABLE 5

| Monomer | Structure | Characterization Data |
|---|---|---|
| M-20 | M-20 | Yield 100%%). ESI-MS m/z: 508 (M+ + 1). |
| M-21 | M-21 | Yield 100% ESI-MS m/z: 507 (M+). |

Example 4.8.13

Preparation of M-22

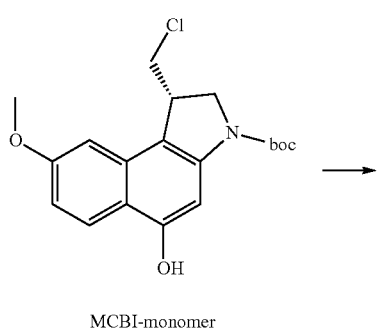

MCBI-monomer

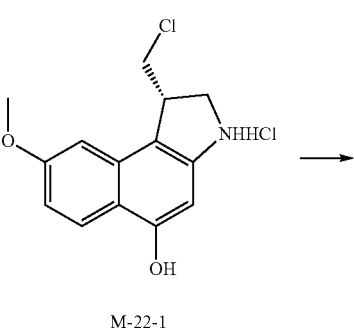

M-22-1

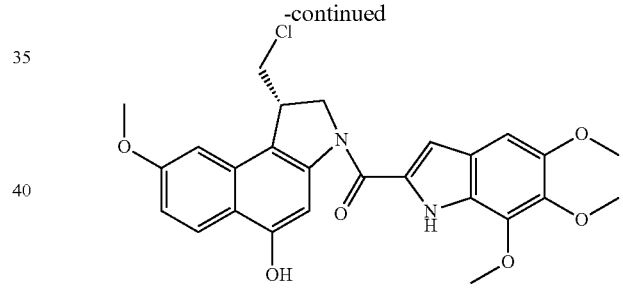

M-22

Preparation of Compound M-22-1

To a solution of MCBI-monomer (100 mg, 0.274 mmol) in dry DCM (5.5 mL) was added hydrogen chloride solution (3 mL, 4.0 M in dioxane) at 0° C. under $N_2$ atmosphere. After stirring for 3 hours at room temperature, the reaction mixture was concentrated under reduced pressure. Producing compound M-22-1 (82 mg, 100%), which was used without further purification.

ESI-MS m/z: 264 (M$^+$+1).

Preparation of Compound M-22

To a solution of M-22-1 (7.0 mg, 0.023 mmol) in DMF (1 mL) was added compound M-11 (8.6 mg, 0.035 mmol) and EDCI (13.2 mg, 0.069 mmol) at room temperature under $N_2$ atmosphere. After stirring for 2 hours at same temperature, the reaction mixture was purified by prep HPLC to obtain compound M-22 (6.5 mg, 58%).

$^1$H NMR (400 MHz, MeOH-d4) δ 8.09 (d, J=9.2 Hz, 1H), 7.60 (brs, 1H), 7.06-6.98 (m, 4H), 4.65 (d, J=4.8 Hz, 2H), 4.10-4.07 (m, 1H), 4.05 (s, 3H), 3.97 (dd, J=11.2, 3.2 Hz, 1H), 3.93 (s, 3H), 3.89 (s, 3H), 3.88 (s, 3H), 3.64 (dd, J=11.2, 9.2 Hz, 1H).

ESI-MS m/z: 496 (M$^+$).

Table 6 below lists the derivatives that were synthesized via a similar synthetic route as described in Example 4.8.13.

TABLE 6

| Monomer | Structure | Characterization Data |
|---|---|---|
| M-23 | 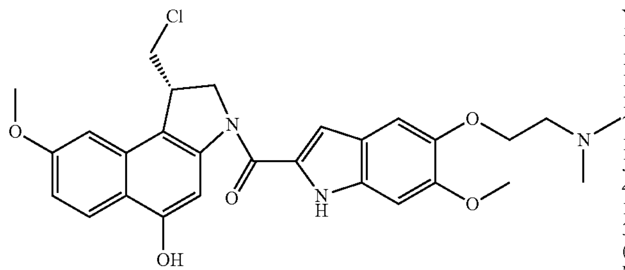 | Yield 68%<br>¹H NMR (400 MHz, DMSO-d6)) δ 11.57 (s, 1H), 10.33 (s, 1H), 9.63 (brs, 1H), 8.01 (d, J = 9.2 Hz, 1H), 7.82 (s, 1H), 7.32 (s, 1H), 7.11-7.09 (m, 2H), 7.03 (s, 1H), 6.98 (dd, J = 9.2, 2.4 Hz, 1H), 4.75 (t, J = 10.4 Hz, 1H), 4.53 (d, J = 10.4 Hz, 1H), 4.29 (t, J = 4.4 Hz, 2H), 4.19 (t, J = 8.4 Hz, 1H), 4.05 (dd, J = 11.2, 3.2 Hz, 1H), 3.91 (s, 3H), 3.85 (s, 3H), 3.82-3.81 (m, 1H), 3.54-3.51 (m, 2H), 2.94 (s, 3H), 2.93 (s, 3H); ESI-MS m/z: 524 (M⁺). |
| M-24 | 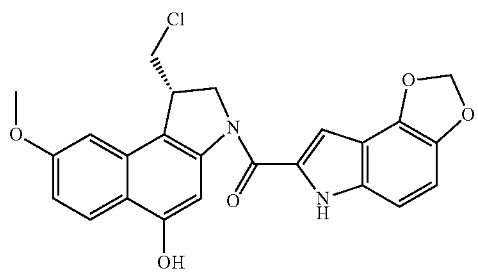 [SMILES: COc1ccc2c(O)cc3c(c2c1)[C@H](CCl)CN3C(=O)c1cc2c3c(ccc2[nH]1)OCO3] | Yield 60%<br>¹H NMR (400 MHz, DMSO-d6)) δ 11.76 (s, 1H), 10.34 (s, 1H), 8.02 (d, J = 9.2 Hz, 1H), 7.80 (s, 1H), 7.12 (d, J = 2.8 Hz, 1H), 7.05 (d, J = 1.6 Hz, 1H), 7.01-6.97 (m, 3H), 6.07 (s, 2H), 4.80 (t, J = 10.4 Hz, 1H), 4.53 (d, J = 9.6 Hz, 1H), 4.19 (t, J = 2.0 Hz, 1H), 4.05 (dd, J = 11.2, 3.2 Hz, 1H), 3.91 (s, 3H), 3.87 (dd, J = 11.2, 7.2 Hz, 1H); ESI-MS m/z: 451 (M⁺ + 1). |
| M-25 | 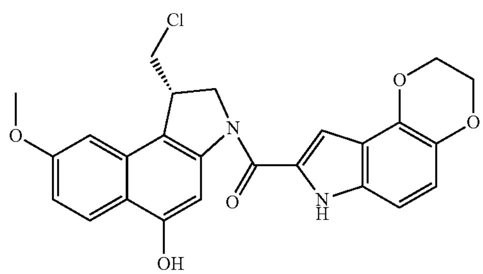 [SMILES: COc1ccc2c(O)cc3c(c2c1)[C@H](CCl)CN3C(=O)c1cc2c3c(ccc2[nH]1)OCCO3] | Yield 62%)<br>¹H NMR (400 MHz, DMSO-d6)) δ δ 8.09 (d, J = 9.2 Hz, 1H), 7.64 (s, 1H), 7.09-6.95 (m, 4H), 6.84 (d, J = 8.8 Hz, 1H), 5.34 (t, J = 4.8 Hz, 1H), 4.70 (d, J = 4.4 Hz, 1H), 4.60 (s, 1H), 4.39-4.37 (m, 2H), 4.29-4.27 (m, 2H), 4.14-4.06 (m, 1H), 4.01-3.97 (m, 1H), 3.94 (s, 3H); ESI-MS m/z: 465 (M⁺ + 1). |
| M-26 | 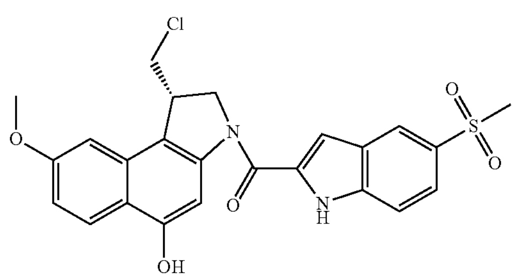 [SMILES: COc1ccc2c(O)cc3c(c2c1)[C@H](CCl)CN3C(=O)c1cc2cc(S(C)(=O)=O)ccc2[nH]1] | Yield 60%<br>¹H NMR (400 MHz, DMSO-d6)) δ 12.31 (s, 1H), 10.37 (s, 1H), 8.33 (s, 1H), 8.03 (d, J = 9.2 Hz, 1H), 7.81 (s, 1H), 7.77 (dd, J = 8.8, 2.0 Hz, 1H), 7.70 (d, J = 8.8 Hz, 1H), 7.44 (s, 1H), 7.13 (d, J = 2.8 Hz, 1H), 7.05 (dd, J = 9.2, 2.4 Hz, 1H), 4.80 (t, J = 10.0 Hz, 1H), 4.55 (d, J = 10.8 Hz, 1H), 4.23 (t, J = 8.0 Hz, 1H), 4.05 (dd, J = 11.2, 3.2 Hz, 1H), 3.92 (s, 3H), 3.87 (dd, J = 11.2, 7.6 Hz, 1H), 3.20 (s, 3H); ESI-MS m/z: 485 (M⁺ + 1). |
| M-27 | 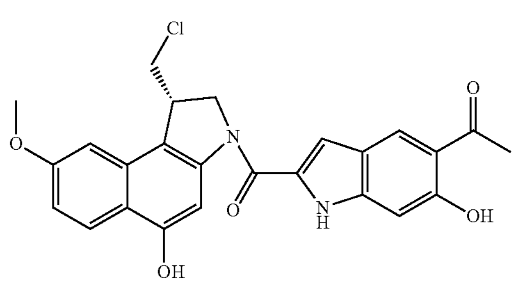 [SMILES: COc1ccc2c(O)cc3c(c2c1)[C@H](CCl)CN3C(=O)c1cc2cc(C(C)=O)c(O)cc2[nH]1] | Yield 59%<br>¹H NMR (400 MHz, DMSO-d6) δ 12.11 (s, 1H), 11.77 (s, 1H), 10.35 (s, 1H), 8.44 (s, 1H), 8.02 (d, J = 9.2 Hz, 1H), 7.82 (s, 1H), 7.28 (s, 1H), 7.12 (d, J = 2.0 Hz, 1H), 7.00 (dd, J = 9.2, 2.4 Hz, 1H), 6.85 (s, 1H), 4.78 (t, J = 9.2 Hz, 1H), 4.54 (dd, J = 10.8, 1.6 Hz, 1H), 4.22 (t, J = 2.0 Hz, 1H), 4.05 (dd, J = 11.2, 3.2 Hz, 1H), 3.92 (s, 3H), 3.85 (dd, J = 10.8, 7.6 Hz, 1H), 2.72 (s, 3H); ESI-MS m/z: 465 (M⁺ + 1). |

TABLE 6-continued

| Monomer | Structure | Characterization Data |
|---|---|---|
| M-28 | (structure shown) | Yield 58%<br>1H NMR (400 MHz, DMSO-d6) δ 11.08 (s, 1H), 10.35 (s, 1H), 8.01 (d, J = 9.2 Hz, 1H), 7.85 (s, 1H), 7.84 (d, J = 8.8 Hz, 1H), 7.25 (d, J = 2.0 Hz, 1H), 7.11 (d, J = 2.0 Hz, 1H), 6.99 (dd, J = 9.2, 2.8 Hz, 1H), 6.89 (d, J = 8.4 Hz, 1H), 6.54 (s, 1H), 4.75 (t, J = 10.8 Hz, 1H), 4.55 (dd, J = 10.8, 1.6 Hz, 1H), 4.23 (t, J = 9.2 Hz, 1H), 4.05 (dd, J = 10.8, 2.8 Hz, 1H), 3.92 (s, 3H), 3.87 (dd, J = 11.2, 7.6 Hz, 1H), 2.71 (s, 3H). ESI-MS m/z: 465 (M ++ 1). |

Example 4.8.14

Preparation of M-29

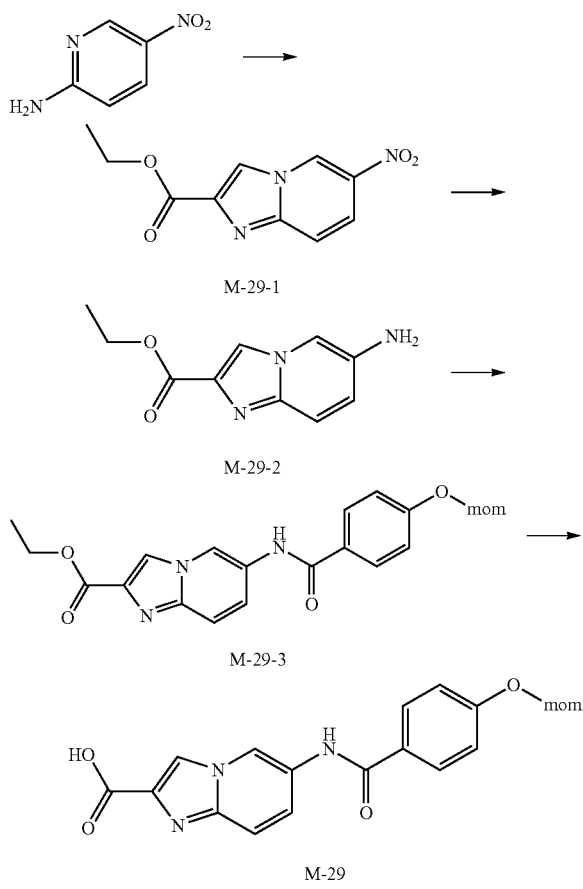

Preparation of Compound M-29-1

To a solution of 2-amino-5-nitropyridine (5.0 g, 35.9 mmol) in ethanol (72.0 mL) was added ethyl bromopyruvate (6.31 mL, 50.3 mmol) under $N_2$ atmosphere. The mixture was refluxed overnight. After the reaction was completed, the mixture was cooled at room temperature. After addition of cold water, the resulting precipitate was collected by filtration. The solid was washed with water and dried in vacuo to obtain compound M-29-1(6.28 g, 74%) as brown solid.

$^1$H NMR (400 Hz, CDCl$_3$) δ 9.30-9.29 (m, 1H), 8.38 (s, 1H), 8.05 (dd, J=10, 2.4 Hz, 1H), 7.81 (d, J=10 Hz, 1H), 4.53-4.47 (m, 2H), 1.44 (t, J=7.2 Hz, 3H)

ESI-MS m/z: 236 (M$^+$+1).

Preparation of Compound M-29-2

A suspension of compound M-29-1 (2.0 g, 8.50 mmol) in methanol (20.0 mL) was cooled to 0° C., and hydrochloric acid (6.4 mL) was added drop by drop, followed by addition of zinc (2.22 g, 34.0 mmol) in small portions. The reaction mixture was stirred for 30 min. Next, methanol (14 mL) was added, and the reaction was quenched with concentrated ammonia. The suspension was filtered and the residue washed with methanol. The combined filtrate was concentrated and the residue suspended in a mixture of chloroform (70 mL), water (30 mL), and concentrated ammonia (30 mL, 30% solution). The mixture was stirred until it became clear. Layers were separated, and the water layer was extracted once with chloroform. The combined organic layers were washed with saturated aqueous NaCl, dried with MgSO$_4$, filtered, and concentrated under reduced pressure. The compound M-29-2 was used in the next step without further purification. (1.12 g, 64%)

$^1$H NMR (400 Hz, CDCl$_3$) δ 8.01 (s, 1H), 7.54-7.51 (m, 2H), 6.86 (dd, J=9.6, 2.4 Hz, 1H), 4.45 (m, 2H), 3.53 (s, 2H), 1.47 (t, J=6.8 Hz, 3H)

Preparation of Compound M-29-3

To a solution of M-29-2 (1.12 g, 5.46 mmol) in DMA (18 mL) were added compound Int-TG4 (995 mg, 5.46 mmol) and EDC.HCl (1.26 g, 6.55 mmol). The resulting mixture was stirred for overnight at room temperature. Subsequently, the reaction mixture was concentrated. The residue was dissolved in water and CH$_2$Cl$_2$, and the layers were separated. The organic layer was washed with water, dried with Na$_2$SO$_4$, and concentrated. The residue was purified by column chromatography to obtain compound M-29-3 (927 mg, 46%).

$^1$H NMR (400 Hz, CDCl$_3$) δ 9.33-9.32 (m, 1H), 8.45 (d, J=0.8 Hz, 1H), 7.97-7.93 (m, 2H), 7.61-7.52 (m, 2H), 7.18-7.15 (m, 2H), 5.28 (s, 1H), 4.62 (s, 1H), 4.44-4.38 (m, 2H), 3.48 (s, 3H), 1.41 (t, J=6.8 Hz, 3H)

Preparation of Compound M-29

To a solution of M-29-3 (300 mg, 0.812 mmol) in 1,4-dioxane/H$_2$O (1.5 mL/1.5 mL) were added 2N NaOH (3.0 mL). The resulting mixture was stirred for 1 h at 70° C. The mixture was stirred at 70° C. for 1 h. Next, the mixture was cooled to room temperature, water was added, and the mixture was acidified with a 4 M hydrochloric acid solution. The resulting suspension was filtered, and the residue was dried to give compound M-29 (242 mg, 87%) as a yellow-brown solid.

¹H NMR (400 Hz, DMSO) δ 10.37 (s, 1H), 9.47 (s, 1H), 7.99 (d, J=8.4 Hz, 2H), 7.67 (t, J=14 Hz, 2H), 7.17 (d, J=8.4 Hz, 2H), 5.26 (s, 2H), 3.38 (s, 3H)
ESI-MS m/z: 342 (M⁺+1).

Example 4.8.15

Preparation of M-30

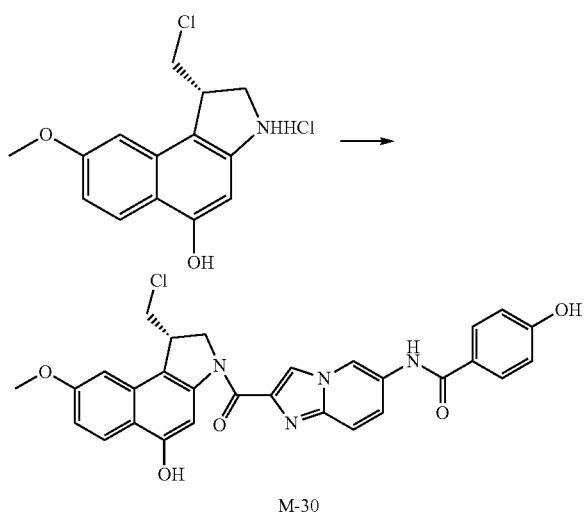

Compound M-30 was synthesized via a similar method as described in Example 4.8.13. Yield 23%; ESI-MS m/z: 588 (M⁺+1).

Example 4.9

Preparation of Benzodiazepine Dimer Derivatives

Example 4.9.1

Preparation of L-1

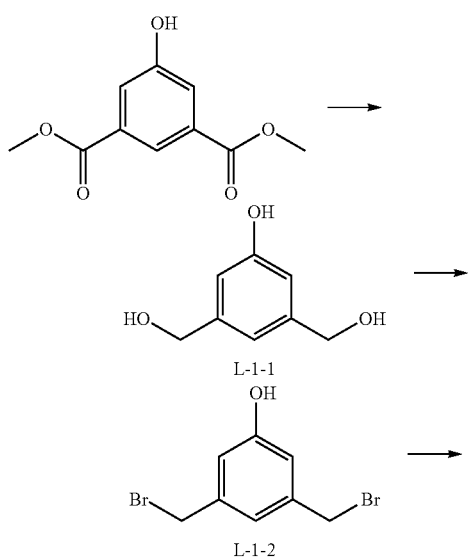

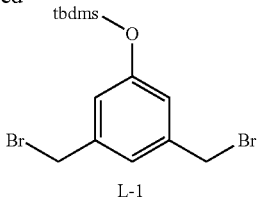

Preparation of Compound L-1-1

To solution of dimethyl 5-hydroxyisophthalate (5 g, 23.79 mmol) in dry THF (300 mL) was added LAH (3.6 g, 95.15 mmol) dropwise at −78° C. under $N_2$ atmosphere. The reaction mixture was stirred at room temperature for 17 hours. After the reaction was completed, 15% NaOH solution (4 mL), $H_2O$ (8 mL) and EA (100 mL) were added and then the reaction mixture was stirred for 1 hour. The mixture was filtered and concentrated under reduced pressure. The residue was purified by column chromatography to obtain compound L-1-1 (3.02 g, 82%).
¹H NMR (400 MHz, DMSO-d6) δ 9.21 (s, 1H), 6.66 (s, 1H), 6.58 (s, 2H), 5.07 (t, J=6.0 Hz, 2H), 4.38 (d, J=4.6 Hz, 4H).
Preparation of Compound L-1-2

To a solution of compound L-1-1 (2 g, 12.97 mmol) was dissolved in HBr (5.0 mL, 33% in AcOH) under $N_2$ atmosphere. After stirring at 60° C. for 18 hours, the reaction was quenched by addition of $NaHCO_3$ solution (pH~8). And then distilled water (50 mL) and EA (100 mL×2) were added in reaction mixture. The organic layer was dried over anhydrous $Na_2SO_4$, filtered and concentrated under reduced pressure. The residue was purified by column chromatography to obtain compound L-1-2 (2.9 g, 80%).
¹H NMR (400 MHz, CDCl₃) δ 6.99 (s, 1H), 6.81 (s, 2H), 4.85 (s, 1H), 4.41 (s, 2H).
Preparation of Compound L-1

To solution of compound L-1-2 (100 mg, 0.36 mmol) in dry DCM (3 mL) was added imidazole (27 mg, 0.39 mmol) and TBDMS-Cl (59 mg, 0.39 mmol) at room temperature under $N_2$ atmosphere. After stirring for 16 hours, distilled water (50 mL) and EA (100 mL) were added in reaction mixture. The organic layer was dried over anhydrous $Na_2SO_4$, filtered and concentrated under reduced pressure. The residue was purified by column chromatography to obtain compound L-1 (110 mg, 79%).
¹H NMR (400 MHz, CDCl₃) δ 7.00 (s, 1H), 6.80 (s, 2H), 4.41 (s, 4H), 0.99 (s, 9H), 0.21 (s, 6H).

Example 4.9.2

Preparation of L-7

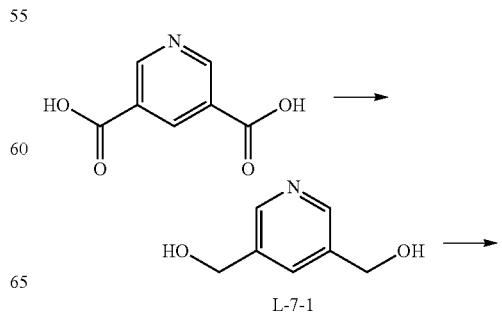

-continued

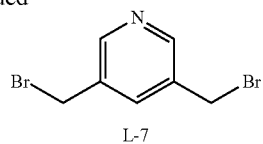

L-7

Preparation of Compound L-7-1

To a solution of 3,5-pyridinedicarboxylic acid (1.0 g, 5.98 mmol) in anhydrous THF (50 mL) at 0° C. under $N_2$ atmosphere was added boron trifluoride tetrahydrofuran complex (30.0 mL, 30.0 mmol, 1M THF). The reaction was allowed to warm up to room temperature and stirred for 18 hours. The mixture was quenched with 2N HCl till pH 2 and extracted with distilled water (20 mL) and EA (50 mL×2). The organic layer was dried over anhydrous $Na_2SO_4$, filtered and concentrated under reduced pressure. The residue was purified by preparative TLC to obtain compound L-7-1 (363 mg, 48%).

$^1$H NMR (400 MHz, DMSO-$d_6$) δ 8.38 (s, 2H), 7.99 (s, 1H), 5.59 (t, J=4.0 Hz, 2H), 4.61 (d, J=5.2 Hz, 2H).

Compound L-7 was synthesized via a similar synthetic route as described in Example 4.9.1.

Preparation of Compound L-7

Yield 65%; $^1$H NMR (400 MHz, CDCl$_3$) δ 8.56 (s, 2H), 7.77 (s, 1H), 4.47(s, 2H).

Example 4.9.3

Preparation of L-8

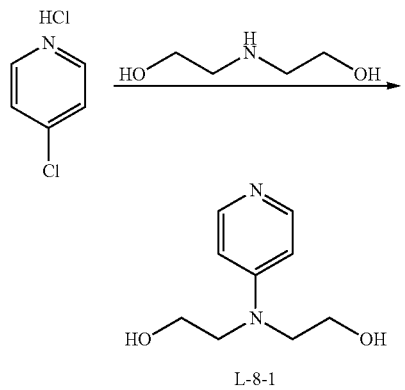

L-8-1

L-8

Preparation of Compound L-8-1

A solution of 4-chloropyridine-hyrochloride (1.0 g, 6.67 mmol) and diethanolamine (1.05 g, 10.00 mmol) in $H_2O$ (12 mL) at room temperature under $N_2$ atmosphere was treated NaOH (1.07 g, 26.67 mmol) and heated to 110° C. for 1 hour using microwave reactor. After the reaction was quenched with distilled water (18 mL)/methanol (10 mL) and extracted with EA (200 mL). The organic layer was dried over anhydrous $Na_2SO_4$, filtered and concentrated under reduced pressure. The residue was purified by column chromatography to obtain compound L-8-1 (160 mg, 13%).

$^1$H NMR (400 MHz, DMSO-d6) δ 8.10 (d, J=5.6 Hz, 2H), 6.83 (d, J=6.0 Hz, 2H), 4.91 (brs, 2H), 3.57 (s, 8H). ESI-MS m/z: 183 (M$^+$+1).

Compound L-8 was synthesized via a similar synthetic route as described in Example 4.9.1.

Preparation of Compound L-8

Yield 70%; ESI-MS m/z: 309 (M$^+$+1).

Example 4.9.4

Preparation of L-9

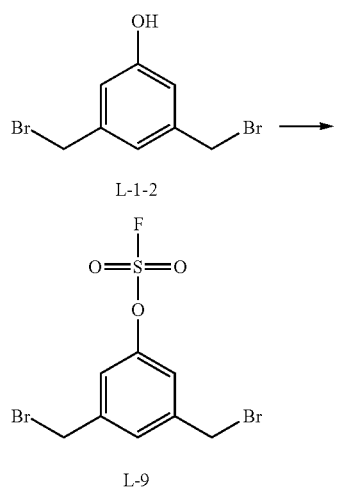

L-1-2

L-9

Compound L-9 was synthesized via a similar manner to the preparation method of the compound OHPAS-D6-1 in Example 3.5.

Yield 73%; $^1$H NMR (400 Hz, CDCl$_3$) δ 7.47 (s, 1H), 7.32 (s, 2H), 4.46 (s, 4H).

Example 4.9.5

Preparation of L-10

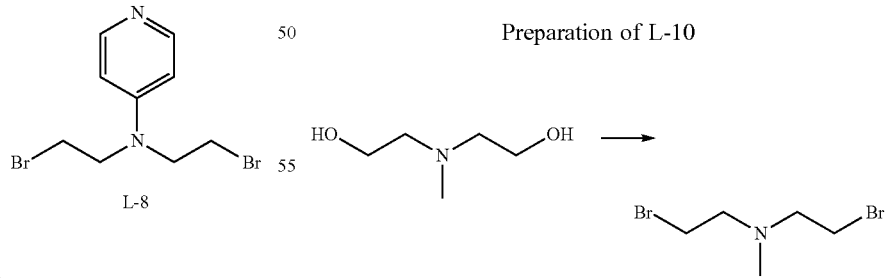

L-10

Compound L-10 was synthesized via a similar manner to the preparation method of the compound L-1-2 in Example 4.9.1.

ESI-MS m/z: 245 (M$^+$+1).

Example 4.9.6

Preparation of Dimer Derivatives

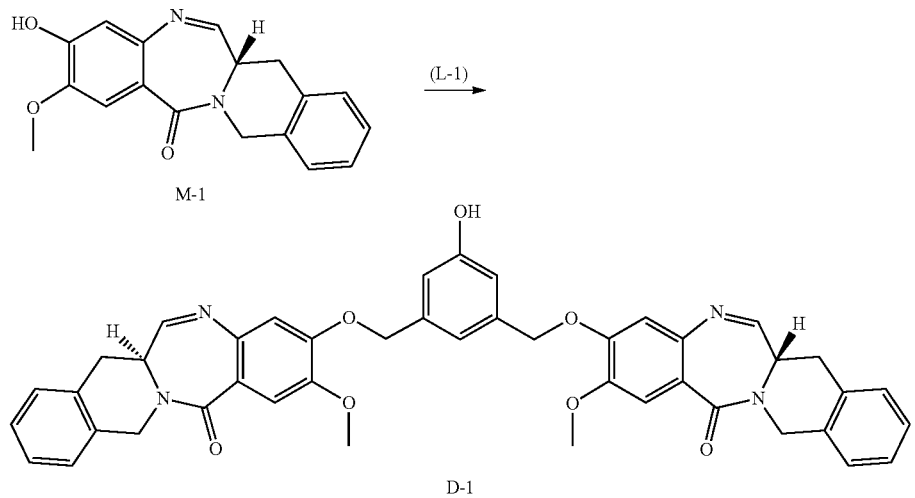

M-1

D-1

To a solution of Compound M-1 (31 mg, 0.10 mmol) and compound L-1 (20 mg, 0.05 mmol) in DMF (1.0 mL) was added $K_2CO_3$ (14 mg, 0.10 mmol) under $N_2$ atmosphere. After stirring for 7 hours at room temperature, the reaction mixture was purified by preparative HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-3 (13 mg, 30%).

ESI-MS m/z: 734 ($M^+$+1).

Example 4.9.7

Preparation of Dimer Derivatives

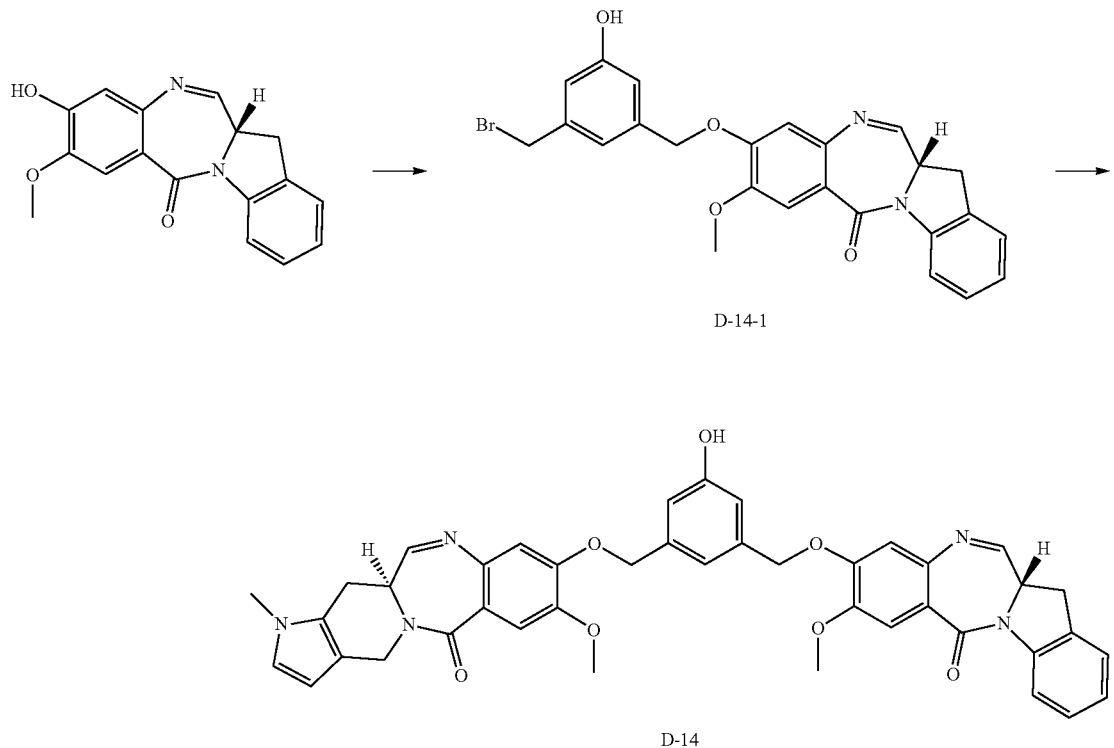

D-14-1

D-14

Compound D-14 was synthesized in a way similar to the synthesis of compound D-1 of Example 4.9.6.

Compound D-14-1

Yield 32%, white solid. ESI-MS m/z: 494 (M⁺+1).

Compound D-14

Yield 7%, white solid. ESI-MS m/z: 725 (M⁺+1)

Table 7 below lists the dimer derivatives that were synthesized via a similar synthetic route as described in Example 4.9.6 or 4.9.7.

TABLE 7

| Dimer | Structure | Characterization Data |
|---|---|---|
| D-2 | 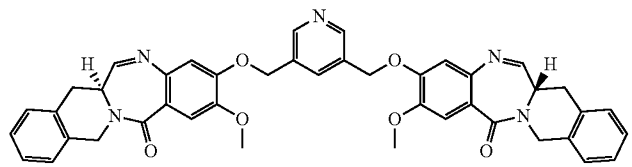 [SMILES: COc1cc2c(cc1OCc1cncc(COc3cc4c(cc3OC)C(=O)N3Cc5ccccc5C[C@H]3C=N4)c1)N=C[C@@H]1Cc3ccccc3CN1C2=O] | Yield 85%, ESI-MS m/z: 720 (M⁺ + 1). |
| D-3 | 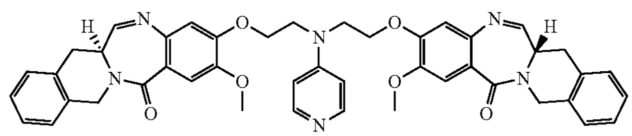 [SMILES: COc1cc2c(cc1OCCN(CCOc1cc3c(cc1OC)C(=O)N1Cc4ccccc4C[C@H]1C=N3)c1ccncc1)N=C[C@@H]1Cc3ccccc3CN1C2=O] | Yield 53%, ESI-MS m/z: 763 (M⁺ + 1). |
| D-4 | 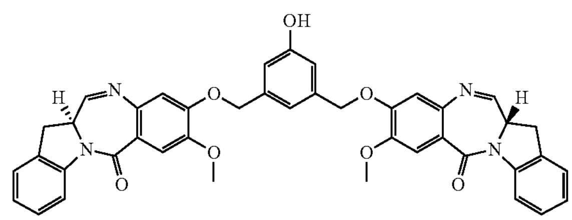 [SMILES: COc1cc2c(cc1OCc1cc(O)cc(COc3cc4c(cc3OC)C(=O)N3c5ccccc5C[C@H]3C=N4)c1)N=C[C@@H]1Cc3ccccc3N1C2=O] | ESI-MS m/z: 707 (M⁺ + 1). |
| D-5 | 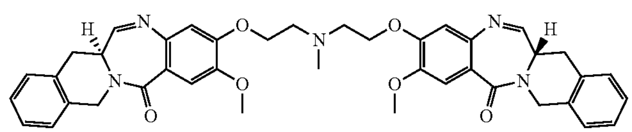 [SMILES: COc1cc2c(cc1OCCN(C)CCOc1cc3c(cc1OC)C(=O)N1Cc4ccccc4C[C@H]1C=N3)N=C[C@@H]1Cc3ccccc3CN1C2=O] | Yield 55%, ESI-MS m/z: 700 (M⁺ + 1). |
| D-6 | 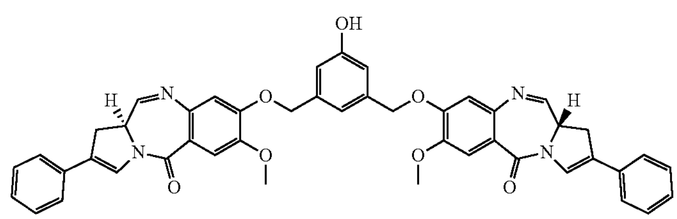 [SMILES: COc1cc2c(cc1OCc1cc(O)cc(COc3cc4c(cc3OC)C(=O)N3C=C(c5ccccc5)C[C@H]3C=N4)c1)N=C[C@@H]1CC(c3ccccc3)=CN1C2=O] | Yield 10%, ESI-MS m/z: 759 (M⁺ + 1) |
| D-7 | 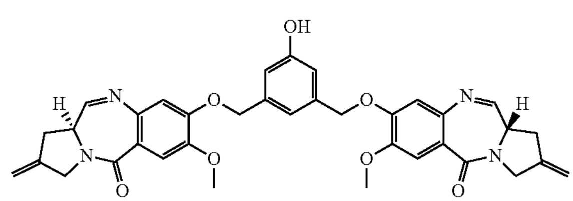 | Yield 51%, ESI-MS m/z: 717 (M⁺ + 1) |
| D-8 | 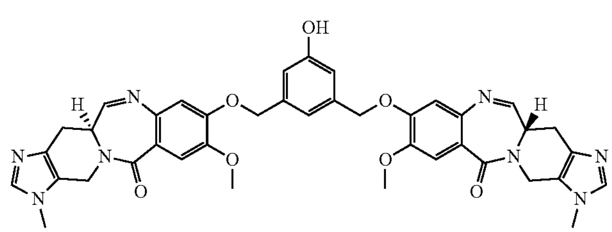 [SMILES: COc1cc2c(cc1OCc1cc(O)cc(COc3cc4c(cc3OC)C(=O)N3Cc5c(ncn5C)C[C@H]3C=N4)c1)N=C[C@@H]1Cc3ncn(C)c3CN1C2=O] | Yield 34%, ESI-MS m/z: 743 (M⁺ + 1) |

TABLE 7-continued

| Dimer | Structure | Characterization Data |
|---|---|---|
| D-9 | 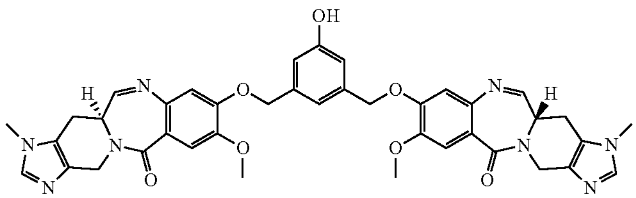 | Yield 34%, ESI-MS m/z: 743 (M+ + 1) |
| D-10 | 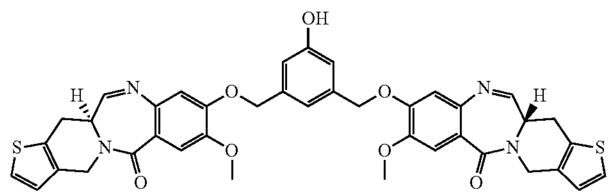 [SMILES: COc1cc2c(cc1OCc1cc(O)cc(COc3cc4c(cc3OC)C(=O)N3Cc5ccsc5C[C@H]3C=N4)c1)N=C[C@@H]1Cc3sccc3CN1C2=O] | Yield 50%, ESI-MS m/z: 747 (M+ + 1) |
| D-11 | 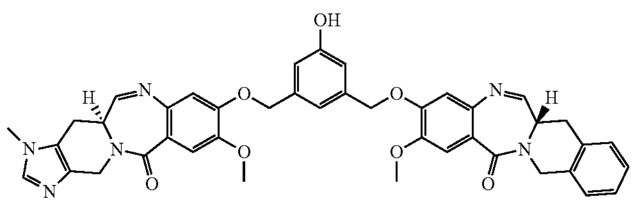 [SMILES: COc1cc2c(cc1OCc1cc(O)cc(COc3cc4c(cc3OC)C(=O)N3Cc5ncn(C)c5C[C@H]3C=N4)c1)N=C[C@@H]1Cc3ccccc3CN1C2=O] | Yield 23%, ESI-MS m/z: 739 (M+ + 1) |
| D-12 | 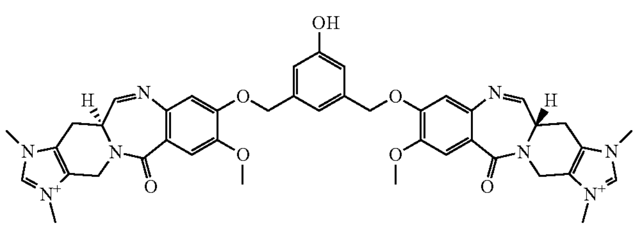 | Yield 33%, ESI-MS m/z: 772 (M+ + 1) |
| D-13 | 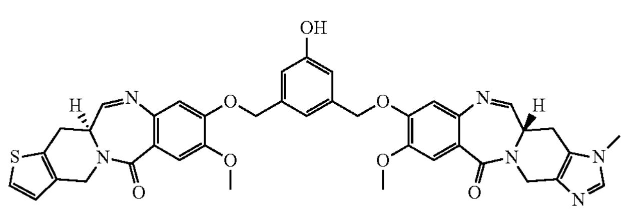 [SMILES: COc1cc2c(cc1OCc1cc(O)cc(COc3cc4c(cc3OC)C(=O)N3Cc5ncn(C)c5C[C@H]3C=N4)c1)N=C[C@@H]1Cc3sccc3CN1C2=O] | Yield 11%, white solid. ESI-MS m/z: 745 (M+ + 1) |
| D-14 | 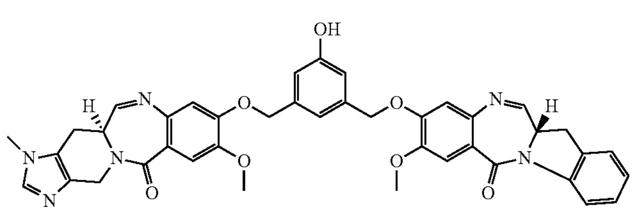 [SMILES: COc1cc2c(cc1OCc1cc(O)cc(COc3cc4c(cc3OC)C(=O)N3c5ccccc5C[C@H]3C=N4)c1)N=C[C@@H]1Cc3c(ncn3C)CN1C2=O] | Yield 7%, white solid. ESI-MS m/z: 725 (M+ + 1) |

Example 4.9.8

Preparation of Dimer Derivatives

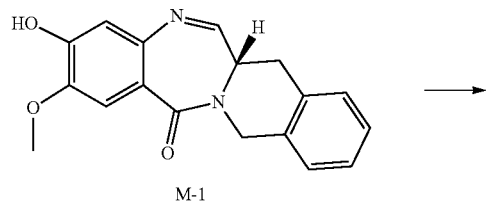

M-1

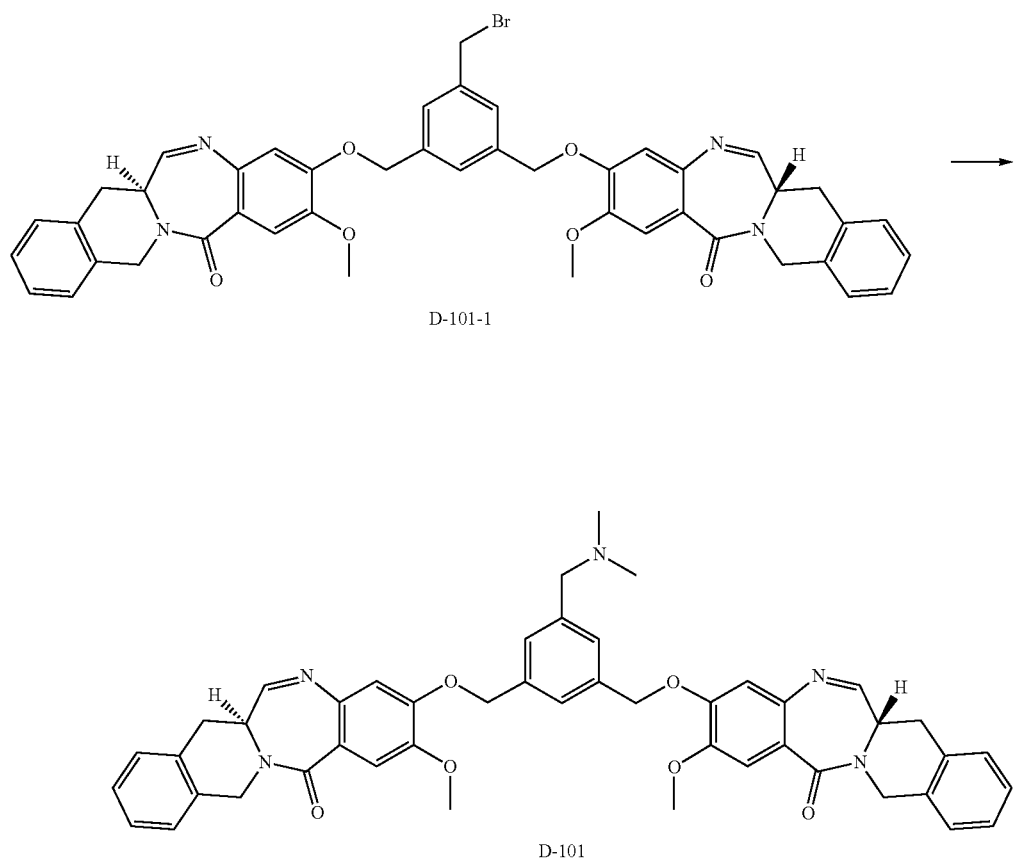

Preparation of Compound D-101-1

To a solution of compound M-1 (100 mg, 0.32 mmol) and 1,3,5-tris(bromomethyl)benzene (57 mg, 0.16 mmol) in DMF (1 mL) was added $K_2CO_3$ (45 mg, 0.32 mmol) at room temperature under $N_2$ atmosphere. After stirring for 4 hours, EA (100 mL), $H_2O$ (50 mL) and 2N HCl aqueous solution (5 mL) were added to perform extraction, the obtained organic layer was dried over anhydrous $Na_2SO_4$, filtered and concentrated under reduced pressure. The residue was purified by column chromatography to obtain compound D-101-1 (54 mg, 42%).

ESI-MS m/z: 812 ($M^+$).

Preparation of Compound D-101

Compound D-101-1 (50 mg, 0.01 mmol) was dissolved in dimethylamine (1 mL) at room temperature under $N_2$ atmosphere. After stirring for 1 h, the mixture was purified by preparative HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-101 (2.2 mg, 17%).

ESI-MS m/z: 776 ($M^+$+1).

Example 4.9.9

Preparation of Dimer Derivatives

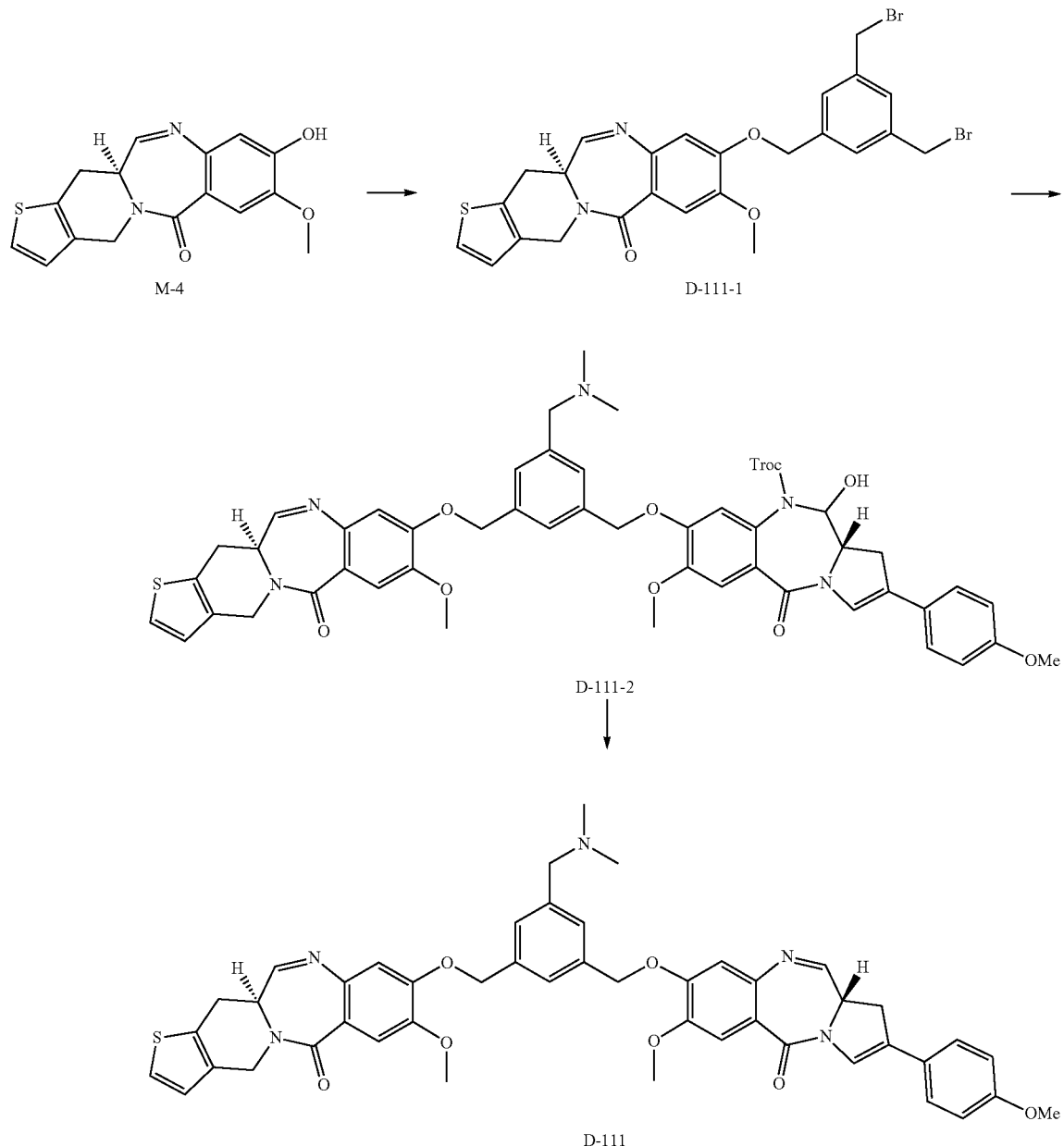

Preparation of Compound D-111-1

A yellow solution of compound M-4 (10 mg, 0.032 mmol) and 1,3,5-tris(bromomethyl)benzene (11.35 mg, 0.032 mmol, 1.0 eq) in DMF (1 mL) at room temperature under $N_2$ atmosphere was treated with $K_2CO_3$ (4.4 mg, 0.032 mmol, 1.0 eq) and stirred for 5 hours. The reaction mixture was purified by prep HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound D-111-1 (20.9 mg, 22%) as white solid.

ESI-MS m/z: 591 ($M^+$+1).

Preparation of Compound D-111-2

A homogeneous solution of compound D-111-1 (20 mg, 0.034 mmol) and M-2 (18.4 mg, 0.034 mmol) in DMF (1 mL) at room temperature under $N_2$ atmosphere was treated with $K_2CO_3$ (4.7 mg, 0.034 mmol) and stirred for 5 hours. The reaction mixture was treated with 1M dimethylamine in THF (0.5 mL) and stirred for 30 minutes. The reaction mixture was purified by prep HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound D-111-2 (3.4 mg, 9.8%) as white solid.
ESI-MS m/z: 1018 (M$^+$+1).

Preparation of Compound D-111

A solution of compound D-111-2 (3.4 mg, 0.003 mmol) and 10% Cd/Pb (100 mg) in THF (0.5 mL) at room temperature under N$_2$ atmosphere was treated with 1N NH$_4$OAc (300 µL) and stirred for 3 days. The reaction mixture was purified by prep HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound D-111 (0.8 mg, 29%) as white solid. ESI-MS m/z: 824 (M$^+$+1).

Table 8 below lists the dimer derivatives that were synthesized via a similar synthetic route as described in Example 4.9.8 or 4.9.9.

TABLE 8

| Dimer | Structure | Characterization Data |
|---|---|---|
| D-102 | 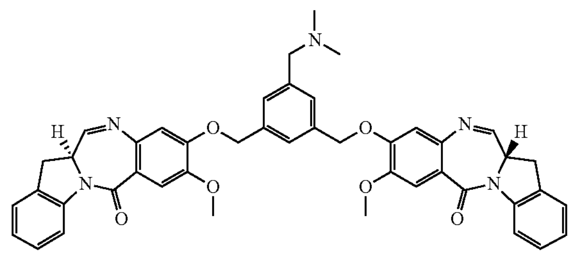 [SMILES: COc1cc2c(cc1OCc1cc(COc3cc4c(cc3OC)C(=O)N3c5ccccc5C[C@H]3C=N4)cc(CN(C)C)c1)N=C[C@@H]1Cc3ccccc3N1C2=O] | Yield 50%, ESI-MS m/z: 748 (M$^+$ + 1) |
| D-103 | 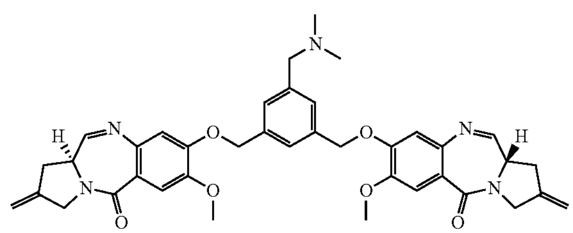 | Yield 23%, ESI-MS m/z: 658 (M$^+$ + 1) |
| D-104 | 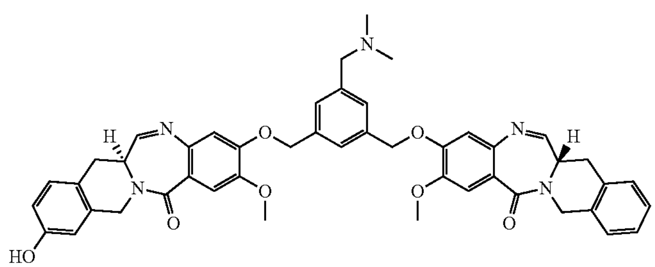 [SMILES: COc1cc2c(cc1OCc1cc(COc3cc4c(cc3OC)C(=O)N3Cc5cc(O)ccc5C[C@H]3C=N4)cc(CN(C)C)c1)N=C[C@@H]1Cc3ccccc3CN1C2=O] | Yield 23%, ESI-MS m/z: 792 (M$^+$ + 1) |
| D-105 | 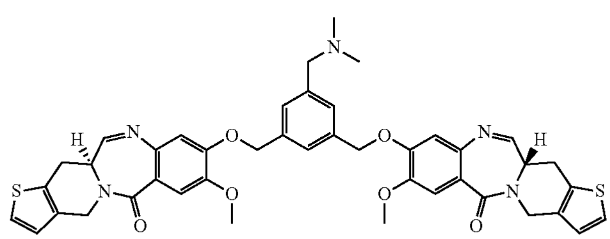 | Yield 60%, ESI-MS m/z: 788 (M$^+$ + 1) |
| D-106 | 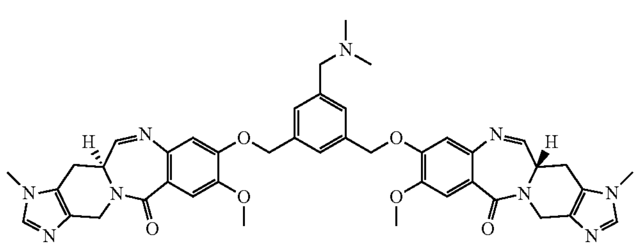 | ESI-MS m/z: 784 (M$^+$ + 1) |

TABLE 8-continued
| Dimer | Structure | Characterization Data |
|---|---|---|
| D-107 | 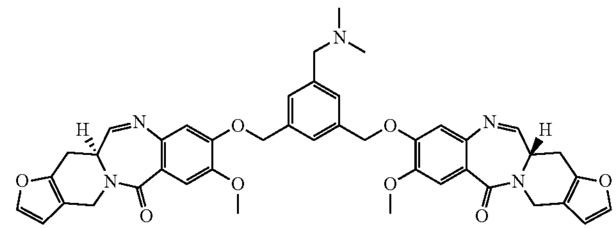 [SMILES: COc1cc2c(cc1OCc1cc(COc3cc4c(cc3OC)C(=O)N3Cc5ccoc5C[C@H]3C=N4)cc(CN(C)C)c1)N=C[C@@H]1Cc3occc3CN1C2=O] | ESI-MS m/z: 756 (M+ + 1) |
| D-108 | 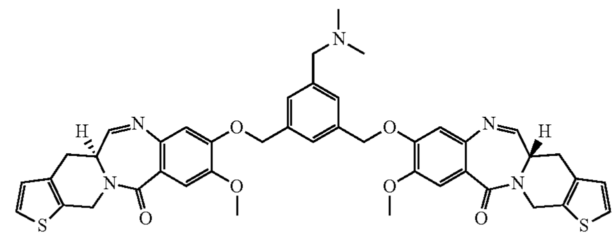 [SMILES: COc1cc2c(cc1OCc1cc(COc3cc4c(cc3OC)C(=O)N3Cc5sccc5C[C@H]3C=N4)cc(CN(C)C)c1)N=C[C@@H]1Cc3ccsc3CN1C2=O] | Yield 16%, ESI-MS m/z: 788 (M+ + 1) |
| D-109 | 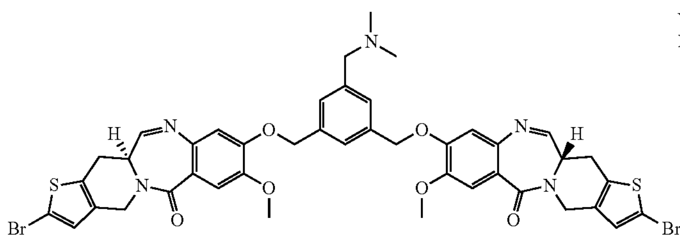 [SMILES: COc1cc2c(cc1OCc1cc(COc3cc4c(cc3OC)C(=O)N3Cc5cc(Br)sc5C[C@H]3C=N4)cc(CN(C)C)c1)N=C[C@@H]1Cc3sc(Br)cc3CN1C2=O] | Yield 56%, ESI-MS m/z: 946 (M+ + 1) |
| D-110 | 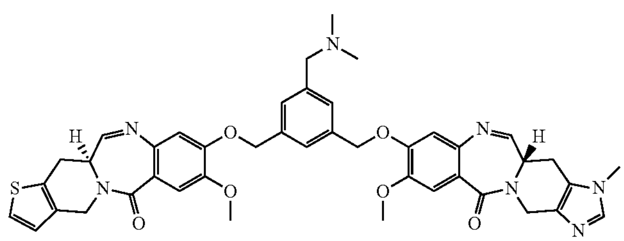 [SMILES: COc1cc2c(cc1OCc1cc(COc3cc4c(cc3OC)C(=O)N3Cc5ncn(C)c5C[C@H]3C=N4)cc(CN(C)C)c1)N=C[C@@H]1Cc3sccc3CN1C2=O] | Yield 9%, ESI-MS m/z: 786 (M+ + 1) |
Example 4.9.10
Preparation of D-112
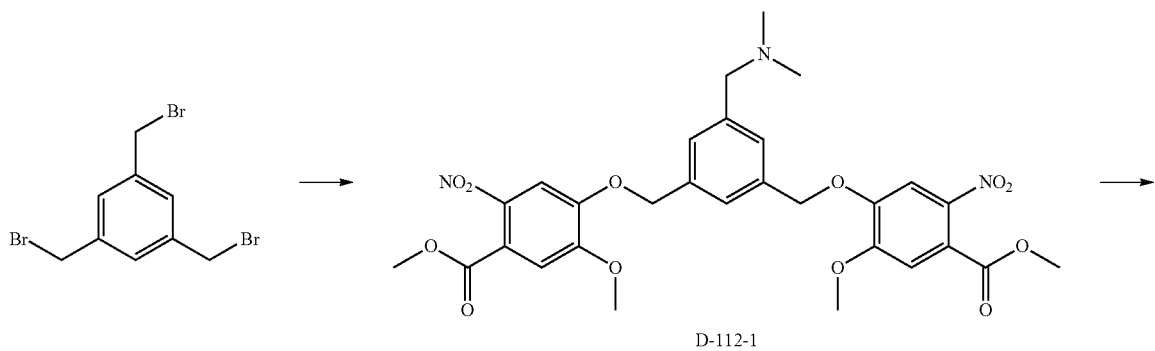
D-112-1

-continued
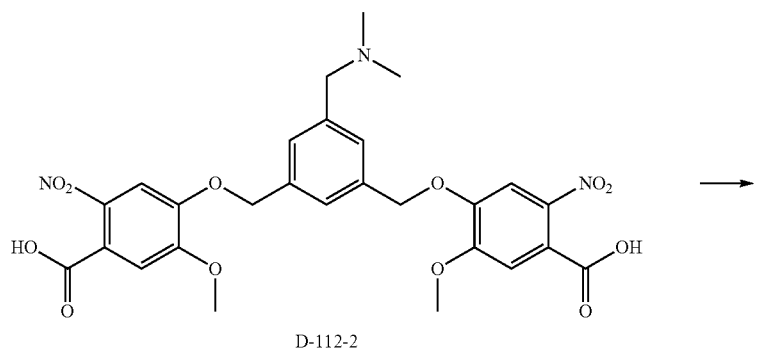
D-112-2
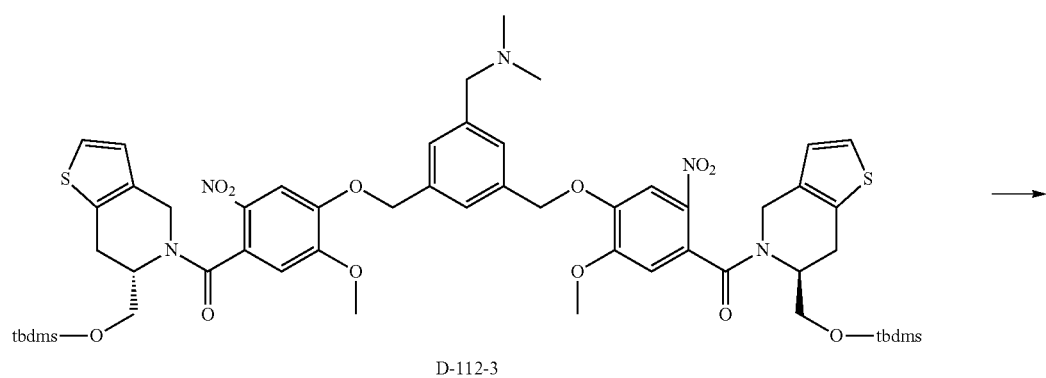
D-112-3
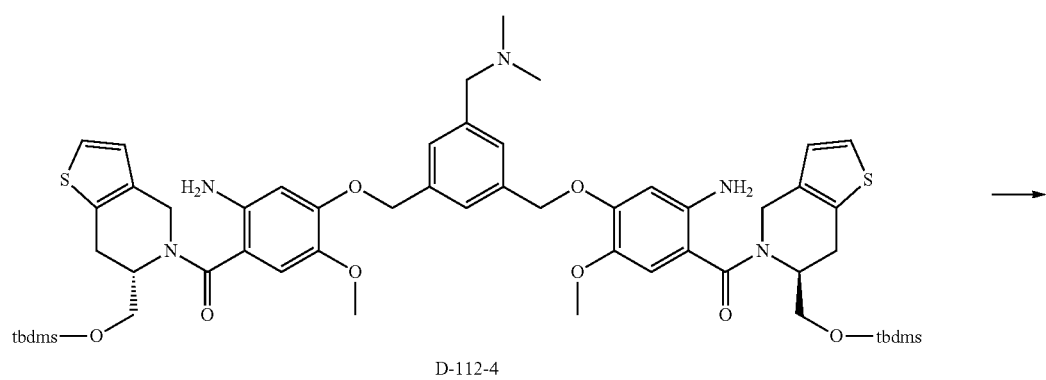
D-112-4

245
246
-continued
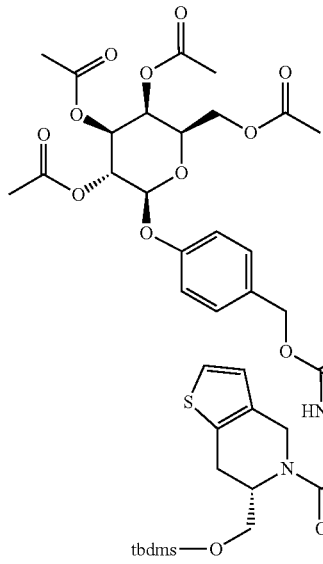
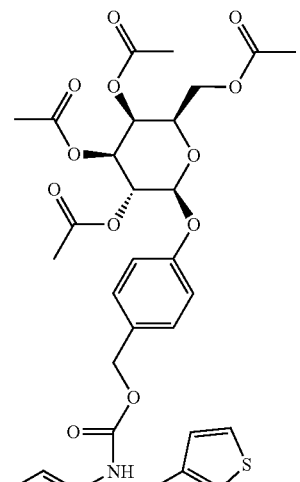
D-112-5
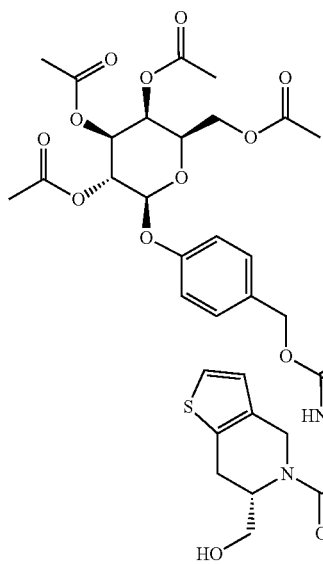
D-112-6
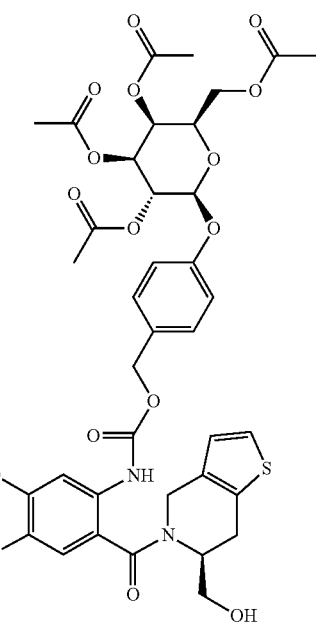

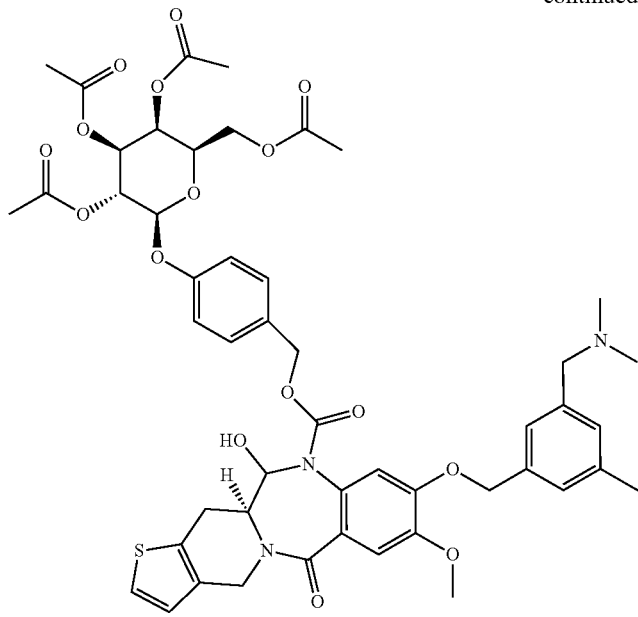
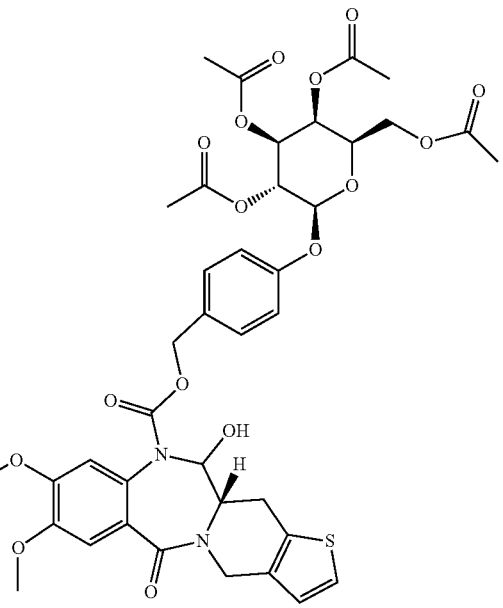

D-112

Preparation of Compound D-112-1

To a solution of 1,3,5-tris(bromomethyl)benzene (3.9 g, 11.0 mmol), compound Int-2 (4.96 g, 21.9 mmol, in DMF (10.0 mL) at room temperature under $N_2$ atmosphere was treated with $K_2CO_3$ (44.2 mg, 0.32 mmol, 1.0 eq) was stirred for 6 hours. The reaction mixture was treated with dimethyl amine (5.0 mL) and stirred for 30 minutes. The reaction mixture was diluted with distilled water (50 mL) and DCM (100 mL×2). The organic layer was dried over anhydrous $Na_2SO_4$, filtered and concentrated under reduced pressure. The residue was purified by column chromatography to obtain compound D-112-1 (2.74 g g, 41%).

$^1$H NMR (400 MHz, $CDCl_3$) δ 7.50 (s, 2H), 7.41 (d, J=12.0 Hz, 3H), 7.08 (s, 2H), 5.20 (s, 4H), 3.97 (s, 6H), 3.91 (s, 6H), 3.47 (s, 2H), 2.25 (s 6H); ESI-MS m/z: 614 (M$^+$1).

Preparation of Compound D-112-2

To a solution of compound D-112-1 (2.74 g, 4.46 mol) in THF (75 mL) and $H_2O$ (50 mL) was added LiOH (937 mg, 22.33 mol). After stirring for 5 hours. The reaction mixture was concentrated under reduced pressure. The residue was cooled to 0° C. and adjusted to have pH 2 by addition of 2N HCl solution, and then solid was filtered and washed with $H_2O$ (30 mL), EA (100 mL) to obtain compound D-112-2 (2.5 g, 96%).

$^1$H NMR (400 MHz, DMSO-d6) δ 7.71 (s, 2H), 7.60 (d, J=17.6 Hz, 3H), 7.32 (s, 2H), 5.30 (s, 4H), 3.91 (s, 6H), 2.67 (s, 6H); ESI-MS m/z: 586 (M$^+$1).

Preparation of Compound D-112-3

To a solution of compound D-112-2 (1.5 g, 2.56 mmol), compound M-4a (1.52 g, 5.38 mmol) in DMF (50.0 ml) at room temperature under $N_2$ atmosphere was treated with PyBop (3.5 g, 6.40 mmol), DIPEA (2.2 mL, 12.8 mmol) was stirred for 2 hours. The reaction mixture was diluted with distilled water (100 mL) and EA (100 mL×2). The organic layer was dried over anhydrous $Na_2SO_4$, filtered and concentrated under reduced pressure. The residue was purified by column chromatography to obtain compound D-112-3 (2.7 g, 94%); ESI-MS m/z: 1116 (M$^+$).

Preparation of Compound D-112-4

To a solution of compound D-112-3 (2.7 g, 2.42 mmol) in EA (50.0 ml) was treated with 5% Pd/C (5.1 g, 2.42 mmol) at room temperature under $H_2$ and stirred for 1 hour. The reaction mixture was filtered through CELITE®, and then concentrated under reduced pressure to obtain compound D-112-4 (1.87 g, 93%); ESI-MS m/z: 1056 (M$^+$).

Preparation of Compound D-112-5

To a solution of compound D-112-4 (100 mg, 0.095 mmol), Int-3 (189 mg, 0.28 mmol) in anhydrous THF (3.0 ml) at room temperature under $N_2$ atmosphere was treated with HOBT (13.0 mg, 0.095 mmol), DIPEA (36 uL, 0.208 mmol) was stirred for 44 hours. The reaction mixture was extracted with distilled water (10 mL) and EA (20 mL×2) and organic layer wash with sat $NH_4Cl$ (50 mL). The organic layer was dried over anhydrous $Na_2SO_4$, filtered and concentrated under reduced pressure. The residue was purified by column chromatography to obtain compound D-112-5 (76 mg, 40%); ESI-MS m/z: 2017 (M$^+$).

Preparation of Compound D-112-6

To a solution of compound D-112-5 (116.7 mg, 0.06 mmol) in ACN (2.0 ml), $H_2O$ (800 uL) at 0° C. under $N_2$ atmosphere was treated with TFA/ACN (1.0 mL) was stirred for 2 hours. The residue was purified by prep HPLC to obtain compound D-112-6 (83.3 mg, 80%); ESI-MS m/z: 1788 (M$^+$).

Preparation of Compound D-2

To a solution of compound D-112-6 (83.3 mg, 0.046 mmol) in anhydrous DCM (3.0 ml) at 0° C. under $N_2$ atmosphere was treated with Dess-Martin periodinane (45.4 mg, 0.11 mmol) was stirred for 4 hours. The reaction mixture was diluted with distilled water (10 mL) and EA (30 mL×2). The organic layer was dried over anhydrous $Na_2SO_4$, filtered and concentrated under reduced pressure. The residue was purified by prep HPLC to obtain compound D-112 (59.3 mg, 71%); ESI-MS m/z: 1784 (M$^+$).

Table 9 below lists the dimer derivatives that were synthesized via a similar synthetic route as described in Example 4.9.10.

TABLE 9
| Dimer | Structure | Characterization Data |
|---|---|---|
| D-113 | 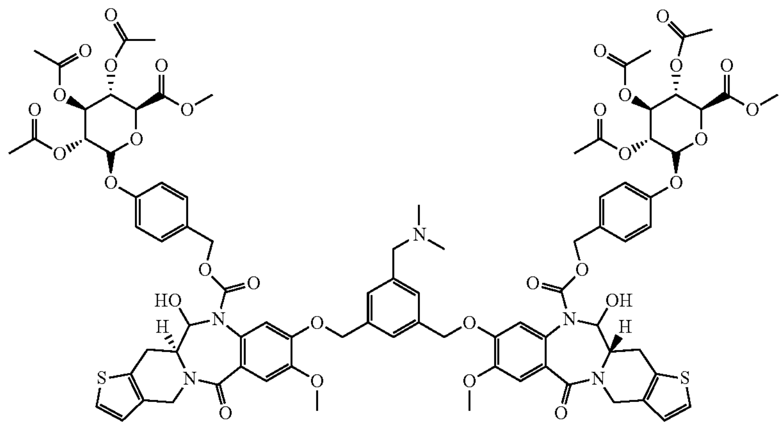 | Yield 48%<br>ESI-MS m/z: 1756 (M+). |
| D-114 | 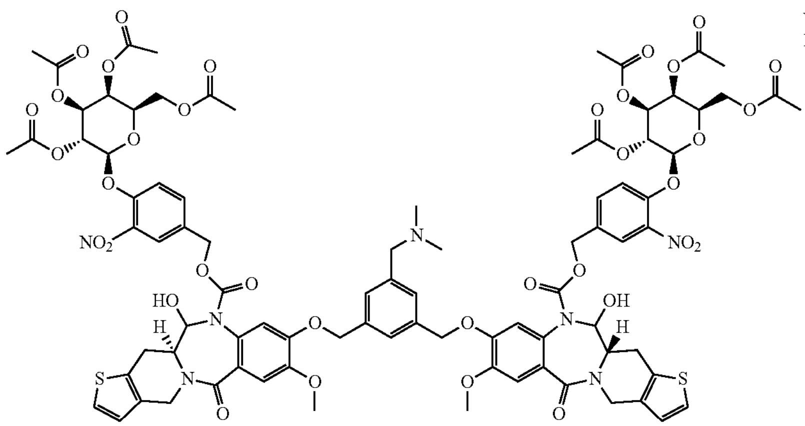 [SMILES: COc1cc2c(cc1OCc1cc(COc3cc4c(cc3OC)C(=O)N3Cc5ccsc5C[C@H]3C(O)N4C(=O)OCc3ccc(O[C@@H]4O[C@H](COC(C)=O)[C@H](OC(C)=O)[C@H](OC(C)=O)[C@H]4OC(C)=O)c([N+](=O)[O-])c3)cc(CN(C)C)c1)N(C(=O)OCc1ccc(O[C@@H]3O[C@H](COC(C)=O)[C@H](OC(C)=O)[C@H](OC(C)=O)[C@H]3OC(C)=O)c([N+](=O)[O-])c1)C(O)[C@@H]1Cc3sccc3CN1C2=O] | Yield 74%<br>ESI-MS m/z: 1874.36 (M+). |
Example 4.10
Example 4.10.1
Preparation of T-Int-1
T-Int-1-1

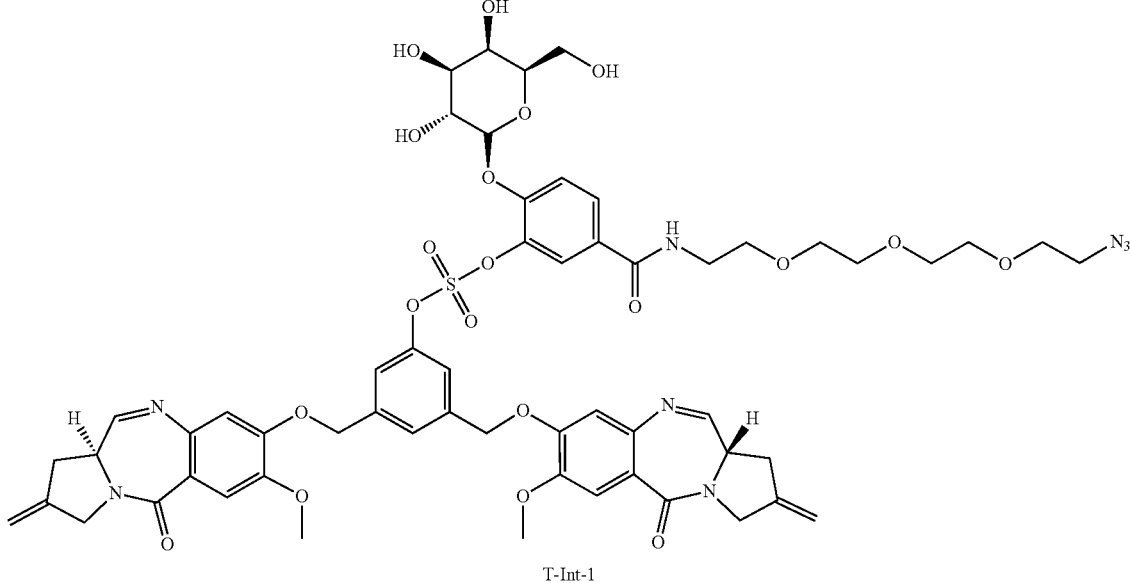

T-Int-1

Preparation of Compound T-Int-1-1

To a solution of compound D-7 (10 mg, 0.01 mmol) and compound OHPAS-D1 (11 mg, 0.01 mmol) in ACN (1 mL) was added BEMP (0.8 mg, 0.003 mmol) at room temperature under $N_2$ atmosphere. After stirring for 1 hour at room temperature, the reaction mixture was purified by HPLC to obtain compound T-Int-1-1 (12 mg, 63%). ESI-MS m/z: 1382 ($M^{+1}$).

Preparation of Compound T-Int-1

To a solution of Compound T-Int-1-1 (10 mg, 0.007 mmol) in MeOH (1.0 mL) was added $K_2CO_3$ (5 mg, 0.036 mmol) under $N_2$ atmosphere. After stirring for 2 hours at room temperature, the mixture was purified by HPLC to obtain compound T-Int-1 (7.4 mg, 85%). ESI-MS m/z: 1214 ($M^{+1}$).

Table 10 below lists the dimer derivatives that were synthesized via a similar synthetic route as described in Example 4.10.1.

TABLE 10

| Dimer | Structure | Characterization Data |
|---|---|---|
| T-Int-2<br>T-Int-3 | ![structure] T-Int-2 (n = 3)<br>T-Int-3 (n = 11) | T-Int-2: Yield 71%,<br>ESI-MS m/z: 1314<br>($M^+$ + 1)<br>T-Int-3: Yield 83%,<br>ESI-MS m/z: 1666<br>($M^+$ + 1) |
| T-Int-4 | ![structure] | Yield 67%,<br>ESI-MS m/z: 1280<br>($M^+$ + 1) |

TABLE 10-continued

| Dimer | Structure | Characterization Data |
|---|---|---|
| T-Int-5 | 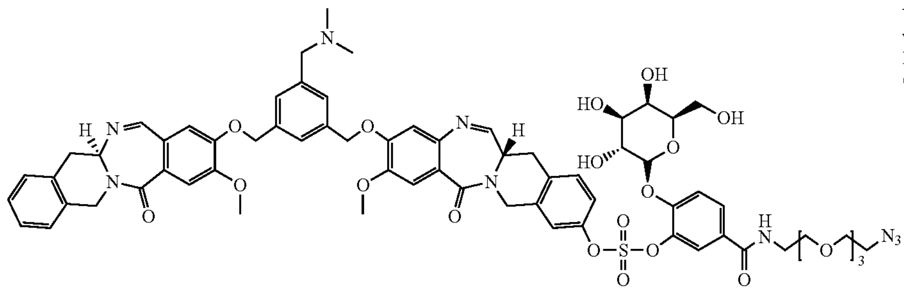 | Yield 72%, white solid ESI-MS m/z: 1371 (M⁺ + 1) |
| T-Int-6 | 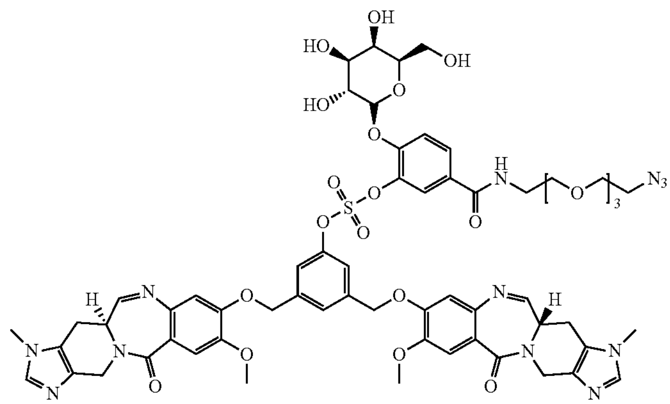 | Yield 76%, ESI-MS m/z: 1322 (M⁺ + 1) |
| T-Int-7 | 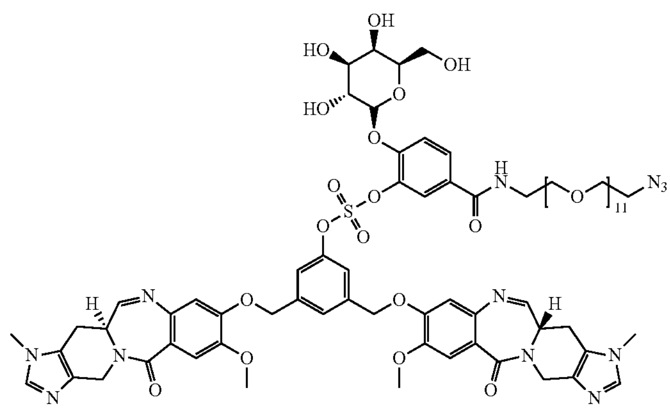 | Yield 62% ESI-MS m/z: 1674 (M⁺ + 1). |
| T-Int-8 | 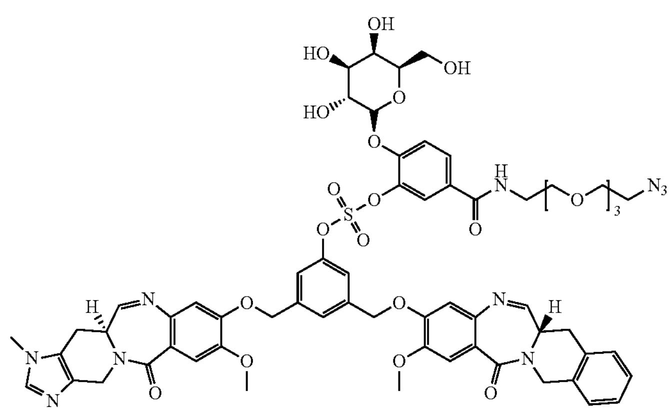 | Yield 63%, white solid. ESI-MS m/z: 1318 (M⁺ + 1). |

TABLE 10-continued
| Dimer | Structure | Characterization Data |
|---|---|---|
| T-Int-9 | 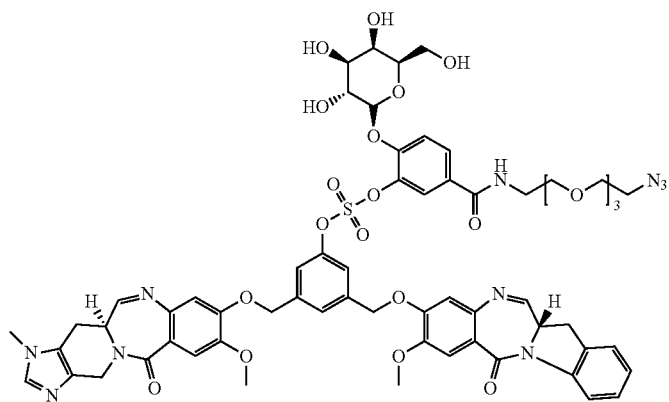 | Yield 57%, yellow solid. ESI-MS m/z: 1304 (M+ + 1). |
| T-Int-10 | 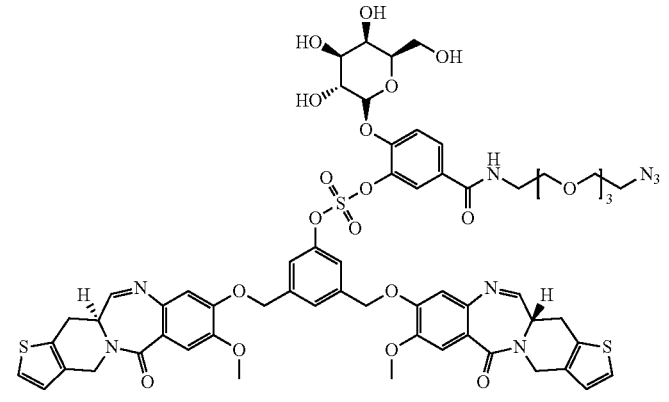 | Yield 71%, yellow solid. ESI-MS m/z: 1326 (M+ + 1). |
| T-Int-11 | 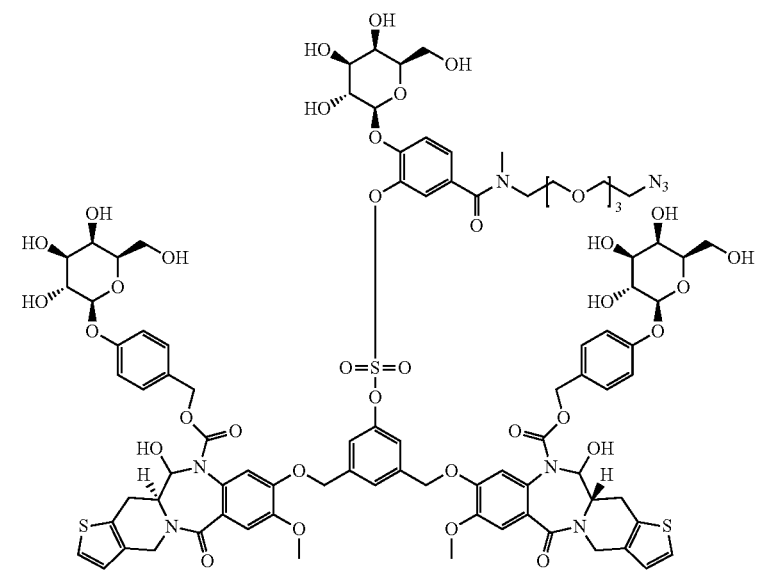 | Yield 66%; ESI-MS m/z: 1000 (M+/2), 2000 (M+). |

Example 4.10.2

Preparation of T-Int-101

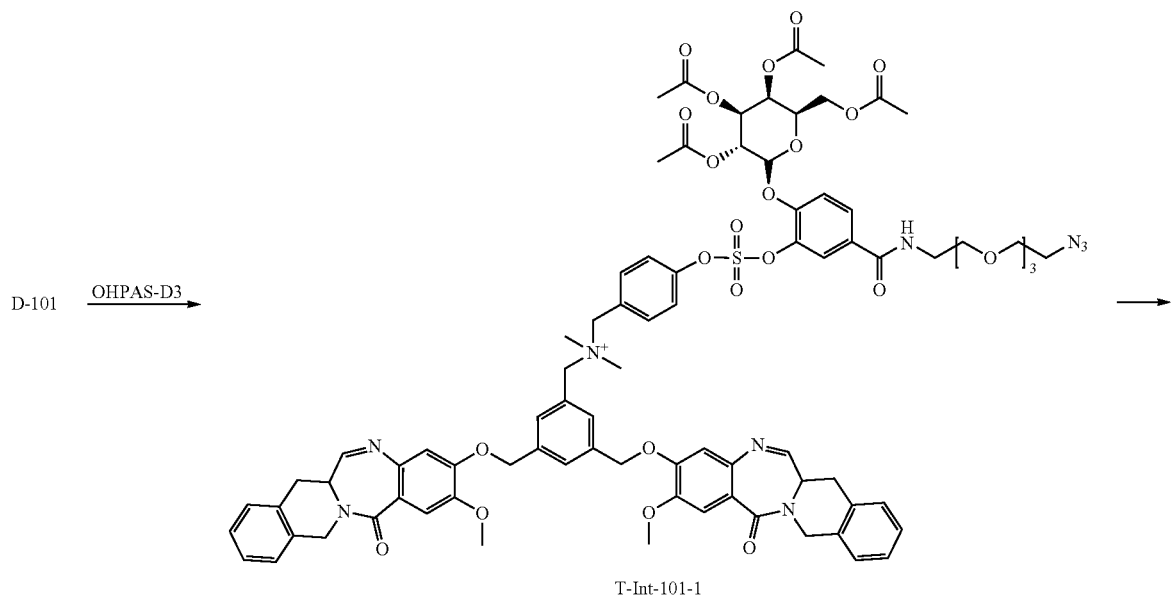

T-Int-101-1

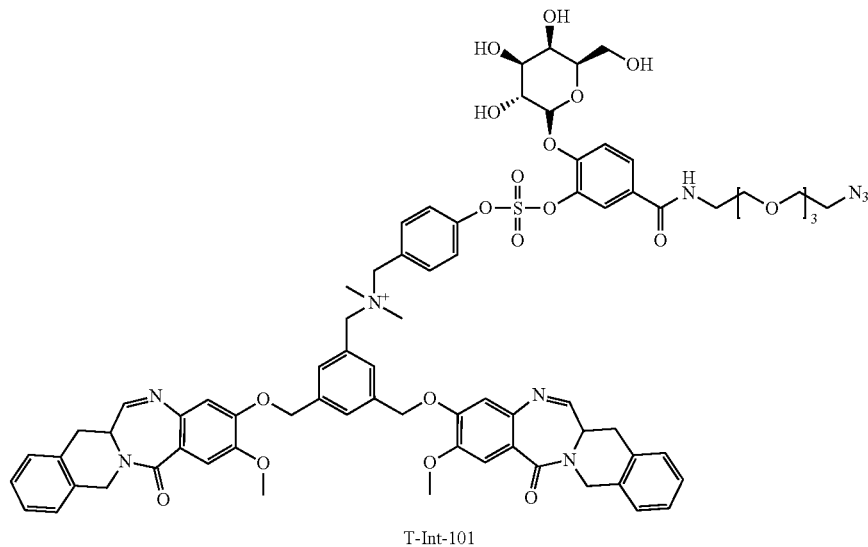

T-Int-101

Preparation of Compound T-Int-101-1

To a solution of compound D-101 (8.0 mg, 0.01 mmol) and compound OHPAS-D3 (11.5 mg, 0.01 mmol) in DMF (1 mL) was added DIPEA (5.4 μL, 0.03 mmol) at room temperature under $N_2$ atmosphere. After stirring for 6 hours at room temperature, the reaction mixture was purified by HPLC to obtain compound T-Int-101-1 (11.9 mg, 71%). ESI-MS m/z: 1630 ($M^{+1}$).

Preparation of Compound T-Int-101

To a solution of Compound T-Int-101-1 (11.9 mg, 0.01 mmol) in MeOH (1 mL) was added $K_2CO_3$ (5 mg, 0.04 mmol) under $N_2$ atmosphere. After stirring for 1 hours at room temperature, the reaction mixture was purified by HPLC (Column: Innoval ODS-2 10 um, 100 Å, 50×250 mm; flow rate: 15 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound T-Int-101 (6.4 mg, 60%). ESI-MS m/z: 1462 ($M^{+1}$).

Example 4.10.3

Preparation of T-Int-102, T-Int-104 and T-Int-105

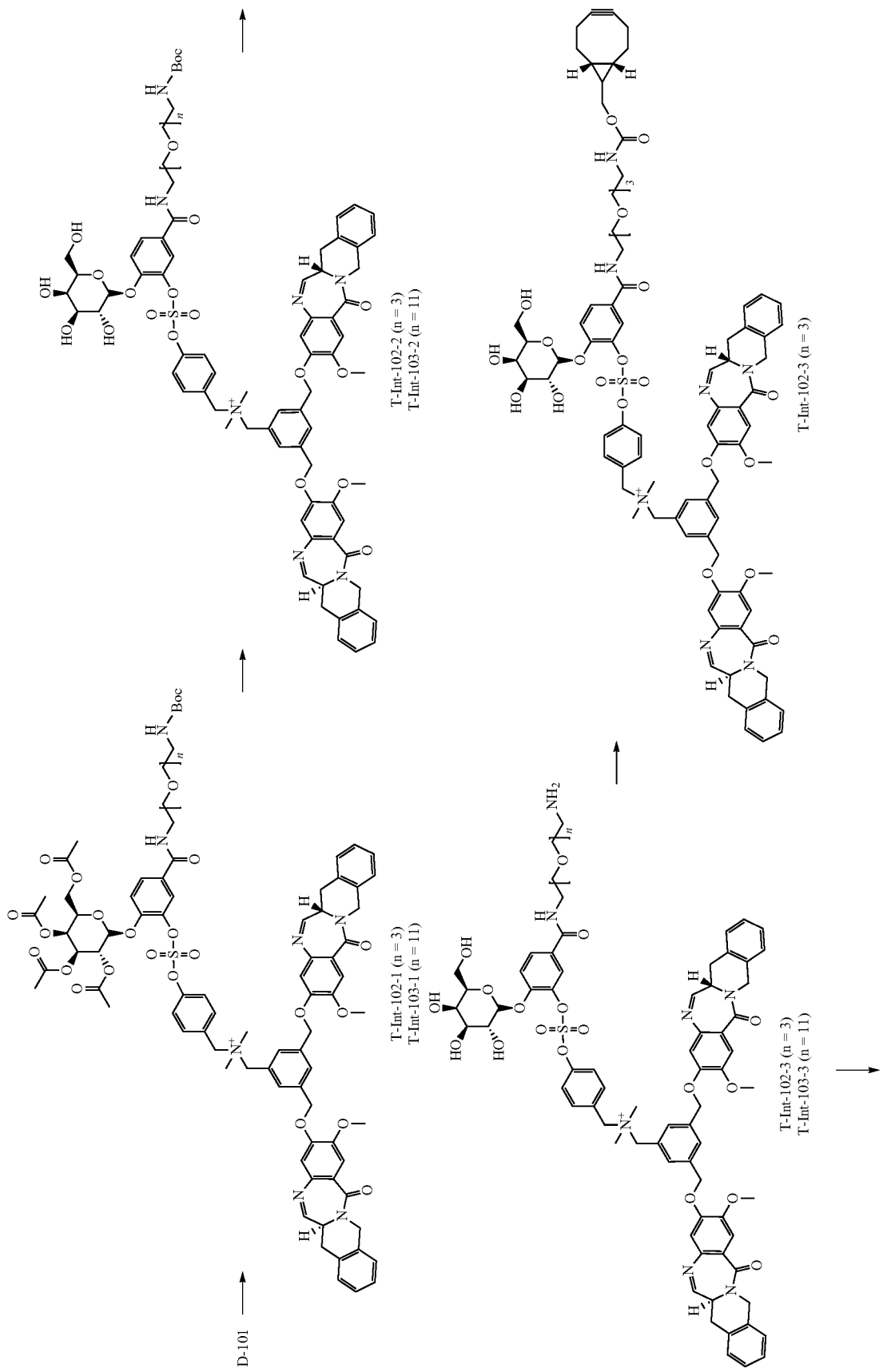

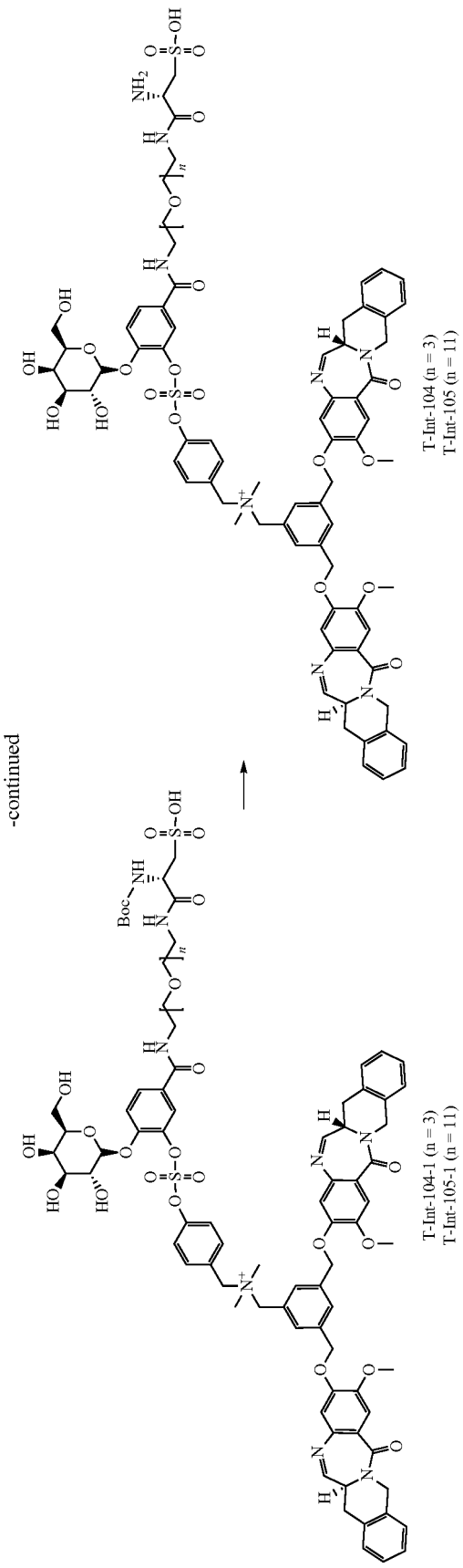

T-Int-102-2 and T-Int-103-2 were synthesized via a similar manner to the preparation method of the compound T-Int-101.

Preparation of Compound T-Int-102-1
Yield 70% as white solid.
ESI-MS m/z: 1704 (M$^+$+1).

Preparation of Compound T-Int-102-2
Yield 81%, white solid
ESI-MS m/z: 1536 (M$^+$+1).

Preparation of Compound T-Int-103-1
Yield 84%, yellow solid
ESI-MS m/z: 2057 (M$^+$+1), 1029 (M/2$^+$+1).

Preparation of Compound T-Int-103-2
Yield 84%, a colorless oil
ESI-MS m/z: 1889 (M$^+$+1), 945 (M/2$^+$+1).

Preparation of Compound T-Int-102-3
A homogeneous solution of compound T-Int-102-2 (56 mg, 0.036 mmol) in anhydrous DCM (1.0 mL) at 0° C. under N$_2$ atmosphere was treated TFA (0.2 mL) in DCM (1 mL) and stirred for 2 hours. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-102-3 (44.4 mg, 82%) as ivory solid.
ESI-MS m/z: 1436 (M$^+$+1).

T-Int-103-3 was synthesized via a similar manner to the preparation method of the compound T-Int-102-3.

Preparation of Compound T-Int-103-3
Yield 74%, ivory solid
ESI-MS m/z: 1789 (M$^+$+1), 895 (M/2$^+$+1).

Preparation of Compound T-Int-102
A homogeneous solution of compound T-Int-102-3 (50 mg, 0.035 mmol) and BCN-PNP (11 mg, 0.035 mmol, 1.0 eq.) in DMF (3.0 mL) at room temperature under N$_2$ atmosphere was treated DIPEA (11 uL, 0.068 mmol, 2.0 eq.) and stirred for 2 hours. The mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-102 (22 mg, 39%) as beige solid.
ESI-MS m/z: 1612 (M$^+$+1).

Preparation of Compound T-Int-104-1
A homogeneous solution of T-Int-103-3 (20 mg, 0.014 mmol) and L-6-5 (5.1 mg, 0.014 mmol, 1.0 eq.) in DMF (2.0 mL) at room temperature under N$_2$ atmosphere was treated DIPEA (7.3 uL, 0.042 mmol, 3.0 eq.) and stirred for 2 hours. The mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-104-1 (19.9 mg, 85%) as yellow solid.
ESI-MS m/z: 1687 (M$^+$+1), 844 (M/2$^+$+1).

Preparation of Compound T-Int-104
T-Int-104 was synthesized via a similar manner to the preparation method of the compound T-Int-102-3.
Yield 72%, ivory solid
ESI-MS m/z: 1789 (M$^+$+1), 895 (M/2$^+$+1).

T-Int-105 was synthesized via a similar manner to the preparation method of the compound T-Int-104.

Preparation of Compound T-Int-105-1
Yield 75%, ivory solid
ESI-MS m/z: 2040 (M$^+$+1), 1010 (M/2$^+$+1).

Preparation of Compound T-Int-105
Yield 60%, ivory solid
ESI-MS m/z: 1940 (M$^+$+1), 970 (M/2$^+$+1).

Table 11 below lists the dimer derivatives that were synthesized via a similar synthetic route as described in Example 4.10.1.

TABLE 11

| Dimer | Structure | Characterization Data |
|---|---|---|
| T-Int-106 | 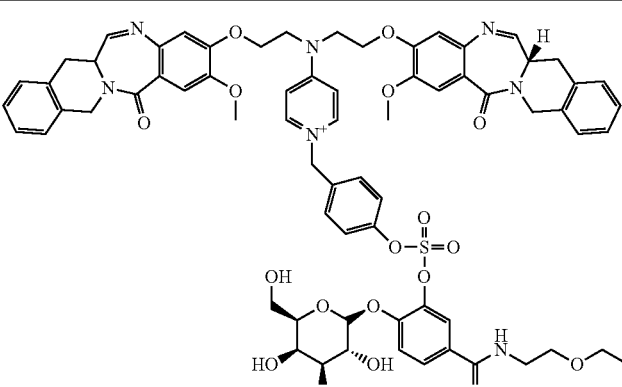 | Yield 68%, ESI-MS m/z: 1449 (M$^+$ + 1) |

TABLE 11-continued
| Dimer | Structure | Characterization Data |
|---|---|---|
| T-Int-107 | 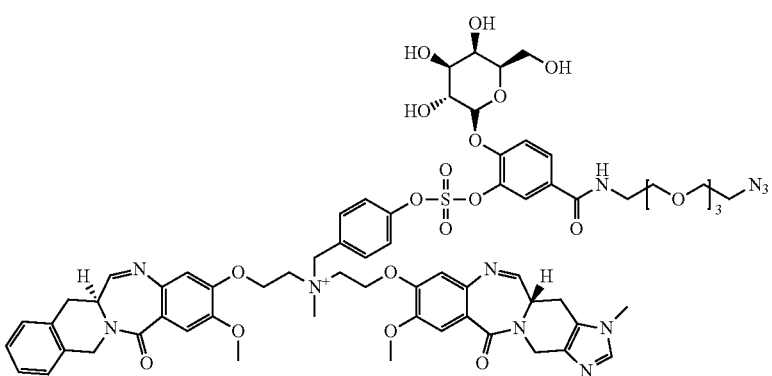 | Yield 74%, yellow solid ESI-MS m/z: 1386 (M$^+$ + 1). |
| T-Int-108 | 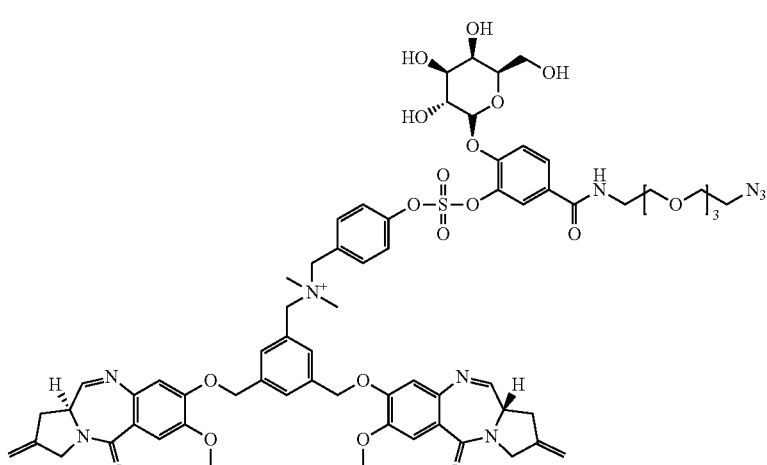 | Yield 81%, yellow solid ESI-MS m/z: 1362 (M$^+$ + 1). |
| T-Int-109 | 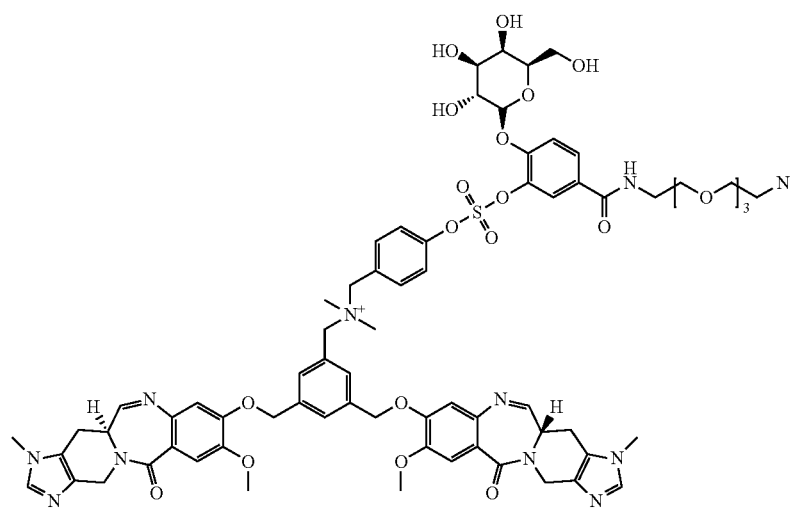 | Yield 72%, ESI-MS m/z: 1469 (M$^+$ + 1). |

TABLE 11-continued

| Dimer | Structure | Characterization Data |
|---|---|---|
| T-Int-110 | 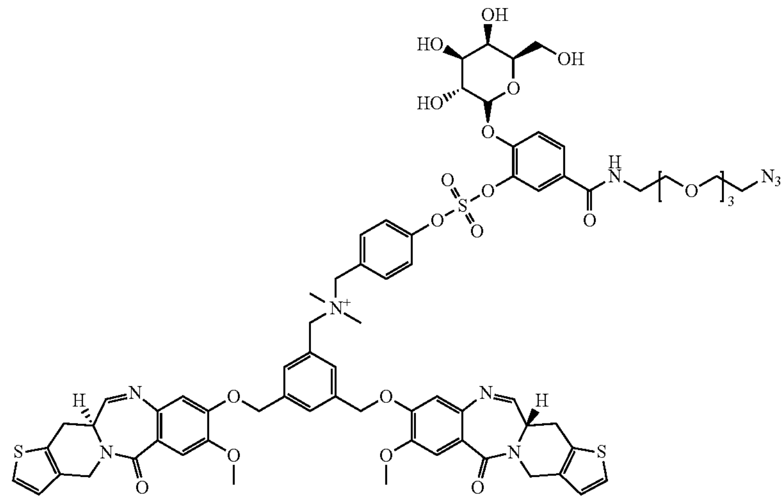 | Yield 71% ESI-MS m/z: 1473 (M$^+$ + 1). |
| T-Int-111 | 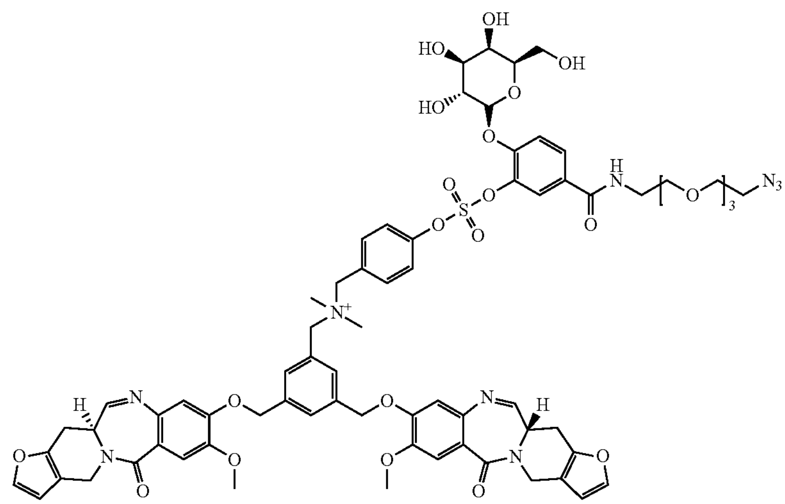 | Yield 55%; ESI-MS m/z: 1441 (M$^+$ + 1). |
| T-Int-112 | 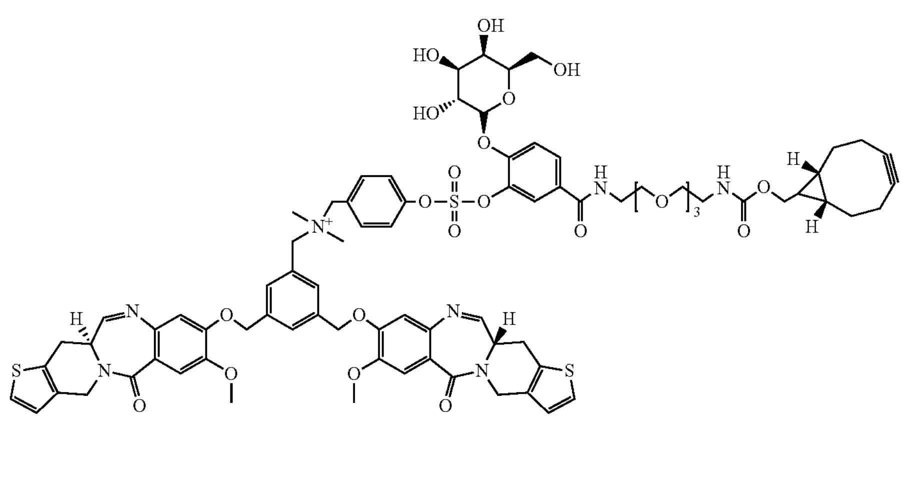 | Yield 62% as light yellow solid; ESI-MS m/z: 1624 (M$^+$ + 1), 812 (M$^+$/2 + 1). |

TABLE 11-continued
| Dimer | Structure | Characterization Data |
|---|---|---|
| T-Int-113 | 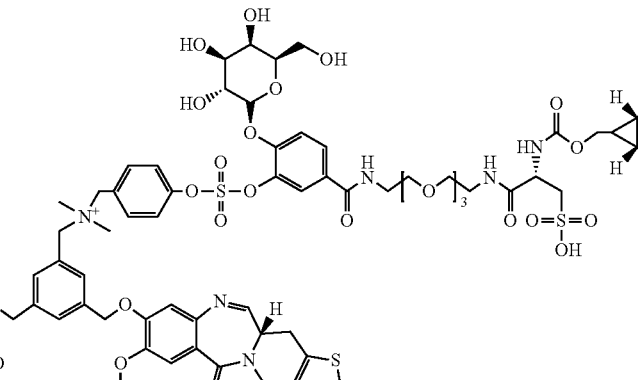 | Yield 35% as light yellow solid. ESI-MS m/z: 1776 (M+ + 1), 888 (M+/2 + 1). |
| T-Int-114 | 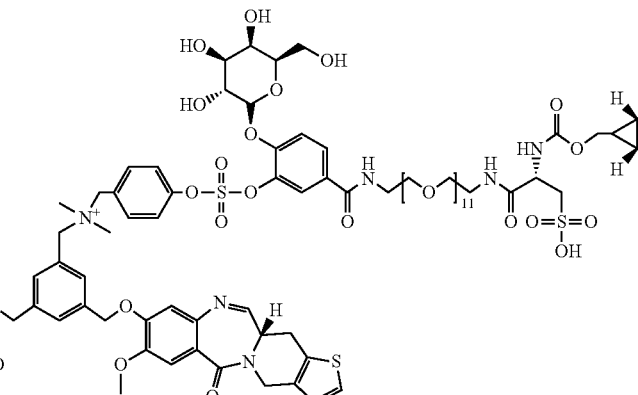 | Yield 31%, white solid. ESI-MS m/z: 2128 (M+ + 1), 1064 (M+/2 + 1) |
| T-Int-115 | 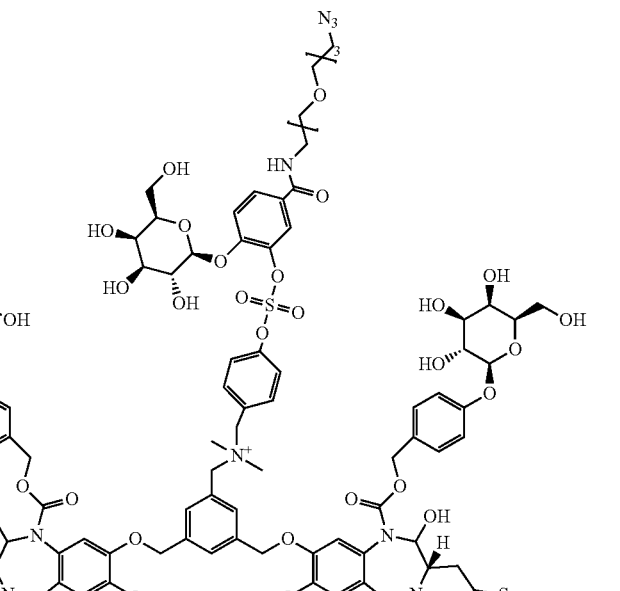 | Yield 68% ESI-MS m/z: 2134 (M+). |

TABLE 11-continued
| Dimer | Structure | Characterization Data |
|---|---|---|
| T-Int-116 | 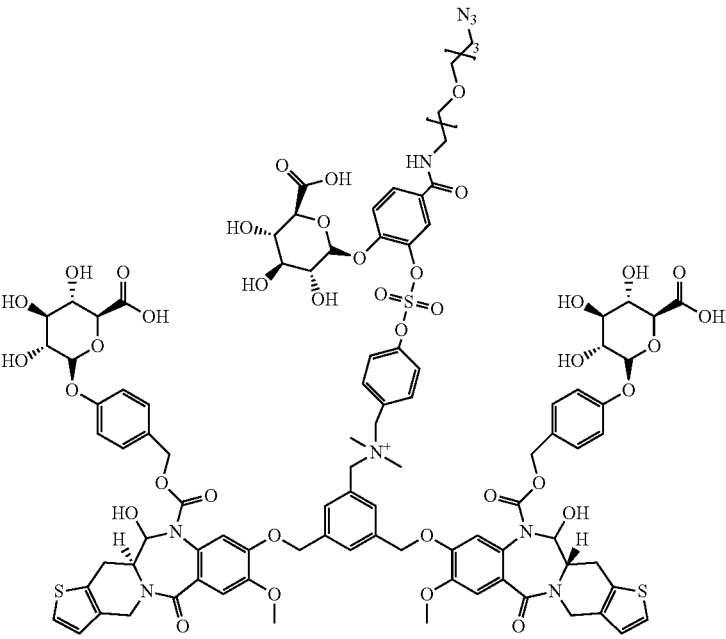 | Yield 64% ESI-MS m/z: 2176 (M+). |
| T-Int-117 | 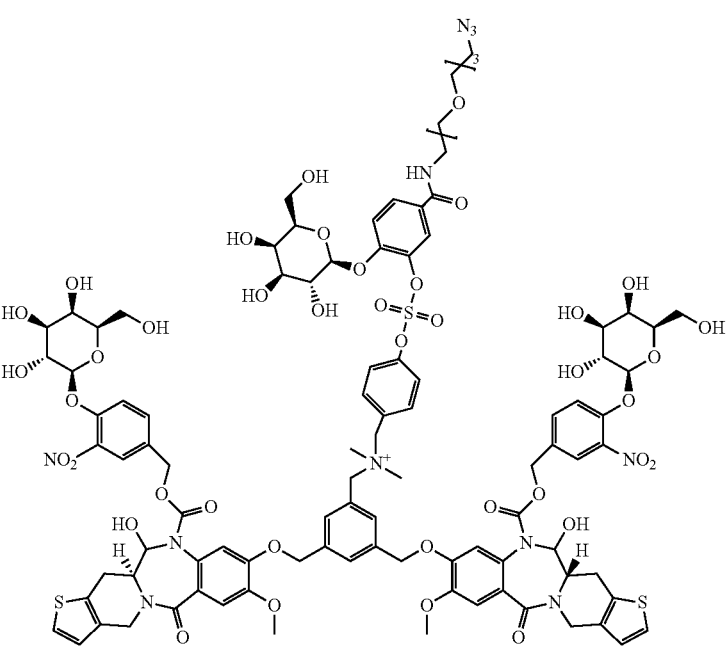 | Yield 63% ESI-MS m/z: 1311 (M+/2), 2623 (M+). |

Example 4.11

Example 4.11.1

Preparation of T-1

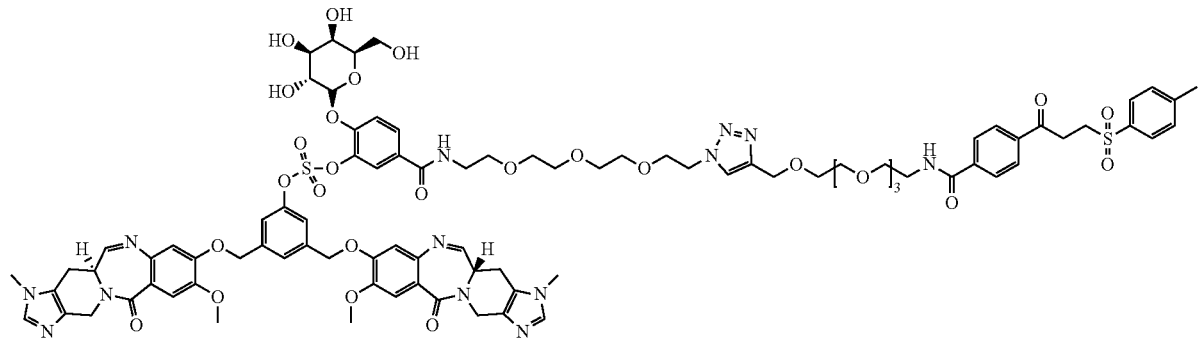

T-1

To a solution of T-Int-1 (2.3 mg, 0.002 mmol) in DMSO (2 mL) was added (BimC$_4$A)$_3$ prepared to have a concentration of 5 mmol. Then, CuBr prepared to have a concentration of 100 mmol was added thereto in an amount of 189 μL. Then, the mixture was stirred for 2 minutes. The compound MPS-D1-2 (3.7 mg, 0.007 mmol) was dissolved in DMSO (674 μL) and added thereto, followed by stirring for 10 minutes. After the reaction was completed, the mixed solution was separated and purified by prep-HPLC to obtain compound T-1 (1.0 mg, 32%).

ESI-MS m/z: 1868 (M$^+$+1).

Table 12 below lists the dimer derivatives that were synthesized via a similar synthetic route as described in Example 4.11.1.

TABLE 12
| Dimer | Structure | Characterization Data |
|---|---|---|
| T-2 | 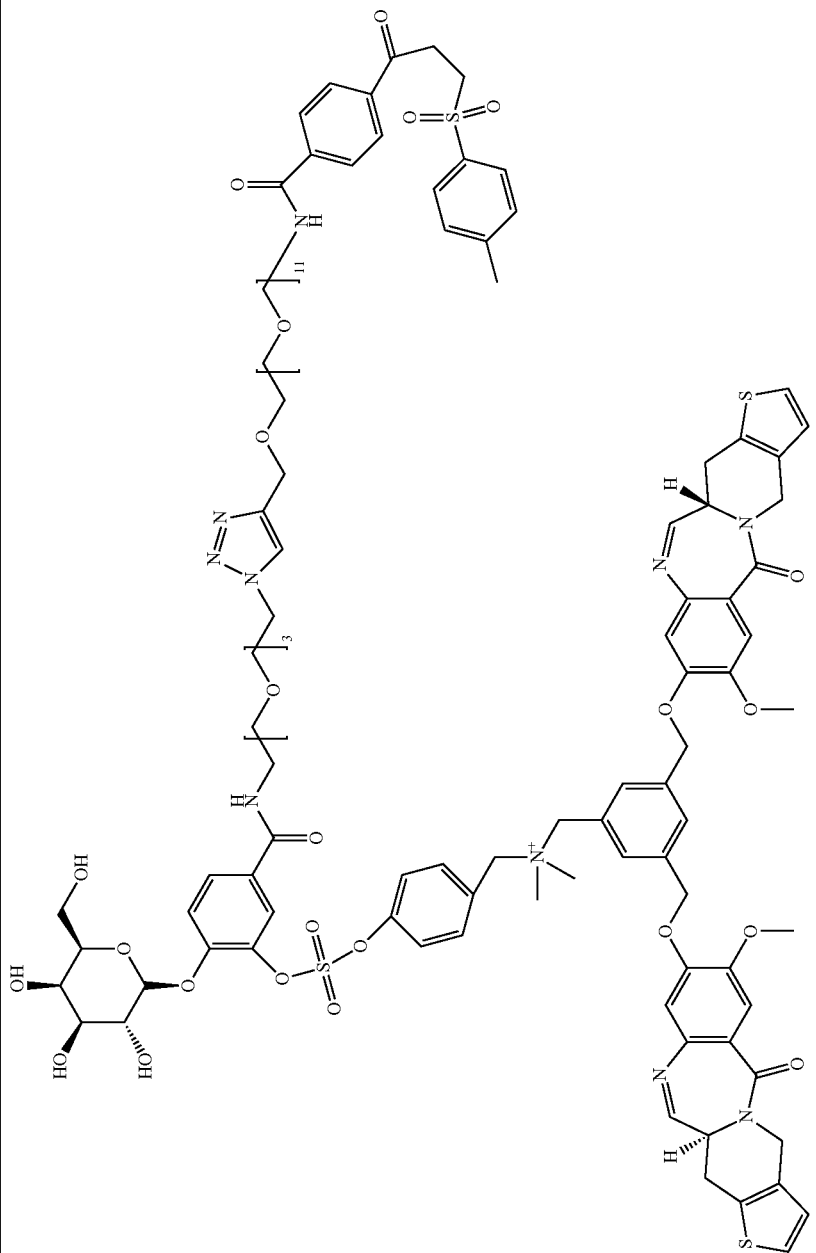 | Yield 34%, ESI-MS m/z: 2371 (M+ + 1) |

TABLE 12-continued
| Dimer | Structure | Characterization Data |
|---|---|---|
| T-3 | 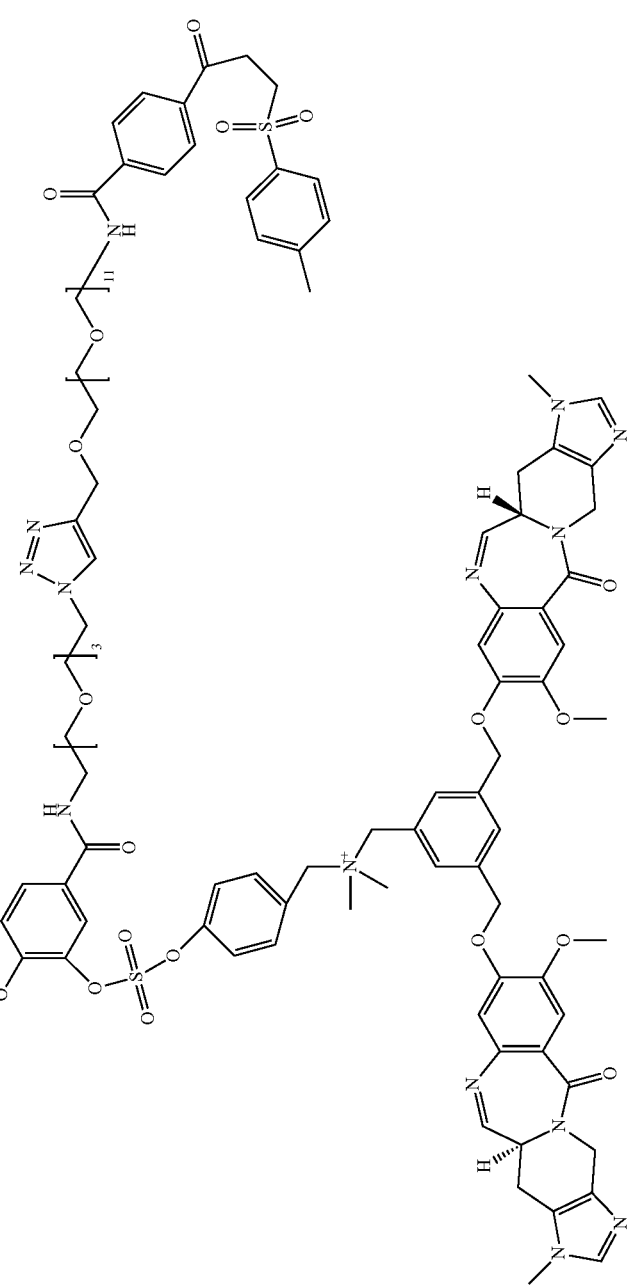<br>T-3 | Yield 34%, ESI-MS m/z: 2371 (M⁺ + 1) |

TABLE 12-continued
| Dimer | Structure | Characterization Data |
|---|---|---|
| T-4 | 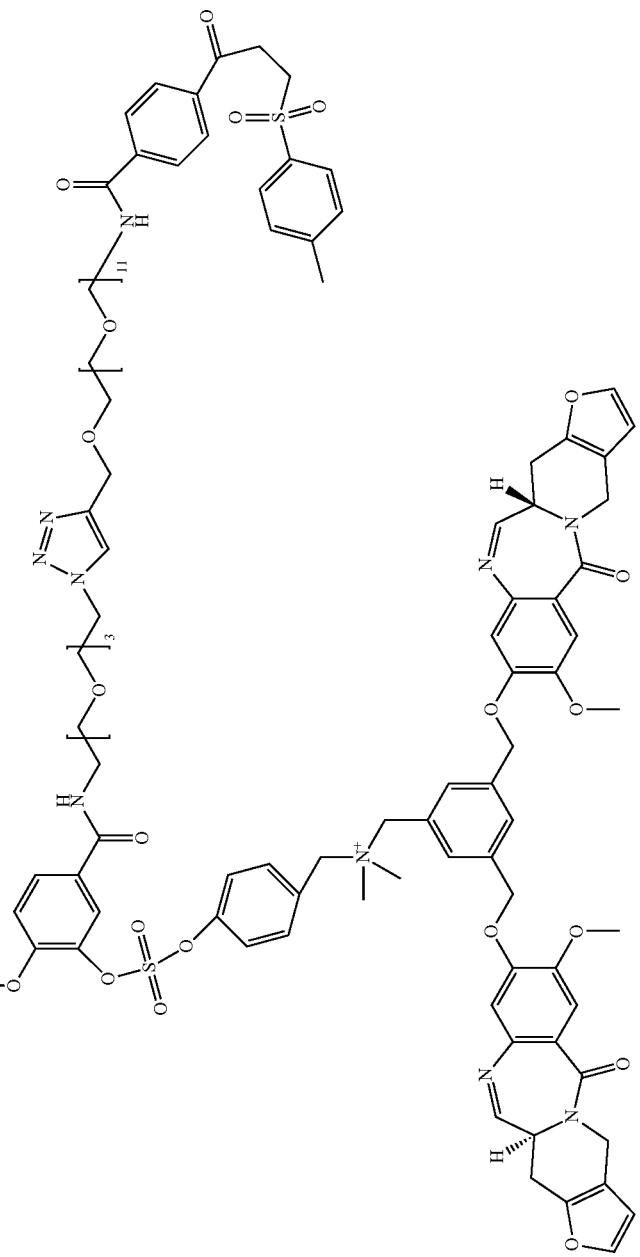 T-4 | Yield 24%, ESI-MS m/z: 2339 (M⁺ + 1) |

TABLE 12-continued
| Dimer | Structure | Characterization Data |
|---|---|---|
| T-5 | 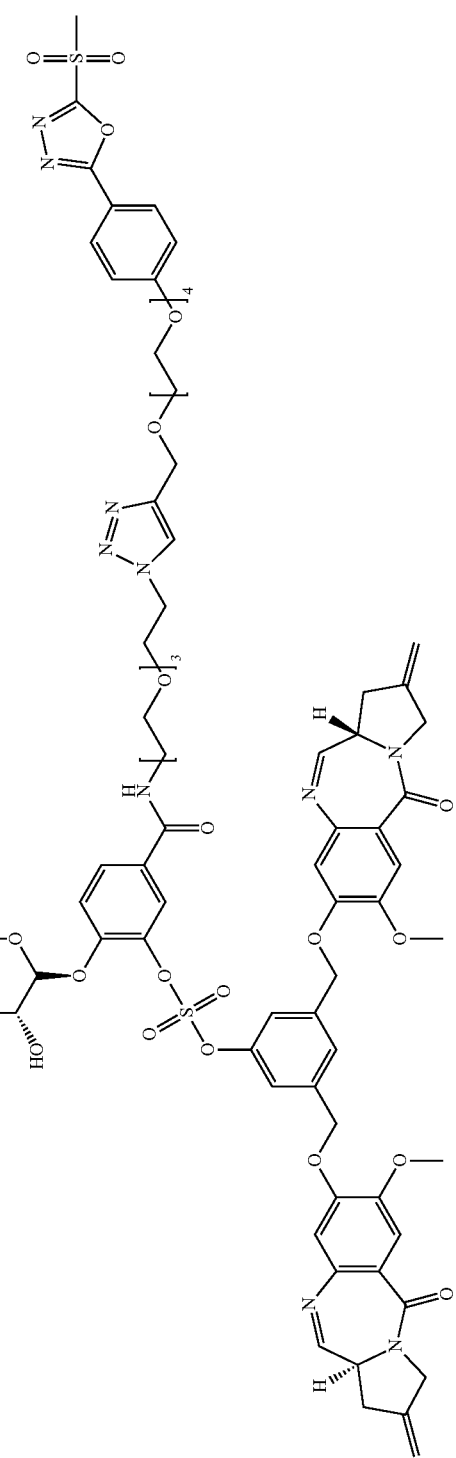 T-5 | Yield 12%, ESI-MS m/z: 1668 (M⁺ + 1) |

TABLE 12-continued
| Dimer | Structure | Characterization Data |
|---|---|---|
| T-6 | 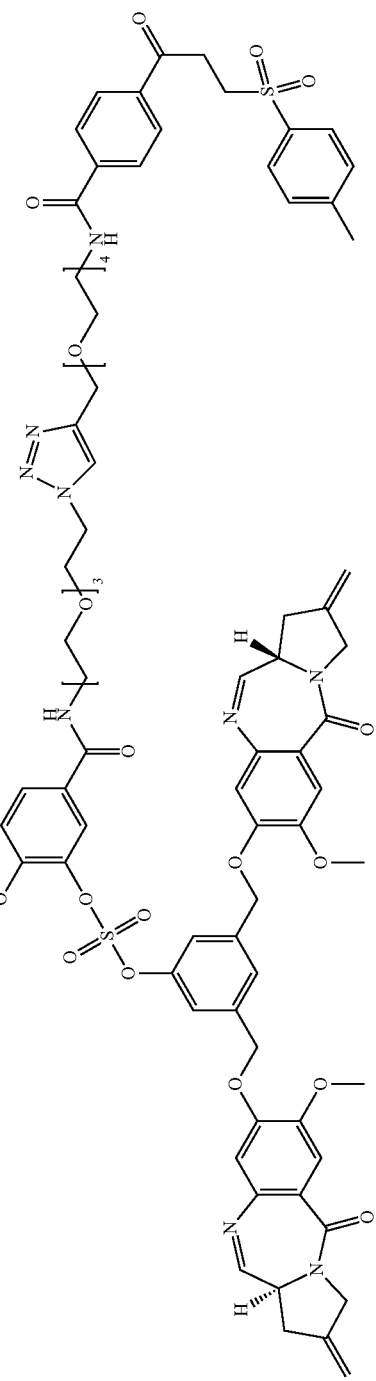 T-6 | Yield 7%, ESI-MS m/z: 1759 (M⁺ + 1) |

TABLE 12-continued
| Dimer | Structure | Characterization Data |
|---|---|---|
| T-7 T-8 | 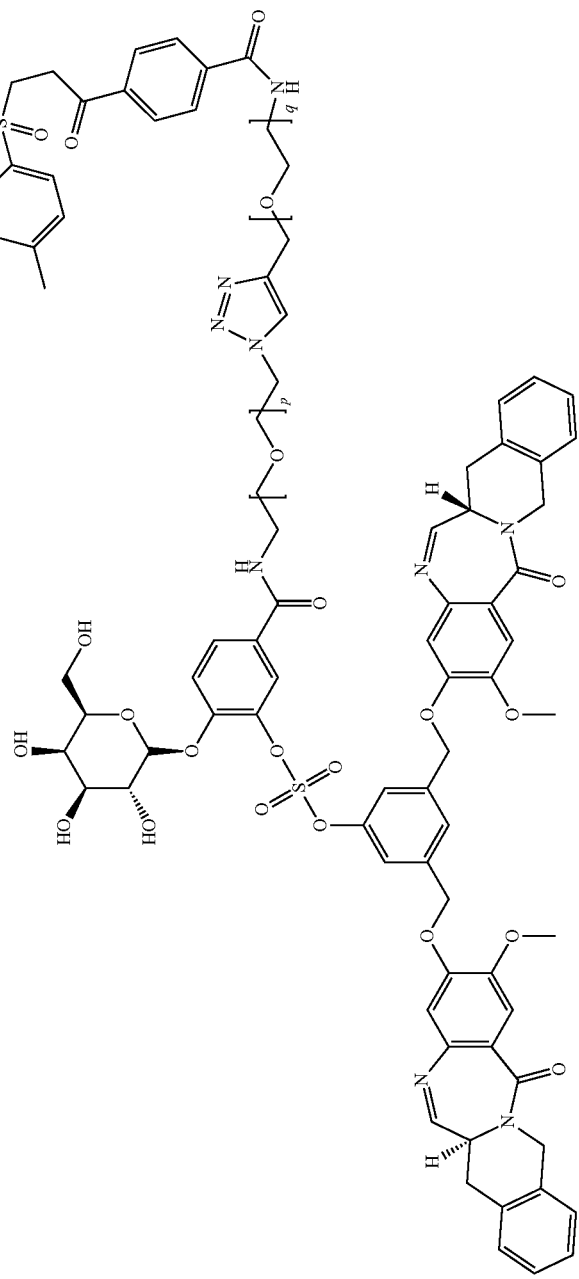 T-7 (p = 3, q = 4) T-8 (p = 11, q = 12) | Compound T-7 Yield 9.0%; ESI-MS m/z: 1860 (M$^{+1}$). Compound T-8 Yield 26%; ESI-MS m/z: 1282 (M/2$^{+1}$). |

TABLE 12-continued

| Dimer | Structure | Characterization Data |
|---|---|---|
| T-9 | 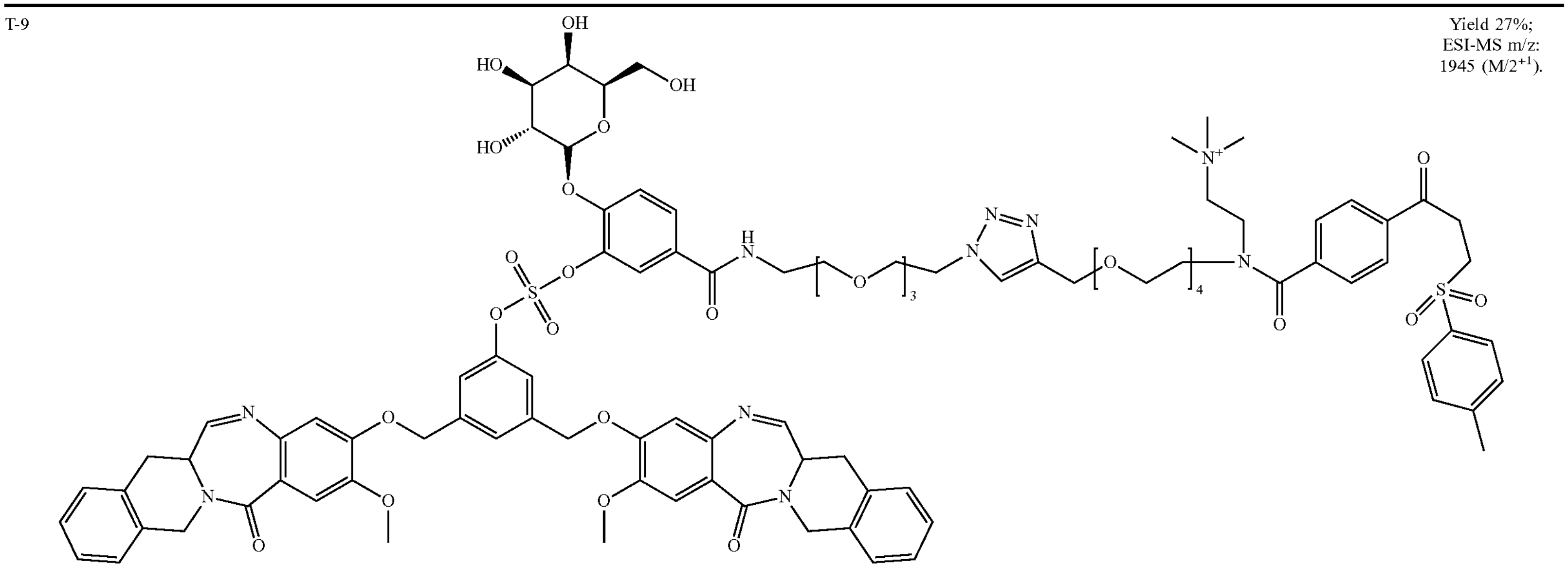 | Yield 27%; ESI-MS m/z: 1945 (M/2+1). |

TABLE 12-continued
| Dimer | Structure | Characterization Data |
|---|---|---|
| T-10 T-11 | 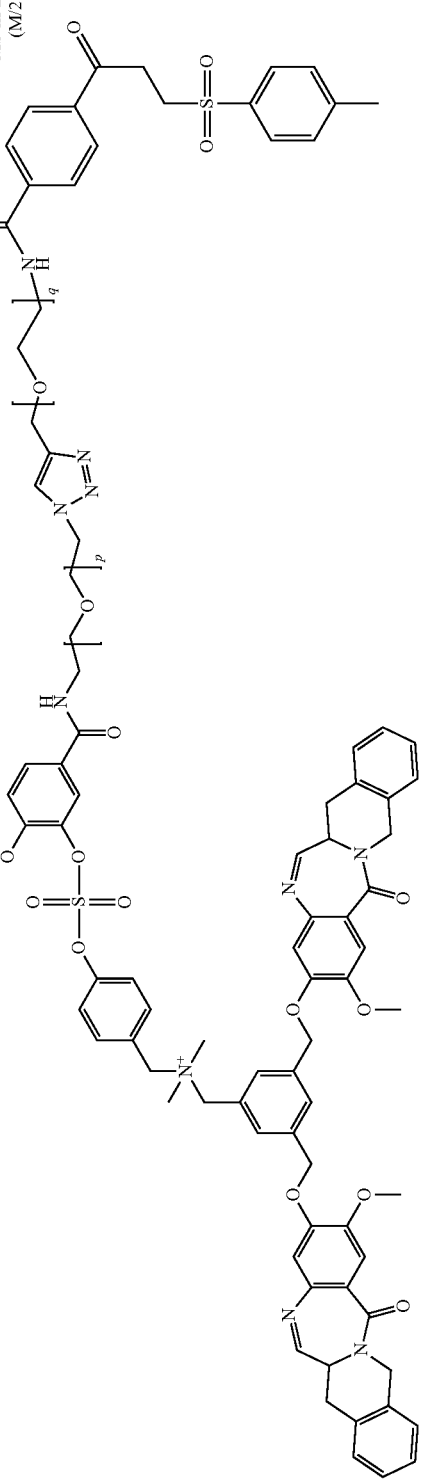 T-10 (p = 3, q = 4) T-11 (p = 3, q = 12) | Compound T-10 Yield 25%; ESI-MS m/z: 1004 (M/2+1). Compound T-11 Yield 62 %; ESI-MS m/z: 1180 (M/2+1). |

TABLE 12-continued
| Dimer | Structure | Characterization Data |
|---|---|---|
| T-12 |  T-12 | Yield 27%; ESI-MS m/z: 1174 (M/2+). |

TABLE 12-continued
| Dimer | Structure | Characterization Data |
|---|---|---|
| T-13 | 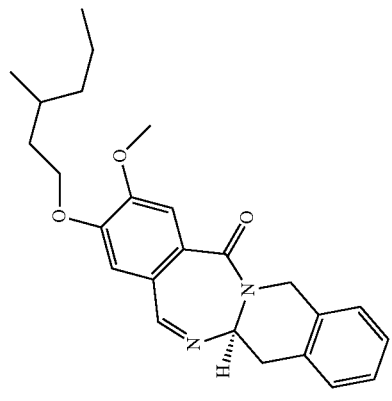 | Yield 64%; ESI-MS m/z: 2178 (M⁺ + 1), 1089 (M²⁺ + 1). |

TABLE 12-continued
| Dimer | Structure | Characterization Data |
|---|---|---|
| T-14 | 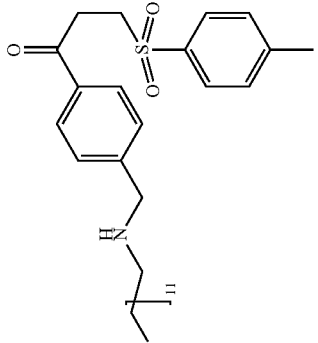 T-14 | Yield 56%; ESI-MS m/z: 2269 ($M^+ + 1$), 1135 ($M^{2+} + 1$). |

TABLE 12-continued
| Dimer | Structure | Characterization Data |
|---|---|---|
| T-15 | 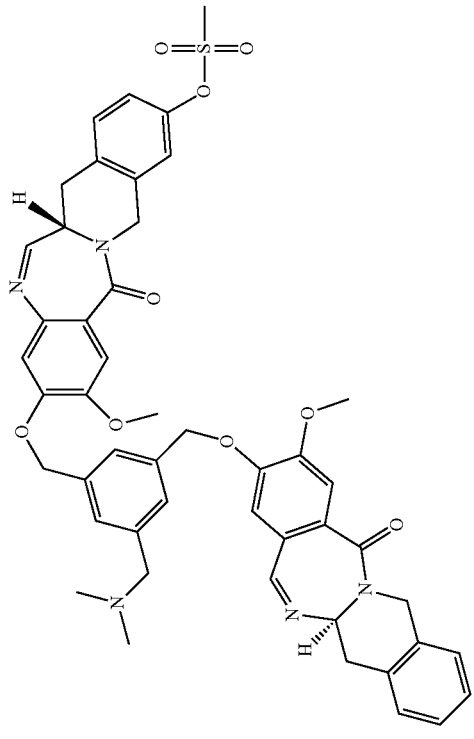 | Yield 64%, white solid. ESI-MS m/z: 2178 (M+ + 1), 1089 (M2+ + 1). |

TABLE 12-continued
| Dimer | Structure | Characterization Data |
|---|---|---|
| T-16 | 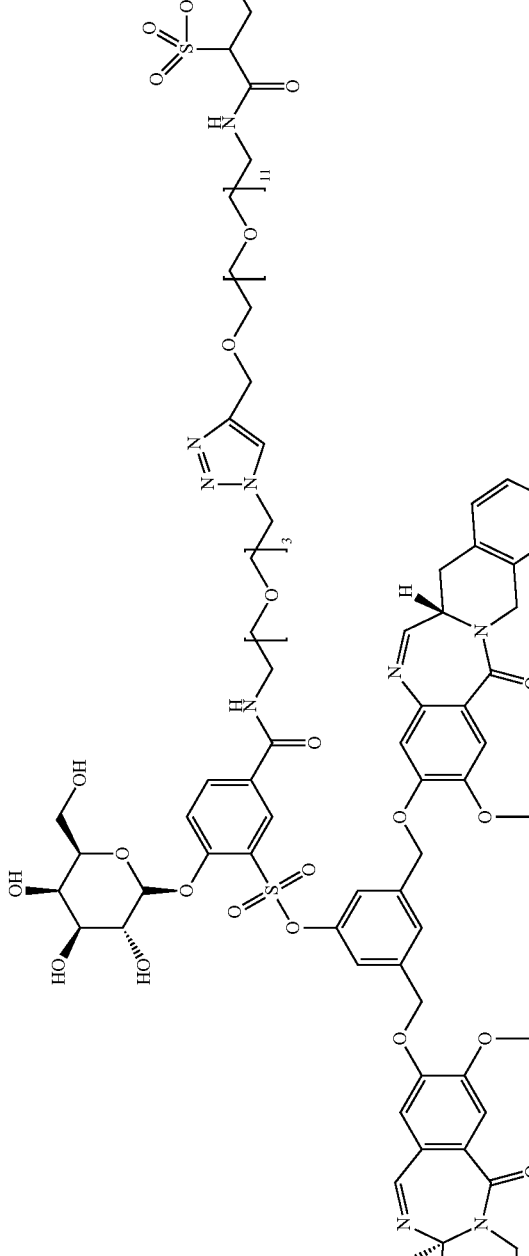 T-16 | Yield 34%; ESI-MS m/z: 2377 ($M^+ + 1$), 1189 ($M^{2+} + 1$). |

TABLE 12-continued
| Dimer | Structure | Characterization Data |
|---|---|---|
| T-17 | 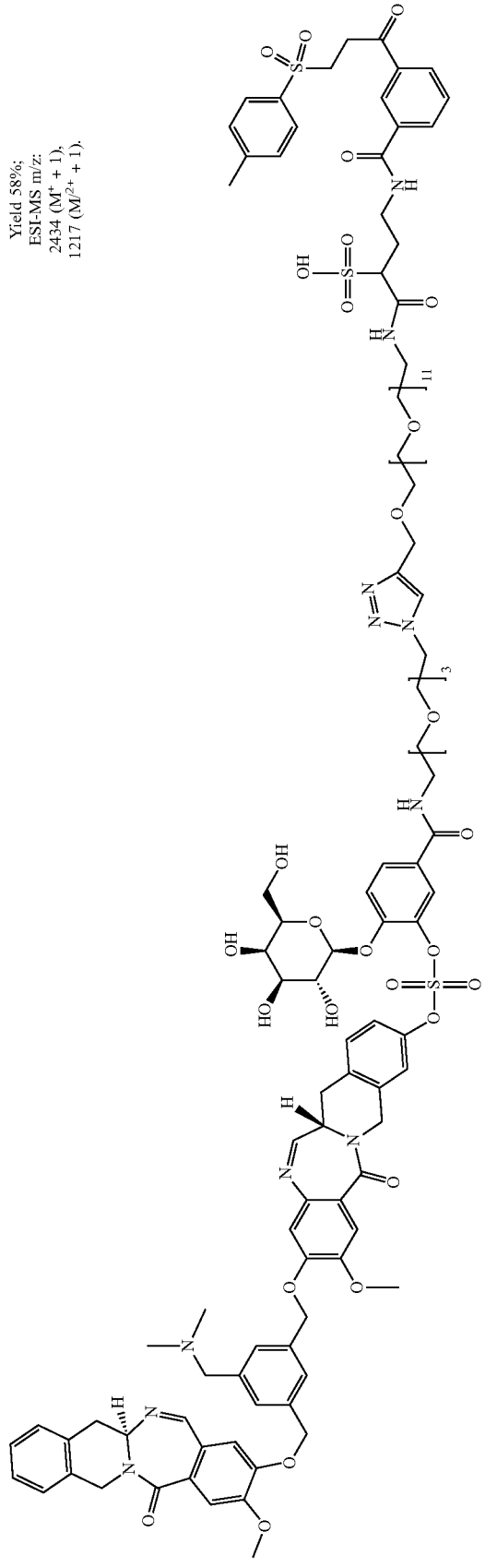 T-17 | Yield 58%; ESI-MS m/z: 2434 ($M^+ + 1$), 1217 ($M^{2+} + 1$). |

TABLE 12-continued
| Dimer | Structure | Characterization Data |
|---|---|---|
| T-18 | 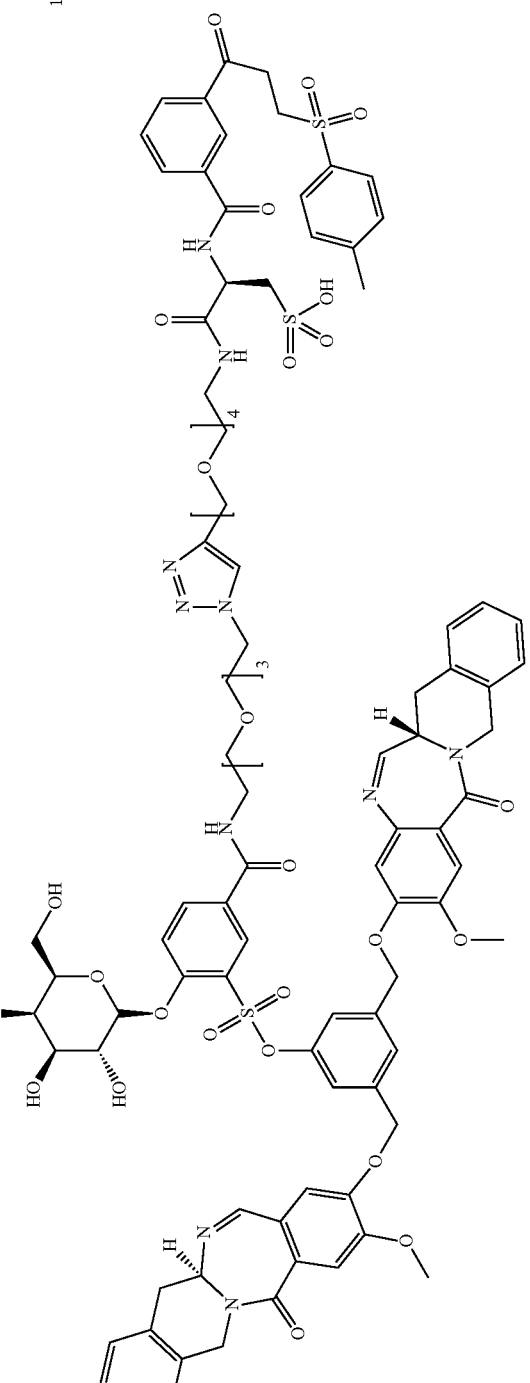 T-18 | Yield 72%; ESI-MS m/z: 2011 ($M^+ + 1$), 1006 ($M^{2+} + 1$). |

TABLE 12-continued
| Dimer | Structure | Characterization Data |
|---|---|---|
| T-19 | 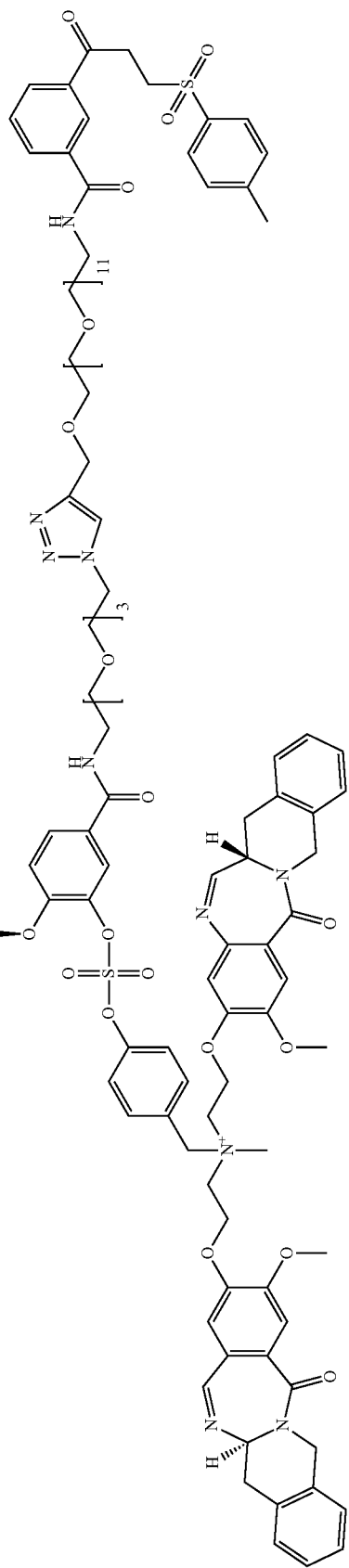 T-19 | Yield 48%; ESI-MS m/z: 2284 (M$^+$ + 1), 1142 (M$^{2+}$ + 1). |

TABLE 12-continued
| Dimer | Structure | Characterization Data |
|---|---|---|
| T-20 | 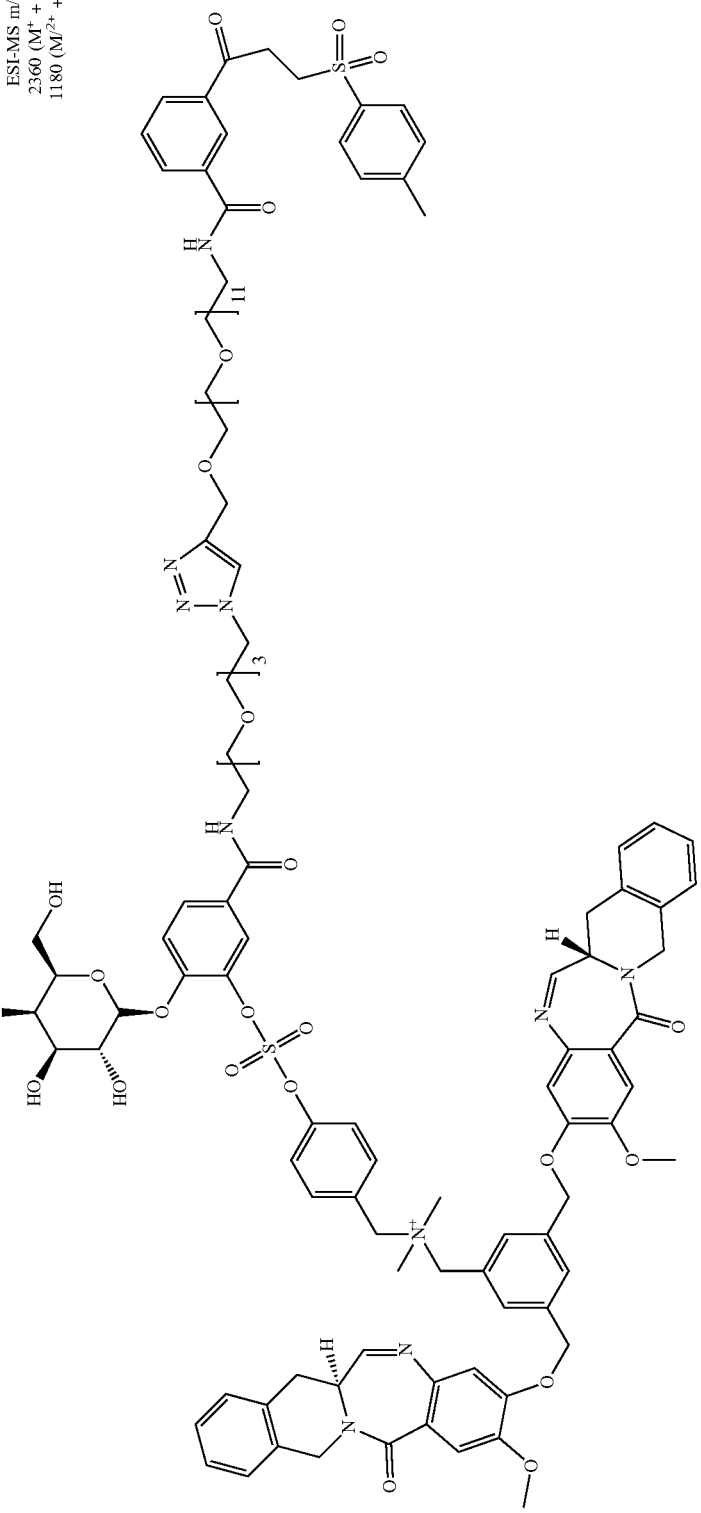 T-20 | Yield 69%; ESI-MS m/z: 2360 (M$^+$ + 1), 1180 (M$^{2+}$ + 1). |

TABLE 12-continued
| Dimer | Structure | Characterization Data |
|---|---|---|
| T-21 | 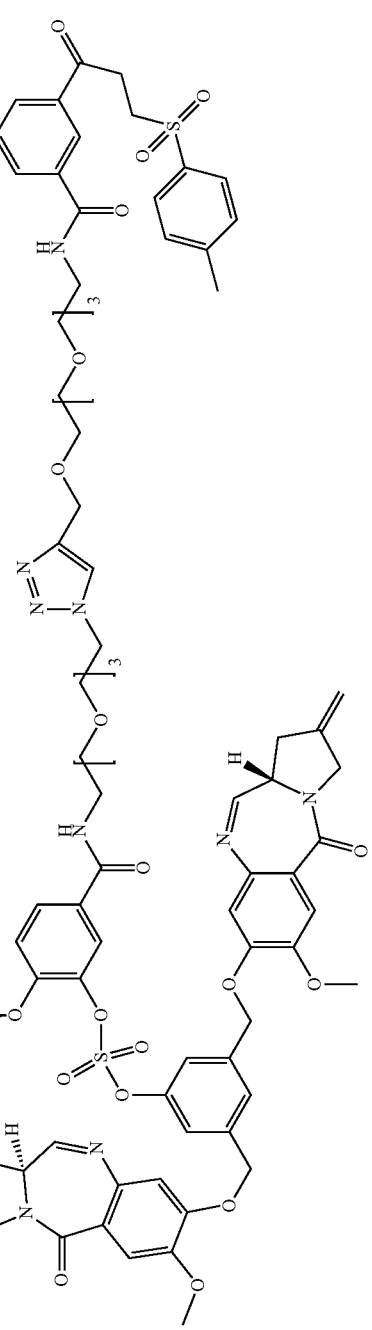 | Yield 40%; ESI-MS m/z: 1759 (M+ + 1), 880 (M/2+ + 1). |

TABLE 12-continued
| Dimer | Structure | Characterization Data |
|---|---|---|
| T-22 | 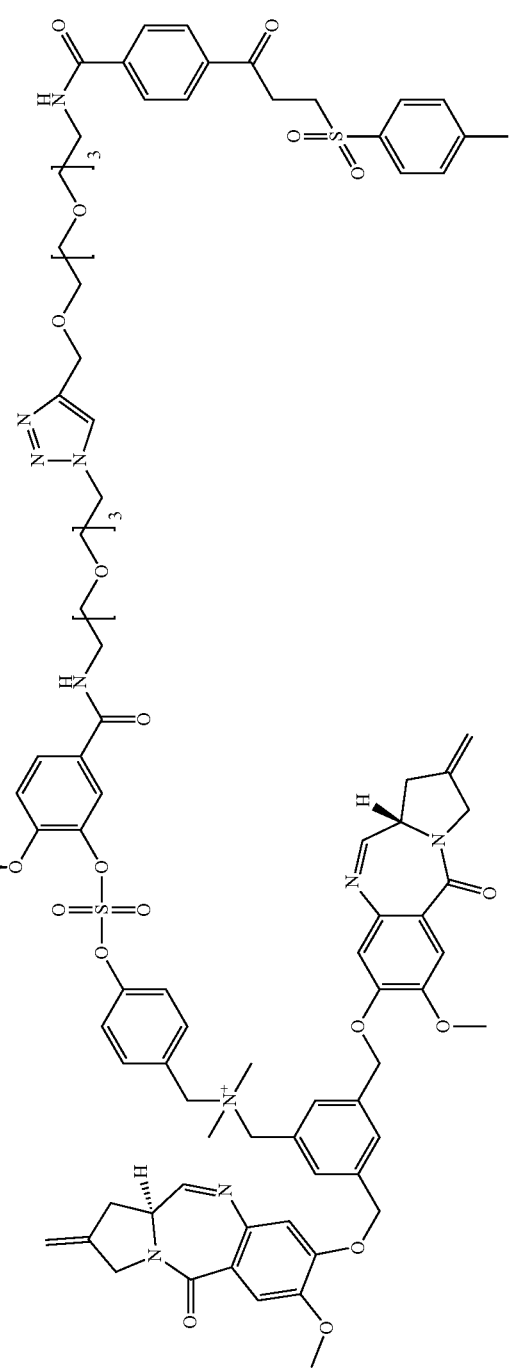<br>T-22 | Yield 71%; ESI-MS m/z: 1908 ($M^+ + 1$), 954 ($M^{2+} + 1$). |

TABLE 12-continued
| Dimer | Structure | Characterization Data |
|---|---|---|
| T-23 | 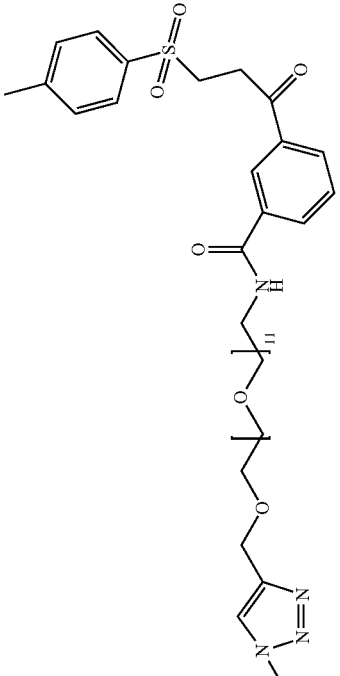 | Yield 79%, white solid. ESI-MS m/z: 2372 (M+ + 1), 1186 (M+/2 + 1). |

TABLE 12-continued

| Dimer | Structure | Characterization Data |
|---|---|---|
| T-24 | 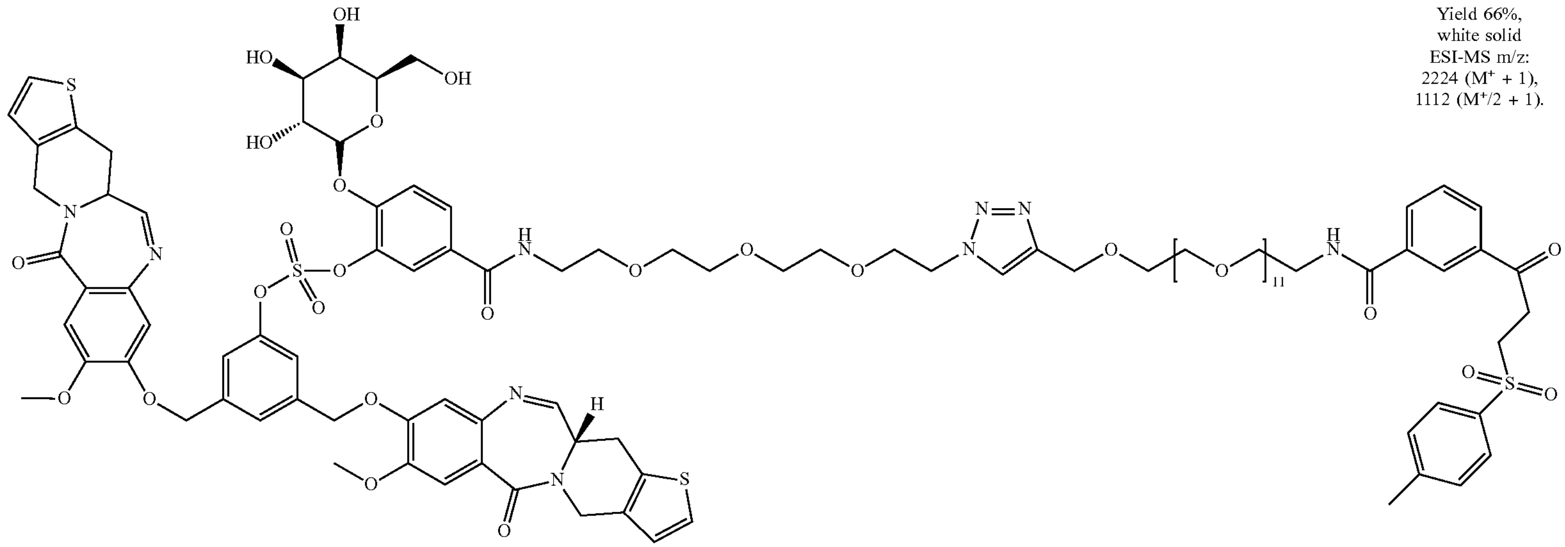 | Yield 66%, white solid ESI-MS m/z: 2224 (M⁺ + 1), 1112 (M⁺/2 + 1). |

TABLE 12-continued
| Dimer | Structure | Characterization Data |
|---|---|---|
| T-25 | 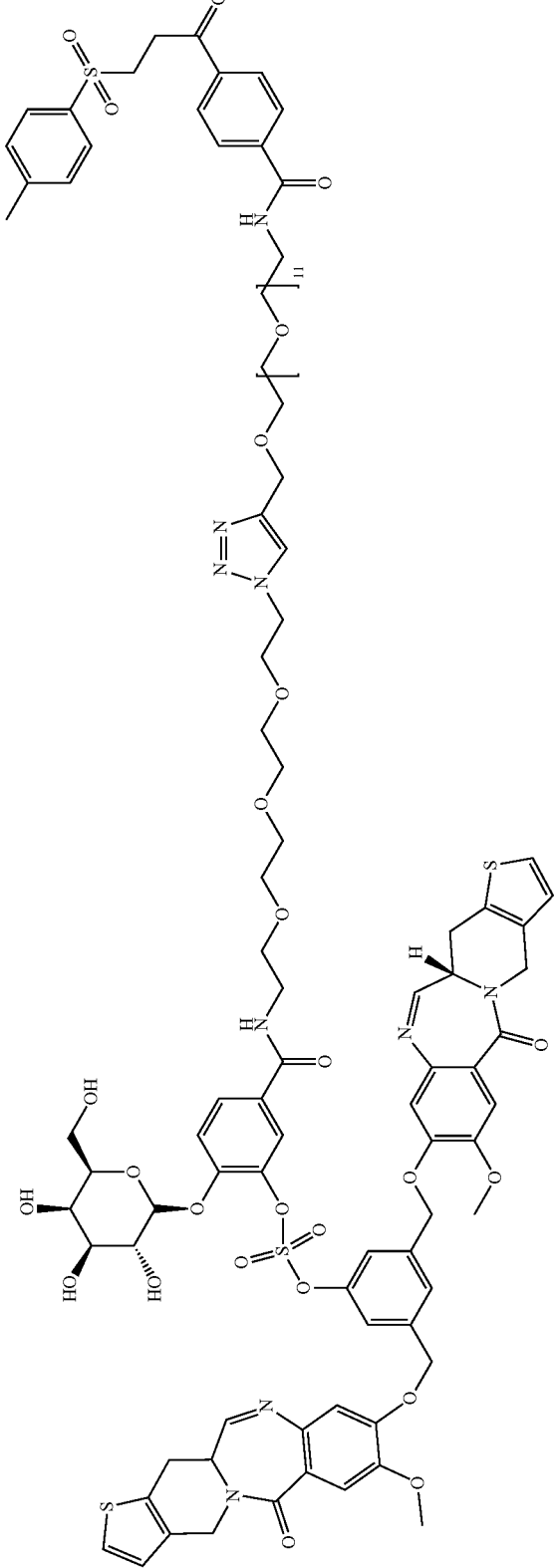 | Yield %: 34% ESI-MS m/z: 2371(M+ + 1). |

TABLE 12-continued
| Dimer | Structure | Characterization Data |
|---|---|---|
| T-26 | 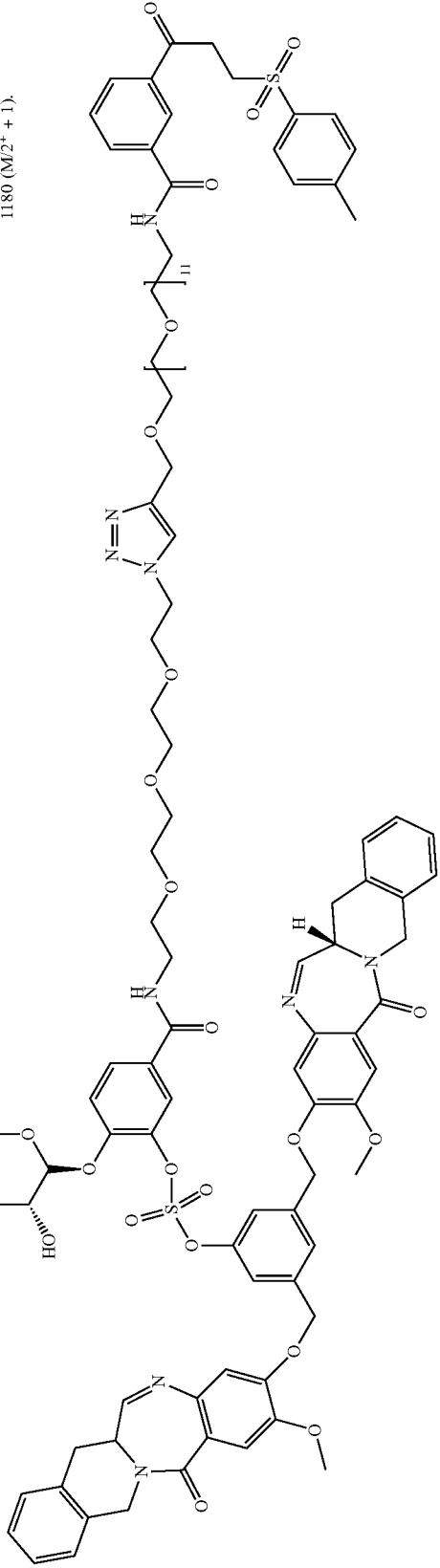 | Yield 69%, pale yellow solid. ESI-MS m/z: 2360 ($M^+$ + 1), 1180 ($M/2^+$ + 1). |

TABLE 12-continued
| Dimer | Structure | Characterization Data |
|---|---|---|
| T-27 | 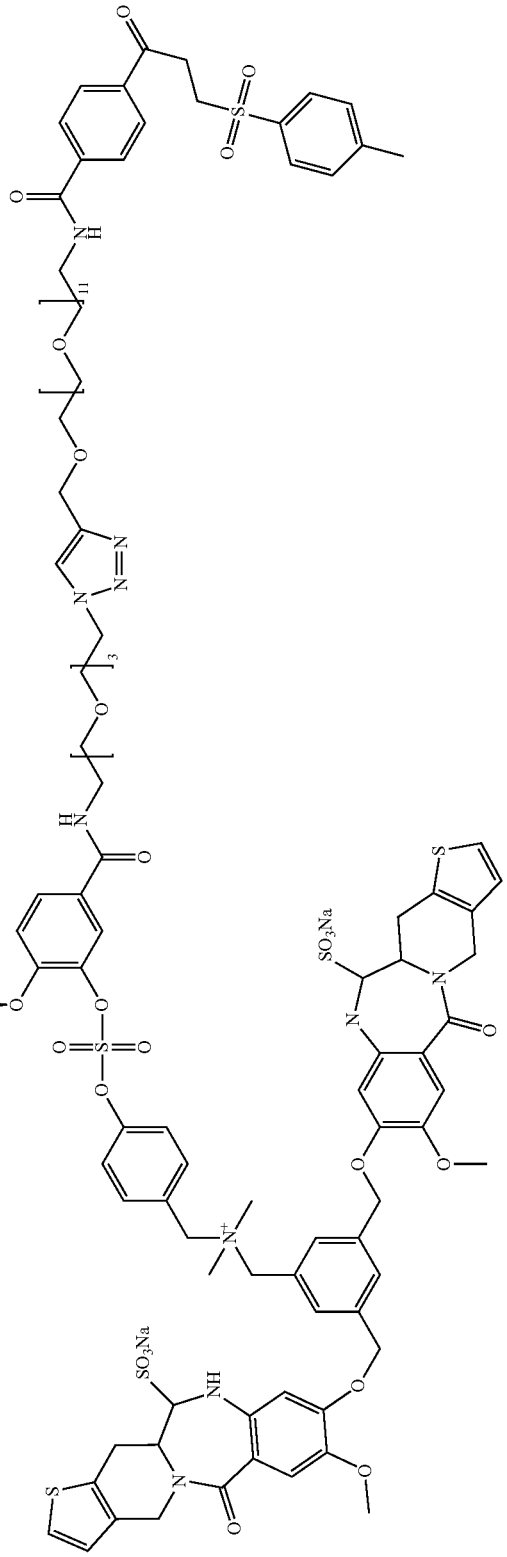 | Yield 92%, white solid. ESI-MS m/z: 2580 (M⁺ + 1). |

TABLE 12-continued
| Dimer | Structure | Characterization Data |
|---|---|---|
| T-28 | 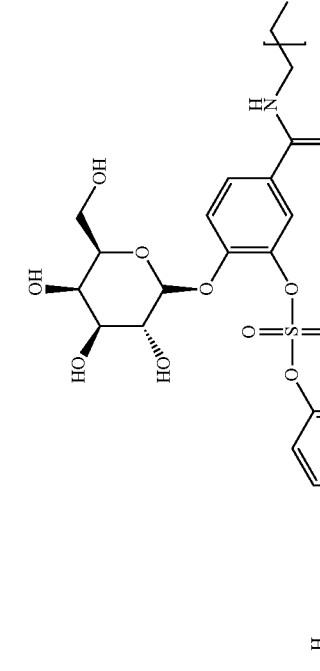 | Yield 40%, white solid. ESI-MS m/z: 1759 (M+ + 1), 880 (M/2+ + 1). |

TABLE 12-continued
| Dimer | Structure | Characterization Data |
|---|---|---|
| T-29 | 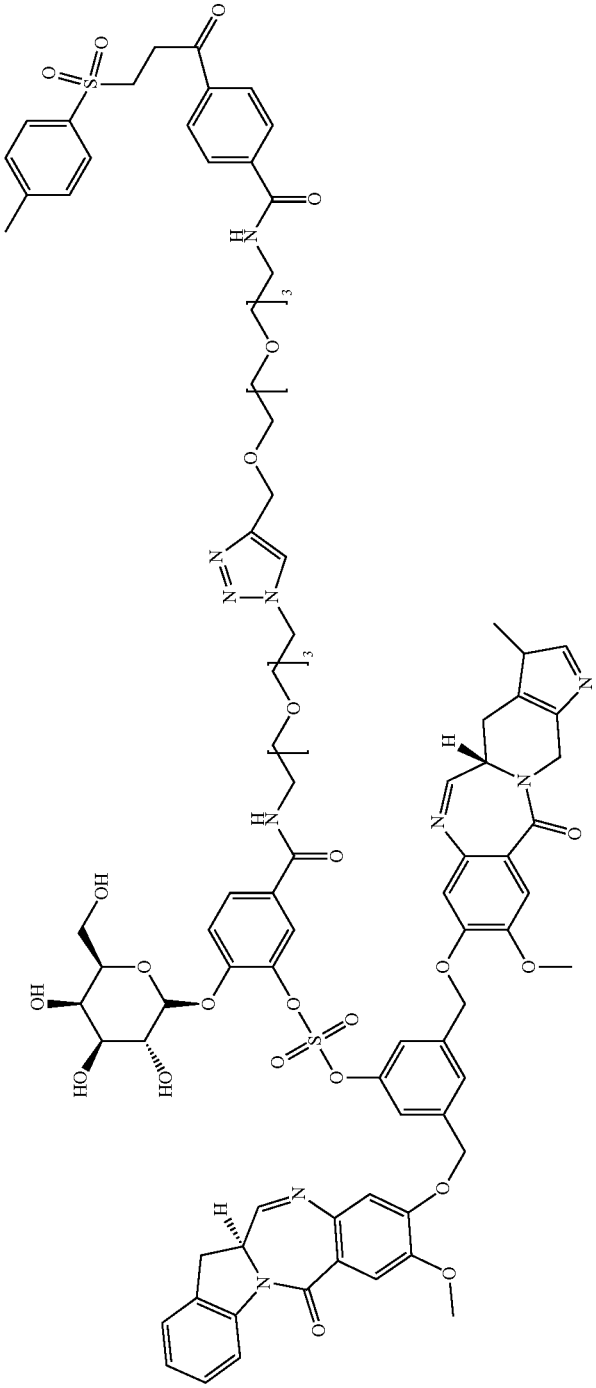 | Yield 75%, white solid. ESI-MS m/z: 1849 (M+ + 1), 925 (M/2+ + 1). |

TABLE 12-continued
| Dimer | Structure | Characterization Data |
|---|---|---|
| T-30 | 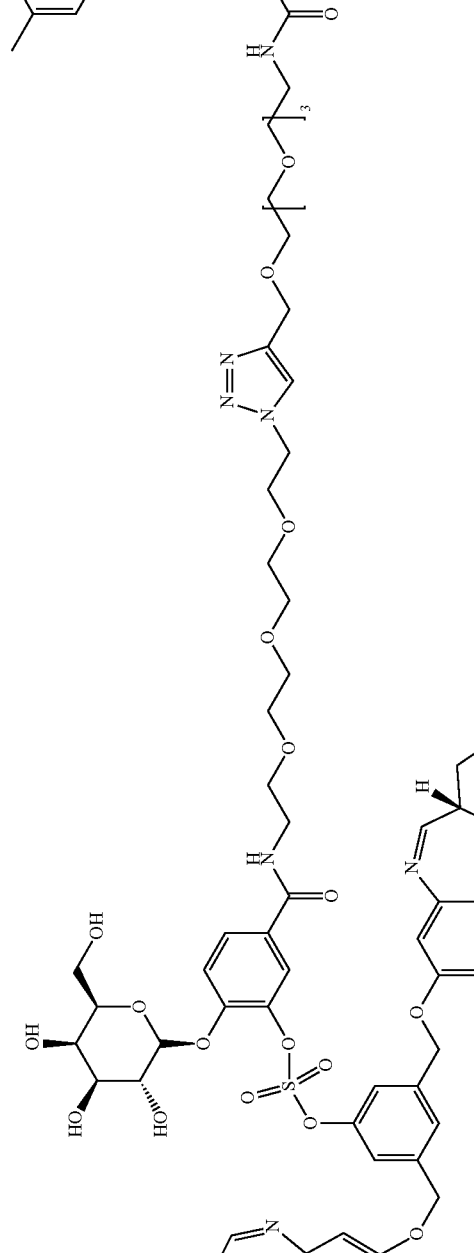 | Yield 59%, white solid ESI-MS m/z: 1864 ($M^+ + 1$), 932 ($M^+/2 + 1$). |

TABLE 12-continued

| Dimer | Structure | Characterization Data |
|---|---|---|
| T-31 | 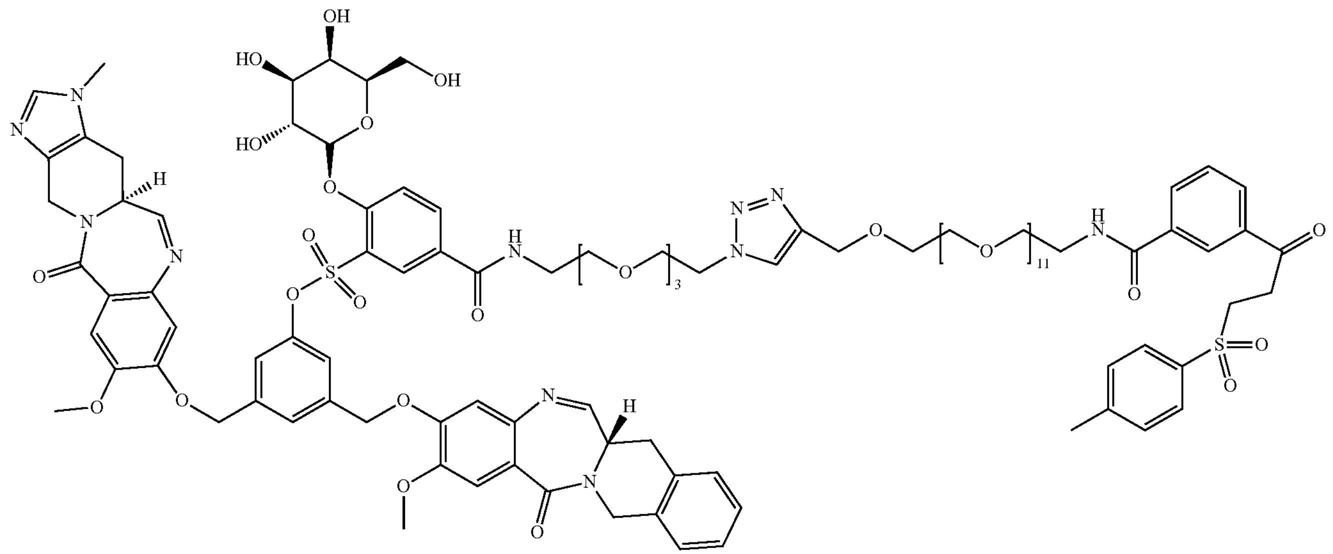 | Yield 50%, white solid ESI-MS m/z: 2216 (M$^+$ + 1), 1108 (M$^+$/2 + 1). |

TABLE 12-continued
| Dimer | Structure | Characterization Data |
|---|---|---|
| T-32 | 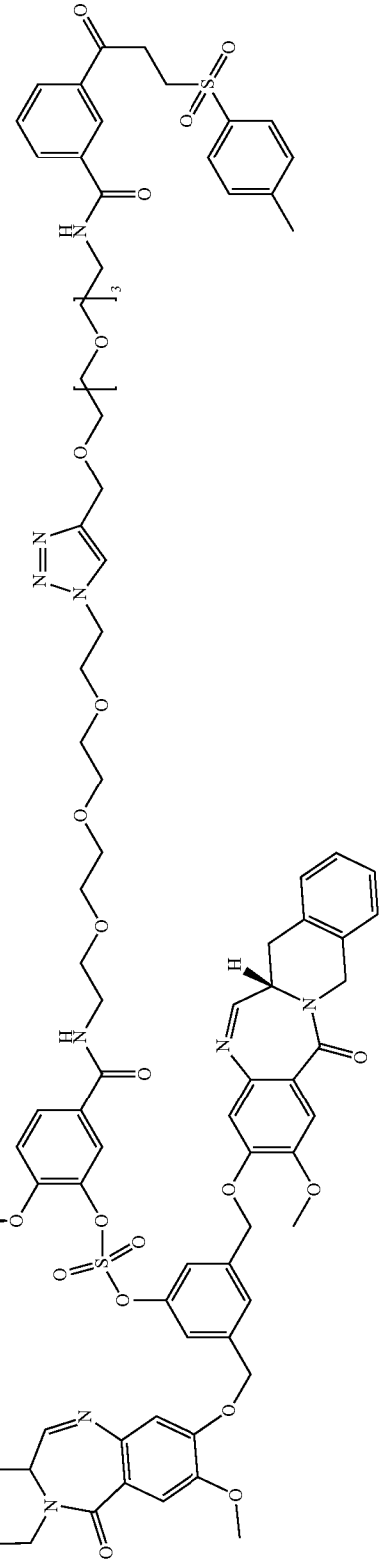 | Yield 32%, white solid ESI-MS m/z: 1864 (M$^+$ + 1), 932 (M$^+$/2 + 1). |

TABLE 12-continued
| Dimer | Structure | Characterization Data |
|---|---|---|
| T-33 | 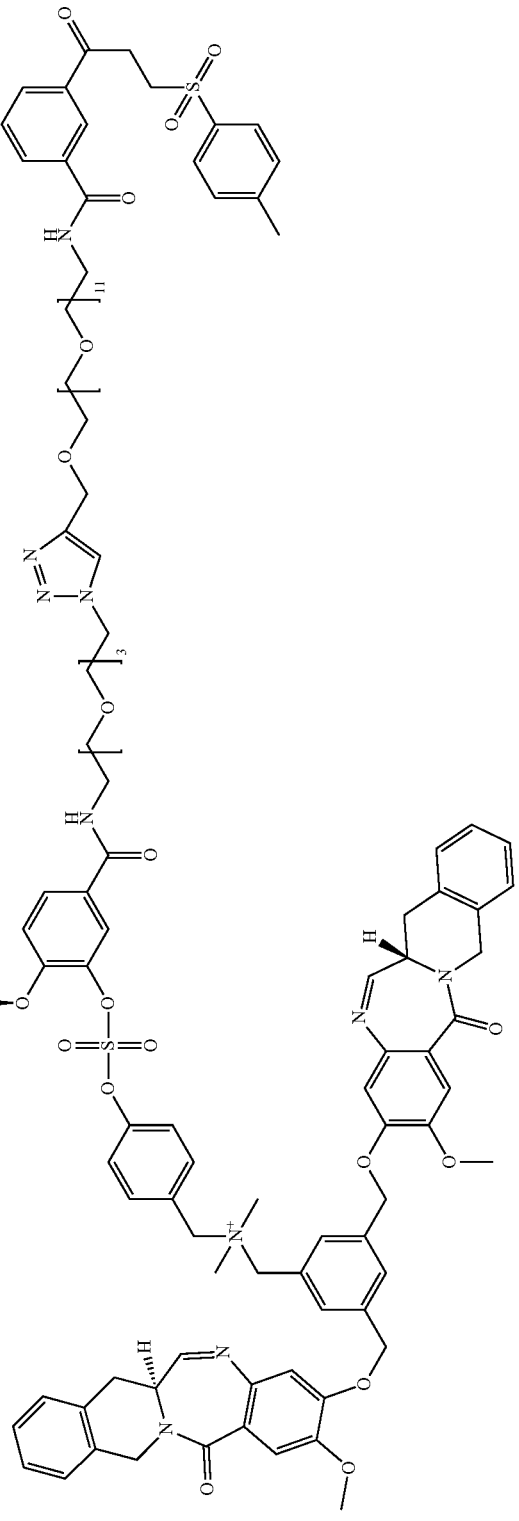 | Yield 53%, white solid. ESI-MS m/z: 1181 (M/2+1). |

TABLE 12-continued
| Dimer | Structure | Characterization Data |
|---|---|---|
| T-34 | 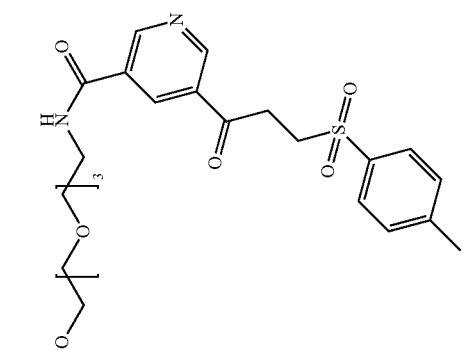 | Yield 15%, white solid. ESI-MS m/z: 935 (M/2+1). |

TABLE 12-continued

| Dimer | Structure | Characterization Data |
|---|---|---|
| T-35 | 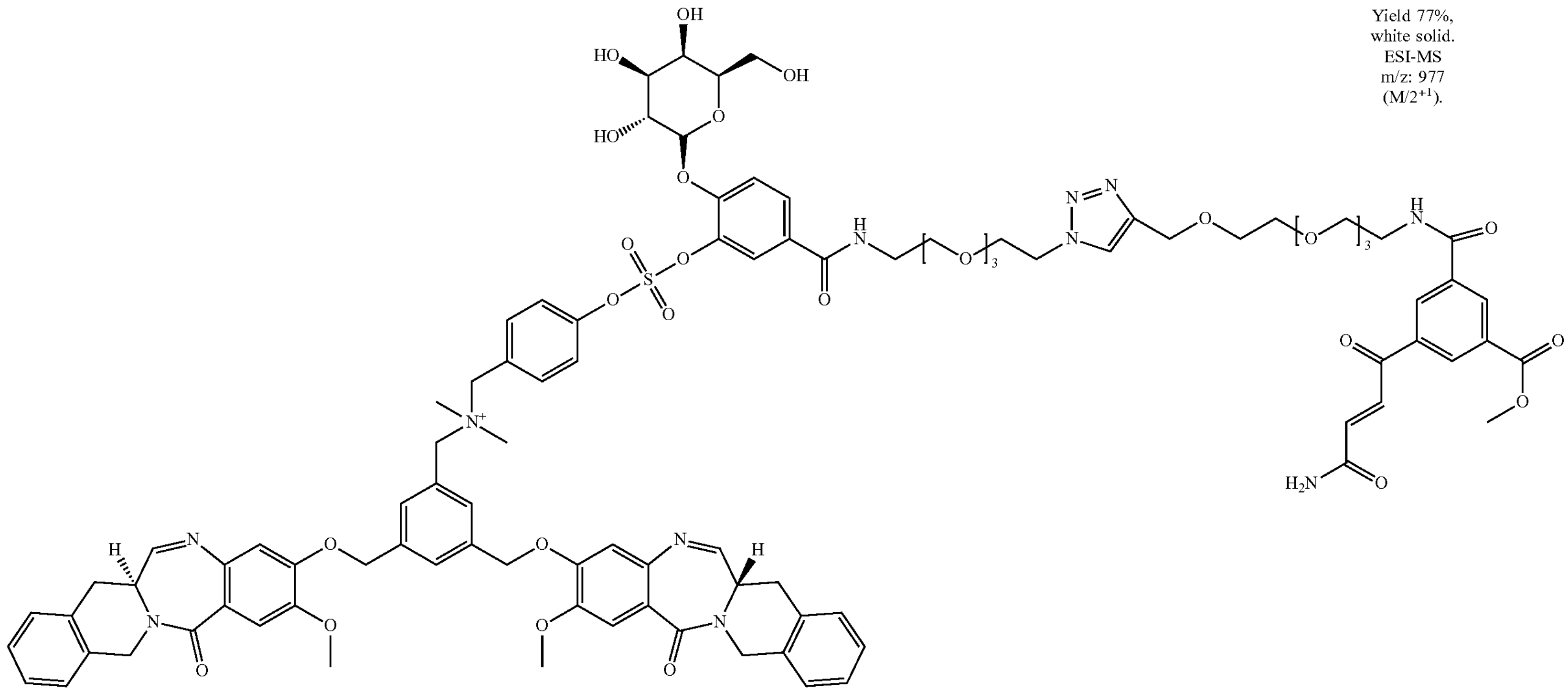 | Yield 77%, white solid. ESI-MS m/z: 977 (M/2+1). |

TABLE 12-continued
| Dimer | Structure | Characterization Data |
|---|---|---|
| T-36 | 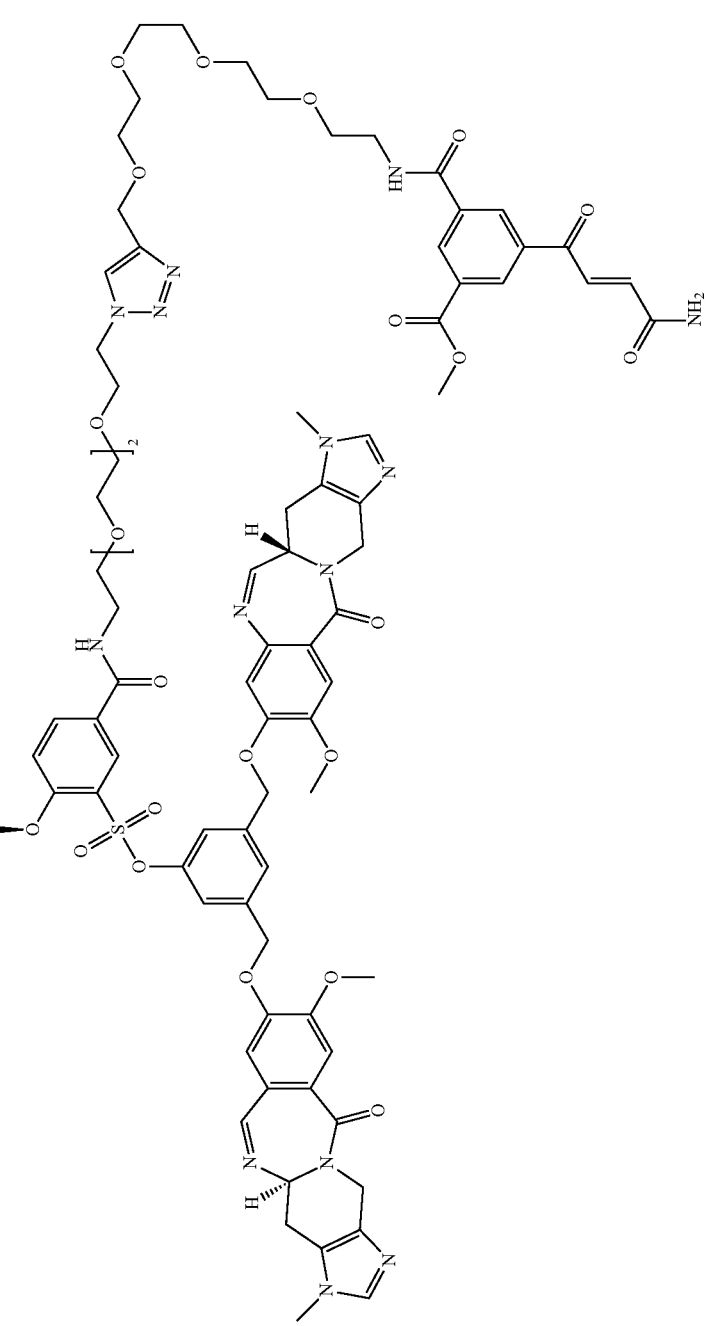 | Yield 40%, ESI-MS m/z: 906 (M/2+1) |

TABLE 12-continued
| Dimer | Structure | Characterization Data |
|---|---|---|
| T-37 | 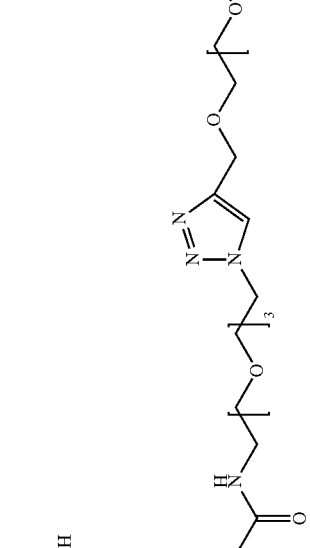 | Yield 61%, white solid. ESI-MS m/z: 957 (M/2+1). |

TABLE 12-continued
| Dimer | Structure | Characterization Data |
|---|---|---|
| T-38 | 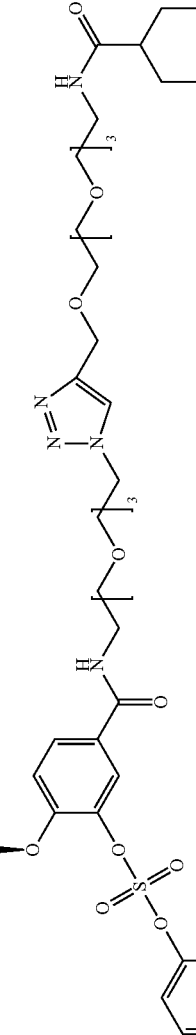 | Yield 65%, white solid. ESI-MS m/z: 963 (M/2+1). |

TABLE 12-continued
| Dimer | Structure | Characterization Data |
|---|---|---|
| T-39 | 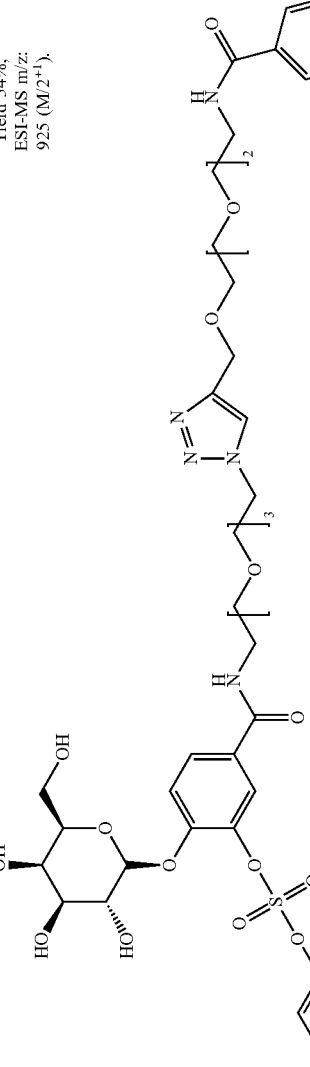 | Yield 54%, ESI-MS m/z: 925 (M/2+1). |

TABLE 12-continued

| Dimer | Structure | Characterization Data |
|---|---|---|
| T-40 | 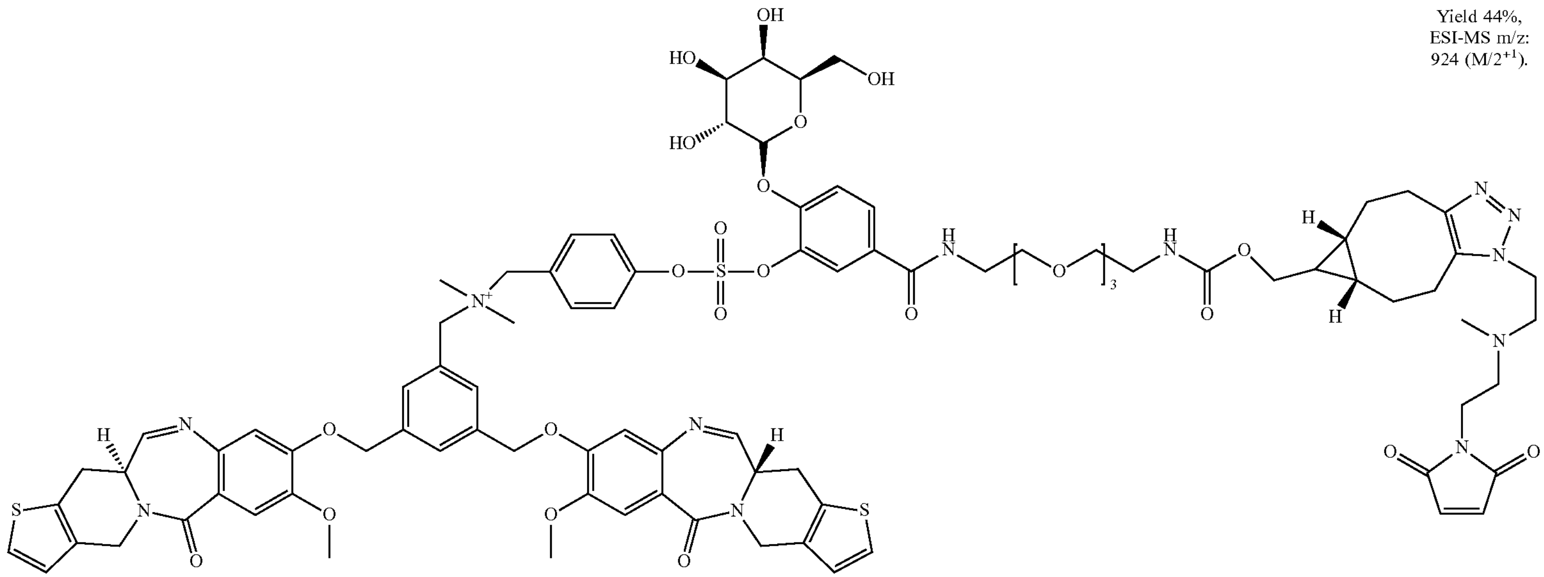 | Yield 44%, ESI-MS m/z: 924 (M/2+1). |

TABLE 12-continued
| Dimer | Structure | Characterization Data |
|---|---|---|
| T-41 | 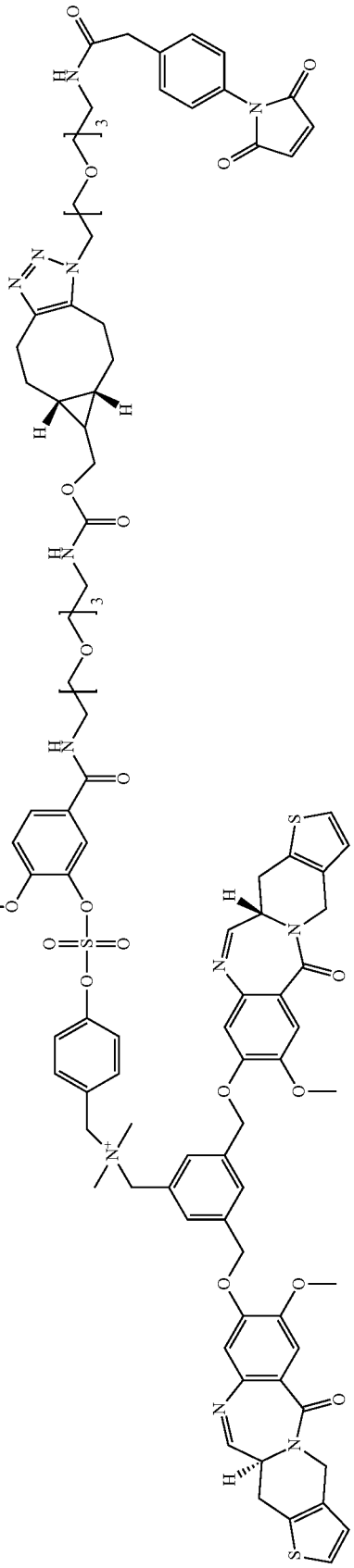 | Yield 28%, ESI-MS m/z: 1028 (M/2+). |
| T-42 | 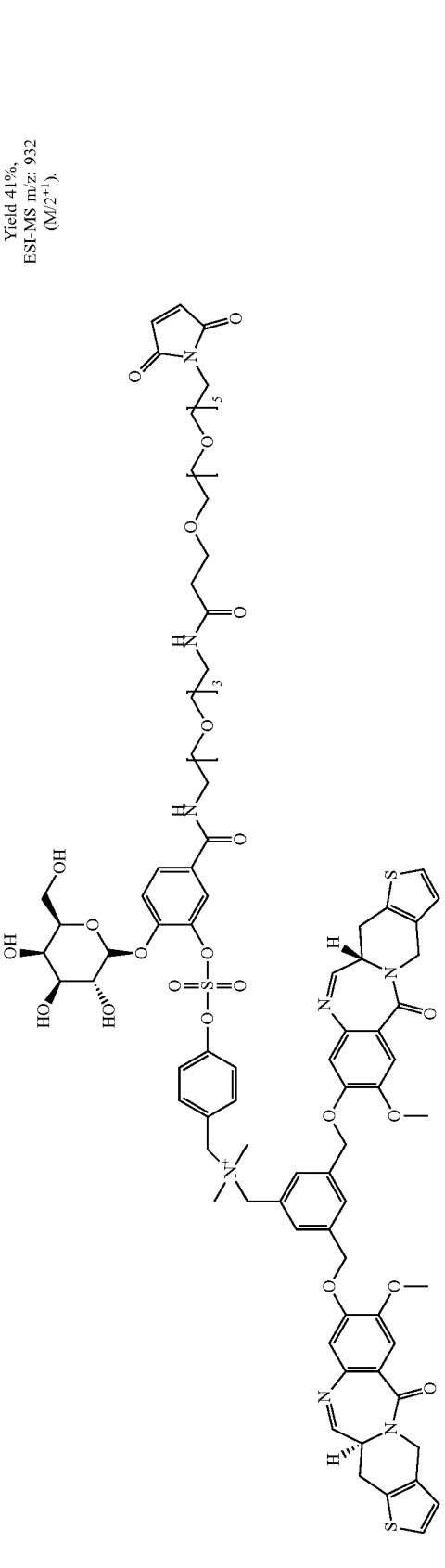 | Yield 41%, ESI-MS m/z: 932 (M/2+). |

TABLE 12-continued
| Dimer | Structure | Characterization Data |
|---|---|---|
| T-43 | 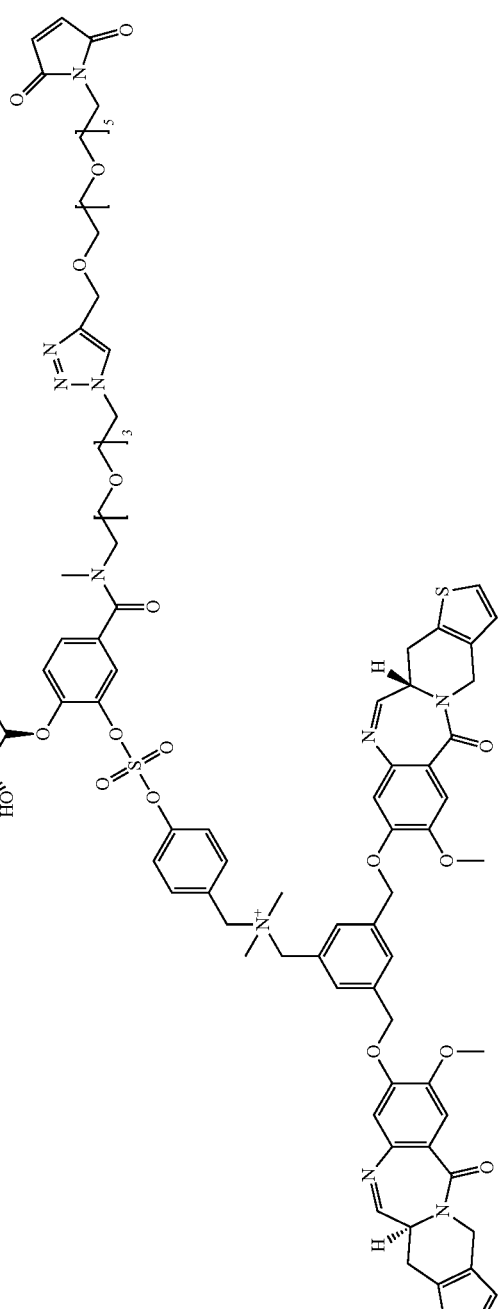 | Yield 48%, ESI-MS m/z: 1888 (M+1). |

TABLE 12-continued
| Dimer | Structure | Characterization Data |
|---|---|---|
| T-44 | 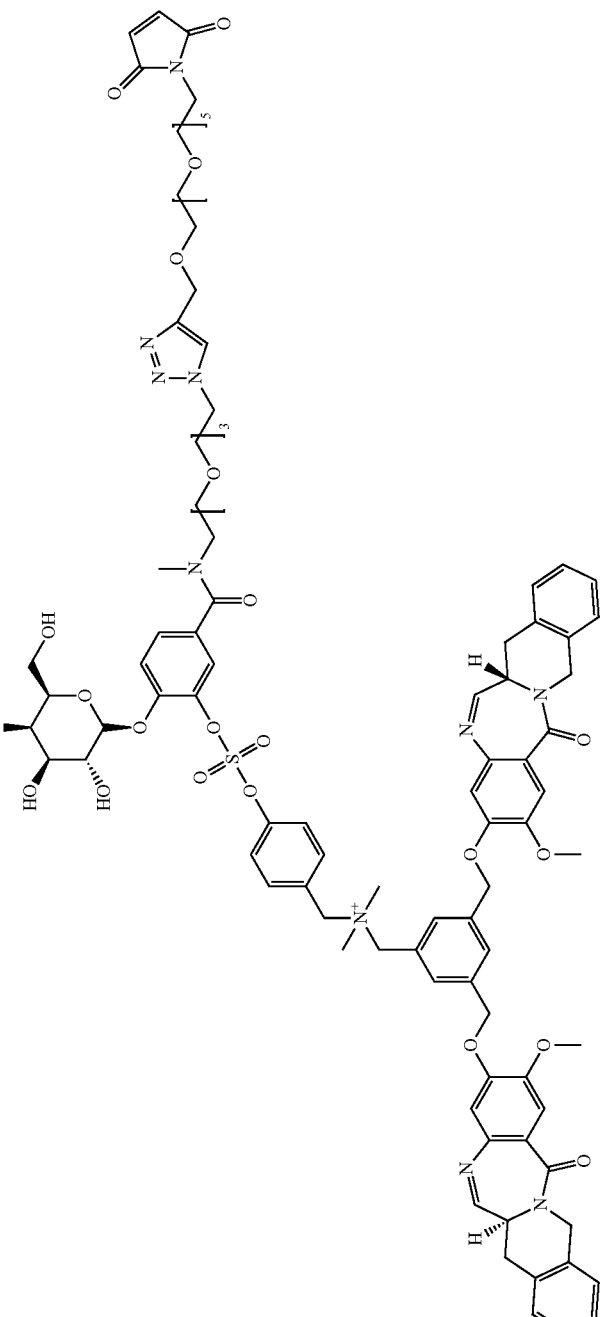 | Yield 26%, ESI-MS m/z: 938 (M/2+1). |

TABLE 12-continued
| Dimer | Structure | Characterization Data |
|---|---|---|
| T-45 | 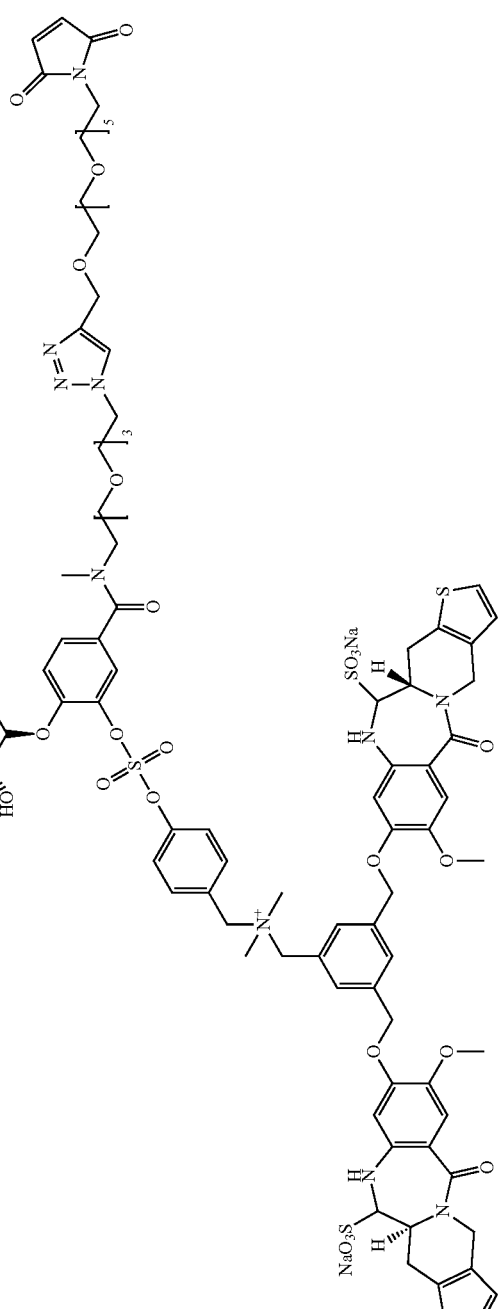 | Yield Quant., white solid. ESI-MS m/z: 1888 (M+1). |

TABLE 12-continued
| Dimer | Structure | Characterization Data |
|---|---|---|
| T-46 | 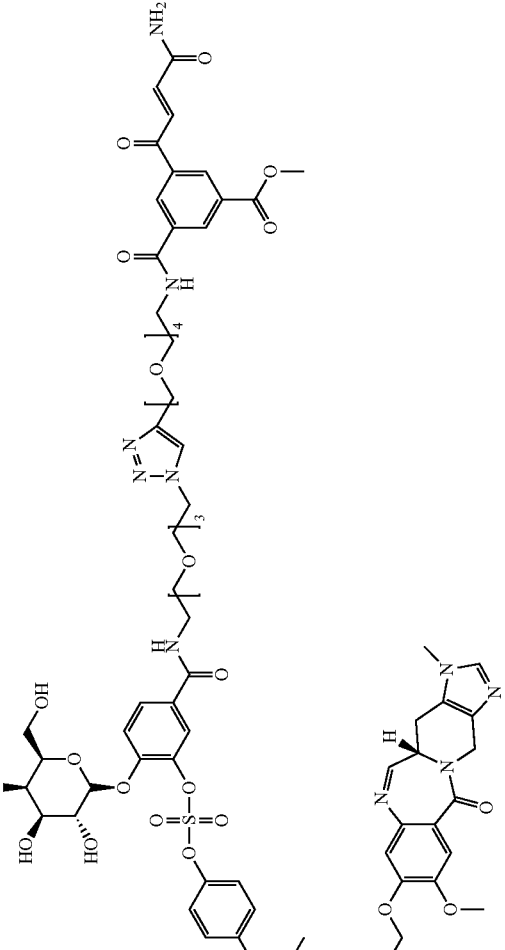 | Yield 40%, white solid. ESI-MS m/z: 906 (M+ + 1). |
| T-47 | 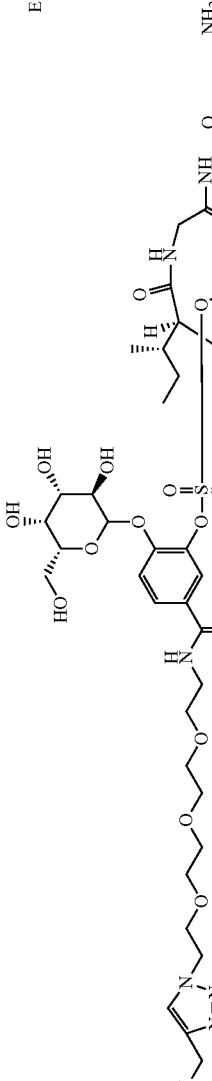 | Yield 35%; ESI-MS m/z: 934 (M/2+1). |

TABLE 12-continued
| Dimer | Structure | Characterization Data |
|---|---|---|
| T-48 | 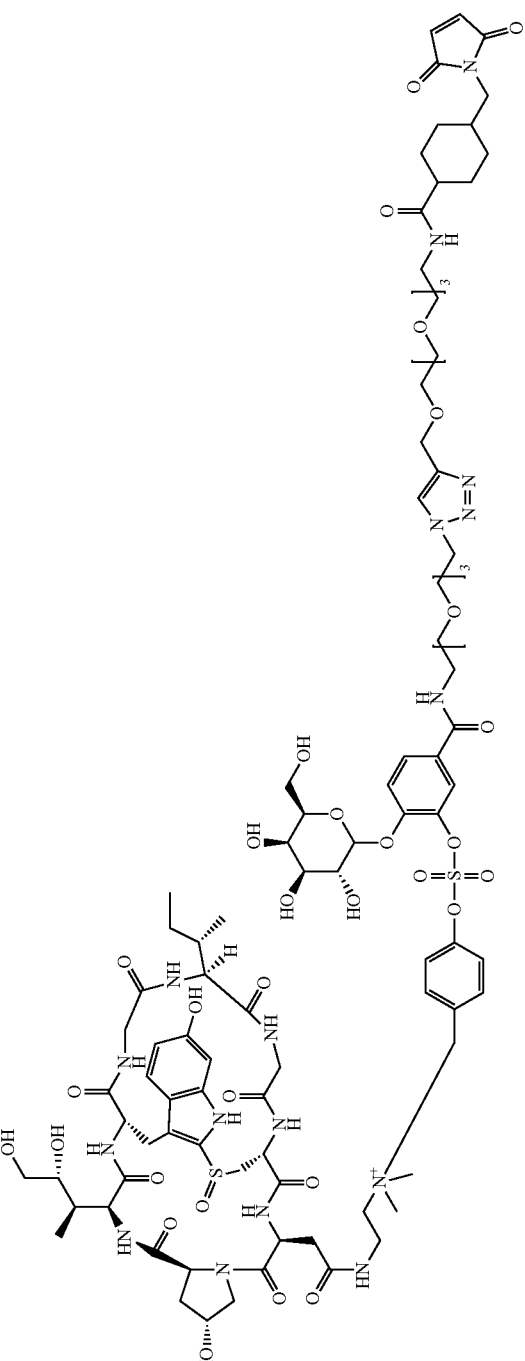 | Yield 16%; ESI-MS m/z: 1063 (M/2+1). |

TABLE 12-continued

| Dimer | Structure | Characterization Data |
|---|---|---|
| T-49 | 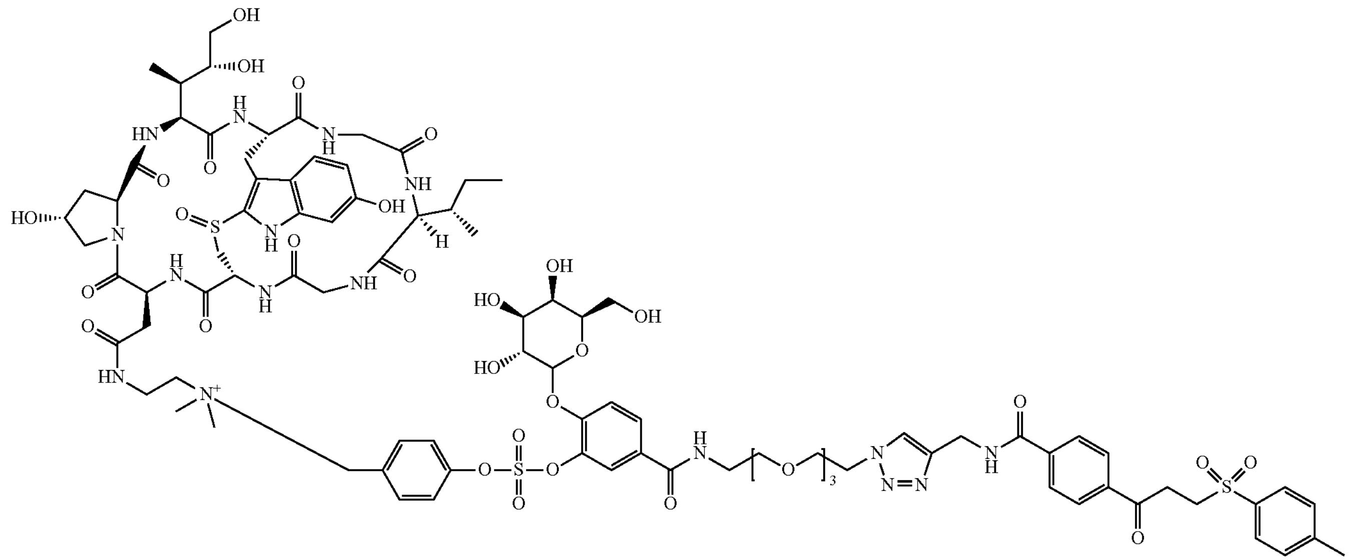 | Yield 39%; ESI-MS m/z: 1023 (M/2+1) |
| T-50 | 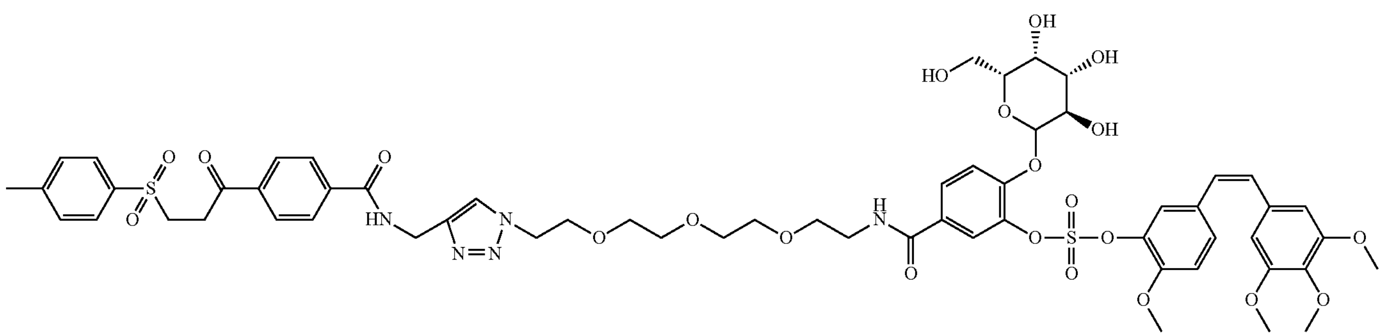 | Yield 50%; ESI-MS m/z: 1264 (M+1). |

TABLE 12-continued
| Dimer | Structure | Characterization Data |
|---|---|---|
| T-51 | 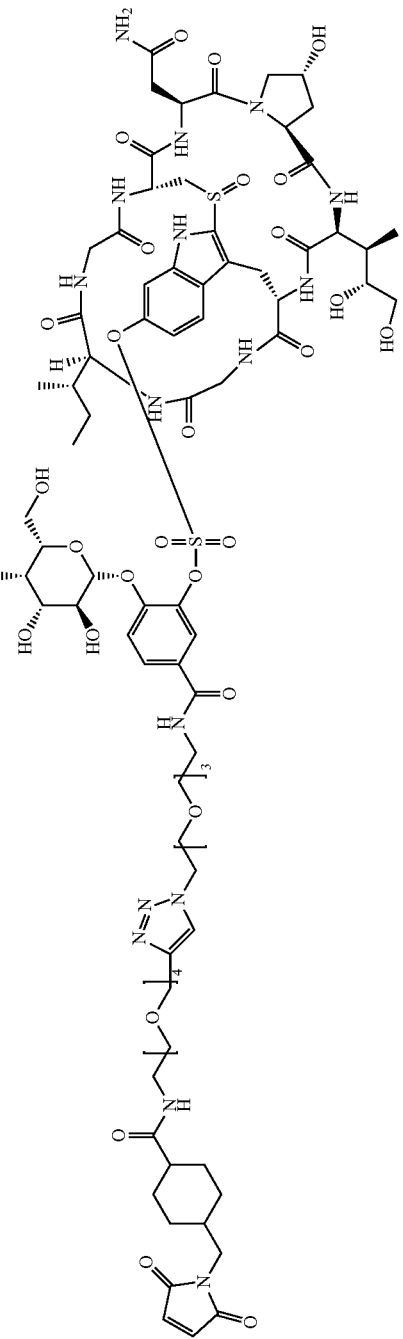 | Yield 64%; ESI-MS m/z: 975 ($M/2^{+1}$). |
| T-52 | 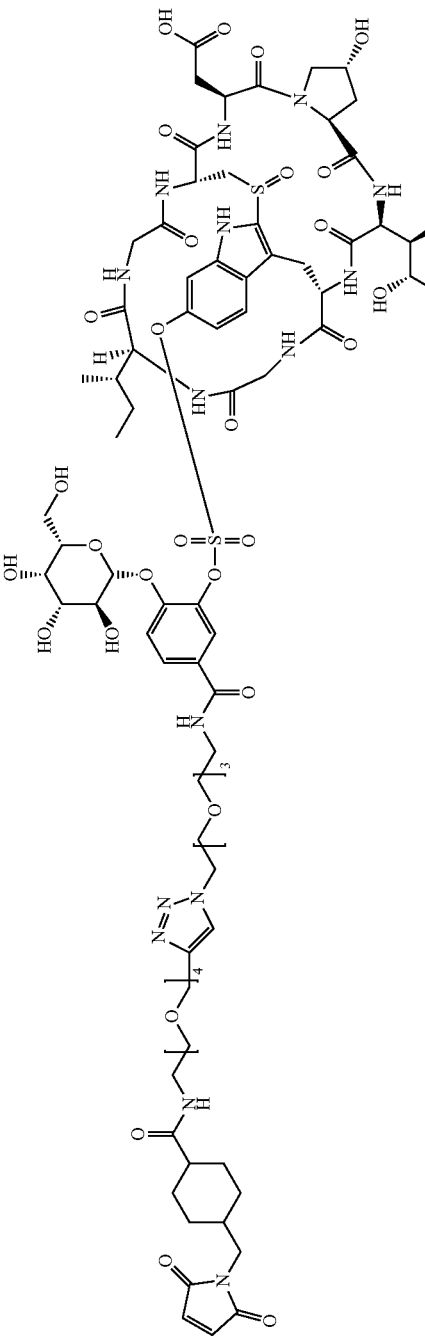 | Yield %: 22% ESI-MS m/z: 975 ($M/2^{+1}$). |

TABLE 12-continued
| Dimer | Structure | Characterization Data |
|---|---|---|
| T-53 | 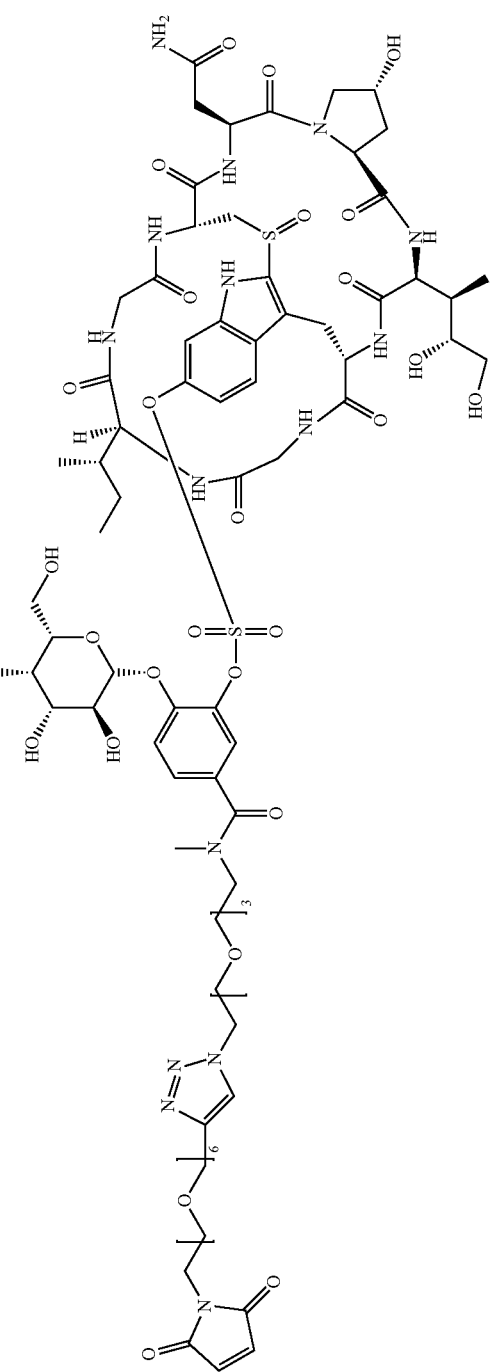 | Yield 48%; ESI-MS m/z: 956 (M/2+1). |
| T-54 | 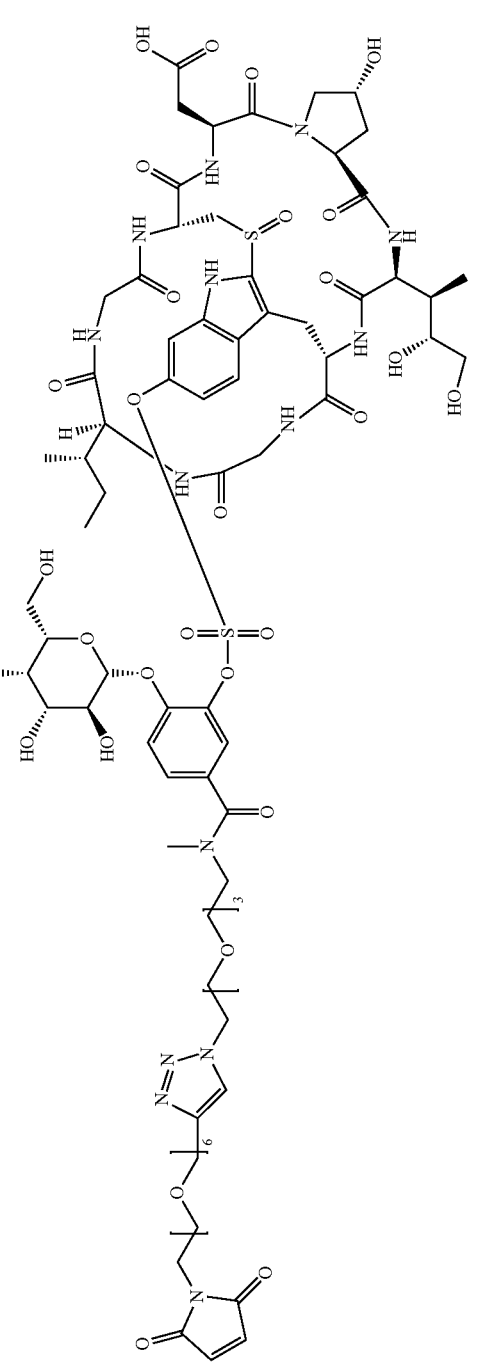 | Yield 68%; ESI-MS m/z: 955 (M/2+1). |

TABLE 12-continued
| Dimer | Structure | Characterization Data |
|---|---|---|
| T-55 | 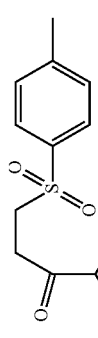 | Yield 43%; ESI-MS m/z: 916 (M/2$^{+1}$). |
| T-56 | 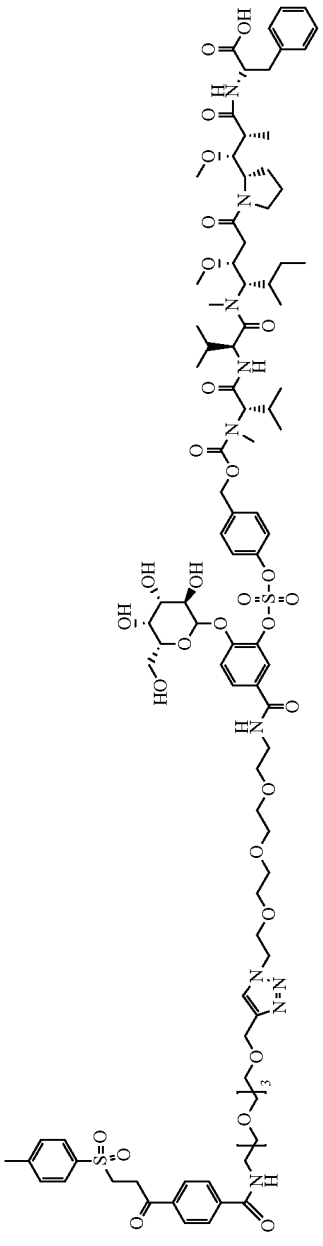 | Yield 70%, white solid. ESI-MS m/z: 1007 (M/2$^{+1}$). |

TABLE 12-continued

| Dimer | Structure | Characterization Data |
|---|---|---|
| T-57 | 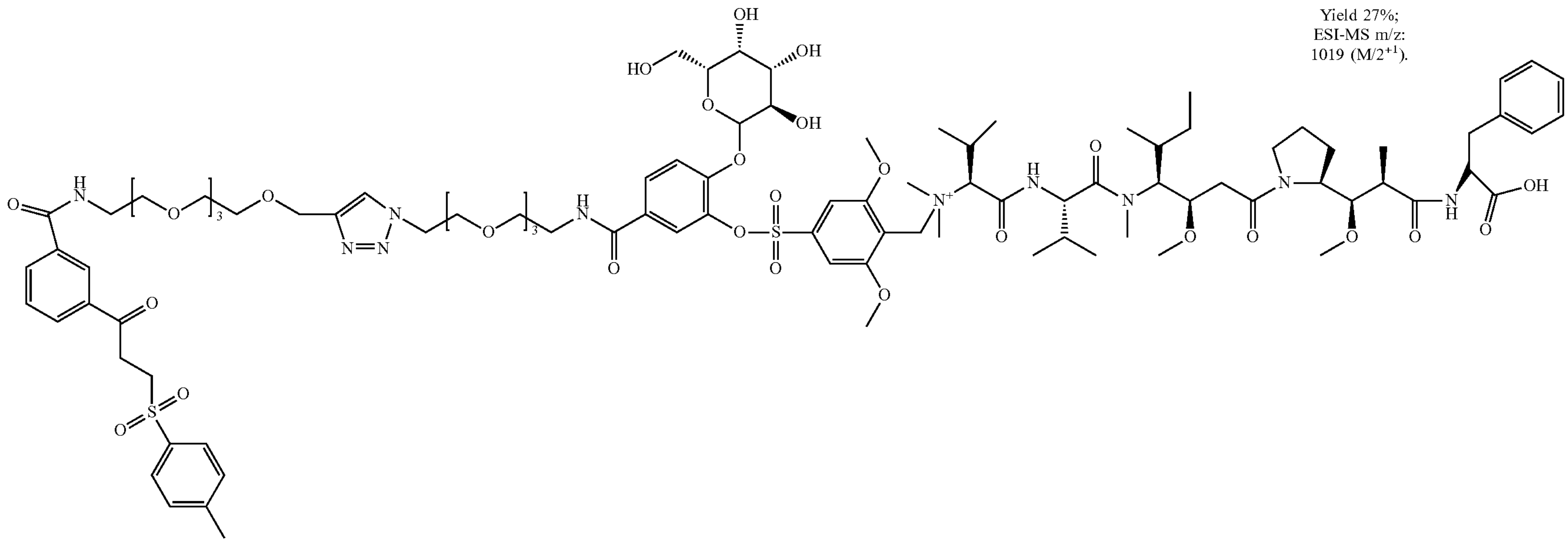 | Yield 27%; ESI-MS m/z: 1019 (M/2+1). |
| T-58 | 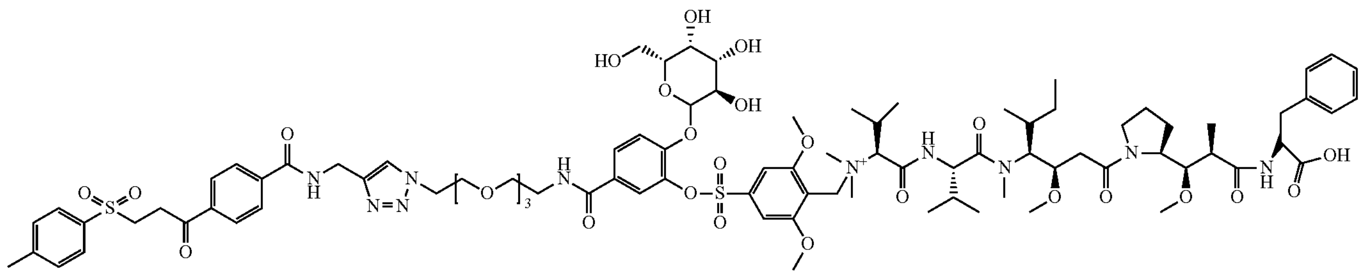 | Yield 18%; ESI-MS m/z: 930 (M/2+1). |

TABLE 12-continued

| Dimer | Structure | Characterization Data |
|---|---|---|
| T-59 | 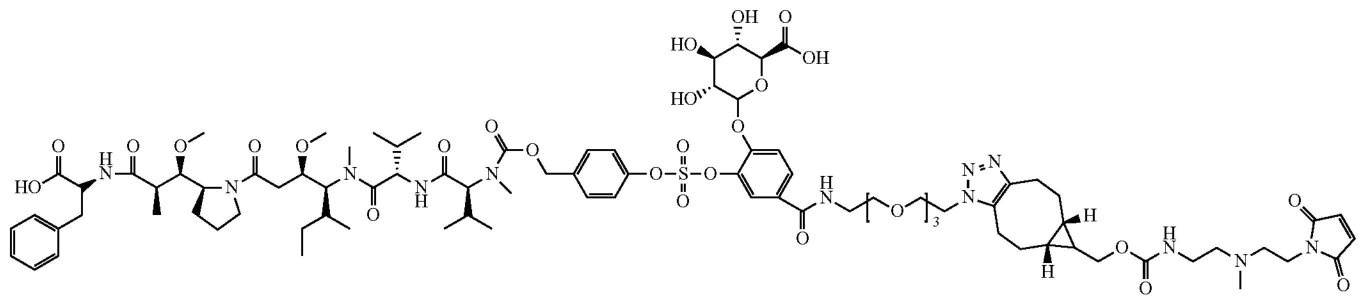 | Yield %; 57%, ESI-MS m/z: 1835 (M+) |
| T-60 | 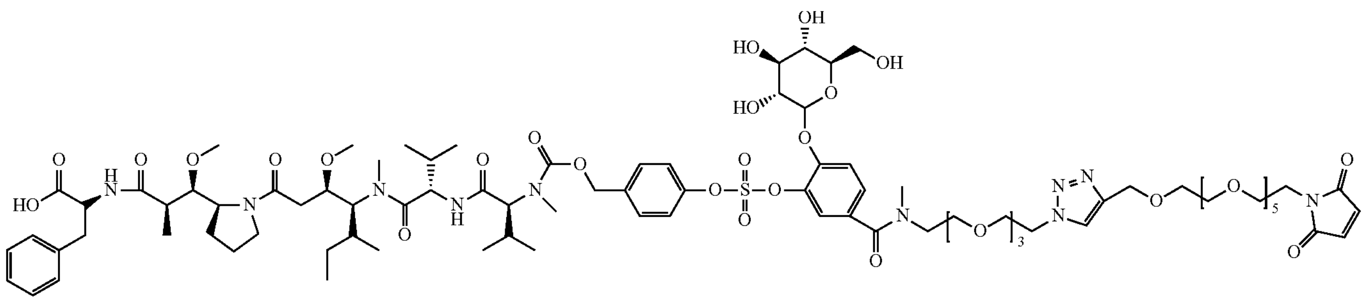 | Yield 44%; ESI-MS m/z: 937 (M/2+1). |
| T-61 | 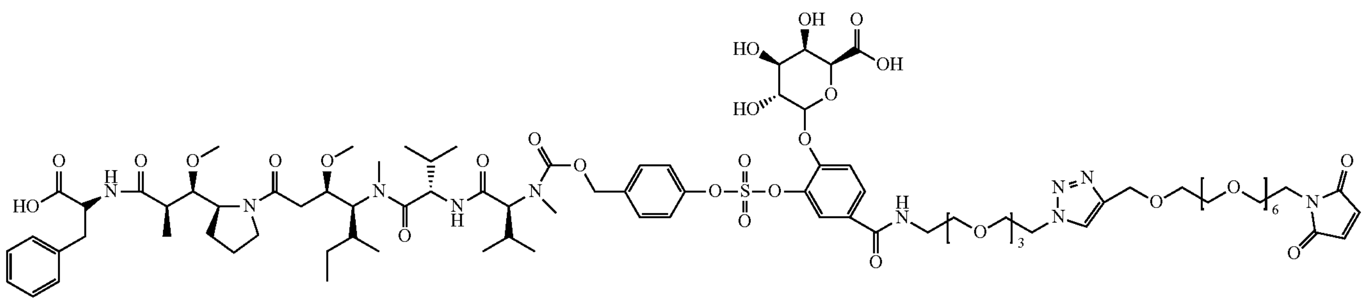 | Yield 17%; ESI-MS m/z: 1861 (M+) |

TABLE 12-continued

| Dimer | Structure | Characterization Data |
|---|---|---|
| T-62 | 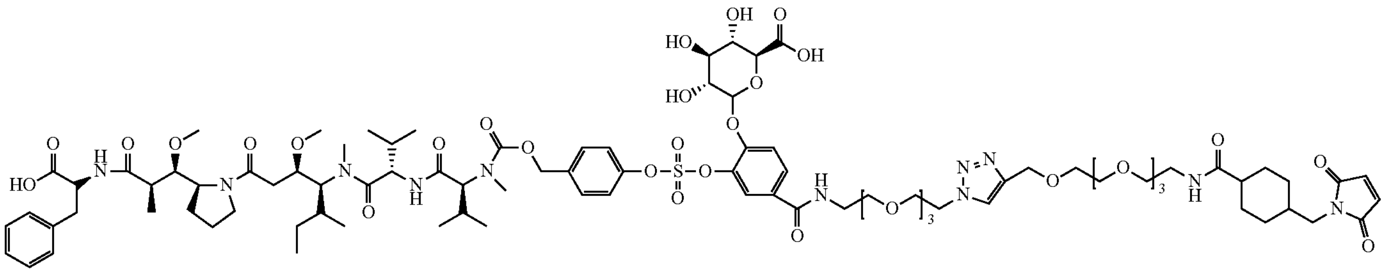 | Yield 64%, white solid. ESI-MS m/z: 957 (M/2+1). |
| T-63 | 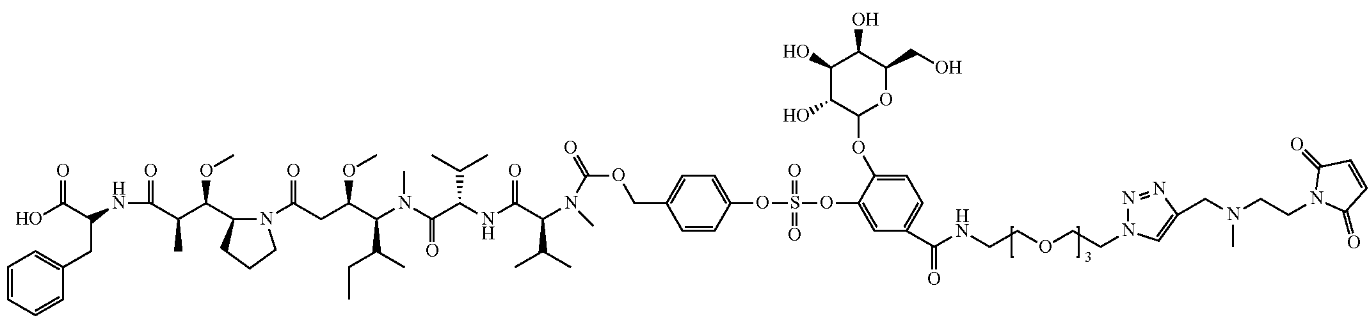 | Yield 57%, ESI-MS m/z: 827 (M/2+1). |
| T-64 | 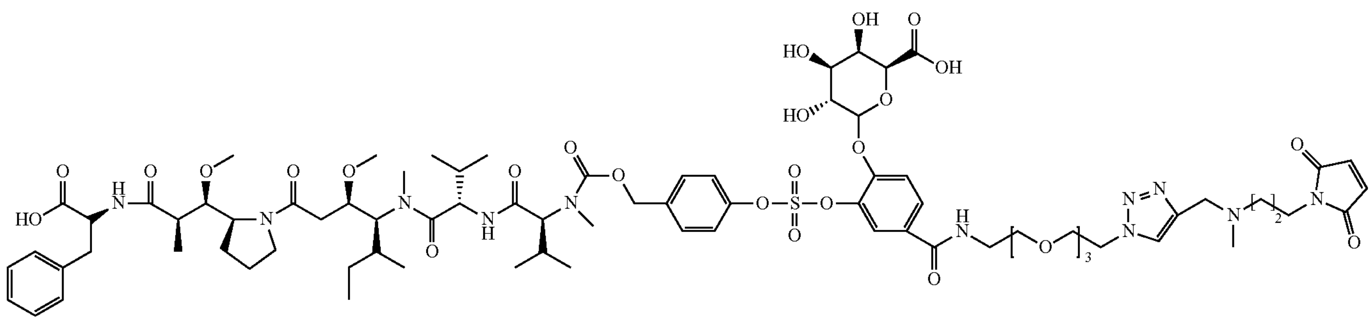 | Yield 70%, ESI-MS m/z: 1667 (M+ + 1). |

TABLE 12-continued
| Dimer | Structure | Characterization Data |
|---|---|---|
| T-65 | 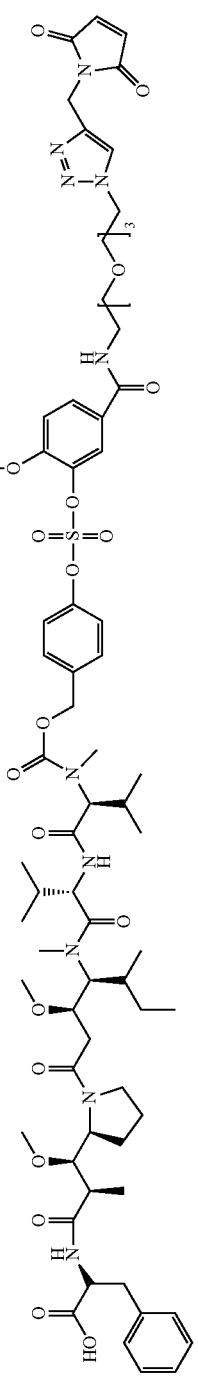 | Yield 68%, ESI-MS m/z: 1596 (M+1). |

TABLE 12-continued
| Dimer | Structure | Characterization Data |
|---|---|---|
| T-67 | 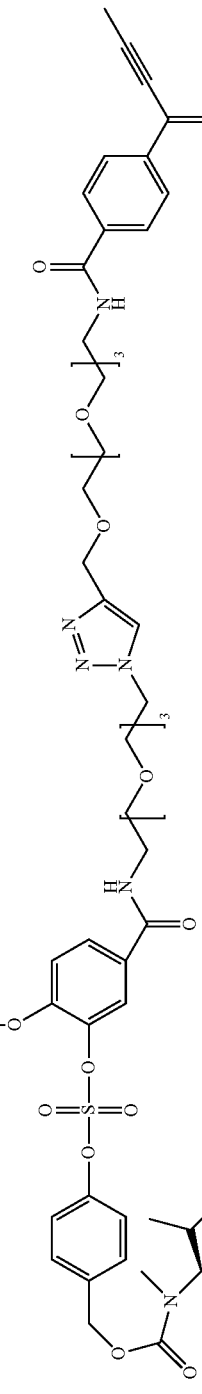 | Yield 25%; ESI-MS m/z: 1863 (M+1). |

TABLE 12-continued
| Dimer | Structure | Characterization Data |
|---|---|---|
| T-68 | 379 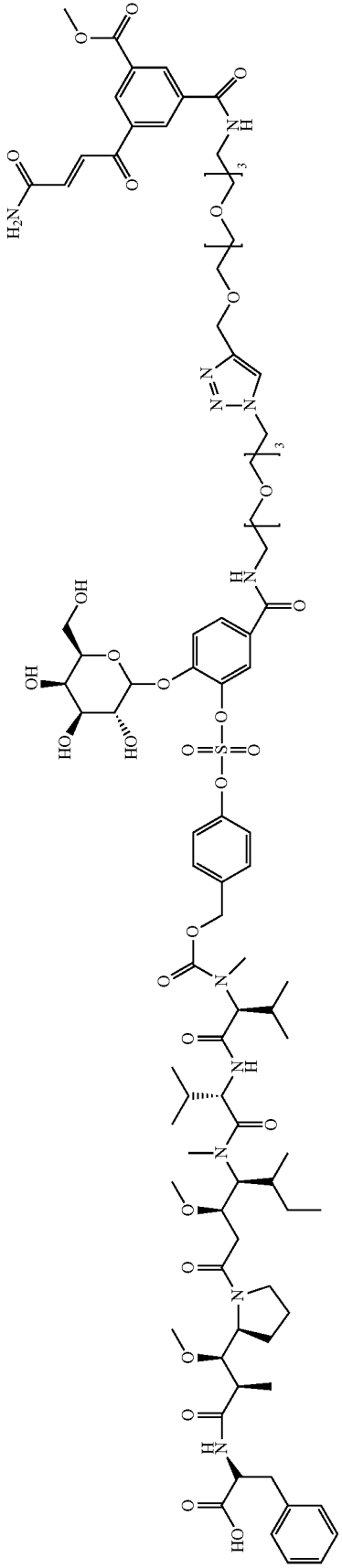 | Yield 44%; ESI-MS m/z: 937 (m/2$^{+1}$) |
| T-69 | 380 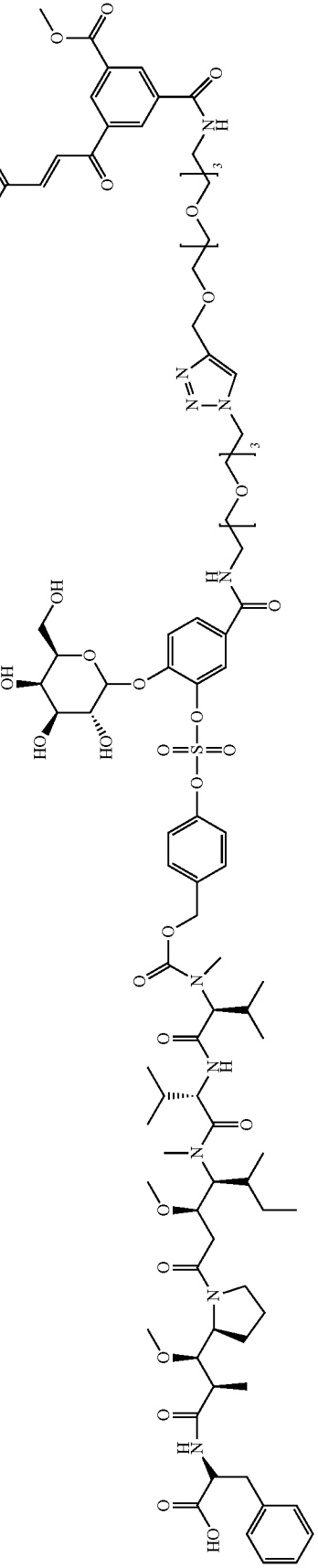 | Yield 33%, white solid. ESI-MS m/z: 976 (M/2$^{+1}$), |

TABLE 12-continued
| Dimer | Structure | Characterization Data |
|---|---|---|
| T-70 | 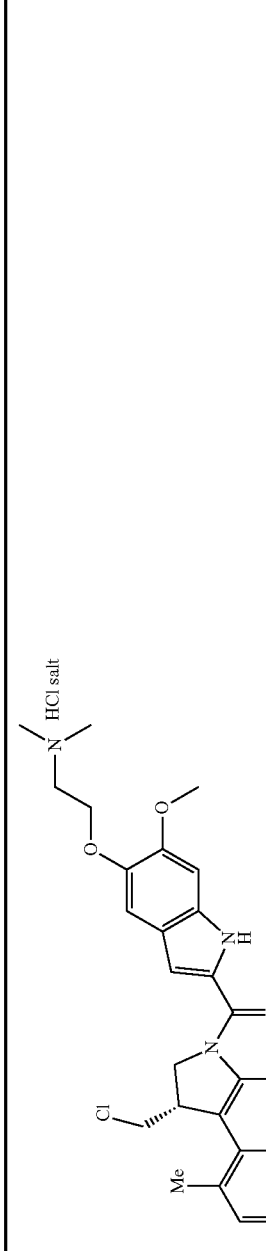 | ESI-MS m/z: 728.8 (M/2+1). |

TABLE 12-continued

| Dimer | Structure | Characterization Data |
|---|---|---|
| T-71 | 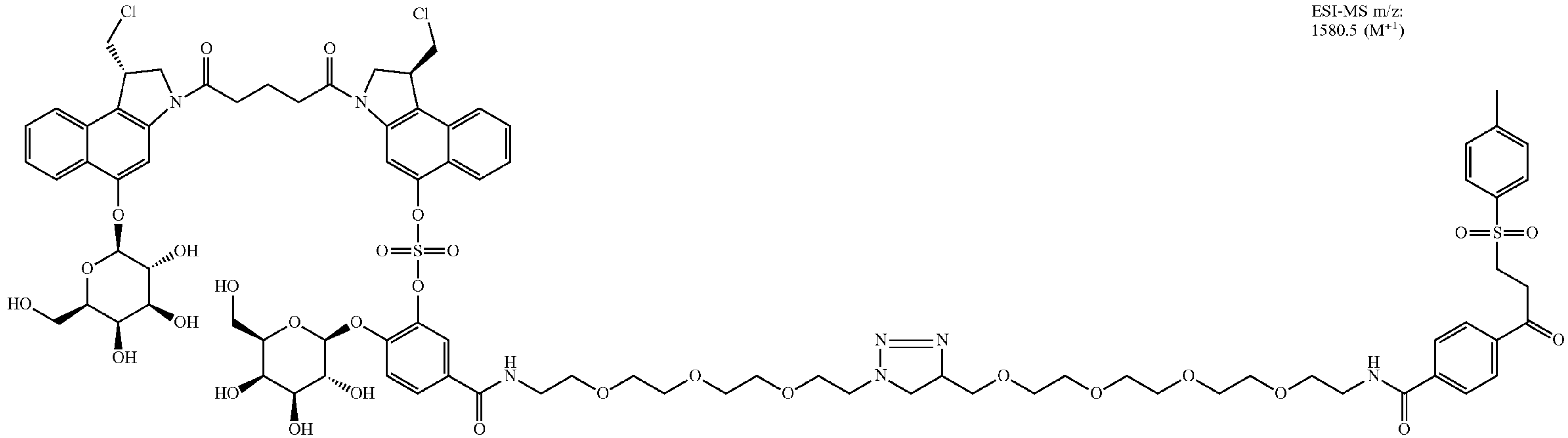 | ESI-MS m/z: 1580.5 (M+1) |
| T-72 | 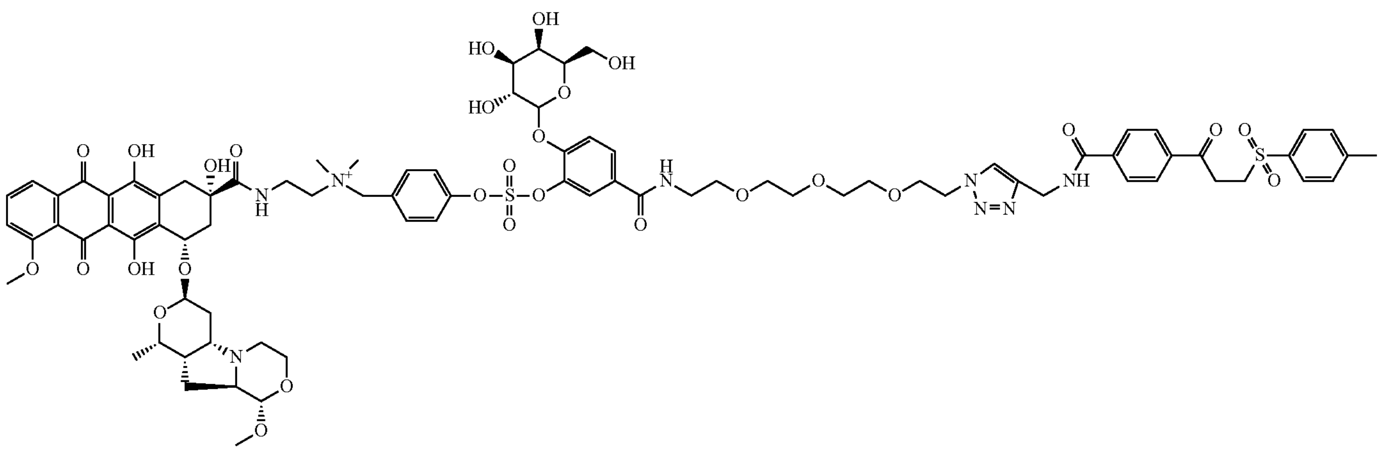 [SMILES: COc1cccc2c1C(=O)c1c(O)c3c(c(O)c1C2=O)C[C@@](O)(C(=O)NCC[N+](C)(C)Cc1ccc(OS(=O)(=O)Oc2cc(C(=O)NCCOCCOCCOCCn4cc(CNC(=O)c5ccc(C(=O)CCS(=O)(=O)c6ccc(C)cc6)cc5)nn4)ccc2OC2O[C@H](CO)[C@H](O)[C@H](O)[C@H]2O)cc1)C[C@@H]3O[C@H]1C[C@H]2[C@H](C[C@@H]3[C@@H](OC)OCCN32)[C@H](C)O1] | Yield 13%; ESI-MS m/z: 1753 (M+1). |

TABLE 12-continued

| Dimer | Structure | Characterization Data |
|---|---|---|
| T-73 | 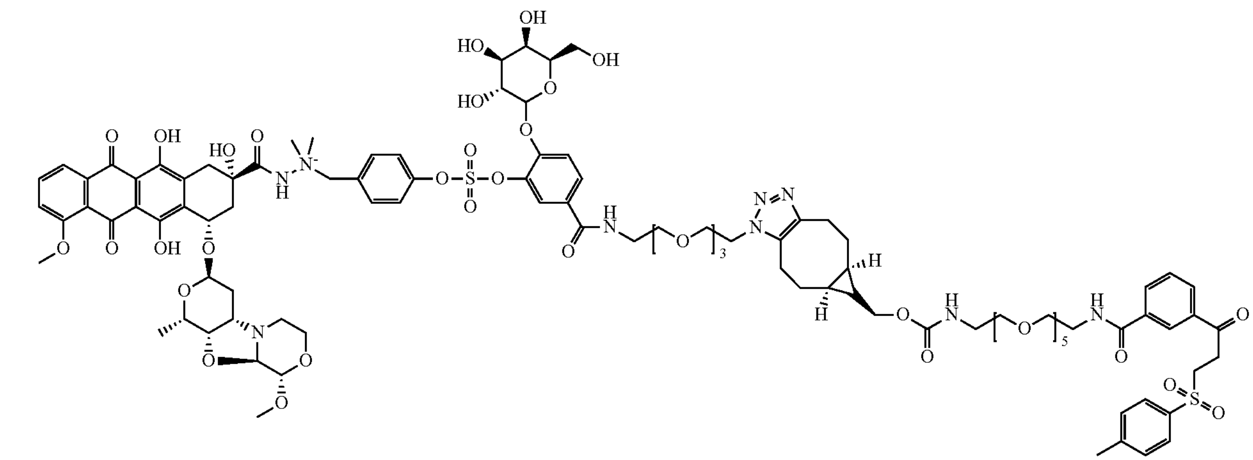 | Yield 32%; ESI-MS m/z: 1077 (M/2+1). |
| T-74 | 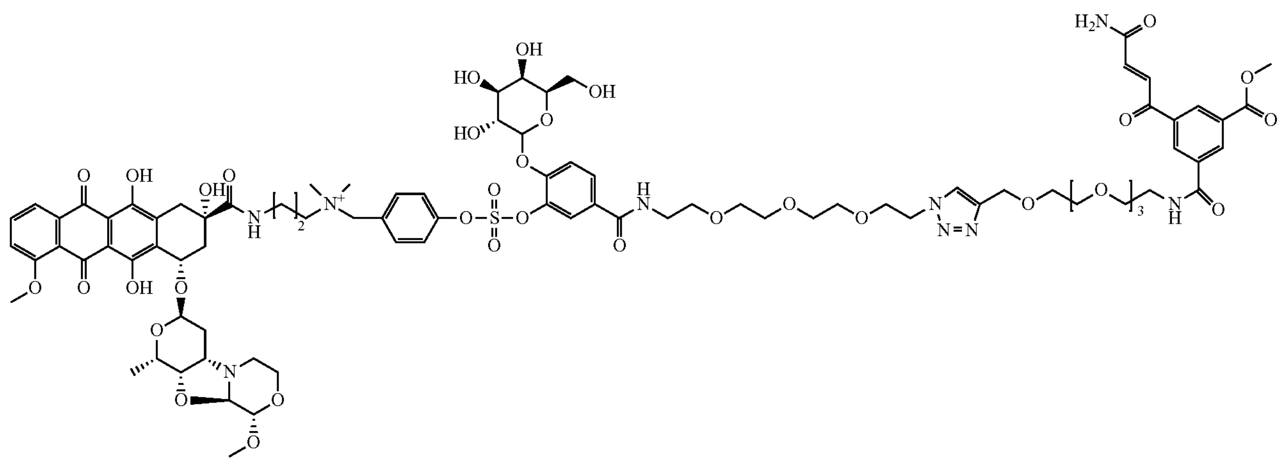 | Yield 21%; ESI-MS m/z: 925 (M/2+1). |

TABLE 12-continued

| Dimer | Structure | Characterization Data |
|---|---|---|
| T-75 | 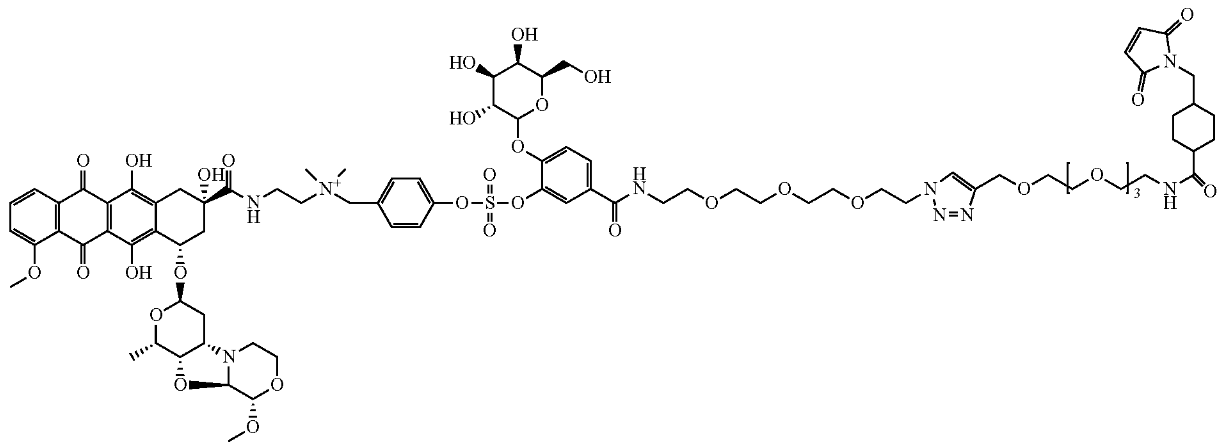 | Yield 35%; ESI-MS m/z: 917 (M/2+1). |
| T-76 | 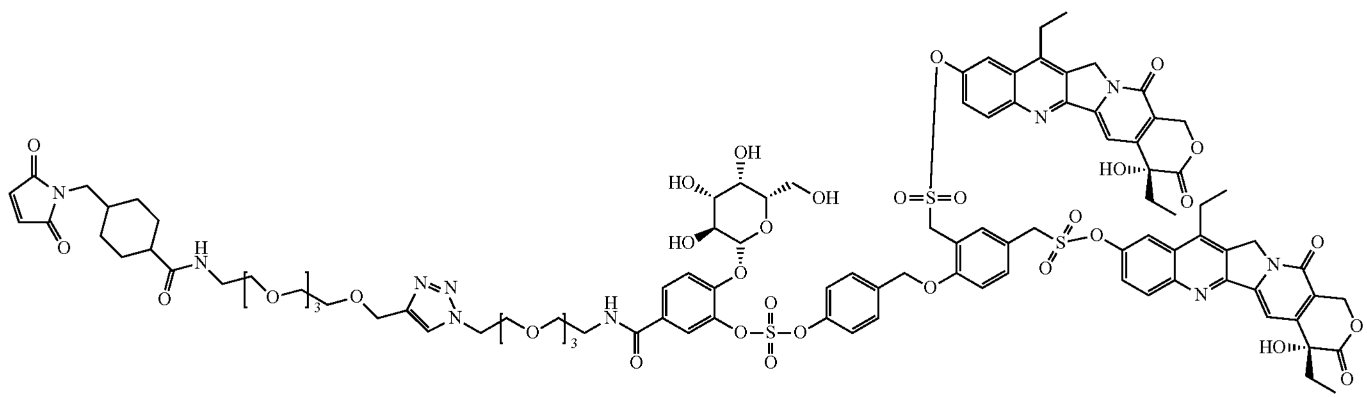 | Yield 81%; ESI-MS m/z: 1084 (M/2+1). |

TABLE 12-continued
| Dimer | Structure | Characterization Data |
|---|---|---|
| T-77 | 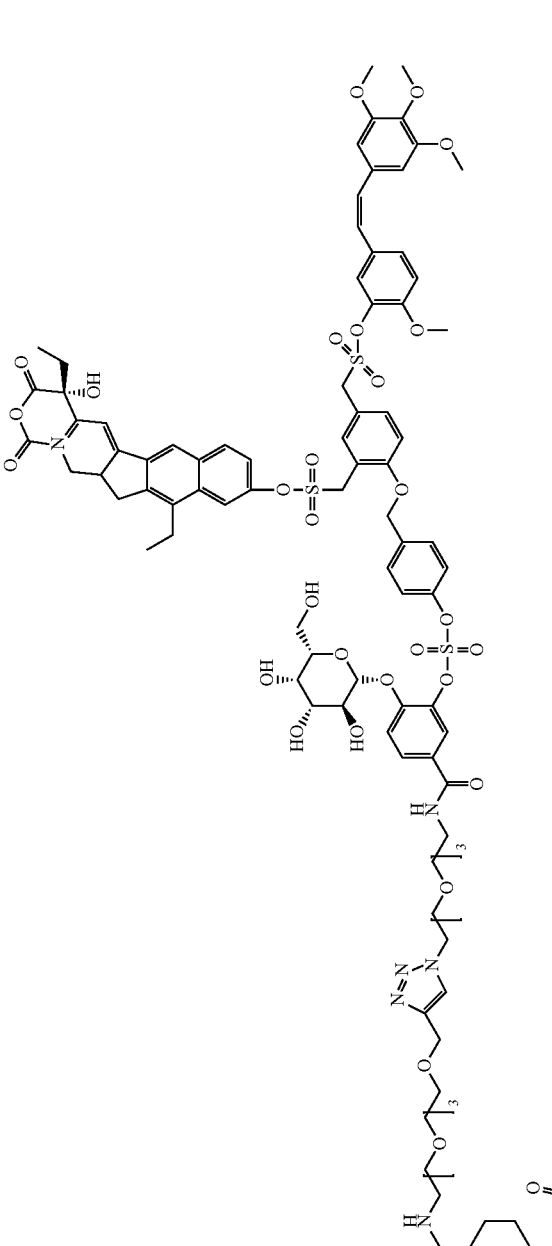 | Yield 55%; ESI-MS m/z: 1046 (M/2+1). |

TABLE 12-continued

| Dimer | Structure | Characterization Data |
|---|---|---|
| T-78 | 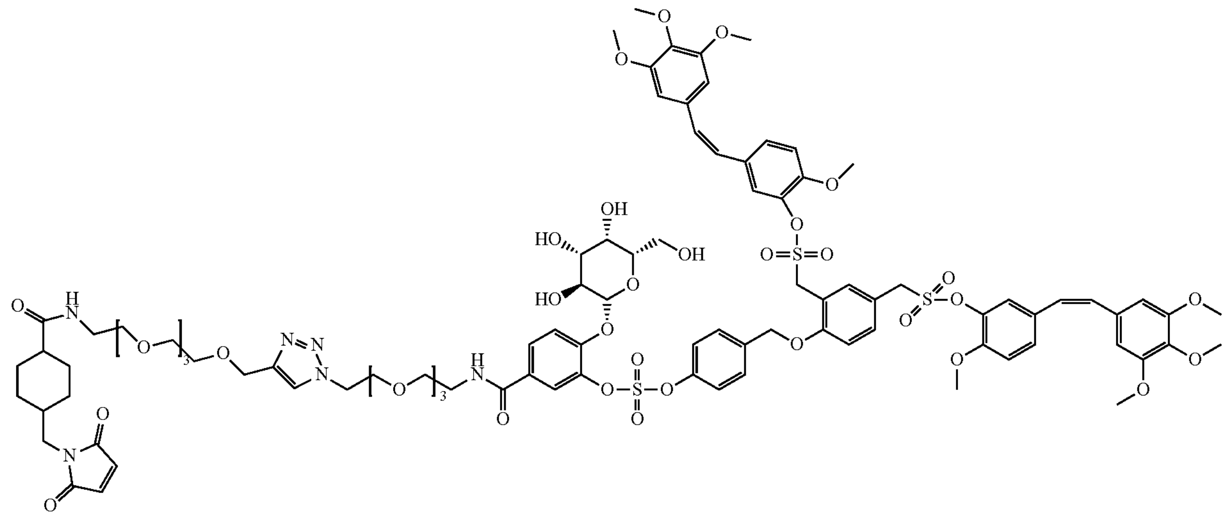 | Yield 50%; ESI-MS m/z: 1008 (M/2+¹). |

TABLE 12-continued
| Dimer | Structure | Characterization Data |
|---|---|---|
| T-79 | 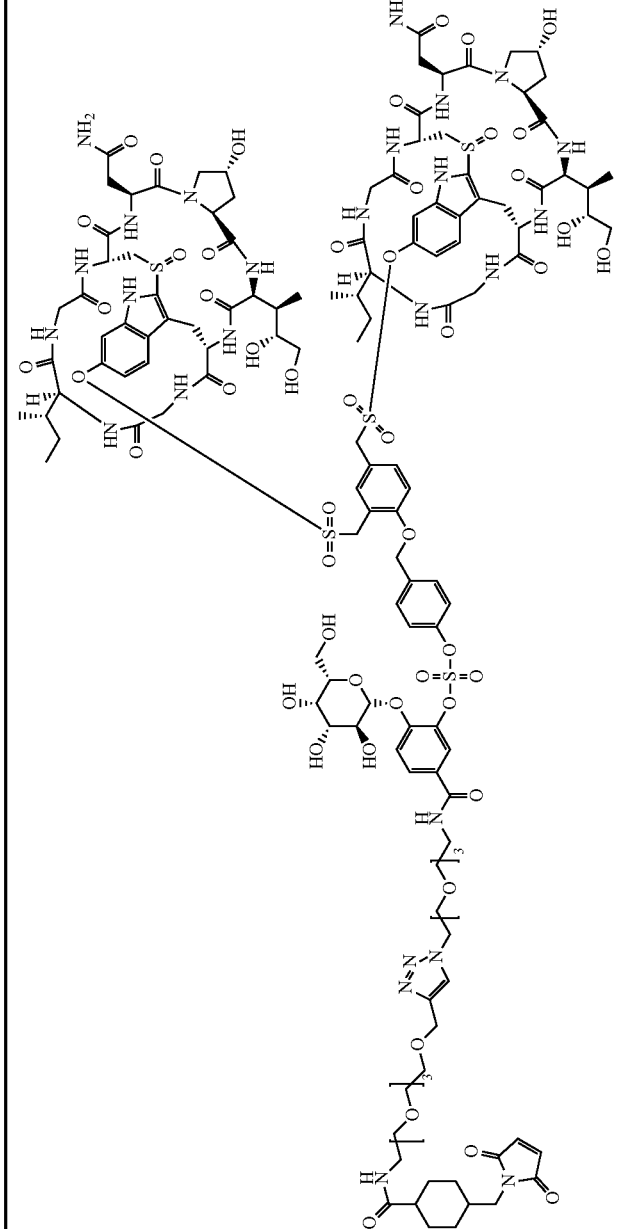 | Yield 54% ESI-MS m/z: 1610 (M/2+1). |

TABLE 12-continued
| Dimer | Structure | Characterization Data |
|---|---|---|
| T-80 | 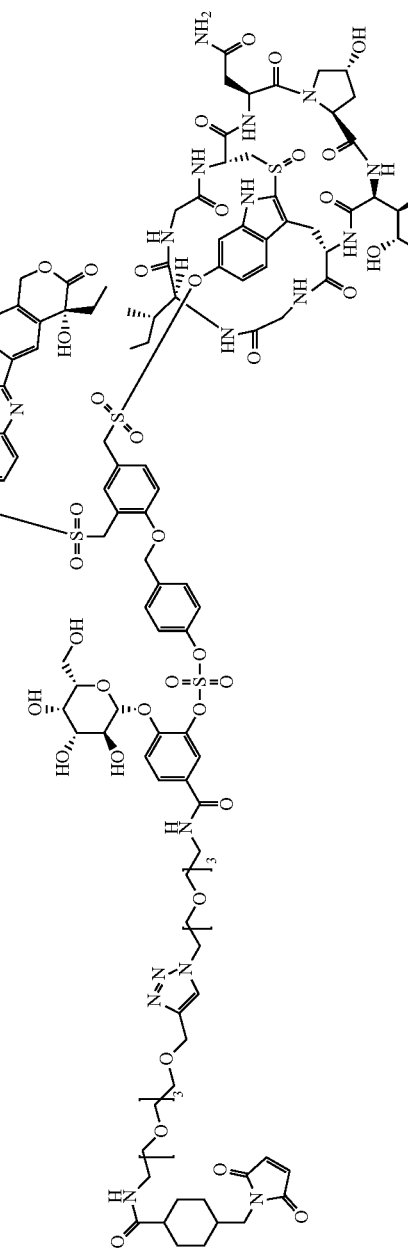 | Yield 73% ESI-MS m/z: 1610 (M/2+1). |
| T-81 | 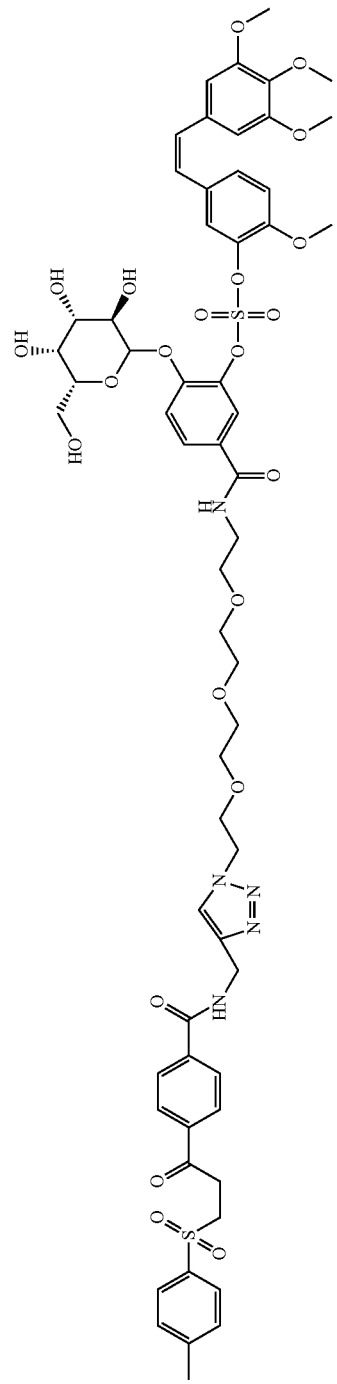 | Yield 50%; ESI-MS m/z: 1347 (M+1). |

TABLE 12-continued
| Dimer | Structure | Characterization Data |
|---|---|---|
| T-82 | 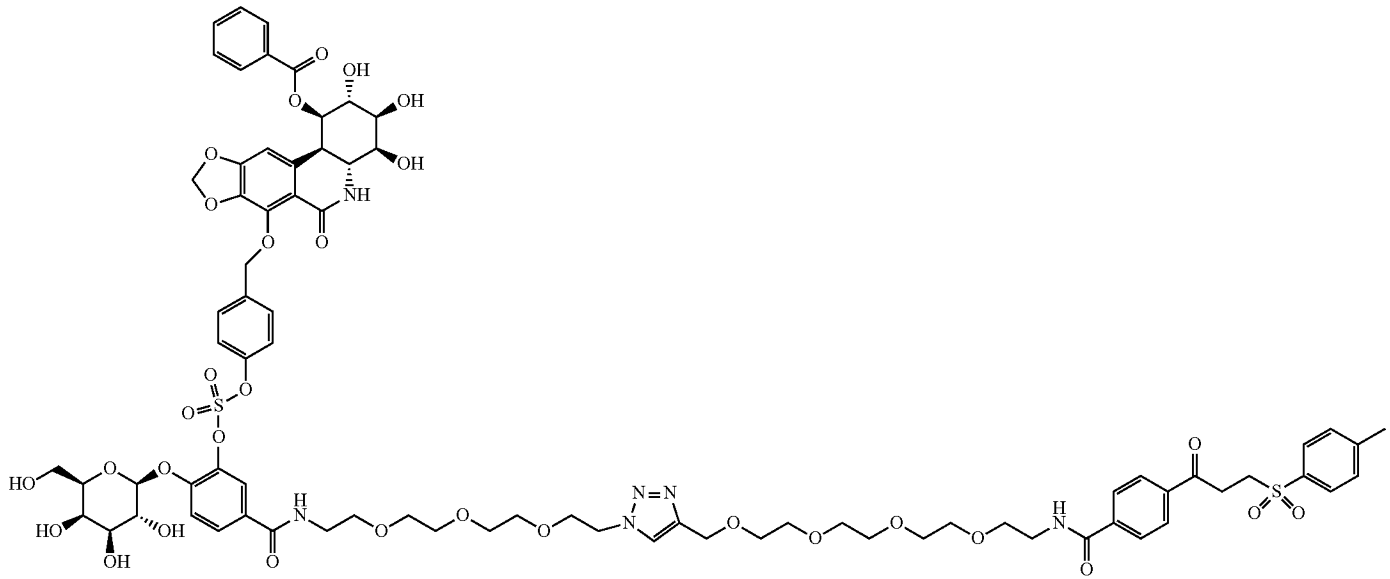 [SMILES: Cc1ccc(S(=O)(=O)CCC(=O)c2ccc(C(=O)NCCOCCOCCOCCOCc3cn(CCOCCOCCOCCNC(=O)c4ccc(O[C@@H]5O[C@H](CO)[C@H](O)[C@H](O)[C@H]5O)c(OS(=O)(=O)Oc5ccc(COc6c7c(cc8c6C(=O)N[C@H]6[C@H](O)[C@H](O)[C@@H](O)[C@H](OC(=O)c9ccccc9)[C@H]86)OCO7)cc5)c4)nn3)cc2)cc1] | Yield 12%; ESI-MS m/z: 830 (M/2+1). |

TABLE 12-continued
| Dimer | Structure | Characterization Data |
|---|---|---|
| T-83 | 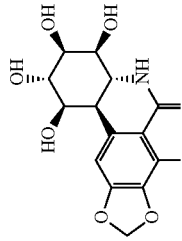 | Yield 19%; ESI-MS m/z: 1556 (M+1), 778 (M/2+1). |

TABLE 12-continued
| Dimer | Structure | Characterization Data |
|---|---|---|
| T-101 | 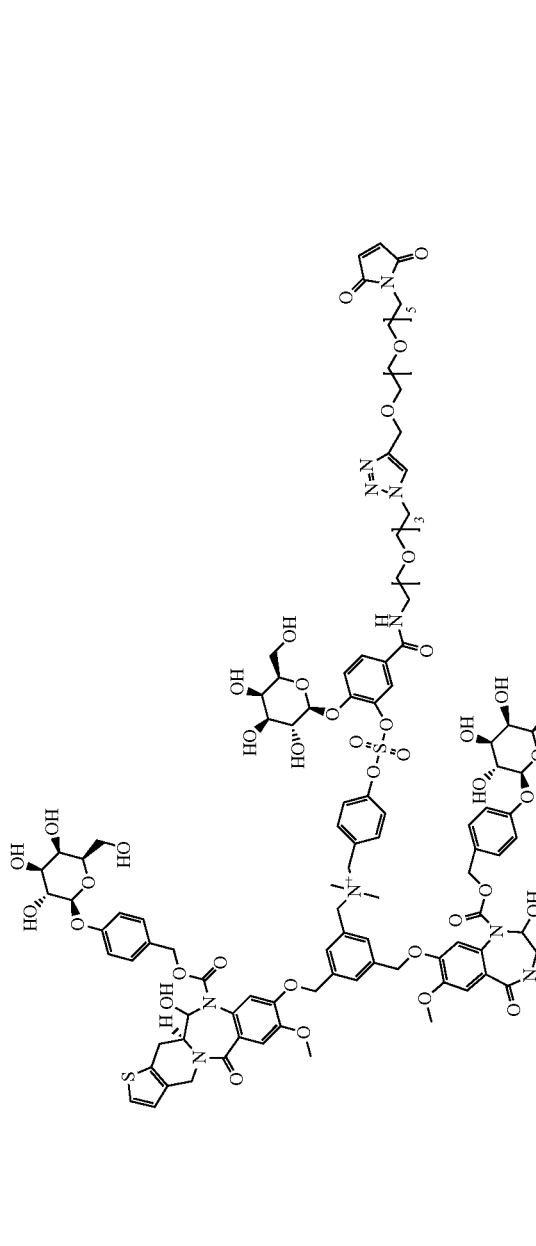 | Yield 61%; ESI-MS m/z: 1267 (M$^+$/2), 2534 (M$^+$ + 1). |

TABLE 12-continued
| Dimer | Structure | Characterization Data |
|---|---|---|
| T-102 | 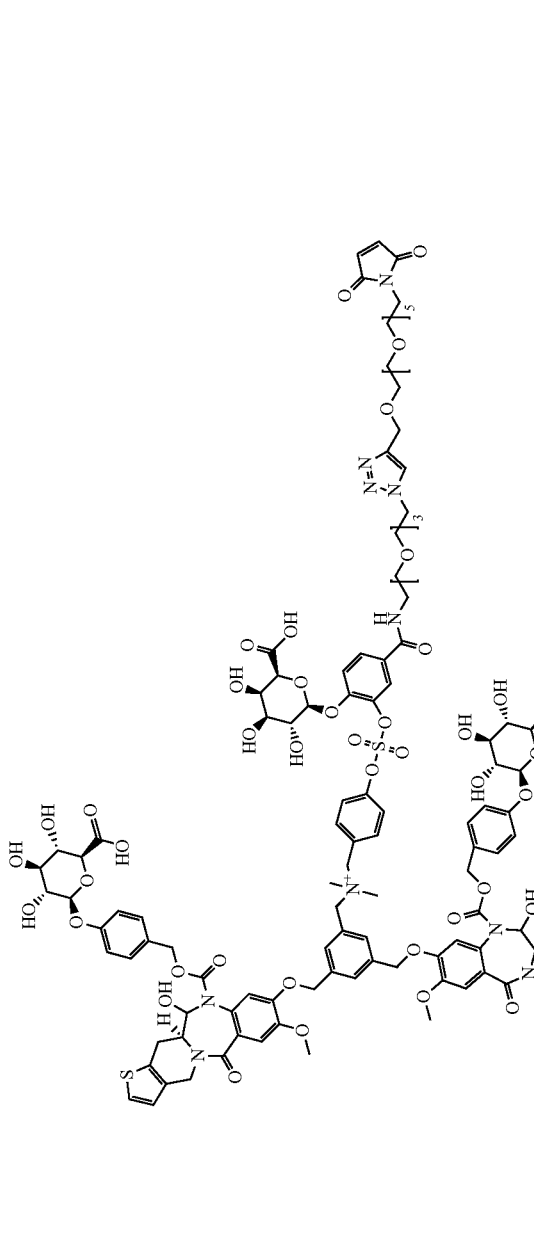 | Yield 58% ESI-MS m/z: 1288 (M+/2), 2576 (M+ + 1). |

TABLE 12-continued
| Dimer | Structure | Characterization Data |
|---|---|---|
| T-103 | 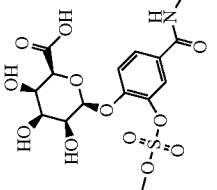 T-103 | Yield 63% ESI-MS m/z: 1312 (M+/2), 2623 (M+). |

TABLE 12-continued
| Dimer | Structure | Characterization Data |
|---|---|---|
| T-104 | 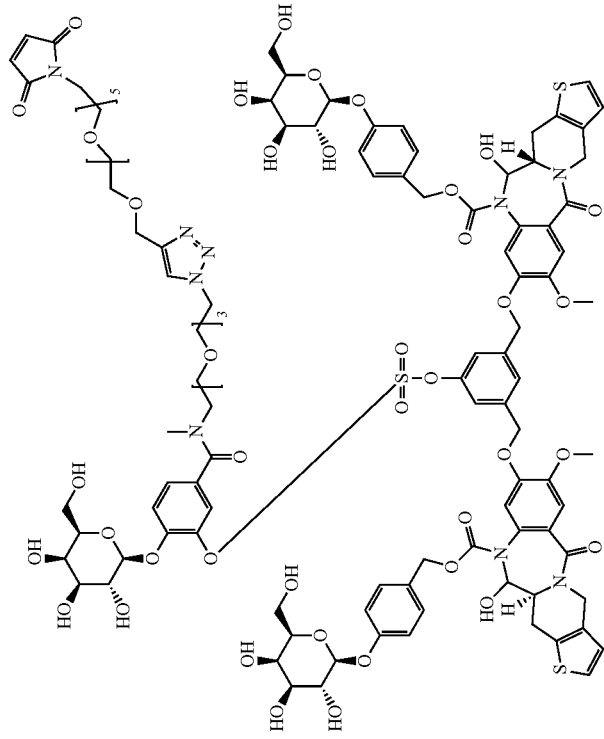 T-104 | Yield 63% ESI-MS m/z: 1200 (M+/2), 2399(M+). |

TABLE 12-continued

| Dimer | Structure | Characterization Data |
|---|---|---|
| T-105 | 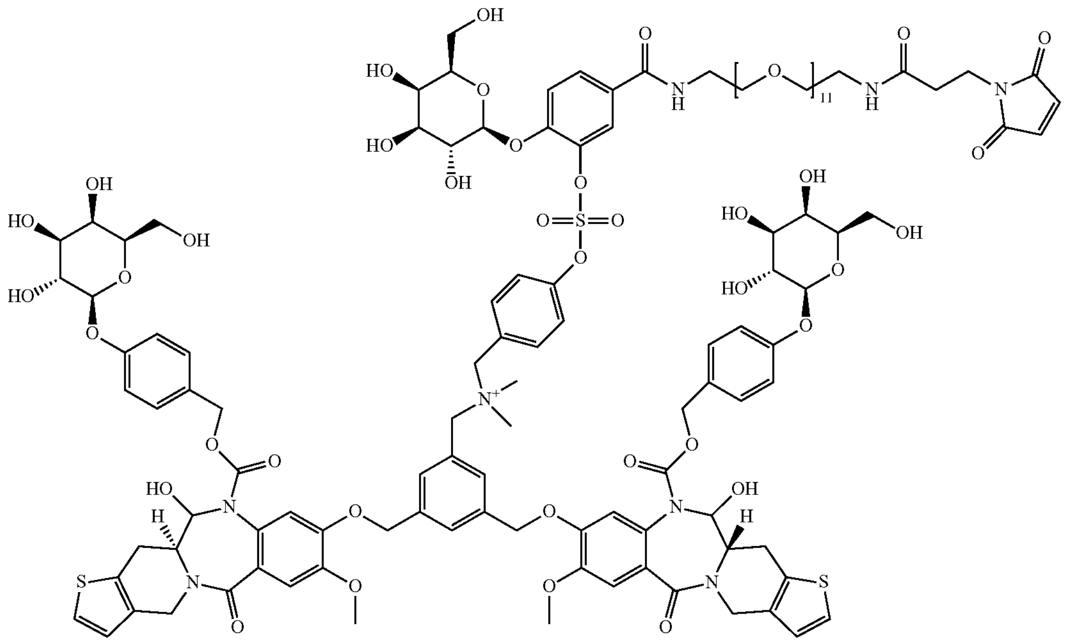 | Yield 60% ESI-MS m/z: 1305 (M$^+$/2). |

TABLE 12-continued
| Dimer | Structure | Characterization Data |
|---|---|---|
| T-106 | 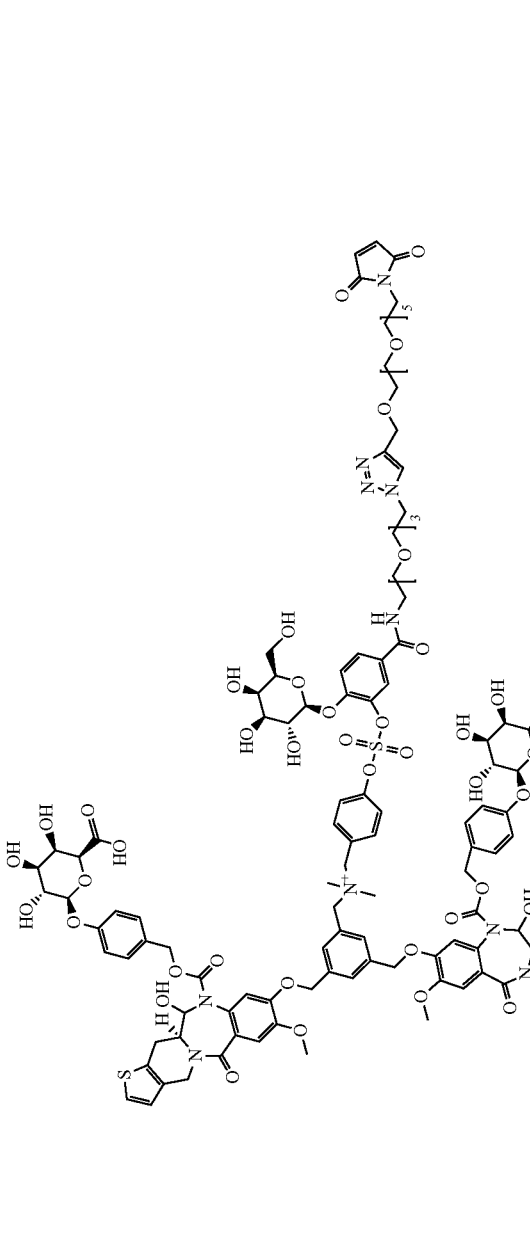 | Yield 54% ESI-MS m/z: 1281 (M/2)$^{+1}$, 2562 (M$^+$ + 1) |

TABLE 12-continued
| Dimer | Structure | Characterization Data |
|---|---|---|
| T-107 | 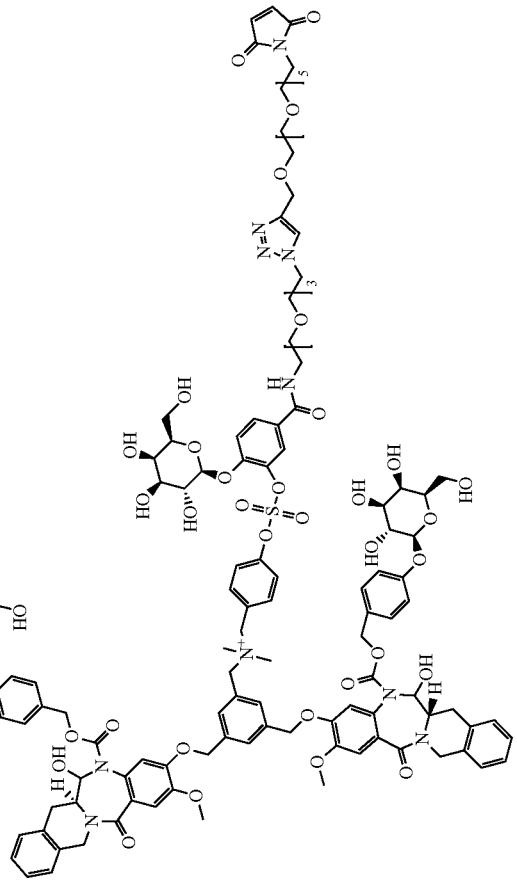 | Yield 74% ESI-MS m/z: 1260 (M+/2 + 1), 2519 (M+). |

TABLE 12-continued
| Dimer | Structure | Characterization Data |
|---|---|---|
| T-108 | 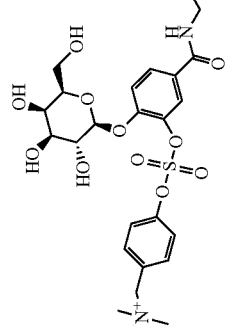 | Yield 63% ESI-MS m/z: 1210 (M+/2). |

TABLE 12-continued
| Dimer | Structure | Characterization Data |
|---|---|---|
| T-109 | 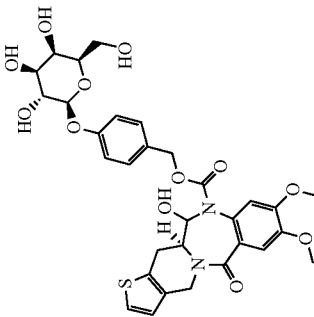 | Yield 70% ESI-MS m/z: 1263 (M+/2). |

TABLE 12-continued
| Dimer | Structure | Characterization Data |
|---|---|---|
| T-110 | 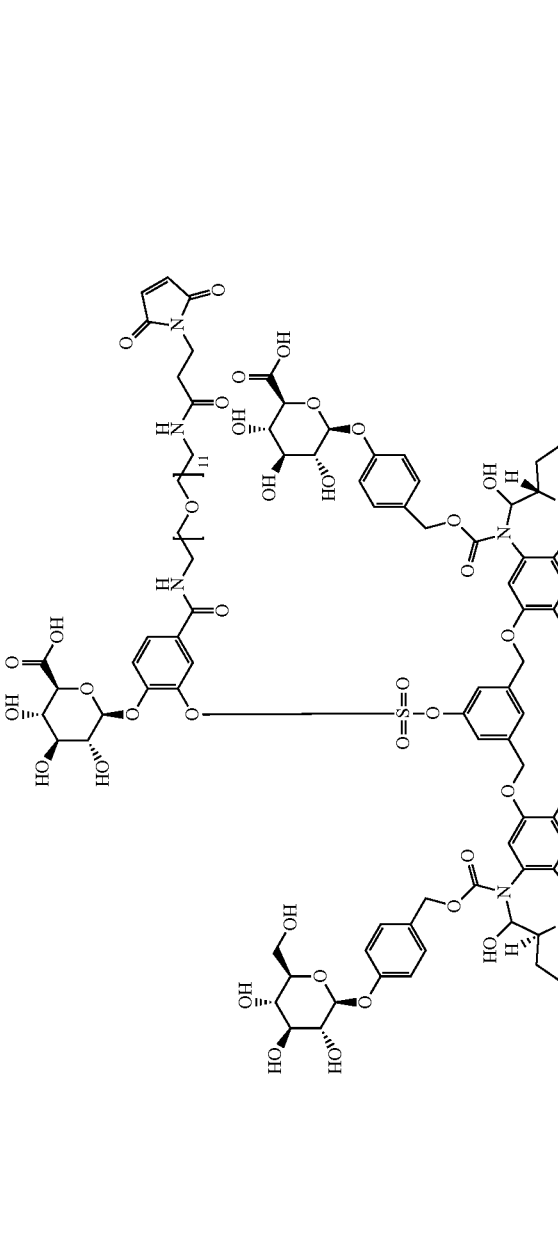 T-8 | Yield 47% ESI-MS m/z: 1177 (M+/2) |

TABLE 12-continued
| Dimer | Structure | Characterization Data |
|---|---|---|
| T-111 | 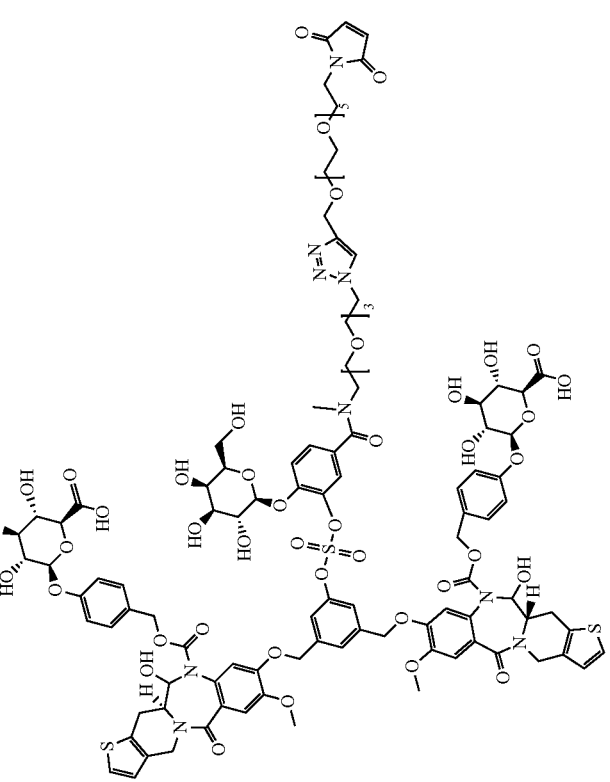 | Yield 78% ESI-MS m/z: 1206 (M+/2), 2413 (M+). |

TABLE 12-continued
| Dimer | Structure | Characterization Data |
|---|---|---|
| T-112 | 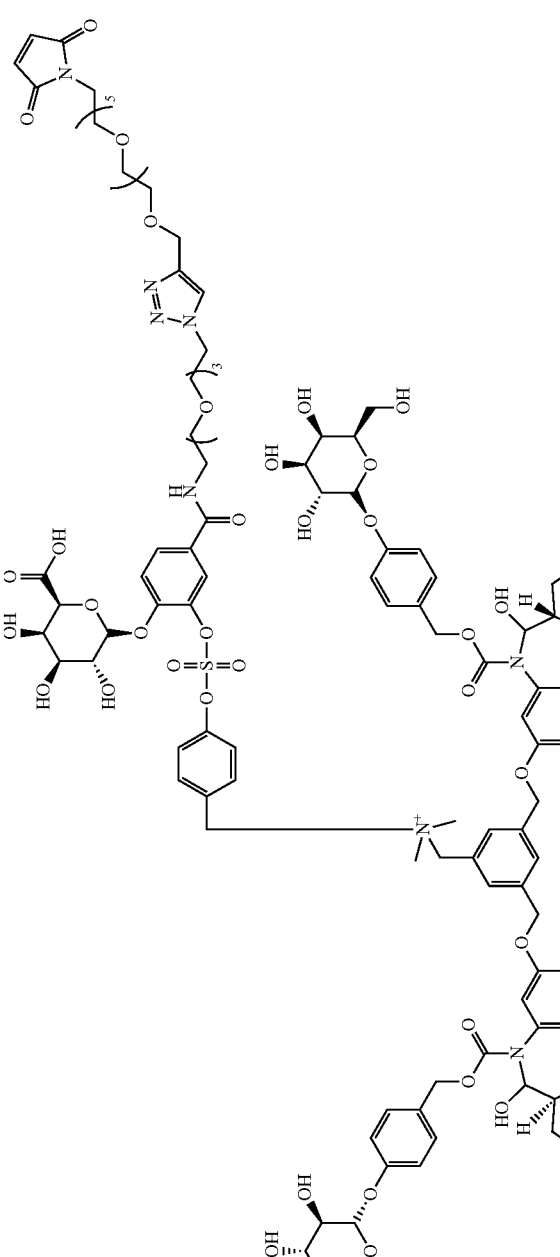 | Yield 68% ESI-MS m/z: 1273 (M+/2) |

Example 4.11.2
Preparation of A4, A5, A6 and A7
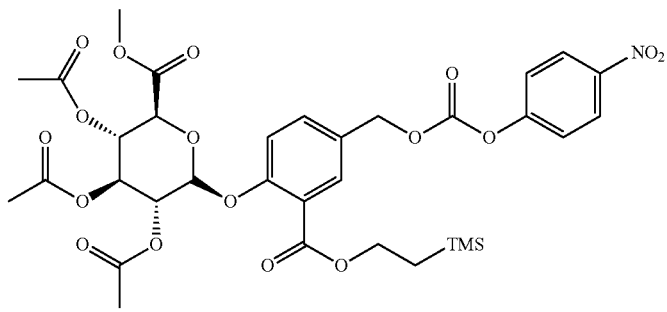
A-1
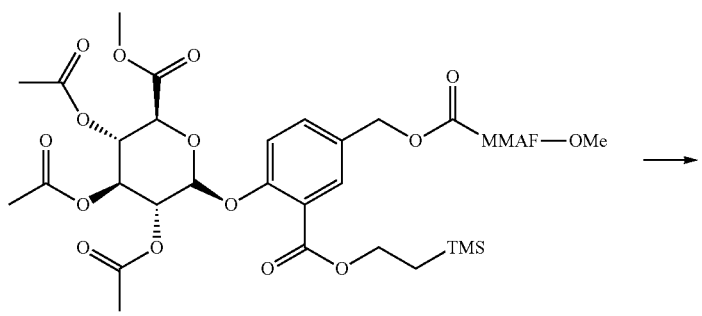
A-2
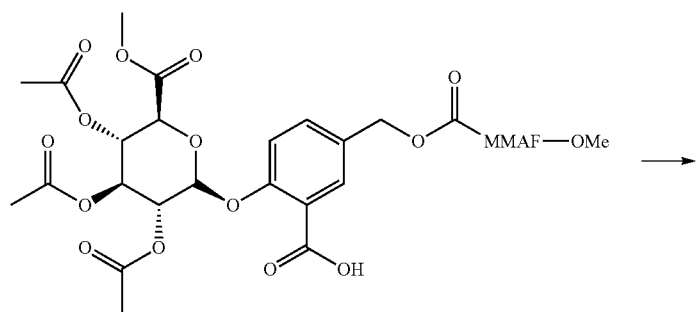
A-3

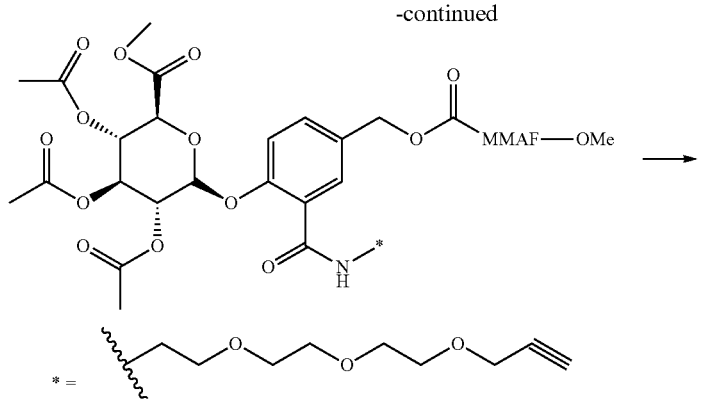
A-4
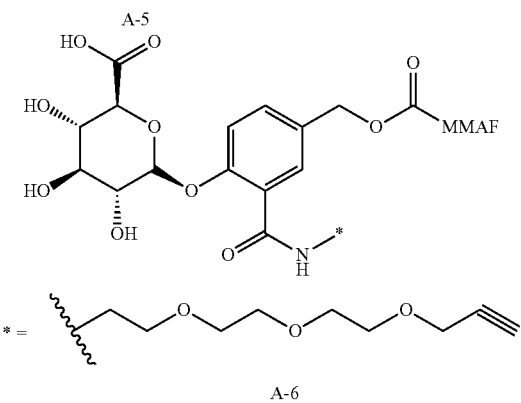
A-6
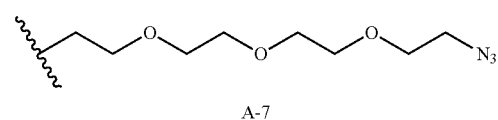
A-7
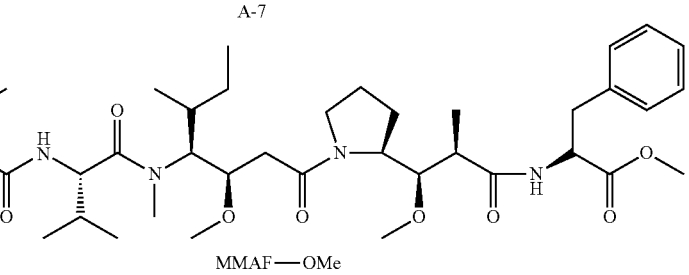
MMAF—OMe
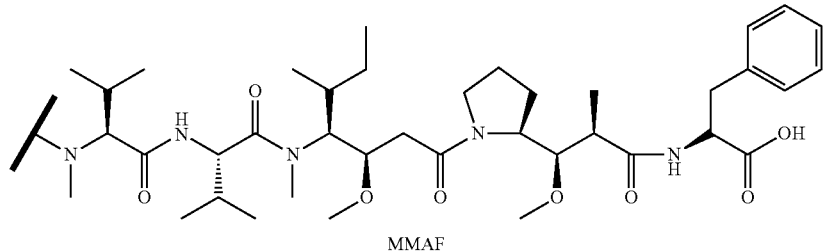
MMAF
Preparation of Compounds A-1, A-2 and A-3
Each substance was obtained by preparing it with a method similar to that described in Examples 2 and 3 of Korean Patent Laid-Open Publication No. 10-2015-0137015.
Compound A-4, A-5, A-6 and A-7 were prepared by a similar synthetic route of preparing compound OHPAS-D1 or Q-1 in Example 3.2 or Example 4.1.1.
Preparation of Compound A-4
ESI-MS m/z: 1426 ($M^{+1}$).

Preparation of Compound A-5
　Yield 75%, ESI-MS m/z: 1457 (M$^{+1}$).
Preparation of Compound A-6
　Yield 63%, ESI-MS m/z: 1272 (M$^{+1}$).
Preparation of Compound A-5
　Yield 89%, ESI-MS m/z: 1303 (M$^{+1}$).

Table 9 below lists the dimer derivatives that were synthesized via a similar synthetic route as described in Example 4.11.1.

TABLE 9
| T-84 | 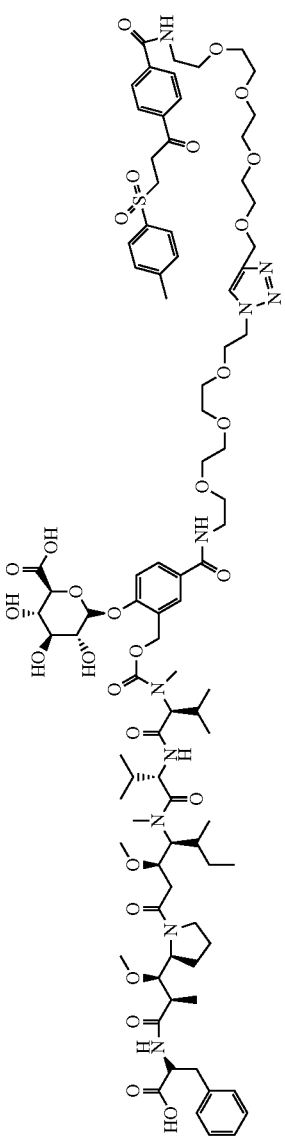 | Yield 71%; ESI-MS m/z: 925(M/2+1). |
| T-85 | 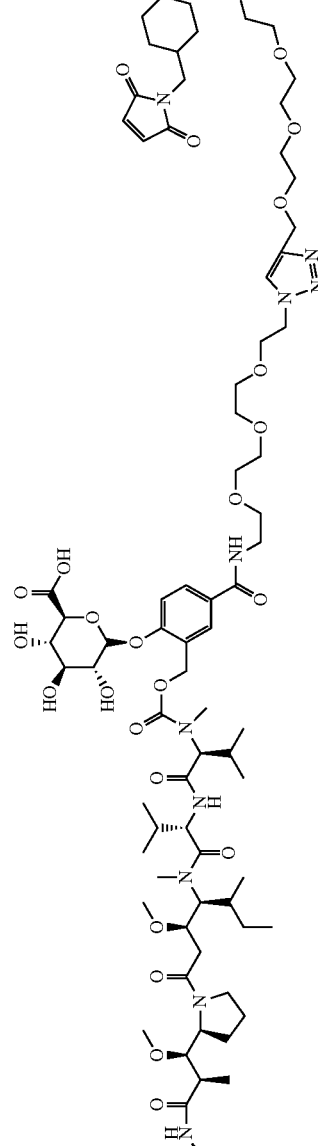 | Yield 56%, white solid. ESI-MS m/z: 877(M/2+1). |
| T-86 | 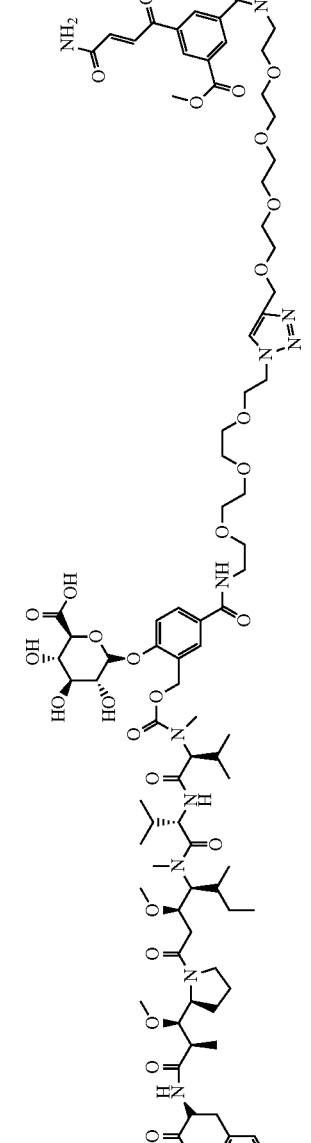 | Yield 70%, white solid. ESI-MS m/z: 897(M/2+1). |

TABLE 9-continued
| T-87 | 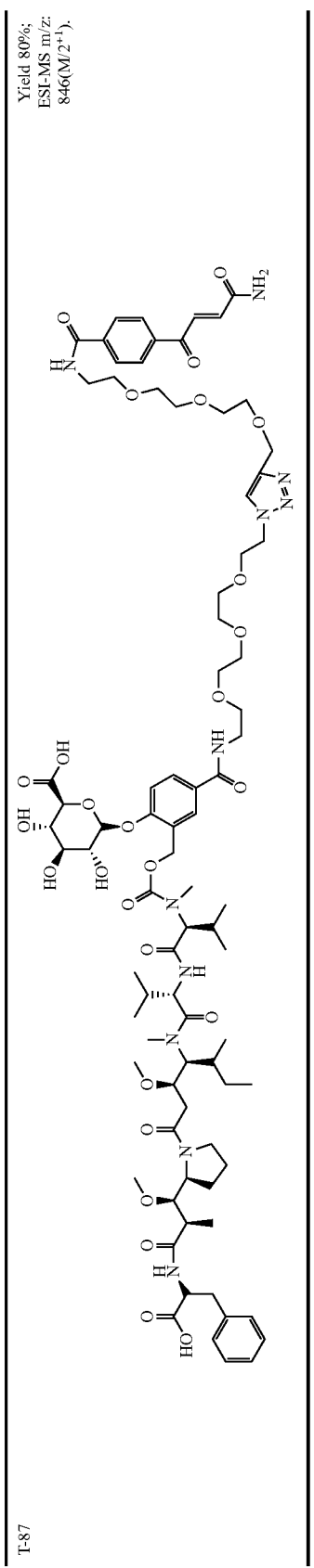 | Yield 80%; ESI-MS m/z: 846(M/2+1). |

Example 4.11.3

Preparation of T-88

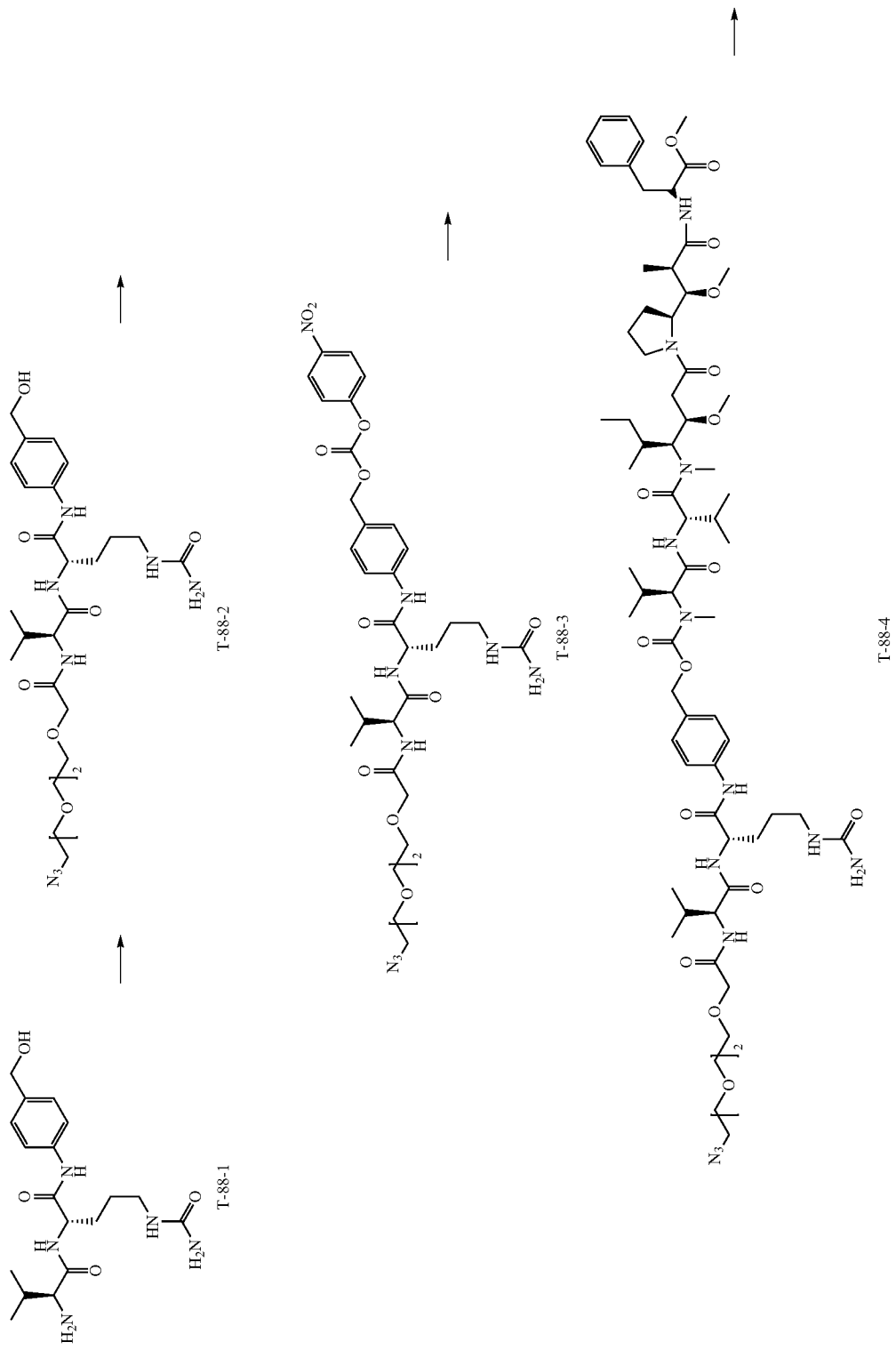

-continued
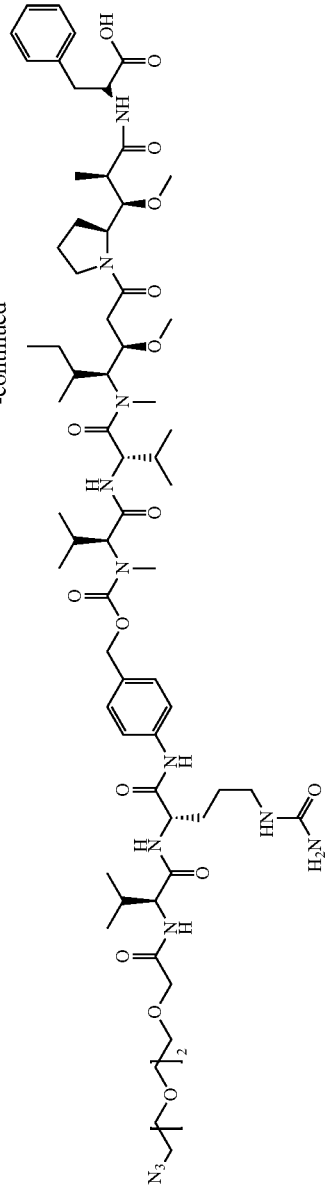
T-88-5
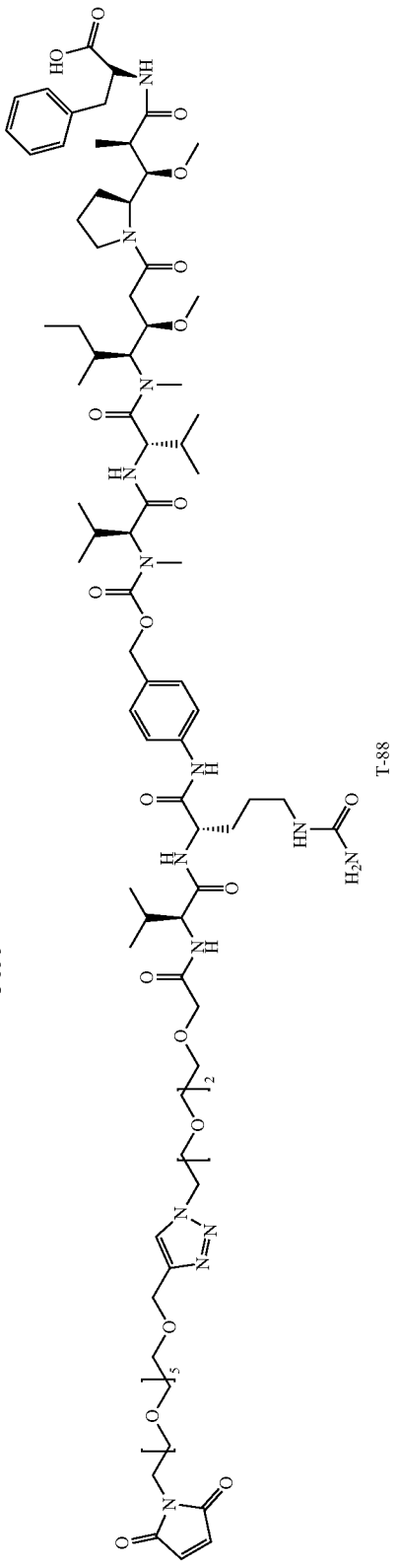
T-88

Compound T-88 was synthesized by a similar synthetic route as described in WO2015/095227 A2, incorporated herein by reference.

Preparation of Compound T-88-2

To a solution of T-88-1 (320 mg, 0.84 mmol) in DMF (5 mL) was added L-2a (280 mg, 0.85 mmol) at 0° C. under $N_2$ atmosphere. The reaction was stirred at room temperature for 1 hour under $N_2$ atmosphere. After the reaction was completed, DMF was removed under reduced pressure. The residue was purified by column chromatography to obtain compound T-88-2 (310 mg, 62%).

ESI-MS m/z: 595 ($M^+$+1).

Preparation of Compound T-88-3

To a solution of T-88-2 (70 mg, 0.12 mmol) in DMF (3 mL) under $N_2$ atmosphere was added Bis(4-nitrophenyl) carbonate (54 mg, 0.18 mmol) and followed by addition of DIPEA (41 µL, 0.24 mmol). The mixture was stirred for 3 hours at room temperature. After the reaction was completed, the mixture was extracted with brine (50 mL) and EA (50 mL). The organic layer was dried over anhydrous $Na_2SO_4$, filtered and concentrated under reduced pressure. The residue was purified by column chromatography to obtain compound T-88-3 (44 mg, 49%).

ESI-MS m/z: 760 ($M^+$+1).

Preparation of Compound T-88-4

To a solution of T-88-3 (40 mg, 0.05 mmol) was dissolved in DMF (1 mL) at room temperature under a nitrogen atmosphere. MMAF-OMe (43 mg, 0.06 mmol) and HOBt (1.4 mg, 0.01 mmol) were added followed by the addition of pyridine (0.33 mL) and DIPEA (10 µL 0.06 mmol). The mixture was stirred for 22 hours at room temperature. After the reaction was completed, the mixture was extracted with EA (100 mL), distilled water (300 mL), brine (100 mL) and 1N hydrochloric acid aqueous solution (20 mL). The organic layer was dried over anhydrous $Na_2SO_4$, filtered and concentrated under reduced pressure. The residue was purified by column chromatography to obtain compound T-88-4 (47 mg, 65%).

ESI-MS m/z: 1367 ($M^+$+1).

Preparation of Compound T-88-5

To a solution of compound T-88-4 (40 mg, 0.03 mmol) in methanol (1 mL) was added $LiOH.H_2O$ (10 mg, 0.23 mmol) dissolved in water (0.5 mL) at 0° C. under $N_2$ atmosphere. The mixture was stirred at 0° C. for 2 hours. After the reaction was completed, the resulting residue was diluted with 2N hydrochloric acid aqueous solution (2 mL) and purified by prep-HPLC to obtain compound T-88-5 (29.5 mg, 75%).

ESI-MS m/z: 1353 ($M^+$+1).

Preparation of Compound T-88

A homogeneous solution of compound T-88-5 (3.0 mg, 2.20 µmol) and Mal-1 (1.85 mg, 4.60 µmol) in DMSO (1.5 mL) and $H_2O$ (0.1 mL) was added at room temperature under a nitrogen atmosphere, and $(BimC_4A)_3$ (5.67 mg, 6.90 µmol), CuBr (3.32 mg, 23.10 µmol) and stirred for 10 minutes. The reaction mixture was purified by Prep HPLC chromatography to give the titled compound T-88 (3.0 mg, 77%).

ESI-MS m/z: 877 ($M/2^{+1}$).

Example 4.11.4

Preparation of T-89

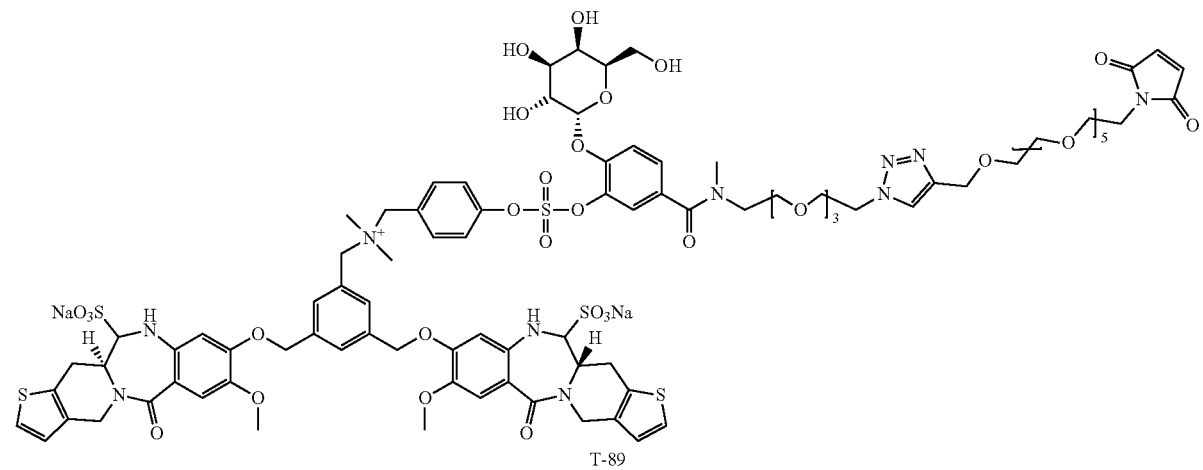

T-89

To a solution of compound T-42 (2.4 mg, 0.0013 mmol) in 0.1% formic acid in $H_2O$ (1.0 mL) at room temperature wat treated with $NaHSO_3$ and stirred for 6 hours. The reaction mixture was freeze dry to obtain compound T-89 (2.7 mg, quant).

Example 4.11.5
Preparation of T-200
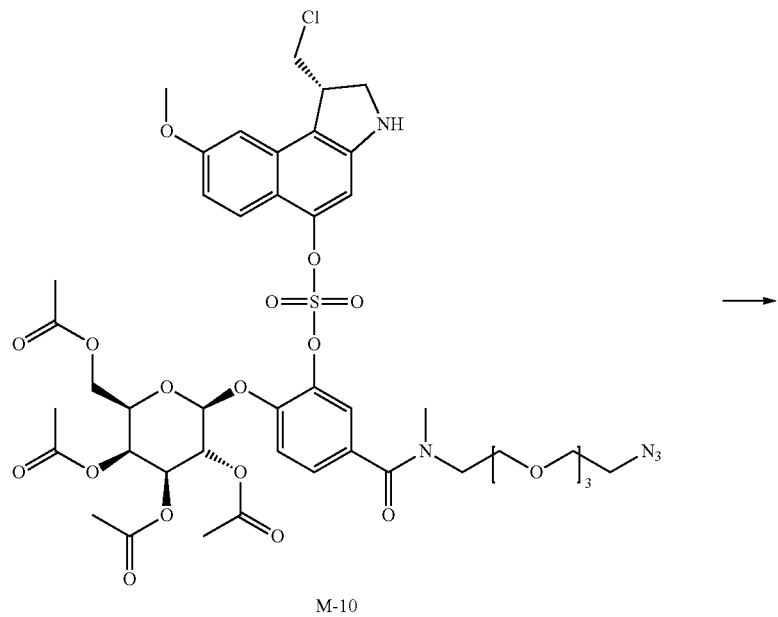
M-10
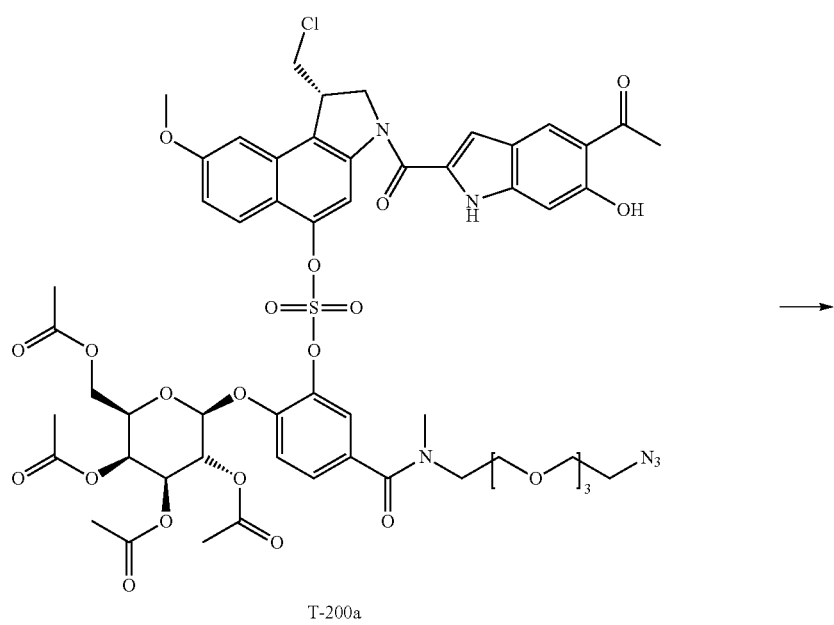
T-200a

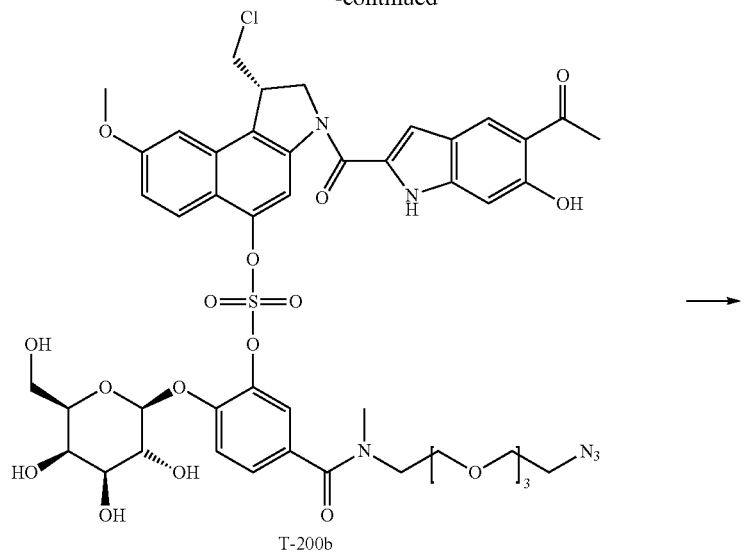

T-200b

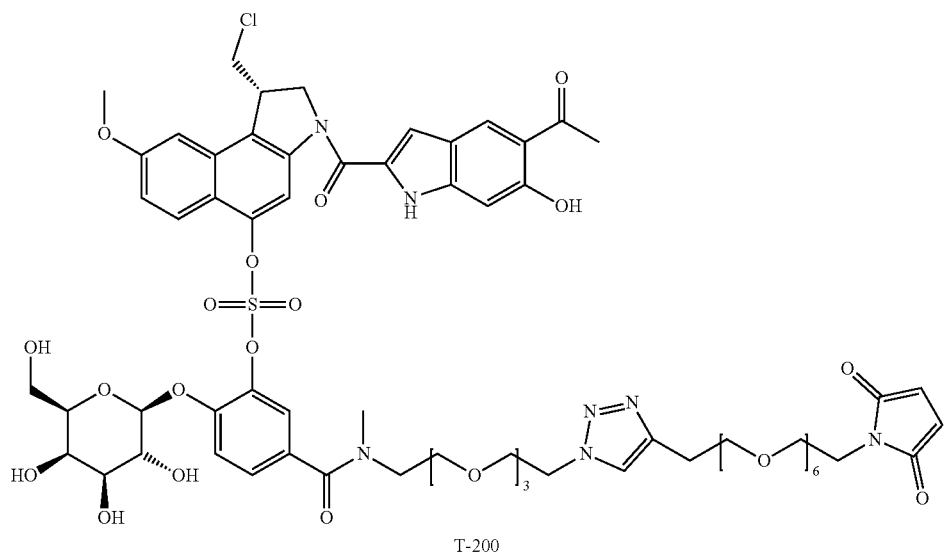

T-200

Preparation of Compound T-200a

To a solution of M-10 (35 mg, 0.033 mmol) in DMF (0.3 mL) was added compound M-17 (8.7 mg, 0.04 mmol) and EDCI (19 mg, 0.099 mmol) at room temperature under $N_2$ atmosphere. After stirring for 1 hour at same temperature, the reaction mixture was purified by prep HPLC to obtain compound T-200a (29 mg, 69%).

ESI-MS m/z: 1225 ($M^+$).

Preparation of Compound T-200b

To a solution of T-200a (4 mg, 0.0032 mmol) in MeOH (0.5 mL) was added potassium carbonate (4.5 mg, 0.032 mmol) at 0° C. under $N_2$ atmosphere. After stirring for 1 hour at same temperature, the reaction mixture was purified by prep HPLC to obtain compound T-200b (2.8 mg, 82%).

ESI-MS m/z: 1057 ($M^+$).

Preparation of Compound T-200

To a solution of compound T-200b (6.3 mg, 0.006 mmol), Mal-1 (4.8 mg, 0.012 mmol) in DMSO (2 mL) at room temperature under $N_2$ nitrogen atmosphere was treated with CuBr (5.1 mg, 0.036 mmol) and stirred for 1 hour. The reaction mixture was purified by Prep-HPLC to obtain compound T-200 (5.3 mg, 61%).

ESI-MS m/z: 1456 ($M^+$).

Table 14 below lists the monomer derivatives that were synthesized via a similar synthetic route as described in Example 4.11.5.

TABLE 14
| Compounds | Structure | Analytical Data |
|---|---|---|
| T-201 | 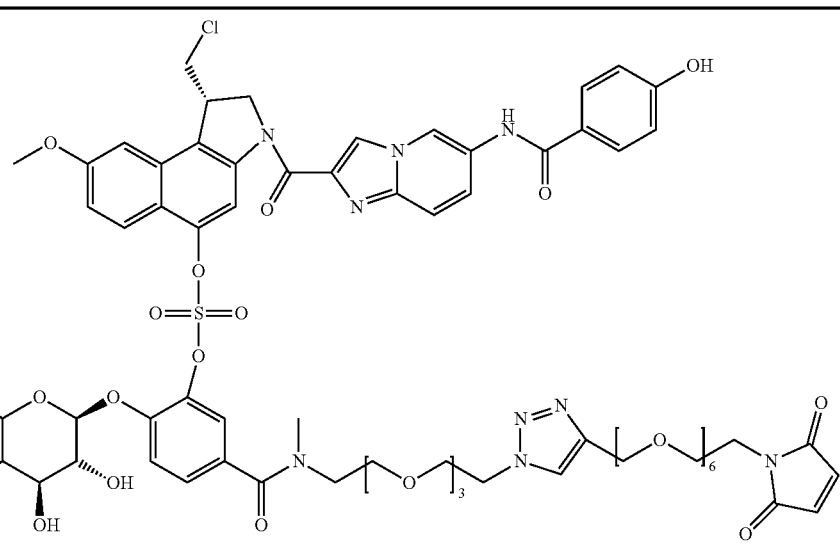 | Yield 64%; ESI-MS m/z: 1535 (M+). |
| T-202 | 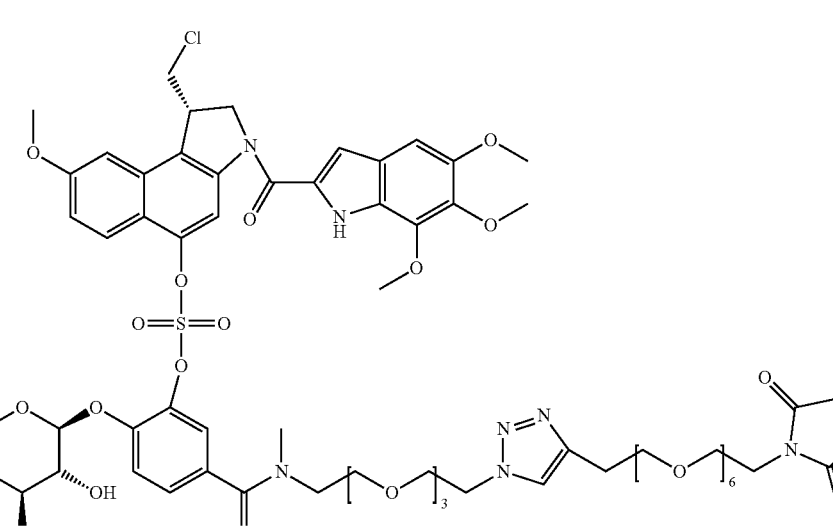 | Yield 43% ESI-MS m/z: 1488 (M+). |
| T-203 | 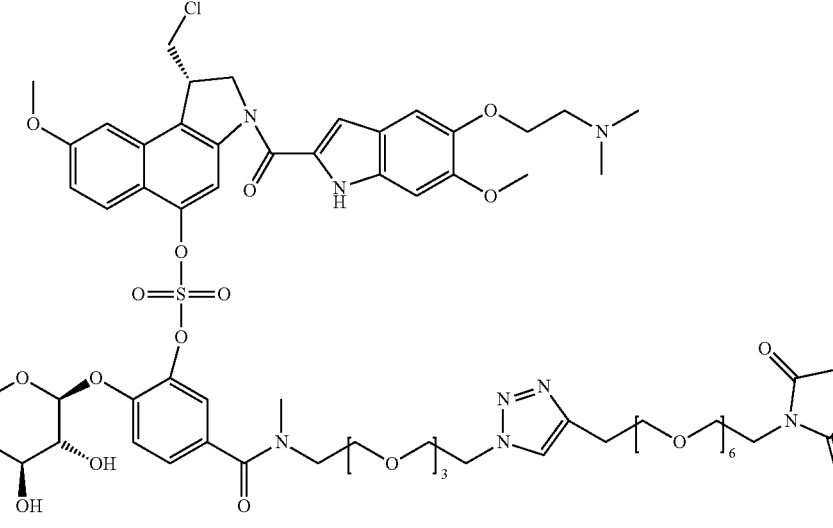 | Yield 64% ESI-MS m/z: 1516 (M+). |

TABLE 14-continued
| Compounds | Structure | Analytical Data |
|---|---|---|
| T-204 | 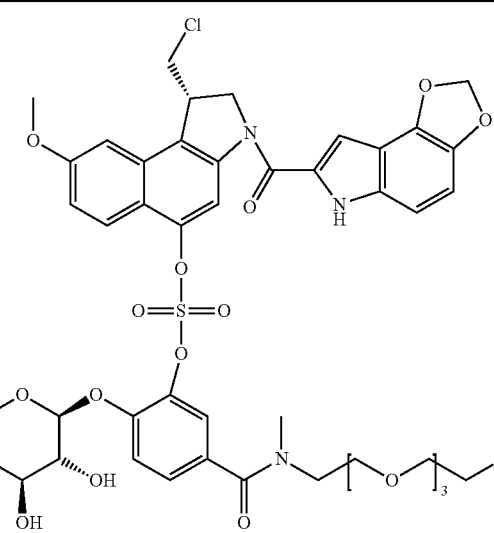 | Yield 32%<br>ESI-MS m/z:<br>1442 (M+). |
| T-205 | 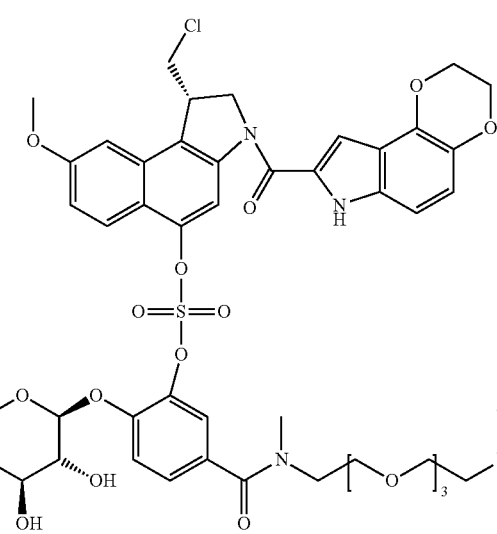 | Yield 32%<br>ESI-MS m/z:<br>1456 (M+). |
| T-206 | 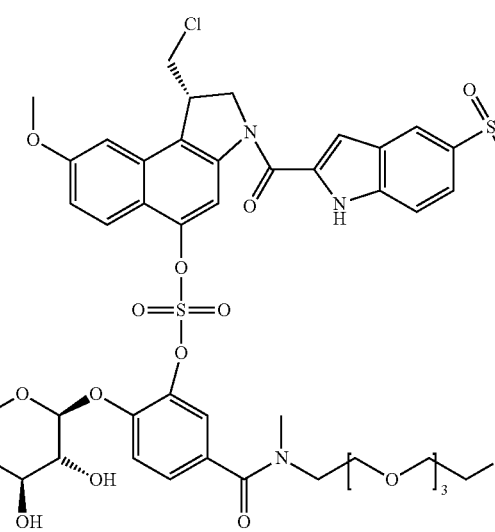 | Yield 70%<br>ESI-MS m/z:<br>1476 (M+). |

TABLE 14-continued
| Compounds | Structure | Analytical Data |
|---|---|---|
| T-207 | 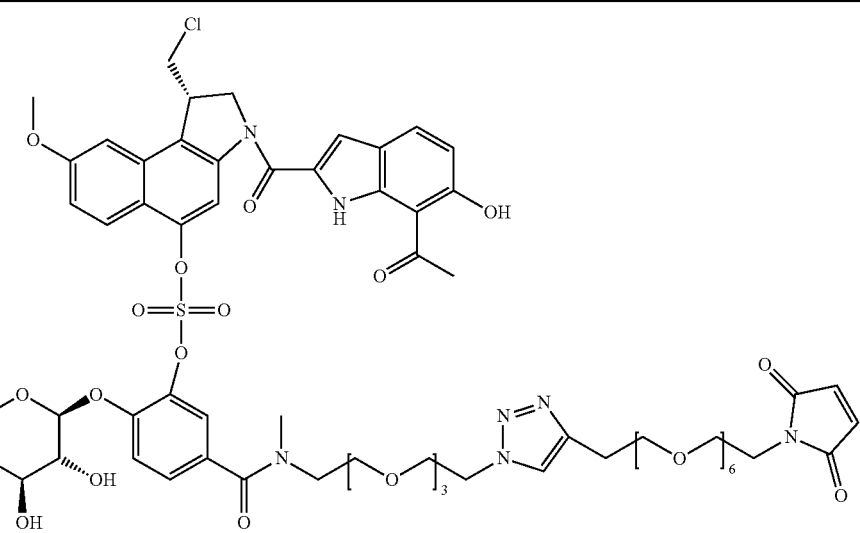 | Yield 66%<br>ESI-MS m/z:<br>456 (M+). |
| T-208 | 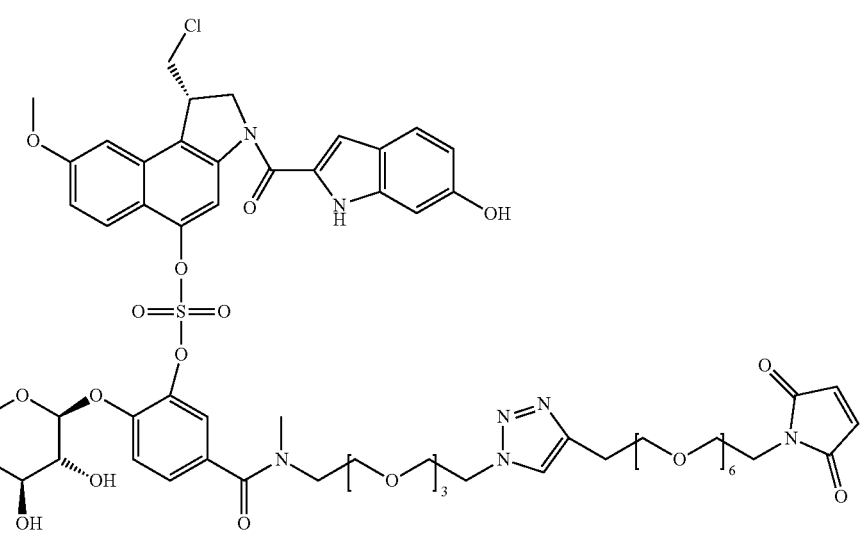 | Yield 84%<br>ESI-MS m/z:<br>1414 (M+). |
| T-209 | 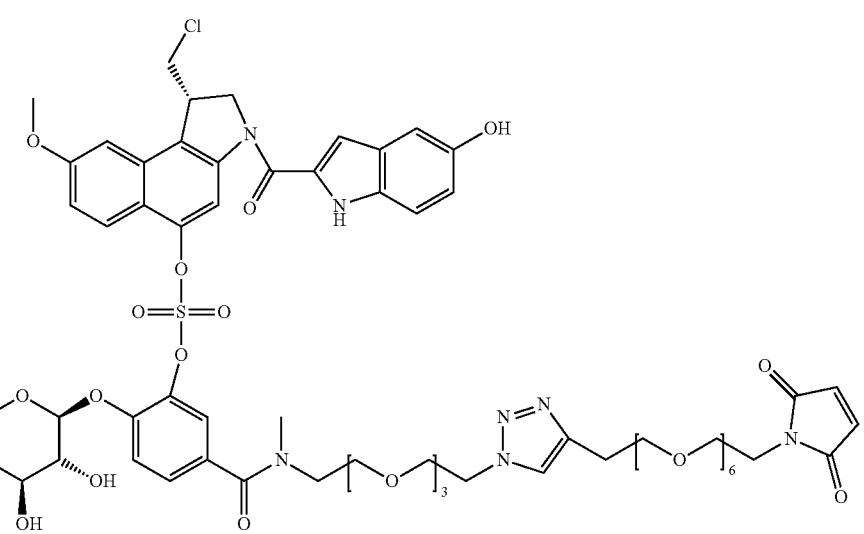 | Yield 68%<br>ESI-MS m/z:<br>1414 (M+). |

TABLE 14-continued
| Compounds | Structure | Analytical Data |
|---|---|---|
| T-210 | 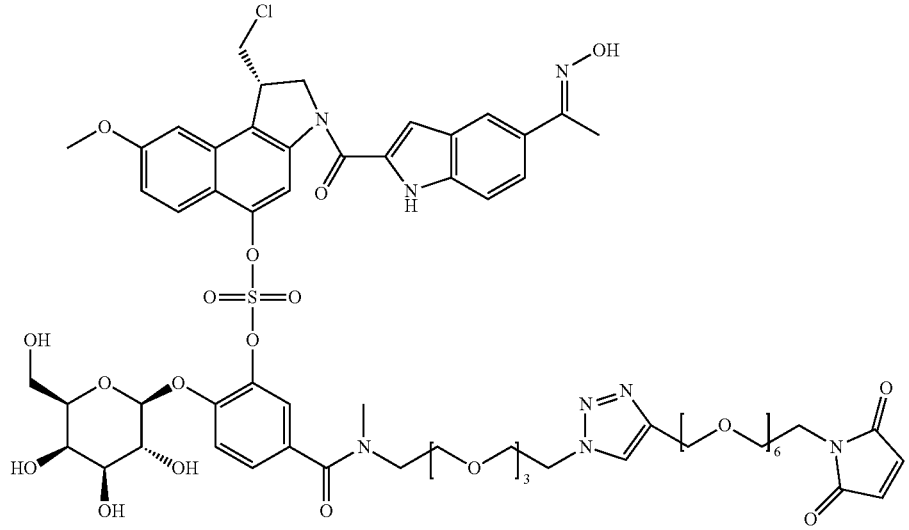 | Yield 80%<br>ESI-MS m/z:<br>1455 (M+) |
| T-211 | 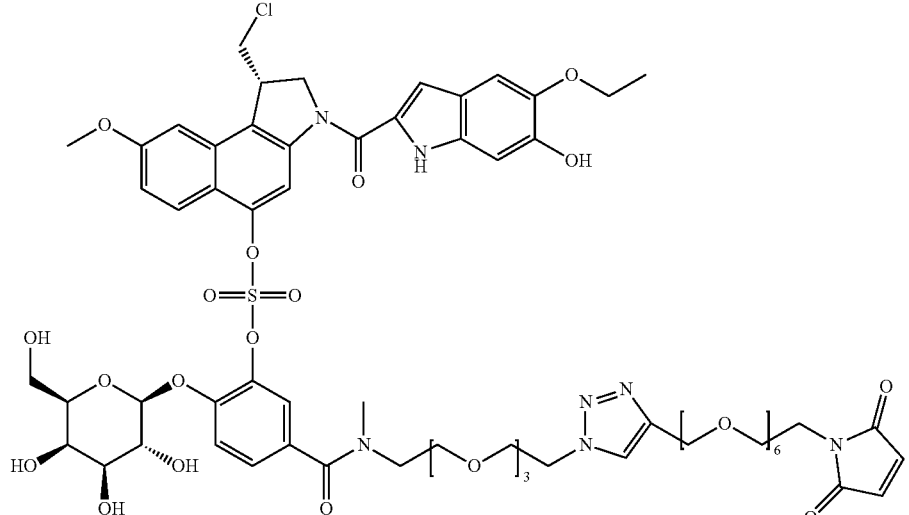 | Yield 60%<br>ESI-MS m/z:<br>1458 (M+). |

Example 4.11.6
Preparation of T-212
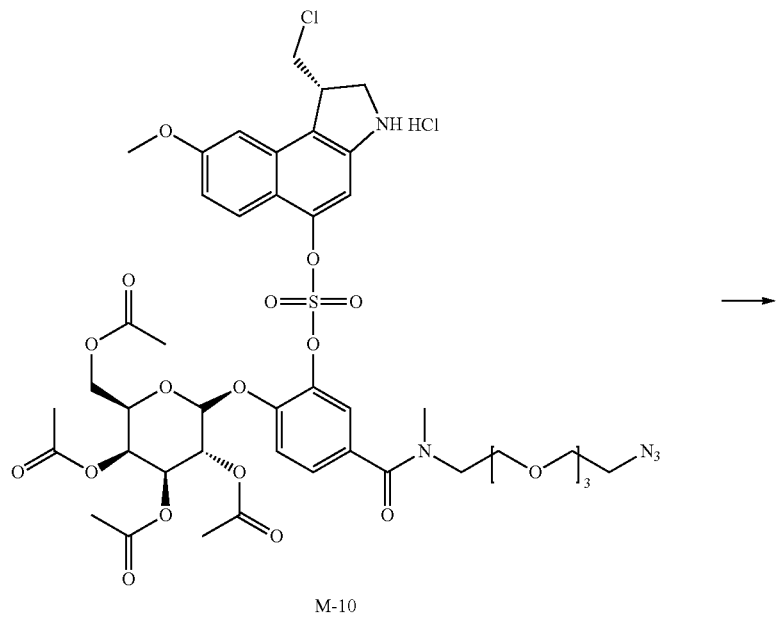
M-10
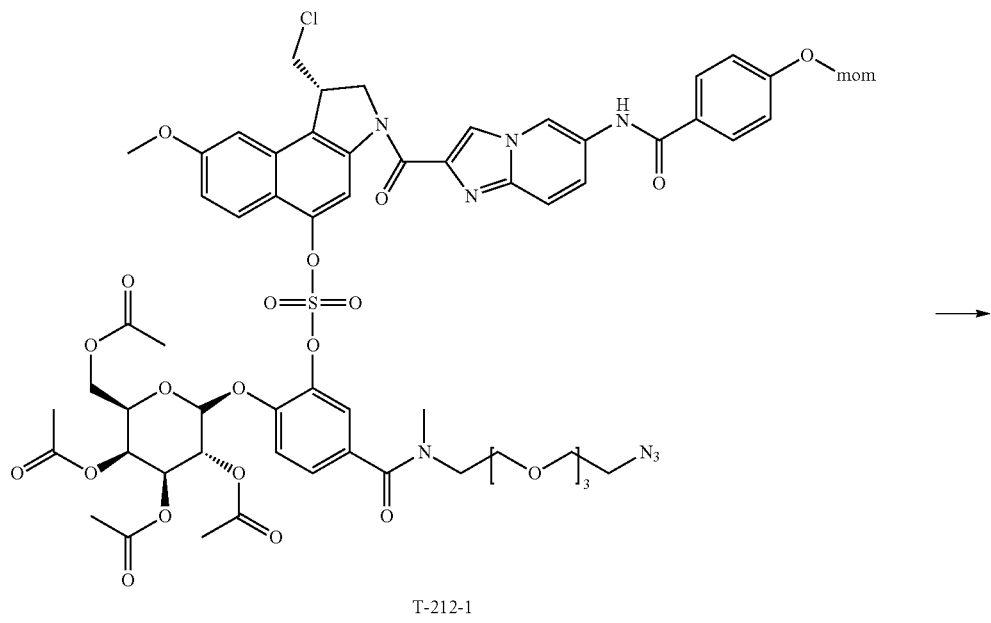
T-212-1

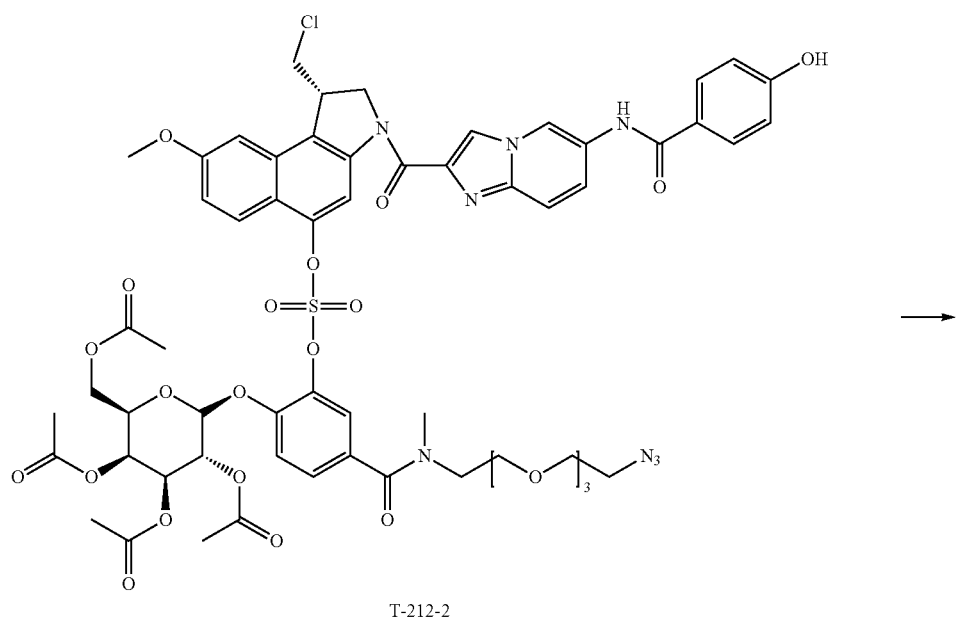
T-212-2
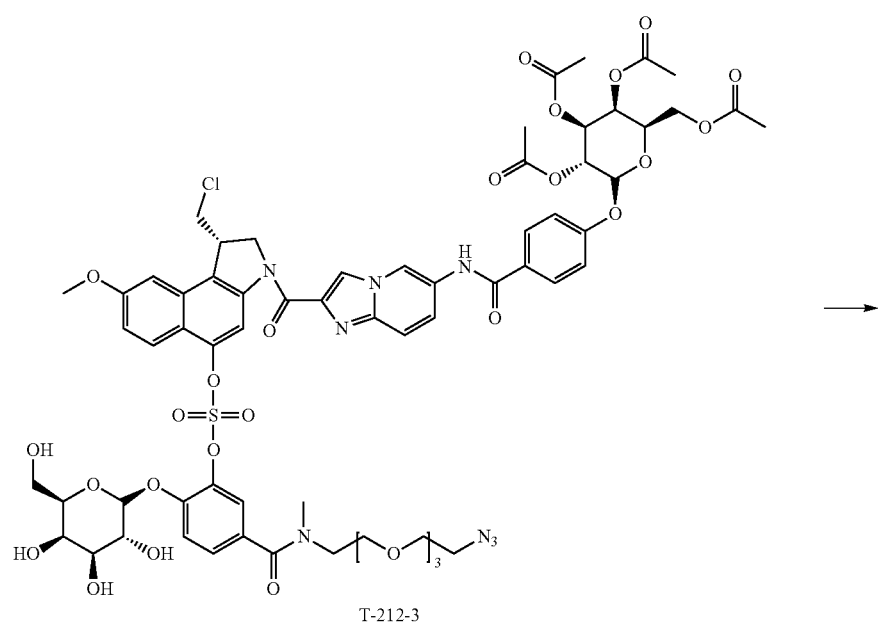
T-212-3

-continued

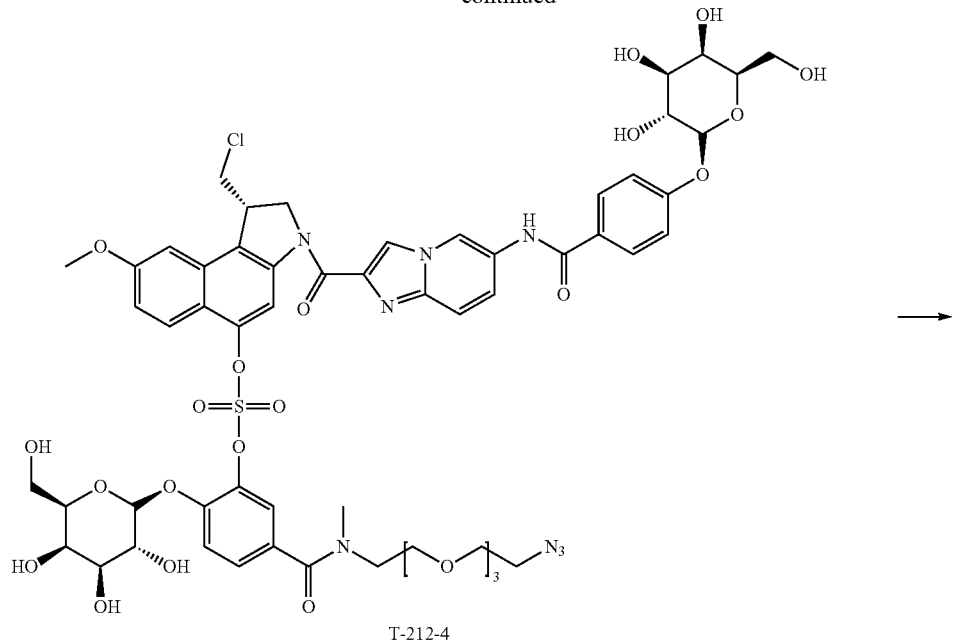
T-212-4

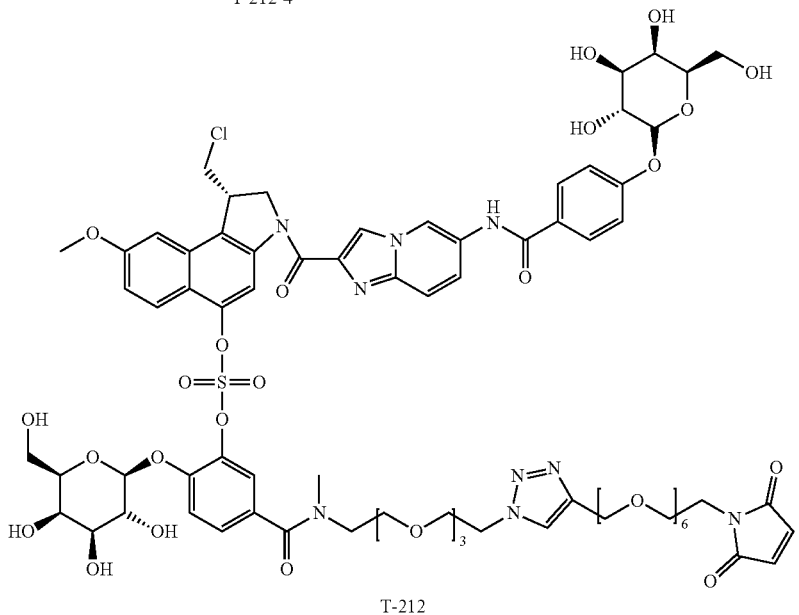
T-212

Preparation of Compound T-212-1

To a solution of M-10 (70 mg, 0.0660 mmol) in DMF (1.2 mL) was added compound M-29 (22.5 mg, 0.0660 mmol) and EDCI (37.9 mg, 0.198 mmol) at room temperature under $N_2$ atmosphere. After stirring for 1 hour at same temperature, the reaction mixture was purified by prep HPLC to obtain compound T-212-1 (48.3 mg, 54%).

ESI-MS m/z: 1347 ($M^+$)

Preparation of Compound T-212-2

To a solution of T-212-1 (48.3 mg, 0.0358 mmol) in DCM (2.0 mL) was added HCl in 4N 1,4-dioxane (0.7 mL) at 0° C. under $N_2$ atmosphere. After stirring for 1 hour at same temperature, the reaction mixture was purified by prep HPLC to obtain compound T-212-2 (43.5 mg, 93%).

ESI-MS m/z: 1303 ($M^+$).

Preparation of Compound T-212-3

To a solution of compound T-212-2 (43.5 mg, 0.0334 mmol) in anhydrous ACN (1.0 mL) was added βGal-Br (192 mg, 0.468 mmol), silver oxide (171 mg, 0.73 mmol) and molecular sieve (90 mg) at room temperature under $N_2$ atmosphere. After stirring at same temperature for overnight, the reaction was filtered through CELITE®, and then concentrated under reduced pressure. The reaction mixture was purified by prep HPLC to obtain compound T-212-3 (33.1 mg, 61%).

ESI-MS m/z: 1635 ($M^+$+1).

Preparation of Compound T-212-4

To a solution of T-212-3 (33.1 mg, 0.0203 mmol) in methanol (2.0 mL) was added potassium carbonate (28.1 mg, 0.203 mmol) at 0° C. under $N_2$ atmosphere. After stirring for 1 hour at same temperature, the reaction mixture was purified by prep HPLC to obtain compound T-212-4 (21.2 mg, 81%).

ESI-MS m/z: 1297 (M+).

Preparation of Compound T-212

To a solution of compound T-212-4 (5.0 mg, 0.00385 mmol), Mal-1 (3.08 mg, 0.00771 mmol) in DMSO (2 mL) at room temperature under $N_2$ nitrogen atmosphere was treated with CuBr (3.3 mg, 0.0231 mmol) and stirred for 1 hour. The reaction mixture was purified by Prep-HPLC to obtain compound T-212 (5.4 mg, 82%).

ESI-MS m/z: 1697 (M+).

Table 15 below lists the monomer derivatives that were synthesized via a similar synthetic route as described in Example 4.11.6.

TABLE 15

| Compounds | Structure | Analytical Data |
|---|---|---|
| T-213 | 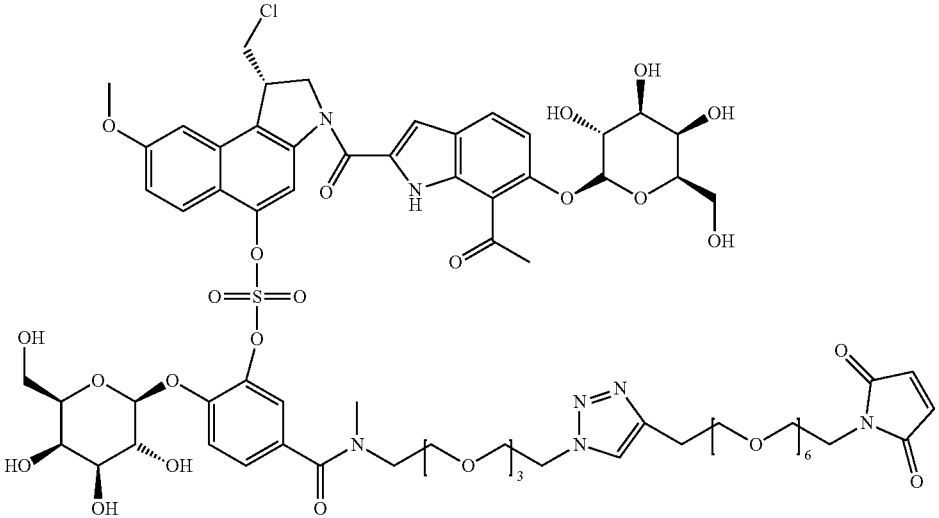 | Yield 67%<br>ESI-MS m/z:<br>1619 (M+). |
| T-214 | 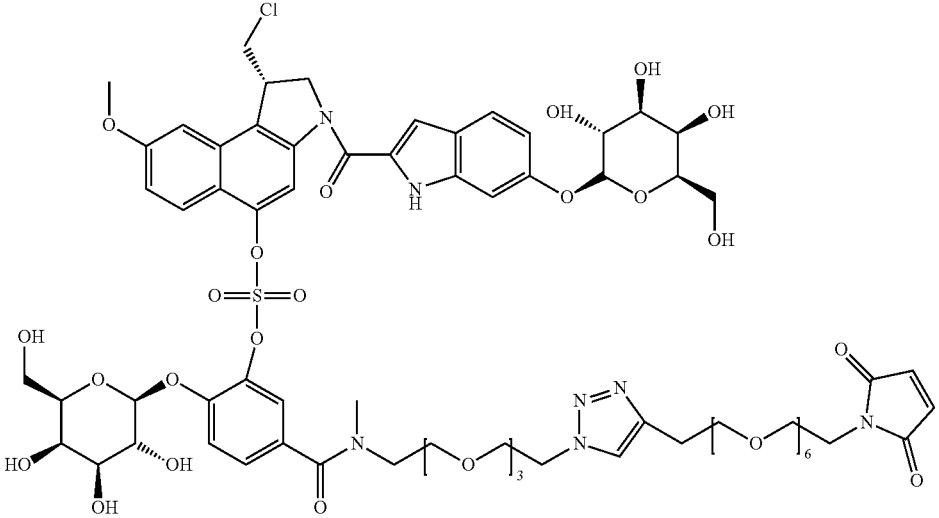 | Yield 83%<br>ESI-MS m/z:<br>1577 (M+). |

TABLE 15-continued

| Compounds | Structure | Analytical Data |
|---|---|---|
| T-215 | 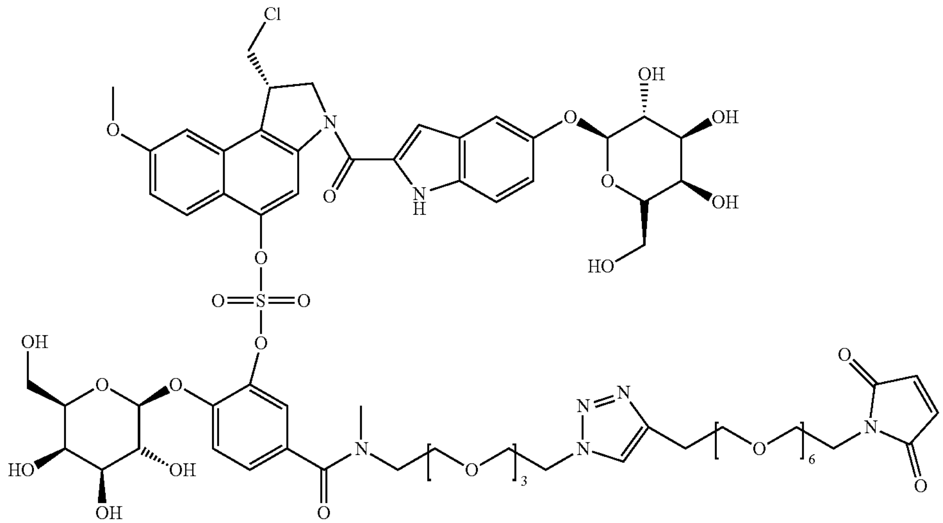 | Yield 84%<br>ESI-MS m/z:<br>1577 (M+). |
| T-216 | 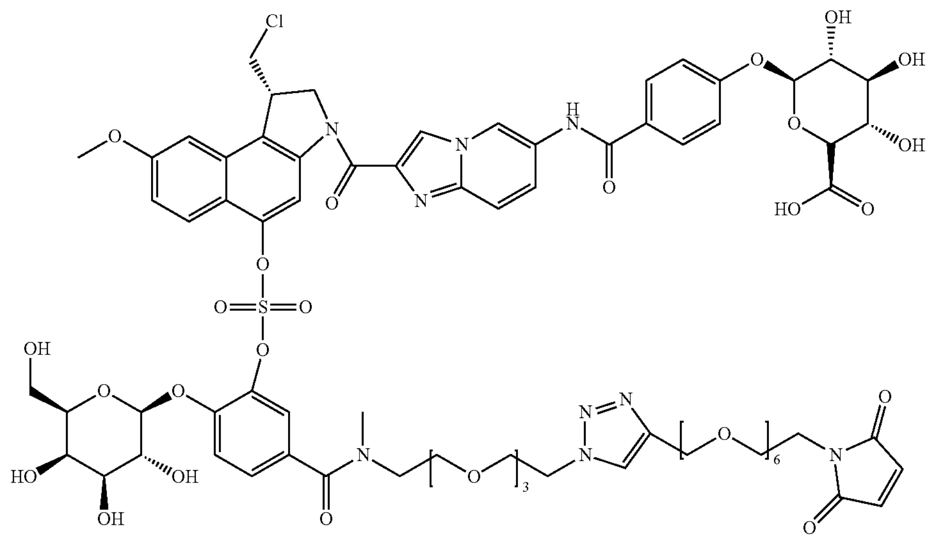 | Yield 97%<br>ESI-MS m/z:<br>1709 (M+). |
| T-217 | 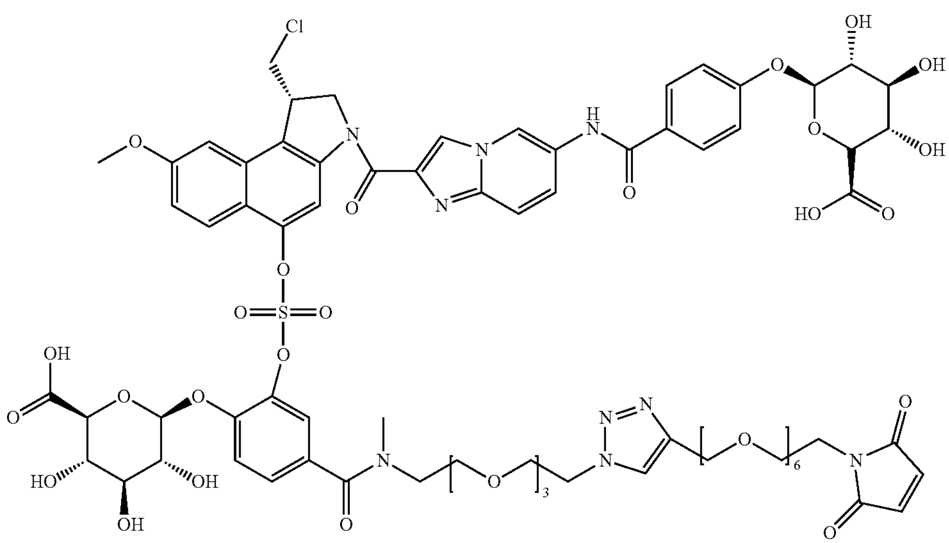 | Yield 30%<br>ESI-MS m/z:<br>1725 (M+). |

TABLE 15-continued

| Compounds | Structure | Analytical Data |
|---|---|---|
| T-218 | 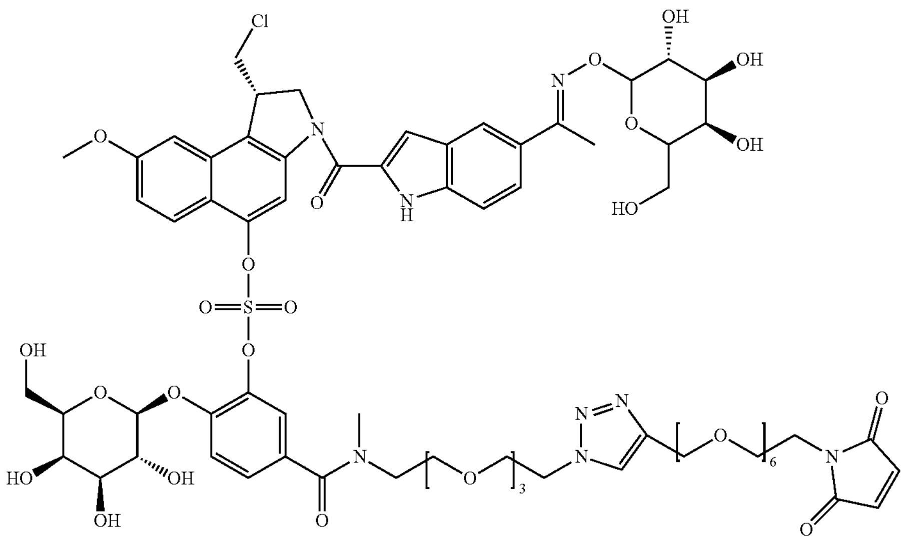 | Yield 45%<br>ESI-MS m/z:<br>1618 (M+). |
| T-219 | 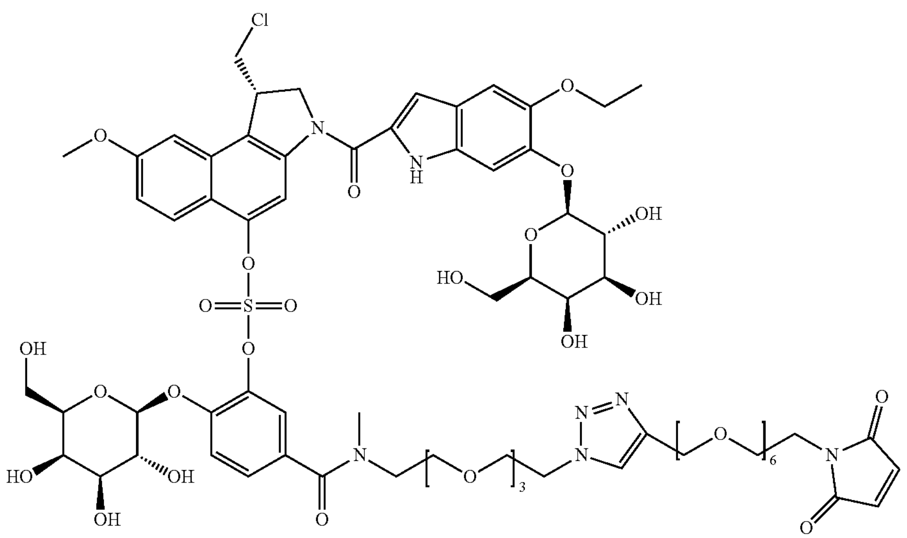 | Yield 60%<br>ESI-MS m/z:<br>1621 (M+). |
| T-220 | 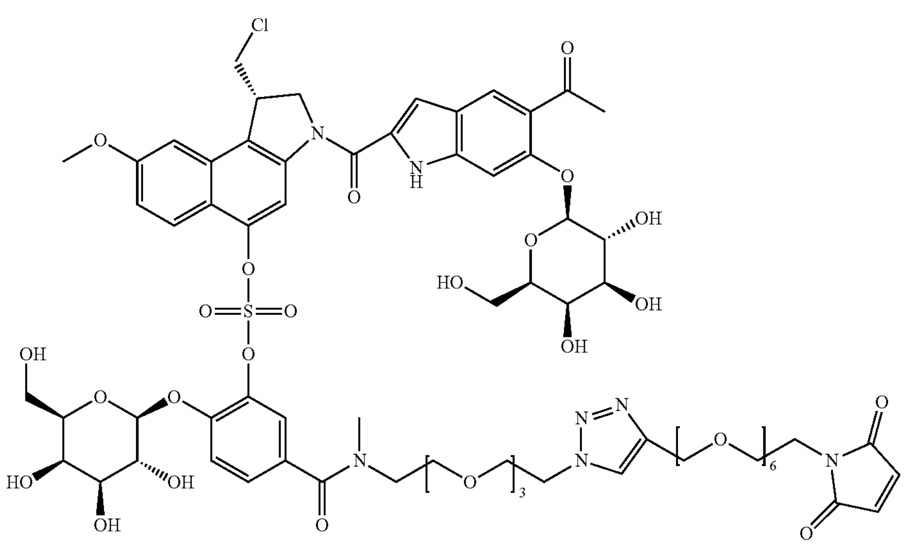 | Yield 62%<br>ESI-MS m/z:<br>1619 (M+). |

Example 5

Reduction/Oxidation of Antibodies for Conjugation

Cysteine engineered monoclonal antibodies were reduced with about a 20-50 fold excess of TCEP (tris(2-carboxyethyl)phosphine hydrochloride or DTT (dithiothreitol) in 4 mM Tris pH 7.3 with 1 mM EDTA for 1 hours at 37° C. The reduced thiomab was diluted and loaded onto a PD-10 column in PBS. The column was eluted with 10 mM PBS pH 7.3. The eluted reduced thiomab was re-established by air oxidation. The thiol/Ab value was checked by determining the reduced antibody concentration form the absorbance at 280 nm of the solution and the thiol concentration by reaction with DTNB (Aldrich, CAS No D8130) and determination of the absorbance at 412 nm.

Example 6

One-Step Conjugation Method for Preparation of ADCs

Example 6.1

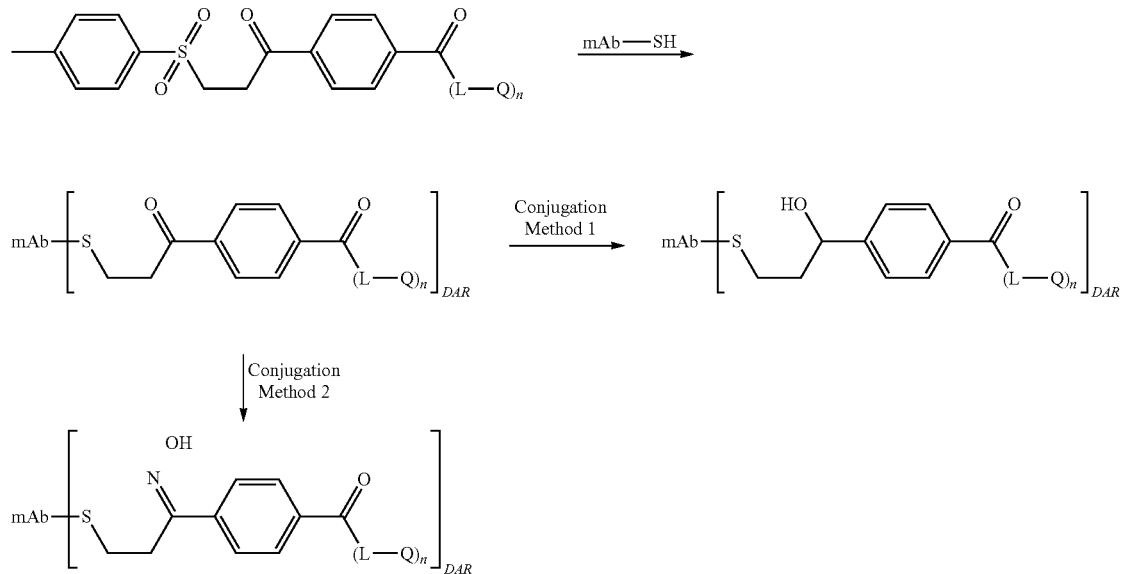

Antibody drug conjugates (ADCs) were synthesized according to the conjugation procedures summarized in Tables 15A-E. Table 15A is shown for conjugation methods 1 and 2; Table 15B shows conjugation methods 2, 3, and 4; Table 15C shows conjugation methods 5 and 6; Table 15D shows conjugation methods 3 and 4; Table 15E shows conjugation methods 3 and 4. In vitro data for ADCs is shown in Tables 15F-J.

Conjugation Method 1: MPS Conjugation Protocol. (NaBH₄)

After the reduction and reoxidation reaction, the antibody was dissolved in PBS. The compound T-47 obtained in Example 4.11.1 (3.80 3.0 mmol, as linker-toxin intermediate) in DMSO was treated with the reduced, reoxidized antibody (45 µL, 0.053 mmol) and agitated gently for 3 hours at room temperature. Sodium borohydride (3.80 µL, 300 mmol) was added to a solution of the reaction mixture and incubated at 37° C. for 1 hour to block a reversible deconjugation reaction. The conjugation mixture was loaded and eluted through PD-10 column to remove excess drug-linker intermediate and other impurities.

Conjugation Method 2: MPS Conjugation Protocol. (NH₂OH)

After the reduction and reoxidation reaction, the antibody was dissolved in PBS. A solution of compound T-11 obtained in Example 4.11.1 (8.86 µL, 3.0 mmol, as linker-toxin intermediate) in DMSO was treated with the reduced, reoxidized antibody (70 µL, 0.053 mmol) and agitated gently for 3 hours at room temperature. Hydroxylamine (8.86 µL, 1,500 mmol) was added to a solution of the reaction mixture and incubated at 37° C. for 8 hours to block a reversible deconjugation reaction. The conjugation mixture was loaded and eluted through PD-10 column to remove excess drug-linker intermediate and other impurities.

Example 6.2

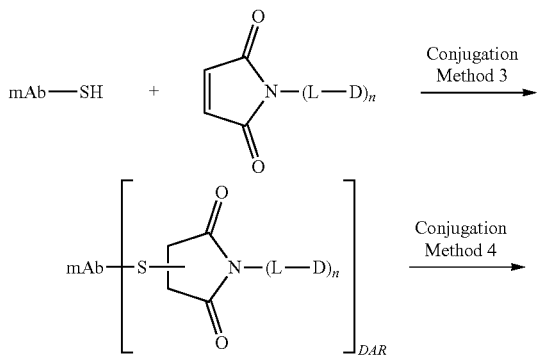

-continued

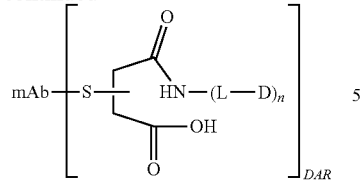

Conjugation Method 3: Maleimide Conjugation Protocol.

After the reduction and reoxidation reaction, the antibody was dissolved in PBS. A solution of compound T-48 obtained in Example 4.11.1 (5.04 μL, 3.0 mmol, as linker-toxin intermediate) in DMSO was treated with the reduced, reoxidized antibody (36 μL, 0.12 mmol) and agitated gently for 1 hours at 40° C. The conjugation mixture was loaded and eluted through PD-10 column to remove excess drug-linker intermediate and other impurities. DAR (drug to antibody ratio) of conjugated antibody was analyzed by HIC.

Conjugation Method 4: Maleimide Conjugation Protocol. (Hydrolysis)

After the maleimide conjugation, the antibody drug conjugate was incubated in borate buffer (pH9.2) for 16 hours at 37° C. to hydrolyze the maleimide ring. And the borate buffer was changed with PBS (pH7.3) through a viva-spin column (GE Healthcare).

Example 7

Two-Step Conjugation Method for Preparation of ADCs

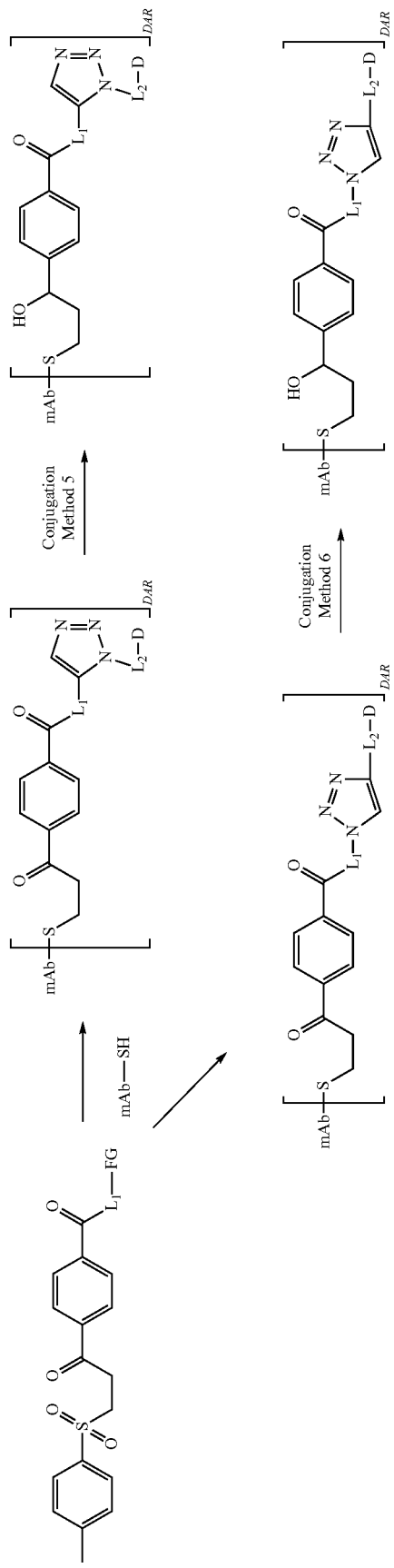

Conjugation Method 5: MPS-N$_3$+BCN-Drug. (NaBH$_4$)

After the reduction and reoxidation reaction, the compound MPS-D1-11 obtained in Example 2 (Table 2) used to perform 1$^{st}$ step conjugation reaction with thiol groups of engineered cysteine of antibody. the antibody in PBS was treated with each compound (6.62 uL, 3.0 mmol) in DMSO. After 3 hours, sodium borohydride (6.62 ul, 300 mmol) was added to the conjugated solution to block a reversible de-conjugation reaction at RT for 1 hour. And 1$^{st}$ conjugated antibodies were purified by PD-10 column. For 2$^{nd}$ conjugation, T-Int-102 (13.24 uL, 3.0 mmol) obtained in Example 4.10.2 with a functional group such as N$_3$ to be promoted cycloaddition in the absence of a Cu(I) catalyst was subjected to T-Int-102-D1-11 AB2.1 conjugated antibody (7.4 uL, 0.117 mmol) and incubated at 37° C. After approximately 24 hours, antibody drug conjugate was purified by PD-10 column and concentrated by centrifugal ultrafiltration. DAR (drug to antibody ratio) of conjugated antibody was analyzed by HIC.

Conjugation Method 6: MPS-BCN+N$_3$-Drug. (NaBH$_4$)

After the reduction and reoxidation reaction, the compound MPS-D1-10 obtained in Example1.9 used to perform 1$^{st}$ step conjugation reaction with thiol groups of engineered cysteine of antibody. the antibody in PBS was treated with each compound (6.62 uL, 3.0 mmol) in DMSO. After 3 hours, sodium borohydride (6.62 ul, 300 mmol) was added to the conjugated solution to block a reversible de-conjugation reaction at RT for 1 hour. And 1$^{st}$ conjugated antibodies were purified by PD-10 column. For 2$^{nd}$ conjugation, Q-7 (13.24 uL, 3.0 mmol) obtained in Example 4.6 with a functional group such as BCN to be promoted cycloaddition in the absence of a Cu(I) catalyst was subjected to Q-7 AB2.1 conjugated antibody (7.4 uL, 0.117 mmol) and incubated at 37° C. After approximately 24 hours, antibody drug conjugate was purified by PD-10 column and concentrated by centrifugal ultrafiltration. DAR (drug to antibody ratio) of conjugated antibody was analyzed by HIC.

TABLE 15A

| ADC | Antibody | Stabilization | Conjugation handle (PEG) | (PEG) Linker | Warhead |
|---|---|---|---|---|---|
| T-11 AB2.1 | SA2107 A121C | NH$_2$OH | MPS (12) | (3) bGal-OHPAS | Q-dTBD |
| T-1 AB2.1 | SA2107 A121C | NH$_2$OH | MPS (4) | (3) bGal-OHPAS | dImBD |
| T-47 AB2.1 | SA2107 A121C | NaBH$_4$ | MPS (0) | (3) bGal-OHPAS | a-amanitin |
| T-6 AB2.1 | SA2107 A121C | NH$_2$OH | MPS (4) | (3) bGal-OHPAS | dPBD |
| T-55 AB2.1 | SA2107 A121C | NaBH$_4$ | MPS (0) | (3) bGal-OHPAS | MMAF |
| T-70 AB2.1 | SA2107 A121C | NaBH$_4$ | MPS (0) | (3) bGal-OHPAS | CBI-indole |
| T-71 AB2.1 | SA2107 A121C | NaBH$_4$ | MPS (4) | (3) bGal-OHPAS | dCBI |
| T-82 AB2.1 | SA2107 A121C | NaBH$_4$ | MPS (4) | (3) bGal-OHPAS | Phenpanstatin |
| T-2 AB2.1 | SA2107 A121C | NH$_2$OH | MPS (12) | (3) bGal-OHPAS | Q-dThBD |
| T-4 AB2.1 | SA2107 A121C | NH$_2$OH | MPS (12) | (3) bGal-OHPAS | Q-dFuBD |
| T-30 AB2.1 | SA2107 A121C | NH$_2$OH | MPS (4) | (3) bGal-OHPAS | ImBD-TBD |
| T-32 AB2.1 | SA2107 A121C | NH$_2$OH | mpMPS (4) | (3) bGal-OHPAS | ImBD-TBD |
| T-33 AB2.1 | SA2107 A121C | NH$_2$OH | mpMPS (12) | (3) bGal-OHPAS | Q-dTBD |
| T-34 AB2.1 | SA2107 A121C | NH$_2$OH | mpMPS (4) | (3) bGal-OHPAS | dImBD |
| T-72 AB2.1 | SA2107 A121C | NH$_2$OH | MPS (0) | (3) bGal-OHPAS | Q-PNU |
| T-21 AB2.1 | SA2107 A121C | NH$_2$OH | mMPS (4) | (3) bGal-OHPAS | dPBD |
| T-22 AB2.1 | SA2107 A121C | NH$_2$OH | MPS (4) | (3) bGal-OHPAS | Q-dPBD |
| T-28 AB2.1 | SA2107 A121C | NH$_2$OH | mMPS (4) | (3) bGal-OHPAS | Q-dPBD |
| T-20 AB2.1 | SA2107 A121C | NH$_2$OH | mMPS (12) | (3) bGal-OHPAS | Q-dTBD |
| T-23 AB2.1 | SA2107 A121C | NH$_2$OH | mMPS (12) | (3) bGal-OHPAS | Q-dThBD |
| T-25 AB2.1 | SA2107 A121C | NH$_2$OH | MPS (12) | (3) bGal-OHPAS | dThBD |
| T-24 AB2.1 | SA2107 A121C | NH$_2$OH | mMPS (12) | (3) bGal-OHPAS | dThBD |

TABLE 15B

| ADC | Antibody | Stabilization | Conjugation handle (PEG) | (PEG) Linker | Warhead |
|---|---|---|---|---|---|
| T-8 AB2.1 | SA2107 A121C | NH$_2$OH | MPS (12) | (11) bGal-OHPAS | dTBD |
| T-26 AB2.1 | SA2107 A121C | NH$_2$OH | mpMPS (12) | (3) bGal-OHPAS | dTBD |
| T-57 AB2.1 | SA2107 A121C | NaBH$_4$ | mMPS (4) | (3) bGal-OHPAS | Q-Auristatin F |
| T-13 AB2.1 | SA2107 A121C | NH$_2$OH | mMPS (12) | (3) bGal-OHPAS | adTBD |
| T-27 AB2.1 | SA2107 A121C | NH$_2$OH | mMPS (12) | (3) bGal-OHPAS | Q-dThBD, NaSO$_3$ |
| T-19 AB2.1 | SA2107 A121C | NH$_2$OH | mMPS (12) | (3) bGal-OHPAS | dTBD, alky amine |
| T-73 AB2.1 | SA2107 A121C | NH$_2$OH | mMPS (5) | (3) bGal-OHPAS | Q-PNU |
| T-31 AB2.1 | SA2107 A121C | NH$_2$OH | mMPS (12) | (3) bGal-OHPAS | ImBD-TBD |
| T-15 AB2.1 | SA2107 A121C | NH$_2$OH | mMPS (12) | (3) bGal-OHPAS | adTBD, DMBA |
| T-17 AB2.1 | SA2107 A121C | NH$_2$OH | mMPS (12), sulfinic acid | (3) bGal-OHPAS | adTBD, DMBA |
| T-38 AB2.1 | SA2107 A121C | — | Mal (4) | (3) bGal-OHPAS | Q-dThBD |
| T-48 AB2.1 | SA2107 A121C | — | Mal (4) | (3) bGal-OHPAS | Q-a-amanitin |
| T-51 AB2.1 | SA2107 A121C | — | Mal (4) | (3) bGal-OHPAS | a-amanitin |
| T-52 AB2.1 | SA2107 A121C | — | Mal (4) | (3) bGal-OHPAS | b-amanitin |
| T-77 AB2.1 | SA2107 A121C | — | Mal (4) | (3) bGal-OHPAS | SN38/CA4 |
| T-78 AB2.1 | SA2107 A121C | — | Mal (4) | (3) bGal-OHPAS | CA4/CA4 |
| T-59 AB2.1 | SA2107 A121C | — | Mal (0) | (3) bGal-OHPAS | MMAF |
| T-43 AB2.1 | SA2107 A121C | — | Mal (6) | (3) bGal-OHPAS | Q-dTBD |
| T-45 AB2.1 | SA2107 A121C | — | Mal (6) | (3) bGal-OHPAS | Q-dThBD_SO$_3$ |
| T-45RO AB2.1 | SA2107 A121C | — | Mal (6) | (3) bGal-OHPAS | Q-dThBD_SO$_3$ |
| T-60 AB2.1 | SA2107 A121C | — | Mal (6) | (3) bGal-OHPAS | MMAF |
| T-88 AB2.1 | SA2107 A121C | — | Mal (6) | (3) VC | MMAF |
| T-6 AB2.1 | SA2566 A121C | NH$_2$OH | MPS (4) | (3) bGal-OHPAS | dPBD |
| T-21 AB2.1 | SA2566 A121C | NH$_2$OH | mMPS (4) | (3) bGal-OHPAS | dPBD |

TABLE 15B-continued

| ADC | Antibody | Stabilization | Conjugation handle (PEG) | (PEG) Linker | Warhead |
|---|---|---|---|---|---|
| T-20 AB2.1 | SA2566 A121C | NH$_2$OH | mMPS (12) | (3) bGal-OHPAS | Q-dTBD |
| T-55 AB2.1 | m8524 A121C | NaBH$_4$ | MPS (0) | (3) bGal-OHPAS | MMAF |
| T-55 AB2.1 | m8524 S442C | NaBH$_4$ | MPS (0) | (3) bGal-OHPAS | MMAF |
| T-6 AB2.1 | m8524 S442C | NH$_2$OH | MPS (4) | (3) bGal-OHPAS | dPBD |
| T-21 AB2.1 | m8524 S442C | NH$_2$OH | mMPS (4) | (3) bGal-OHPAS | dPBD |

TABLE 15C

| ADC | Antibody | Conjugation handle (PEG) | (PEG) Linker | Warhead |
|---|---|---|---|---|
| T-Int-102-D3-1 AB2.1 | SA2107 A121C | mpMPS-N$_3$ (5) | (3) BCN-bGal-OHPAS | Q-dTBD |
| Q-7 AB2.1 | SA2107 A121C | MPS-BCN (5) | (3) N$_3$-bGal-OHPAS | Q-PNU |
| T-Int-1 AB2.1 | SA2107 A121C | MPS-BCN (5) | (3) N$_3$-bGal-OHPAS | dPBD |
|  | SA2107 A121C | mpMPS-N$_3$ (5) | (3) BCN-bGal-OHPAS | Q-dThBD |
| T-Int-102-D1-17AB2.1 | SA2107 A121C | MPS-N$_3$ (5) | (3) BCN-bGal-OHPAS | Q-dTBD |
| T-Int-102-D1-11 AB2.1 | SA2107 A121C | MPS-N$_3$ (11) | (3) BCN-bGal-OHPAS | Q-dTBD |
| T-Int-102-D1-5 AB2.1 | SA2107 A121C | MPS-N$_3$ (2) | (3) BCN-bGal-OHPAS | Q-dTBD |
| T-Int-113 AB2.1 | SA2107 A121C | MPS-N$_3$ (2) | (3) BCN-SO$_3$H-bGal-OHPAS | Q-dTBD |
| T-Int-112 AB2.1 | SA2107 A121C | MPS-N$_3$ (2) | (3) BCN-bGal-OHPAS | Q-dThBD |

TABLE 15D

| ADC | Antibody | Conjugation handle (PEG) | (PEG) Linker | Warhead |
|---|---|---|---|---|
| T-101 AB2.1 | SA2107 A121C | maleimide (6) | (3) bGal-OHPAS | Q dThBD_bGal |
| T-102 AB2.1 | SA2107 A121C | maleimide (6) | (3) bGal-OHPAS | Q dThBD_bG |
| T-103 AB2.1 | SA2107 A121C | maleimide (6) | (3) bGal-OHPAS | NO$_2$_bGal dThBD_bGal |
| T-104 AB2.1 | SA2107 A121C | maleimide (6) | (3) bGal-OHPAS | dThBD_bGal |
| T-105 AB2.1 | SA2107 A121C | maleimide (11) | bGal-OHPAS | Q dThBD_bGal |
| T-106 AB2.1 | SA2107 A121C | maleimide (6) | (3) bGal-OHPAS | Q dThBD_bG |
| T-107 AB2.1 | SA2107 A121C | maleimide (6) | (3) bGal-OHPAS | Q dTBD_bGal |
| T-108 AB2.1 | SA2107 A121C | maleimide (6) | (3) bGal-OHPAS | Q PBD_bGal |
| T-109 AB2.1 | SA2107 A121C | maleimide (6) | (3) bGal-OHPAS | Q ThBD-TBD_bGal |
| T-110 AB2.1 | SA2107 A121C | maleimide (11) | bG-OHPAS | Q dThBD_bG |
| T-111 AB2.1 | SA2107 A121C | maleimide (6) | (3) bGal-OHPAS | Q dThBD_bG |

TABLE 15E

| ADC | Antibody | Conjugation handle (PEG) | (PEG) Linker | Warhead |
|---|---|---|---|---|
| T-201 AB2.1 | SA2107 A121C | maleimide (6) | (3) bGal-OHPAS | seco DUBA |
| T-203 AB2.1 | SA2107 A121C | maleimide (6) | (3) bGal-OHPAS | seco MCBI DEI |
| T-206 AB2.1 | SA2107 A121C | maleimide (6) | (3) bGal-OHPAS | seco MCBI MSI |
| T-207 AB2.1 | SA2107 A121C | maleimide (6) | (3) bGal-OHPAS | seco MCBI 6H7AI |
| T-208 AB2.1 | SA2107 A121C | maleimide (6) | (3) bGal-OHPAS | seco MCBI 6HI |
| T-209 AB2.1 | SA2107 A121C | maleimide (6) | (3) bGal-OHPAS | seco MCBI 5HI |
| T-210 AB2.1 | SA2107 A121C | maleimide (6) | (3) bGal-OHPAS | seco MCBI 6H7AI-bGal |
| T-211 AB2.1 | SA2107 A121C | maleimide (6) | (3) bGal-OHPAS | seco MCBI 6HI-bGal |
| T-212 AB2.1 | SA2107 A121C | maleimide (6) | (3) bGal-OHPAS | seco MCBI 5HI-bGal |
| T-213 AB2.1 | SA2107 A121C | maleimide (6) | (3) bGal-OHPAS | seco MCBI-bGal |
| T-214 AB2.1 | SA2107 A121C | maleimide (6) | (3) bGal-OHPAS | seco DUBA-bG |
| T-215 AB2.1 | SA2107 A121C | maleimide (6) | (3) bG-OHPAS | seco DUBA-bG |

TABLE 15F

| ADC | Antibody | Warhead | mDAR | HEK293/B7-H3 | JIMT1 (6.7 × 10$^5$) | Calu-6 (4.6 × 10$^5$) | H460 (3.0 × 10$^5$) | A549 (2.3 × 10$^5$) | HCT-116 (2.1 × 10$^5$) | NCI-N87 (1.5 × 10$^5$) | DU-145 (8.5 × 10$^4$) | NCI-H23 (8.2 × 10$^4$) |
|---|---|---|---|---|---|---|---|---|---|---|---|---|
| T-11 AB2.1 | SA2107 A121C | Q-dTBD | 0.62 | 0.002 | 0.063 | — | 0.268 | — | 0.052 | 0.222 | — | — |
| T-1 AB2.1 | SA2107 A121C | dImBD | 0.78 | 0.055 | >100 | — | — | — | >100 | >100 | — | — |
| T-47 AB2.1 | SA2107 A121C | a-amanitin | 2.0 | 0.059 | 0.1-1.0 | — | — | — | >100 | >100 | — | — |
| T-6 AB2.1 | SA2107 A121C | dPBD | 1.94 | 0.011 | 0.079 | — | — | — | 0.557 | 4.641 | — | — |
| T-55 AB2.1 | SA2107 A121C | MMAF | 1.62 | — | — | — | — | — | — | — | — | — |
| T-70 AB2.1 | SA2107 A121C | CBI-indole | 0.88 | — | — | — | — | — | — | — | — | — |
| T-71 AB2.1 | SA2107 A121C | dCBI | 2.0 | — | 0.019 | 0.024 | 0.014 | 0.176 | — | — | 0.035 | 0.046 |
| T-82 AB2.1 | SA2107 A121C | Phen-panstatin | 1.67 | — | — | — | — | — | — | — | — | — |

TABLE 15F-continued

| ADC | Antibody | Warhead | mDAR | HEK293/B7-H3 | JIMT1 (6.7 × $10^5$) | Calu-6 (4.6 × $10^5$) | H460 (3.0 × $10^5$) | A549 (2.3 × $10^5$) | HCT-116 (2.1 × $10^5$) | NCI-N87 (1.5 × $10^5$) | DU-145 (8.5 × $10^4$) | NCI-H23 (8.2 × $10^4$) |
|---|---|---|---|---|---|---|---|---|---|---|---|---|
| T-2 AB2.1 | SA2107 A121C | Q-dThBD | 1.89 | — | 0.012 | 0.003 | — | — | 0.004 | 0.098 | — | — |
| T-4 AB2.1 | SA2107 A121C | Q-dFuBD | 0.62 | — | — | — | — | — | — | — | — | — |
| T-30 AB2.1 | SA2107 A121C | ImBD-TBD | 0.39 | 0.043 | >100 | — | — | — | >100 | >100 | — | — |
| T-32 AB2.1 | SA2107 A121C | ImBD-TBD | 0.16 | — | — | — | — | — | — | — | — | — |
| T-33 AB2.1 | SA2107 A121C | Q-dTBD | 0.24 | — | — | — | — | — | — | — | — | — |
| T-34 AB2.1 | SA2107 A121C | dImBD | 0.08 | — | — | — | — | — | — | — | — | — |
| T-72 AB2.1 | SA2107 A121C | Q-PNU | — | — | — | — | — | — | — | — | — | — |
| T-21 AB2.1 | SA2107 A121C | dPBD | 1.93 | — | 0.034 | 0.039 | 0.120 | 4.084 | 0.200 | 0.494 | 0.198 | 3.727 |
| T-22 AB2.1 | SA2107 A121C | Q-dPBD | 1.33 | — | 0.023 | — | — | — | — | — | — | — |
| T-28 AB2.1 | SA2107 A121C | Q-dPBD | 2.00 | — | 0.011 | 0.025 | 0.178 | 0.398 | 0.143 | 0.660 | 0.069 | 0.142 |
| T-20 AB2.1 | SA2107 A121C | Q-dTBD | 1.98 | — | 0.011 | 0.008 | 0.039 | 0.107 | — | — | 0.021 | 0.018 |
| T-23 AB2.1 | SA2107 A121C | Q-dThBD | 1.99 | — | 0.011 | 0.010 | 0.055 | 0.074 | — | — | 0.034 | 0.025 |
| T-25 AB2.1 | SA2107 A121C | dThBD | 1.03 | — | 0.043 | — | — | — | — | — | — | — |
| T-24 AB2.1 | SA2107 A121C | dThBD | 0.50 | — | 0.047 | — | — | — | — | — | — | — |

TABLE 15G

| CODE | Antibody | Warhead | mDAR | HEK293/B7-H3 (1.2 × $10^7$) | JIMT1 (6.7 × $10^5$) | Calu-6 (4.6 × $10^5$) | H460 (3.0 × $10^5$) | A549 (2.3 × $10^5$) | HCT-116 (2.1 × $10^5$) | DU-145 (1.5 × $10^5$) | NCI-1123 (8.2 × $10^4$) |
|---|---|---|---|---|---|---|---|---|---|---|---|
| T-57 AB2.1 | SA2107 A121C | Q-AuristatinF | 1.73 | — | 0.040 | — | — | — | — | — | — |
| T-13 AB2.1 | SA2107 A121C | adTBD | 0.69 | — | 0.015 | — | — | — | — | — | — |
| T-19 AB2.1 | SA2107 A121C | dTBD, alky amine | 1.10 | — | 0.604 | — | — | — | — | — | — |
| T-31 AB2.1 | SA2107 A121C | ImBD-TBD | 1.40 | — | 0.278 | — | — | — | — | — | — |
| T-15 AB2.1 | SA2107 A121C | adTBD, DMBA | 0.82 | — | 0.044 | — | — | — | — | — | — |
| T-17 AB2.1 | SA2107 A121C | adTBD, DMBA | 0.56 | — | 0.126 | 0.143 | 0.513 | — | — | 0.256 | 0.780 |
| T-21 AB2.1 | SA2566 A121C | dPBD | 1.12 | — | 0.219 | 0.801 | 2~20 | 2~20 | 3.374 | 2.0 | 3.521 |
| T-55 AB2.1 | m8524 A121C | MMAF | 0.98 | 0.103 | — | 0.589 | — | — | — | — | — |
| T-45RO AB2.1 | SA2107 A121C | Q-dThBD_$SO_3$ | 1.98 | | | | | | | 0.011 | |
| T-6 AB2.1 | m8524 S442C | dPBD | 1.01 | — | — | — | 1~10 | — | 3.373 | — | 3.327 |
| T-21 AB2.1 | m8524 S442C | dPBD | 1.94 | — | 0.007- | — | — | 0.599 | — | — | — |

TABLE 15H

| CODE | Antibody | Warhead | mDAR | HEK293/ B7-H3 (1.27 × 10^7) | JIMT 1 (6.7 × 10^5) | Calu-6 (4.6 × 10^5) | H460 (3.0 × 10^5) | A549 (2.3 × 10^5) | HCT-116 (2.1 × 10^5) | NCI-N87 (1.5 × 10^5) | DU-145 (1.5 × 10^5) | NCI-H23 (8.2 × 10^4) |
|---|---|---|---|---|---|---|---|---|---|---|---|---|
| T-Int-102-D3-1 AB2.1 | SA2107 A121C | Q-dTBD | 0.26 | — | — | — | — | — | — | 0.045 | — | — |
| Q-7 AB2.1 | SA2107 A121C | Q-PNU | 0.43 | 0.191 | — | — | — | — | — | 3.626 | — | — |
| T-Int-102-D1-5 AB2.1 | SA2107 A121C | Q-dTBD | 1.52 | — | — | 0.103 | — | 0.023 | — | — | — | 0.039 |
| T-Int-113 AB2.1 | SA2107 A121C | Q-dTBD | 1.40 | — | — | — | 0.046 | — | 0.012 | — | — | 0.020 |
| T-Int-102-D1-5 AB2.1 | SA2107 A121C | Q-dTBD | 1.99 | — | 0.020 | — | 0.094 | 0.474 | — | — | — | 0.043 |
| T-Int-113 AB2.1 | SA2107 A121C | Q-dTBD | 1.94 | — | — | — | 0.042 | — | 0.020 | — | — | 0.010 |
| T-Int-112 AB2.1 | SA2107 A121C | Q-dThBD | 1.96 | — | 0.018 | — | 0.041 | 0.483 | — | 0.031 | — | 0.042 |

TABLE 15I

| CODE | Antibody | Warhead | DAR | JIMT1 (6.7 × 10^5) | Calu-6 (4.6 × 10^5) |
|---|---|---|---|---|---|
| T-101 AB2.1 | SA2107 A121C | QdThBD | 2.0 | 0.023 ± 0.013 | 0.038 ± 0.004 |
| T-102 AB2.1 | SA2107 A121C | Q dThBD | 2.0 | 0.066 ± 0.019 | 0.066 ± 0.010 |
| T-103 AB2.1 | SA2107 A121C | Q dThBD | 2.0 | 0.016 ± 0.003 | 0.024 ± 0.004 |
| T-104 AB2.1 | SA2107 A121C | dThBD | 2.0 | 0.023 ± 0.006 | 0.044 ± 0.006 |
| T-105 AB2.1 | SA2107 A121C | Q dThBD | 2.0 | 0.029 ± 0.023 | 0.093 ± 0.018 |
| T-106 AB2.1 | SA2107 A121C | Q dThBD | 2.0 | 0.019 ± 0.004 | 0.066 ± 0.005 |
| T-107 AB2.1 | SA2107 A121C | Q dTBD | 2.0 | 0.042 ± 0.004 | 0.027 ± 0.001 |
| T-108 AB2.1 | SA2107 A121C | Q PBD | 2.0 | 0.072 ± 0.016 | 0.291 ± 0.033 |
| T-109 AB2.1 | SA2107 A121C | Q ThBD-TBD | 2.0 | 0.029 ± 0.023 | 0.093 ± 0.018 |
| T-110 AB2.1 | SA2107 A121C | Q dThBD | 2.0 | 0.036 ± 0.002 | 0.044 ± 0.003 |
| T-111 AB2.1 | SA2107 A121C | Q dThBD | 2.0 | 0.020 ± 0.009 | 0.066 ± 0.007 |

TABLE 15J

| CODE | Antibody | Warhead | DAR | JIMT1 (6.7 × 10^5) | Calu-6 (4.6 × 10^5) |
|---|---|---|---|---|---|
| T-201 AB2.1 | SA2107 A121C | seco DUBA | 2.0 | 0.337 ± 0.036 | 0.075 ± 0.001 |
| T-203 AB2.1 | SA2107 A121C | seco MCBI DEI | 2.0 | 0.016 ± 0.010 | |
| T-207 AB2.1 | SA2107 A121C | seco MCBI 6H7AI | 2.0 | 0.070 ± 0.003 | 0.265 ± 0.011 |
| T-208 AB2.1 | SA2107 A121C | seco MCBI 6HI | 2.0 | 0.081 ± 0.002 | 0.053 ± 0.005 |
| T-209 AB2.1 | SA2107 A121C | seco MCBI 5HI | 2.0 | 0.086 ± 0.005 | 0.045 ± 0.002 |
| T-210 AB2.1 | SA2107 A121C | seco MCBI 6H-bGal7AI | 2.0 | 0.500 ± 0.045 | 0.167 ± 0.015 |
| T-211 AB2.1 | SA2107 A121C | seco MCBI 6HIbGal | 2.0 | 0.085 ± 0.006 | 0.415 ± 0.024 |
| T-212 AB2.1 | SA2107 A121C | seco MCBI 5HIbGal | 2.0 | 0.101 ± 0.009 | 0.061 ± 0.001 |
| T-213 AB2.1 | SA2107 A121C | seco MCBI | 2.0 | 0.114 ± 0.008 | 0.092 ± 0.009 |
| T-214 AB2.1 | SA2107 A121C | seco DUBA | 2.0 | | 1.275 ± 0.195 |
| T-215 AB2.1 | SA2107 A121C | seco DUBA | 2.0 | | 2.351 ± 0.670 |

TABLE 16

Antibody-Drug Conjugates (ADCs): refer to Table 12 or Table 15

| ADCs | DAR | Conjugation method | Linker-Toxin |
|---|---|---|---|

(Please refer to Table 12 or Table 15 that show the toxin derivatives for preparation of ADCs)

| T-11-AB2.1 | 0.62 | 2 | T-11, |
| T-1-AB2.1 | 0.78 | 2 | T-1, |
| T-47-AB2.1 | 1.43 | 1 | T-47 |
| T-6-AB2.1 | 1.08 | 2 | T-6 |
| T-55-AB2.1 | 1.62 | 1 | T-55 |
| T-70-AB2.1 | 0.88 | 1 | T-70 |
| T-71-AB2.1 | 0.90 | 1 | T-71 |
| T-82-AB2.1 | 1.67 | 1 | T-82 |
| T-2-AB2.1 | 1.36 | 2 | T-2 |
| T-4-AB2.1 | 0.62 | 2 | T-4 |
| T-30-AB2.1 | 0.39 | 2 | T-30 |

TABLE 16-continued

Antibody-Drug Conjugates (ADCs): refer to Table 12 or Table 15

| ADCs | DAR | Conjugation method | Linker-Toxin |
|---|---|---|---|
| (Please refer to Table 12 or Table 15 that show the toxin derivatives for preparation of ADCs) | | | |
| T-32-AB2.1 | 0.16 | 2 | T-32 |
| T-33-AB2.1 | 0.24 | 2 | T-33 |
| T-34-AB2.1 | 0.08 | 2 | T-34 |
| T-21-AB2.1 | 1.12 | 2 | T-21 |
| T-22-AB2.1 | 1.33 | 2 | T-22 |
| T-28-AB2.1 | 1.45 | 2 | T-28 |
| T-20-AB2.1 | 0.97 | 2 | T-20 |
| T-23-AB2.1 | 0.95 | 2 | T-23 |
| T-25-AB2.1 | 1.03 | 2 | T-25 |
| T-24-AB2.1 | 0.50 | 2 | T-24 |
| T-8-AB2.1 | 0.95 | 2 | T-8 |
| T-26-AB2.1 | 0.40 | 2 | T-26 |
| T-57-AB2.1 | 1.73 | 1 | T-57 |
| T-13-AB2.1 | 0.69 | 2 | T-13 |
| T-19-AB2.1 | 1.10 | 2 | T-19 |
| T-31-AB2.1 | 1.40 | 2 | T-31 |
| T-15-AB2.1 | 0.82 | 2 | T-15 |
| T-17-AB2.1 | 0.56 | 2 | T-17 |
| T-48-AB2.1 | 1.54 | 3 | T-48 |
| T-51-AB2.1 | 1.84 | 3 | T-51 |
| T-52-AB2.1 | 0.38 | 3 | T-52 |
| T-77-AB2.1 | 1.41 | 3 | T-77 |
| T-78-AB2.1 | 1.65 | 3 | T-78 |
| T-59-AB2.1 | 1.84 | 3 | T-59 |
| T-43-AB2.1 | 1.81 | 3 | T-43 |
| T-45-AB2.1 | 1.88 | 3, 4 | T-45 |
| T-45RO-AB2.1 | 1.88 | 4 | T-45 |
| T-60-AB2.1 | 1.88 | 3 | T-60 |
| T-88-AB2.1 | 1.83 | 3 | T-88 |
| T-21-AB6.1 | 1.12 | 2 | T-21 |
| T-20-AB6.1 | 0.44 | 2 | T-20 |
| T-55-AB9.1 | 0.98 | 1 | T-55 |
| T-55-AB9.2 | 1.71 | 1 | T-55 |
| T-6-AB9.2 | 1.01 | 2 | T-6 |
| T-21-AB9.2 | 1.03 | 2 | T-21 |
| T-1-AB1.1 | 1.20 | 2 | T-1 |
| T-1-AB3.1 | — | 2 | T-1 |
| T-8-AB1.1 | 1.20 | 2 | T-8 |
| T-11-AB9.1 | 0.66 | 2 | T-11 |
| T-11-AB1.2 | 0.54 | 2 | T-11 |
| T-21-AB7.1 | 0.40 | 2 | T-21 |
| T-21-AB8.1 | — | 2 | T-21 |
| T-21-AB4.1 | 0.31 | 2 | T-21 |
| T-21-AB5.1 | — | 2 | T-11 |
| T-55-AB1.1 | 1.79 | 1 | T-55 |
| T-55-AB1.2 | 1.69 | 1 | T-55 |
| T-89-AB2.1 | 2.0 | 3, 4 | T-89 |
| T-101 AB2.1 | 2.0 | 3, 4 | T-101 |
| T-102 AB2.1 | 2.0 | 3, 4 | T-102 |
| T-103 AB2.1 | 2.0 | 3, 4 | T-103 |
| T-104 AB2.1 | 2.0 | 3, 4 | T-104 |
| T-105 AB2.1 | 2.0 | 3, 4 | T-105 |
| T-106 AB2.1 | 2.0 | 3, 4 | T-106 |
| T-107 AB2.1 | 2.0 | 3, 4 | T-107 |
| T-108 AB2.1 | 2.0 | 3, 4 | T-108 |
| T-109 AB2.1 | 2.0 | 3, 4 | T-109 |
| T-110 AB2.1 | 2.0 | 3, 4 | T-110 |
| T-111 AB2.1 | 2.0 | 3, 4 | T-111 |
| T-Int-102-D3-1 AB2.1 | 0.62 | 5 | MPS-D3-1, Example 2 T-Int-102, Example4.10.3 |
| Q-7 AB2.1 | 0.43 | 6 | MPS-D1-10, Example 1.9 Q-7, Example 4.6 |
| T-Int-1 AB2.1 | 0.56 | 6 | MPS-D1-10, Example 1.9 T-Int-1, Example4.10.1 |
| T-Int-102-D1-7 AB2.1 | 1.15 | 5 | MPS-D1-7, Example 2 T-Int-102, Example4.10.3 |
| T-Int-102-D1-11 AB2.1 | 0.56 | 5 | MPS-D1-11, Example 2 T-Int-102, Example4.10.3 |
| T-Int-102-D1-5 AB2.1 | 1.52 | 5 | MPS-D1-5, Example 2 T-Int-102, Example4.10.3 |
| T-Int-113 AB2.1 | 1.40 | 5 | MPS-D1-5, Example 2 T-Int-113, Example4.10.1 |
| T-Int-112 AB2.1 | 1.15 | 5 | MPS-D1-5, Example 2 T-Int-112, Example 4.10.3 |
| T-200 AB2.1 | 2 | 3, 4 | T-200 |
| T-201 AB2.1 | 2 | 3, 4 | T-201 |
| T-202 AB2.1 | 2 | 3, 4 | T-202 |
| T-203 AB2.1 | 2 | 3, 4 | T-203 |
| T-204 AB2.1 | 2 | 3, 4 | T-204 |
| T-205 AB2.1 | 2 | 3, 4 | T-205 |
| T-206 AB2.1 | 2 | 3, 4 | T-206 |
| T-207 AB2.1 | 2 | 3, 4 | T-207 |
| T-208 AB2.1 | 2 | 3, 4 | T-208 |
| T-209 AB2.1 | 2 | 3, 4 | T-209 |
| T-210 AB2.1 | 2 | 3, 4 | T-210 |
| T-211 AB2.1 | 2 | 3, 4 | T-211 |
| T-212 AB2.1 | 2 | 3, 4 | T-212 |
| T-213 AB2.1 | 2 | 3, 4 | T-213 |
| T-214 AB2.1 | 2 | 3, 4 | T-214 |
| T-215 AB2.1 | 2 | 3, 4 | T-215 |
| T-216 AB2.1 | 2 | 3, 4 | T-216 |
| T-217 AB2.1 | 2 | 3, 4 | T-217 |
| T-218 AB2.1 | 2 | 3, 4 | T-218 |

Example 8

Purification of Antibody Drug Conjugate

The mixture was concentrated by centrifugal ultrafiltration and the conjugate was purified with HIC NPR column (TOSOH #0007656 TSKgel Phenyl-5PW, 21.5×150 mm, 13 μm) and eluted with a linear gradient from 40 to 100% B at 0.8 ml/min (A buffer 1.5 M ammonium sulfate in 50 mM sodium phosphate (pH 7.0); B buffer 20% acetonitrile in 50 mM sodium phosphate (pH 7.0)). DAR (drug to antibody ratio) of conjugated antibody was analyzed by HIC.

Example 9

In Vitro Analysis of Protein-Drug Conjugates

HEK293(B7-H3 overexpressed), NCI-N87, Calu-6, NCI-H460, A549, HCT-116, DU-145, NCI-H23 and NCI-H358 cancer cells were seeded in 96-well plates at a density of 2,000 to 8,000 cells per well in 100 μL of medium, and cultured for 24 hours. The ADCs were treated by serial dilutions of 1:4 from 50 nM to 0.0003 nM, and the antibody drug conjugate T-DM1 was treated by serial dilutions of 1:4 from 50 nM to 0.0007 nM. The series of compound dilutions in DMSO were added to triplicate wells of 24-well plates at 5 μL per well. Three wells on each individual plate received 5 μL of DMSO without compound as controls. The final concentration of DMSO per well was 0.5%. The plates were incubated for 6 days at 37° C. in a humidified 5% CO$_2$-in-air atmosphere. Cell viability was determined by the MTT assay. 0.2 mL of 3-(4,5-dimethylthiazol-2-yl)-2,5-diphenyltetrazolium bromide (MTT) dye, dissolved in PBS buffer solution (5 mg/mL), was added to each well of the plates. The formazans formed by reduction of the MTT dye by mitochondrial oxidoreductases in the living cells were dissolved in DMSO, and measured using the absorbance at 550 nm. $IC_{50}$ was generated using a sigmoidal dose-response nonlinear regression curve fit (GraphPad software Inc.) and the results are shown in FIGS. 1-9 and Tables 17-27 below.

TABLE 17

Cell cytotoxicity of antibody-drug conjugates (B7-H3 over-expressed HEK293)

| ADCs | DAR | HEK293/B7-H3 ($IC_{50}$ nM) |
|---|---|---|
| T-11-AB2.1 | 0.62 | 0.002 |
| T-1-AB2.1 | 0.78 | 0.055 |
| T-47-AB2.1 | 1.43 | 0.059 |
| T-6-AB2.1 | 1.08 | 0.011 |
| T-30-AB2.1 | 0.39 | 0.043 |
| T-55-AB9.1 | 0.98 | 0.103 |
| T-11-AB9.2 | 0.58 | 0.015 |
| T-11-AB1.2 | 0.54 | 0.008 |
| T-55-AB1.1 | 1.79 | 0.346 |
| Q-7-AB2.1 | 0.43 | 0.191 |

TABLE 18

Cell cytotoxicity of antibody-drug conjugates (Calu-6)

| ADCs | DAR | Calu-6 ($IC_{50}$ nM) |
|---|---|---|
| T-21-AB2.1 | 1.12 | 0.111 |
| T-17-AB2.1 | 0.56 | 0.143 |
| T-21-AB6.1 | 1.12 | 0.801 |
| T-55-AB9.1 | 0.98 | 0.589 |
| T-1-AB1.1 | 1.20 | >100 |
| T-8-AB1.1 | 1.20 | 8,384 |
| T-11-AB9.1 | 0.66 | 0.009 |
| T-11-AB1.1 | 1.58 | 0.005 |
| T-11-AB9.2 | 0.58 | 0.012 |

TABLE 19

Cell cytotoxicity of antibody-drug conjugates (JIMT-1)

| ADCs | DAR | JIMT-1 ($IC_{50}$ nM) |
|---|---|---|
| T-11-AB2.1 | 0.62 | 0.063 |
| T-1-AB2.1 | 0.78 | >100 |
| T-47-AB2.1 | 1.43 | 0.1~1.0 |
| T-6-AB2.1 | 1.08 | 0.079 |
| T-71-AB2.1 | 0.90 | 0.001 |
| T-2-AB2.1 | 1.36 | 0.009 |
| T-30-AB2.1 | 0.39 | >100 |
| T-21-AB2.1 | 1.12 | 0.095 |
| T-22-AB2.1 | 1.33 | 0.023 |
| T-28-AB2.1 | 1.45 | 0.020 |
| T-20-AB2.1 | 0.97 | 0.002 |
| T-23-AB2.1 | 0.95 | 0.011 |
| T-25-AB2.1 | 1.03 | 0.043 |
| T-24-AB2.1 | 0.50 | 0.047 |
| T-57-AB2.1 | 1.73 | 0.040 |
| T-13-AB2.1 | 0.69 | 0.015 |
| T-19-AB2.1 | 1.10 | 0.604 |
| T-31-AB2.1 | 1.40 | 0.278 |
| T-15-AB2.1 | 0.82 | 0.044 |
| T-17-AB2.1 | 0.56 | 0.126 |
| T-21-AB6.1 | 1.12 | 0.219 |

TABLE 20

Cell cytotoxicity of antibody-drug conjugates (NCI-H23)

| ADCs | DAR | NCI-H23 ($IC_{50}$ nM) |
|---|---|---|
| T-21-AB2.1 | 1.12 | 5.203 |
| T-17-AB2.1 | 0.56 | 0.780 |
| T-21-AB6.1 | 1.12 | 3.521 |
| T-Int-102-D1-5 AB2.1 | 1.52 | 0.039 |
| T-Int-113 AB2.1 | 1.40 | 0.020 |

TABLE 21

Cell cytotoxicity of antibody-drug conjugates (HCT-116)

| ADCs | DAR | HCT-116 ($IC_{50}$ nM) |
|---|---|---|
| T-11-AB2.1 | 0.62 | 0.052 |
| T-1-AB2.1 | 0.78 | >100 |
| T-47-AB2.1 | 1.43 | >100 |
| T-6-AB2.1 | 1.08 | 0.557 |
| T-2-AB2.1 | 1.36 | 0.014 |
| T-30-AB2.1 | 0.39 | >100 |
| T-21-AB2.1 | 1.12 | 0.264 |
| T-23-AB2.1 | 0.95 | 0.048 |
| T-21-AB6.1 | 1.12 | 3.374 |
| T-6-AB9.2 | 1.01 | 4.865 |
| T-21-AB9.2 | 1.03 | 0.599 |
| T-Int-102-D1-5 AB2.1 | 1.52 | 0.023 |
| T-Int-113 AB2.1 | 1.40 | 0.012 |

TABLE 22

Cell cytotoxicity of antibody-drug conjugates (NCI-H460)

| ADCs | DAR | NCI-H460 ($IC_{50}$ nM) |
|---|---|---|
| T-11-AB2.1 | 0.62 | 0.268 |
| T-21-AB2.1 | 1.12 | 0.2-2.0 |
| T-23-AB2.1 | 0.95 | 0.157 |
| T-17-AB2.1 | 0.56 | 0.513 |
| T-21-AB6.1 | 1.12 | 2-20 |
| T-6-AB9.2 | 1.01 | 1-10 |
| T-Int-102-D1-5 AB2.1 | 1.52 | 0.103 |
| T-Int-113 AB2.1 | 1.40 | 0.046 |

TABLE 23

Cell cytotoxicity of antibody-drug conjugates (NCI-N87)

| ADCs | DAR | NCI-N87 ($IC_{50}$ nM) |
|---|---|---|
| T-11-AB2.1 | 0.62 | 0.222 |
| T-1-AB2.1 | 0.78 | >100 |
| T-47-AB2.1 | 1.43 | >100 |
| T-6-AB2.1 | 1.08 | 4.641 |
| T-2-AB2.1 | 1.36 | 0.014 |
| T-30-AB2.1 | 0.39 | >100 |
| T-8-AB1.1 | 1.20 | 0.567 |
| T-11-AB9.1 | 0.66 | 0.760 |
| T-11-AB9.2 | 0.58 | 0.116 |
| T-Int-102-D3-2 AB2.1 | 0.26 | 0.045 |
| Q-7-AB2.1 | 0.43 | 3.626 |

TABLE 24

Cell cytotoxicity of the purified antibody-drug conjugates (IC$_{50}$, nM)

| ADCs | JIMT-1 | NCI-N87 | HCT-116 | NCI-H23 | NCI-H460 |
|---|---|---|---|---|---|
| T-47-AB2.1 | 0.315 | — | — | — | 0.612 |
| T-6-AB2.1 | — | — | 0.313 | 7.896 | 10 |
| T-71-AB2.1 | 0.019 | — | — | 0.46 | 0.014 |
| T-2-AB2.1 | 0.012 | 0.098 | 0.004 | — | — |
| T-21-AB2.1 | 0.034 | 0.494 | 0.200 | 3.727 | 0.120 |
| T-28-AB2.1 | 0.011 | 0.660 | 0.143 | 0.142 | 0.178 |
| T-20-AB2.1 | 0.011 | — | — | 0.018 | 0.039 |
| T-23-AB2.1 | 0.011 | — | — | 0.025 | 0.055 |
| T-57-AB2.1 | 0.142 | — | >100 | >100 | >100 |
| T-21-AB9.2 | — | — | 3.373 | 3.327 | 10 |
| T-43-AB2.1 | — | 0.015 | — | — | — |
| T-45-AB2.1 | — | 0.026 | — | — | — |
| T-45R0-AB2.1 | 0.007 | 0.063 | — | 0.011 | — |
| T-Int-102-D1-5 AB2.1 | 0.020 | — | 0.029 | 0.043 | 0.094 |
| T-Int-113 AB2.1 | — | — | 0.020 | 0.010 | 0.042 |
| T-Int-112 AB2.1 | 0.018 | 0.031 | 0.026 | 0.042 | 0.041 |
| D-101 | 0.016 | 0.026 | 0.007 | 0.010 | 0.015 |

TABLE 25

Cell cytotoxicity of antibody-drug conjugates (CCRF-CEM)

| ADCs | DAR | CCRF-CEM (IC$_{50}$) nM |
|---|---|---|
| T-101 AB2.1 | 2.0 | 2.837 ± 0.115 |
| T-102 AB2.1 | 2.0 | 32.35 ± 0.520 |
| T-103 AB2.1 | 2.0 | 1.759 ± 0.381 |
| T-104 AB2.1 | 2.0 | 11.42 ± 1.978 |
| T-105 AB2.1 | 2.0 | 4.563 ± 0.707 |
| T-106 AB2.1 | 2.0 | 45.05 ± 3.124 |
| T-107 AB2.1 | 2.0 | 7.610 ± 0.512 |
| T-108 AB2.1 | 2.0 | 197.2 ± 41.11 |
| T-109 AB2.1 | 2.0 | 8.932 ± 1.144 |
| T-110 AB2.1 | 2.0 | 76.31 ± 10.95 |
| T-111 AB2.1 | 2.0 | 62.09 ± 0.430 |
| T-201 AB2.1 | 2.0 | 5.848 ± 0.520 |
| T-207 AB2.1 | 2.0 | 3.726 ± 0.072 |
| T-208 AB2.1 | 2.0 | 3.356 ± 0.057 |
| T-209 AB2.1 | 2.0 | 3.497 ± 0.101 |
| T-210 AB2.1 | 2.0 | 24.45 ± 2.639 |
| T-211 AB2.1 | 2.0 | 3.688 ± 0.065 |
| T-212 AB2.1 | 2.0 | 1.200 ± 0.239 |
| T-213 AB2.1 | 2.0 | 3.457 ± 0.030 |
| T-214 AB2.1 | 2.0 | 333.4 ± 80.82 |
| T-215 AB2.1 | 2.0 | 1013 ± 43.49 |

TABLE 26

Cell cytotoxicity of antibody-drug conjugates (Raji)

| ADCs | DAR | Raji (IC$_{50}$ nM) |
|---|---|---|
| T-101 AB2.1 | 2.0 | 8.540 ± 1.188 |
| T-103 AB2.1 | 2.0 | 2.670 ± 0.317 |
| T-104 AB2.1 | 2.0 | 10.94 ± 1.837 |
| T-105 AB2.1 | 2.0 | 3.075 ± 0.605 |
| T-106 AB2.1 | 2.0 | 211.1 ± 34.95 |
| T-107 AB2.1 | 2.0 | 5.467 |
| T-108 AB2.1 | 2.0 | 500~1000 |
| T-109 AB2.1 | 2.0 | 5.253 ± 0.453 |
| T-110 AB2.1 | 2.0 | 254.8 |
| T-111 AB2.1 | 2.0 | 272.2 ± 17.64 |
| T-201 AB2.1 | 2.0 | 3.187 ± 1.902 |
| T-210 AB2.1 | 2.0 | 10.99 ± 2.846 |
| T-214 AB2.1 | 2.0 | 175.4 |
| T-215 AB2.1 | 2.0 | 3018 |

TABLE 27

Cell cytotoxicity of antibody-drug conjugates (CHO-K1)

| ADCs | DAR | CHO-K1 (IC$_{50}$ nM) |
|---|---|---|
| T-101 AB2.1 | 2.0 | 34.1 ± 7.37 |
| T-102 AB2.1 | 2.0 | 150~500 |
| T-103 AB2.1 | 2.0 | 9.47 ± 0.61 |
| T-104 AB2.1 | 2.0 | 100~500 |
| T-207 AB2.1 | 2.0 | 14.49 ± 0.11 |
| T-208 AB2.1 | 2.0 | 8.935 ± 0.683 |
| T-209 AB2.1 | 2.0 | 12.09 ± 0.176 |
| T-210 AB2.1 | 2.0 | 51.36 ± 1.08 |
| T-211 AB2.1 | 2.0 | 15.72 ± 0.29 |
| T-212 AB2.1 | 2.0 | 6.293 ± 0.566 |
| T-213 AB2.1 | 2.0 | 16.95 ± 0.685 |

Example 10

In Vivo Efficacy

T-20-AB2.1, T-23-AB2.1, T-Int-102-D1-5 AB2.1, and T-Int0112-AB2.1 were prepared with 20 mg scale reaction. After purification by HIC column, final samples were concentrated to 5-10 mg/ml protein.

Figure 10:
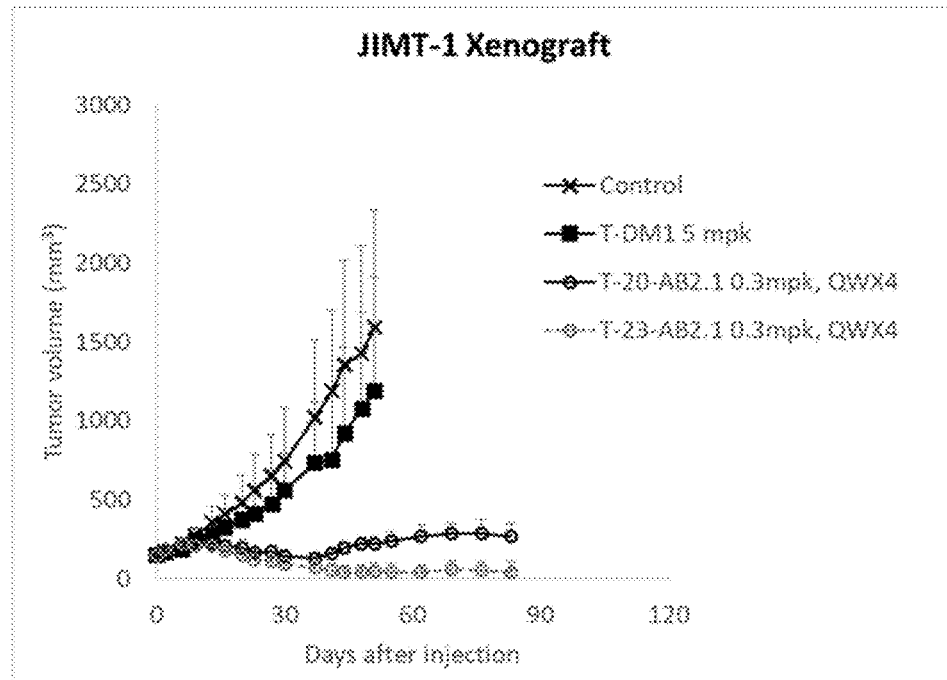
FIG. 10 shows effect of T-20-AB2.1 and T-21-AB2.1 on tumor volume in JIMT-1 xenograft.
Figure 11:
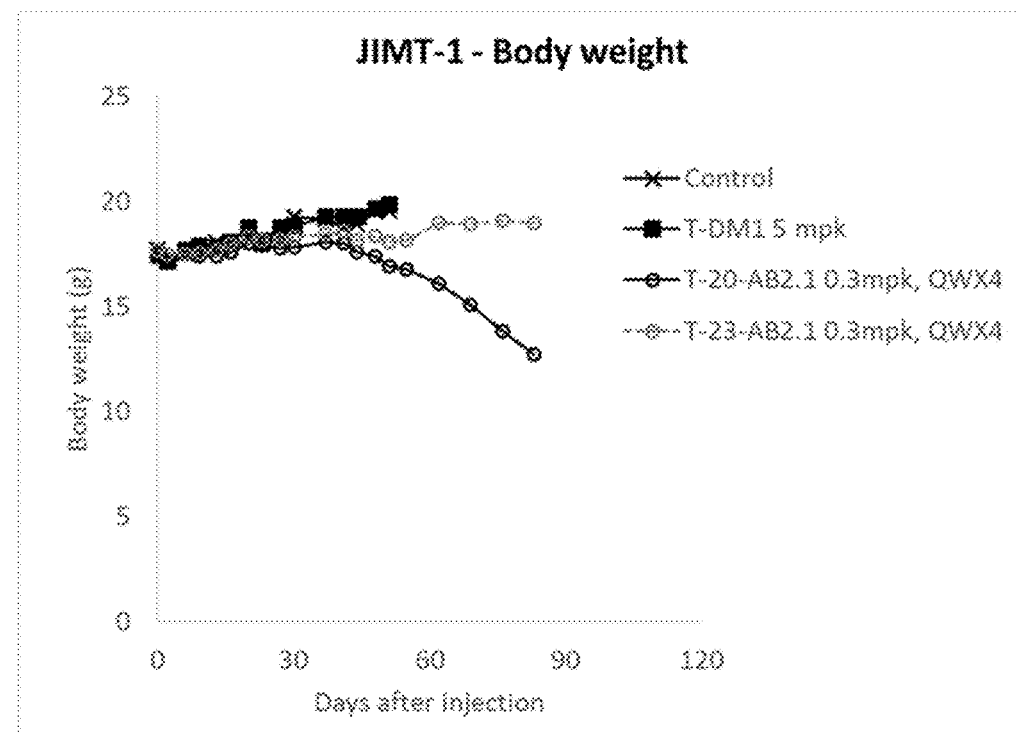
FIG. 11 shows effect of T-20-AB2.1 and T-21-AB2.1 on body weight in JIMT-1 xenograft.
Figure 12:
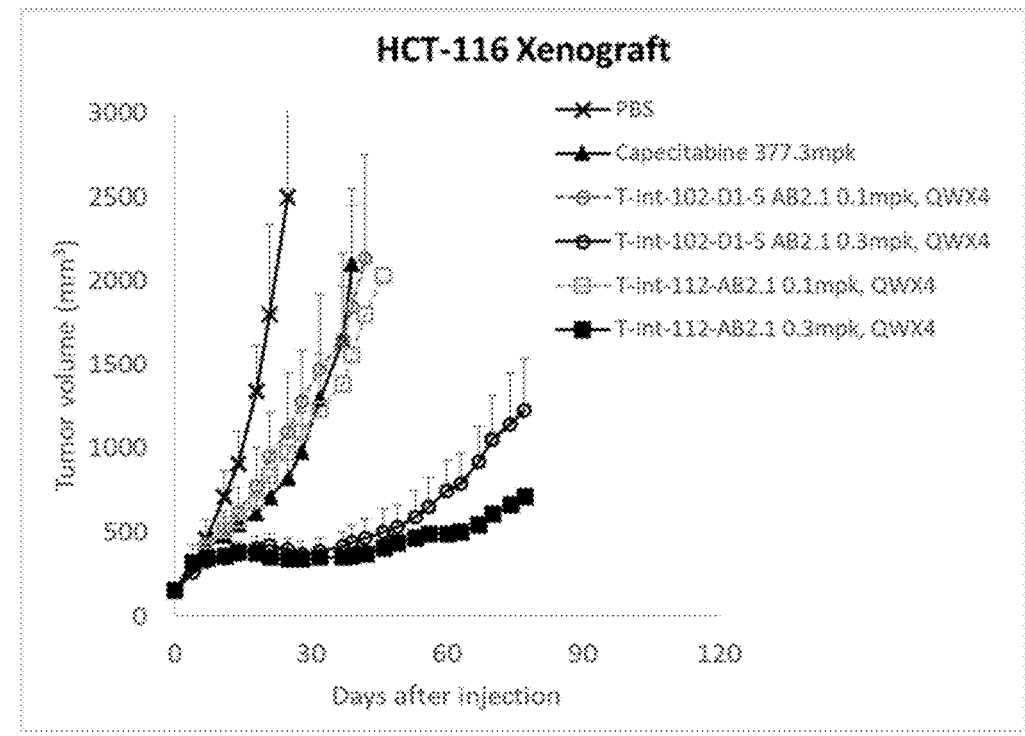
FIG. 12 shows effect of T-Int-102-D1-5 AB2.1 and T-Int-112-AB2.1 on tumor volume in HCT-116 xenograft.
Figure 13:
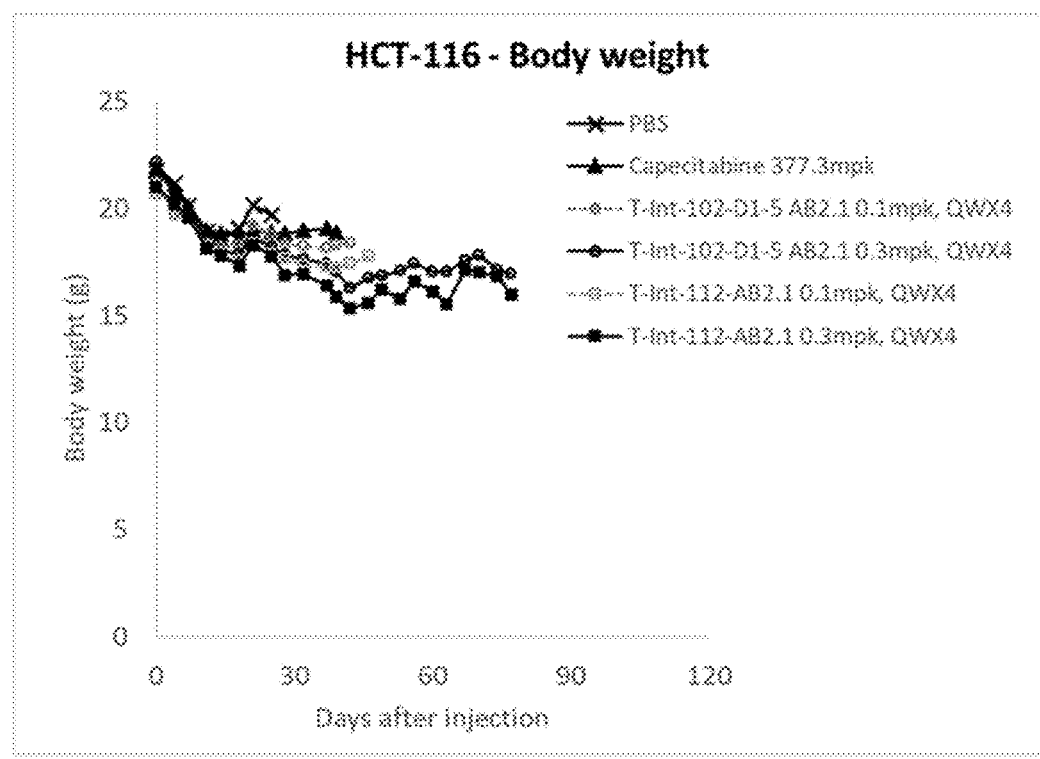
FIG. 13 shows effect of T-Int-102-D1-5 AB2.1 and T-Int-112-AB2.1 on body weight in HCT-116 xenograft.
Figure 14:
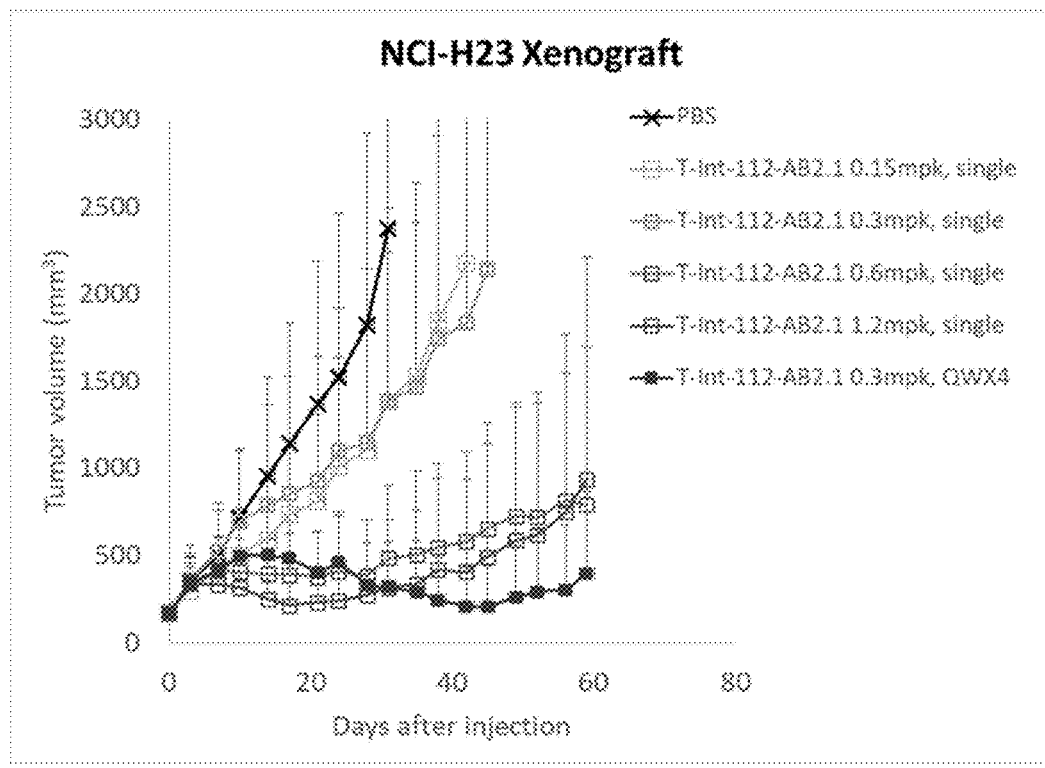
FIG. 14 shows effect of T-Int-112-AB2.1 on tumor volume in NCI-H23 xenograft.
Figure 15:
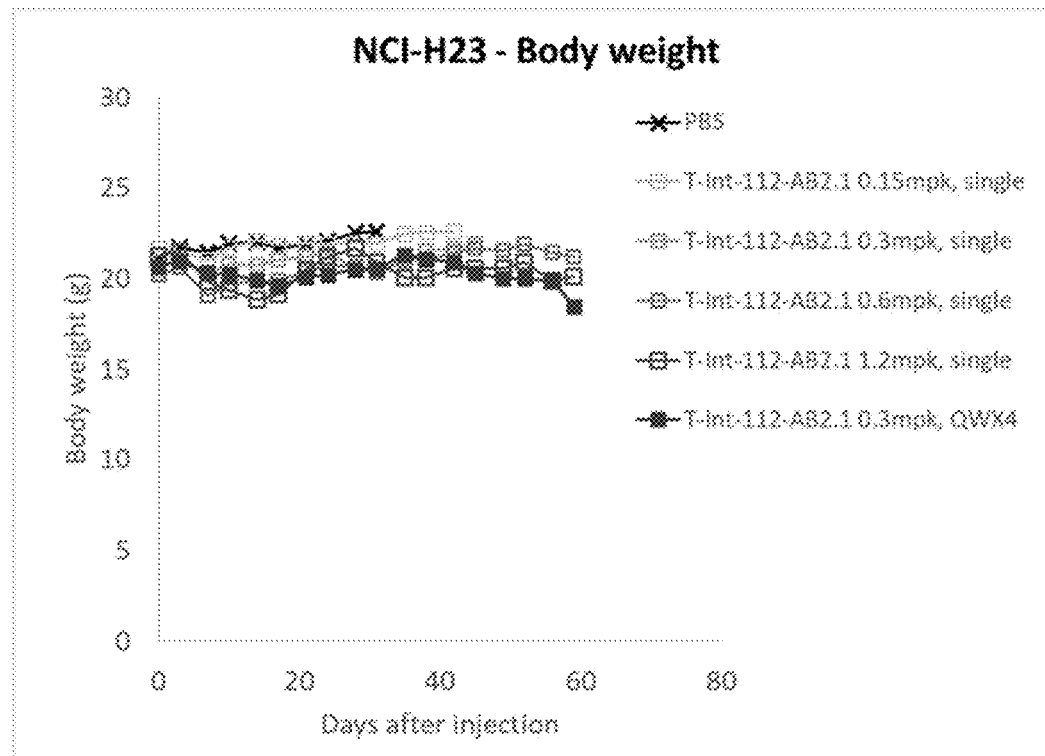
FIG. 15 shows effect of T-Int-112-AB2.1 on body weight in NCI-H23 xenograft.
Figure 16:
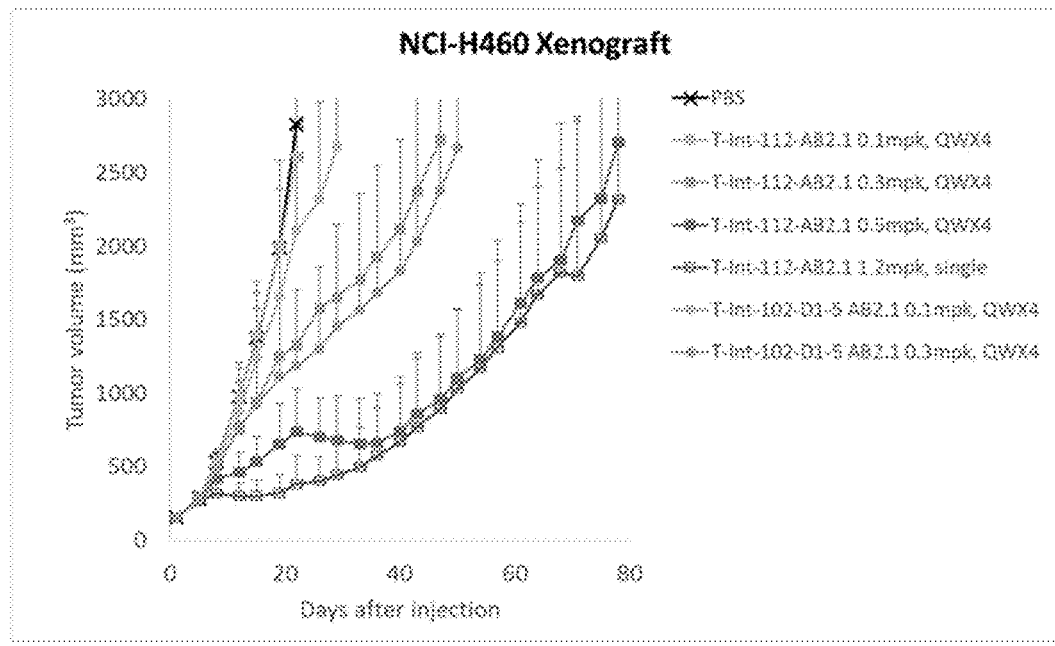
FIG. 16 shows effect of T-Int-112-AB2.1 on tumor volume in NCI-H460 xenograft.
Figure 17:
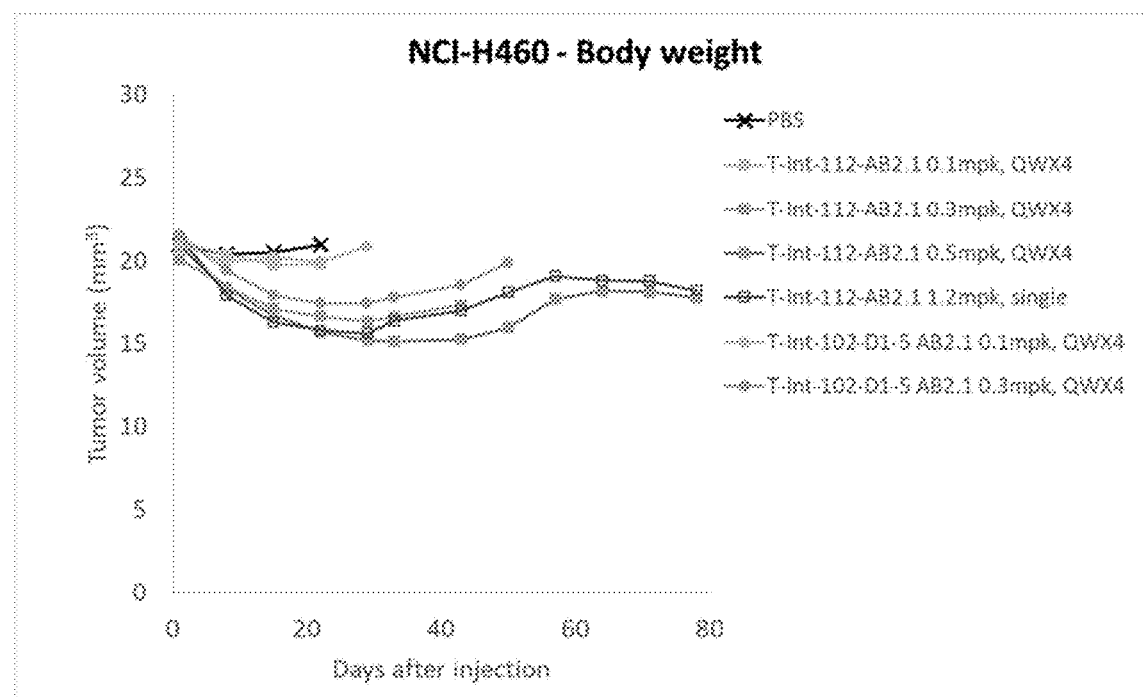
FIG. 17 shows effect of T-Int-112-AB2.1 on body weight in NCI-H460 xenograft.

In vivo efficacy of T-20-AB2.1 and T-23-AB2.1 was measured by tumor xenograft studies in mice. Female BALB/c nu/nu were injected subcutaneously in the right flank with suspensions of $5\times10^6$ of JIMT-1 cells respectively in PBS. Mice were randomized into study groups when tumors reached approximately 150 mm$^3$. T-DM1 (5 mg/kg) and T-20-AB2.1 and T-23-AB2.1 conjugates (0.3 mg/kg, QW X4) were given i.v. All treatment groups consisted of 6 to 10 animals per group, and tumor size was monitored twice weekly using caliper measurement. The tumor mass was calculated as volume=(width×width×length)/2. Conjugates of the disclosure led to tumor regression within the period of observation, i.e. 80 days from the initiation of the experiment. The control conjugate, T-DM1 was less active than our conjugates. These results were shown in FIG. 10 and FIG. 11.

HCT-116, NCI-H23 and NCI-H460 model were progressed in the similar method for T-Int-102-D1-5 AB2.1 and T-Int-112-AB2.1.

The conjugates made the tumor regressed during 60~90 days from the initiation of the experiment. These results were shown in FIGS. 12-17.

These in vivo experiments were performed by CACT (center for advancing cancer therapeutics, Asan Medical Center, project code number: HI15C0972) and Biotoxtech Example 11

Generation of Anti-B7-H3 Monoclonal Antibody

B7-H3 specific antibodies were discovered, by Ymax-ABL library (Y-Biologics Inc.), through three consecutive biopanning processes and additional affinity-maturation technology.

After about 140 scFv antibody hits with different base sequences as well as specific to B7-H3 were screened, they were converted to a complete human IgG form and produced using the Ymax-tEXPRESS system (Y-Biologics Inc.).

B7-H3 specific antibodies were selected by DNA sequence analysis and in vitro characterization assay and produced in the form of the thiomab IgG (IgG_A1C) (Tables 28, 29, 30 and 31).

TABLE 28

List of anti-B7-H3 antibodies generated using a fully human antibody phage library technology

| Clone ID | SID | Clone name | Isotype | GERMVH | HOMOVH | GERMVL | HOMOVL |
|---|---|---|---|---|---|---|---|
| AB1 | SA1319 | CD276-033E03 | Human IgG1, Kappa-T2S | IGHV3-23*04 | 95.9% (93/97) | IGLV2-14*01 | 93.8% (91/97) |
| AB2 | SA2107 | CD276-040F10 | Human IgG1, Kappa-T2S | IGHV1-3*01 | 85.4% (82/96) | IGKV1-12*01 | 91.6% (87/95) |
| AB3 | SA2103 | CD276-039C05 | Human IgG1, Kappa-T2S | IGHV1-69*04 | 99.0% (96/97) | IGKV1-5*03 | 89.4% (84/94) |
| AB4 | SA2545 | CD276-039C05_LS_001E10 | Human IgG1, Kappa-T2S | IGHV1-69*04 | 99.0% (96/97) | IGKV1-5*03 | 92.6% (88/95) |
| AB5 | SA2563 | CD276-039C05_LS_002A11 | Human IgG1, Kappa-T2S | IGHV1-69*04 | 99.0% (96/97) | IGKV1-5*03 | 90.3% (84/93) |
| AB6 | SA2566 | CD276-039C05_LS_002B07 | Human IgG1, Kappa-T2S | IGHV1-69*04 | 99.0% (96/97) | IGKV1-16*01 | 93.7% (89/95) |
| AB7 | SA2571 | CD276-039C05_LS_002D03 | Human IgG1, Kappa-T2S | IGHV1-69*04 | 99.0% (96/97) | IGKV1-5*03 | 95.7% (90/94) |
| AB8 | SA2579 | CD276-039C05_LS_002H07 | Human IgG1, Kappa-T2S | IGHV1-69*04 | 99.0% (96/97) | IGKV1-5*03 | 94.6% (88/93) |

Antibodies including the heavy and light-chain CDR sequences of the selected antibodies, and the heavy chain variable regions and light chain variable regions including the same are shown in Tables 29 and 30.

TABLE 29

CDR sequences of anti-B7-H3 antibodies

| Clone ID | Clone name | CDR | Sequence |
|---|---|---|---|
| AB1 | CD276-033E03 | CDRH1 | GFTFSSYA (SEQ ID NO: 1) |
| | | CDRH2 | ISGSGGSR (SEQ ID NO: 2) |
| | | CDRH3 | ASHTIPGAWDV (SEQ ID NO: 3) |
| | | CDRL1 | TRDVGGYNY (SEQ ID NO: 4) |
| | | CDRL2 | DVN (SEQ ID NO: 5) |
| | | CDRL3 | SSYTTSSRRV (SEQ ID NO: 6) |
| AB2 | CD276-040F10 | CDRH1 | GYTFSSYW (SEQ ID NO: 7) |
| | | CDRH2 | INPGNGHT (SEQ ID NO: 8) |
| | | CDRH3 | VADPRRPKVPTALFVY (SEQ ID NO: 9) |
| | | CDRL1 | QGIGTW (SEQ ID NO: 10) |
| | | CDRL2 | AAS (SEQ ID NO: 11) |
| | | CDRL3 | QQAINFPIT (SEQ ID NO: 12) |
| AB3 | CD276-039C05 | CDRH1 | GGTFSSYA (SEQ ID NO: 13) |
| | | CDRH2 | IIPILGIA (SEQ ID NO: 14) |
| | | CDRH3 | ANGGDSSSWYTFDY (SEQ ID NO: 15) |
| | | CDRL1 | QSISRW (SEQ ID NO: 16) |
| | | CDRL2 | KAS (SEQ ID NO: 17) |
| | | CDRL3 | QQYNTFPLT (SEQ ID NO: 18) |
| AB4 | CD276-039C05_LS_001E10 | CDRH1 | GGTFSSYA (SEQ ID NO: 19) |
| | | CDRH2 | IIPILGIA (SEQ ID NO: 20) |
| | | CDRH3 | ANGGDSSSWYTFDY (SEQ ID NO: 21) |
| | | CDRL1 | QTINSW (SEQ ID NO: 22) |
| | | CDRL2 | KAS (SEQ ID NO: 23) |
| | | CDRL3 | QQYNSYSLT (SEQ ID NO: 24) |

TABLE 29-continued

CDR sequences of anti-B7-H3 antibodies

| Clone ID | Clone name | CDR | Sequence |
|---|---|---|---|
| AB5 | CD276-039C05_LS_002A11 | CDRH1 | GGTFSSYA (SEQ ID NO: 25) |
| | | CDRH2 | IIPILGIA (SEQ ID NO: 26) |
| | | CDRH3 | ANGGDSSSWYTFDY (SEQ ID NO: 27) |
| | | CDRL1 | QNINSW (SEQ ID NO: 28) |
| | | CDRL2 | KAS (SEQ ID NO: 29) |
| | | CDRL3 | QQYDSNPLT (SEQ ID NO: 30) |
| AB6 | CD276-039C05_LS_002B07 | CDRH1 | GGTFSSYA (SEQ ID NO: 31) |
| | | CDRH2 | IIPILGIA (SEQ ID NO: 32) |
| | | CDRH3 | ANGGDSSSWYTFDY (SEQ ID NO: 33) |
| | | CDRL1 | QGISSY (SEQ ID NO: 34) |
| | | CDRL2 | AAS (SEQ ID NO: 35) |
| | | CDRL3 | QQYYSFPLT (SEQ ID NO: 36) |
| AB7 | CD276-039C05_LS_002D03 | CDRH1 | GGTFSSYA (SEQ ID NO: 37) |
| | | CDRH2 | IIPILGIA (SEQ ID NO: 38) |
| | | CDRH3 | ANGGDSSSWYTFDY (SEQ ID NO: 39) |
| | | CDRL1 | ETISSW (SEQ ID NO: 40) |
| | | CDRL2 | KAS (SEQ ID NO: 41) |
| | | CDRL3 | QQYYSYPIT (SEQ ID NO: 42) |
| AB8 | CD276-039C05_LS_002H07 | CDRH1 | GGTFSSYA (SEQ ID NO: 43) |
| | | CDRH2 | IIPILGIA (SEQ ID NO: 44) |
| | | CDRH3 | ANGGDSSSWYTFDY (SEQ ID NO: 45) |
| | | CDRL1 | QSIDNW (SEQ ID NO: 46) |
| | | CDRL2 | KAS (SEQ ID NO: 47) |
| | | CDRL3 | QQYDSNPLT (SEQ ID NO: 48) |

TABLE 30

Variable sequences of anti-B7-H3 antibodies

| Clone ID | Clone name | Variable | Sequence |
|---|---|---|---|
| AB1 | CD276-033E03 | Heavy | QVQLVESGGGLVQSGGSLRLSCAASGFTFSSYAMSWVRQ APGKGLEWVSVISGSGGSRYYADSVKGRFTISRDNSKNTL YLQMNSLRAEDTAVYYCASHTIPGAWDVWGQGTLVTVS S (SEQ ID NO: 49) |
| | | Light | QSALTQPASVSGSPGQSITISCTGTTRDVGGYNYVSWYQQ HPKAPKLMIYDVNNRPSGVSYRFSGSKSGNTASLTISGL QAEDEADYYCSSYTTSSRRVFGTGTKVTVL (SEQ ID NO: 50) |
| AB2 | CD276-040F10 | Heavy | QVQLVESGAEVKKPGASVKLSCKASGYTFSSYWMHWVR QAPGQRLEWMGEINPGNGHTNYNEKFKSRVTITVDKSAS TAYMELSSLRSEDTAVYYCVADPRRPKVPTALFVYWGQG TLVTVSS (SEQ ID NO: 51) |
| | | Light | DIQMTQSPSSVSASVGDRVTISCRASQGIGTWLAWYQQKP GKAPRLLIYAASSLDSGVPSRFSASGSGTDFTLTISSLQPED FATYYCQQAINFPITFGQGTRLEIK (SEQ ID NO: 52) |
| AB3 | CD276-039C05 | Heavy | QVQLVESGAEVKKPGSSVKVSCKASGGTFSSYAISWVRQ APGQGLEWMGRIIPILGIANYAQKFQGRVTITADKSTSTAY MELSSLRSEDTAVYYCANGGDSSSWYTFDYWGQGTLITV SS (SEQ ID NO: 53) |
| | | Light | DIQMTQSPSTLSASVGDKLTLTCRASQSISRWLAWYQQKP GKAPKLLIYKASYLQTGVPSRFSGSGTGTEFTLTISSLQPD DFATYYCQQYNTFPLTFAGGTKVEIK (SEQ ID NO: 54) |
| AB4 | CD276-039C05_LS_001E10 | Heavy | QVQLVESGAEVKKPGSSVKVSCKASGGTFSSYAISWVRQ APGQGLEWMGRIIPILGIANYAQKFQGRVTITADKSTSTAY MELSSLRSEDTAVYYCANGGDSSSWYTFDYWGQGTLITV SS (SEQ ID NO: 55) |
| | | Light | DIQMTQSPSTLSASVGDRVNITCRASQTINSWLAWYQQKP GKAPKLLIYKASYLQTGVPSRFSGSGAGTEFTLTISSLQPD DFATYYCQQYNSYSLTFGGGTKVEIK (SEQ ID NO: 56) |
| AB5 | CD276-039C05_LS_002A11 | Heavy | QVQLVESGAEVKKPGSSVKVSCKASGGTFSSYAISWVRQ AP GQ GLEWMGRIIPILGIANYAQKFQGRVTITADKSTSTAY MELSSLRSEDTAVYYCANGGDSSSWYTFDYWGQGTLITV SS (SEQ ID NO: 57) |

TABLE 30-continued

Variable sequences of anti-B7-H3 antibodies

| Clone ID | Clone name | Variable | Sequence |
|---|---|---|---|
| | | Light | DIQMTQSPSTLSASVGDRLTITCRASQNINSWLAWYQQKP GKAPKLLIYKASYLQTGVPSRFSGSGSGTEFTLTITSLQPD DFASYYCQQYDSNPLTFGGGTKVEIK (SEQ ID NO: 58) |
| AB6 | CD276-039C05_LS_002B07 | Heavy | QVQLVESGAEVKKPGSSVKVSCKASGGTFSSYAISWVRQ APGQGLEWMGRIIPILGIANYAQKFQGRVTITADKSTSTAY MELSSLRSEDTAVYYCANGGDSSSWYTFDYWGQGTLITV SS (SEQ ID NO: 59) |
| | | Light | DIQMTQSPSSLSASVGDRVTITCRASQGISSYLAWYQQKP GKAPKLLIYAASTLQSGVPSRFSGSGSGTDFTLTISSLQPED FATYYCQQYYSFPLTFGGGTKVEIK (SEQ ID NO: 60) |
| AB7 | CD276-039C05_LS_002D03 | Heavy | QVQLVESGAEVKKPGSSVKVSCKASGGTFSSYAISWVRQ APGQGLEWMGRIIPILGIANYAQKFQGRVTITADKSTSTAY MELSSLRSEDTAVYYCANGGDSSSWYTFDYWGQGTLITV SS (SEQ ID NO: 61) |
| | | Light | DIQMTQSPSTLSASVGDRVTITCRASETISSWLAWYQQKP GKAPKLLIYKASSLQSGVPSRFSGSGSGTEFTLTISSLQPDD FATYYCQQYYSYPITFGQGTRLEIK (SEQ ID NO: 62) |
| AB8 | CD276-039C05_LS_002H07 | Heavy | QVQLVESGAEVKKPGSSVKVSCKASGGTFSSYAISWVRQ APGQGLEWMGRIIPILGIANYAQKFQGRVTITADKSTSTAY MELSSLRSEDTAVYYCANGGDSSSWYTFDYWGQGTLITV SS (SEQ ID NO: 63) |
| | | Light | DIQMTQSPSTLSASVGDRVTITCRASQSIDNWLAWYQQKP GKAPKLLIYKASSLQSGVPSRFSGSGSGTEFTLTISSLQPDD FASYYCQQYDSNPLTFGGGTKVEIK (SEQ ID NO: 64) |

Method: Biopanning Using Ymax-ABL Library

E. coli cells were infected with a human scFv phage library (Y-Biologics Inc.) having a variety of about 3×10E10 and then cultured at 30° C. for 16 hours. After culturing, the culture solution was centrifuged, and the resulting supernatant was concentrated with PEG and then dissolved in PBS buffer to obtain a human scFv phage display. The library phages were charged into an immune tube coated with human B7-H3 protein (Sino biological Inc. biological Inc. or Y-Biologics Inc.), followed by reaction at room temperature for 2 hours. After washing with 1× PBS/T and 1× PBS, only the scFv-phages specifically bound to the antigen were eluted.

The eluted phages were infected into E. coli cells again and amplified (panning process) to obtain a pool of positive phages. The second and third panning processes were conducted using the phages amplified in the first panning process in the same manner as described, except that only the number of times of the PBST washing step was increased up to 25 times. The number of phages bound to the antigen (output) was increased during the third panning process.

Poly-phage ELISA (enzyme linked immunoassay) was conducted to investigate the antigenic specificity of the positive poly scFv-phage antibody pool obtained in respectively, each round of the panning process. The cell stock frozen after the first to third panning processes was added to a medium containing 5 ml of 2× YTCM, 2% glucose and 5 mM MgCl$_2$ to OD$_{600}$ of 0.1 and then cultured at 37° C. for 2 to 3 hours (OD$_{600}$=0.5 to 0.7). The cells were infected with M1 helper phages and cultured in a medium containing 2× YTCMK, 5 mM MgCl$_2$, and 1 mM IPTG at 30° C. for 16 hours. The resulting cell culture was centrifuged (4,500 rpm, 15 min, 4° C.), and the supernatant was transferred to a new tube (first to third-panned poly scFv-phages). The antigen was coated at a density of 100 ng/well on 96-well immuno-plates (NUNC 439454) with coating buffer at 4° C. for 16 hours, and each well was blocked using 4% skim milk dissolved in PBS. Each well was washed with 0.2 ml of PBS/T, and 100 µl of the first to third-panned poly scFv-phage was added to each well, followed by reaction at room temperature for 2 hours. Then, each well was washed 4 times with 0.2 ml of PBS/T, and the secondary antibody, anti-M13-HRP (Amersham 27-9421-01) diluted with 4% skim milk/PBS at 1:2000(v/v) was added to each well and reacted at room temperature for 1 hour. After washing with PBS/T, a solution of OPD tablet (Sigma. 8787-TAB) dissolved in PC buffer was added to the wells at a concentration of 100 µl/well to induce color development for 10 minutes. Then, absorbance was measured at 490 nm with a spectrophotometer (Molecular Device). ELISA showed that binding affinity to B7-H3 antigens was enriched in the third panned poly scFv-phages.

Colonies obtained from the polyclonal phage antibody group (the third panning) with high binding affinity were cultured in a 1 ml 96-deep well plate (Bioneer 90030) at 37° C. for 16 hours. 100 to 200 µl of the cells grown thus were added to a medium containing 2× YTCM, 2% glucose and 5 mM MgCl$_2$, to OD$_{600}$ of 0.1, and were added to a medium containing 1 ml of 2× YTCM, 2% glucose and 5 mM MgCl$_2$, and then cultured in a 96-deep well plate at 37° C. for 2 to 3 hours to OD$_{600}$ of 0.5 to 0.7. The cells were infected with M1 helper phages at an MOI of 1:20 and cultured in a medium containing 2× YTCMK, 5 mM MgCl$_2$, 1 mM IPTG at 30° C. for 16 hours. The antigen B7-H3 was coated at a density of 100 ng/well on a 96-well immunoplate at 4° C. for 16 hours and each well was blocked using 4% skim milk dissolved in PBS. Each monoclonal scFv-phage (100 of scFv-phage) washed with 0.2 ml PBS/T and cultured for 16 hours was added in a dose of 100 µl to each well and reacted at room temperature for 2 hours. Then, each well was washed 4 times with 0.2 ml of PBS/T, and the secondary antibody, anti-M13-HRP, diluted with 4% skim milk/PBS to 1/2000 (v/v) and reacted at room temperature for 1 hour. After washing with 0.2 ml of PBS/T, color development was performed and absorbance was measured at 490 nm. A total of several tens of single-phage clones for B7-H3 were obtained as single-phage clones having high binding affinity to each antigen.

Method: Selection by DNA Sequence Analysis

The selected single clones were subjected to DNA-prep using a DNA purification kit (Qiagen, Germany) to obtain DNAs, and sequence analysis for the DNAs was conducted by (Solgent). The CDR regions of VH and VL of the selected antibodies were identified based on the results of sequence analysis, and the similarity (identity) between these antibodies and germ line antibody groups was investigated using an Ig BLAST program (*Nucleic Acids Res.*, 2013, 41, W34-40). Nine species of phage antibodies specific to B7-H3 were obtained and are summarized in Tables 18, 19 and 20.

Method: Construction and Production of B7-H3 Specific Antibodies

PCR (iCycler iQ, BIO-RAD) was performed on the heavy and light chains of the selected antibody clones. As a result, heavy and light chains were obtained, and the vectors (pNATVH and pNATVL) and the two chains were cut (digested) with restriction enzymes. DNAs were eluted with a DNA-gel extraction kit (Qiagen). Ligation was performed by mixing 1 µl (10 ng) of the vectors, 15 µl (100-200 ng) of the heavy or light chain, 2 µl of 10× ligation buffer, 1 µl of ligase (1 U/µl) and distilled water, allowing the mixture to stand at room temperature for 1 to 2 hours, injecting the resulting mixture into competent cells (XL1-blue), placing the cells on ice for 5 minutes and subjecting the cells to heat-shock at 42° C. for 90 seconds. After the heat shock, 1 ml of the medium was added to the cells, and then the cells were grown at 37° C. for 1 hour, spread on an LB Amp plate and incubated at 37° C. for 16 hours. The colony obtained was inoculated into 5 ml of LB Amp medium, cultured at 37° C. for 16 hours and subjected to DNA-prep using a DNA-prep kit (Nuclogen). Sequence analysis of the obtained DNAs was conducted by (Solgent). Each thiomab IgG of selected antibody clones was constructed by site-mutagenesis method. The converted whole IgG clone constructs including thiomabs corresponding to the sequences of phage antibodies of the selected clones were confirmed by sequence analysis (Table 21 and 22). In order to transfect into HEK 293F cells, the heavy (pNATVH) and light chains (pNATVL) of respective clones converted into whole IgG or thiomab IgG were grown in 100 ml of LB Amp medium, and DNAs were obtained using a Midi-prep kit (QIAgen).

The cloned pNATVH and pNATVL vectors were co-transfected at a ratio of 6:4 into HEK293F cells and the supernatant was collected on the 7th day, the cells and debris were removed through centrifugation and a 0.22 µm top filter, and the supernatant was collected and subjected to protein A affinity chromatography to purify the IgG antibody. During purification process, the antibody was separated using a glycine buffer, and buffer was changed such that the final resuspension buffer was PBS. Purified antibodies were quantitated by BCA and nano drop, and each antibody was loaded on to a gel in a dose of 5 ug under reducing and non-reducing conditions, and analyzed by SDS-PAGE to determine purity and mobility of the purified protein. All of the selected antibodies were detected at a molecular weight of 150 kDa or more under non-reducing conditions, and SC0041 or SC0041.01 were produced as a control antibody (Tables 33 and 34).

TABLE 31

Thiomab heavy chain sequences of anti-B7-H3 antibodies generated using the Ymax-tEXPRESS system

| Clone ID | SID | Clone name | Isoheavy | VH | CH |
|---|---|---|---|---|---|
| AB1.1 | SA1319.01 | CD276-033E03_IgG1_A1C | Human IgG1-A1C | QVQLVESGGGLVQSG GSLRLSCAASGFTFSS YAMSWVRQAPGKGLE WVSVISGSGGSRYYAD SVKGRFTISRDNSKNT LYLQMN SLR A EDTAV YYCASHTIPGAYVDVW GQGTLVTVSS (SEQ ID NO: 65) | CSTKGPSVFPLAPSSKST SGGTAALGCLVKDYFPE PVTVSWNSGALTSGVHT FPAVLQSSGLYSLSSVVT VPSSSLGTQTYICNVNH KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEWESNGQPENN YKTTPPVLDSDGSFFLYS KLTVDKSRYVQQGNVFS CSVMHEALHNHYTQKS LSLSPGK (SEQ ID NO: 66) |
| AB1.2 | SA1319.02 | CD276-033E03_IgG1_S325C | Human IgG1-S325C | QVQLVESGGGLVQSG GSLRLSCAASGFTFSS YAMSWVRQAPGKGL EWVSVISGSGGSRYY ADSVKGRFTISRDNSK NTLYLQMNSLRAEDT AVYYCASHTIPGAWD VWGQGTLVTVSS (SEQ ID NO: 67) | ASTKGPSVFPLAPSSKST SGGTAALGCLVKDYFPE PVTVSWNSGALTSGVH TFPAVLQSSGLYSLSSV VTVPSSSLGTQTYICNV NHKPSNTKVDKKVEPK SCDKTHTCPPCPAPELL GGPSVFLFPPKPKDTLMI SRTPEVTCVVVDVSHED PEVKFNWYVDGVEVHN AKTKPREEQYNSTYRV |

TABLE 31-continued

Thiomab heavy chain sequences of anti-B7-H3 antibodies generated using the Ymax-tEXPRESS system

| Clone ID | SID | Clone name | Isoheavy | VH | CH |
|---|---|---|---|---|---|
| | | | | | VSVLTVLHQDWLNGKE YKCKVSNKALPAPIEKTI SKAKGQPREPQVYTLPP SREEMTKNQVSLTCLVK GFYPSDIAVEWESNGQP ENNYKTTPPVLDSDGSF IFLYSKLTVDKSRWQQG NVFSCSVMHEALHNHY TQKSLCLSPGK (SEQ ID NO: 68) |
| AB2.1 | SA2107.01 | CD276-040F10_IgG1_A1C | Human IgG1-A1C | QVQLVESGAEVKKPG ASVKLSCKASGYTFSS YWMHWVRQAPGQRL EWMGEINPGNGHTNY NEKFKSRVTITVDKSA STAYMELSSLRSEDTA VYYCVADPRRPKVPT ALFVYWGQGTLVTVS S (SEQ ID NO: 69) | CSTKGPSVFPLAPSSKST SGGTAALGCLVKDYFPE PVTVSWNSGALTSGVHT FPAVLQSSGLYSLSSVVT VPSSSLGTQTYICNVNH KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEWESNGQPENN YKTTPPVLDSDGSFFLYS KLTVDKSRWQQGNVFS CSVMHEALHNHYTQKS LSLSPGK (SEQ ID NO: 70) |
| AB3.1 | SA2103.01 | CD276-039C05_IgG1_A1C | Human IgG1-A1C | QVQLVESGAEVKKPG SSVKVSCKASGGTFSS YAISWVRQAPGQLE WMGRIIPILGIANYAQ KFQGRVTITADKSTST AYMELSSLRSEDTAVY YCANGGDSSSWYTFD YWGQGTLITVSS (SEQ ID NO: 71) | CSTKGPSVFPLAPSSKST SGGTAALGCLVKDYFPE PVTVSWNSGALTSGVHT FPAVLQSSGLYSLSSVVT VPSSSLGTQTYICNVNH KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEVVESNGQPENN YKTTPPVLDSDGSFFLYS KLTVDKSRWQQGNVFS CSVMHEALHNHYTQKS LSLSPGK (SEQ ID NO: 72) |
| AB4.1 | SA2545.01 | CD276-039C05_LS_001E10_IgG1_A1C | Human IgG1-A1C | QVQLVESGAEVKKPG SSVKVSCKASGGTFSS YAISWVRQAPGQLE WMGRIIPILGIANYAQ KFQGRVTITADKSTST AYMELSSLRSEDTAVY YCANGGDSSSWYTFD YWGQGTLITVSS (SEQ ID NO: 73) | CSTKGPSVFPLAPSSKST SGGTAALGCLVKDYFPE PVTVSWNSGALTSGVHT FPAVLQSSGLYSLSSVVT VPSSSLGTQTYICNVNH KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEWESNGQPENN YKTTPPVLDSDGSFFLYS KLTVDKSRWQQGNVFS CSVMHEALHNHYTQKS |

TABLE 31-continued

Thiomab heavy chain sequences of anti-B7-H3 antibodies
generated using the Ymax-tEXPRESS system

| Clone ID | SID | Clone name | Isoheavy | VH | CH |
|---|---|---|---|---|---|
| | | | | | LSLSPGK (SEQ ID NO: 74) |
| AB5.1 | SA2563.01 | CD276-039C05_LS_002A11_IgG1_A1C | Human IgG1-A1C | QVQLVESGAEVKKPG SSVKVSCKASGGTFSS YAISWVRQAPGQGLE WMGRIIPILGIANYAQ KFQGRVTITADKSTST AYMELSSLRSEDTAVY YCANGGDSSSWYTFD YWGQGTLITVSS (SEQ ID NO: 75) | CSTKGPSVFPLAPSSKST SGGTAALGCLVKDYFPE PVTVSWNSGALTSGVHT FPAVLQSSGLYSLSSVVT VPSSSLGTQTYICNVNH KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEWESNGQPENN YKTTPPVLDSDGSFFLYS KLTVDKSRWQQGNVFS CSVMHEALHNHYTQKS LSLSPGK (SEQ ID NO: 76) |
| AB6.1 | SA2566.01 | CD276-039C05_LS_002B07_IgG1_A1C | Human IgG1-A1C | QVQLVESGAEVKKPG SSVKVSCKASGGTFSS YAISWVRQAPGQGLE WMGRIIPILGIANYAQ KFQGRVTITADKSTST AYMELSSLRSEDTAVY YCANGGDSSSWYTFD YWGQGTLITVSS (SEQ ID NO: 77) | CSTKGPSVFPLAPSSKST SGGTAALGCLVKDYFPE PVTVSWNSGALTSGVHT FPAVLQSSGLYSLSSVVT VPSSSLGTQTYICNVNH KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEWESNGQPENN YKTTPPVLDSDGSFFLYS KLTVDKSRWQQGNVFS CSVMHEALHNHYTQKS LSLSPGK (SEQ ID NO: 78) |
| AB7.1 | SA2571.01 | CD276-1 039C05_LS_002D03_IgG1_A1C | Human IgG1-A1C | QVQLVESGAEVKKPG SSVKVSCKASGGTFSS YAISWVRQAPGQGLE WMGRIIPILGIANYAQ KFQGRVTITADKSTST AYMELSSLRSEDTAVY YCANGGDSSSWYTFD YWGQGTLITVSS (SEQ ID NO: 79) | CSTKGPSVFPLAPSSKST SGGTAALGCLVKDYFPE PVTVSWNSGALTSGVHT FPAVLQSSGLYSLSSVVT VPSSSLGTQTYICNVNH KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEWESNGQPENN YKTTPPVLDSDGSFFLYS KLTVDKSRWQQGNVFS CSVMHEALHNHYTQKS LSLSPGK (SEQ ID NO: 80) |
| AB8.1 | SA2579.01 | CD276-039C05_LS_002H07_I | Human IgG1-A1C | QVQLVESGAEVKKPG SSVKVSCKASGGTFSS YAISWVRQAPGQGLE WMGRIIPILGIANYAQ KFQGRVTITADKSTST | CSTKGPSVFPLAPSSKST SGGTAALGCLVKDYFPE PVTVSWNSGALTSGVHT FPAVLQSSGLYSLSSVVT VPSSSLGTQTYICNVNH |

TABLE 31-continued

Thiomab heavy chain sequences of anti-B7-H3 antibodies generated using the Ymax-tEXPRESS system

| Clone ID | Clone SID | Clone name | Isoheavy | VH | CH |
|---|---|---|---|---|---|
| | | | | AYMELSSLRSEDTAVY YCANGGDSSSWYTFD YWGQGTLITVSS (SEQ ID NO 81) | KPSNTKVDKKVEPKSCD KTHTCPPCPAPELLGGPS VFLFPPKPKDTLMISRTP EVTCVVVDVSHEDPEV KFNWYVDGVEVHNAK TKPREEQYNSTYRVVSV LTVLHQDWLNGKEYKC KVSNKALPAPIEKTISKA KGQPREPQVYTLPPSRE EMTKNQVSLTCLVKGFY PSDIAVEWESNGQPENN YKTTPPVLDSDGSFFLYS KLTVDKSRWQQGNVFS CSVMHEALHNHYTQKS LSLSPGK (SEQ ID NO: 82) |

TABLE 32

Thiomab light chain sequences of anti-B7-H3 antibodies generated using the Ymax-tEXPRESS system

| Clone ID | Clone SID | Clone name | Isolight | VL | CL |
|---|---|---|---|---|---|
| AB1.1 AB1.2 | SA1319.01 | CD276-033E03_IgG1_A1C | Human Kappa-T2S | QSALTQPASVSGSPGQ SITISCTGTTRDVGGY NYVSWYQQHPGKAP KLMIYDVNNRPSGVS YRFSGSKSGNTASLTIS GLQAEDEADYYCSSY TTSSRRVFGTGTKVTV L (SEQ ID NO: 83) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 84) |
| AB2.1 | SA2107.01 | CD276-040F10_IgG1_A1C | Human Kappa-T2S | DIQMTQSPSSVSASVG DRVTISCRASQGIGTW LAWYQQKPGKAPRLL IYAASSLDSGVPSRFS ASGSGTDFTLTISSLQP EDFATYYCQQAINFPI TFGQGTRLEIK (SEQ ID NO: 85) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 86) |
| AB3.1 | SA2103.01 | CD276-039C05_IgG1_A1C | Human Kappa-T2S | DIQMTQSPSTLSASVG DKLTLTCRASQSISRW LAWYQQKPGKAPKLL IYKASYLQTGVPSRFS GSGTGTEFTLTISSLQP DDFATYYCQQYNTFP LTFAGGTKVEIK (SEQ ID NO: 87) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 88) |
| AB4.1 | SA2545.01 | CD276-039C05_LS_001E10_IgG1_A1C | Human Kappa-T2S | DIQMTQSPSTLSASVG DRVNITCRASQTINSW LAWYQQKPGKAPKLL IYKASYLQTGVPSRFS GSGAGTEFTLTISSLQP DDFATYYCQQYNSYS LTFGGGTKVEIK (SEQ ID NO 89) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 90) |
| AB5.1 | SA2563.01 | CD276-039C05_LS_002A11_1 | Human Kappa-T2S | DIQMTQSPSTLSASVG DRLTITCRASQNINSW LAWYQQKPGKAPKLL IYKASYLQTGVPSRFS GSGSGTEFTLTITSLQP DDFASYYCQQYDSNP LTFGGGTKVEIK (SEQ ID NO: 91) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 92) |

TABLE 32-continued

Thiomab light chain sequences of anti-B7-H3 antibodies generated using the Ymax-tEXPRESS system

| Clone ID | Clone SID | Clone name | Isolight | VL | CL |
|---|---|---|---|---|---|
| AB6.1 | SA2566.01 | CD276-039C05_LS_002B07_IgG1_A1C | Human Kappa-T2S | DIQMTQSPSSLSASVG DRVTITCRASQGISSYL AWYQQKPGKAPKLLI YAASTLQSGVPSRFSG SGSGTDFTLTISSLQPE DFATYYCQQYYSFPLT FGGGTKVEIK (SEQ ID NO: 93) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 94) |
| AB7.1 | SA2571.01 | CD276-039C05_LS_002D03_IgG1_A1C | Human Kappa-T2S | DIQMTQSPSTLSASVG DRVTITCRASETISSWL AWYQQKPGKAPKLLI YKASSLQSGVPSRFSG SGSGTEFTLTISSLQPD DFATYYCQQYYSYPIT FGQGTRLEIK (SEQ ID NO: 95) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 96) |
| AB8.1 | SA2579.01 | CD276-039C05_LS_002H07_IgG1_A1C | Human Kappa-T2S | DIQMTQSPSTLSASVG DRVTITCRASQSIDNW LAWYQQKPGKAPKLL IYKASSLQSGVPSRFS GSGSGTEFTLTISSLQP DDFASYYCQQYDSNP LTFGGGTKVEIK (SEQ ID NO: 97) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 98) |

TABLE 33

Heavy chain sequences of control anti-B7-H3 antibody

| Clone ID | Clone SID | Clone name | ISOHEAVY | VH | CH |
|---|---|---|---|---|---|
| AB9 | SC0041 | CD276-m8524 | Human IgG1 | QVQLQQSGAEVKKPG SSVKVSCKASGGTFSS YAISWVRQAPGQGLE WMGGIIPILGIANYAQ KFQGRVTITADESTST AYMELSSLRSEDTAV YYCARGGSGSYEIMD VWGKGTTVTVSS (SEQ ID NO: 99) | ASTKGPSVFPLAPSSKSTSG GTAALGCLVKDYFPEPVTV SWNSGALTSGVHTFPAVLQ SSGLYSLSSVVTVPSSSLGT QTYICNVNHKPSNTKVDKK VEPKSCDKTHTCPPCPAPEL LGGPSVFLFPPKPKDTLMIS RTPEVTCVVVDVSHEDPEV KFNWYVDGVEVHNAKTKP iREEQYNSTYRVVSVLTVLH QDWLNGKEYKCKVSNKAL PAPIEKTISKAKGQPREPQV YTLPPSREEMTKNQVSLTC LVKGFYPSDIAVEWESNGQ PENNYKTTPPVLDSDGSFFL YSKLTVDKSRWQQGNVFS CSVMHEALHNHYTQKSLSL SPGK (SEQ ID NO: 100) |
| AB9.1 | SC0041.01 | CD276-m8524_IgG1_A1C | Human IgG1-A1C | QVQLQQSGAEVKKPG SSVKVSCKASGGTFSS YAISWVRQAPGQGLE WMGGIIPILGIANYAQ KFQGRVTITADESTST AYIVIELSSLRSEDTAV YYCARGGSGSYEIMD VWGKGTTVTVSS (SEQ ID NO 101) | CSTKGPSVFPLAPSSKSTSG GTAALGCLVKDYFPEPVTV SWNSGALTSGVHTFPAVLQ SSGLYSLSSVVTVPSSSLGT QTYICNVNHKPSNTKVDKK VEPKSCDKTHTCPPCPAPEL LGGPSVFLFPPKPKDTLMIS RTPEVTCVVVDVSHEDPEV KFNWYVDGVEVHNAKTKP REEQYNSTYRVVSVLTVLH QDWLNGKEYKCKVSNKAL PAPIEKTISKAKGQPREPQV YTLPPSREEMTKNQVSLTC LVKGFYPSDIAVEWESNGQ PENNYKTTPPVLDSDGSFFL YSKLTVDKSRWQQGNVFS |

TABLE 33-continued

Heavy chain sequences of control anti-B7-H3 antibody

| Clone ID | Clone SID | Clone name | ISOHEAVY | VH | CH |
|---|---|---|---|---|---|
| | | | | | CSVMHEALHNHYTQKSLSL SPGK (SEQ ID NO: 102) |
| AB9.2 | SC0041.02 | CD276-m8524_IgG1_S325C | Human IgG1-S325C | QVQLQQSGAEVKKPG SSVKVSCKASGGTFSS YAISWVRQAPGQGLE WMGGIIPILGIANYAQ KFQGRVTITADESTST AYMELSSLRSEDTAV YYCARGGSGSYHMD VWGKGTTVTVSS (SEQ ID NO: 103) | ASTKGPSVFPLAPSSKSTSG GTAALGCLVKDYFPEPVTV SWNSGALTSGVHTFPAVLQ SSGLYSLSSVVTVPSSSLGT QTYICNVNHKPSNTKVDKK VEPKSCDKTHTCPPCPAPEL LGGPSVFLFPPKPKDTLMIS RTPEVTCVVVDVSHEDPEV KFNWYVDGVEVHNAKTKP REEQYNSTYRVVSVLTVLH QDWLNGKEYKCKVSNKAL PAPIEKTISKAKGQPREPQV YTLPPSREEMTKNQVSLTC LVKGFYPSDIAVEWESNGQ PENNYKTTPPVLDSDGSFFL YSKLTVDKSRWQQGNVFS CSVMHEALHNHYTQKSLC LSPGK (SEQ ID NO: 104) |

TABLE 34

Light chain sequences of control anti-B7-H3 antibody

| Clone ID | Clone SID | Clone name | ISOLIGHT | VL | CL |
|---|---|---|---|---|---|
| AB9 | SC0041 | CD276-m8524 | Human Kappa-T2S | EIVLTQSPATLSLSPGE RATLSCRASQSVSSYL AWYQQKPGQAPRLLI YDASNRATGIPARFSG SGSGTDFTLTISSLEPE DFAVYYCQQRSNWPP RITFGQGTRLEIK (SEQ ID NO: 105) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 106) |
| AB9.1 AB9.2 | SC0041.01 | CD276-m8524_IgG1_A1C | Human Kappa-T2S | EIVLTQSPATLSLSPGE RATLSCRASQSVSSYL AWYQQKPGQAPRLLI YDASNRATGIPARFSG SGSGTDFTLTISSLEPE DFAVYYCQQRSNWPP RITFGQGTRLEIK (SEQ ID NO 107) | RSVAAPSVFIFPPSDEQLKS GTASVVCLLNNFYPREAKV QWKVDNALQSGNSQESVT EQDSKDSTYSLSSTLTLSKA DYEKHKVYACEVTHQGLS SPVTKSFNRGEC (SEQ ID NO: 108) |

TABLE 35

Summary of anti-B7-H3 Antibodies and Thiomabs

| Clone ID | SID | Engineered cysteine | Clone name |
|---|---|---|---|
| AB1 | SA1319 | — | CD276-033E03 |
| AB1.1 | SA1319.01 | A1C | CD276-033E03_IgG1_A1C |
| AB1.2 | SA1319.02 | S325C | CD276-033E03_IgG1_S325C |
| AB2 | SA2107 | — | CD276-040F10 |
| AB2.1 | SA2107.01 | A1C | CD276-040F10_IgG1_A1C |
| AB3 | SA2103 | — | CD276-039C05 |
| AB3.1 | SA2103.01 | A1C | CD276-039C05_IgG1_A1C |
| AB4 | SA2545 | — | CD276-39C05-LS-001E10 |
| AB4.1 | SA2545.01 | A1C | CD276-39C05-LS-001E10_IgG1_A1C |
| AB5 | SA2563 | — | CD276-39C05-LS-002A11 |
| AB5.1 | SA2563.01 | A1C | CD276-39C05-LS-002A11_IgG1_A1C |
| AB6 | SA2566 | — | CD276-39C05-LS-002B07 |
| AB6.1 | SA2566.01 | A1C | CD276-39C05-LS-002B07_IgG1_A1C |
| AB7 | SA2571 | — | CD276-39C05-LS-002D03 |
| AB7.1 | SA2571.01 | A1C | CD276-39C05-LS-002D03_IgG1_A1C |
| AB8 | SA2579 | — | CD276-39C05-LS-002H07 |
| AB8.1 | SA2579.01 | A1C | CD276-39C05-LS-002H07_IgG1_A1C |
| AB9 | SC0041 | — | CD276-m8524 |
| AB9.1 | SC0041.01 | A1C | CD276-m8524_IgG1_A1C |
| AB9.2 | SC0041.02 | S325C | CD276-m8524_IgG1_S325C |

Example 12: In Vitro Binding Affinity of Anti-B7-H3 Monoclonal Antibody

The binding affinity of the purified anti-B7-H3 monoclonal antibodies was determined by BLI-based OCTET or SPR-based Biacore. The binding kinetics of the selected anti-B7-H3 mAbs by OCTET are shown in Table 36. Further the binding kinetics of the antibodies binding to human, cynomolgus monkey and mouse B7-H3 antigen are shown in Table 37.

TABLE 36

OCTET kinetics of anti-B7-H3 antibodies

| Clone ID | SID | Clone name | $K_D$ (M) | Kon (1/Ms) | Koff (1/s) |
|---|---|---|---|---|---|
| AB1 | SA1319 | CD276-033E03 | $2 \times 10E - 9$ | $1 \times 10E + 6$ | $2 \times 10E - 4$ |
| AB2 | SA2107 | CD276-040F10 | $5 \times 10E - 11$ | $7 \times 10E + 5$ | $4 \times 10E - 5$ |
| AB2.1 | SA2107.01 | CD276-040F10_IgG1_A1C | $5 \times 10E - 11$ | $5 \times 10E + 5$ | $12 \times 10E - 5$ |
| AB3 | SA2103 | CD276-039C05 | $4 \times 10E - 11$ | $6 \times 10E + 5$ | $13 \times 10E - 5$ |
| AB4 | SA2545 | CD276-39C05-LS-001E10 | $6 \times 10E - 11$ | $1 \times 10E + 6$ | $17 \times 10E - 5$ |
| AB5 | SA2563 | CD276-39C05_LS_002A11 | $1 \times 10E - 10$ | $1 \times 10E + 6$ | $2 \times 10E - 4$ |
| AB6 | SA2566 | CD276-39C05-LS-002B07 | $2 \times 10E - 10$ | $3 \times 10E + 6$ | $16 \times 10E - 4$ |
| AB7 | SA2571 | CD276-39C05_LS_002D03 | $3 \times 10E - 10$ | $2 \times 10E + 6$ | $15 \times 10E - 4$ |
| AB8 | SA2579 | CD276-39C05-LS-002H07 | $3 \times 10E - 10$ | $9 \times 10E + 5$ | $3 \times 10E - 4$ |
| AB9 | SC0041 | CD276-m8524 | $3 \times 10E - 10$ | $5 \times 10E + 5$ | $2 \times 10E - 4$ |

Method: OCTET Binding Kinetics

A ForteBio Octet QKe instrument was used to measure binding kinetics of human B7-H3 to anti-B7-H3 antibodies. The Octet QKe system is based on BLI (Bio-Layer Interferometry), a label-free biosensor technology that measures molecular interactions in real-time for the purpose of kinetic analysis.

AHC (Anti-hIgG capture) biosensors (ForteBio Inc, 18-5060) were equilibrated in 1× Kinetic Buffer (Fortebio Inc.) for 10 minutes, and human B7-H3 (Y-Biologics Inc.) were prepared as a 2-fold serial dilution (0.94 nM~30 nM) in 1× Kinetic Buffer. B7-H3 antibody ligands were loaded onto AHC biosensors at 10 μg/ml until an optical shift of 1.5 nanometer was achieved. After loading, the biosensors were baselined and associated in defined concentrations of human B7-H3 for 10 minutes, and then dissociated in the buffer for 10 minutes. The entire experiment was performed at 30° C. with the 96-well, black, flat bottom, polypropylene microplate (Greiner Bio-One part no. 655209) shaking at the speed of 1,000 rpm. The final volume for all solutions was 200 μl per well.

All measurements were corrected for baseline drift by subtracting a control sensor exposed to running buffer only. A non-specific binding test was performed by using a blank sensor to check if there is a binding of an anti-B7-H3 antibody to the sensor surface.

Data analysis and curve fitting were carried out using Octet data analysis software 9.0. The data obtained was processed to determine the overlaid fits and the $K_D$, Kon and Koff values. The reference well was subtracted from the analyte wells for buffer artifacts. Then y-axis alignment, inter-step correction, and Savitzky-Golay filtering were also applied to the data. The processed data was then allowed to fit a curve for association and dissociation using a 1:1 model fitting with global fitting. The baseline-corrected binding curves were analyzed with GraphPad Prism 8.

TABLE 37

Biacore kinetics of anti-B7-H3 antibodies binding to human, cynomolgus monkey, and mouse B7-H3

| Immobilized ligand | Analyte | Ka ($M^{-1}s^{-1}$) | Kd ($s^{-1}$) | $K_D$ (M) |
|---|---|---|---|---|
| SC0041 | Human 4IgB7-H3 | 1.19E + 06 | 6.17E − 04 | 5.18E − 10 |
|  | Human 2IgB7-H3 | 5.15E + 05 | 1.07E − 01 | 2.08E − 07 |
| SA2107 | Cyno B7-H3 | 8.71E + 05 | 2.42E − 04 | 2.78E − 10 |
|  | Mouse B7-H3 | 6.00E + 05 | 2.94E − 02 | 4.90E − 08 |
|  | Human 4IgB7-H3 | 4.46E + 05 | 1.99E − 04 | 4.46E − 10 |
|  | Human 2IgB7-H3 | 2.06E + 05 | 5.15E − 03 | 2.50E − 08 |
| SA2107.01 | Cyno B7-H3 | 4.81E + 05 | 4.42E − 04 | 9.19E − 10 |
|  | Mouse B7-H3 | 4.08E + 05 | 1.93E − 02 | 4.73E − 08 |
|  | Human 4IgB7-H3 | 4.42E + 05 | 4.70E − 04 | 1.06E − 09 |
|  | Human 2IgB7-H3 | 2.17E + 05 | 4.69E − 03 | 2.16E − 08 |
|  | Cyno B7-H3 | 4.80E + 05 | 5.04E − 04 | 1.05E − 09 |
|  | Mouse B7-H3 | 4.20E + 05 | 1.78E − 02 | 4.24E − 08 |

Method: Biacore Binding Kinetics

A Biacore 8K (GE Life science) instrument was used to measure the binding kinetics about several B7-H3 variants (analyte) binding to various mAbs (ligands). Antibodies were captured onto the immobilized anti-human Fc antibody (GE Life science). Anti-Fc antibodies were immobilized to approximately 7,000 RU on CM5 sensor chip using a standard amine coupling method on both active cell and reference cell. For binding kinetic measurements, the HBS-EP+ was used for running buffer (10 mM Hepes, pH7.4, 150 mM NaCl, 3 mM EDTA, 0.05% polysorbate20). Anti-B7-H3 antibodies were diluted to 0.5 ug/mL in running buffer and injected for 110 s on active cells only. After capturing ligand, various B7-H3 antigens were analyzed for 120 s and the dissociation was monitored for 600 s at a flow rate of 30 ul/min. 3M $MgCl_2$ solution was injected on both active cell and reference cell for 30 s at 30 ul/min for regeneration. For the kinetic analysis, 5 points of 2-fold diluted analytes were flown over the captured ligand ranging from 20 nM of human 4Ig B7-H3 (Y-Biologics Inc.), 320 nM of human 2Ig B7-H3 (Acrobiosystems), 40 nM of cynomolgus monkey B7-H3 (Sino biological Inc.), and 160 nM of mouse B7-H3

(Sino biological Inc.). Kinetic information was calculated by fitting data to a 1:1 binding model using Biacore Insight Evaluation software (GE Life Science) to determine ka (association constant), kd (dissociation constant), and KD (equilibrium dissociation constant).

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. A antibody conjugate represented by Formula I or pharmaceutically acceptable salt or solvate thereof:

$$Ab-(G)_n \qquad \text{Formula I}$$

wherein:
Ab is an anti-B7-H3 antibody or antigen-binding fragment thereof comprising a variable heavy chain complementarity determining region 1 (CDRH1), a variable heavy chain complementarity determining region 2 (CDRH2), a variable heavy chain complementarity determining region 3 (CDRH3), a variable light chain complementarity determining region 1 (CDRL1), a variable light chain complementarity determining region 2 (CDRL2), and a variable light chain complementarity determining region 3 (CDRL3); wherein,
CDRH1 comprises an amino acid sequence of SEQ ID NO: 1,
CDRH2 comprises an amino acid sequence of SEQ ID NO: 2,
CDRH3 comprises an amino acid sequence of SEQ ID NO: 3,
CDRL1 comprises an amino acid sequence of SEQ ID NO: 4,
CDRL2 comprises an amino acid sequence of SEQ ID NO: 5, and
CDRL3 comprises an amino acid sequence of SEQ ID NO: 6; or
CDRH1 comprises an amino acid sequence of SEQ ID NO: 7,
CDRH2 comprises an amino acid sequence of SEQ ID NO: 8,
CDRH3 comprises an amino acid sequence of SEQ ID NO: 9,
CDRL1 comprises an amino acid sequence of SEQ ID NO: 10,
CDRL2 comprises an amino acid sequence of SEQ ID NO: 11, and
CDRL3 comprises an amino acid sequence of SEQ ID NO: 12; or
CDRH1 comprises an amino acid sequence of SEQ ID NO: 13,
CDRH2 comprises an amino acid sequence of SEQ ID NO: 14,
CDRH3 comprises an amino acid sequence of SEQ ID NO: 15,
CDRL1 comprises an amino acid sequence of SEQ ID NO: 16,
CDRL2 comprises an amino acid sequence of SEQ ID NO: 17, and
CDRL3 comprises an amino acid sequence of SEQ ID NO: 18; or
CDRH1 comprises an amino acid sequence of SEQ ID NO: 19,
CDRH2 comprises an amino acid sequence of SEQ ID NO: 20,
CDRH3 comprises an amino acid sequence of SEQ ID NO: 21,
CDRL1 comprises an amino acid sequence of SEQ ID NO: 22,
CDRL2 comprises an amino acid sequence of SEQ ID NO: 23, and
CDRL3 comprises an amino acid sequence of SEQ ID NO: 24; or
CDRH1 comprises an amino acid sequence of SEQ ID NO: 25,
CDRH2 comprises an amino acid sequence of SEQ ID NO: 26,
CDRH3 comprises an amino acid sequence of SEQ ID NO: 27,
CDRL1 comprises an amino acid sequence of SEQ ID NO: 28,
CDRL2 comprises an amino acid sequence of SEQ ID NO: 29, and
CDRL3 comprises an amino acid sequence of SEQ ID NO: 30; or CDRH1 comprises an amino acid sequence of SEQ ID NO: 31,
CDRH2 comprises an amino acid sequence of SEQ ID NO: 32,
CDRH3 comprises an amino acid sequence of SEQ ID NO: 33,
CDRL1 comprises an amino acid sequence of SEQ ID NO: 34,
CDRL2 comprises an amino acid sequence of SEQ ID NO: 35, and
CDRL3 comprises an amino acid sequence of SEQ ID NO: 36; or
CDRH1 comprises an amino acid sequence of SEQ ID NO: 37,
CDRH2 comprises an amino acid sequence of SEQ ID NO: 38,
CDRH3 comprises an amino acid sequence of SEQ ID NO: 39,
CDRL1 comprises an amino acid sequence of SEQ ID NO: 40,
CDRL2 comprises an amino acid sequence of SEQ ID NO: 41, and
CDRL3 comprises an amino acid sequence of SEQ ID NO: 42; or
CDRH1 comprises an amino acid sequence of SEQ ID NO: 43,
CDRH2 comprises an amino acid sequence of SEQ ID NO: 44,
CDRH3 comprises an amino acid sequence of SEQ ID NO: 45,
CDRL1 comprises an amino acid sequence of SEQ ID NO: 46,
CDRL2 comprises an amino acid sequence of SEQ ID NO: 47,
CDRL3 comprises an amino acid sequence of SEQ ID NO: 48;
and further wherein:
each G is, independently, a chemical moiety comprising one or more active agents and a linker, wherein the linker links Ab to the active agent(s); and
n is an integer between 1 to 20.

2. The antibody conjugate of claim 1, wherein Ab further comprises a combination of a variable heavy chain sequence and a variable light chain sequence selected from:
   (a) a variable heavy chain comprising the amino acid sequence of SEQ ID NO: 49 and a variable light chain comprising the amino acid sequence of SEQ ID NO: 50;
   (b) a variable heavy chain comprising the amino acid sequence of SEQ ID NO: 51, and a variable light chain comprising the amino acid sequence of SEQ ID NO: 52;
   (c) a variable heavy chain comprising the amino acid sequence of SEQ ID NO: 53 and a variable light chain comprising the amino acid sequence of SEQ ID NO: 54;
   (d) a variable heavy chain comprising the amino acid sequence of SEQ ID NO: 55 and a variable light chain comprising the amino acid sequence of SEQ ID NO: 56;
   (e) a variable heavy chain comprising the amino acid sequence of SEQ ID NO: 57 and a variable light chain comprising the amino acid sequence of SEQ ID NO: 58;
   (f) a variable heavy chain comprising the amino acid sequence of SEQ ID NO: 59 and a variable light chain comprising the amino acid sequence of SEQ ID NO: 60;
   (g) a variable heavy chain comprising the amino acid sequence of SEQ ID NO: 61 and a variable light chain comprising the amino acid sequence of SEQ ID NO: 62; and
   (h) a variable heavy chain comprising the amino acid sequence of SEQ ID NO: 63 and a variable light chain comprising the amino acid sequence of SEQ ID NO: 64.

3. The antibody conjugate of claim 1, wherein the anti-B7-H3 antibody is AB1, AB2, AB3, AB4, AB5, AB6, AB7, AB8, AB1.1, AB2.1, AB3.1, AB4.1, AB5.1, AB6.1, AB7.1, or AB8.1.

4. The antibody conjugate of claim 1, wherein the B7-H3 is human B7-H3.

5. The antibody conjugate of claim 1, wherein Ab is a monoclonal antibody, a domain antibody (dAb), a single chain antibody (scAb), a Fab fragment, a F (ab') 2 fragment, a single chain variable fragment (scFv), a scFv-Fc fragment, a single domain heavy chain antibody, a single domain light chain antibody, a variant antibody, or a multimeric antibody.

6. The antibody conjugate of claim 1, wherein Ab is a rabbit, mouse, chimeric, humanized or fully human monoclonal antibody.

7. The antibody conjugate of claim 1, wherein Ab is an IgG isotype.

8. The antibody conjugate of claim 1, wherein Ab is an IgG1 isotype.

9. The antibody conjugate of claim 1, wherein the link between Ab and the active agent is cleavable.

10. The antibody conjugate of claim 1, wherein G is represented by Formula II:

$$(Q')_q-(L')_w-\overset{\overset{TG}{\underset{\|}{O}}}{\underset{\underset{\|}{O}}{S}}-X-\overset{\overset{(Y')_x}{|}}{Ar}-Z'-\xi \quad , \tag{II}$$

wherein:
each Q' is independently an active agent linked to L' by a heteroatom;
Z' is a linking group;
L' is a spacer moiety attached to the $SO_2$ via a heteroatom selected from O, S, and N, and is selected such that cleavage of the bond between L' and $SO_2$ promotes cleavage of the bond between L' and Q' to release the active agent;
X is —O—, —$C(R^b)_2$—, or —$N(R^c)$—;
Ar represents a ring, such as aryl, heteroaryl, cycloalkyl, or heterocycloalkyl;
Y' is —$(CR^b{}_2)_y N(R^a)$—, —$(CR^b{}_2)_y O$—, or —$(CR^b{}_2)_y S$—, positioned such that the N, O, or S atom is attached to TG if y is 1;
X and Y' are positioned on adjacent atoms of Ar;
TG is a triggering group that, when activated, generates an N, O, or S atom capable of reacting with the $SO_2$ to displace $(Q')_q-(L')_w$ and form a 5-6-membered ring including X-$SO_2$ and the intervening atoms of Ar;
q is an integer having a value from 1 to about 20;
w, x, and y are each independently an integer having a value of 0 or 1;

each $R^a$ and $R^c$ is independently hydrogen or lower alkyl; and each $R^b$ is independently hydrogen or lower alkyl; or two $R^b$, together with the atom to which they are attached, form a 3-5-membered ring;

provided that when w is 0, q is 1.

11. The antibody conjugate of claim 1, wherein Ab-(G)$_n$ is represented by a compound of formula (III):

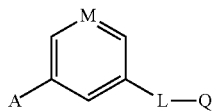
(III)

or a salt thereof, wherein:

A is

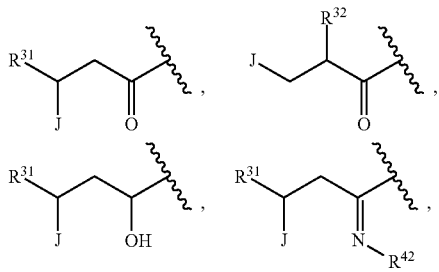

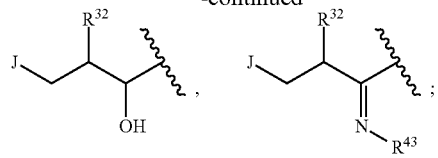

M is N, $CR^{30}$, or C (-L-Q);

each L is independently a spacer moiety;

each Q is independently an active agent;

J is the anti-B7-H3 antibody or antigen-binding fragment thereof;

$R^{30}$ and $R^{31}$ are each independently selected from an electron-withdrawing group, hydrogen, alkyl, alkenyl, alkynyl, aryl, heteroaryl, carbocyclyl, heterocyclyl, and haloalkyl;

$R^{42}$ and $R^{43}$ are each independently selected from —OH, alkoxy, —$NR^{44}R^{45}$, alkyl, alkenyl, alkynyl, aryl, heteroaryl, carbocyclyl, and heterocyclyl, wherein $R^{44}$ and $R^{45}$ together with the nitrogen atom to which they are attached can form a 5-8-membered cycle, optionally fused with an aryl or a heteroaryl ring;

$R^{32}$, $R^{44}$, and $R^{45}$ are each independently selected from hydrogen, alkyl, alkenyl, alkynyl, aryl, heteroaryl, carbocyclyl, heterocyclyl, and haloalkyl; and n is 1 to 4.

12. The antibody conjugate of claim 10, wherein Z' is selected from

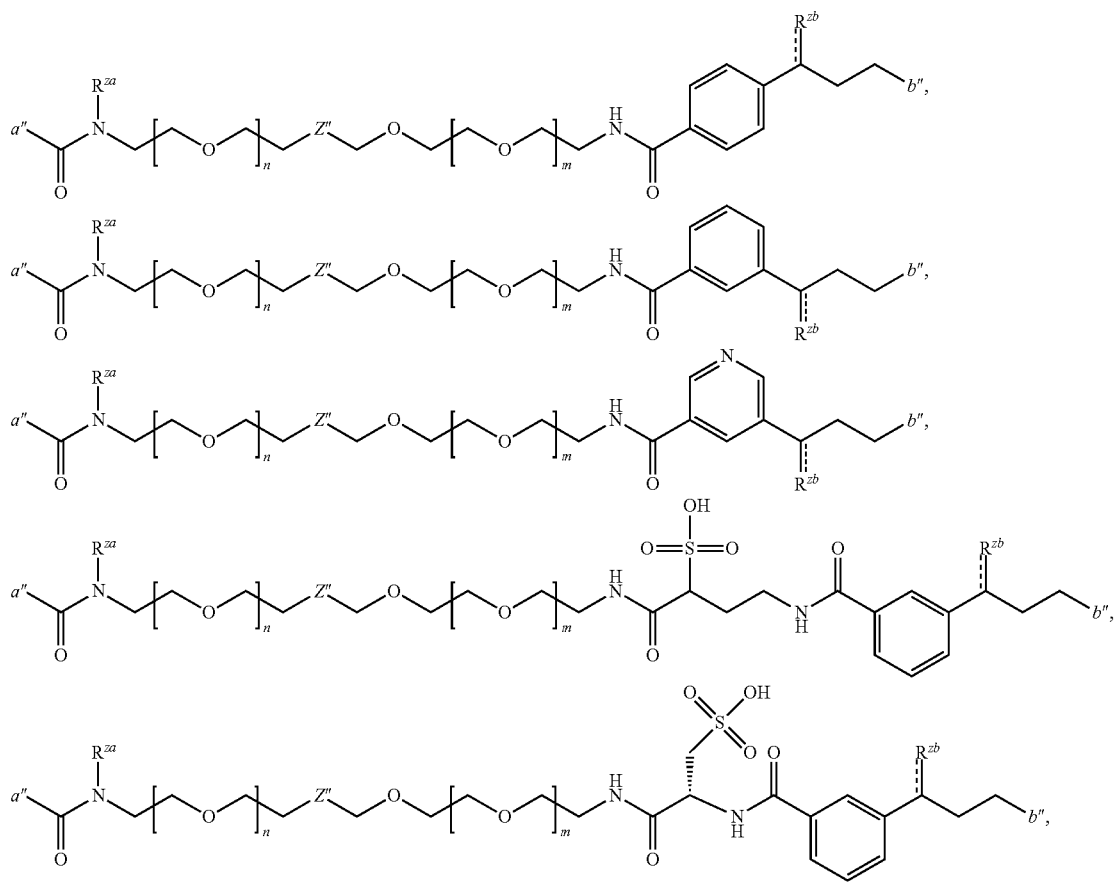

-continued
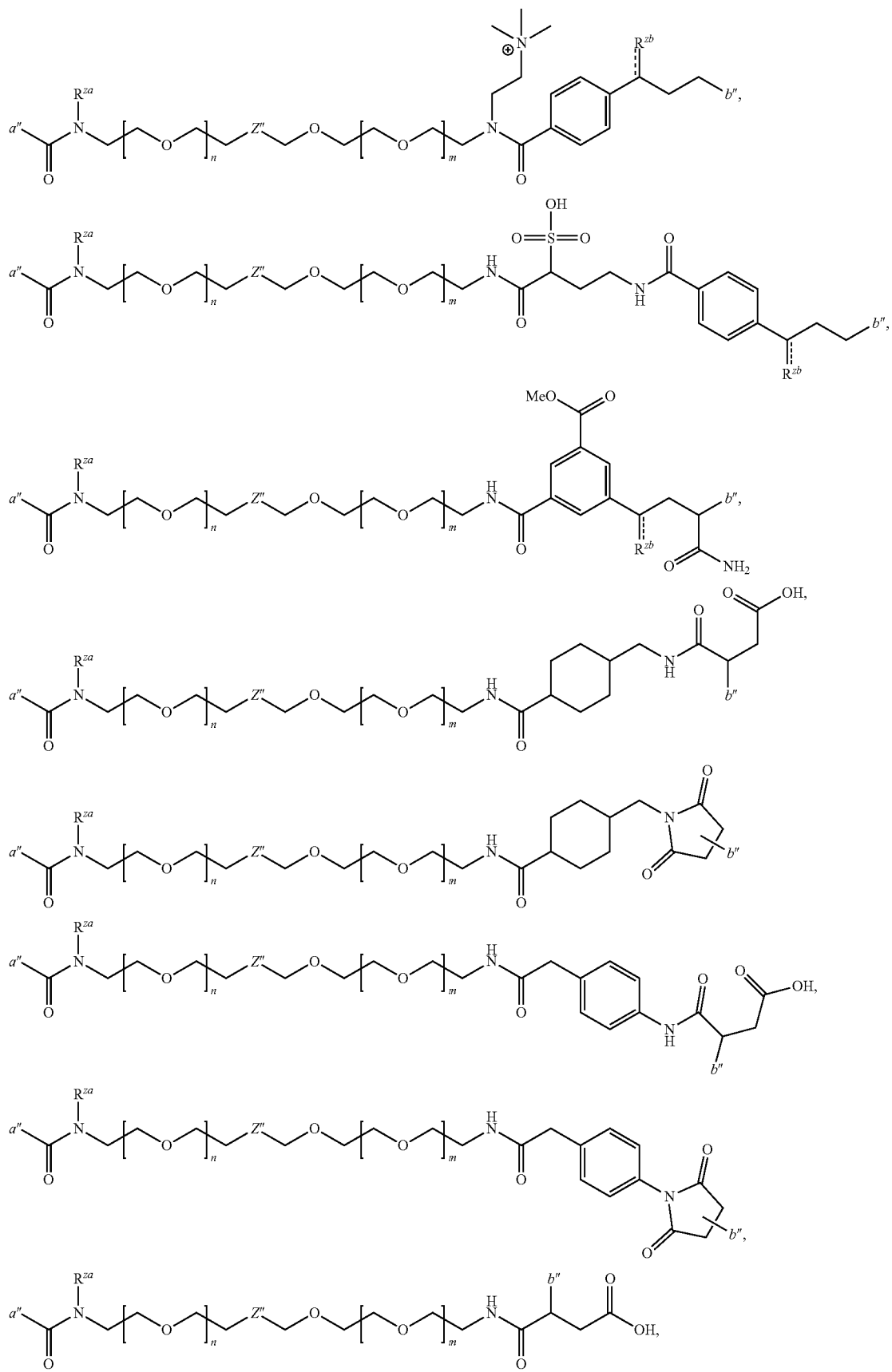

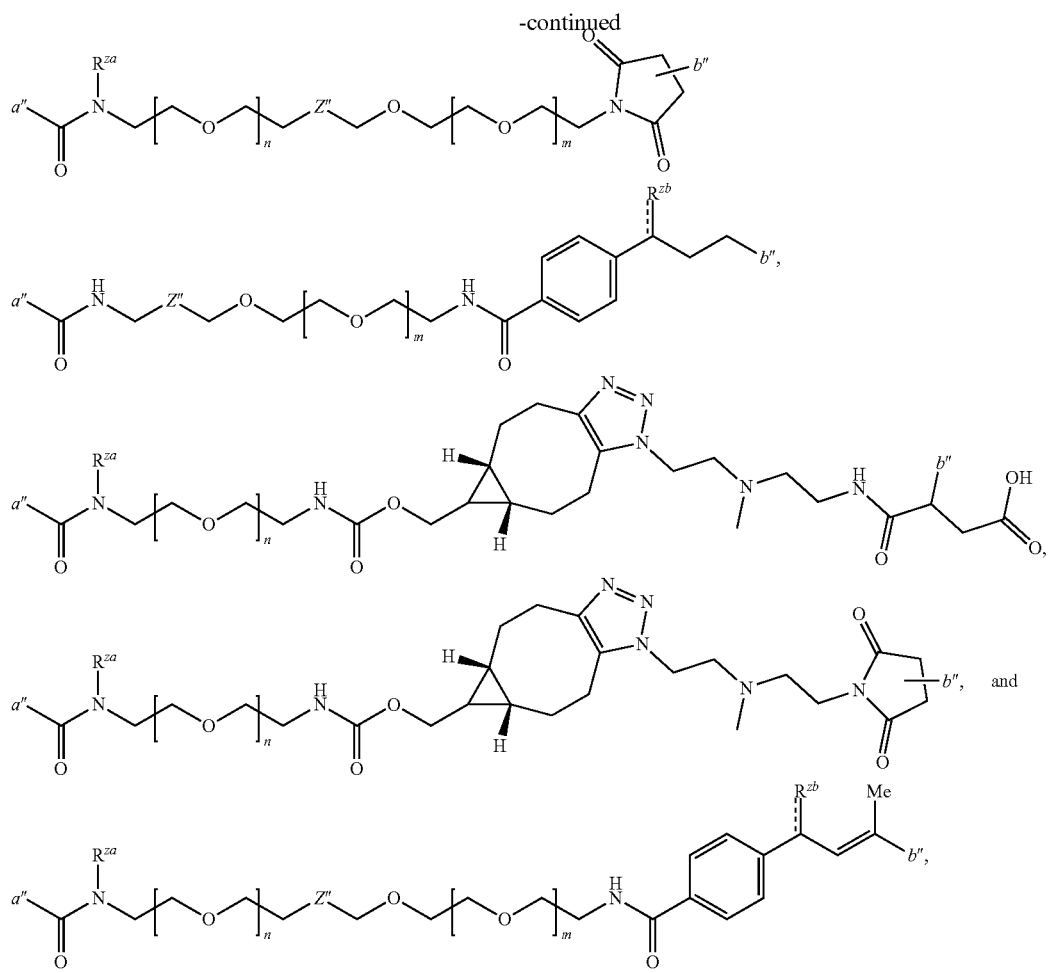
wherein
$R^{za}$ is H or methyl;
$R^{zb}$ is —OH, =O, or =NHOH;
------- a single bond or a double bond;
a" represents the bond between Z' and Ar of Formula (II);
b" represents the bond between Z' and Ab; and
Z" is selected from
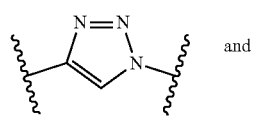 and
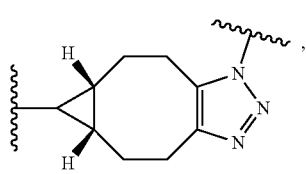
oriented in either direction.
13. The antibody conjugate of claim 10, wherein G comprises a moiety selected from the following:
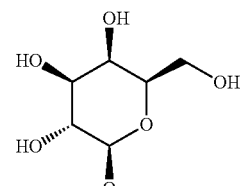
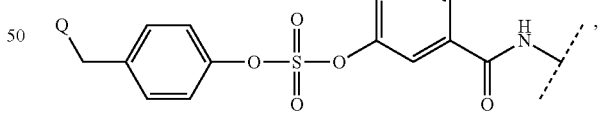
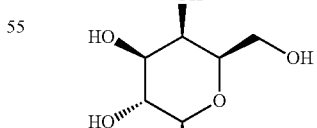
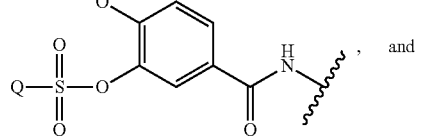, and -continued
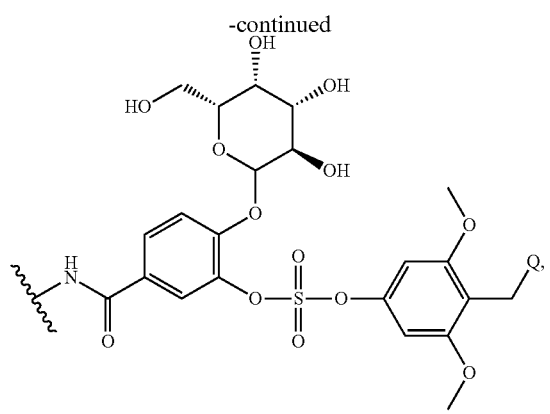
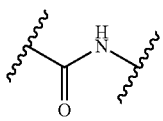
wherein
Q is an active agent, and
is a fragment of Z' connecting Z' to Ar.
14. The antibody conjugate of claim 10, wherein G comprises a moiety selected from the following:
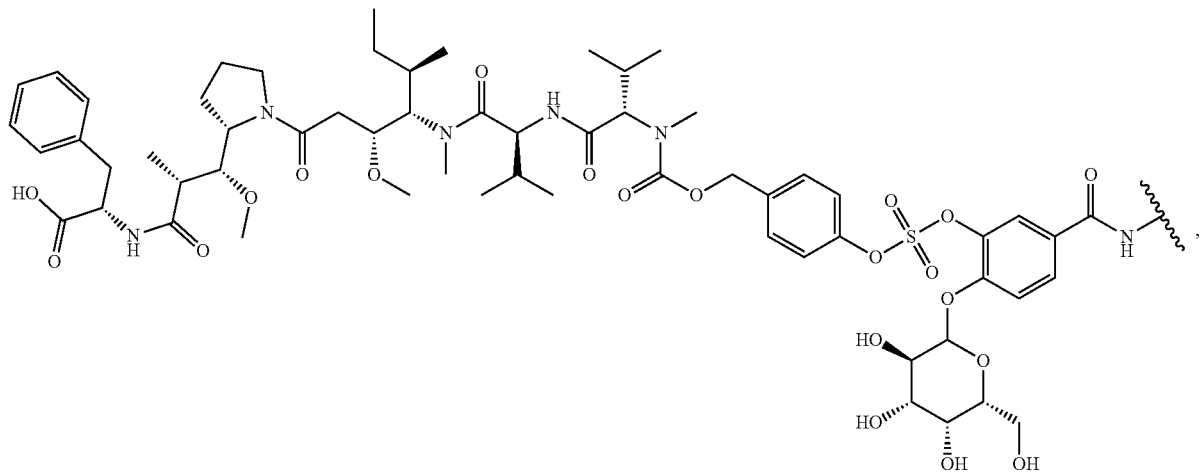
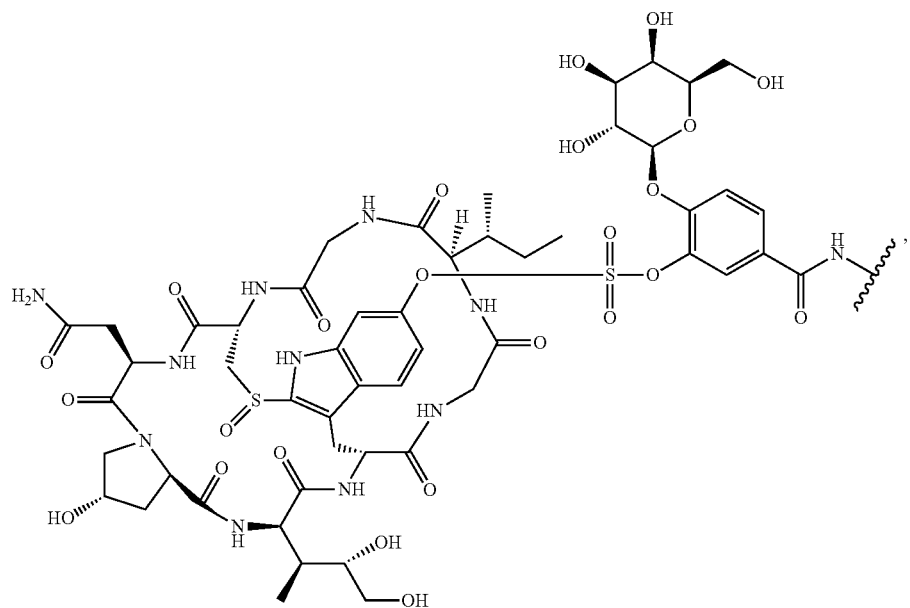

-continued
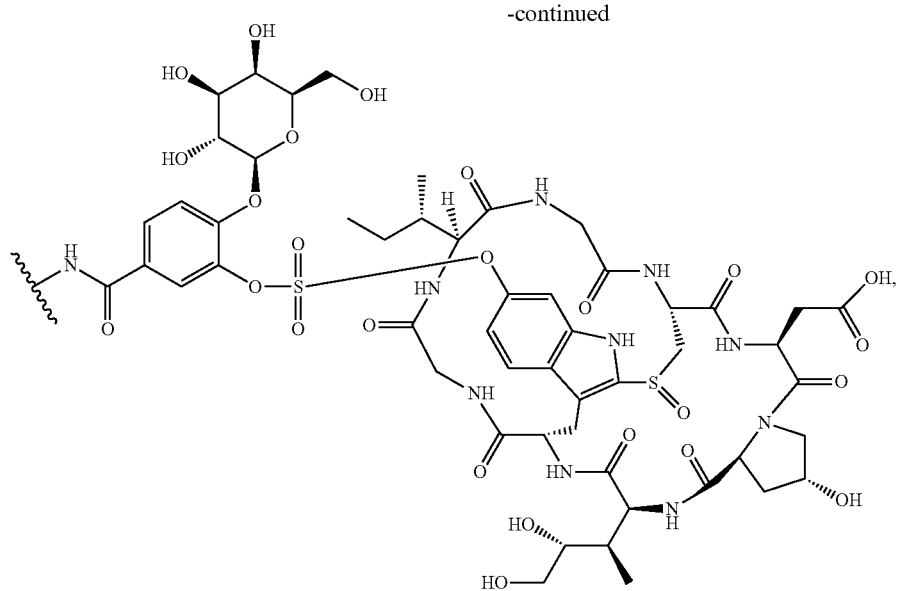
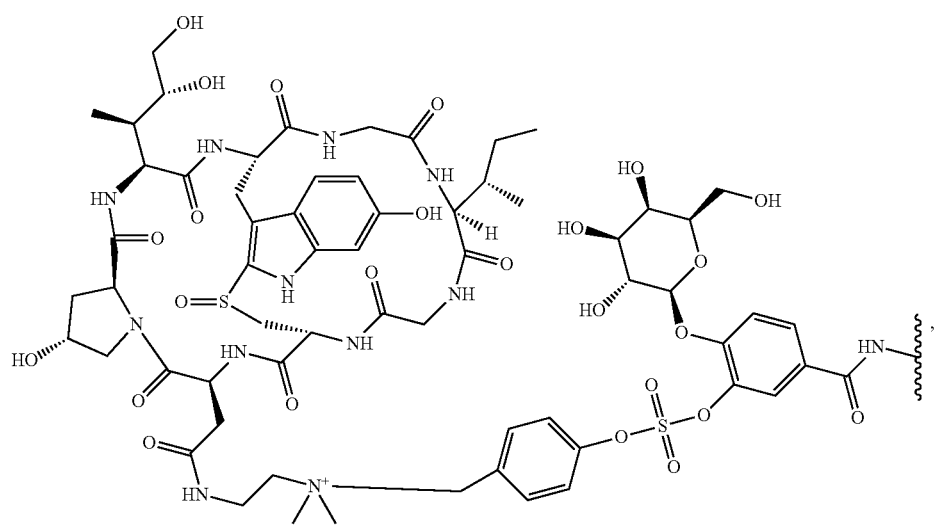
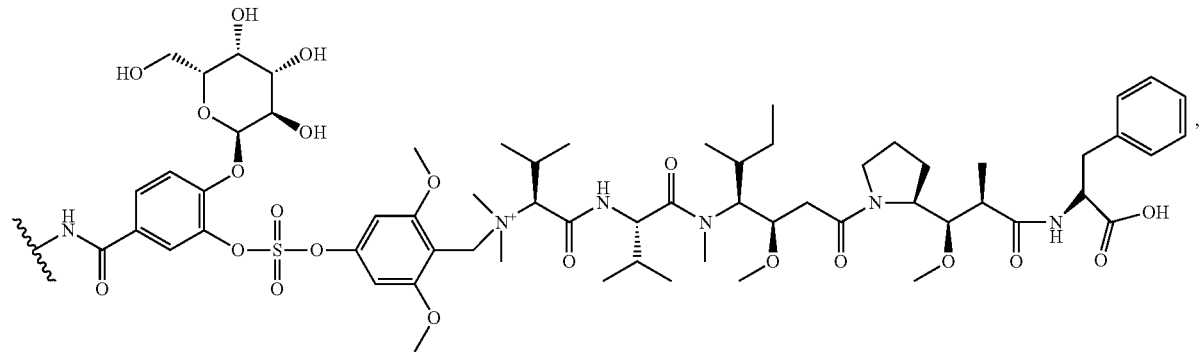

601
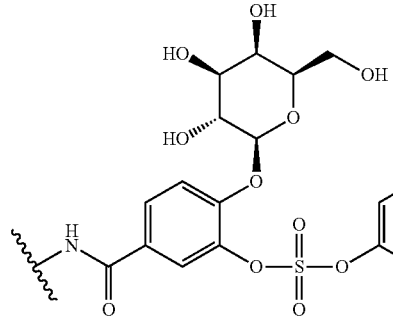
602
-continued
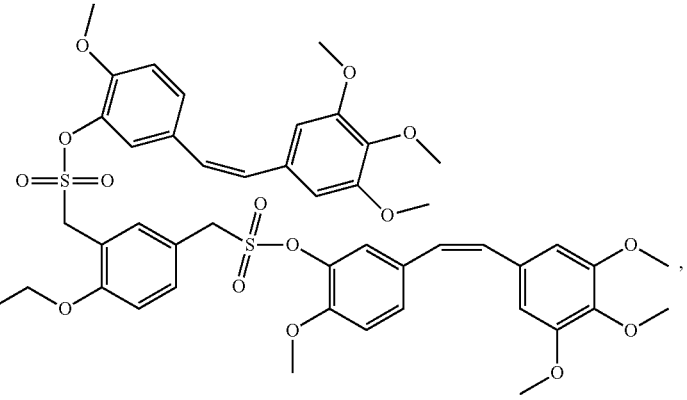
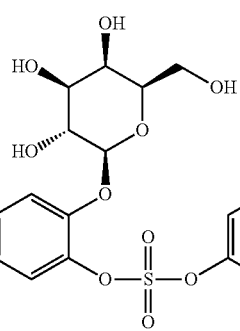
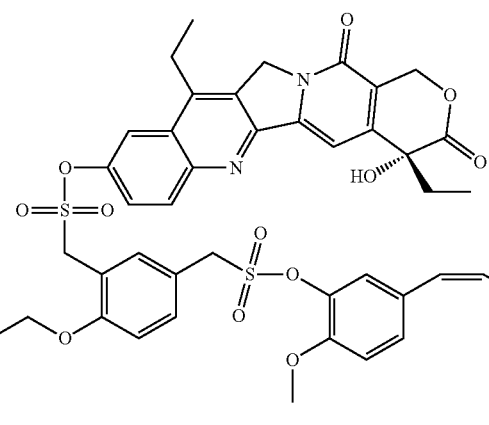
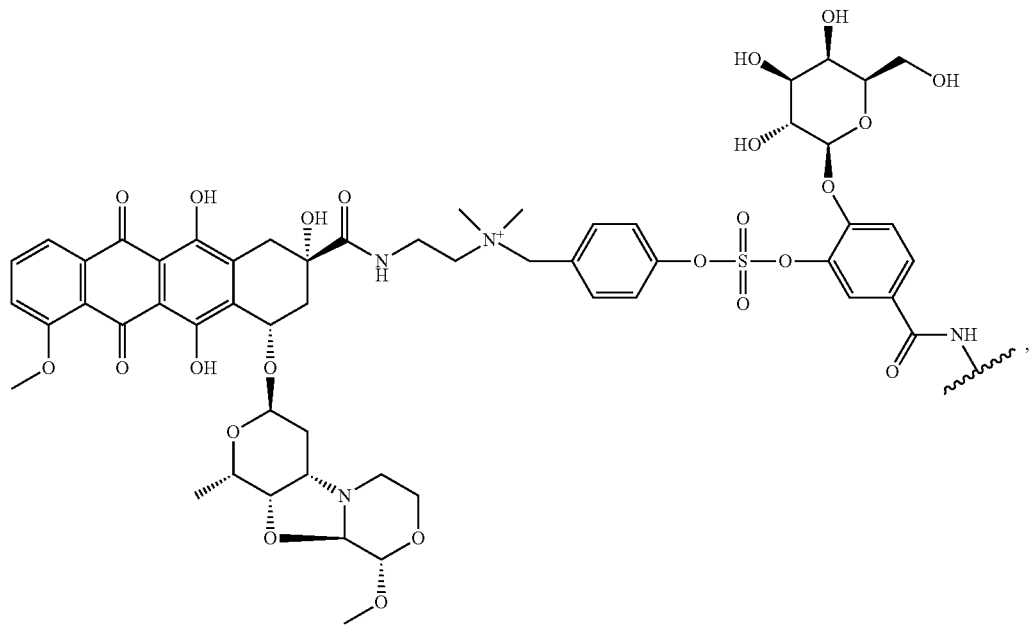

-continued
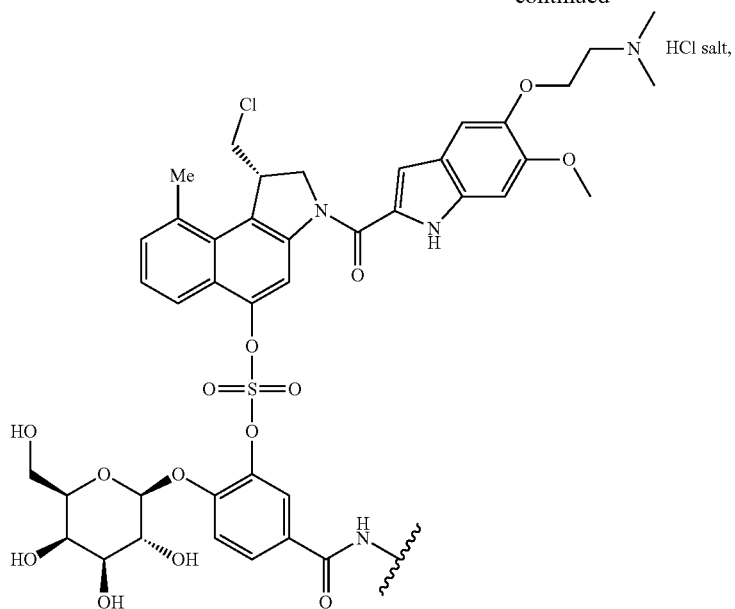 HCl salt,
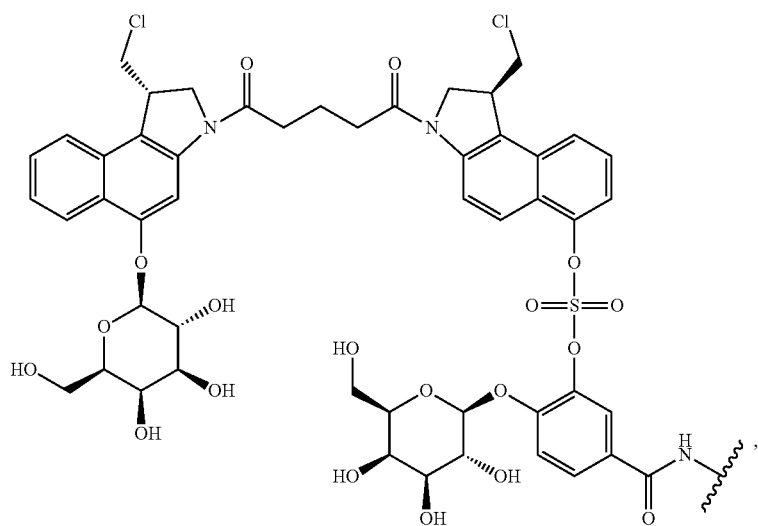
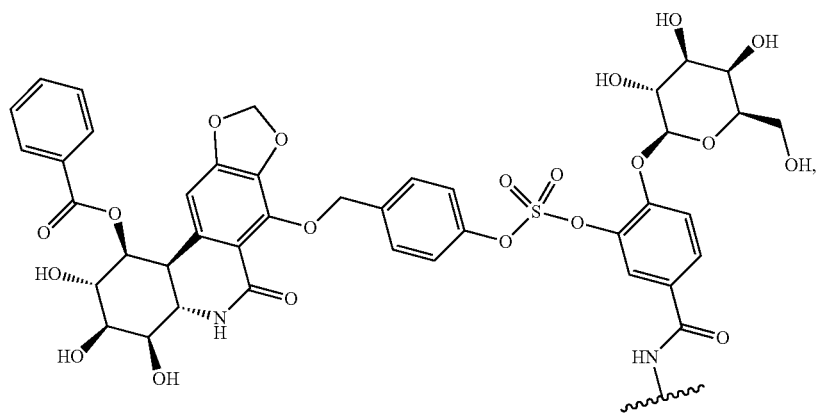

-continued
605
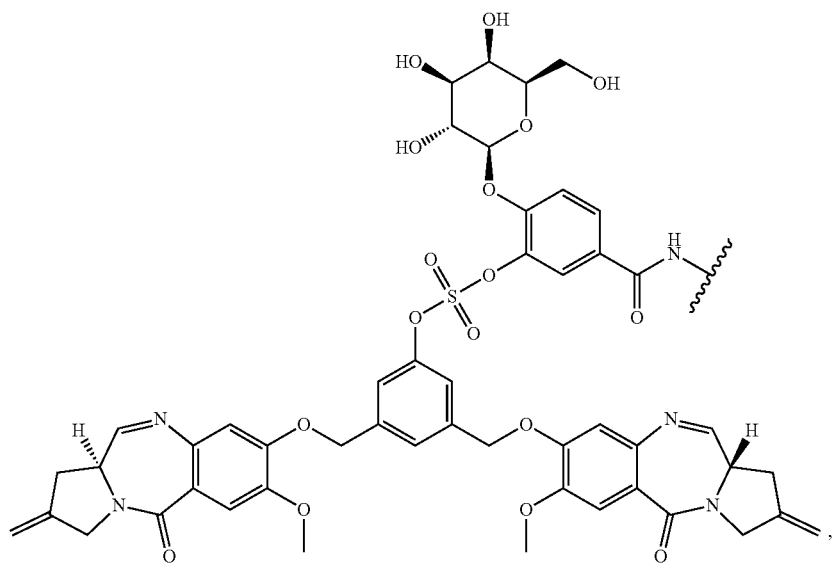
606
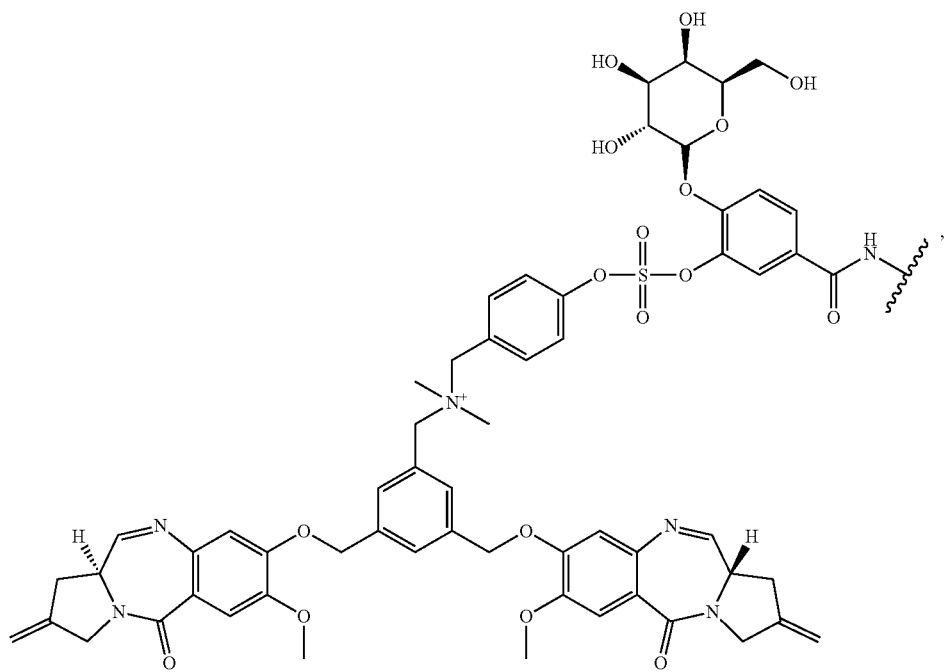

-continued
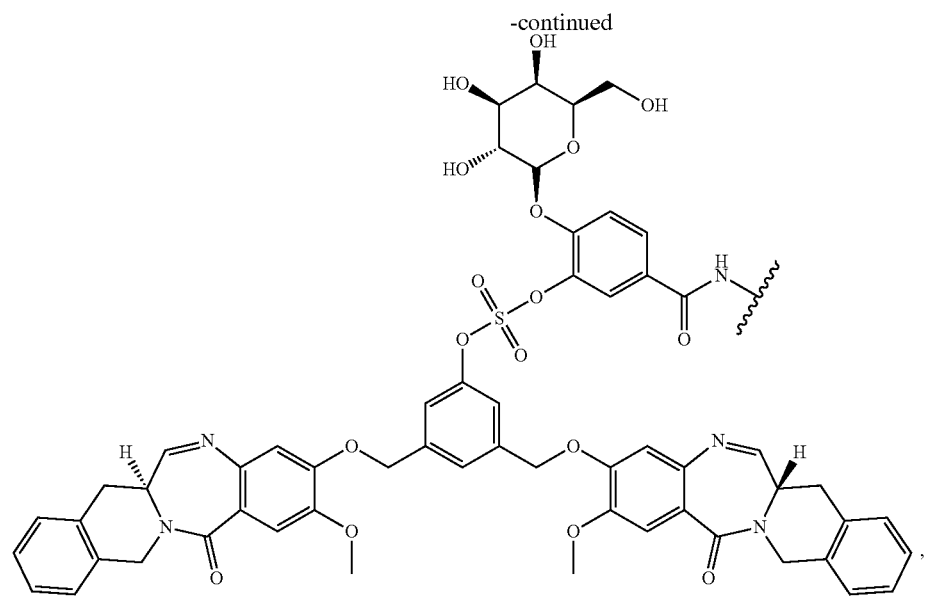
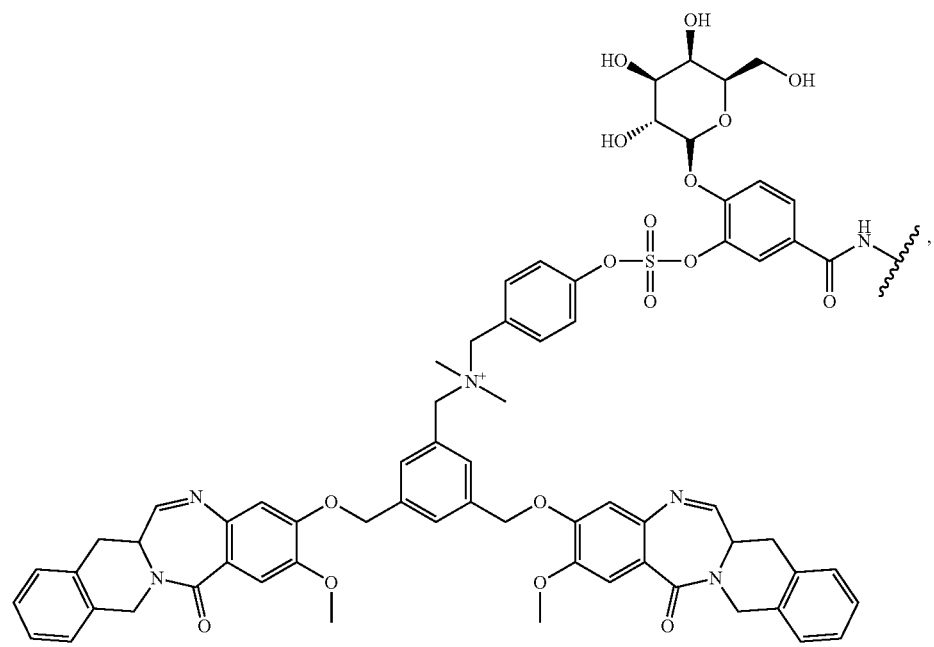
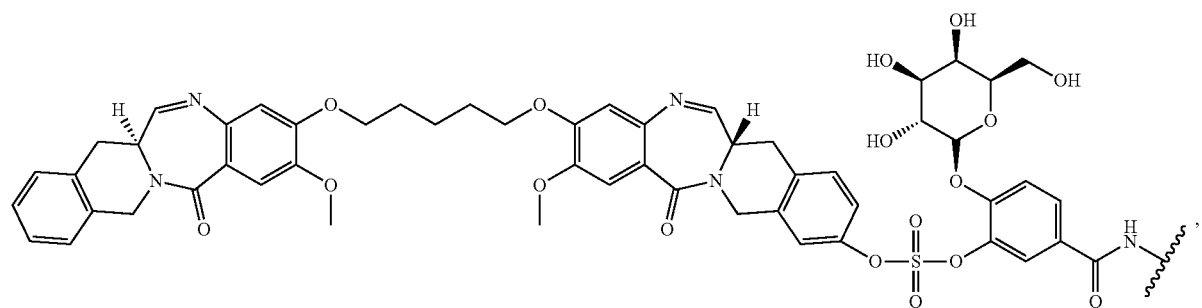

-continued
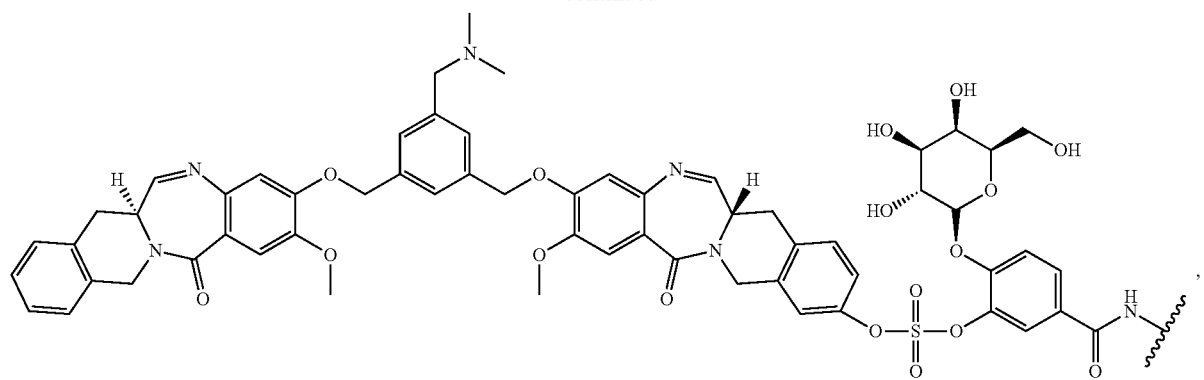
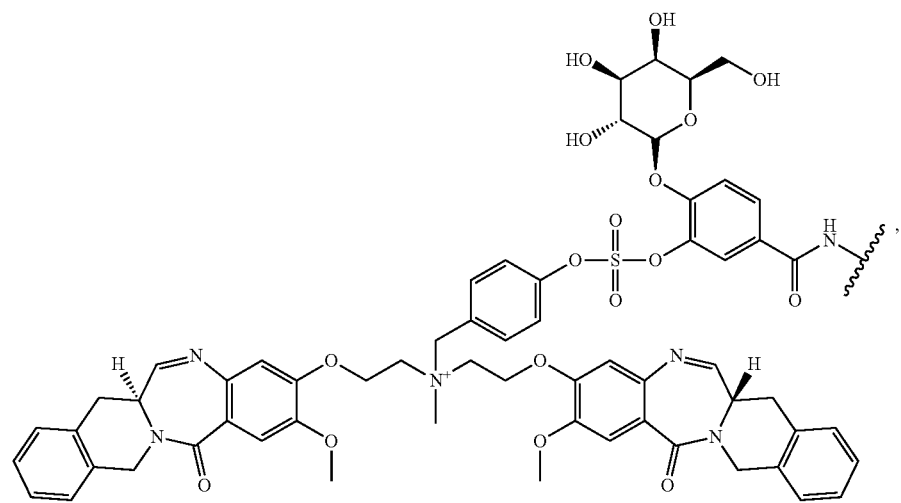
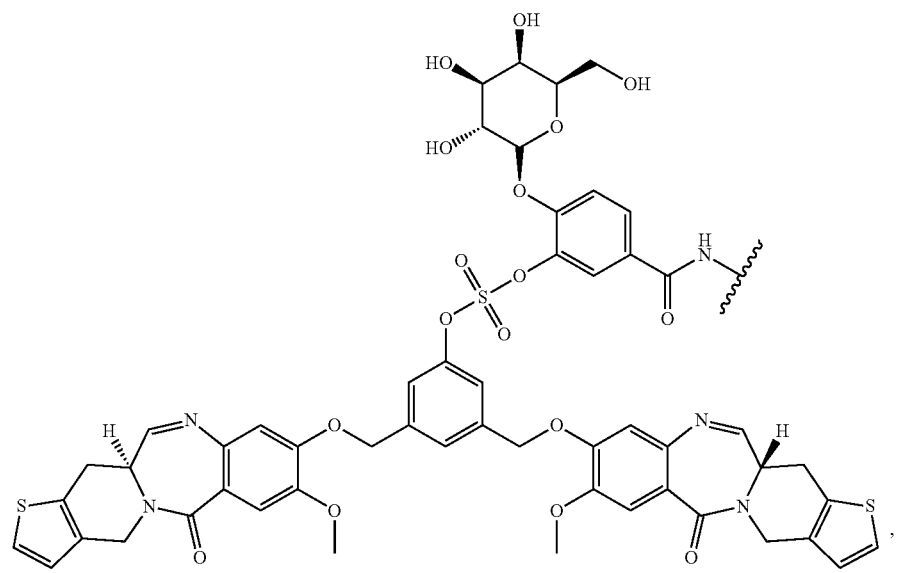

611                                          612
-continued
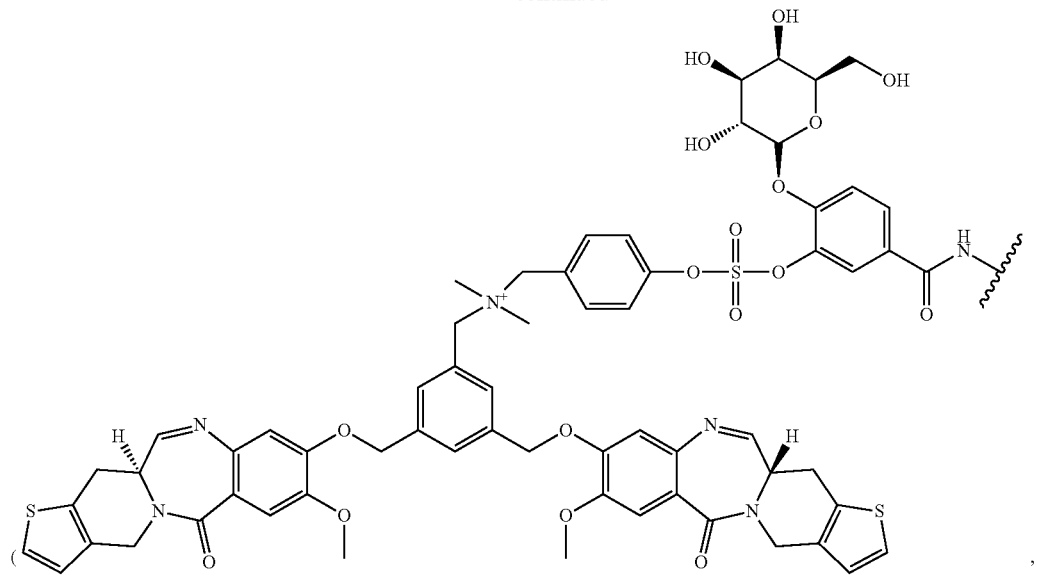
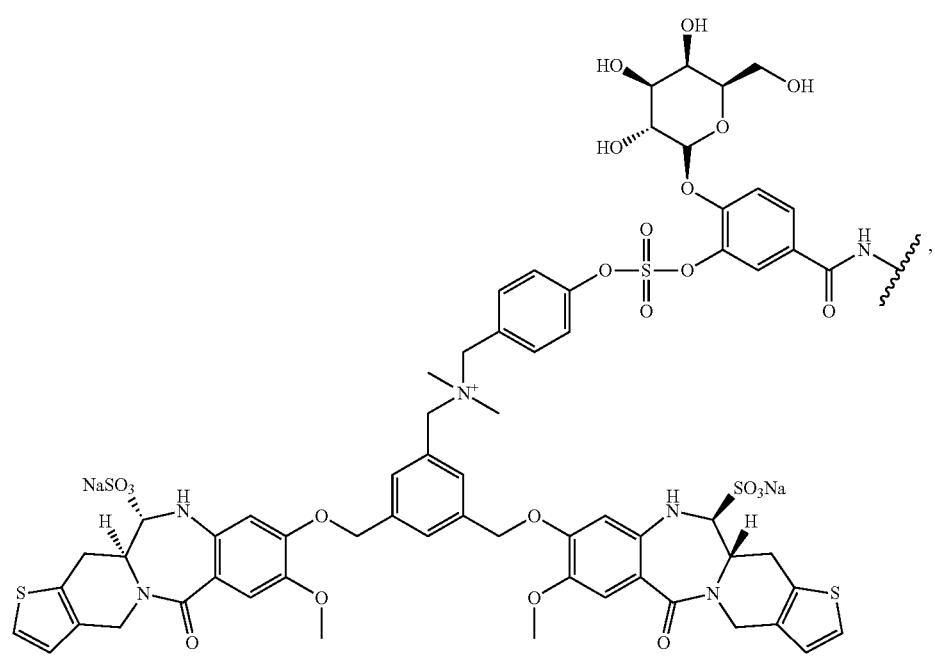

-continued
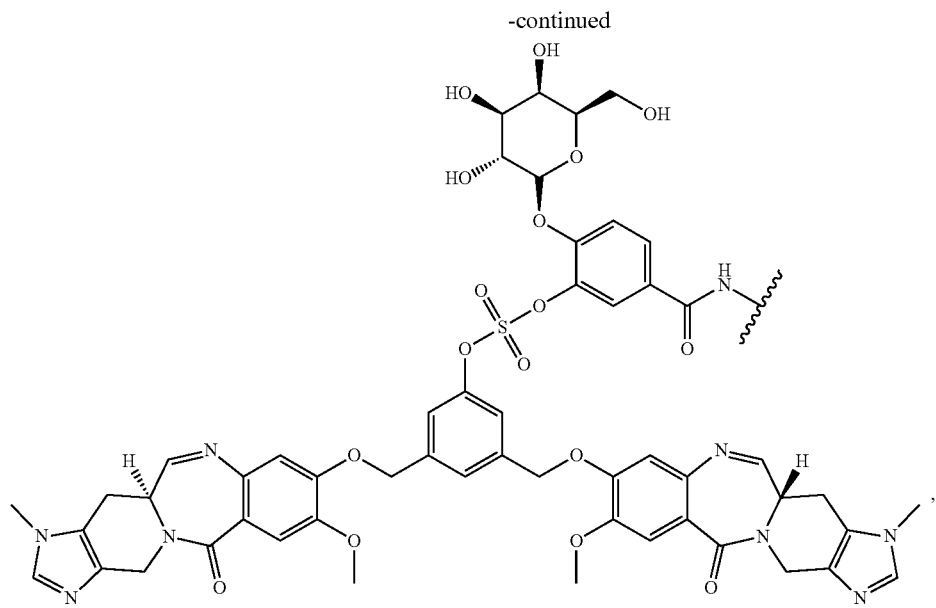
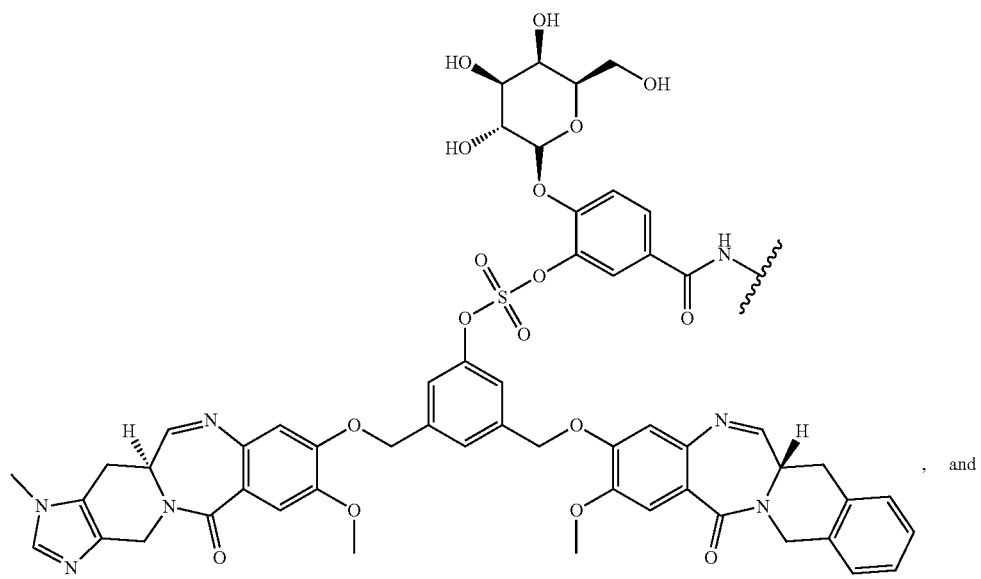
, and

-continued

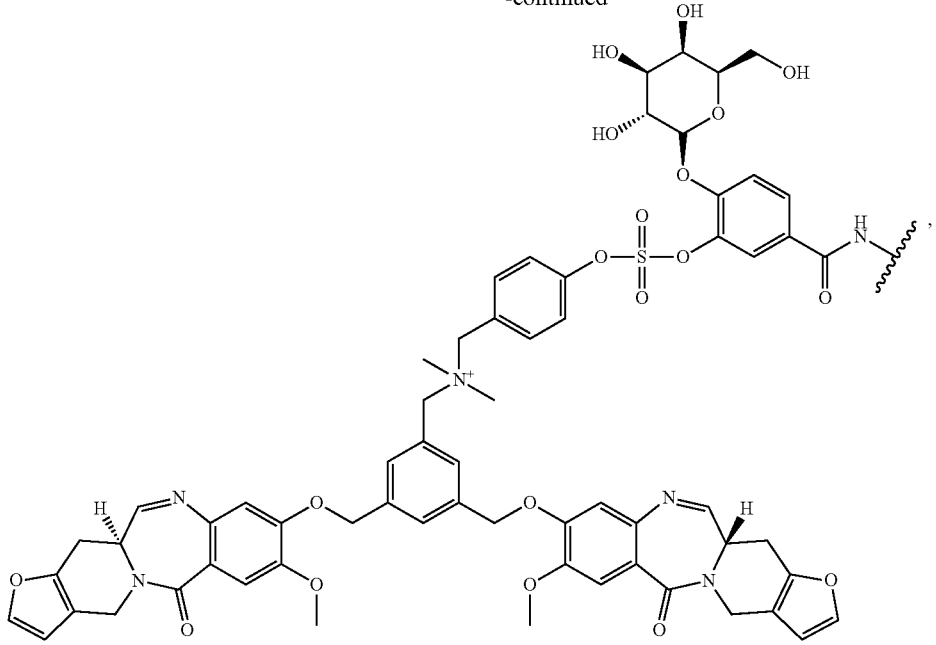

wherein

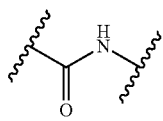 [SMILES: *NC(*)=O]

is a fragment of Z' connecting Z' to Ar.

15. The antibody conjugate of claim 1, wherein the active agent is an immunomodulatory compound, an anticancer agent, an antiviral agent, an antibacterial agent, an antifungal agent, an antiparasitic agent, or a combination thereof.

16. The antibody conjugate of claim 1, wherein the active agent is selected from:

(a) erlotinib, bortezomib, fulvestrant, sutent, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, trietylenephosphormide, triethiylenethiophosphoramide, trimethylolomelamine, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, antrmycin, azaserine, bleomycins, cactinomycin, carabicin, carninomycin, carzinophilin, chromomycins, dactinomycin, daunorubicin, detorubucin, 6-diazo-5-oxo-L-norleucine, doxorubicin, morpholino-doxorubicin, cyanomorpholino-doxorubicin, 2-pyrrolino-doxorubucin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2,2 trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albuminengineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;

(b) monokine, a lymphokine, a traditional polypeptide hormone, parathyroid hormone, thyroxine, relaxin, pro-relaxin, a glycoprotein hormone, follicle stimulating hormone, thyroid stimulating hormone, luteinizing hormone, hepatic growth factor fibroblast growth factor, prolactin, placental lactogen, tumor necrosis factor-a, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-a, interferon-β, interferon-y, a colony stimulating factor ("CSF"), macrophage-CSF, granulocyte-macrophage-CSF, granulocyte-CSF, an interleukin ("IL"), IL-1, IL-1α, IL-2, IL-3, IL-4, IL-5, IL-6, IL-7, IL-8, IL-9, IL-10, IL-11, IL-12, a tumor necrosis factor, TNF-α, TNF-β, a polypeptide factor, LIF, kit ligand, or a combination of any of the foregoing;

(c) diphtheria toxin, botulium toxin, tetanus toxin, dysentery toxin, cholera toxin, amanitin, amanitin derivatives, a-amanitin, pyrrolobenzodiazepine, pyrrolobenzodiazepine derivatives, tetrodotoxin, brevetoxin, ciguatoxin, ricin, AM toxin, auristatin, tubulysin, geldanamycin, maytansinoid, calicheamicin, daunomycin, doxorubicin, methotrexate, exatecan, exatecan derivatives, vindesine, SG2285, dolastatin, a dolastatin analog, cryptophycin, camptothecin, camptothecin derivatives and metabolites, rhizoxin, a rhizoxin derivative, CC-1065, a CC-1065 analogue or derivative, duocarmycin, an enediyne antibiotic, esperamicin, epothilone, azonafide, aplidine, a toxoid, or a combination of any of the foregoing;

(d) an affinity ligand, wherein the affinity ligand is a substrate, an inhibitor, a stimulating agent, a neurotransmitter, a radioisotope, or a combination of any of the foregoing;

(e) a radioactive label, $^{32}$P, $^{35}$S, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;

(f) an immunomodulatory compound, an anti-cancer agent, an anti-viral agent, an anti-bacterial agent, an anti-fungal agent, and an anti-parasitic agent, or a combination of any of the foregoing;

(g) tamoxifen, raloxifene, droloxifene, 4-hydroxytamoxifen, trioxifene, keoxifene, LY117018, onapristone, or toremifene;

(h) 4 (5)-imidazoles, aminoglutethimide, megestrol acetate, exemestane, letrozole, or anastrozole;

(i) flutamide, nilutamide, bicalutamide, leuprolide, goserelin, or troxacitabine;

(j) an aromatase inhibitor;

(k) a protein kinase inhibitor;

(l) a lipid kinase inhibitor;

(m) an antisense oligonucleotide;

(n) a ribozyme;

(o) a vaccine; and (p) an anti-angiogenic agent.

17. A pharmaceutical composition comprising the antibody conjugate of claim 1.

18. A method of treating a cancer, comprising administering the antibody conjugate of claim 1 to a subject in need thereof.

19. A method of treating an autoimmune disease or an inflammatory disease, comprising administering the antibody conjugate of claim 1 to a subject in need thereof.

20. The antibody conjugate of claim 1, having a structure selected from:

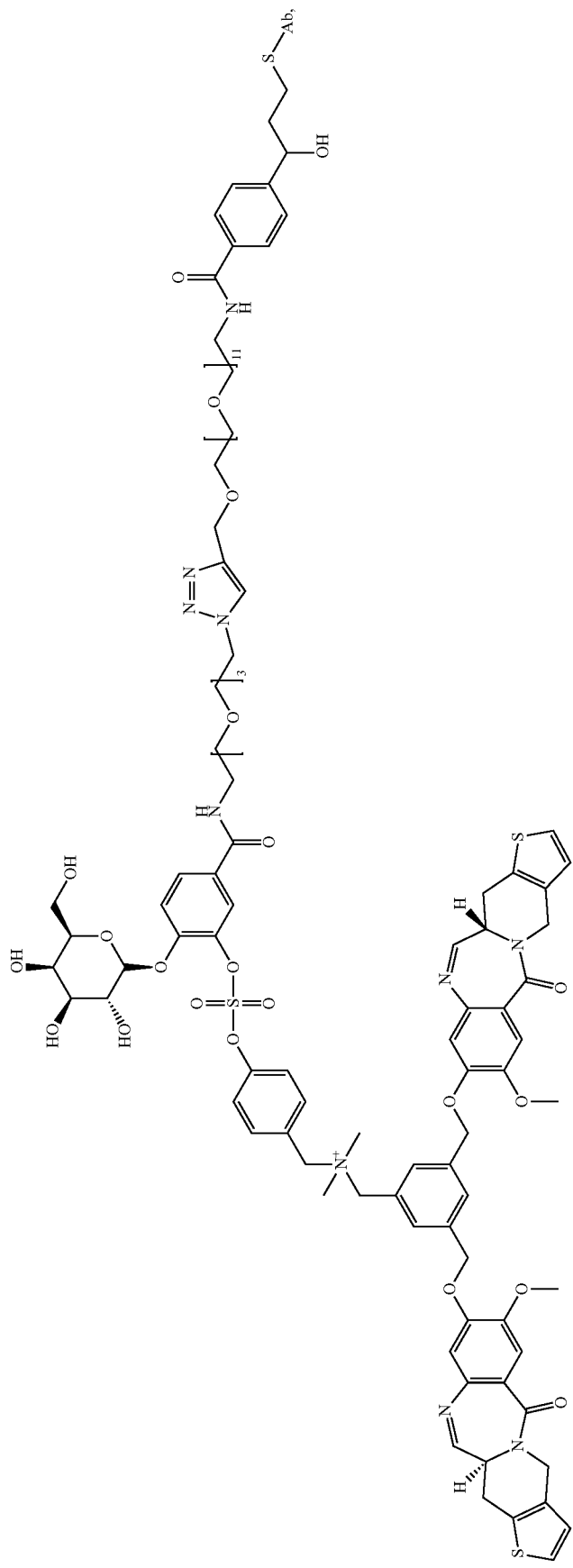

621 622
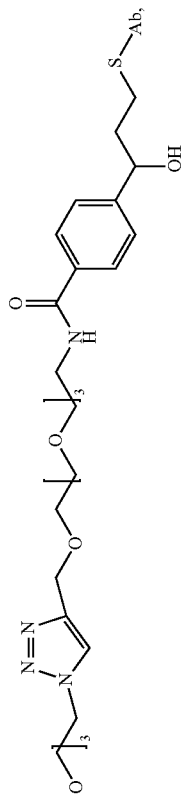
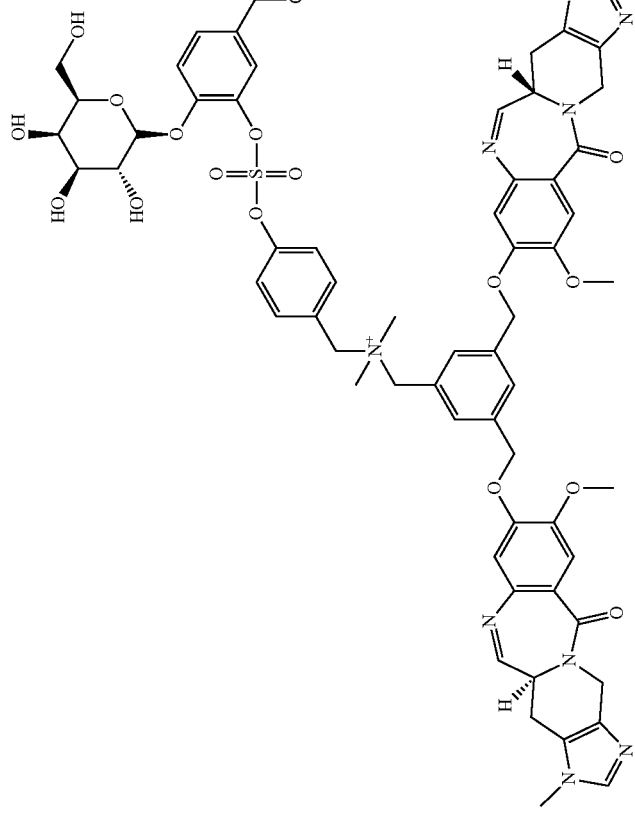

623 624
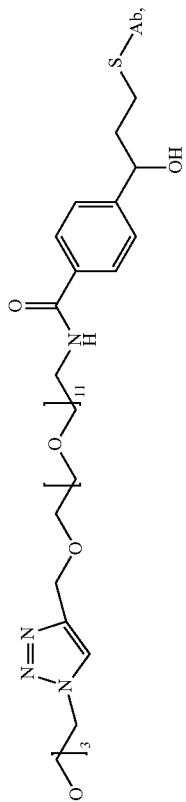
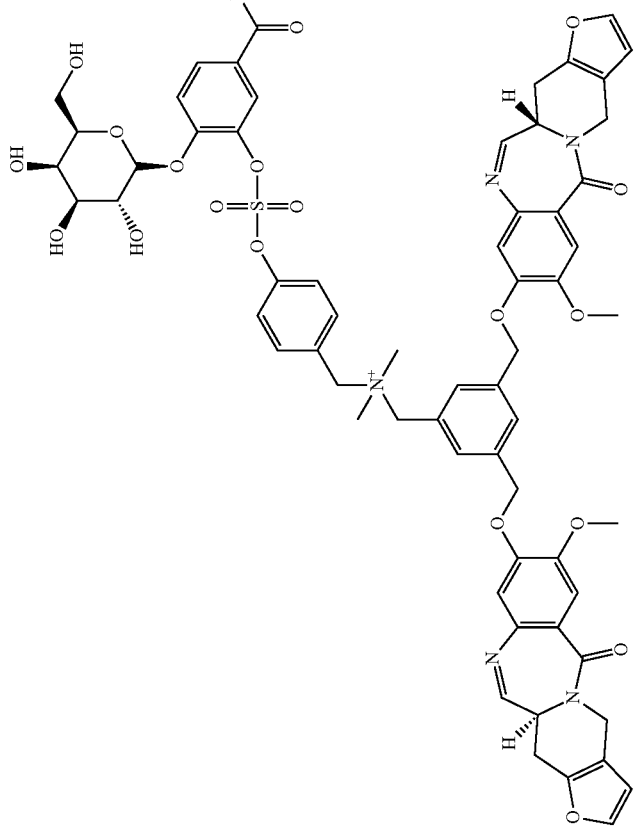

625
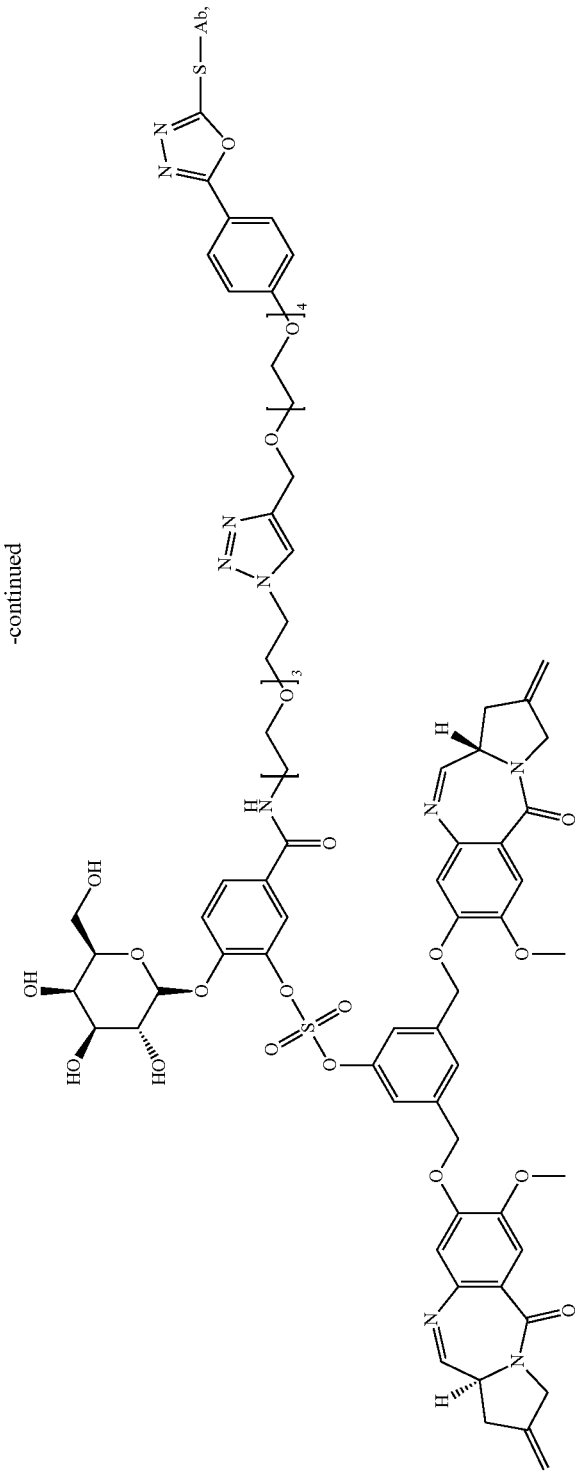
626
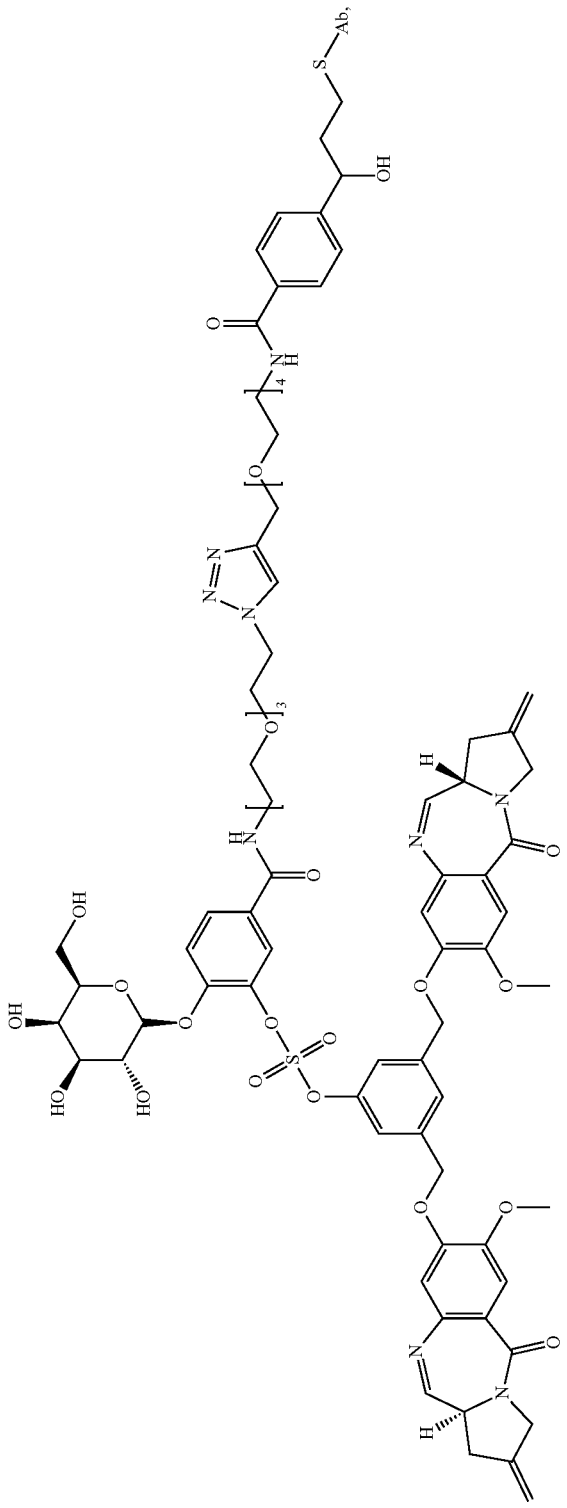

-continued
627
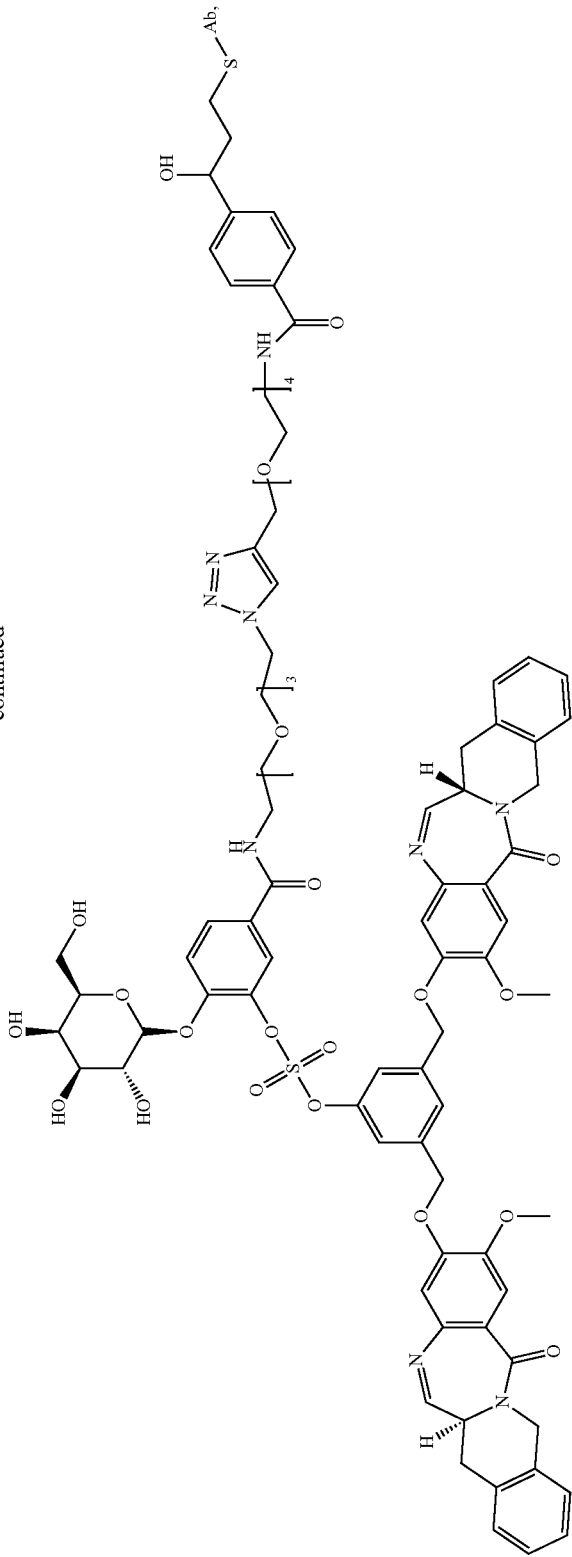
628
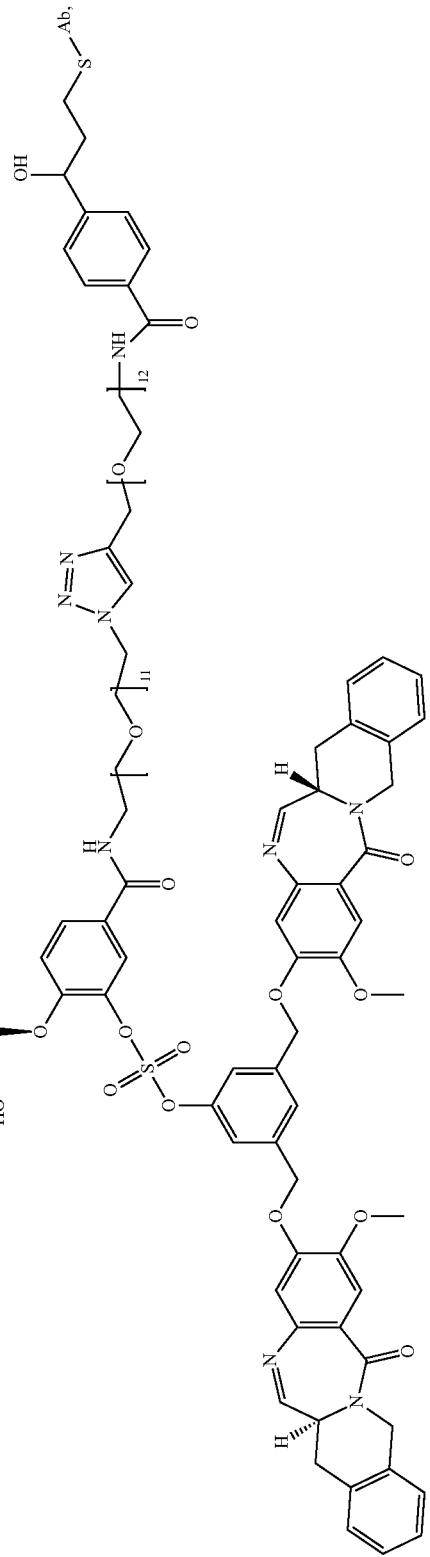

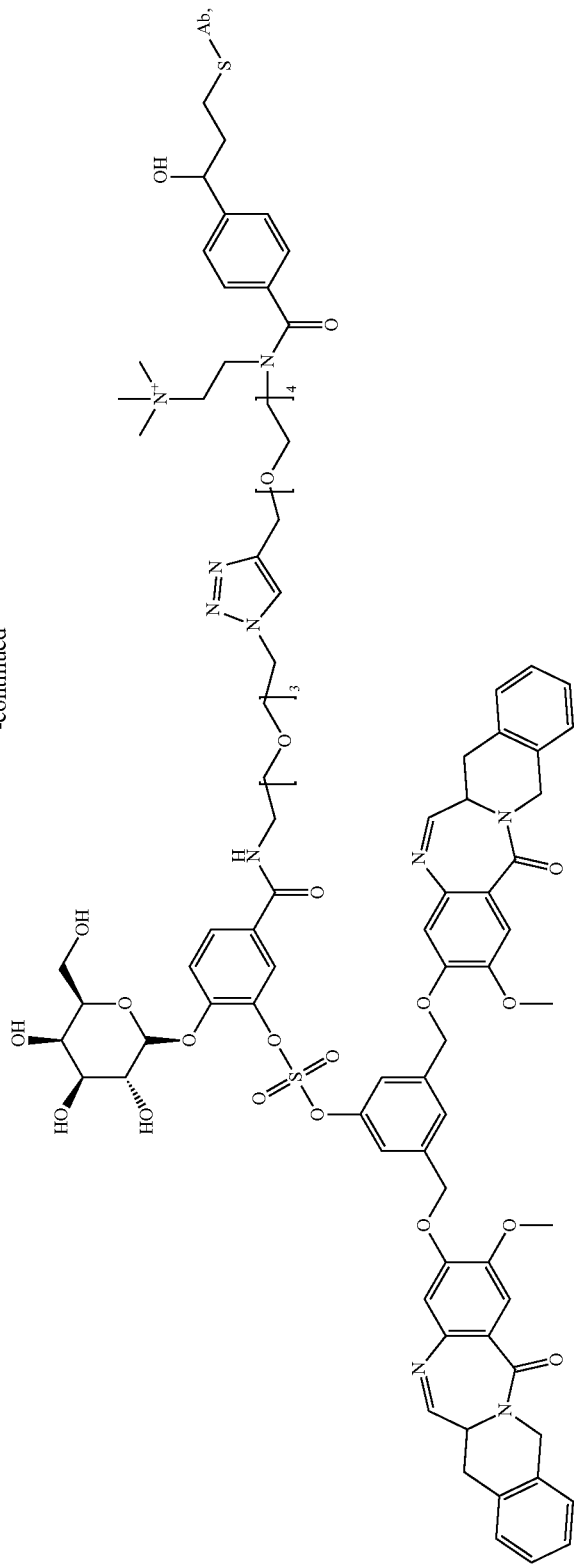

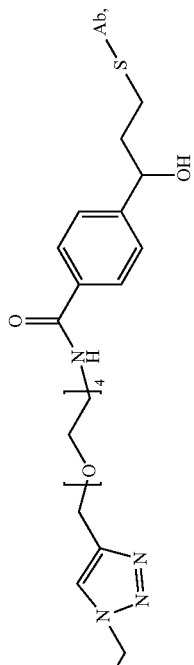
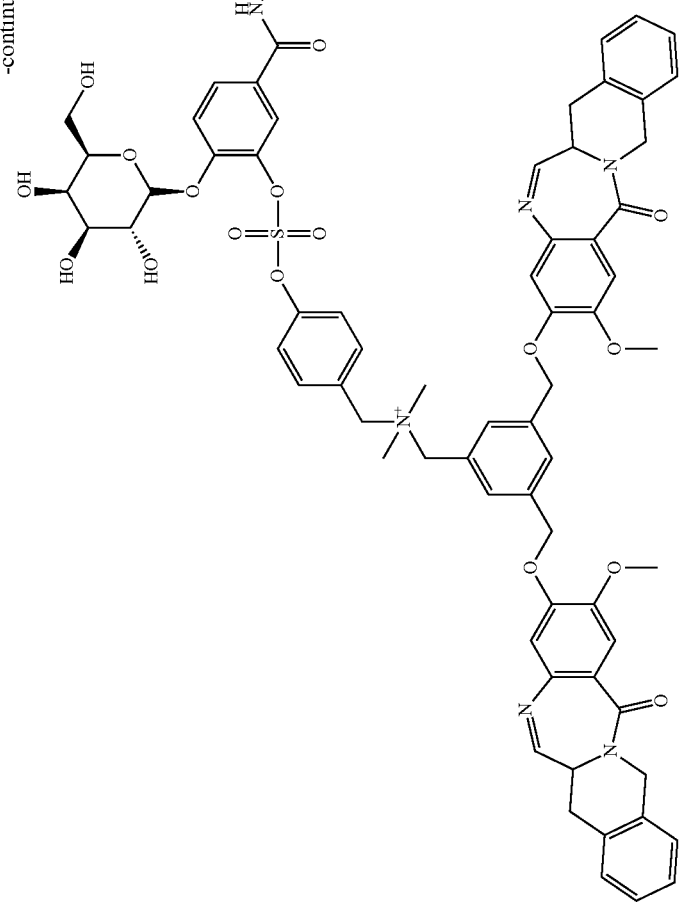

633
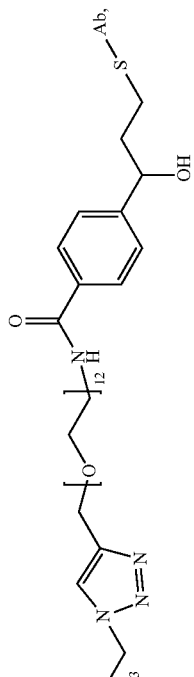
634
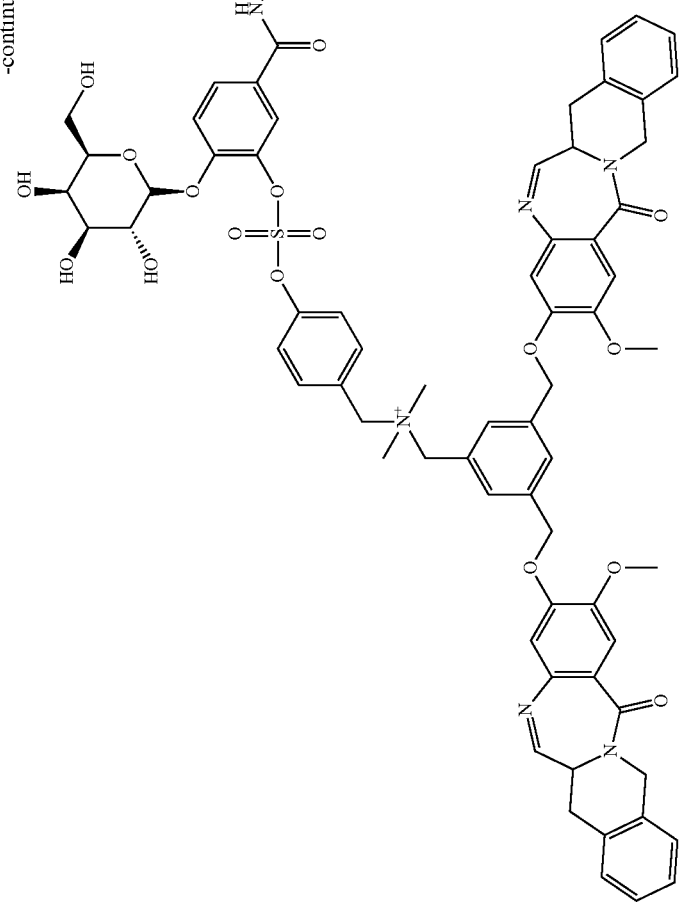

-continued
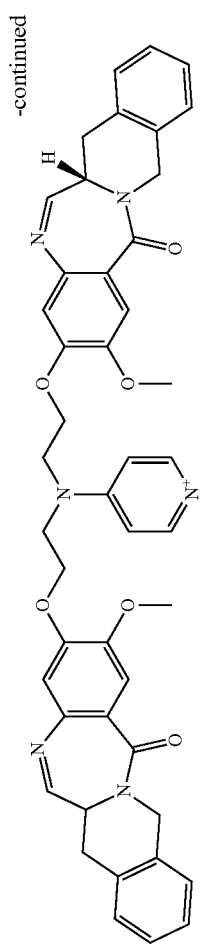

637 638
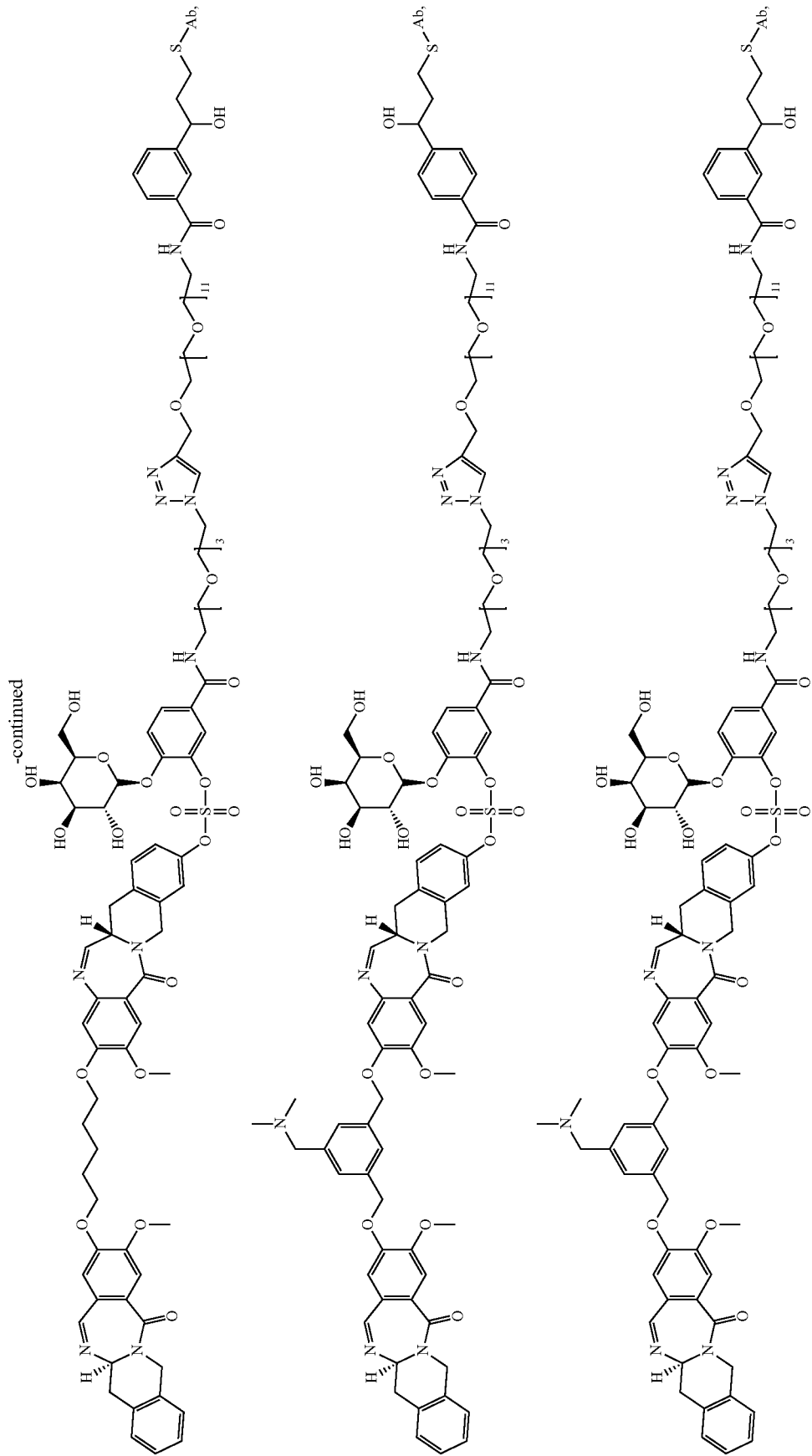

639 640
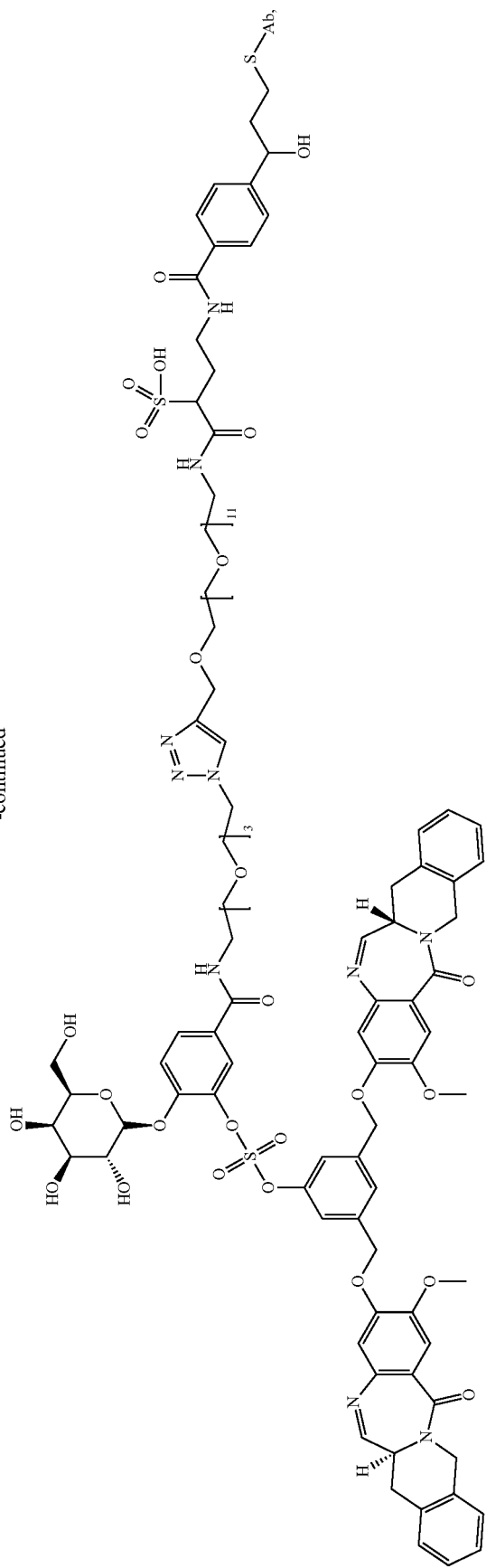
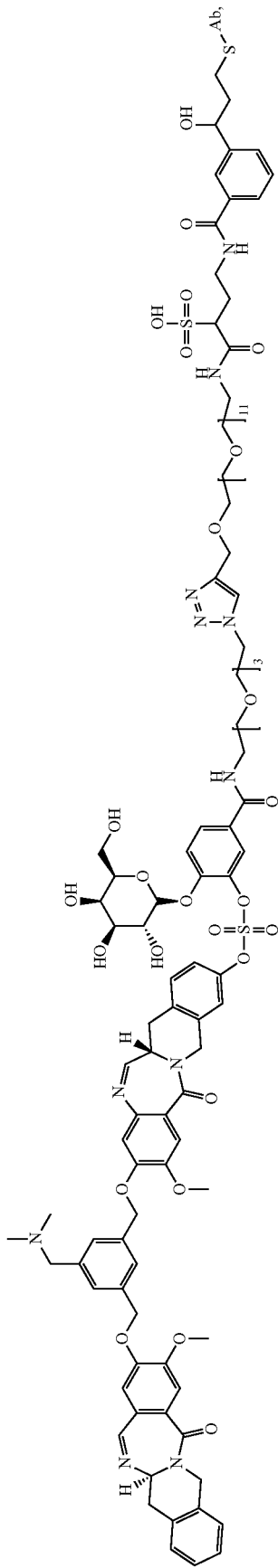

641
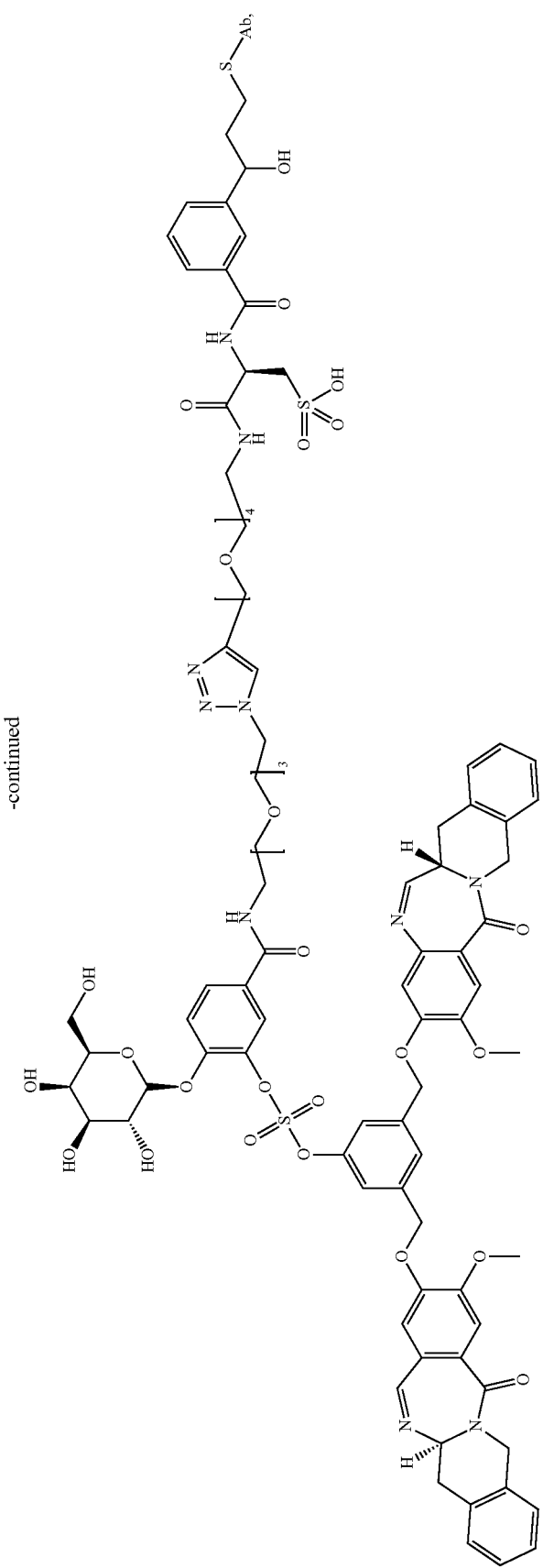
642
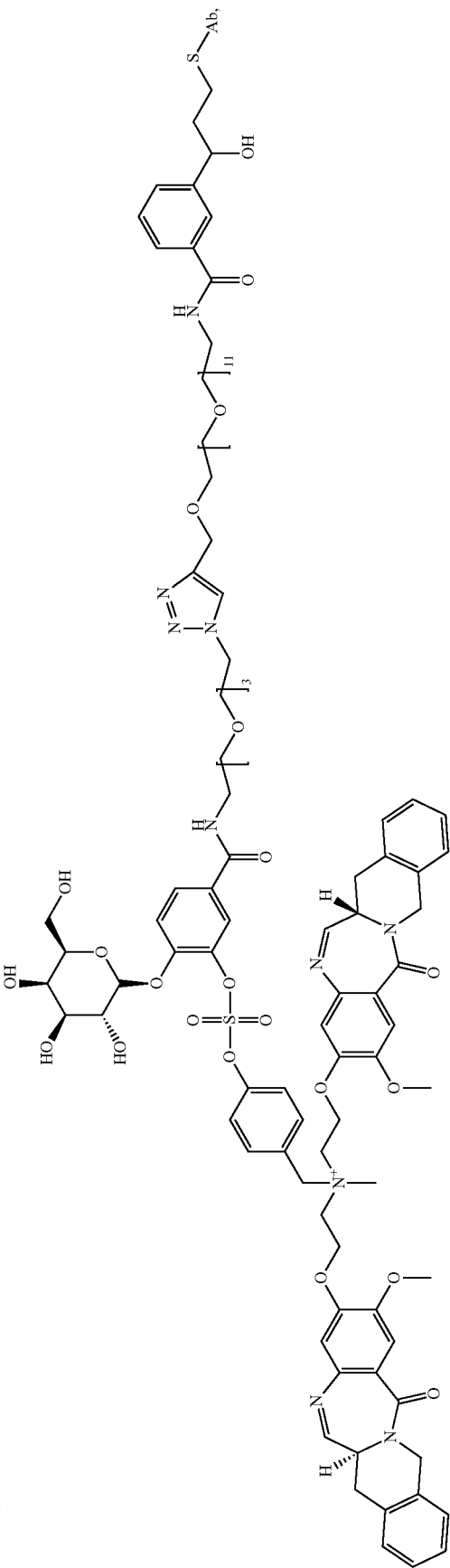

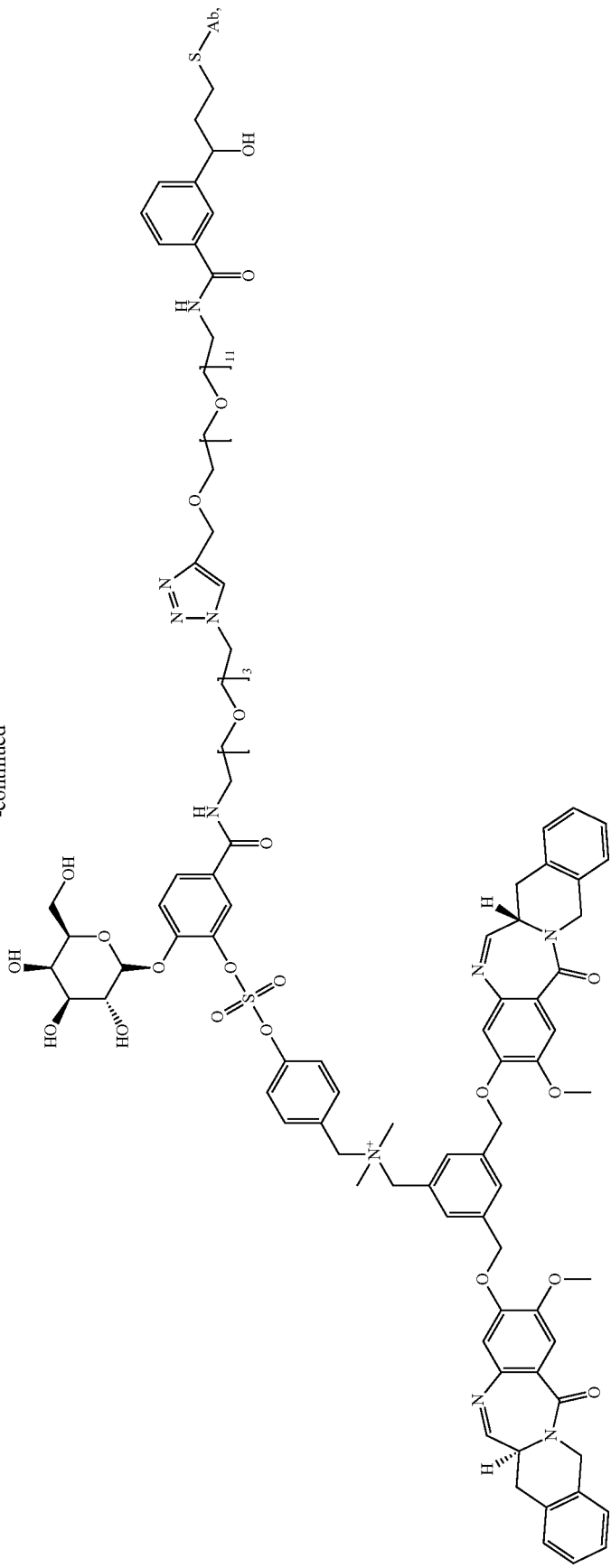

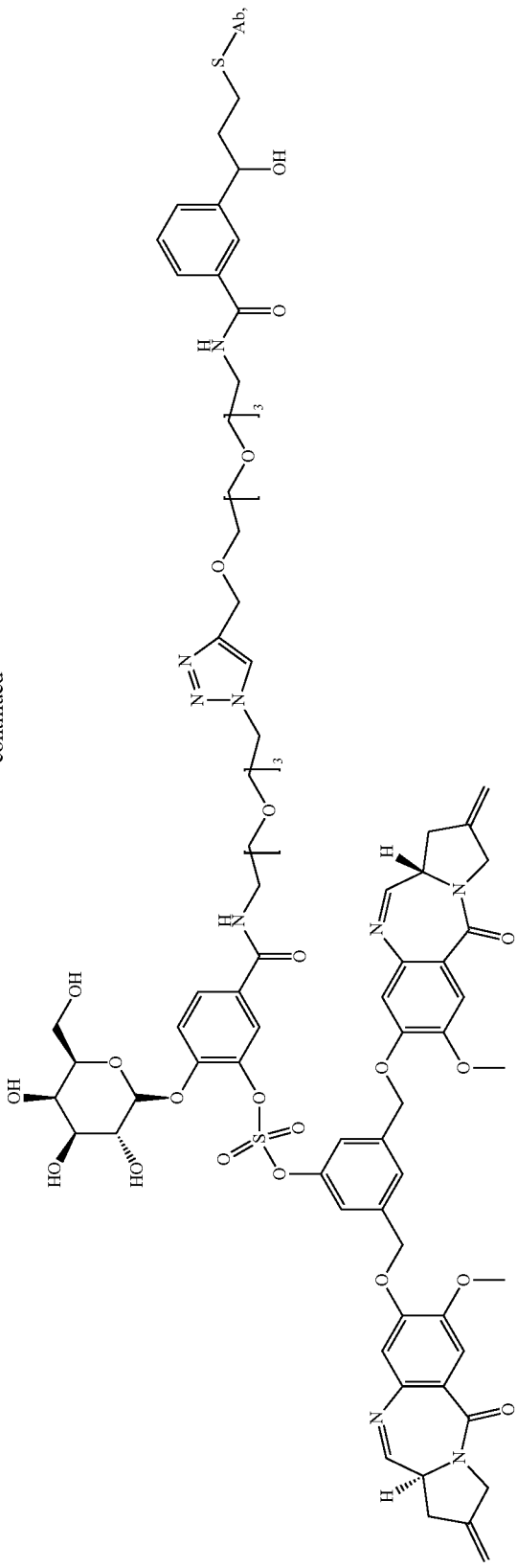

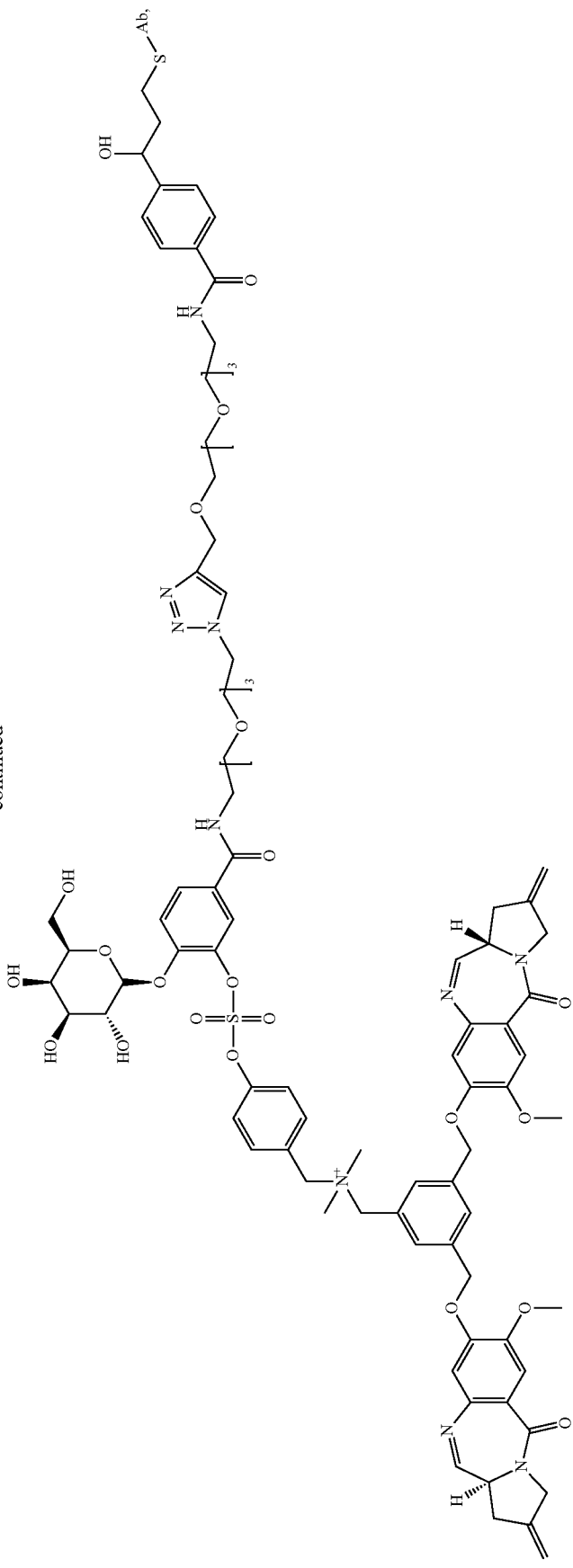

649 650
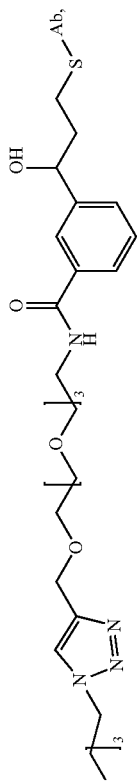
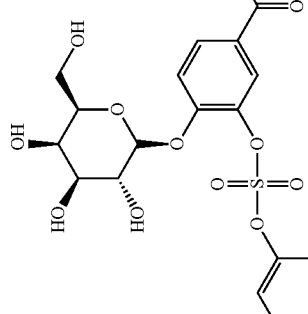
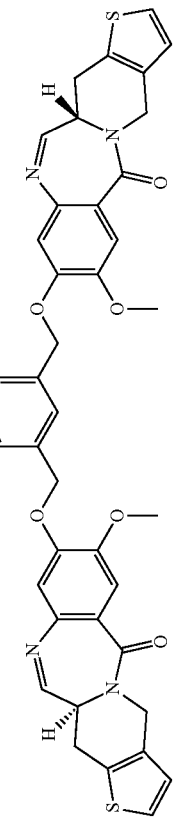
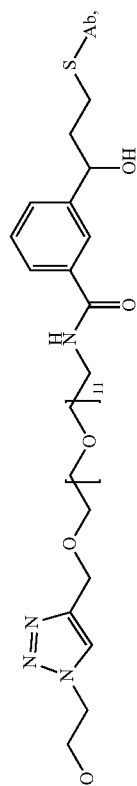
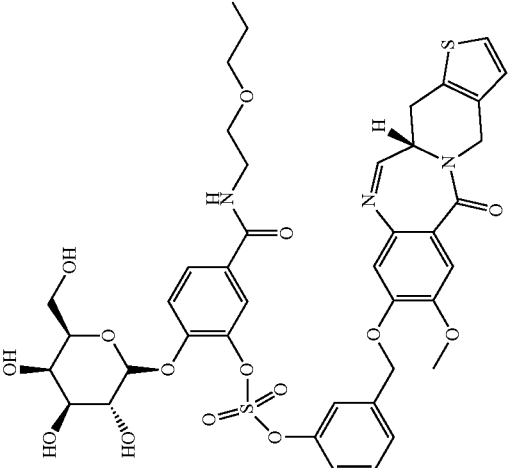
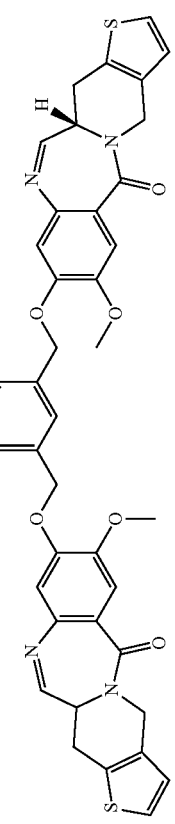

651 652
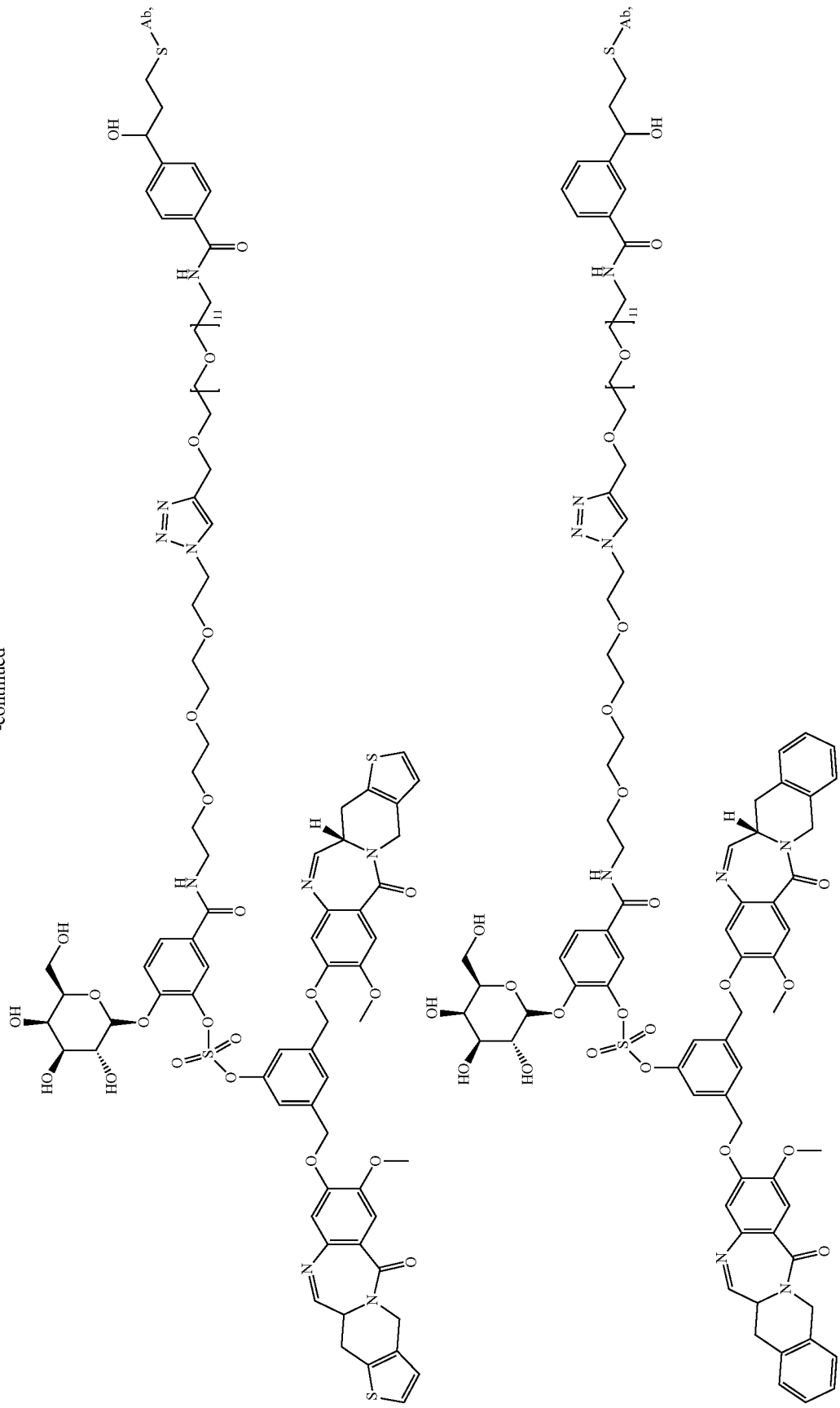

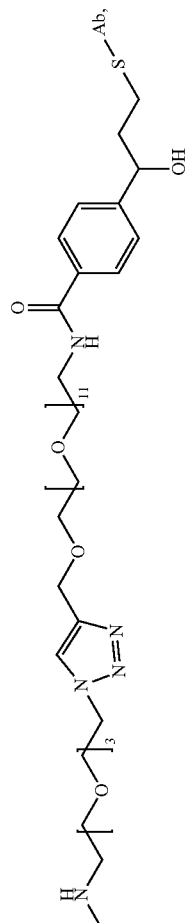
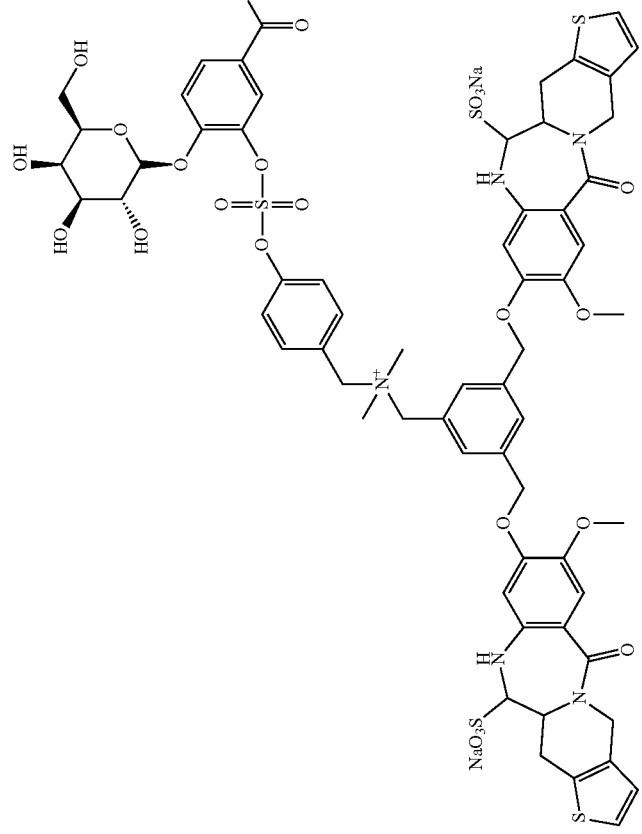

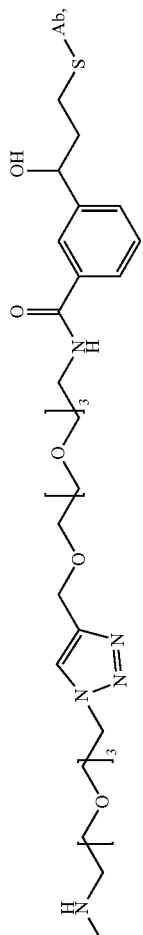
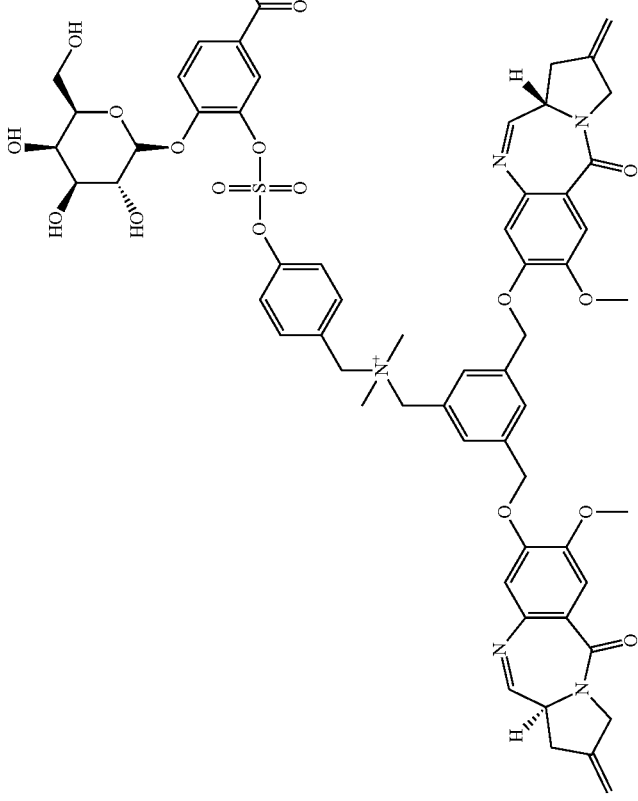

657
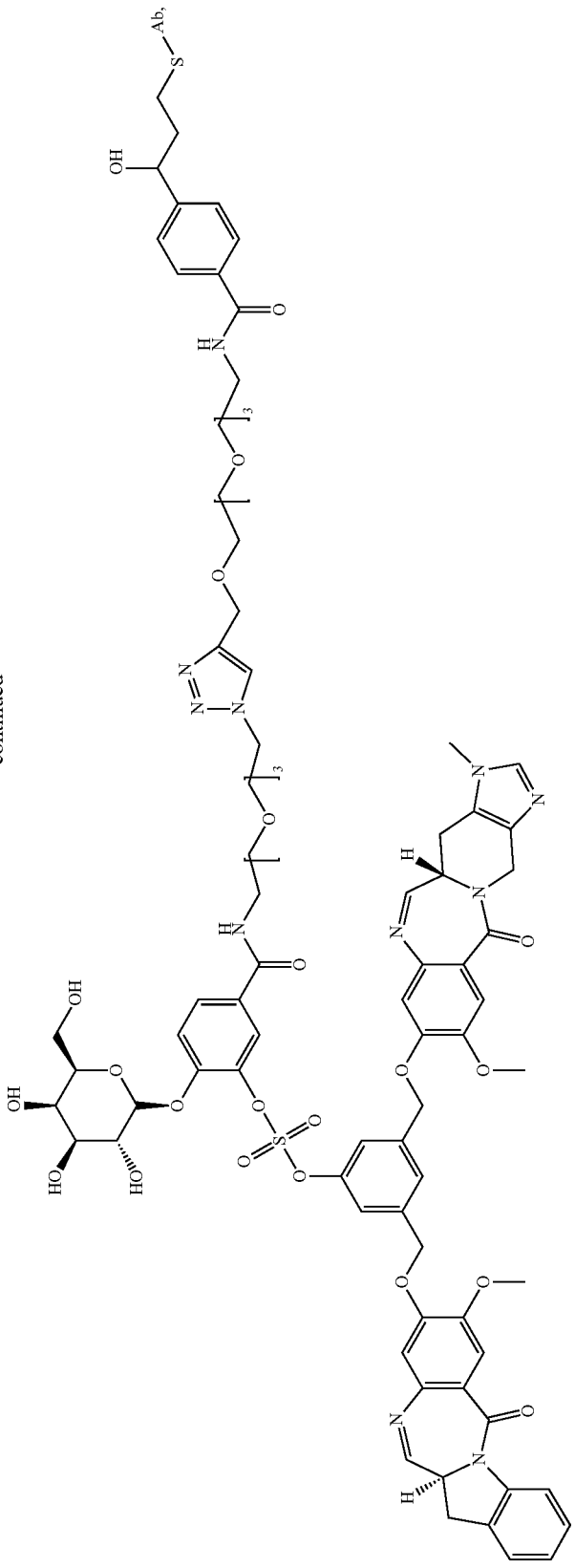
658
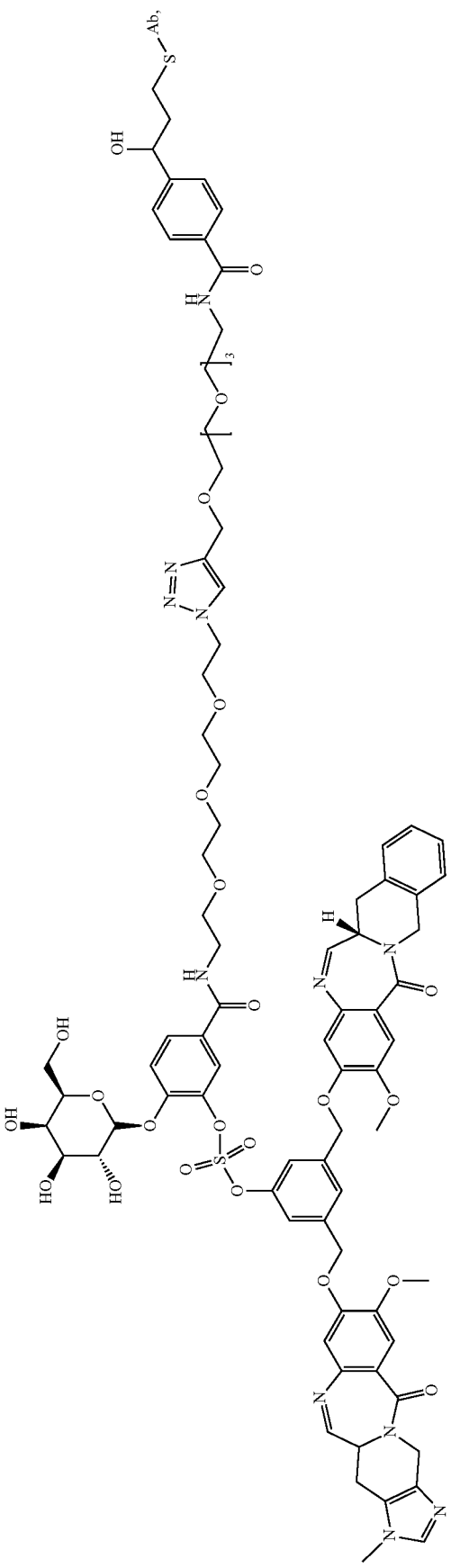

659
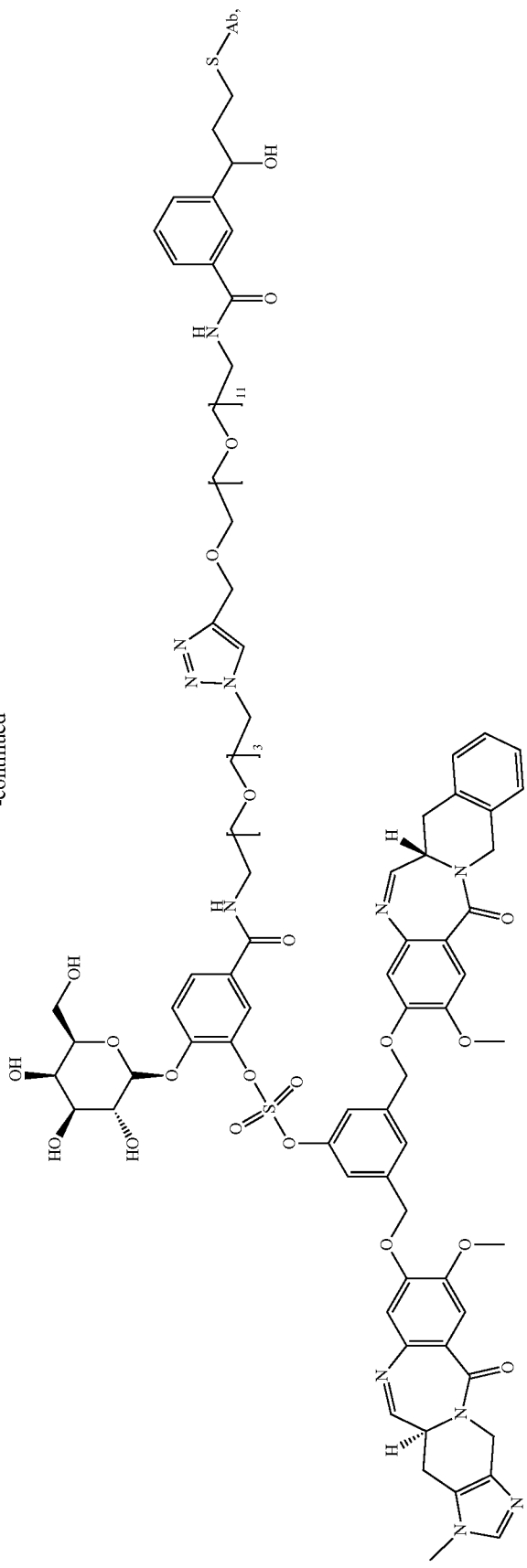
660
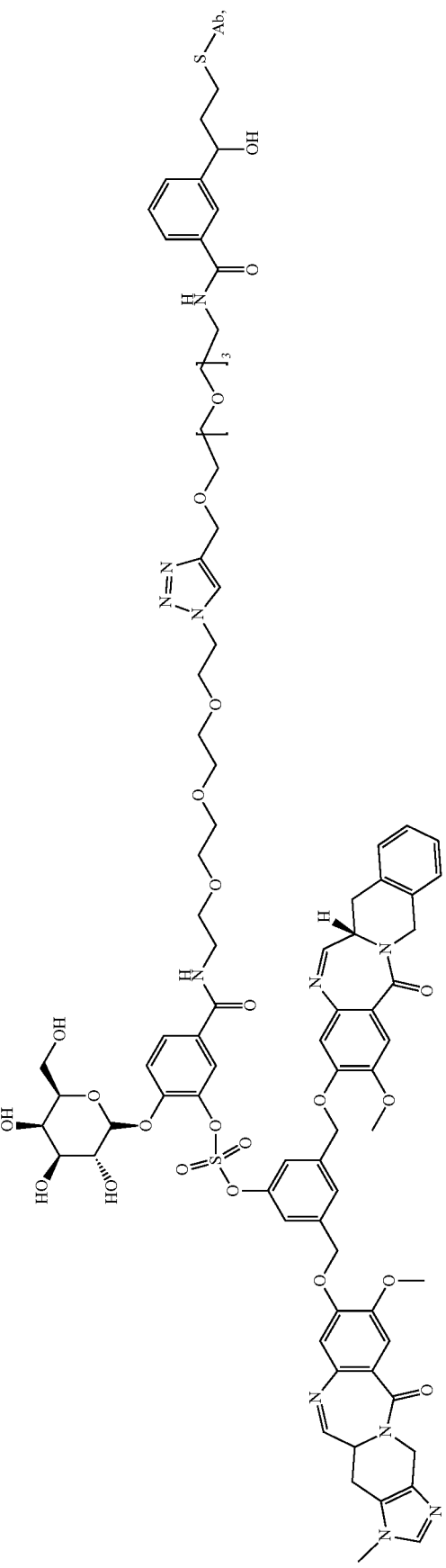

661 662
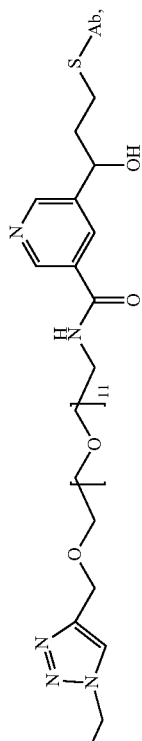
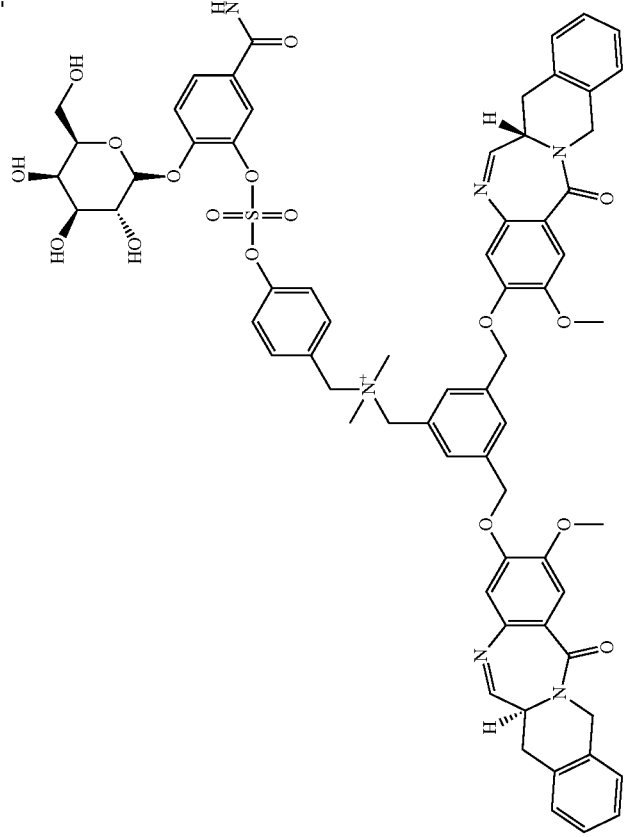
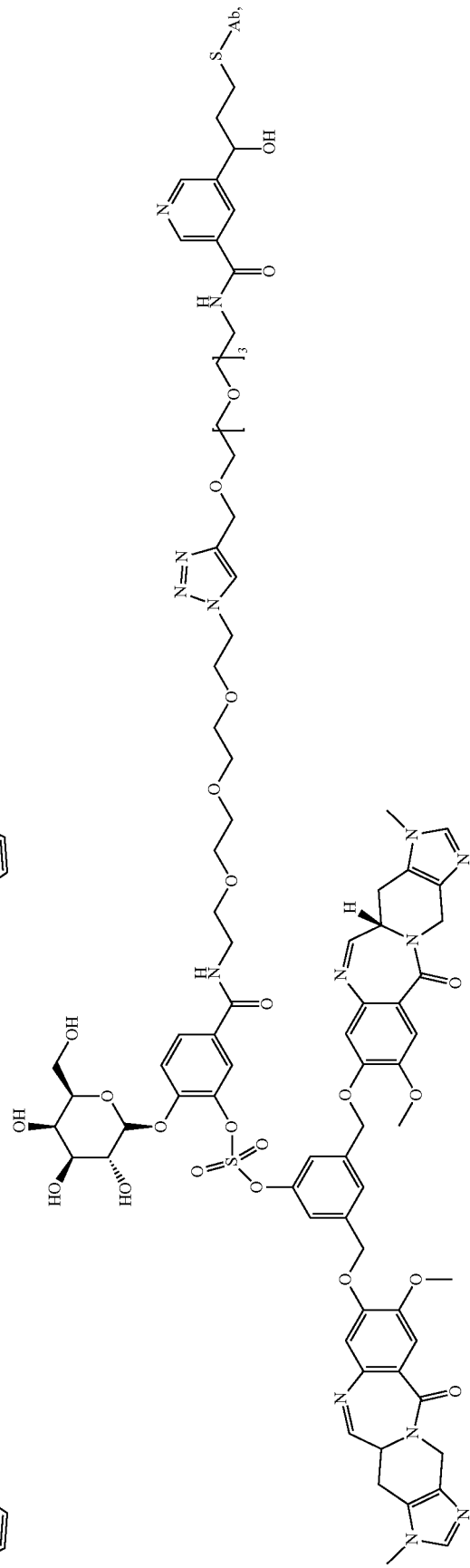

-continued
663
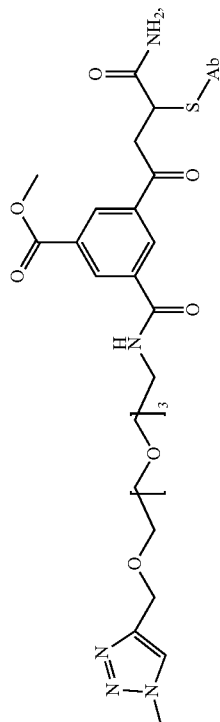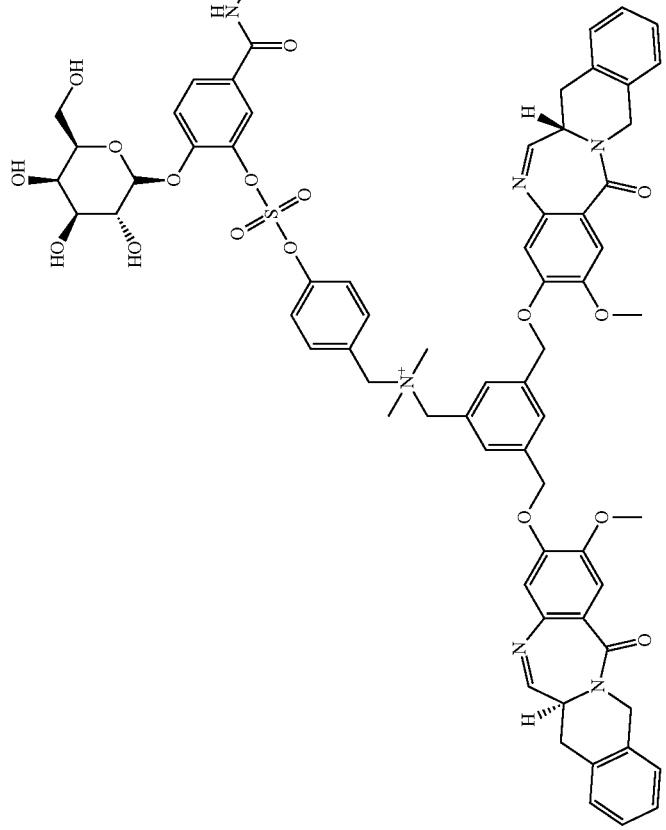
664
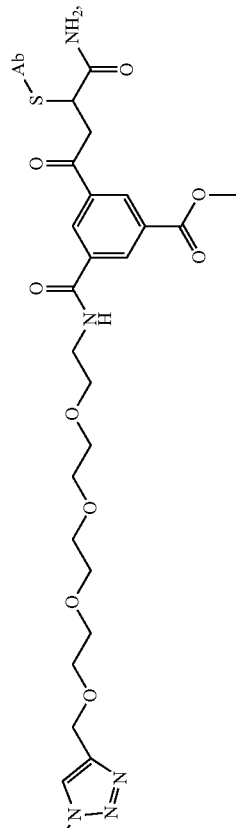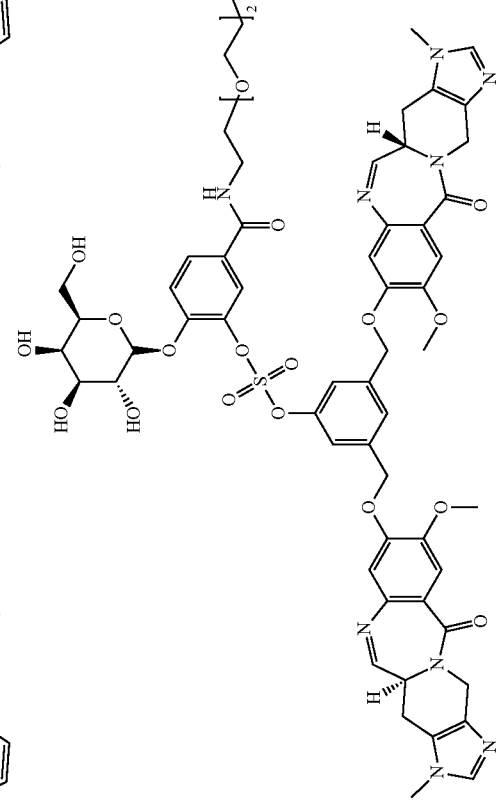

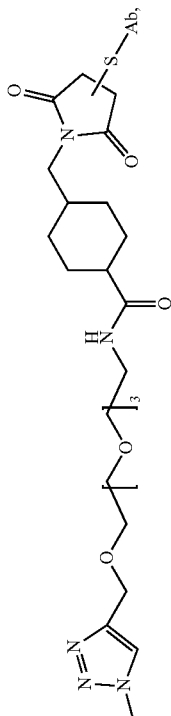
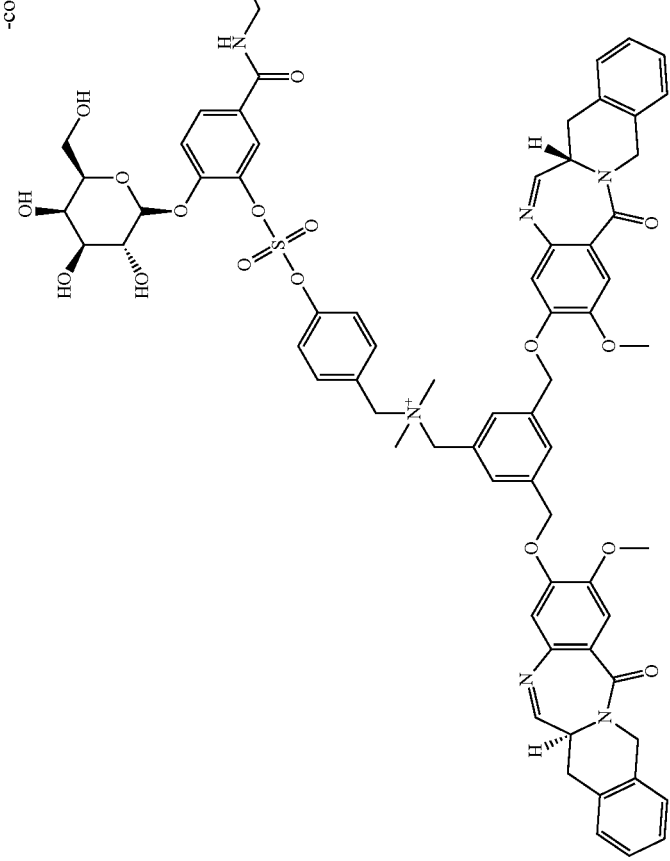

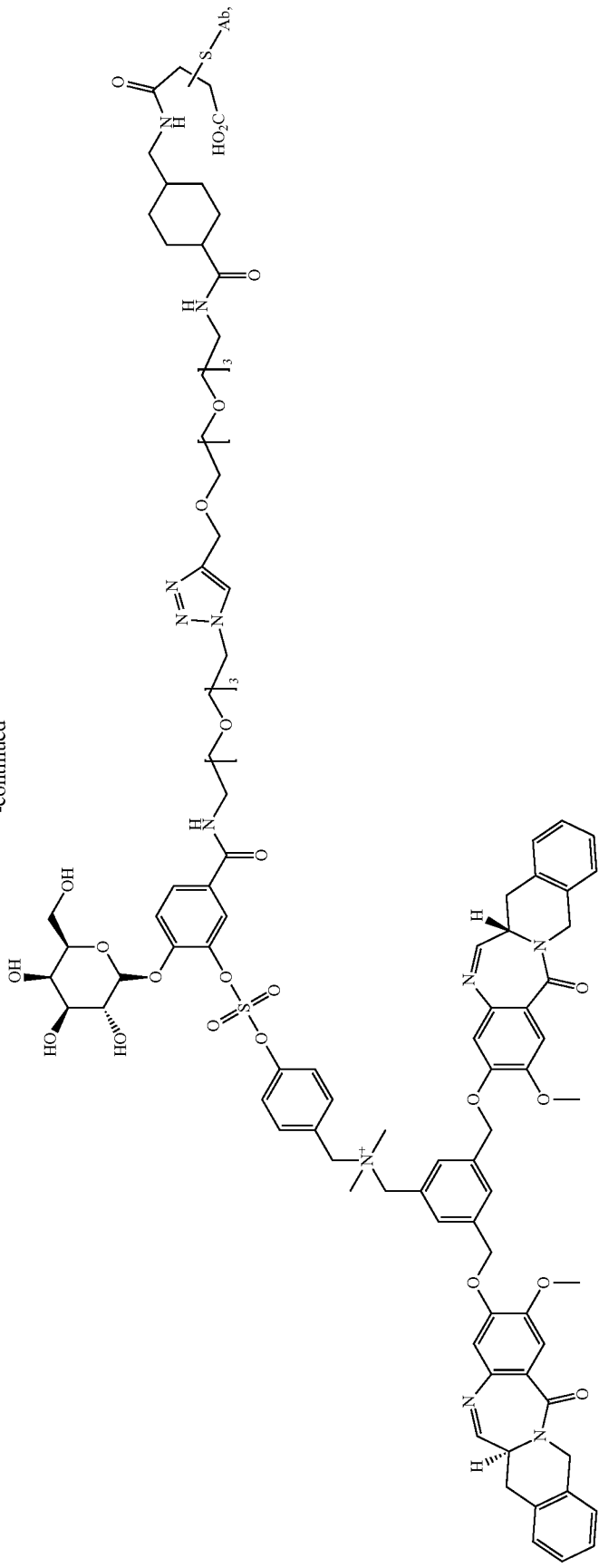

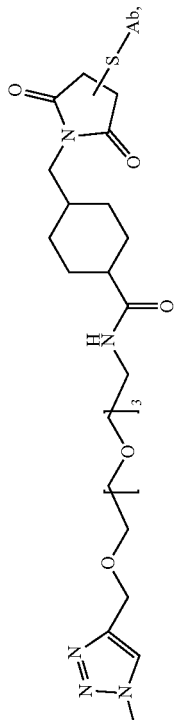
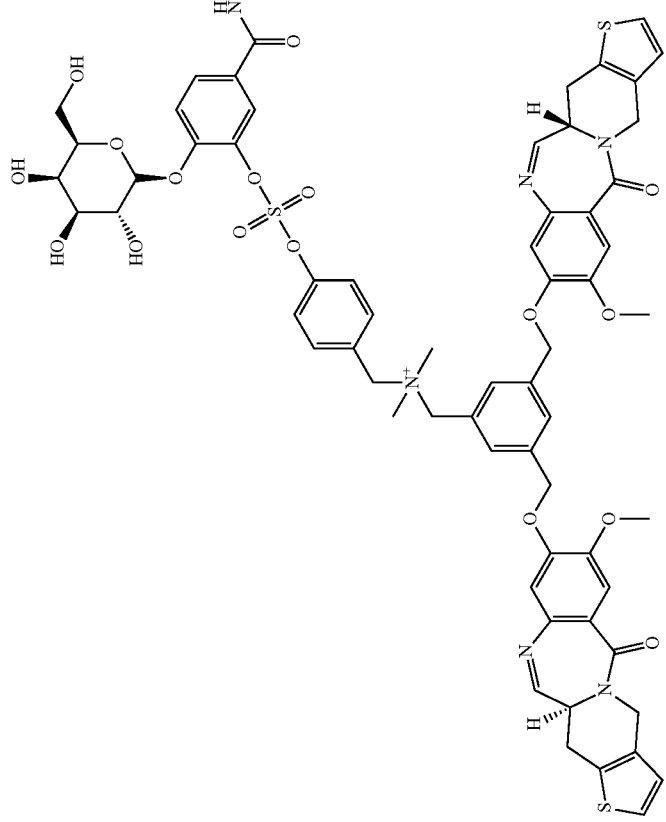

-continued
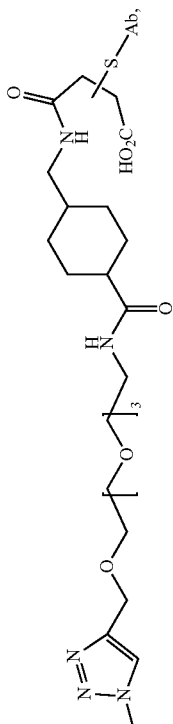
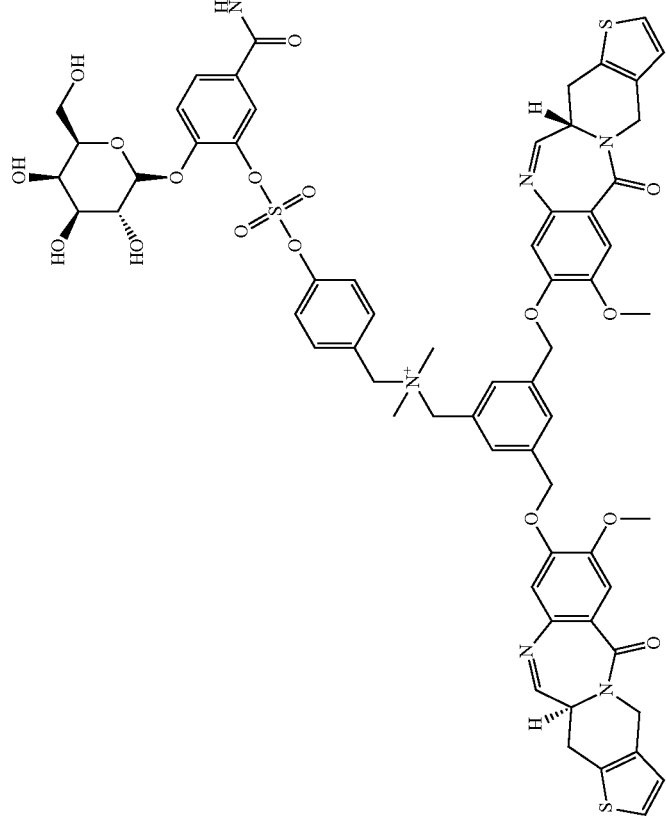

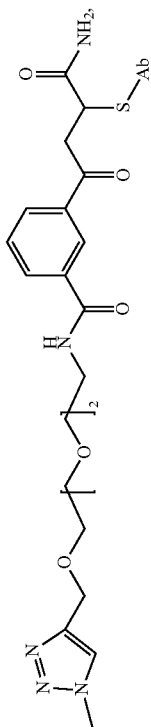
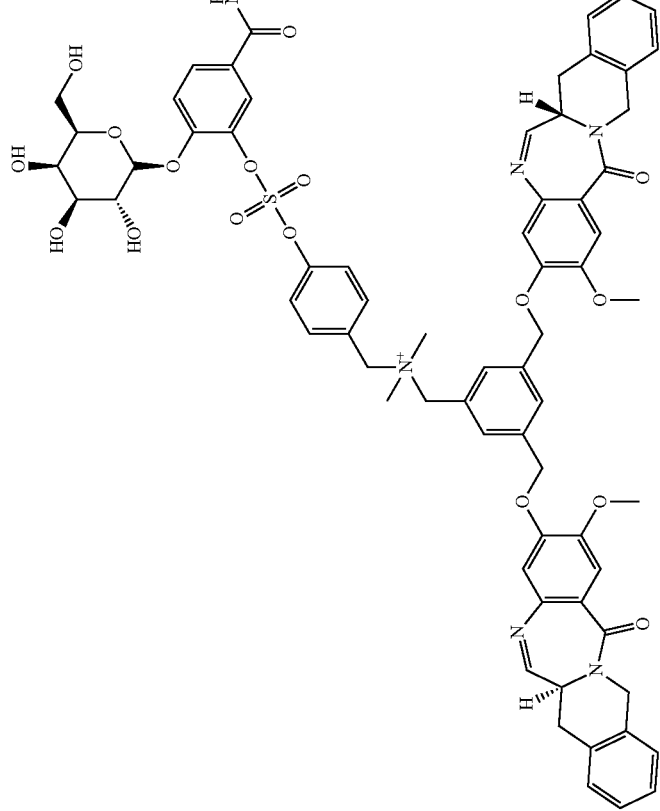

675 676
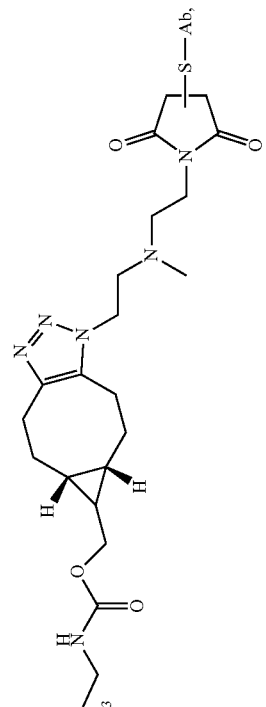
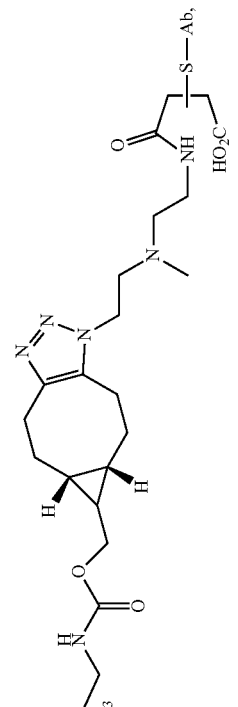
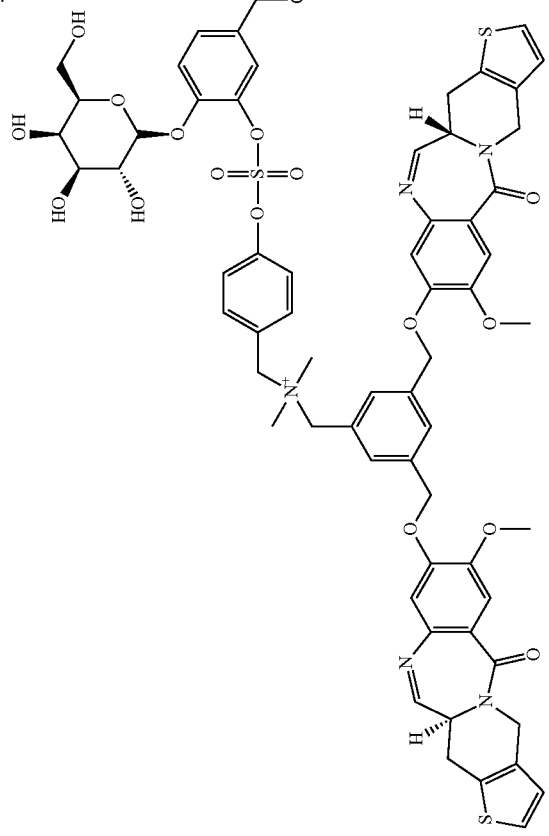
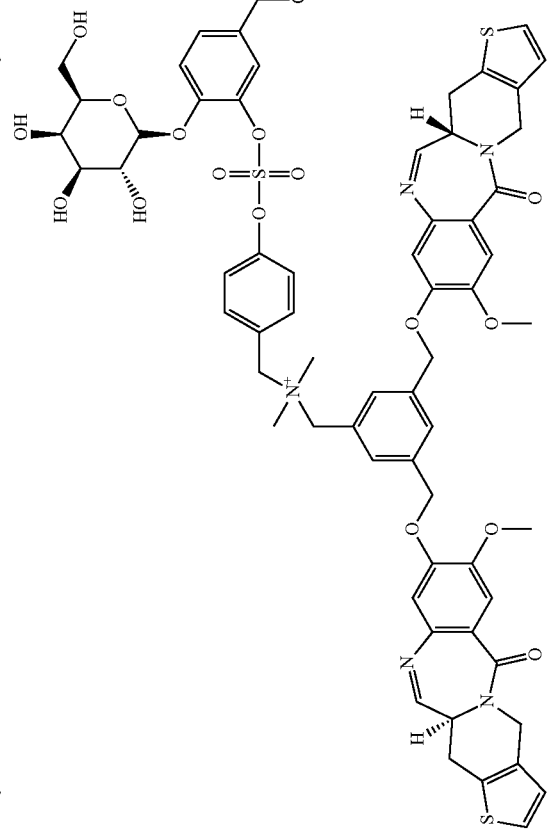

677
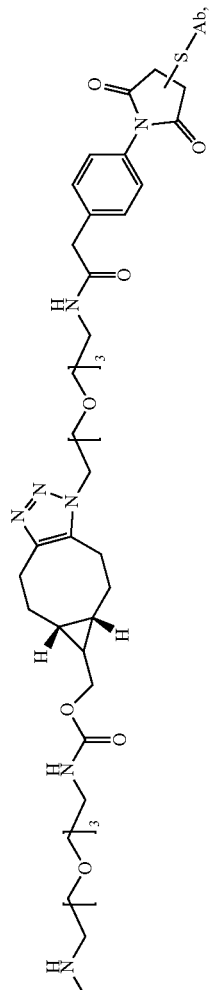
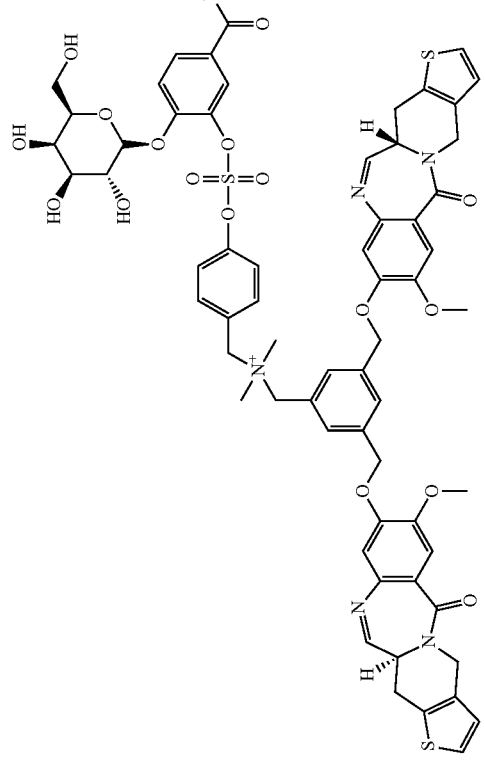
678
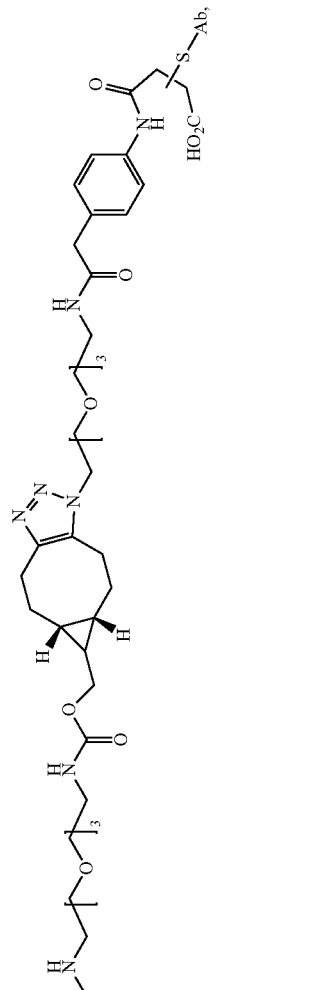
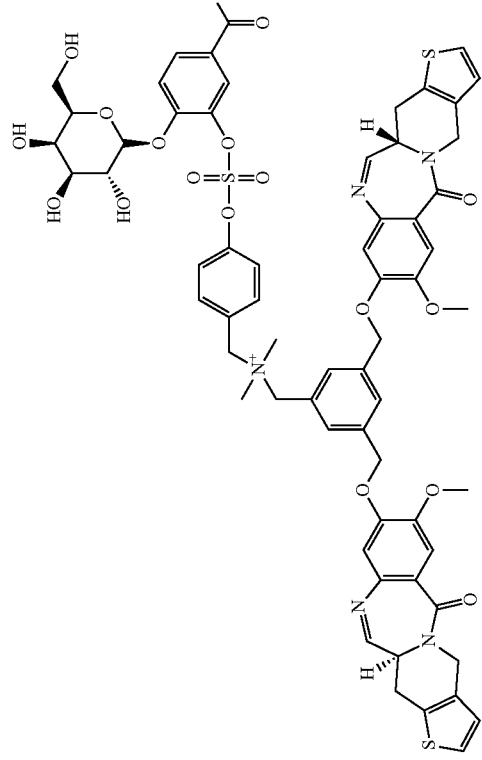

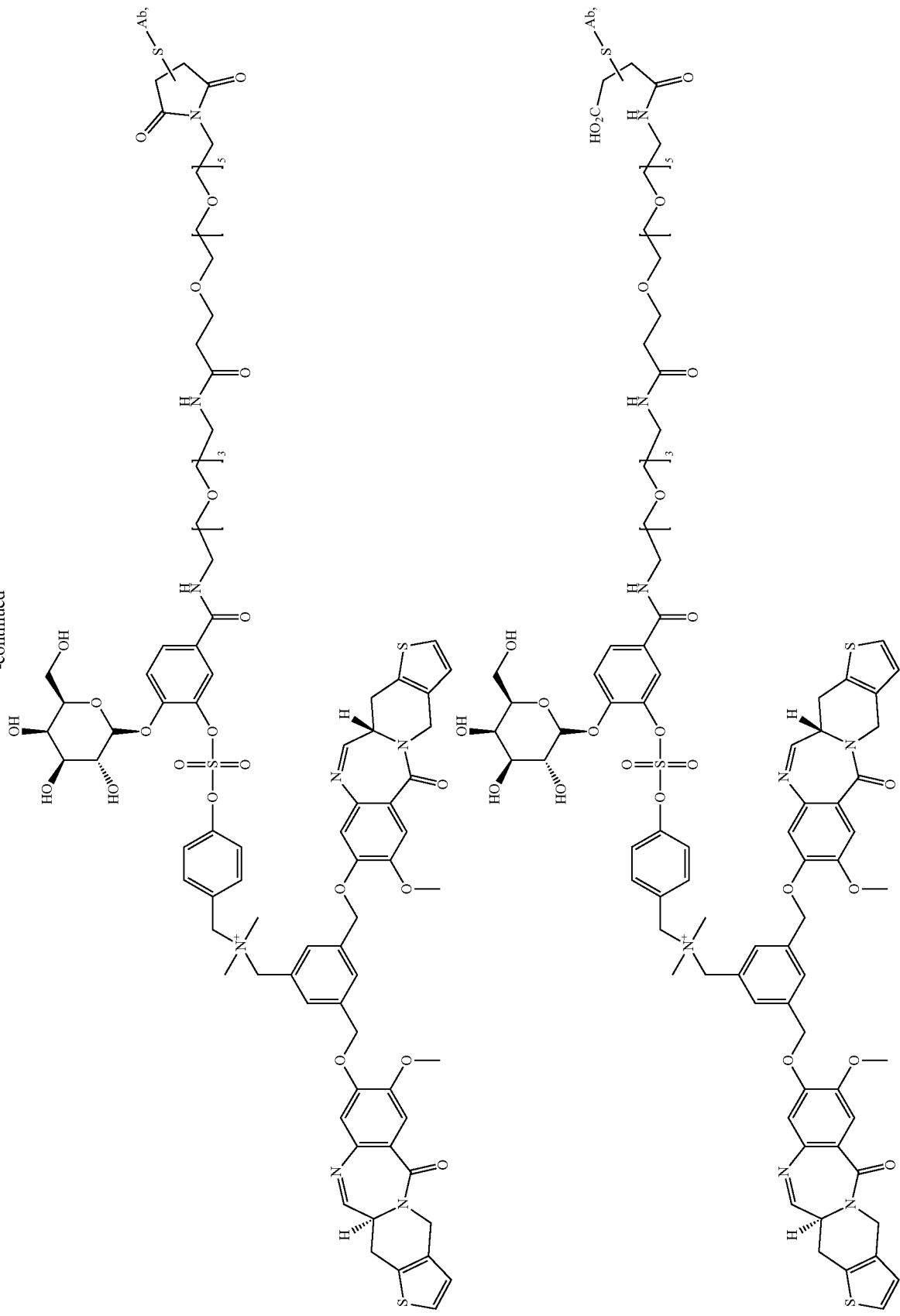

-continued
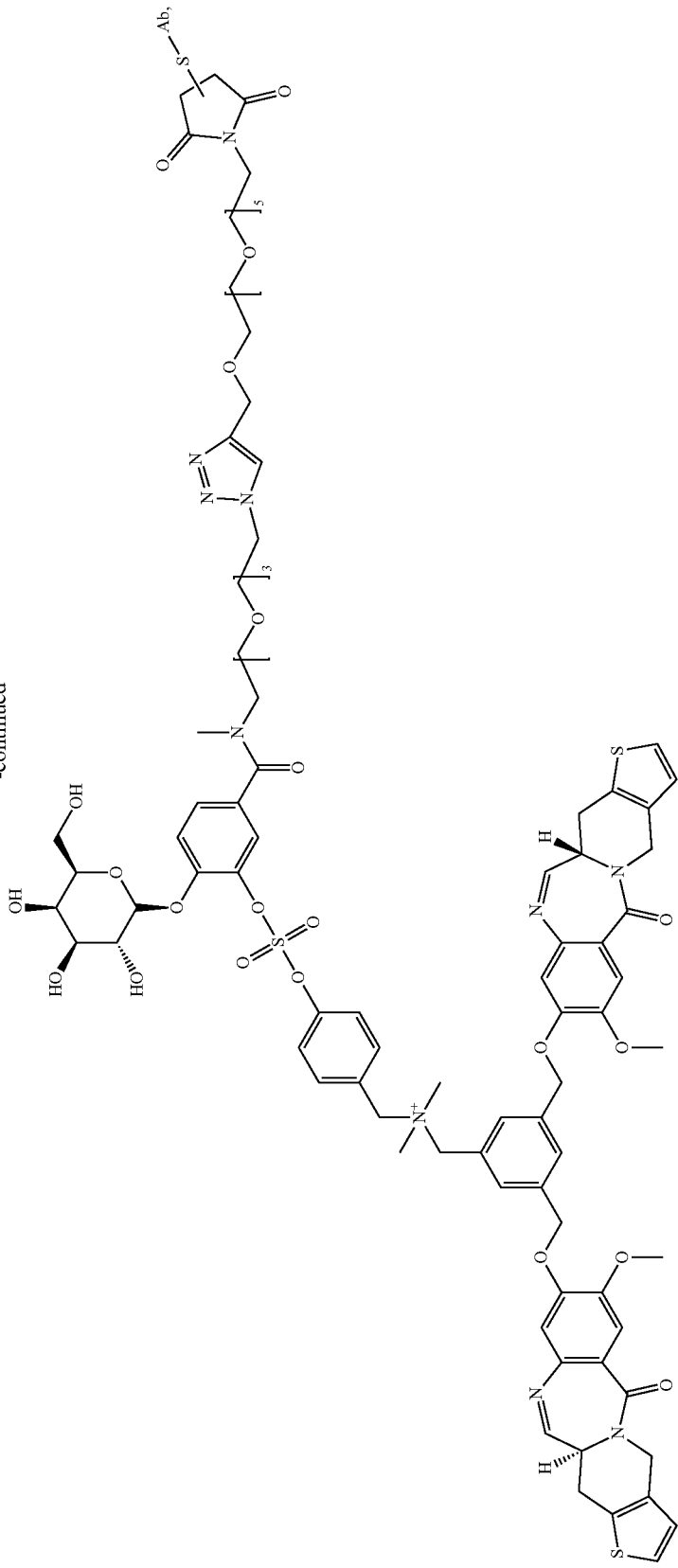

-continued
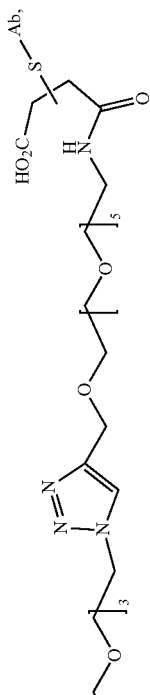
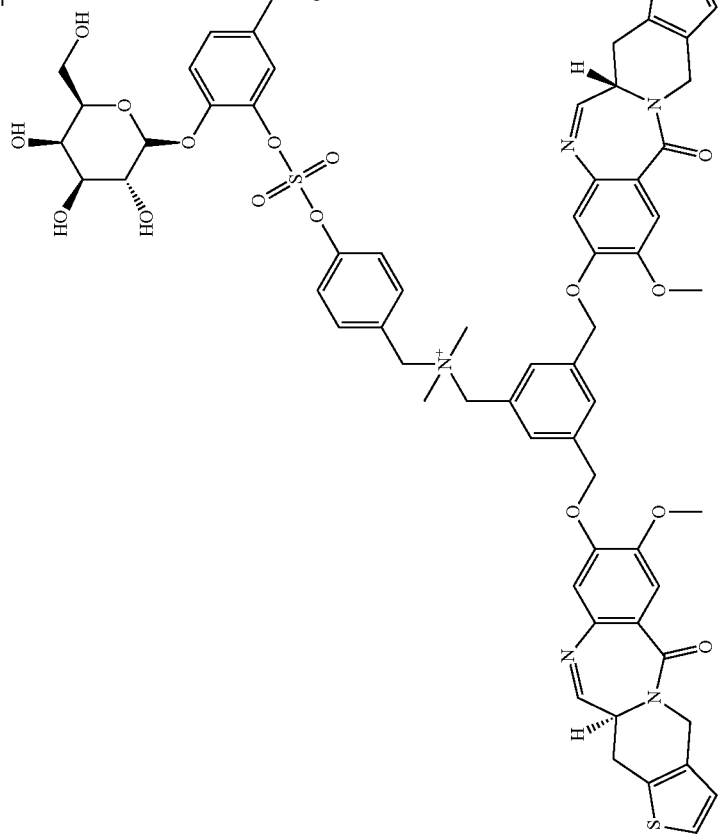

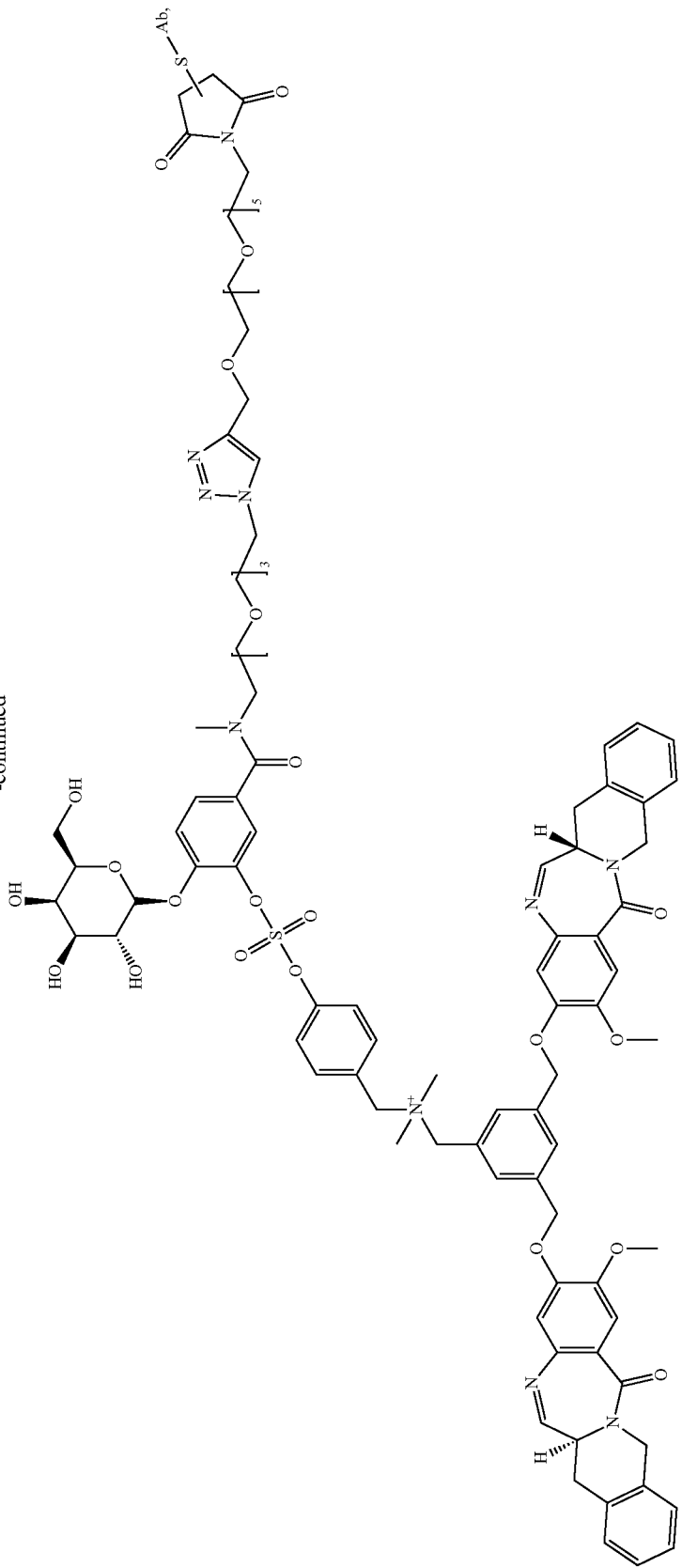

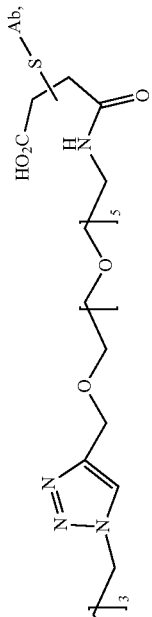
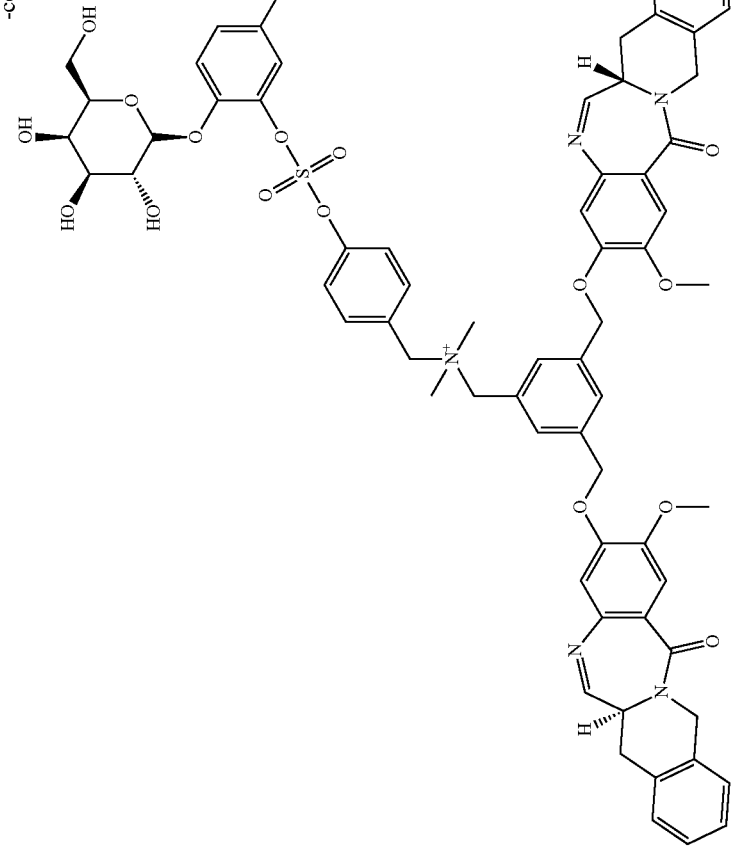

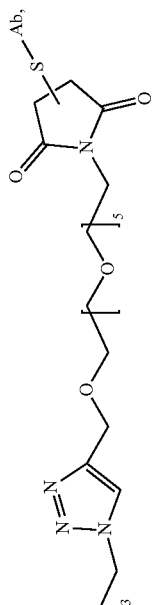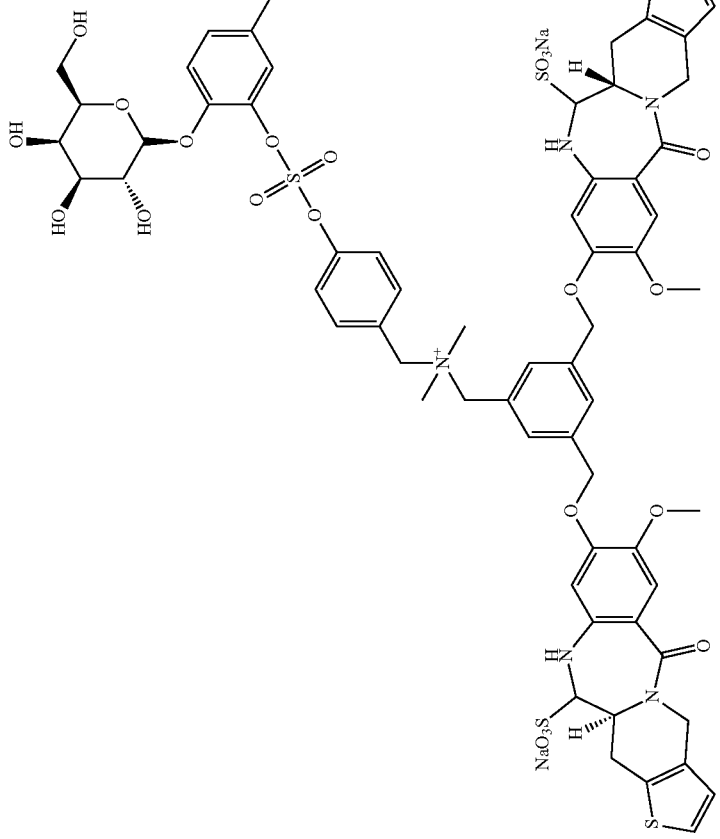

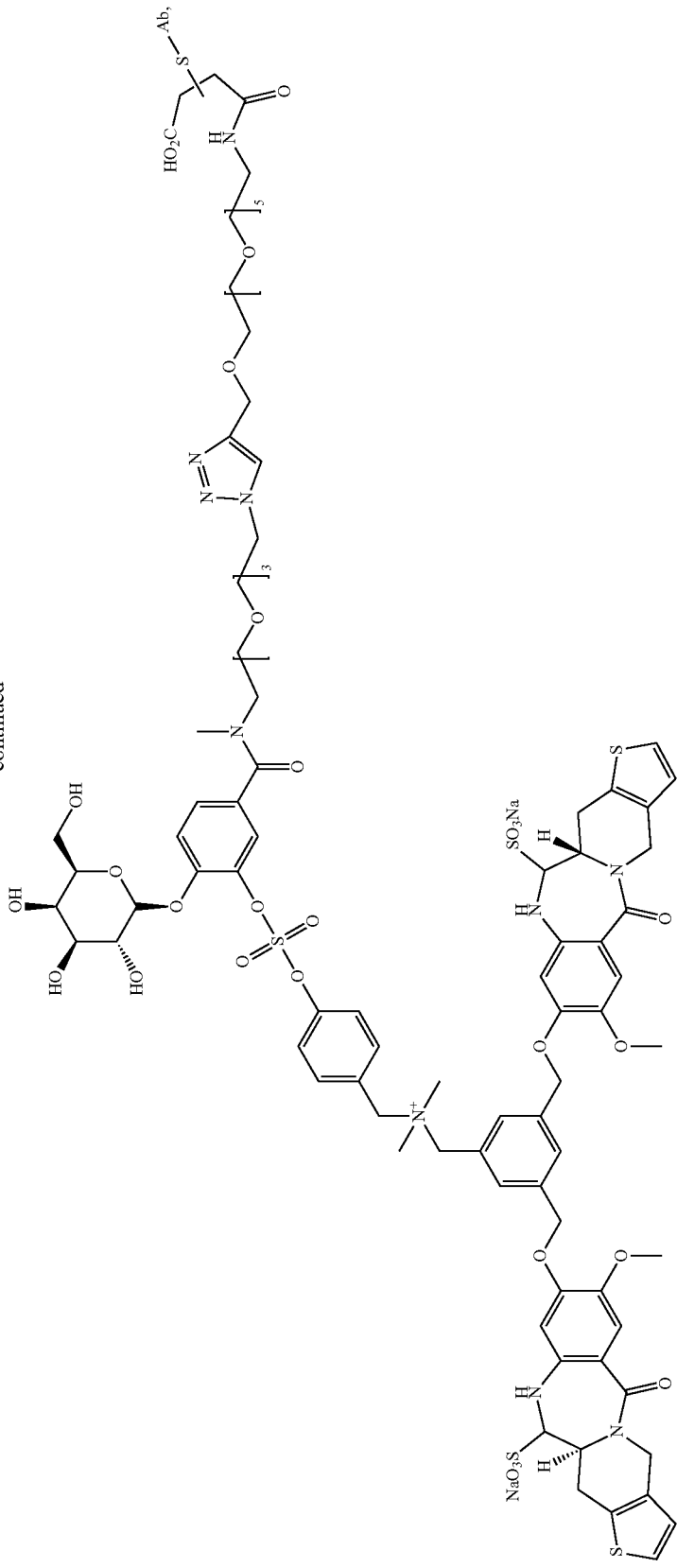

-continued
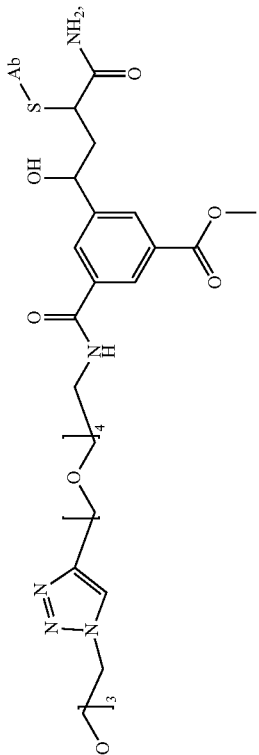
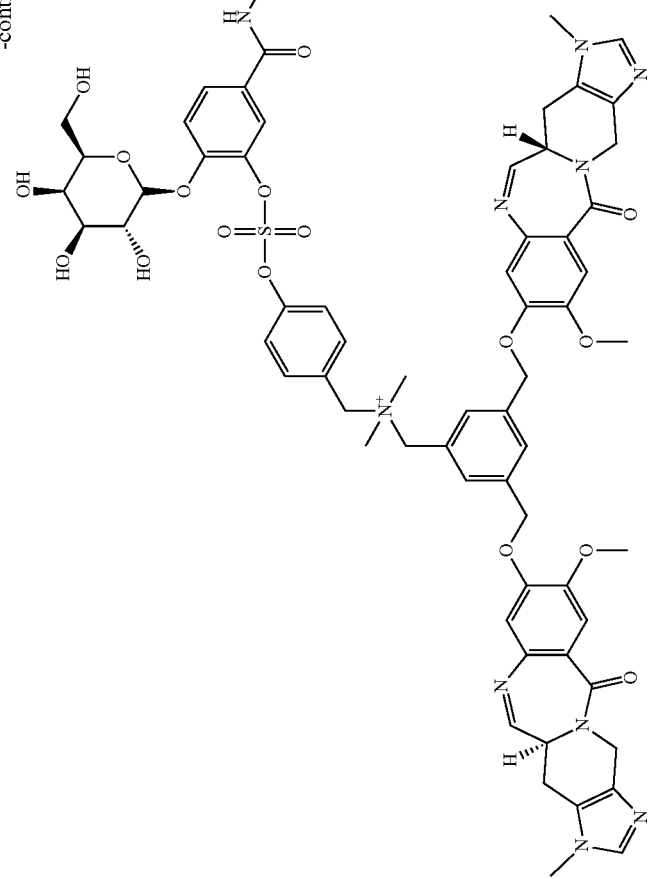

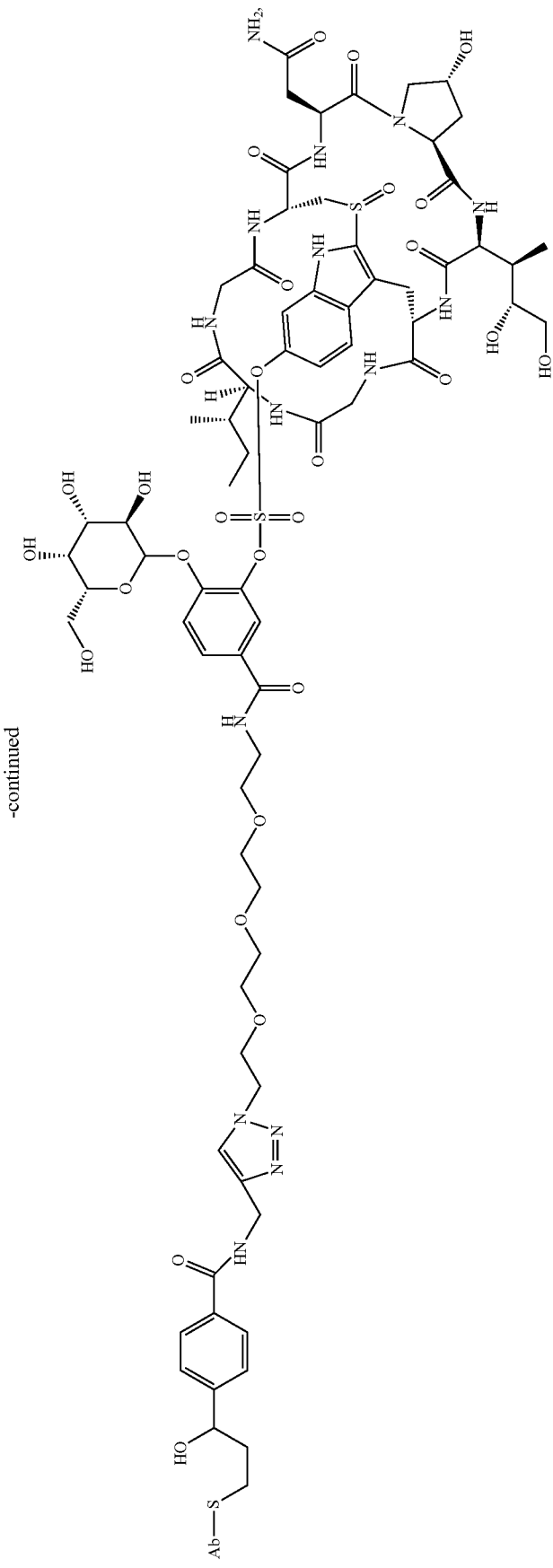

-continued
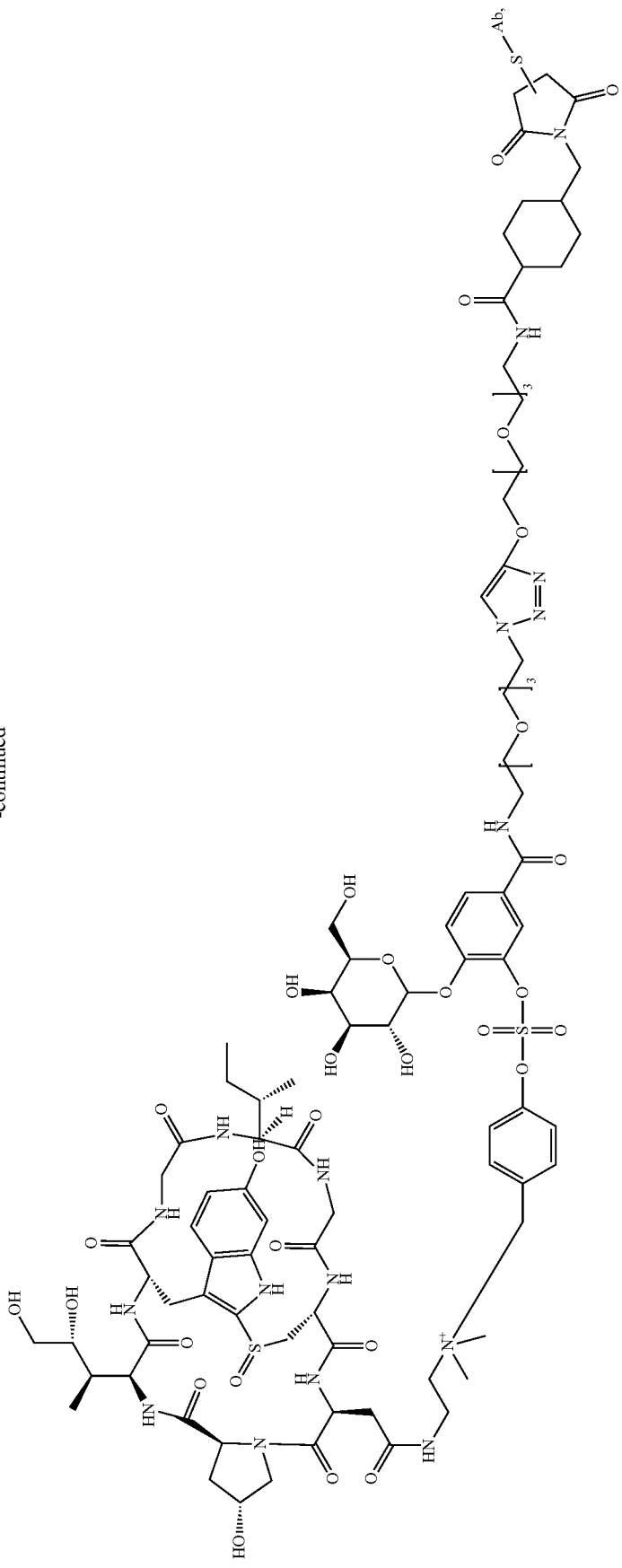

-continued
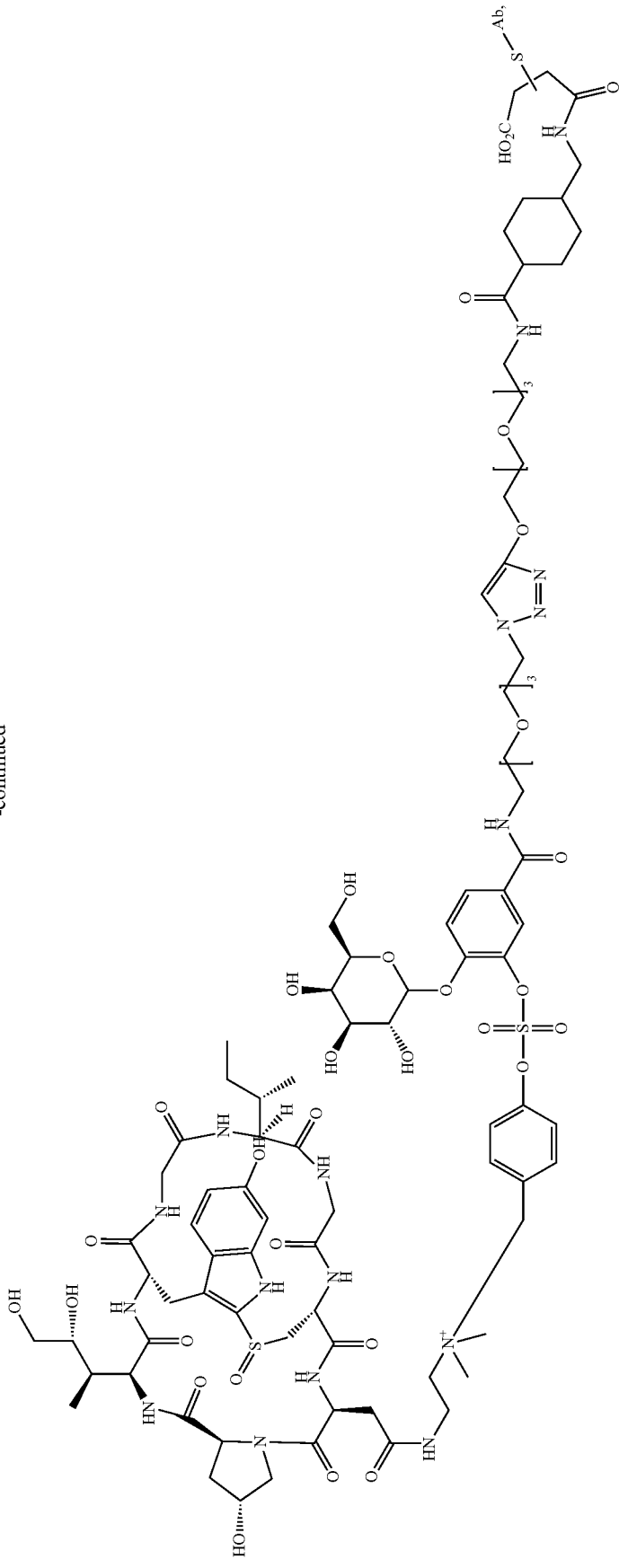

-continued
701
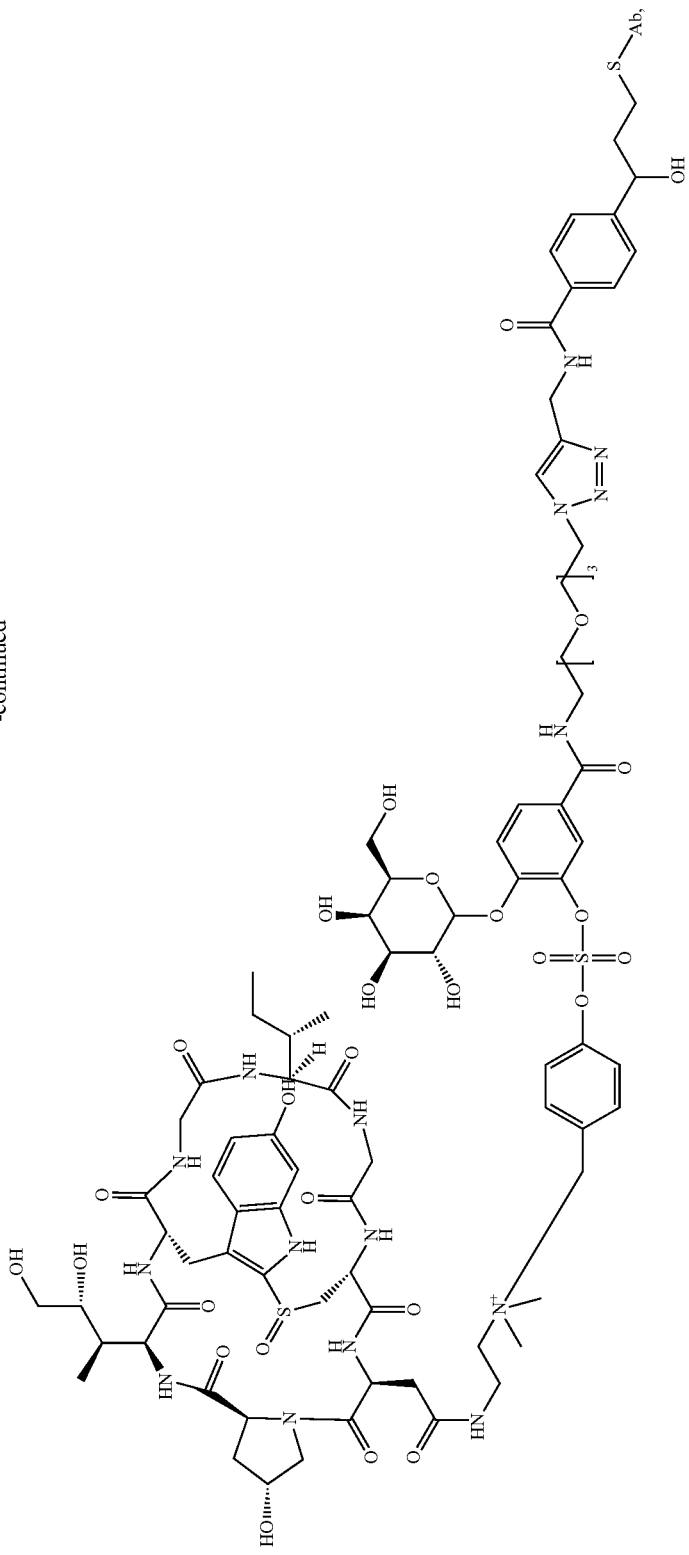
702
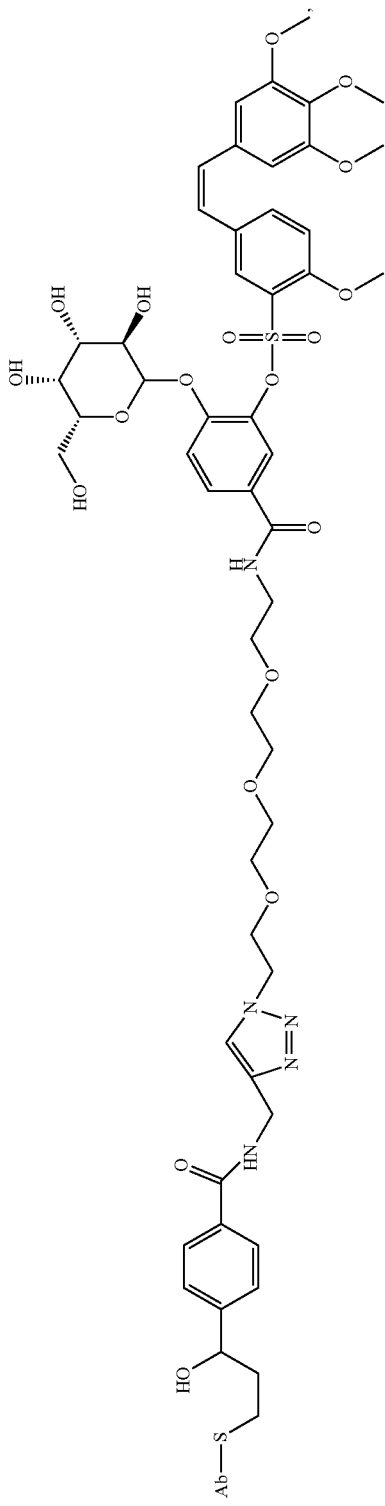

703 704
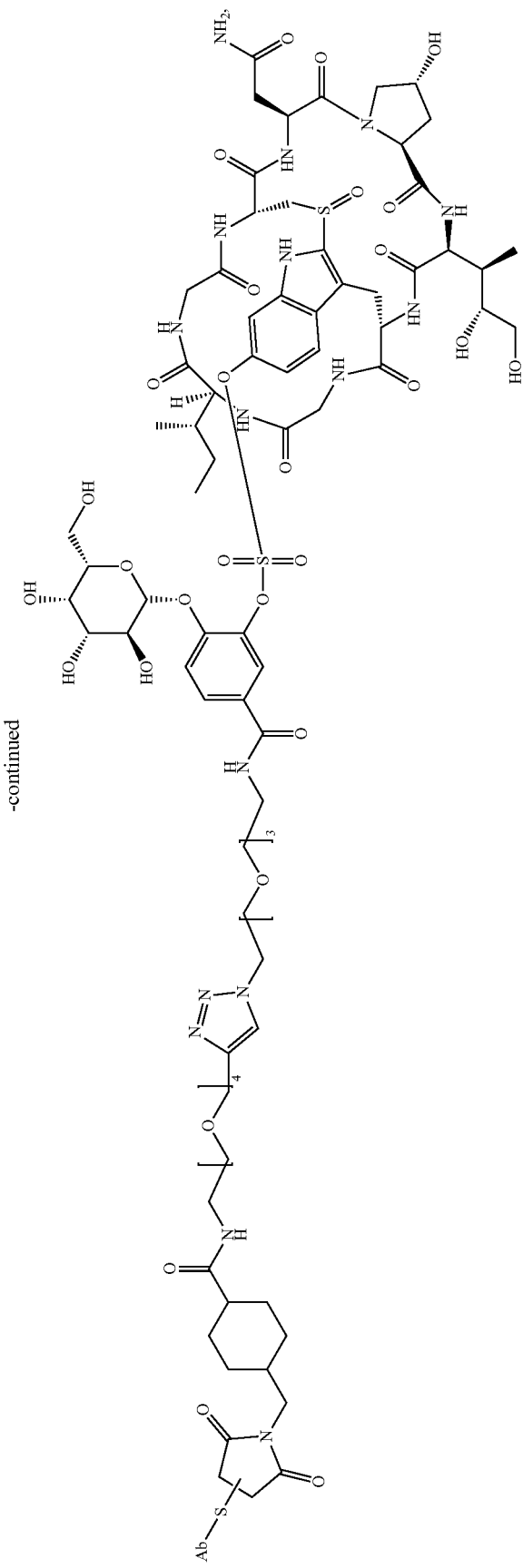
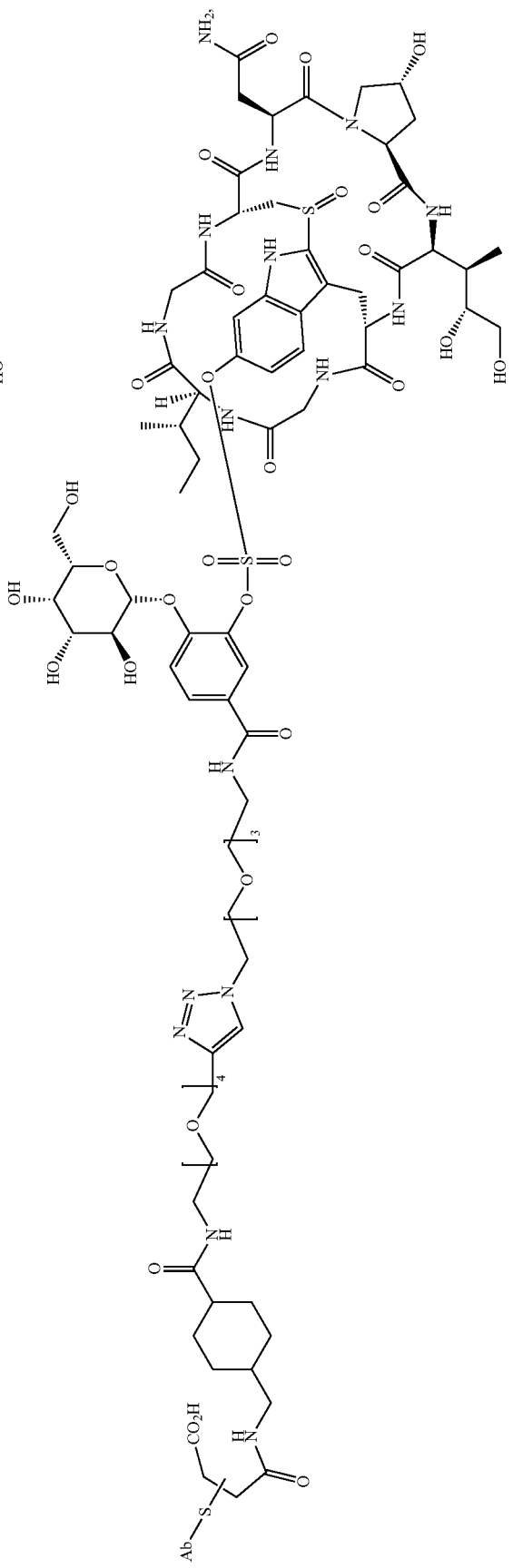

705 706
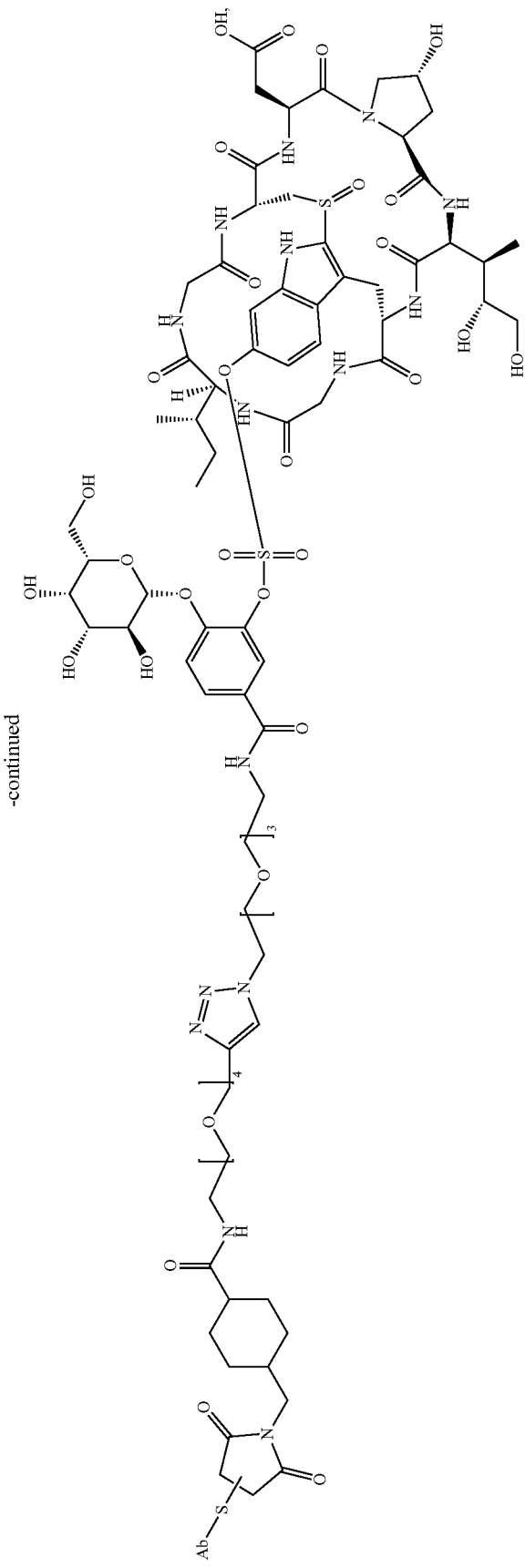
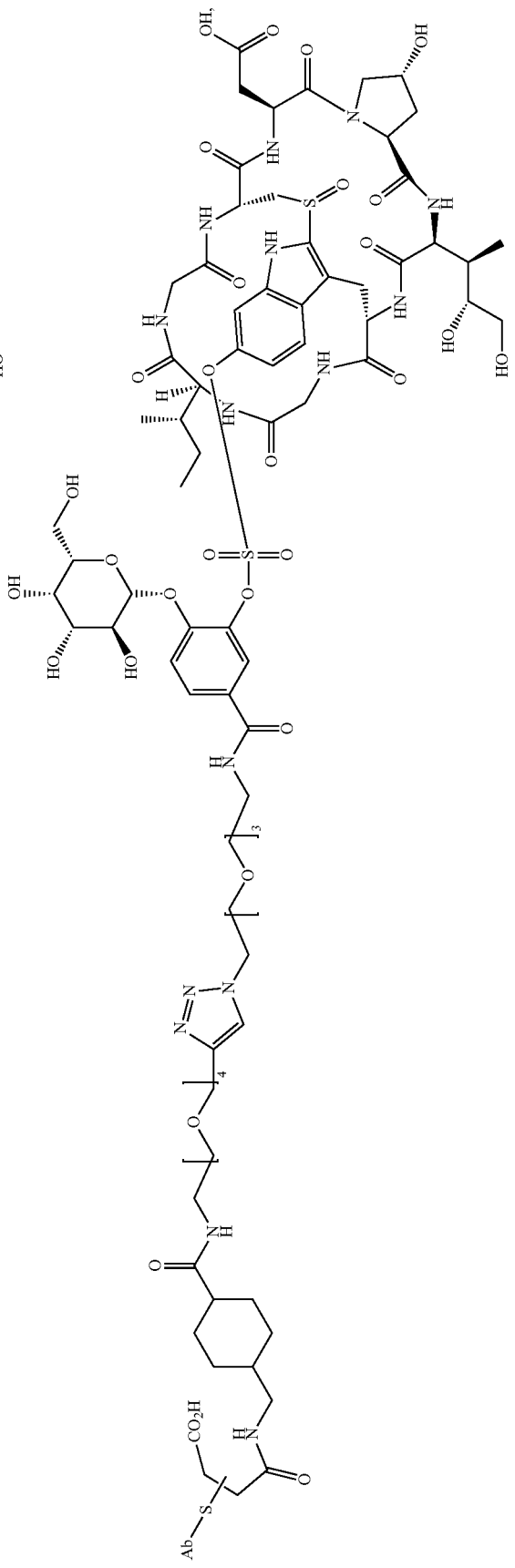

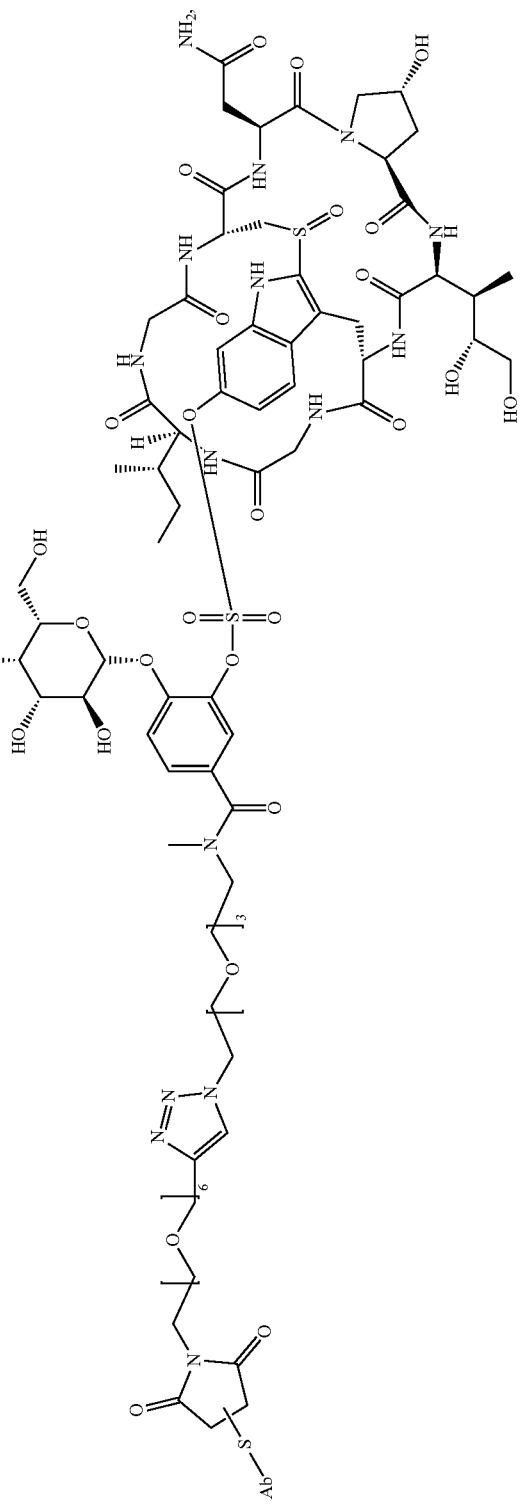

709
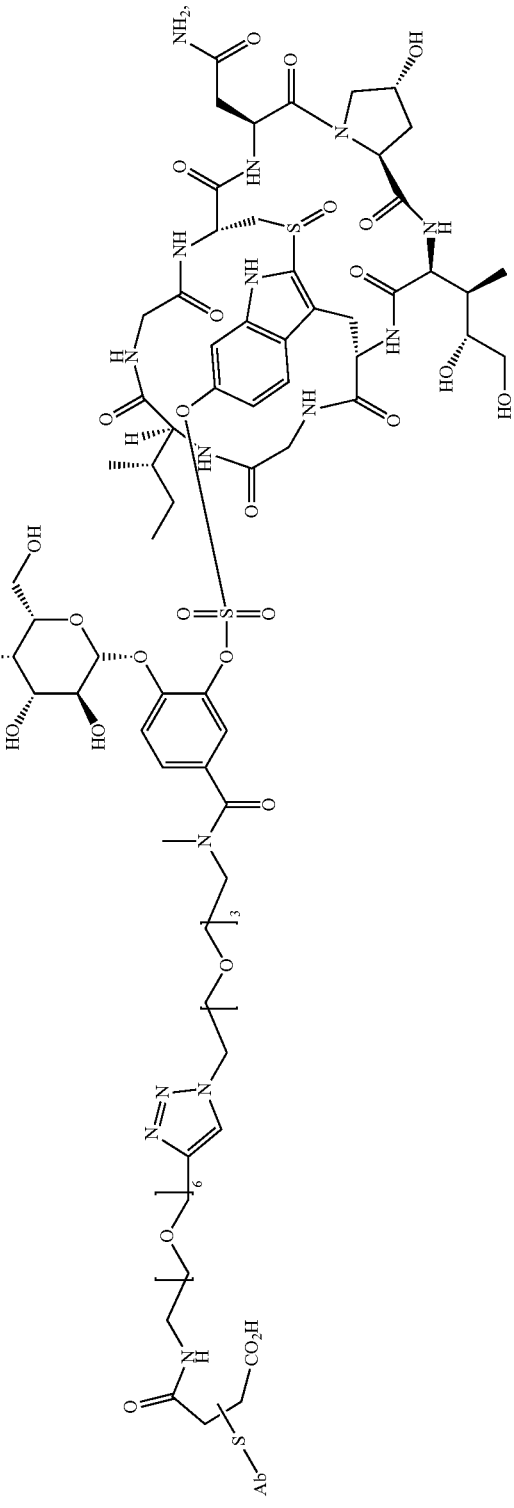
710
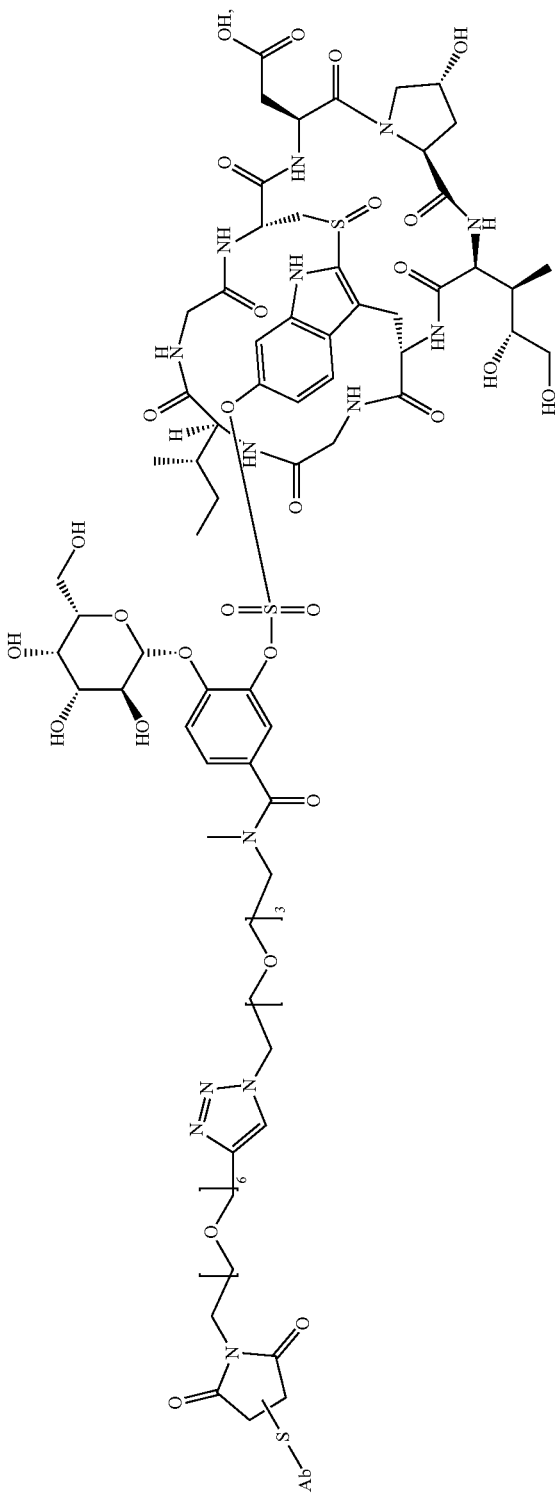

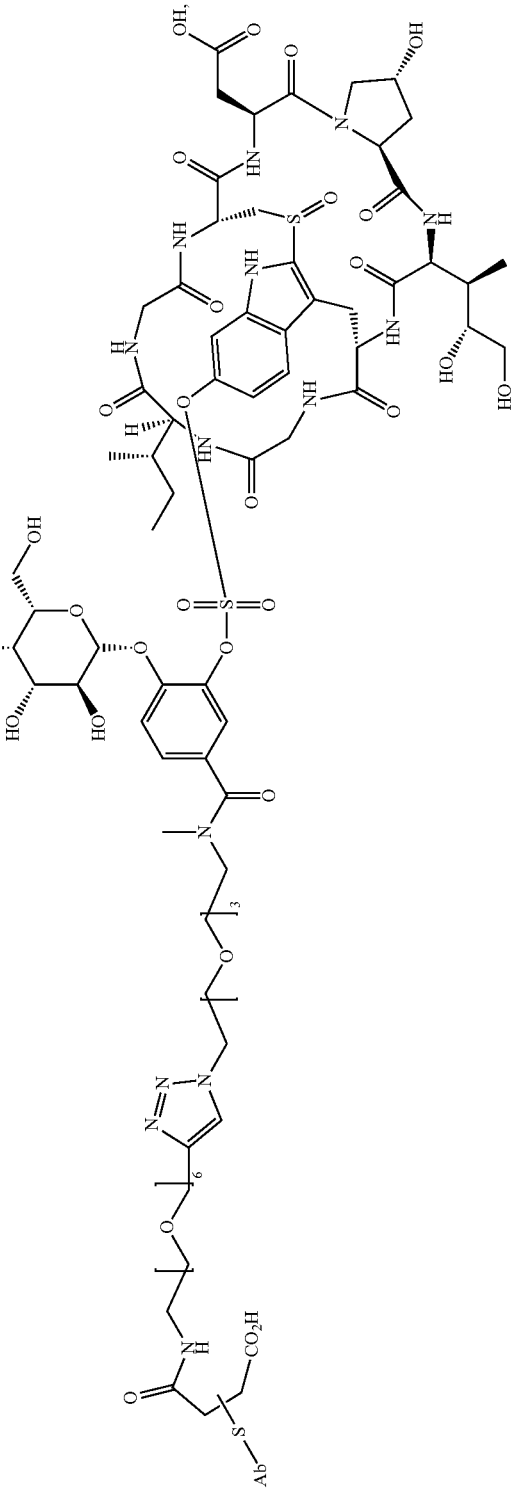
711
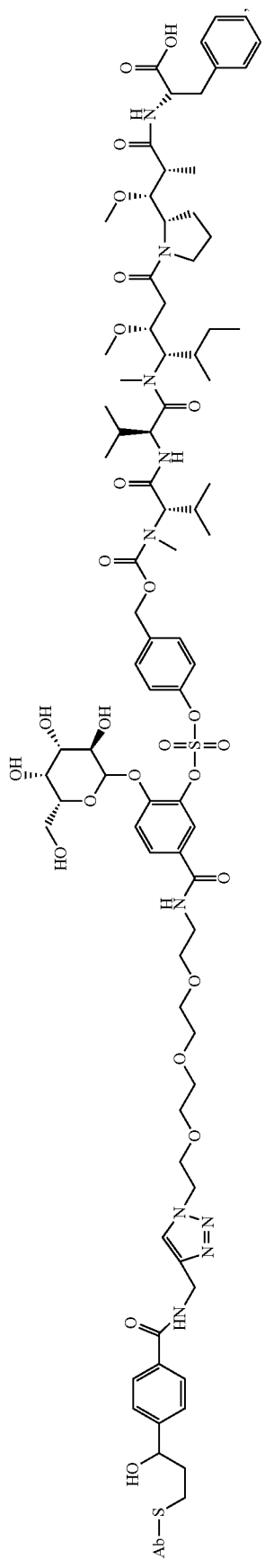
712

713
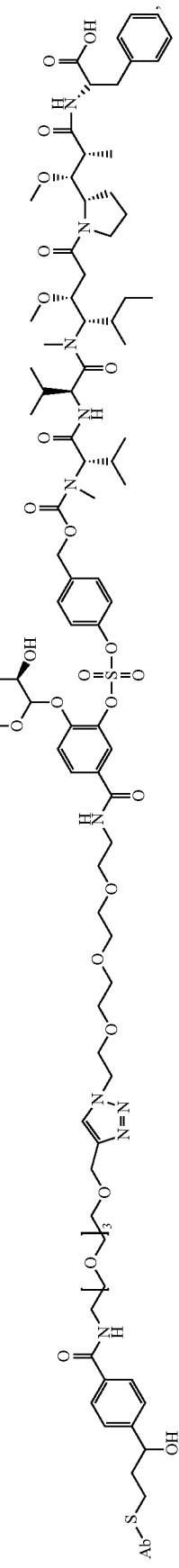
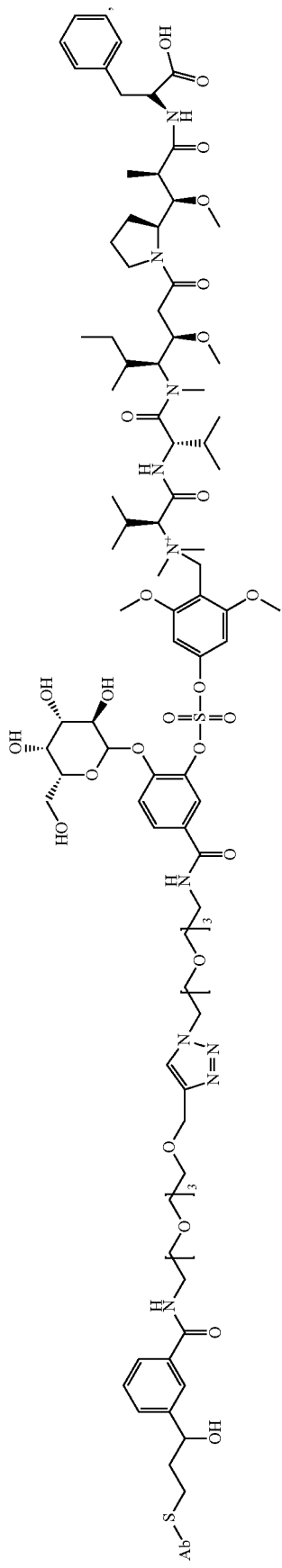
714
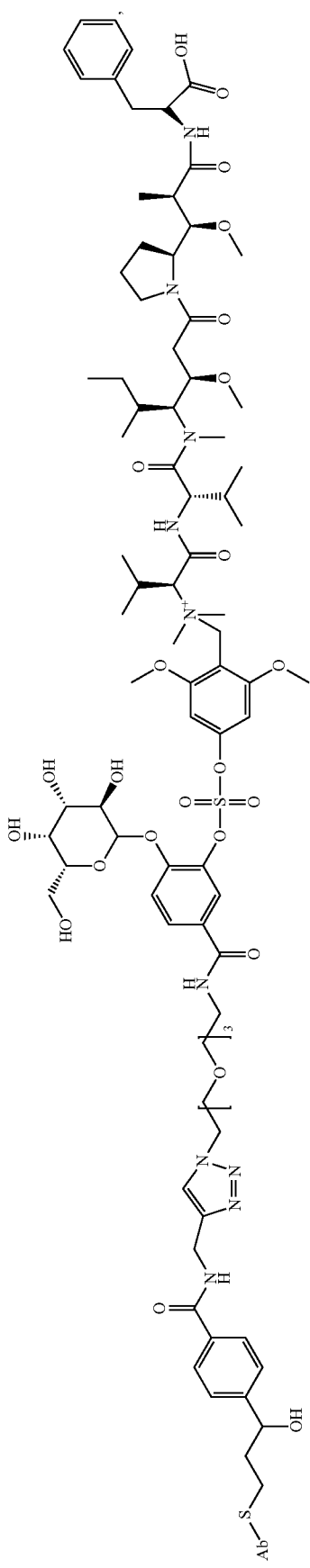

715
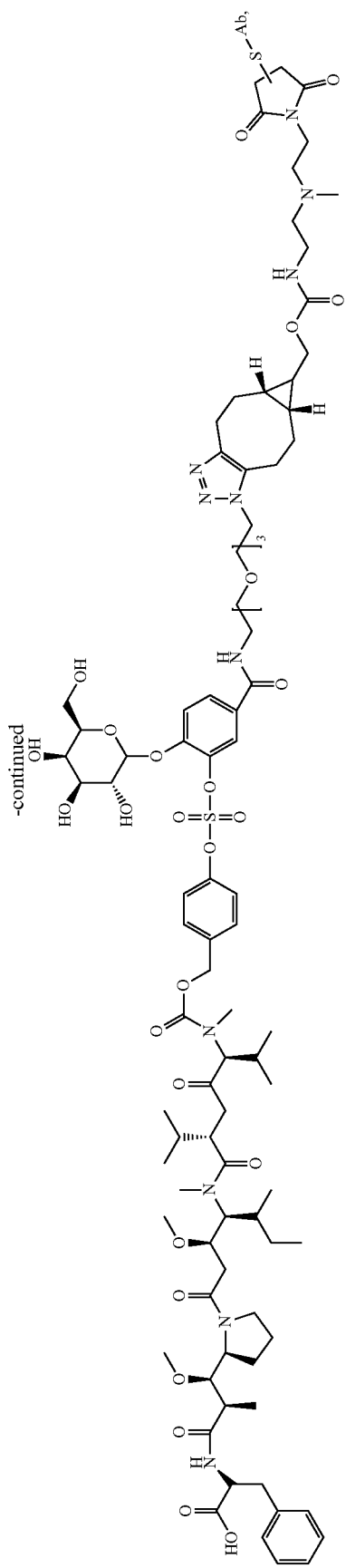
716
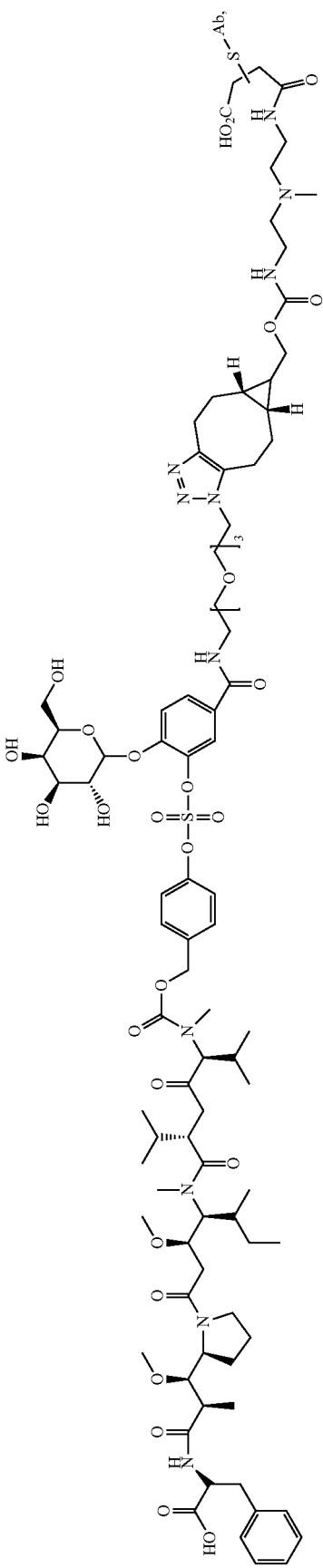

717 718
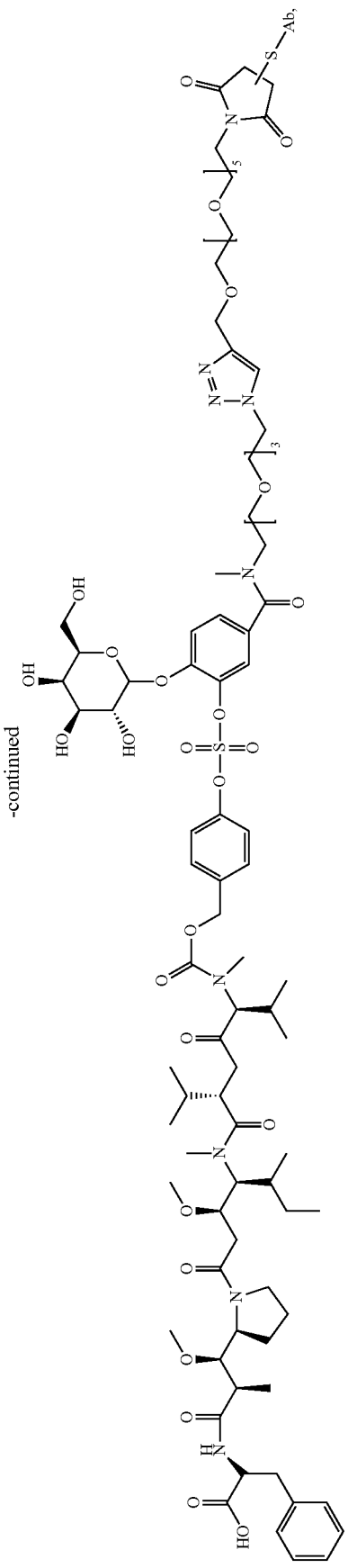
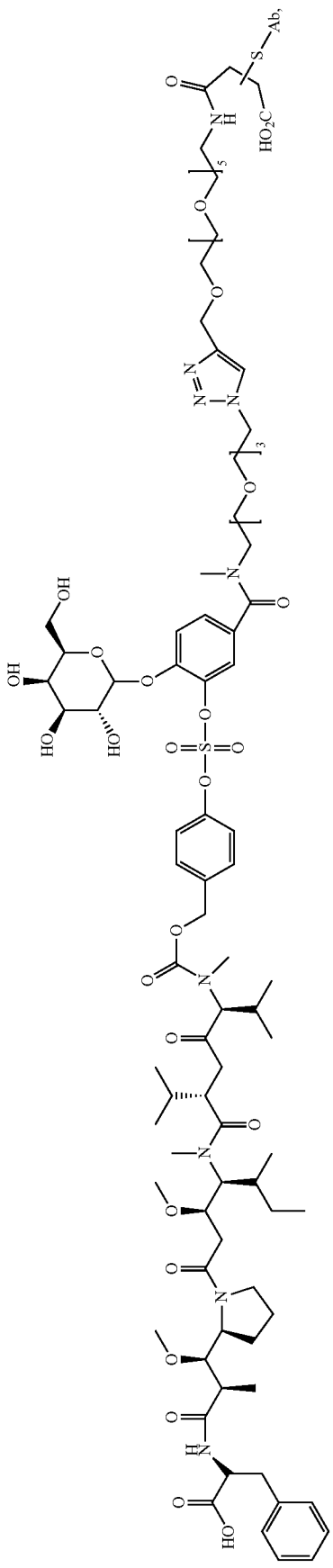
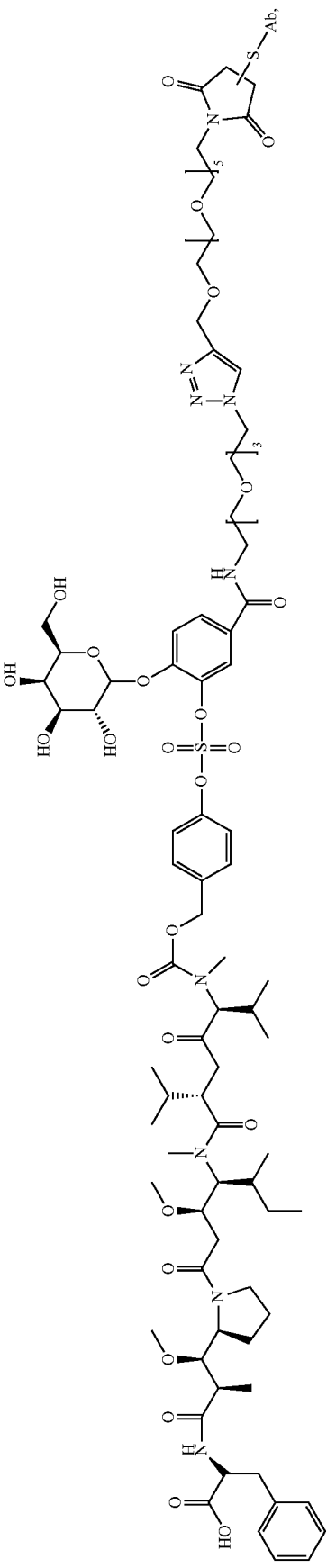

719
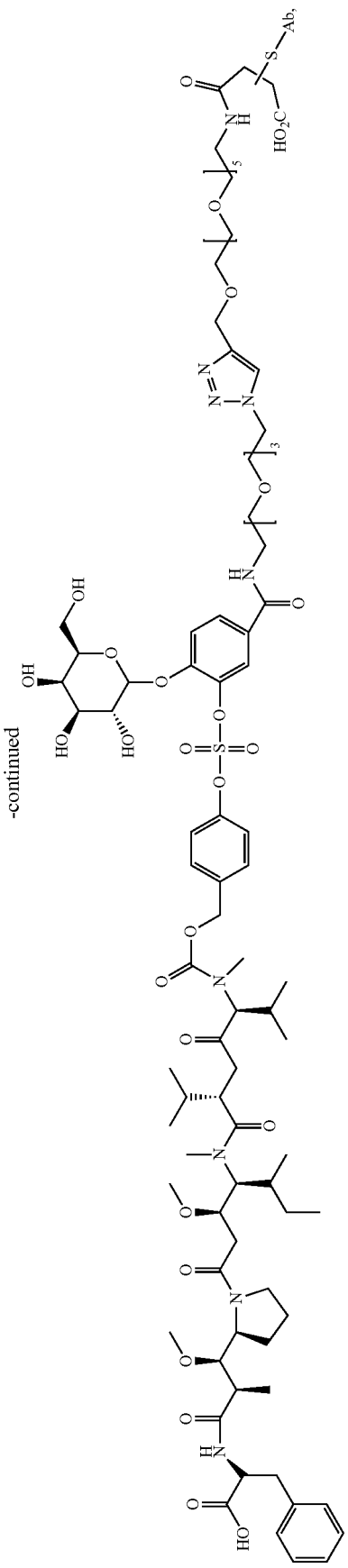
720
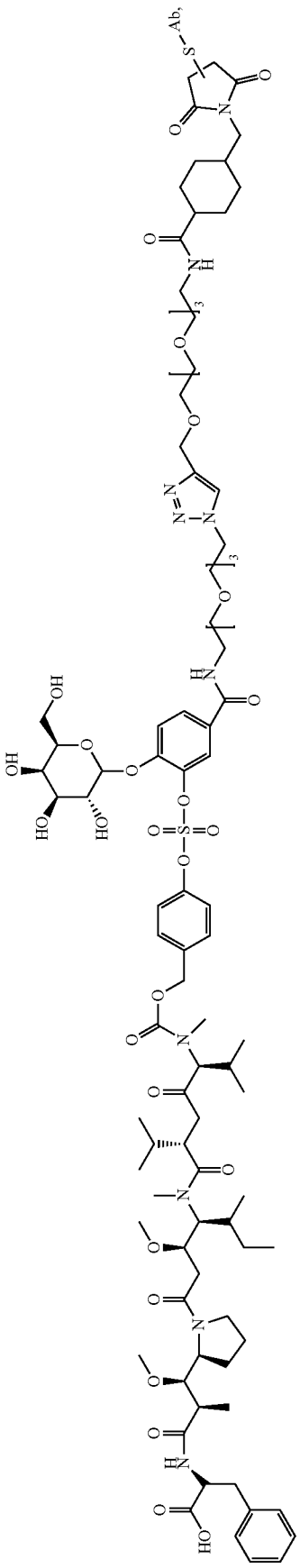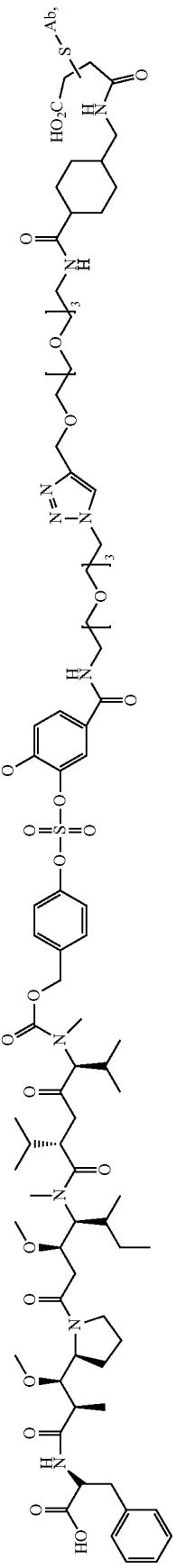

721
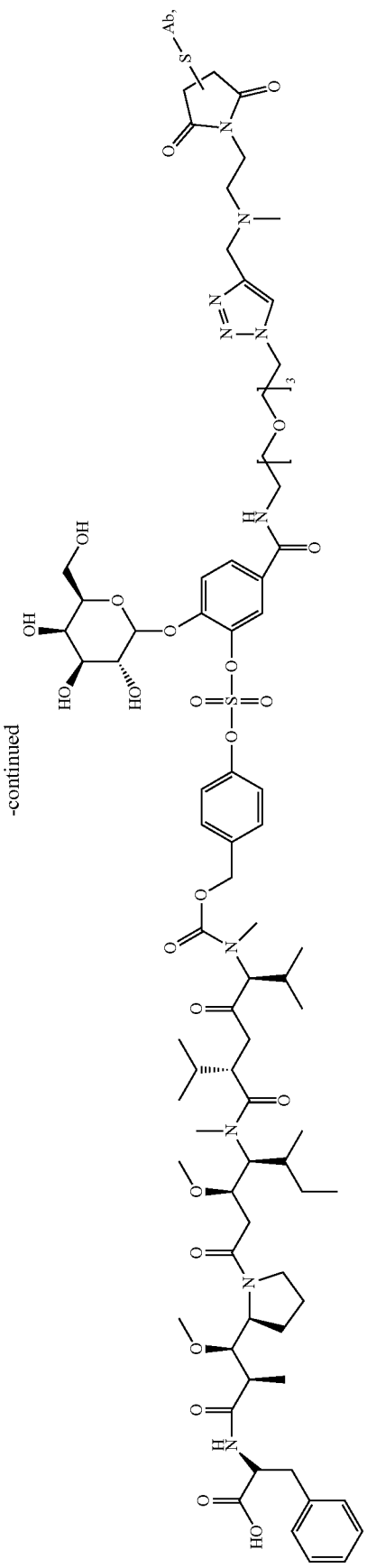
722
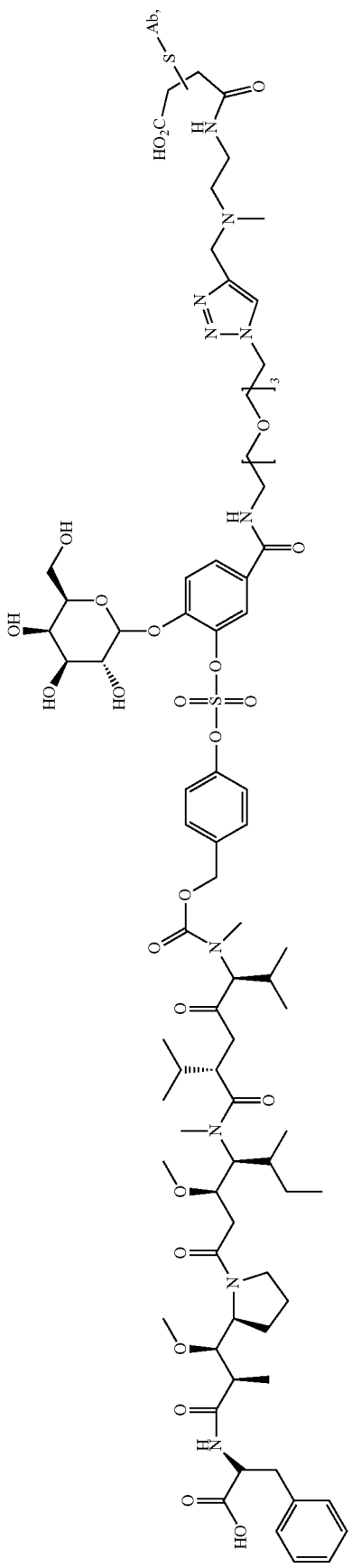

723
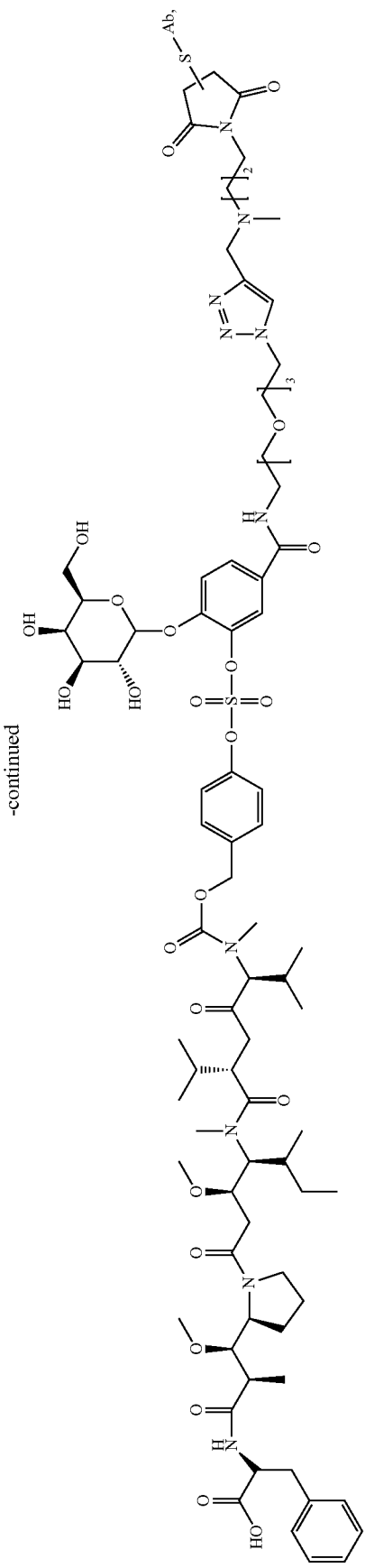
724
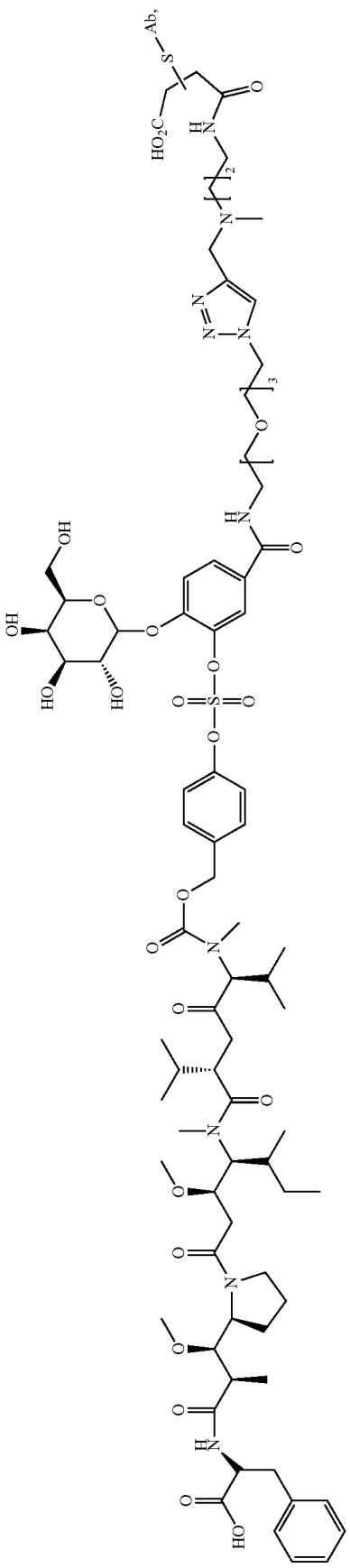

725
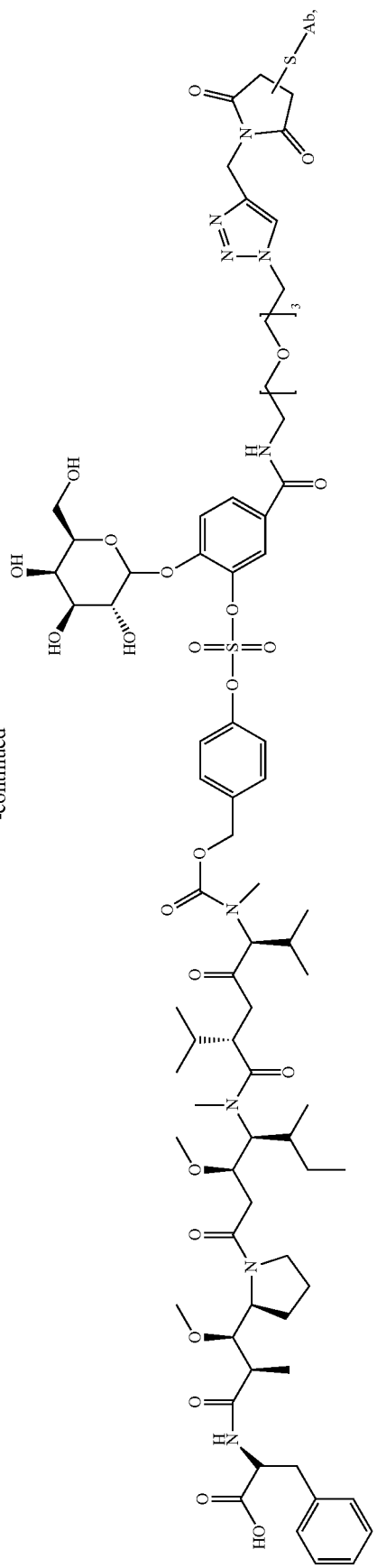
726
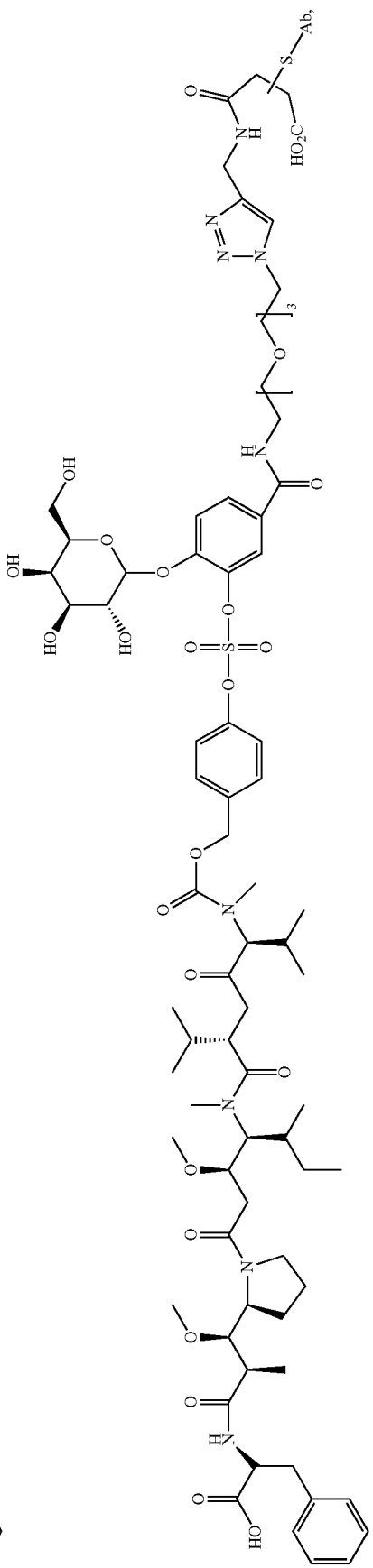
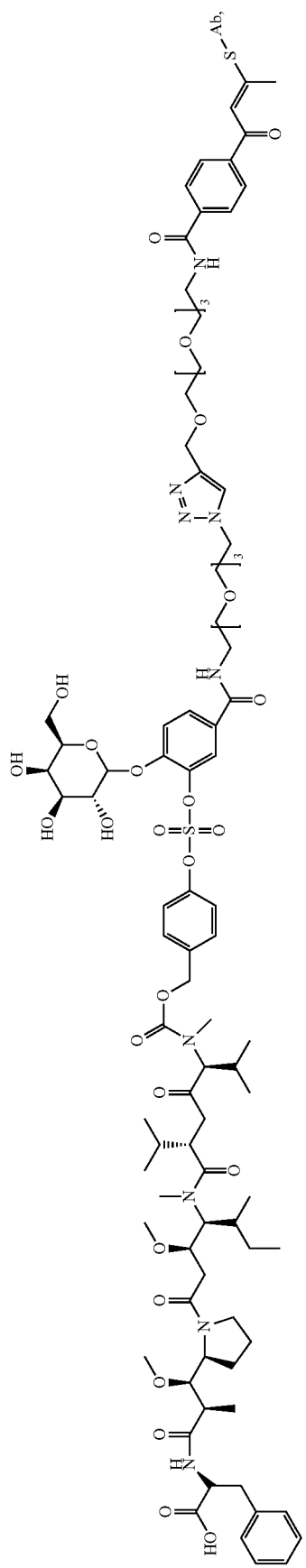

727
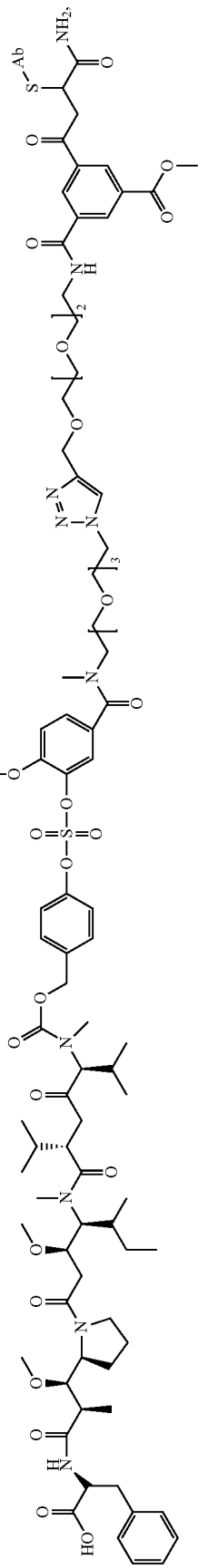
728
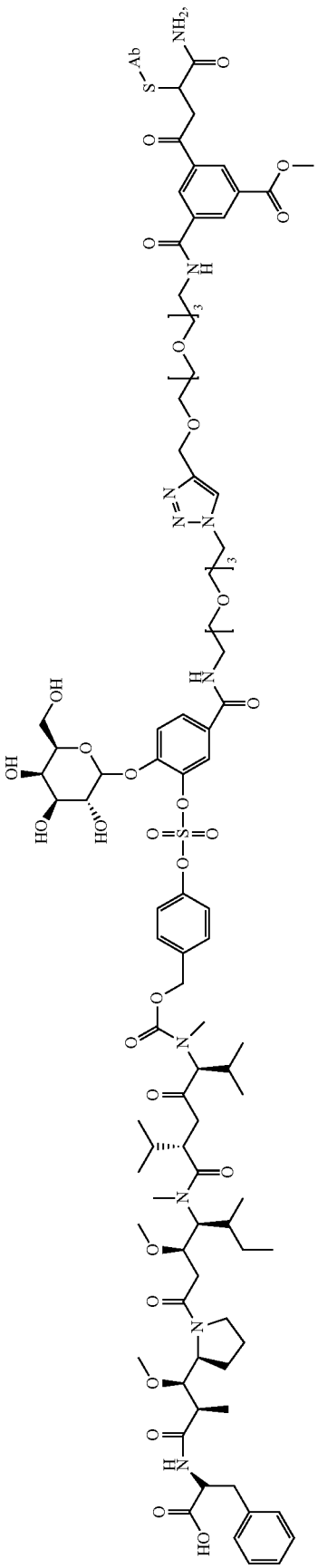

-continued
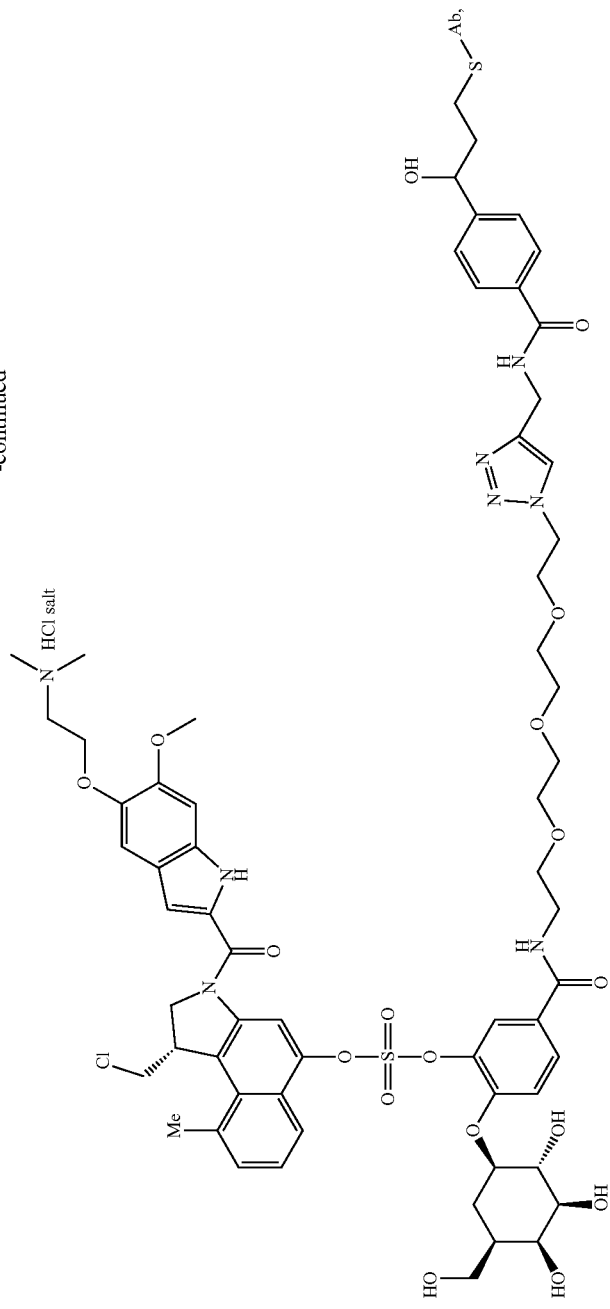

731
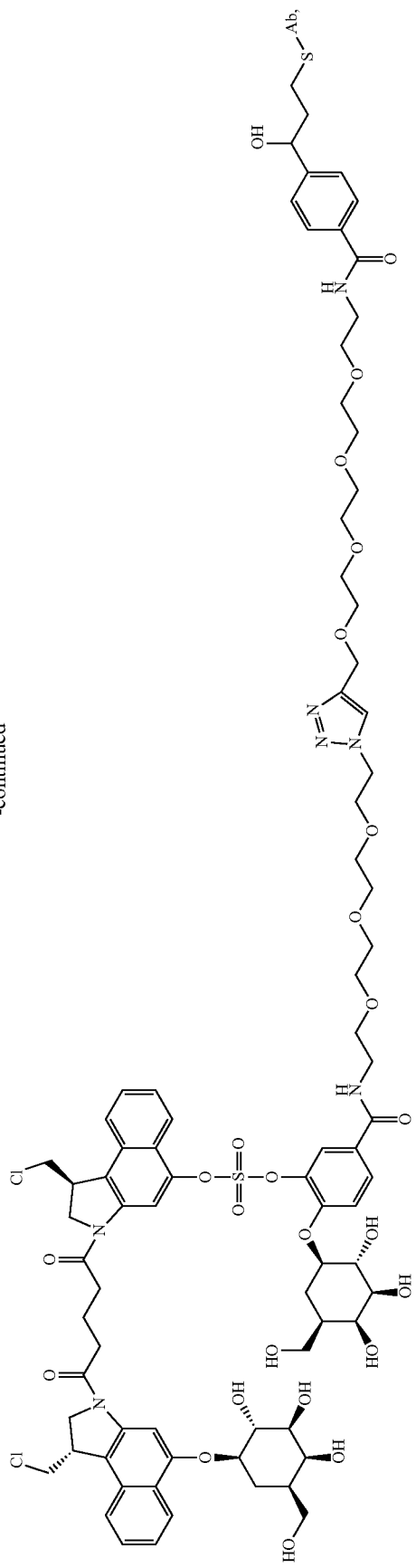
732
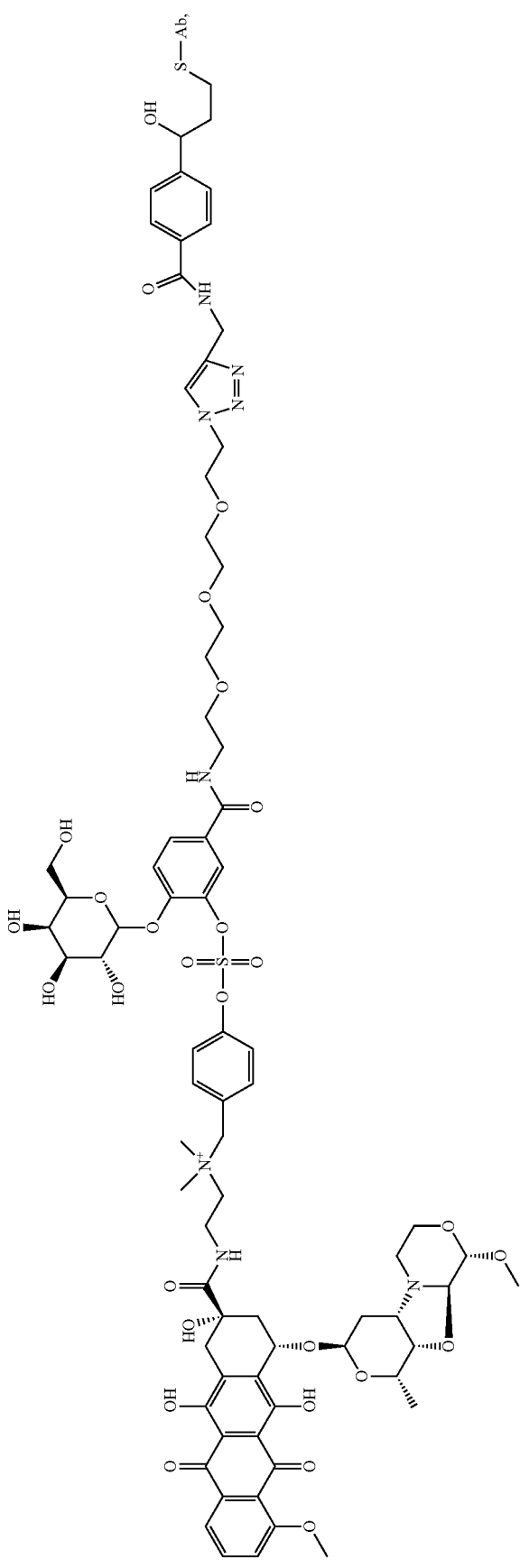

-continued
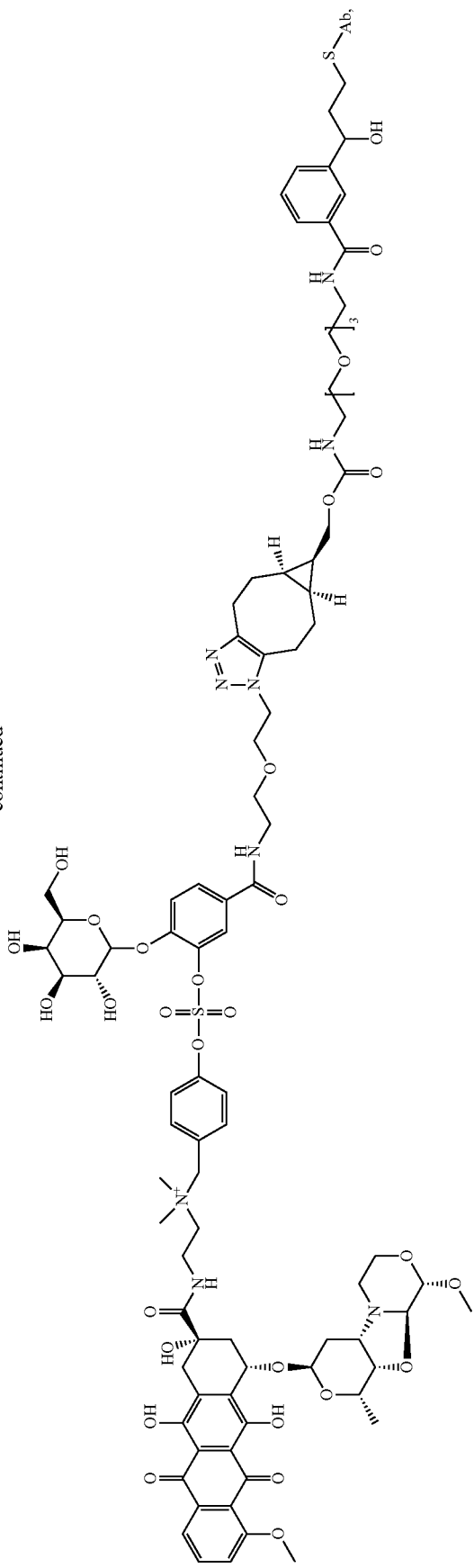

735
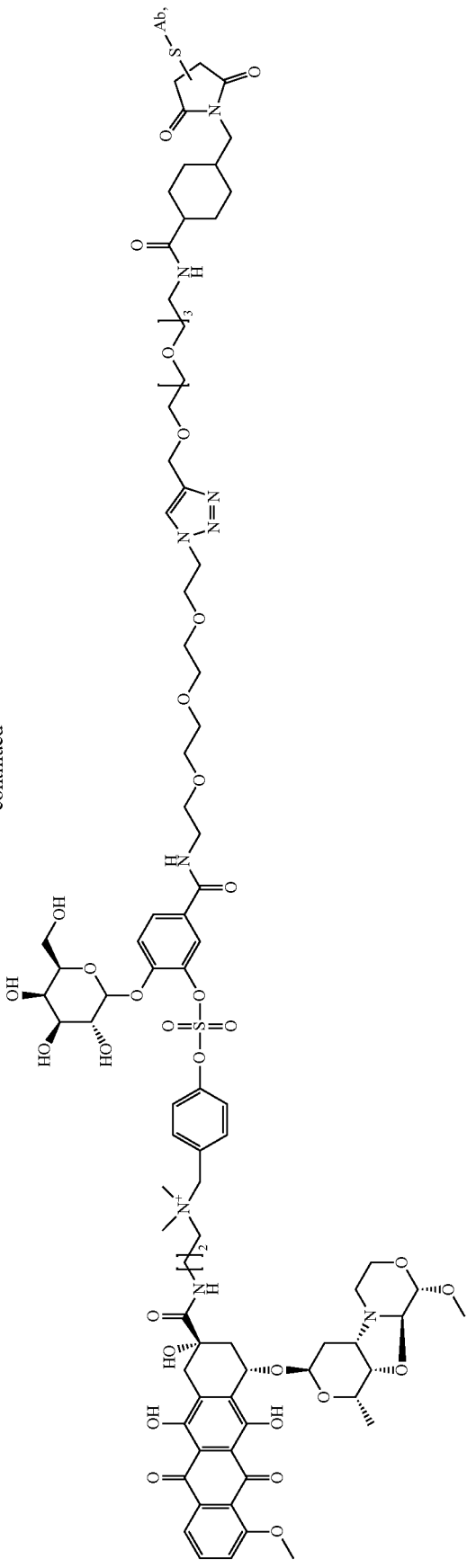
736
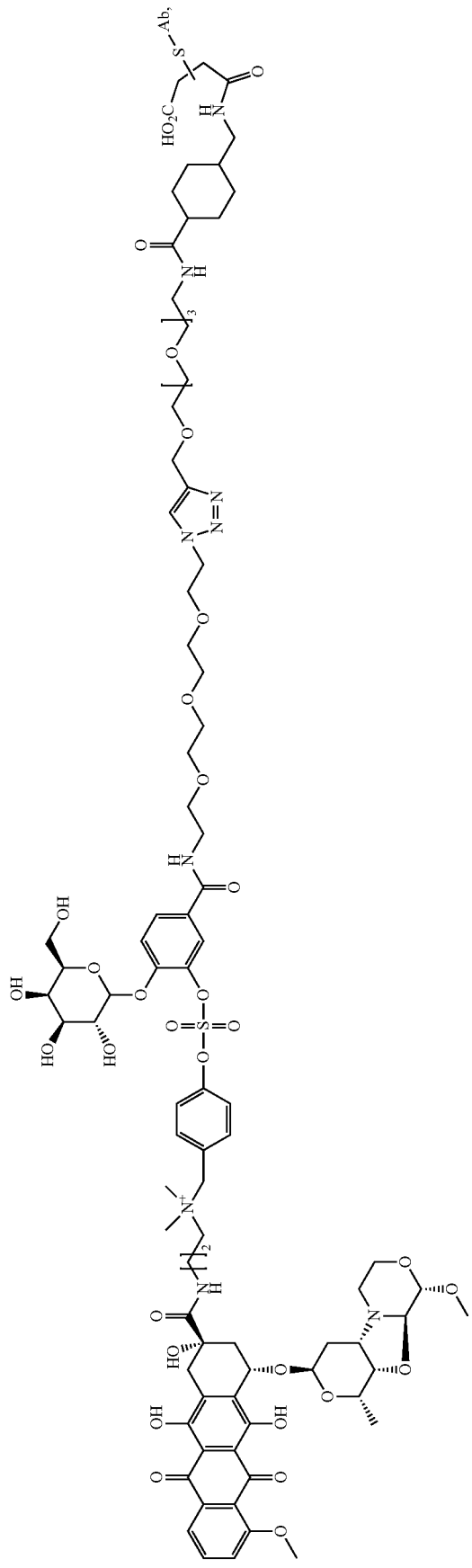

737 738
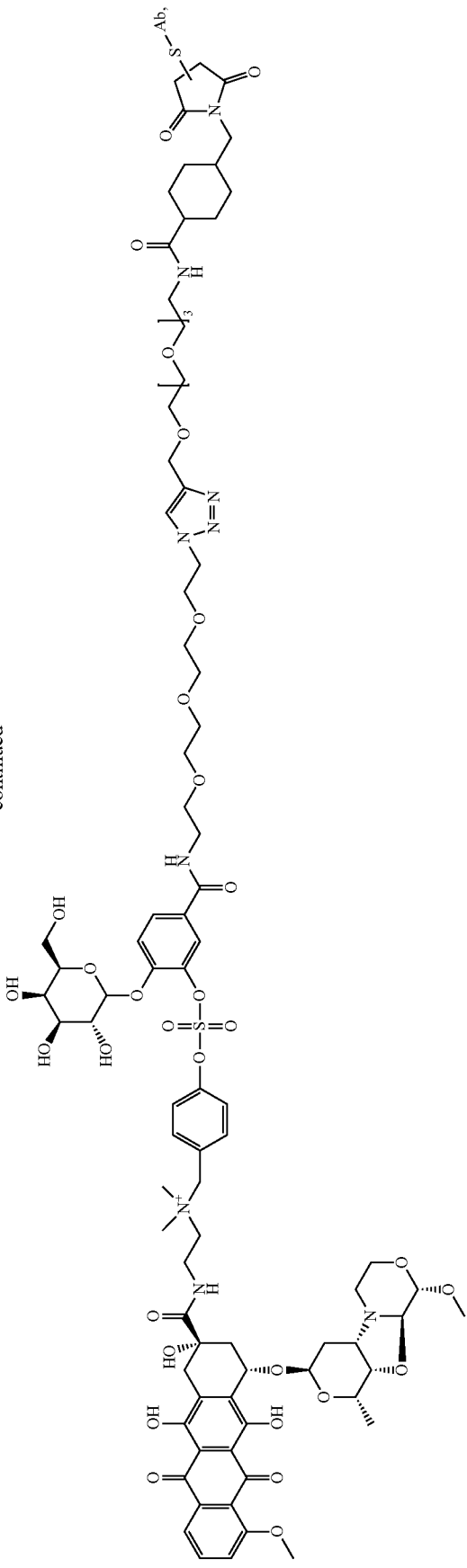
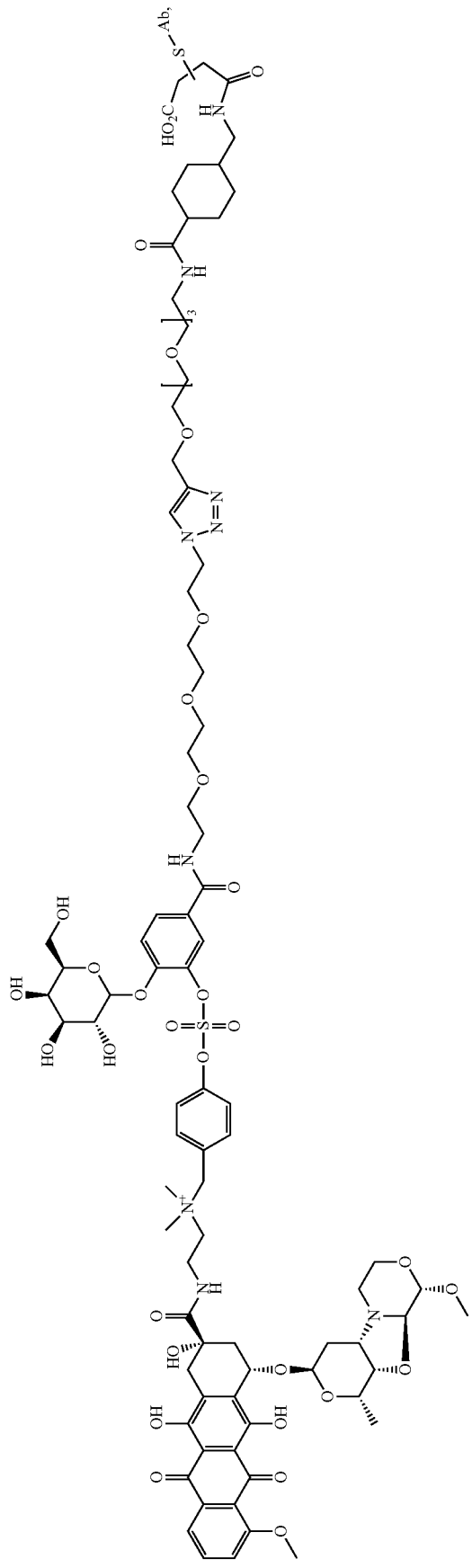

739 740
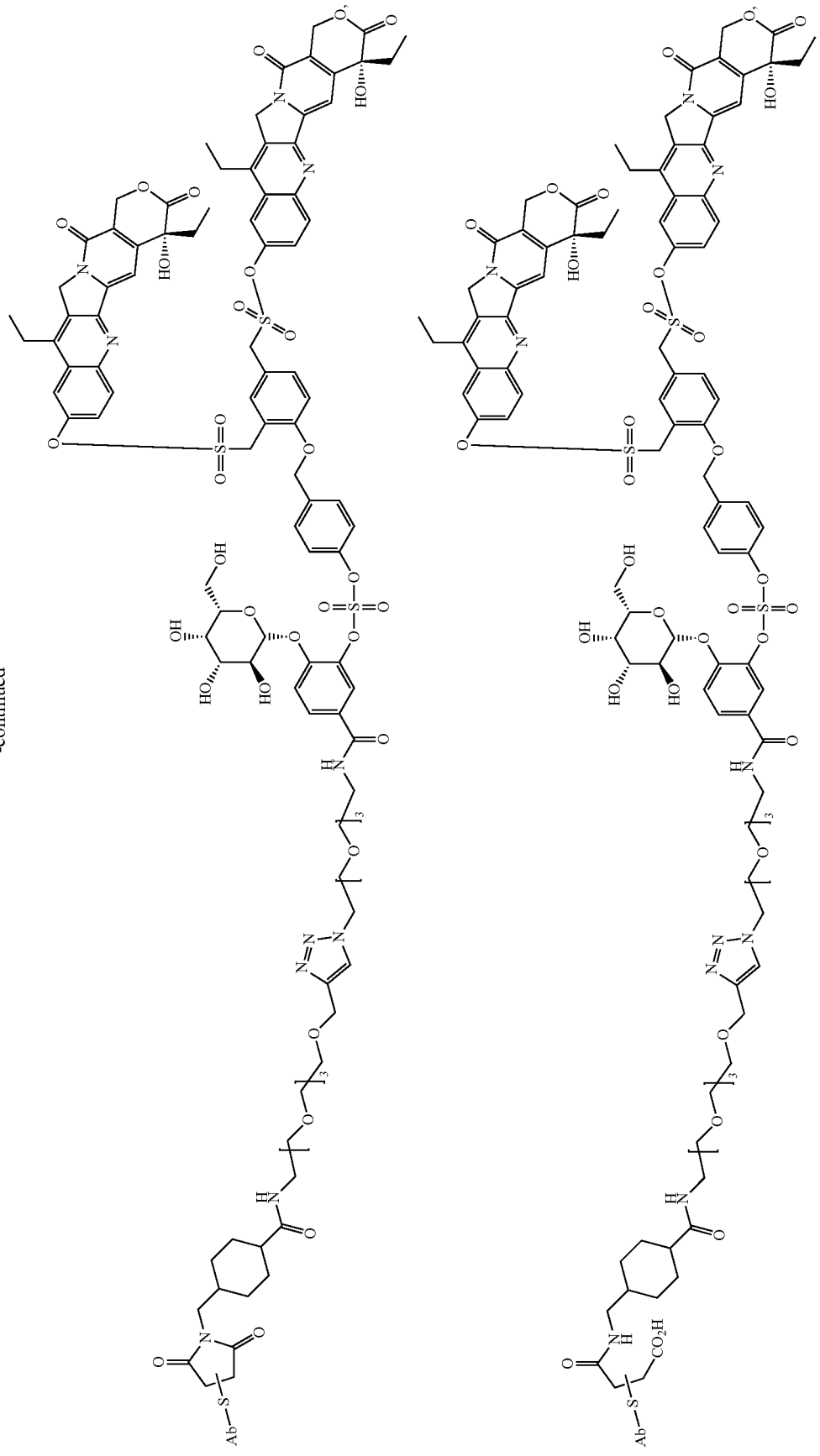

741 742
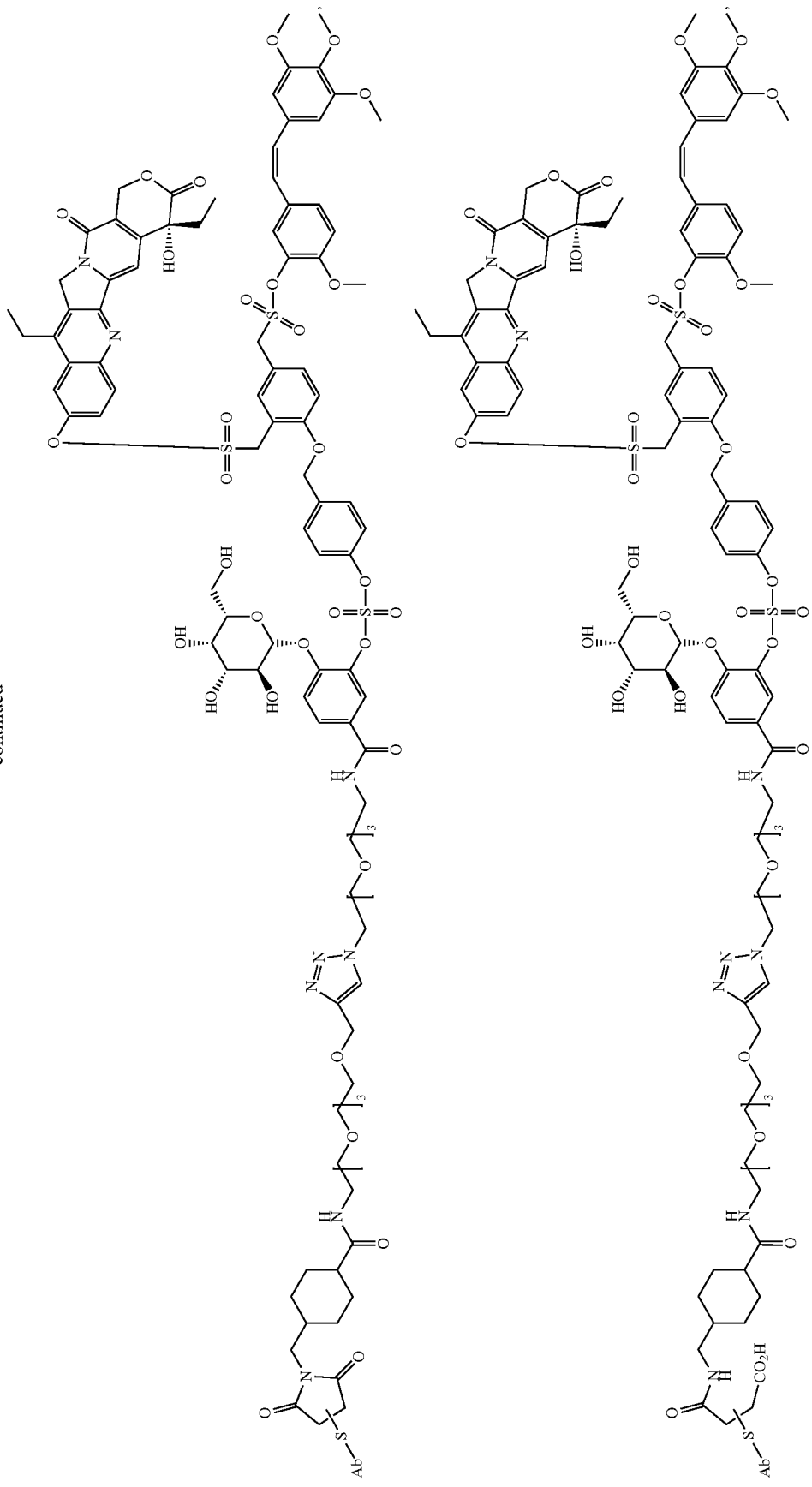

743 744
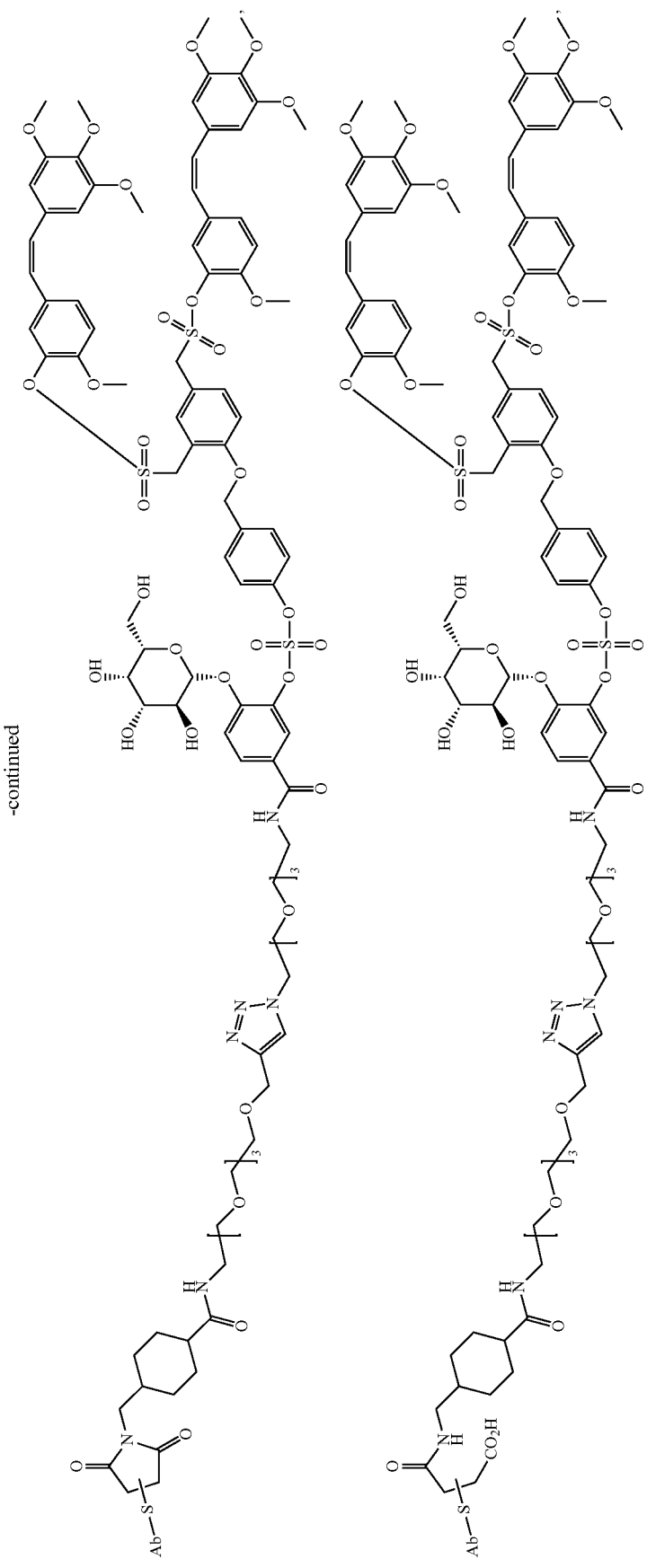

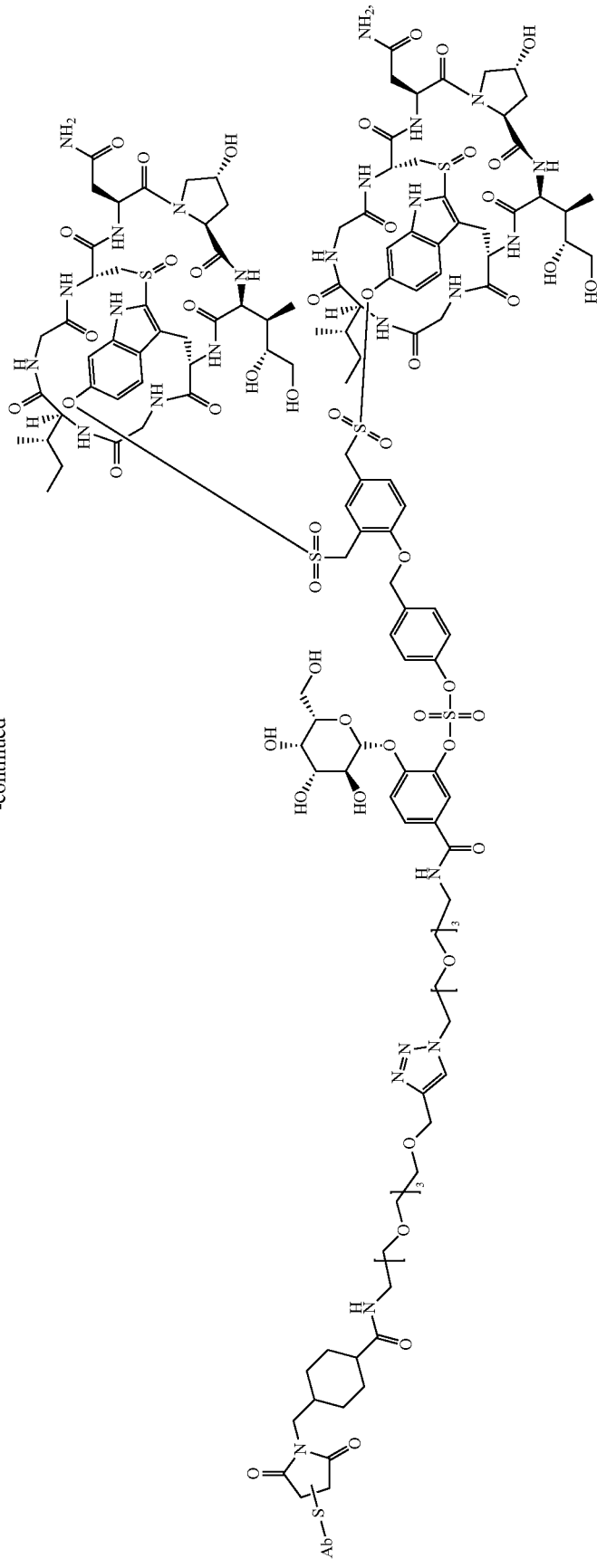

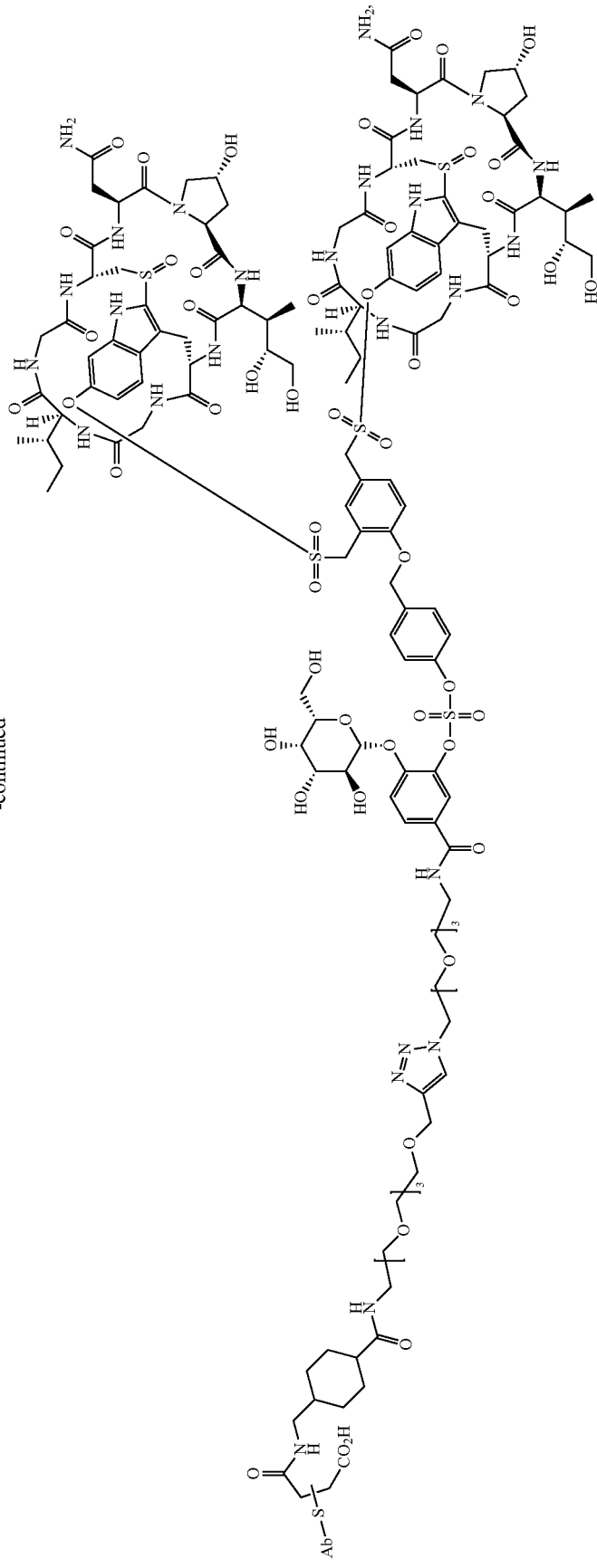

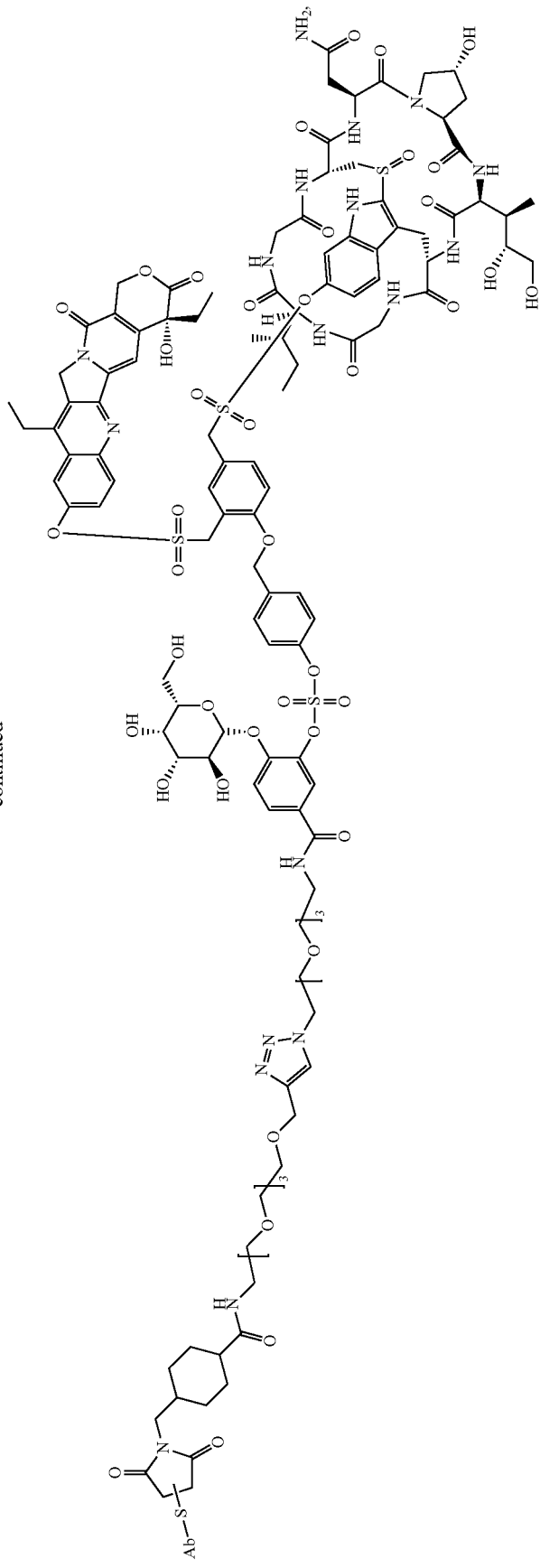

751
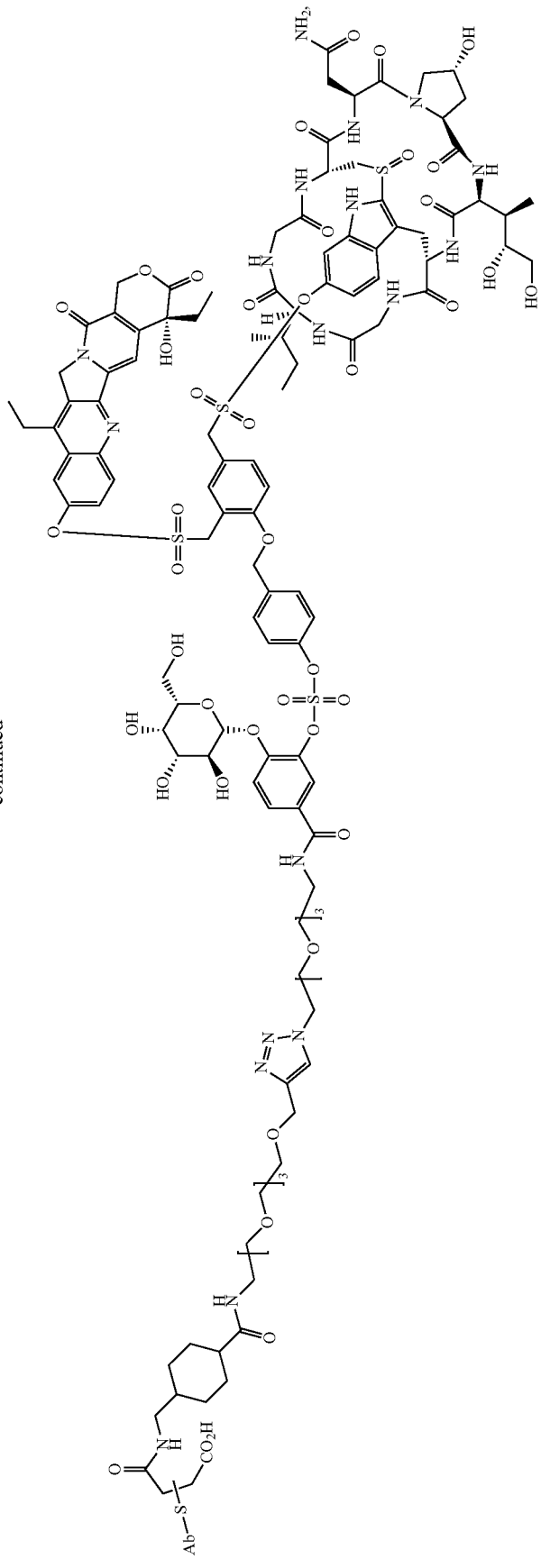
752
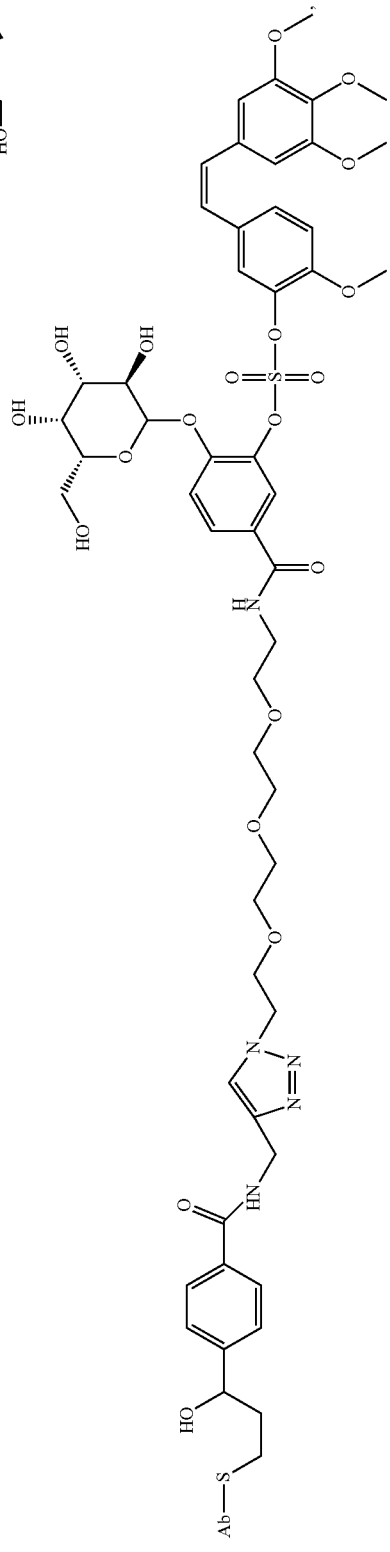

-continued
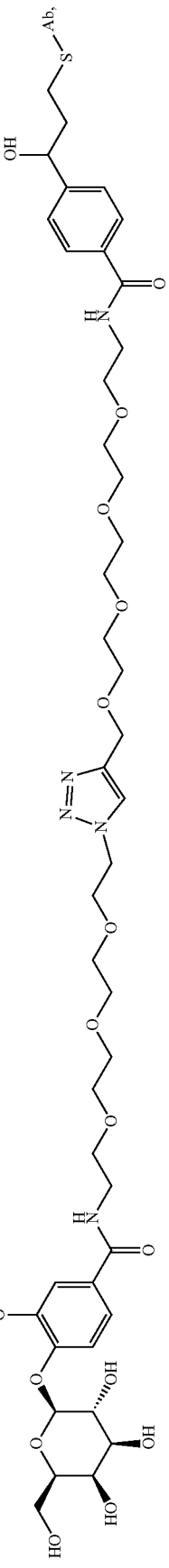

-continued
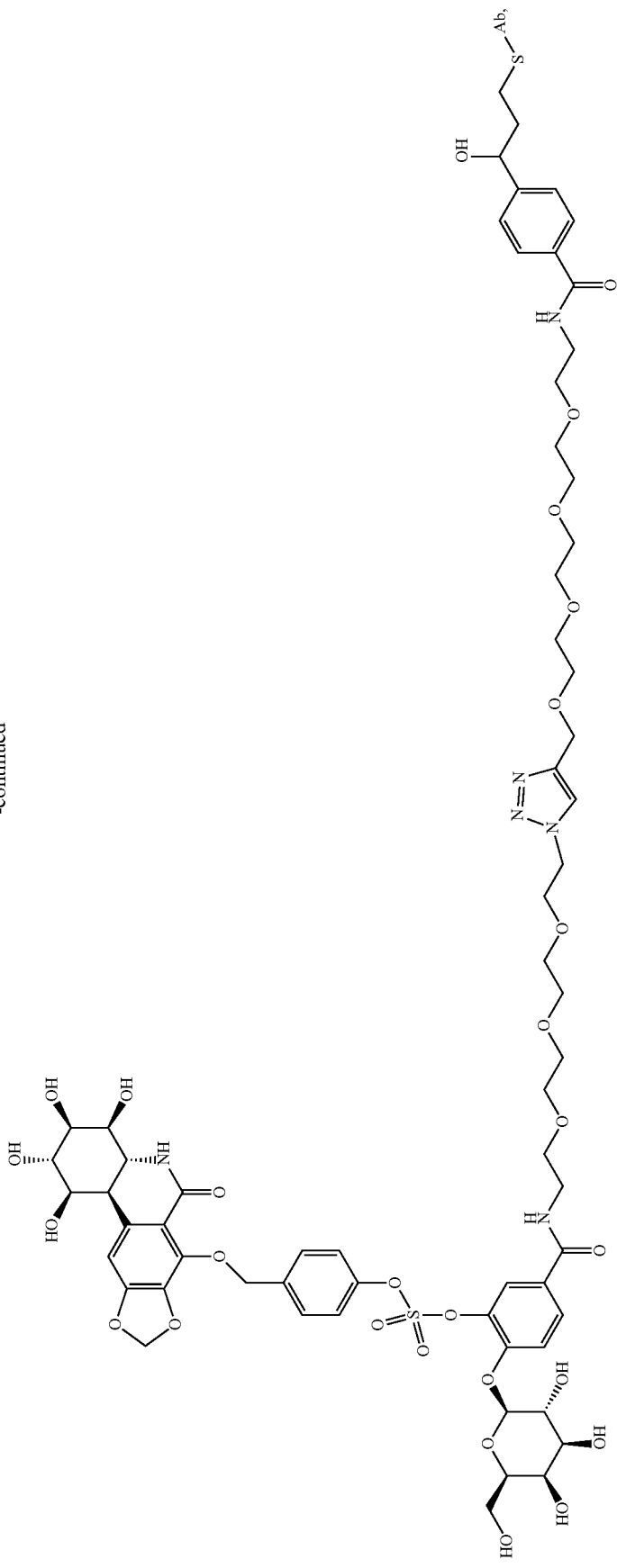

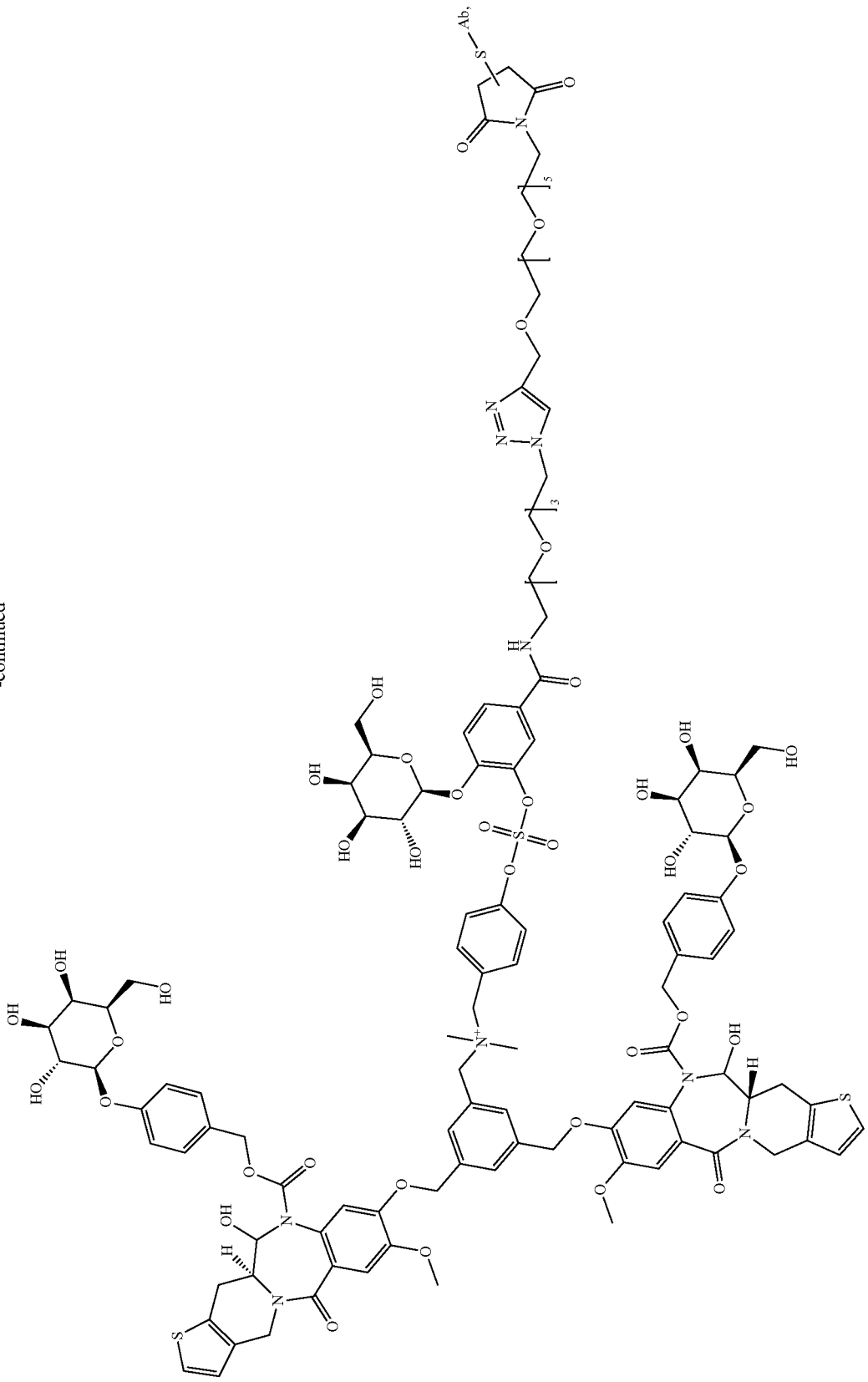

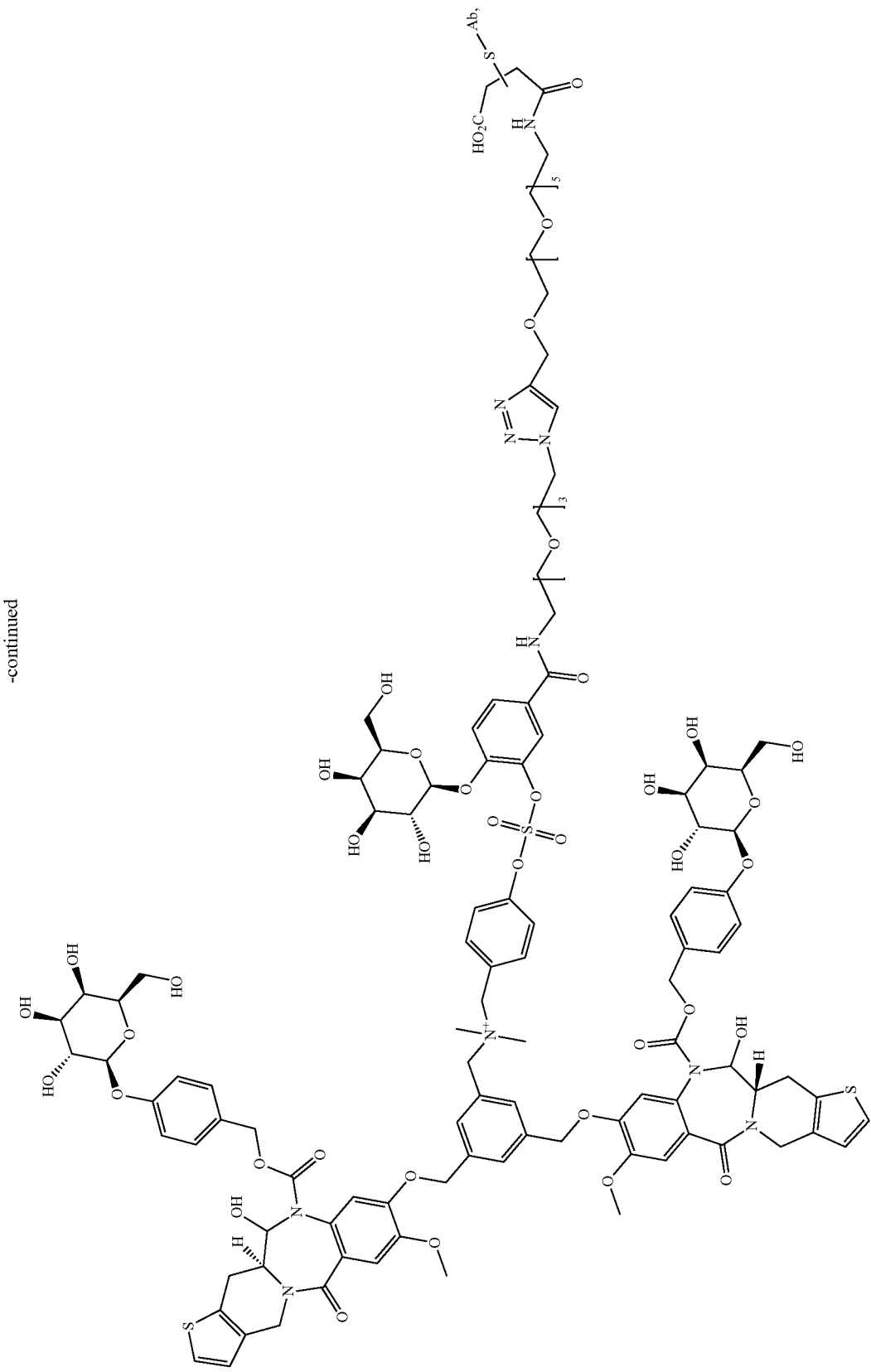

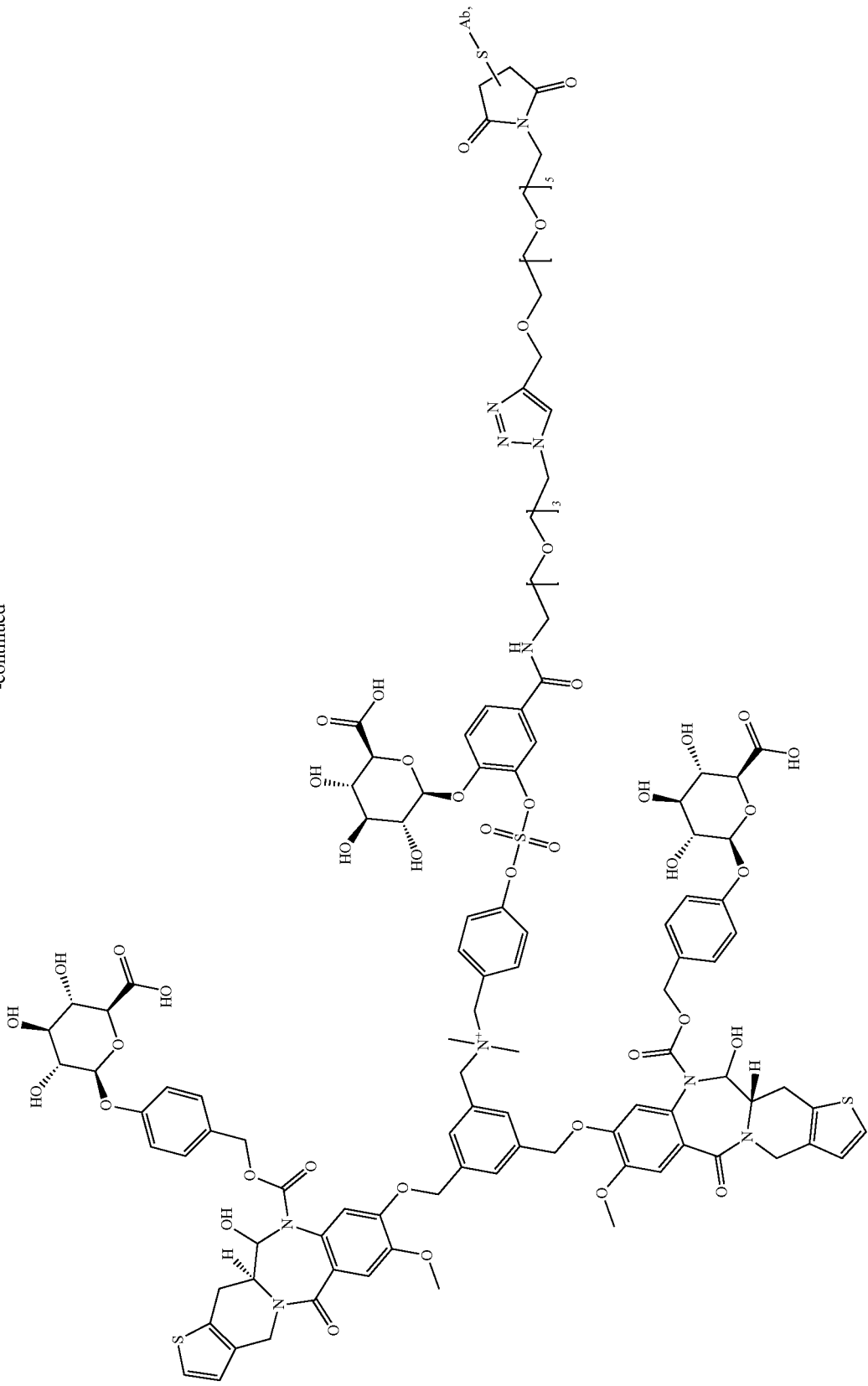

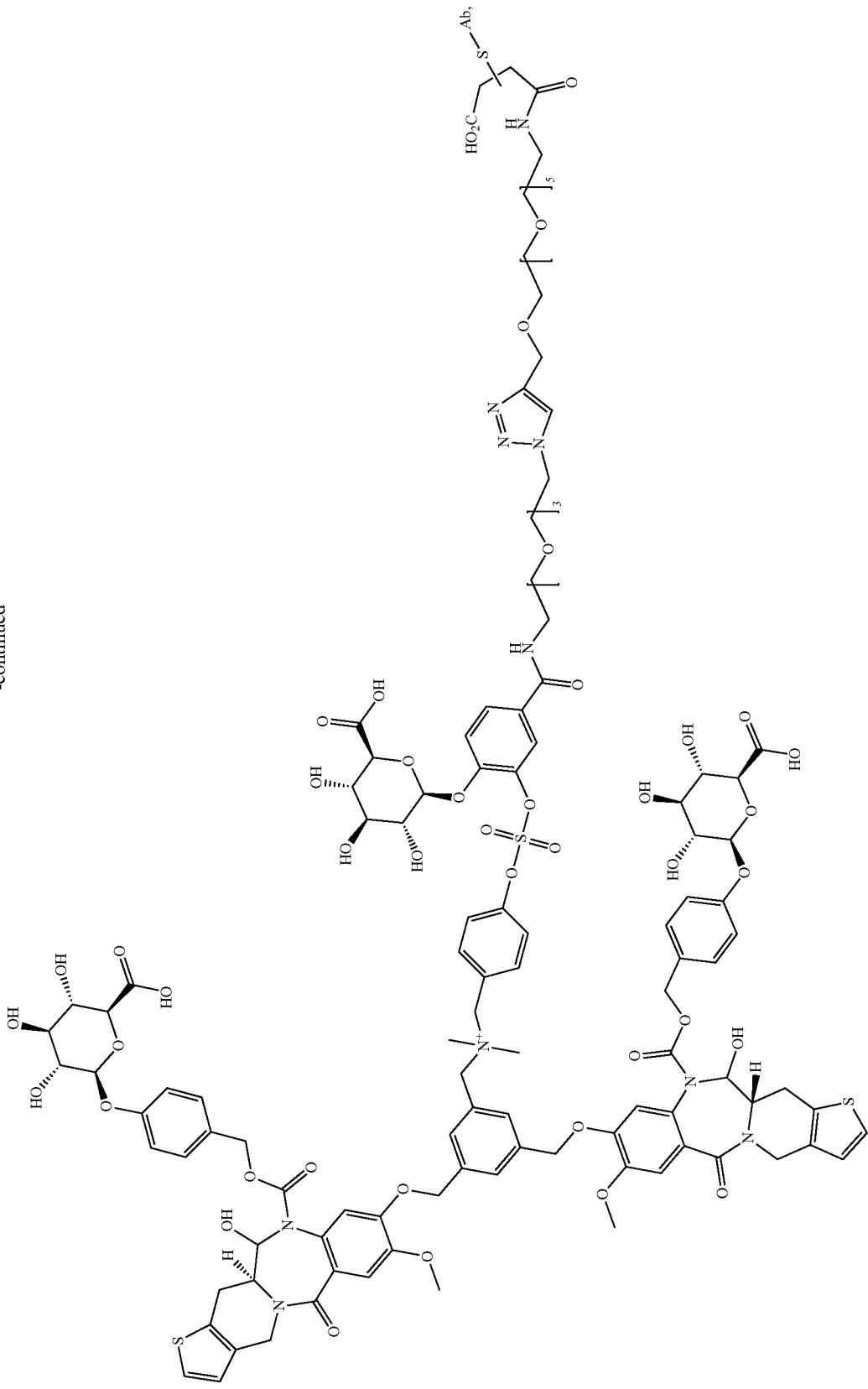

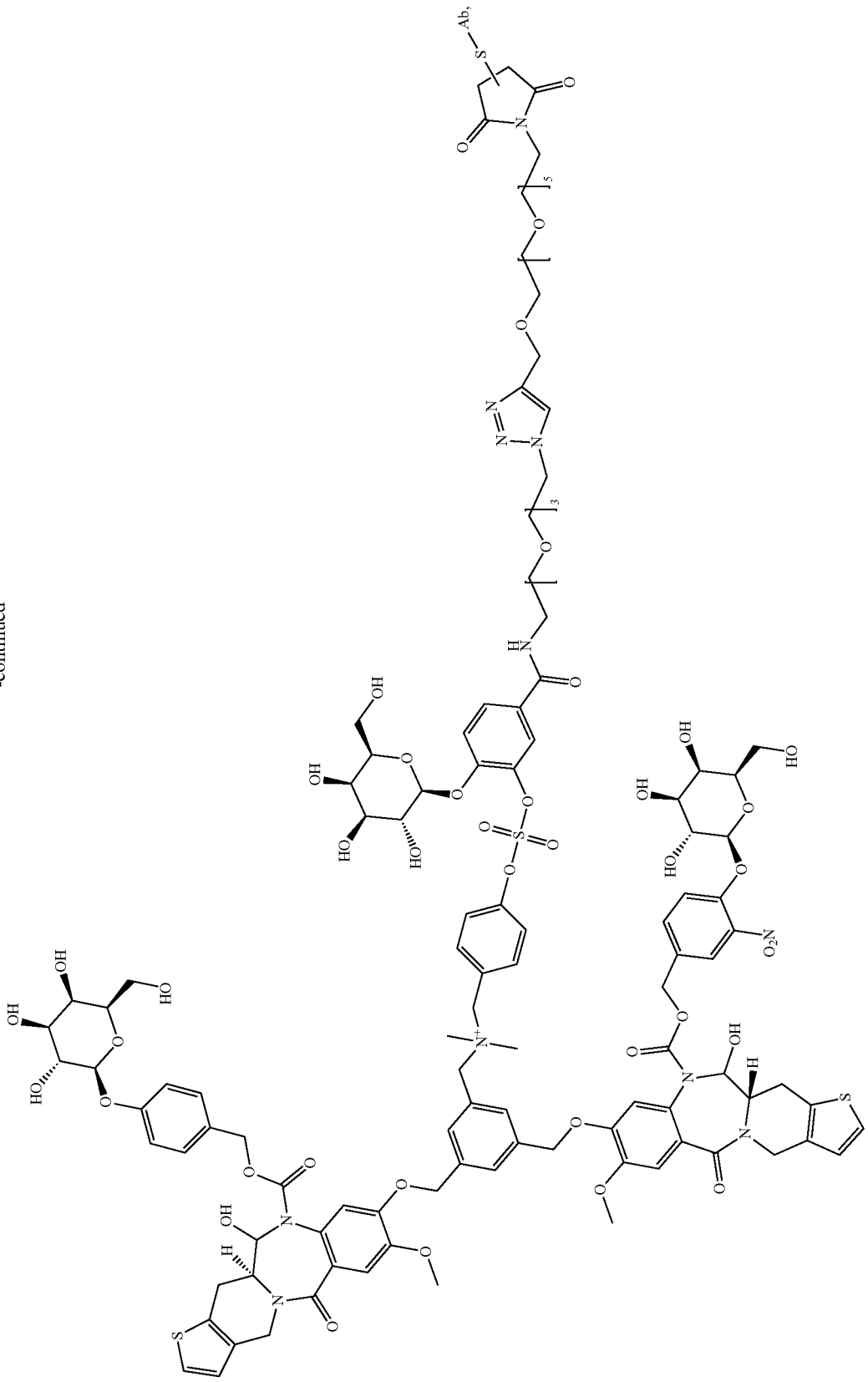

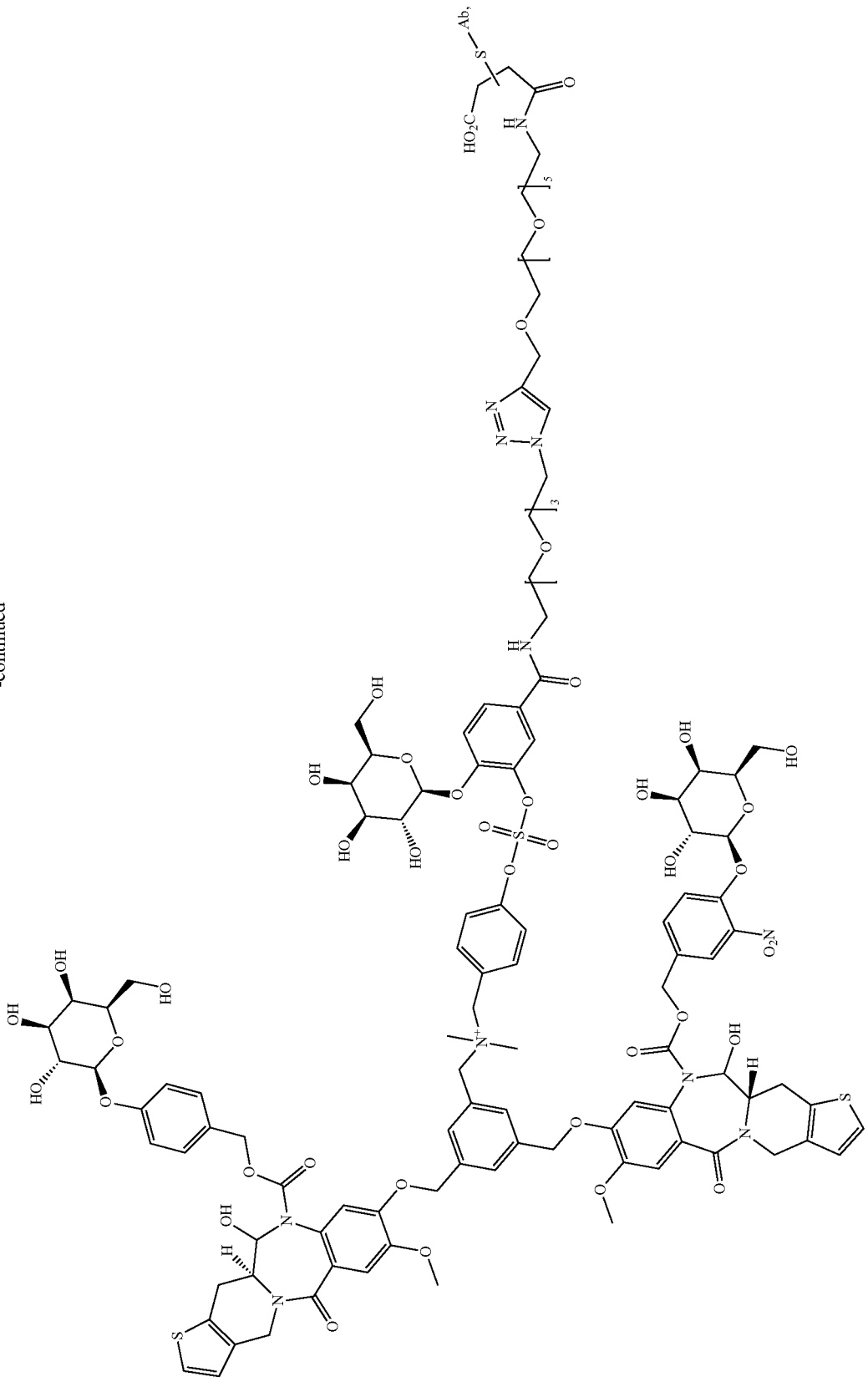

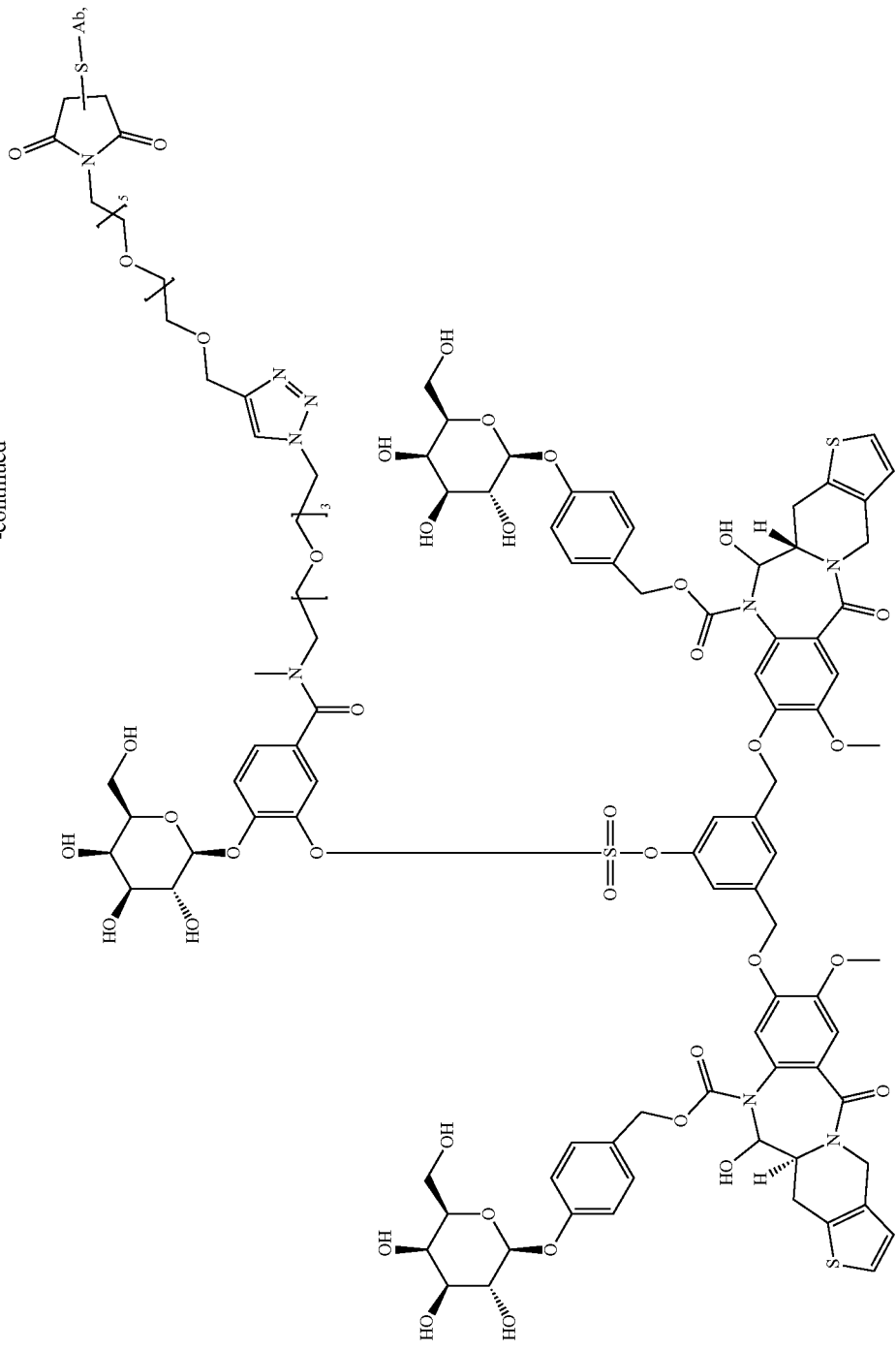

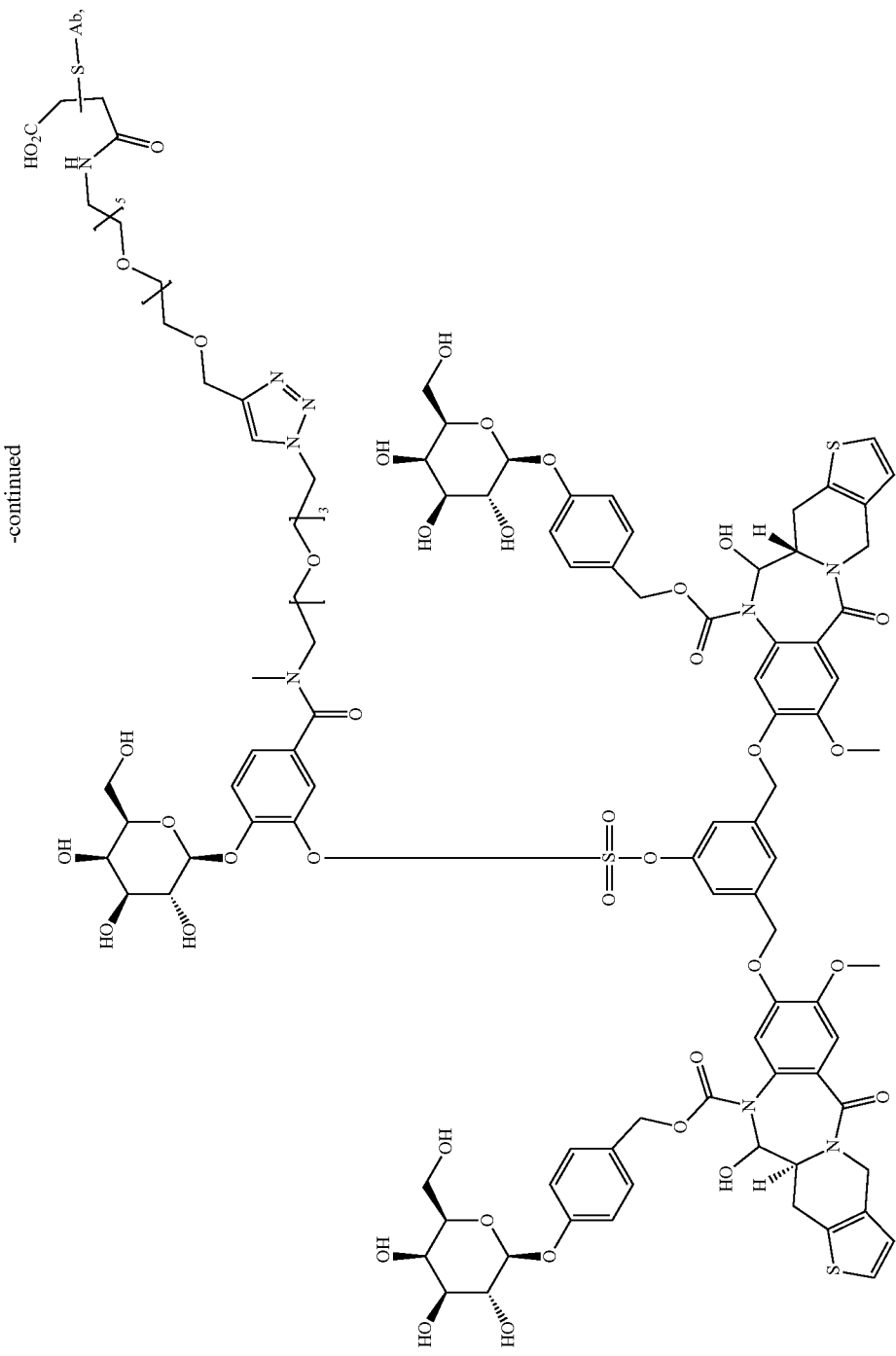

-continued
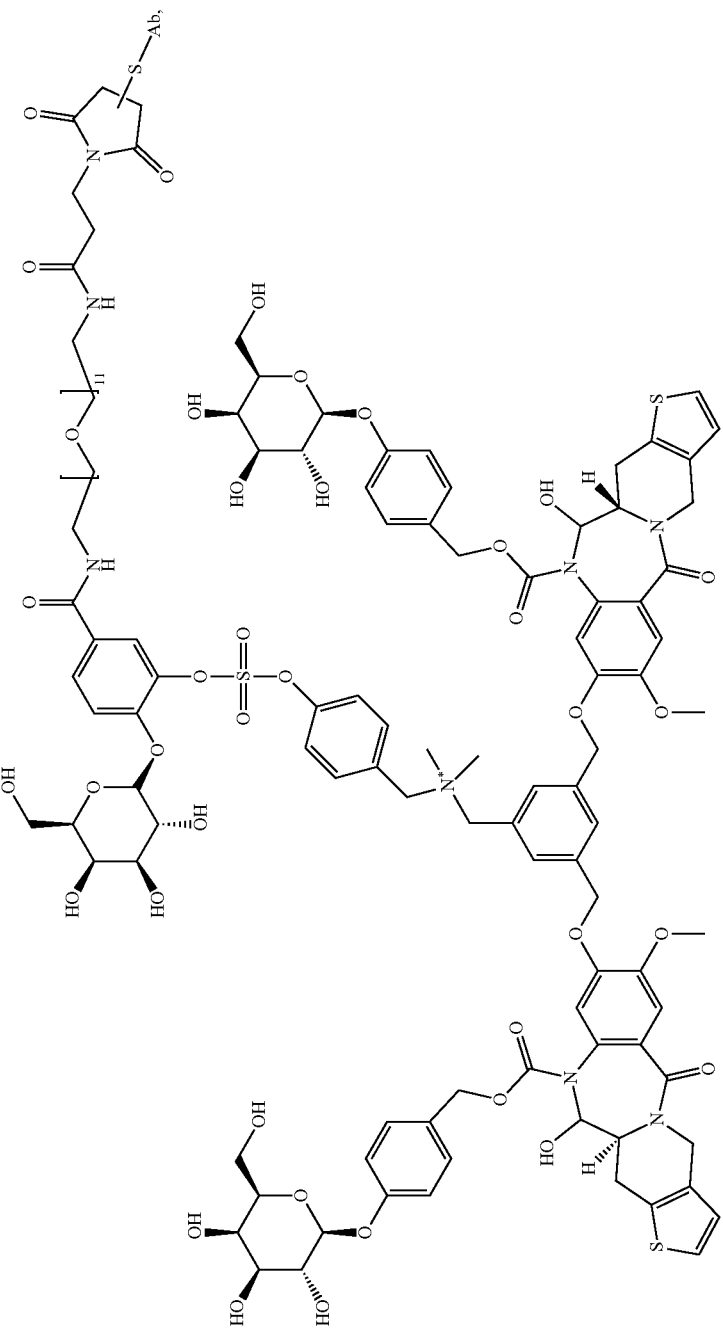

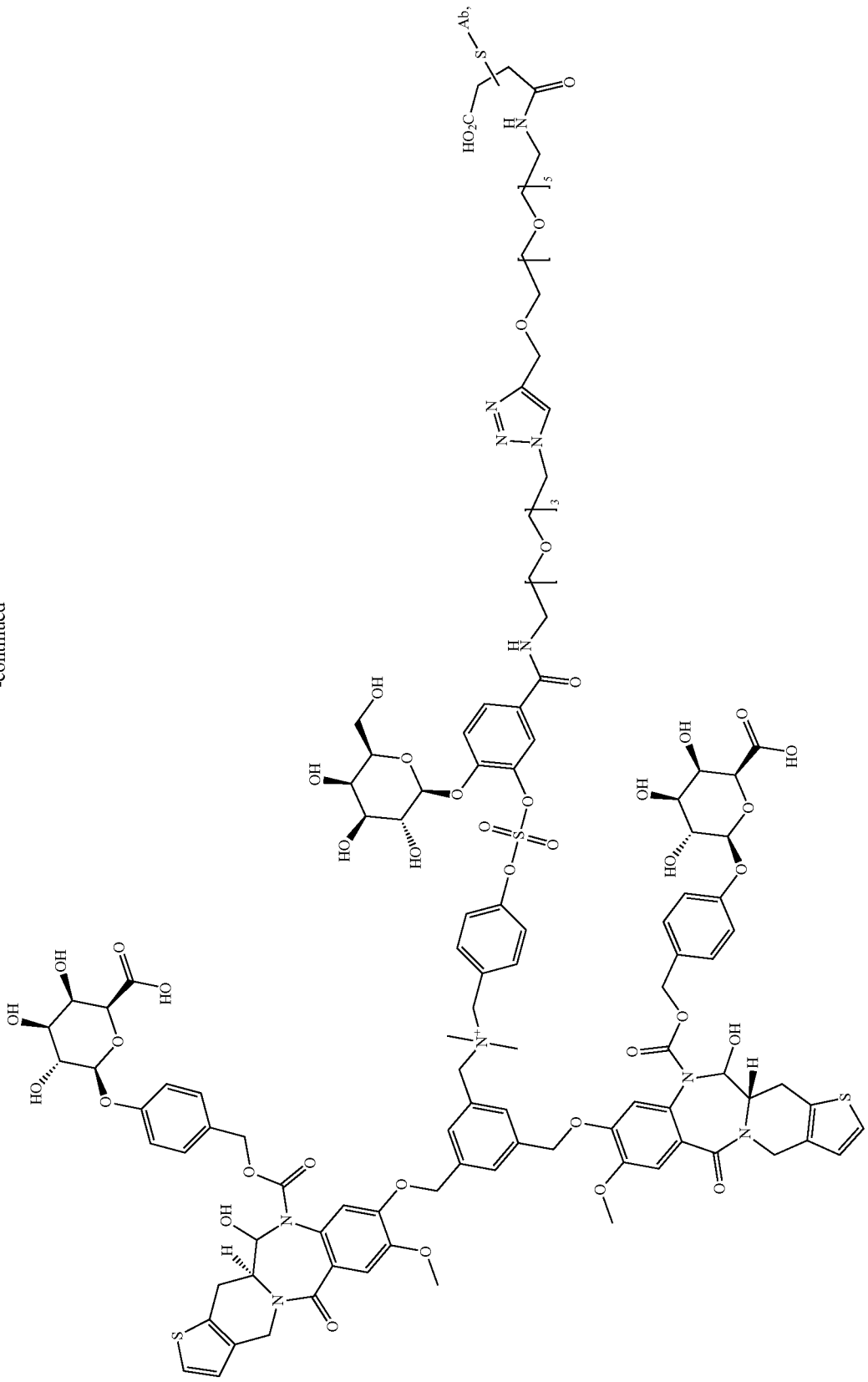

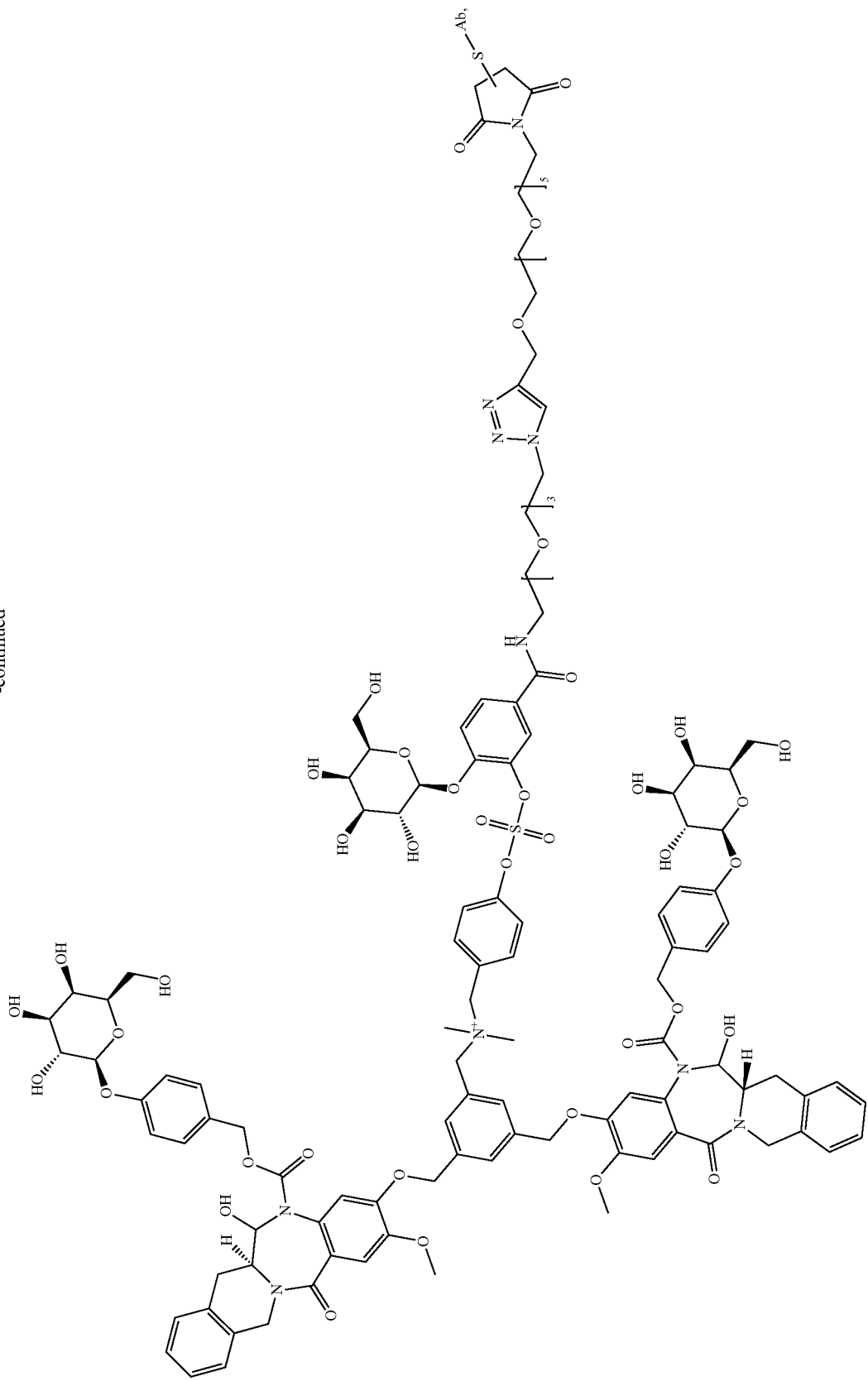

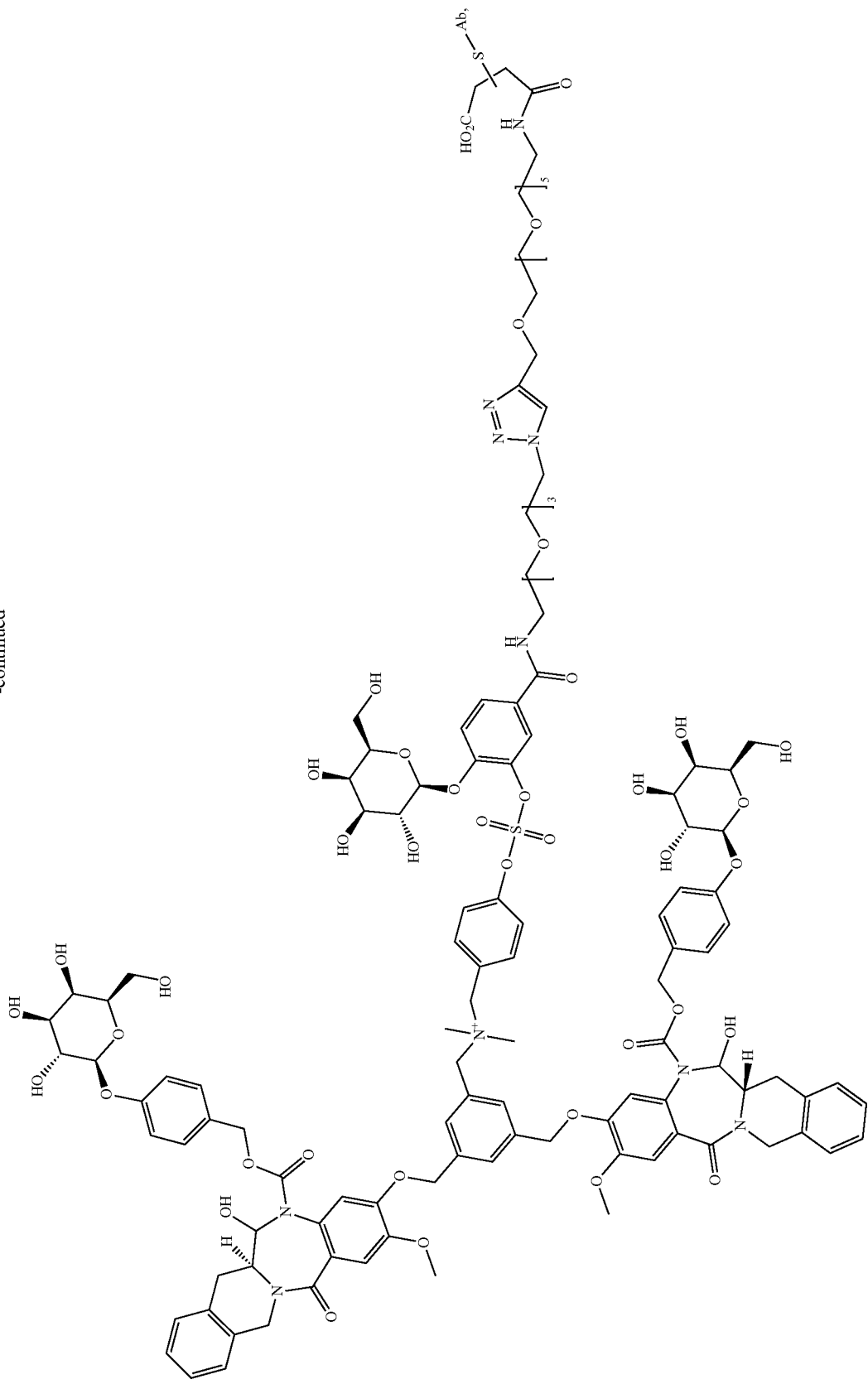

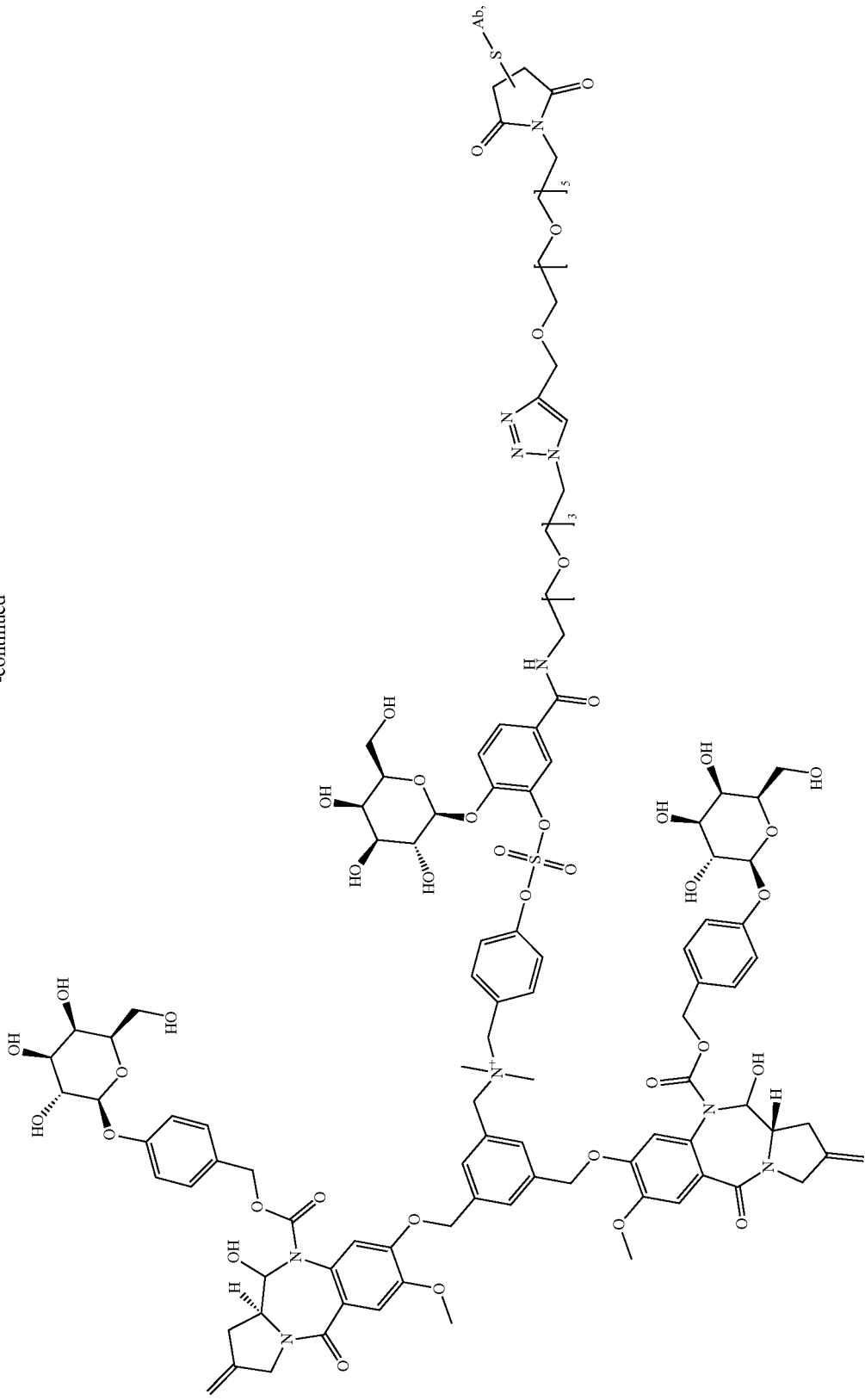

783 784
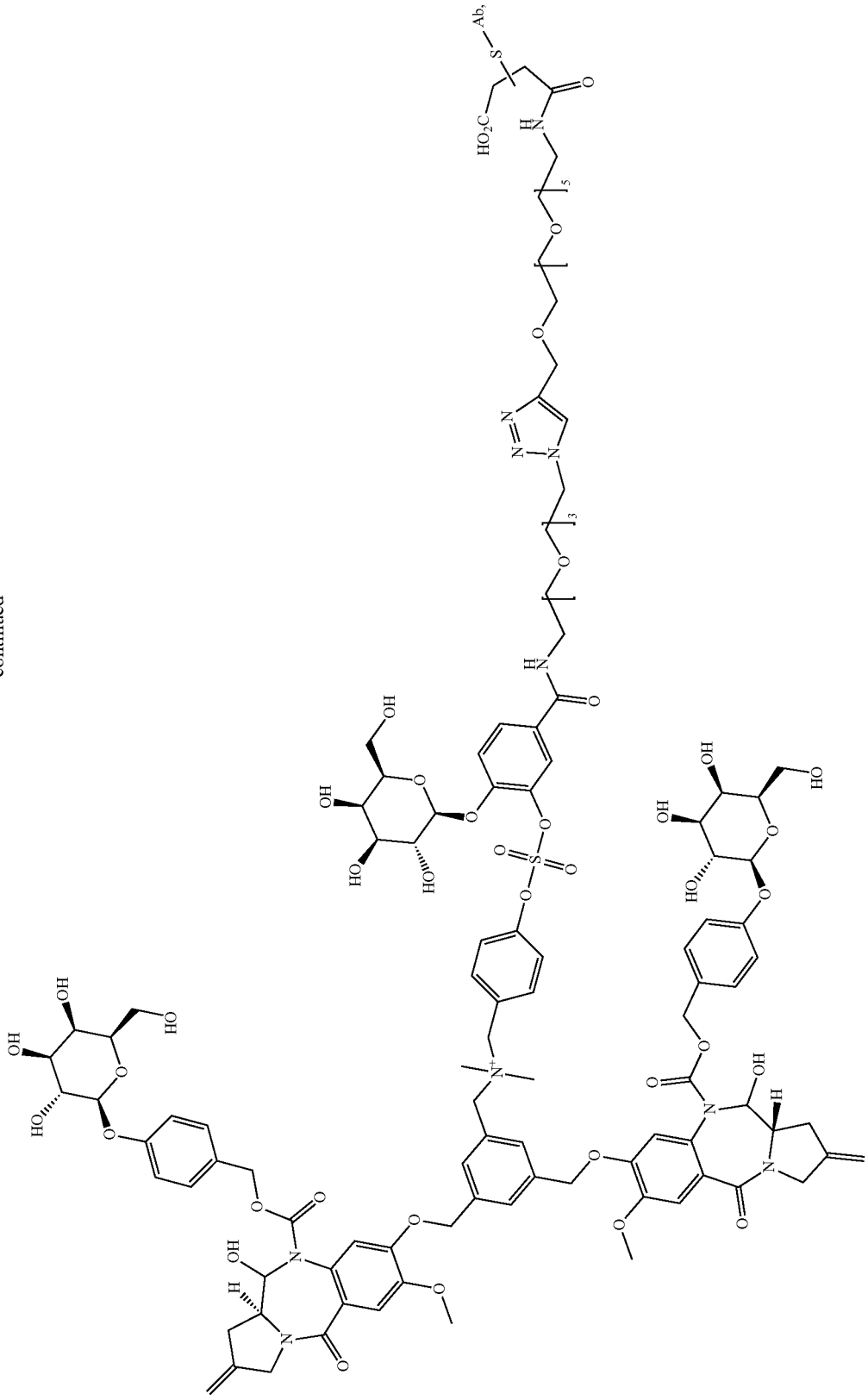

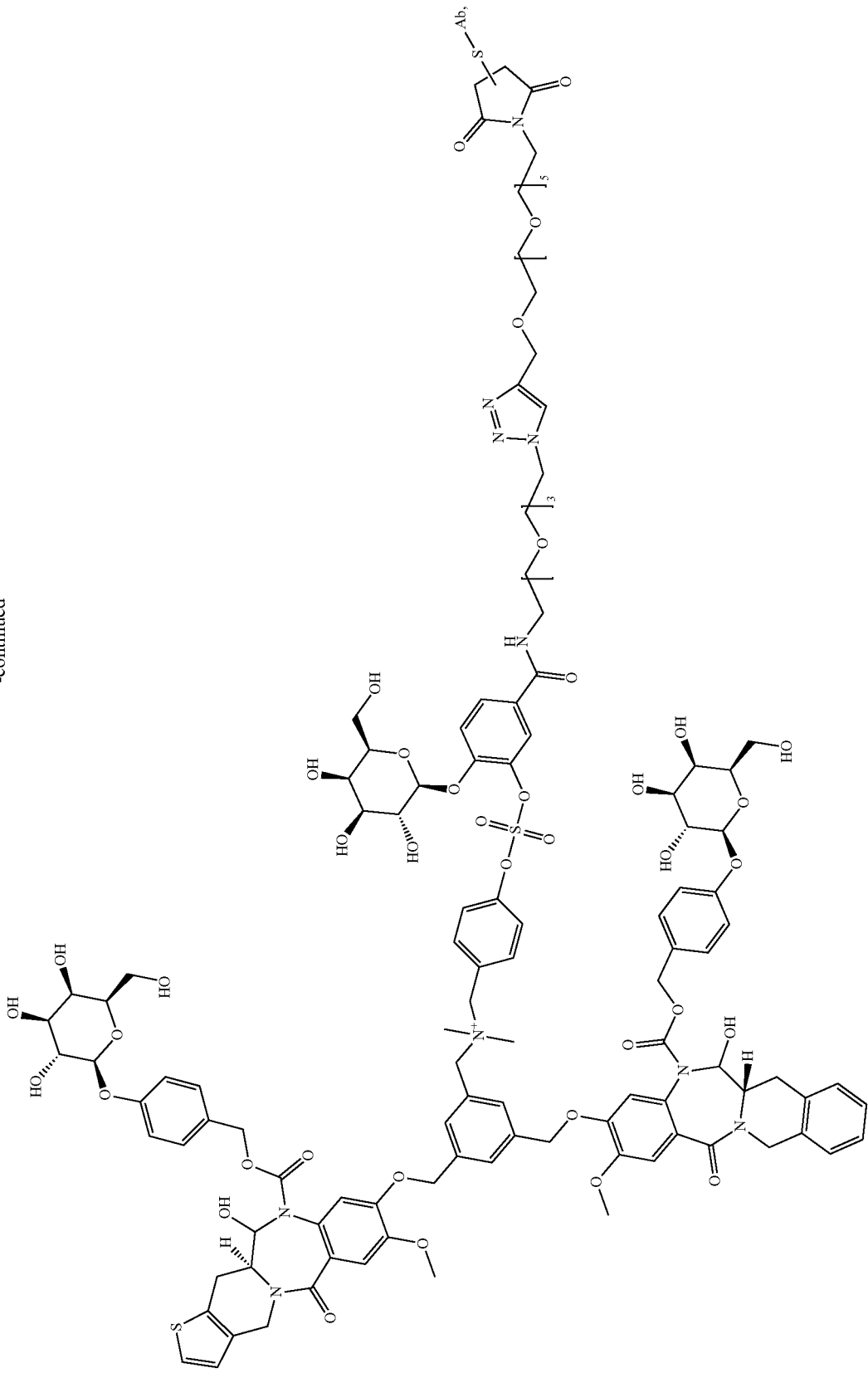

787 788
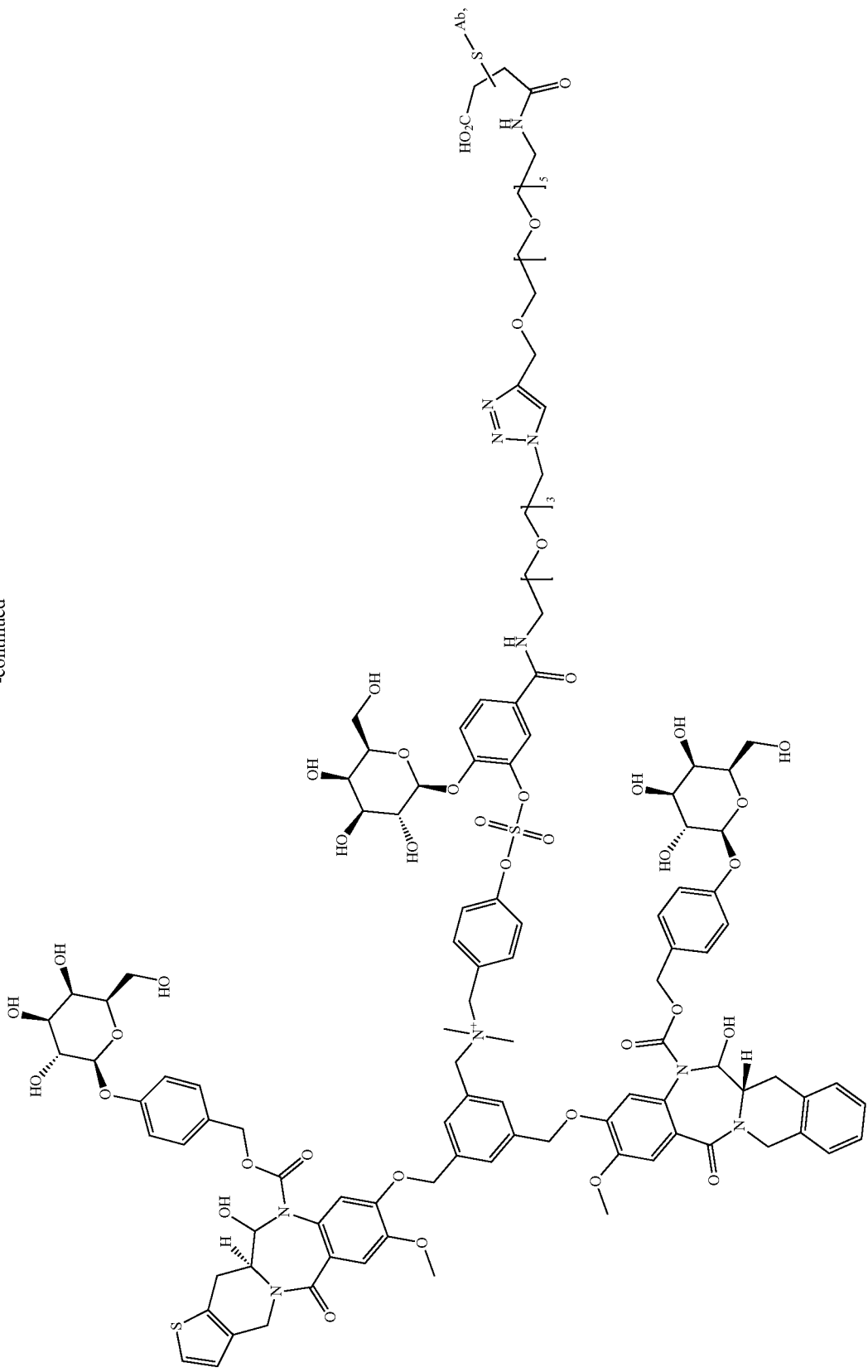
-continued

-continued
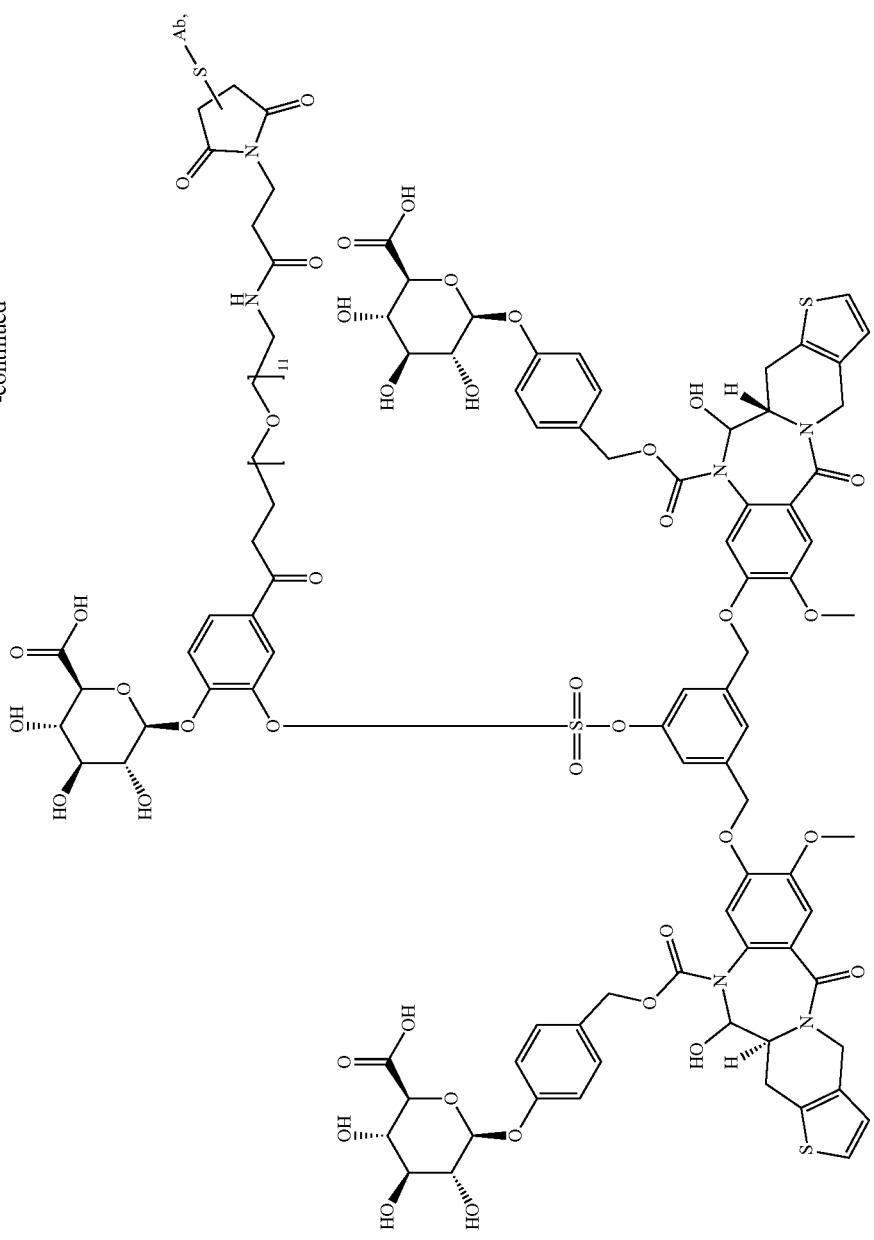

-continued
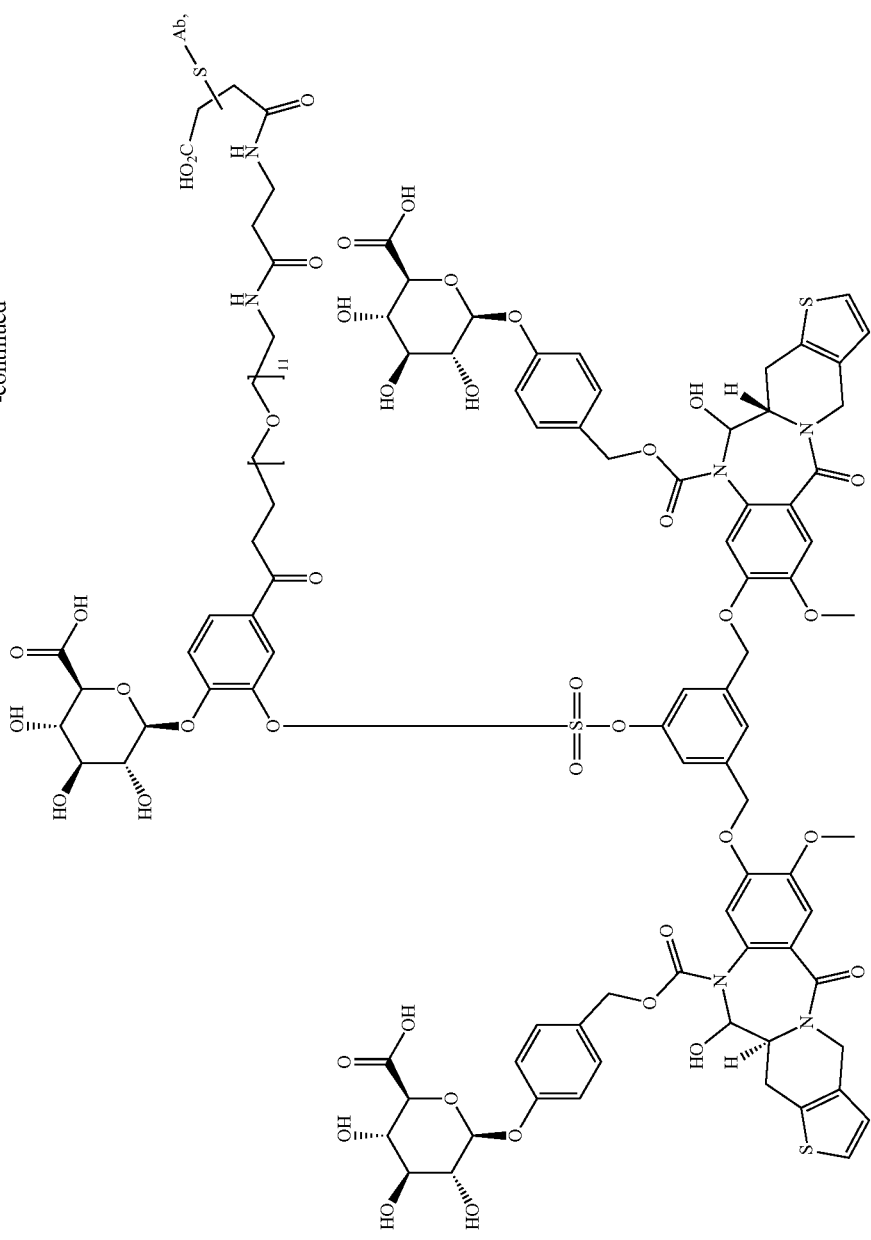

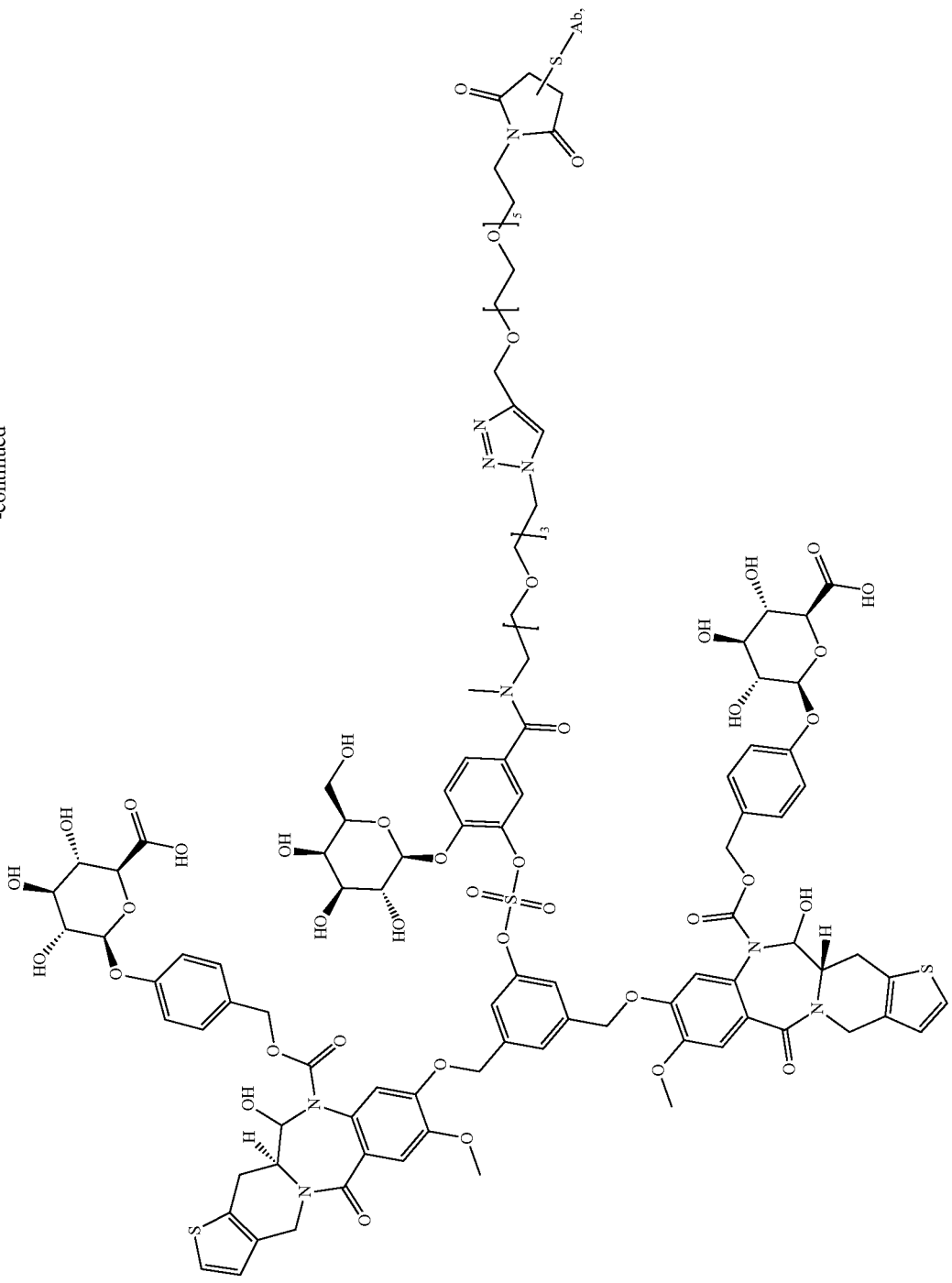

795 796
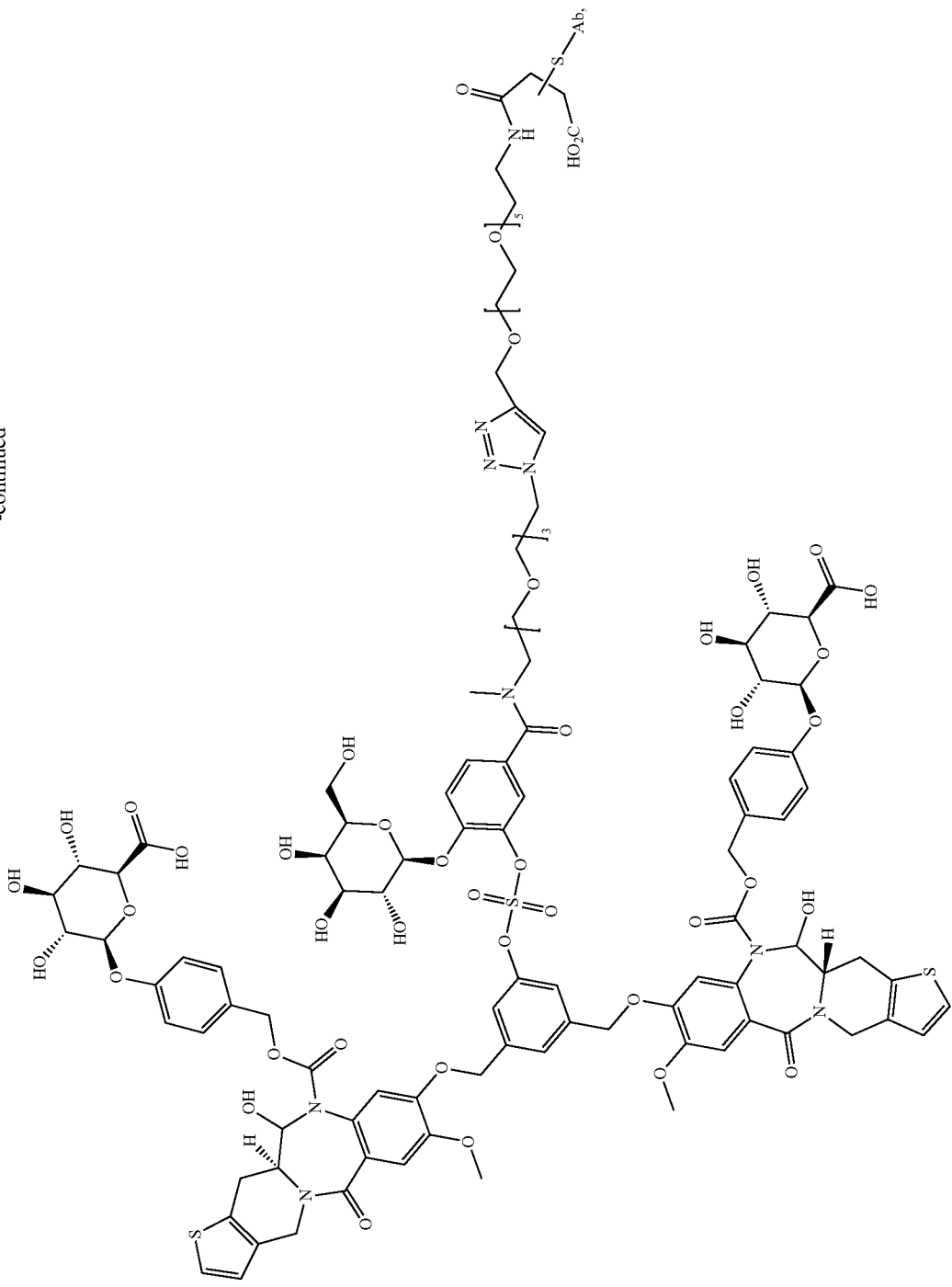
-continued

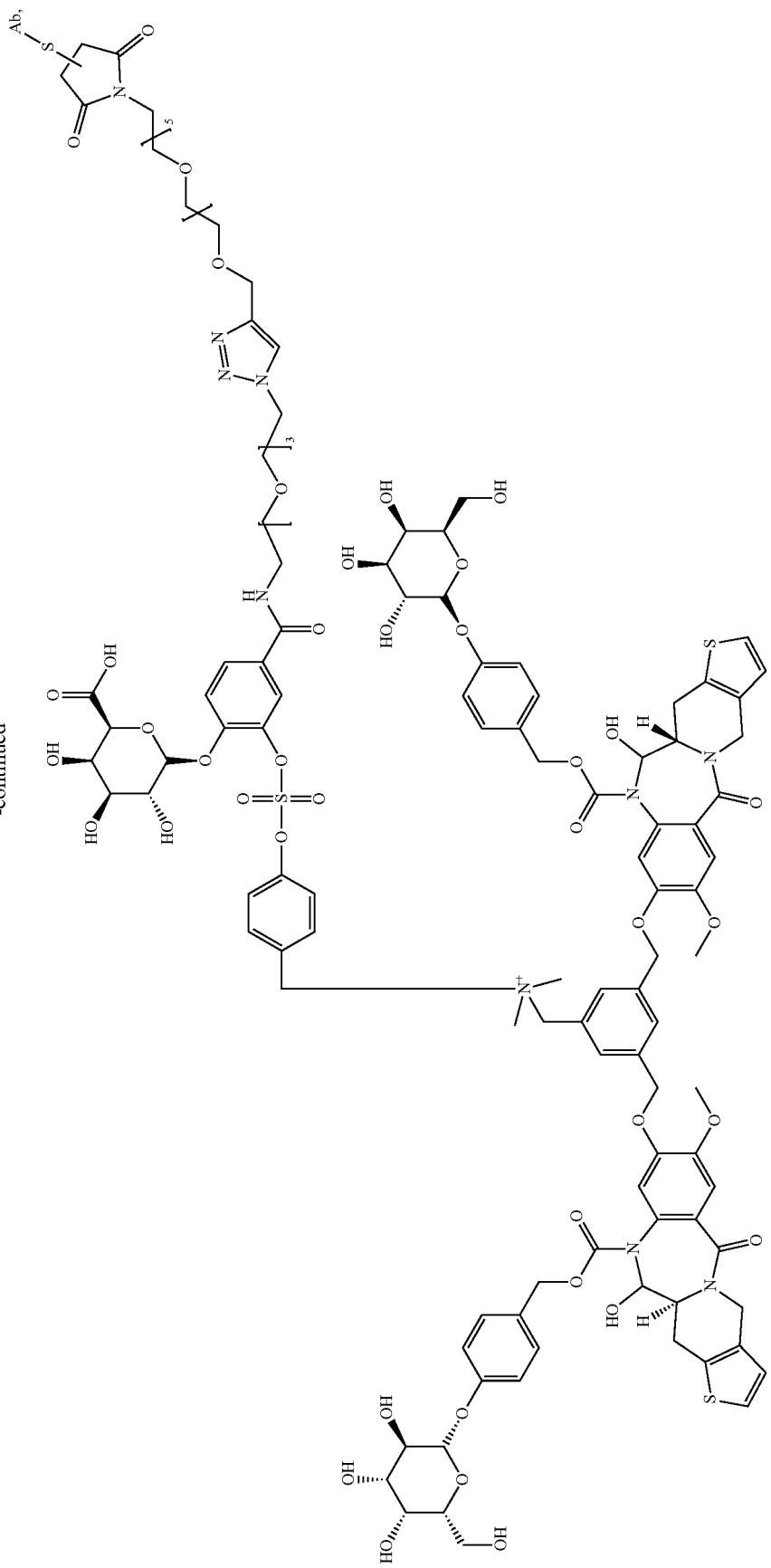

-continued
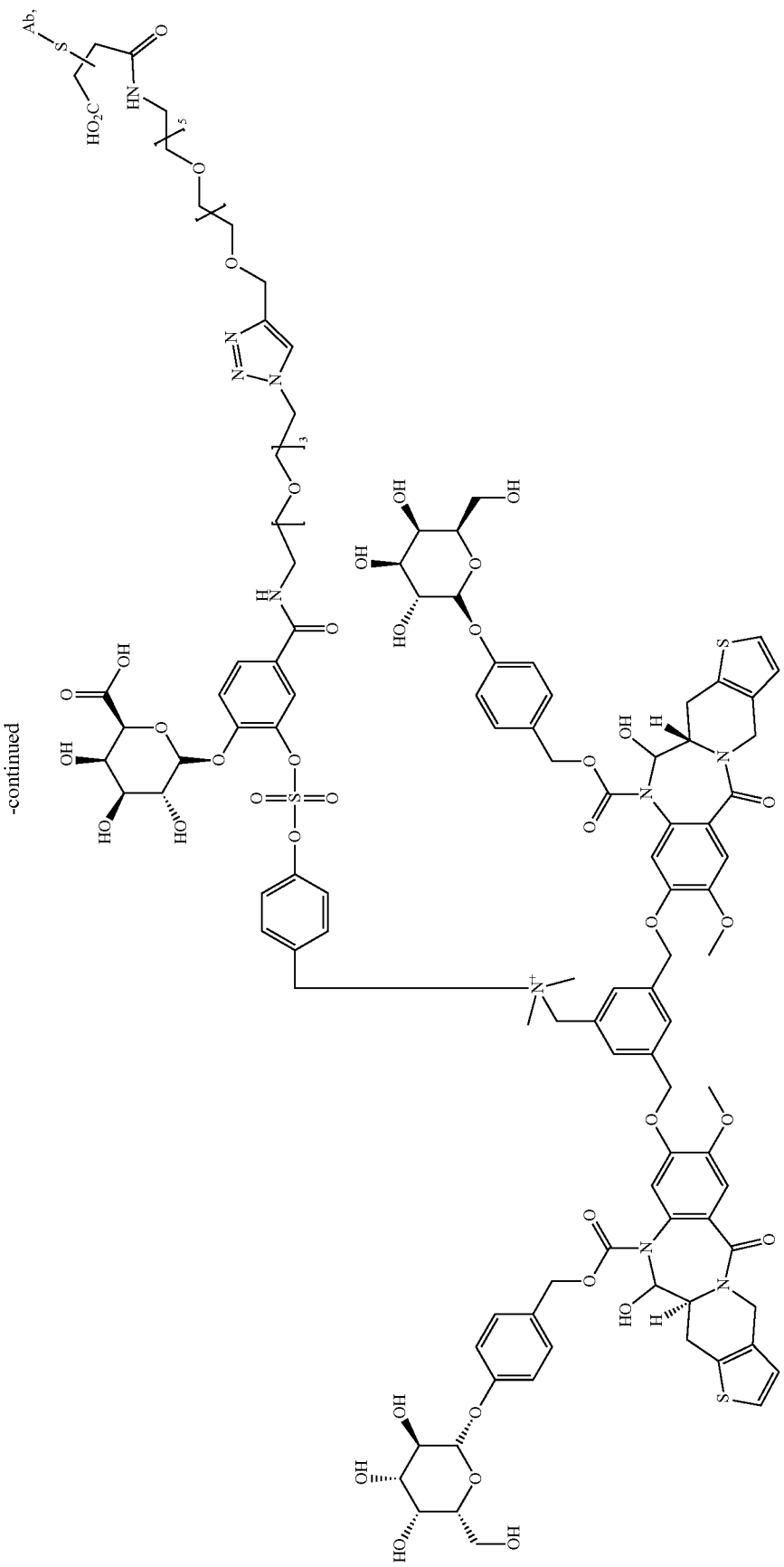

801 802
-continued
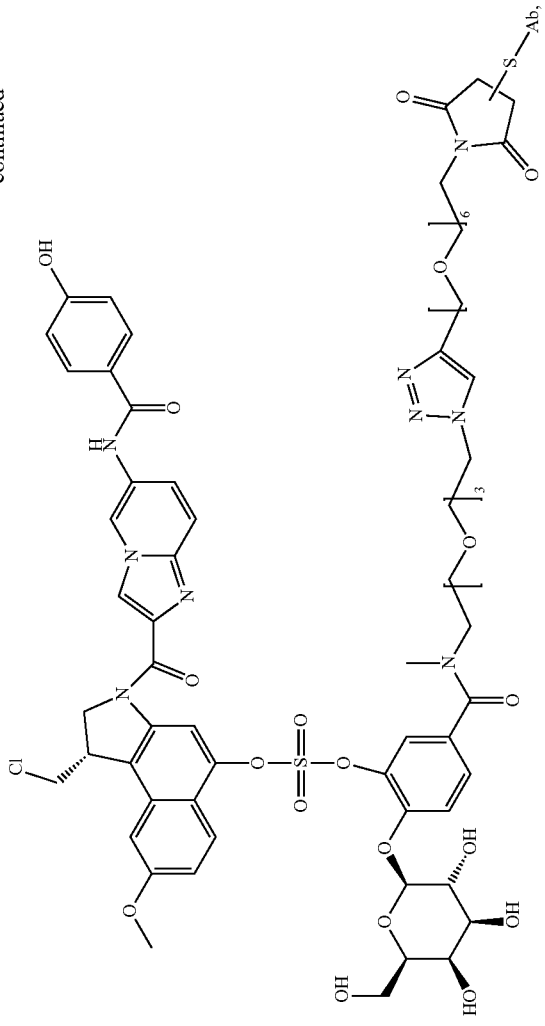

803 804
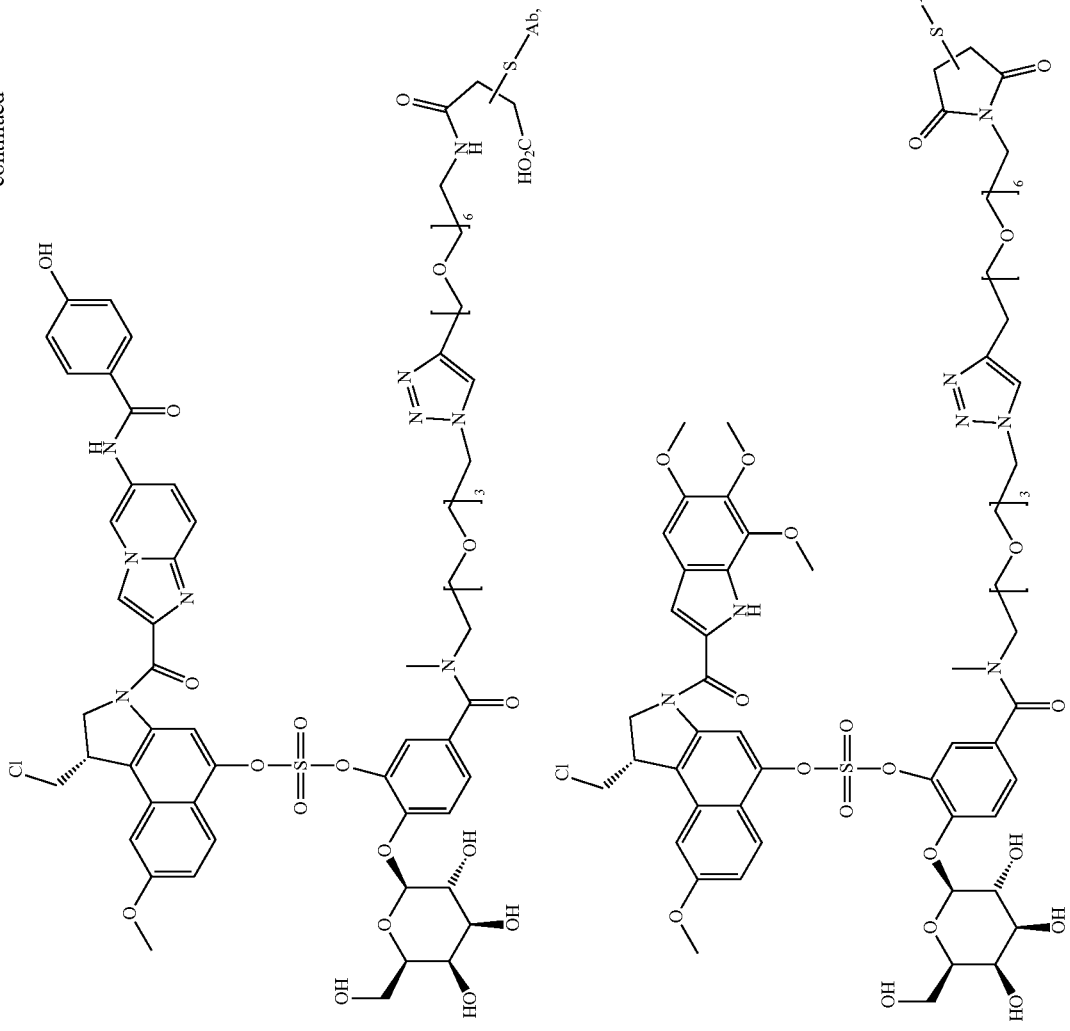

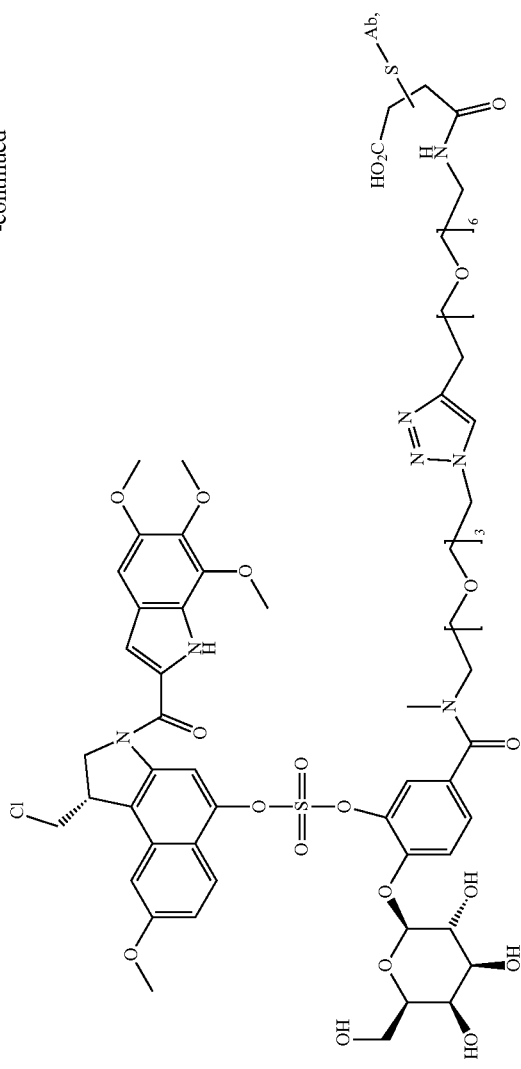

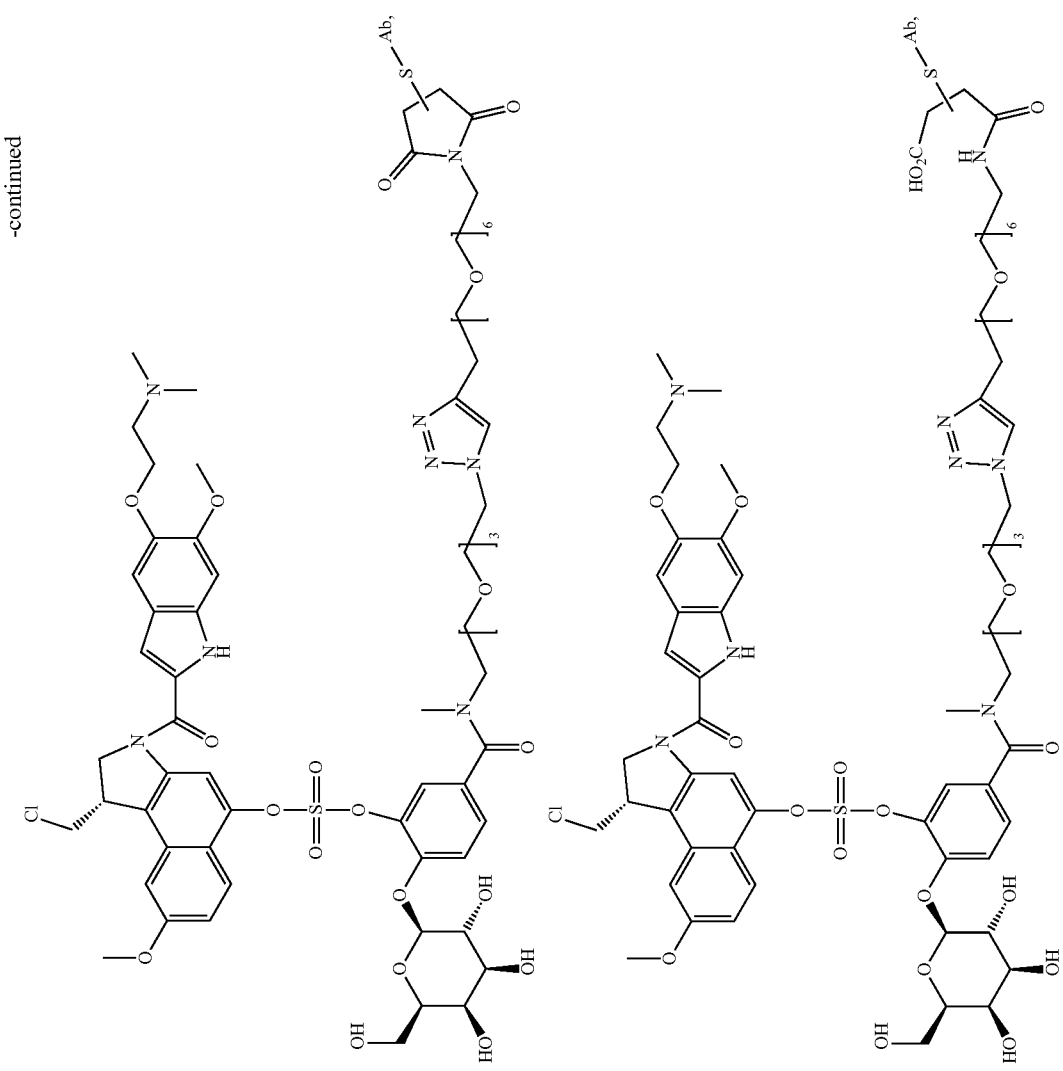

-continued
809 810
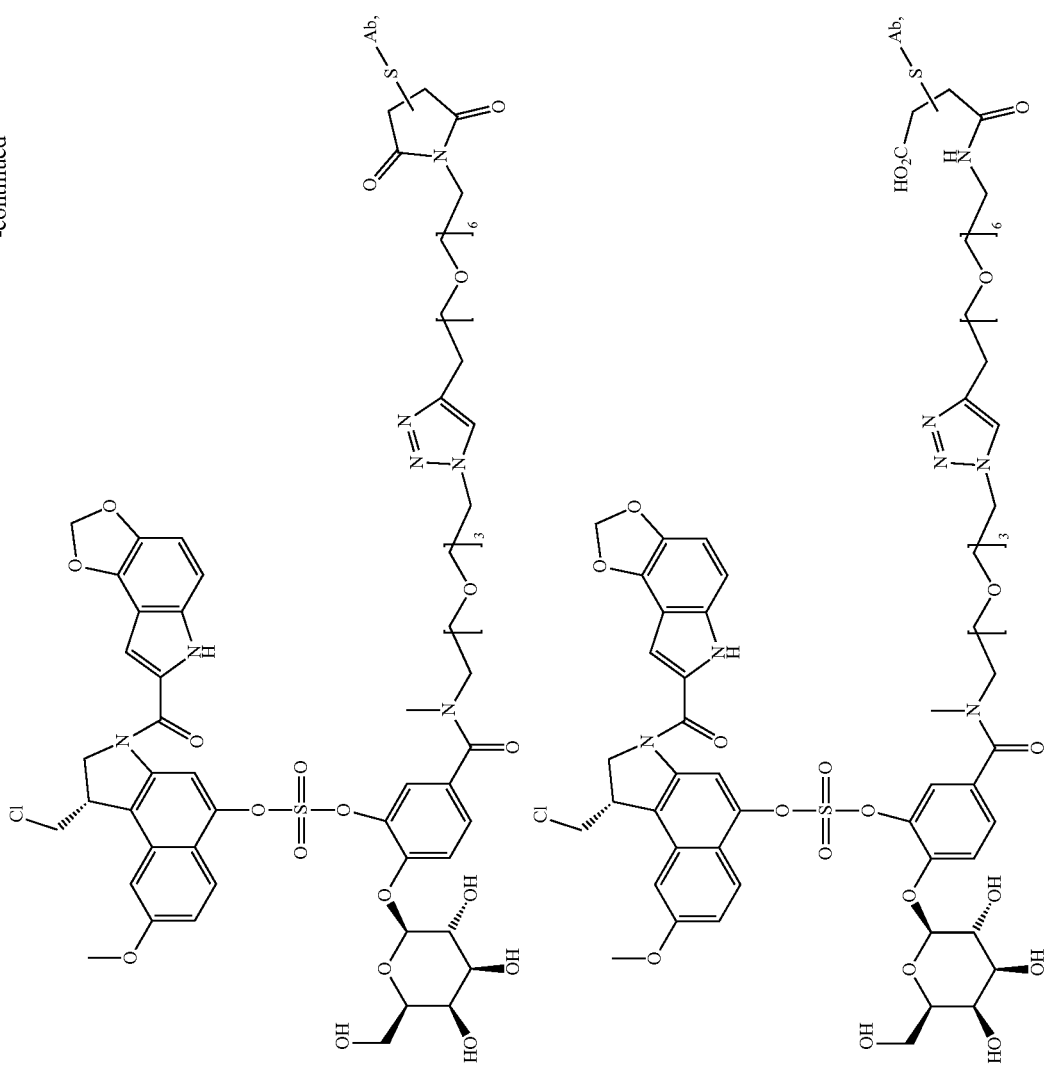

811 812
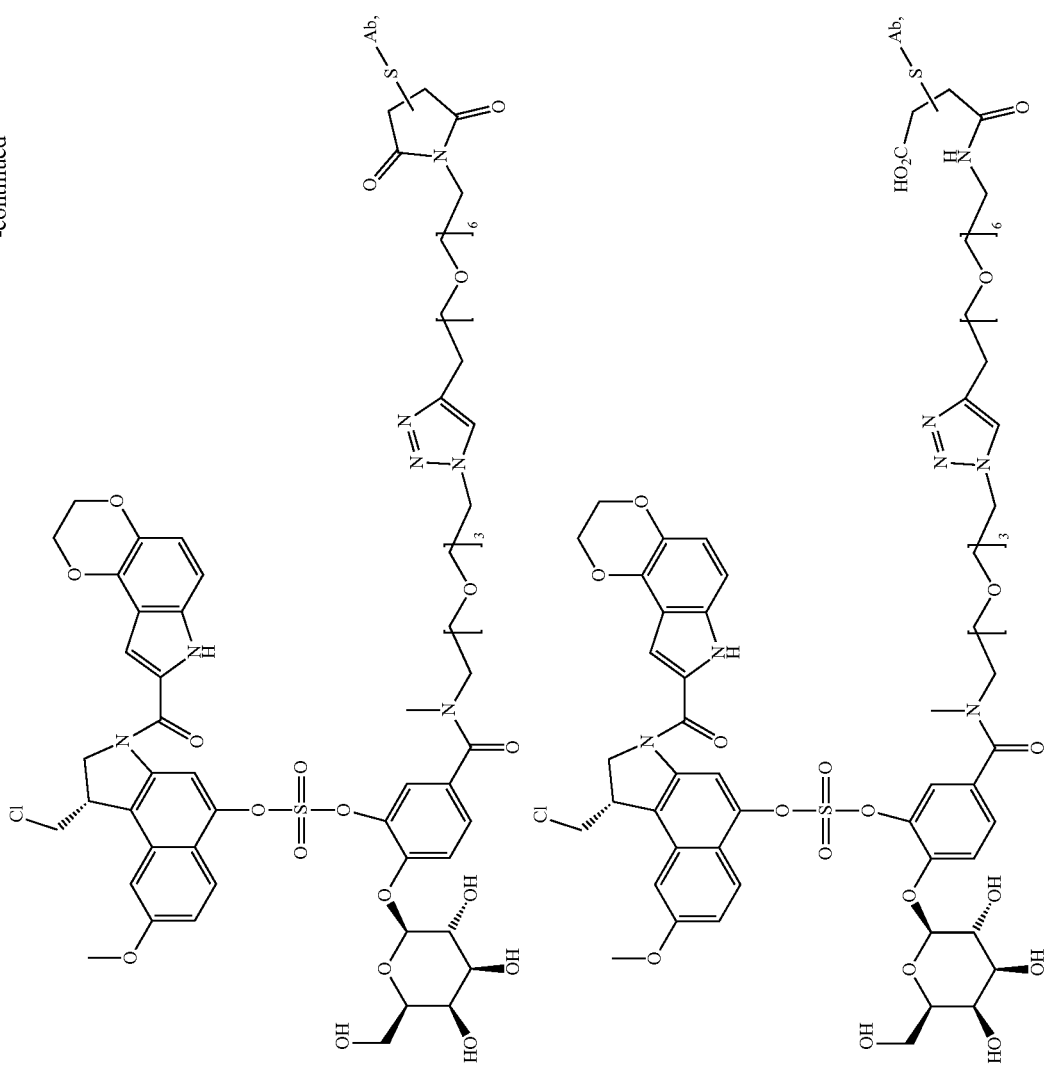

-continued
813 814
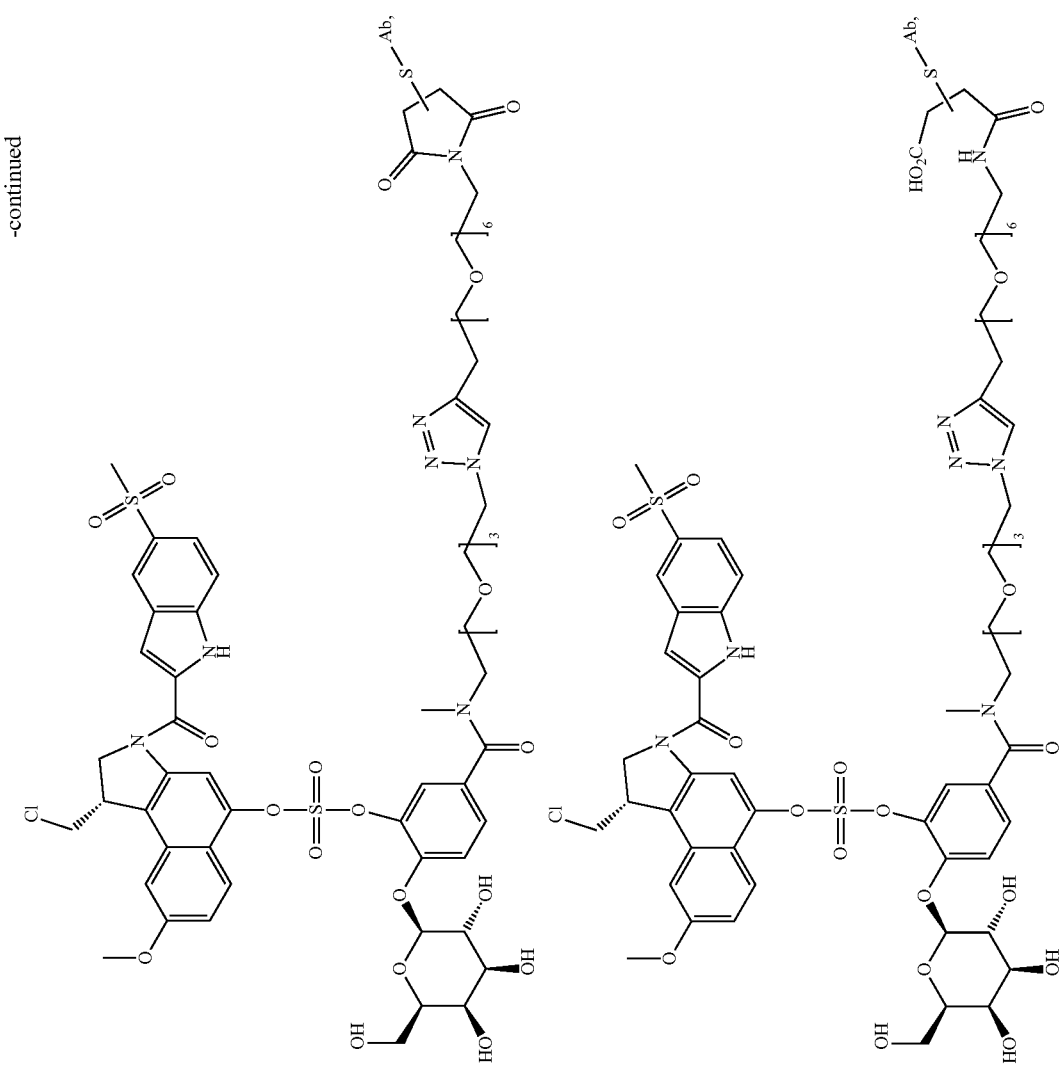

815 816
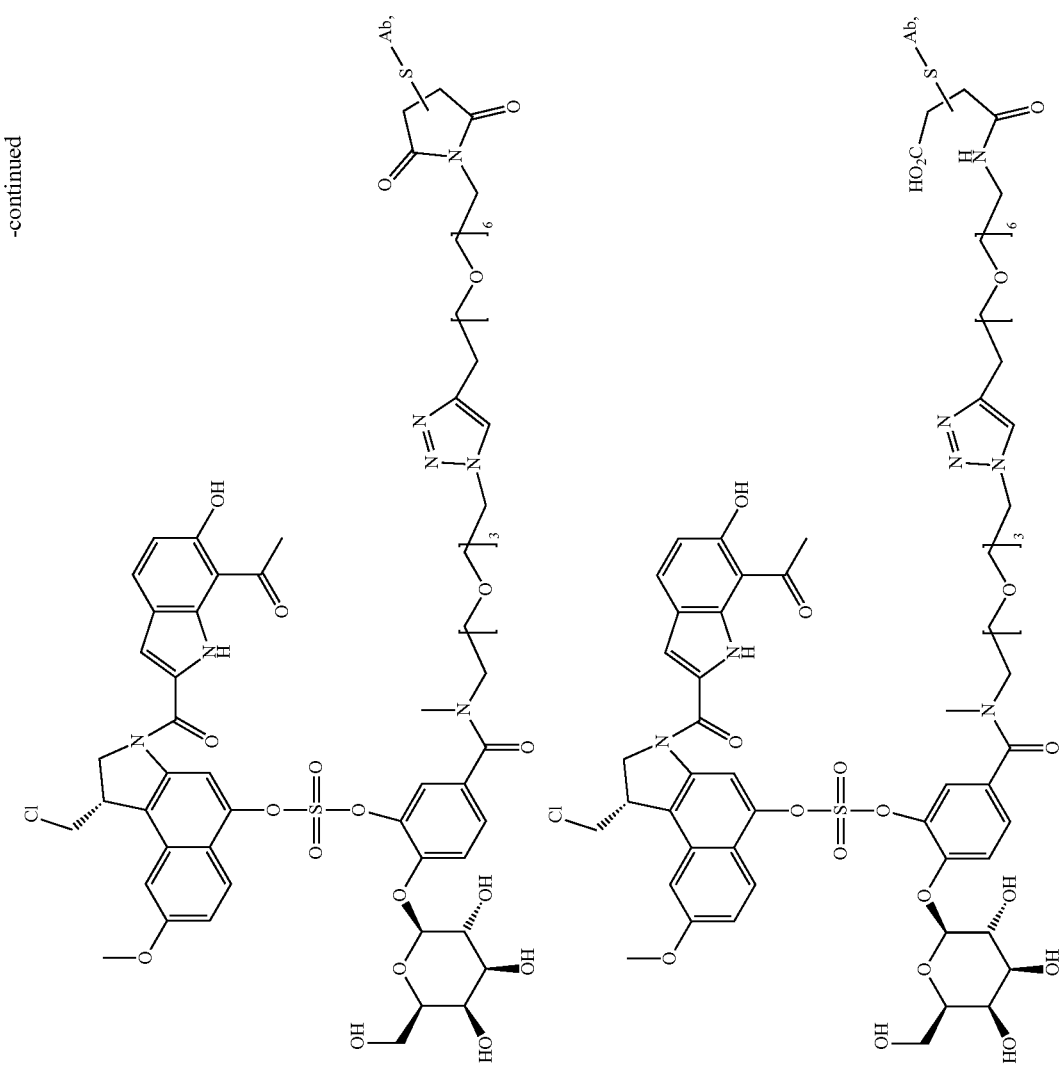

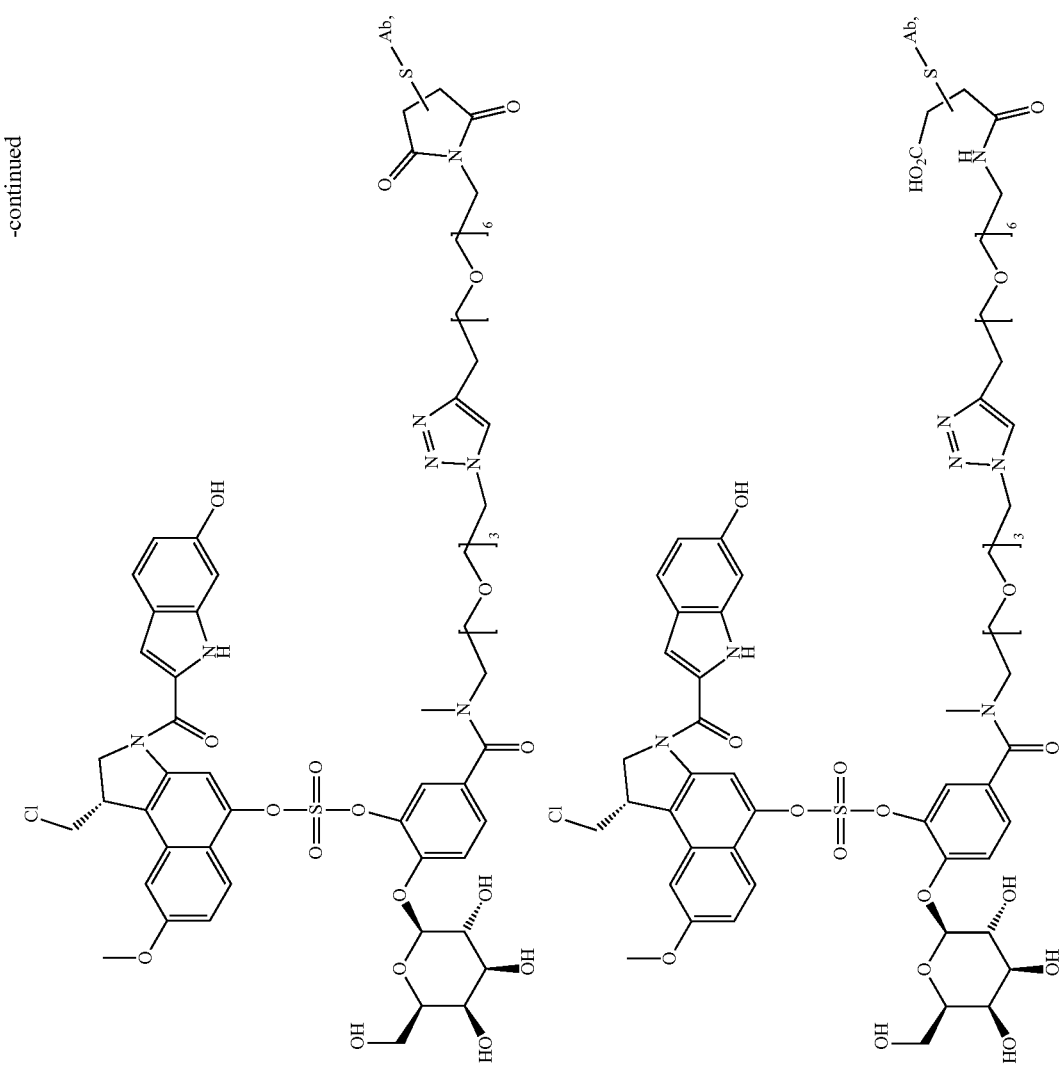

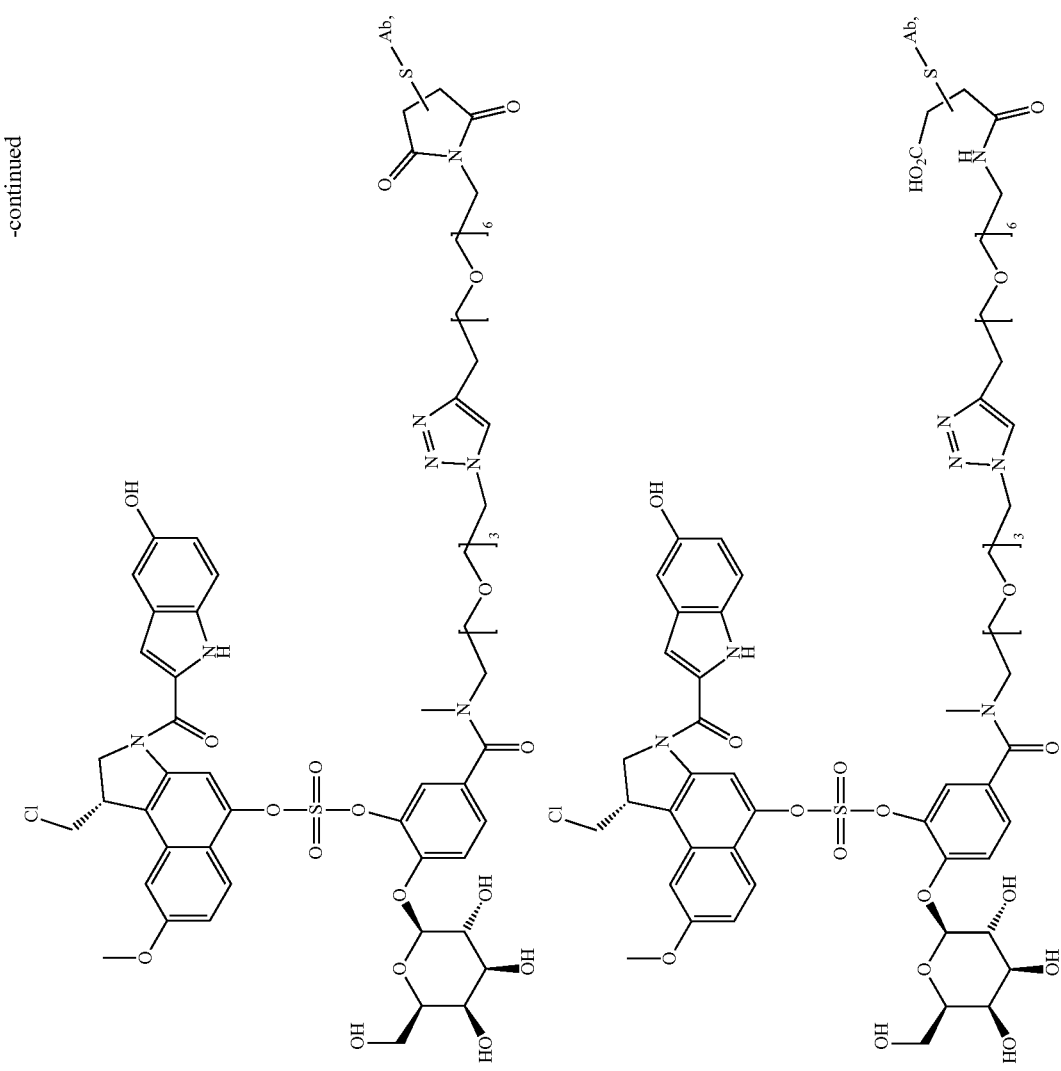

821 822
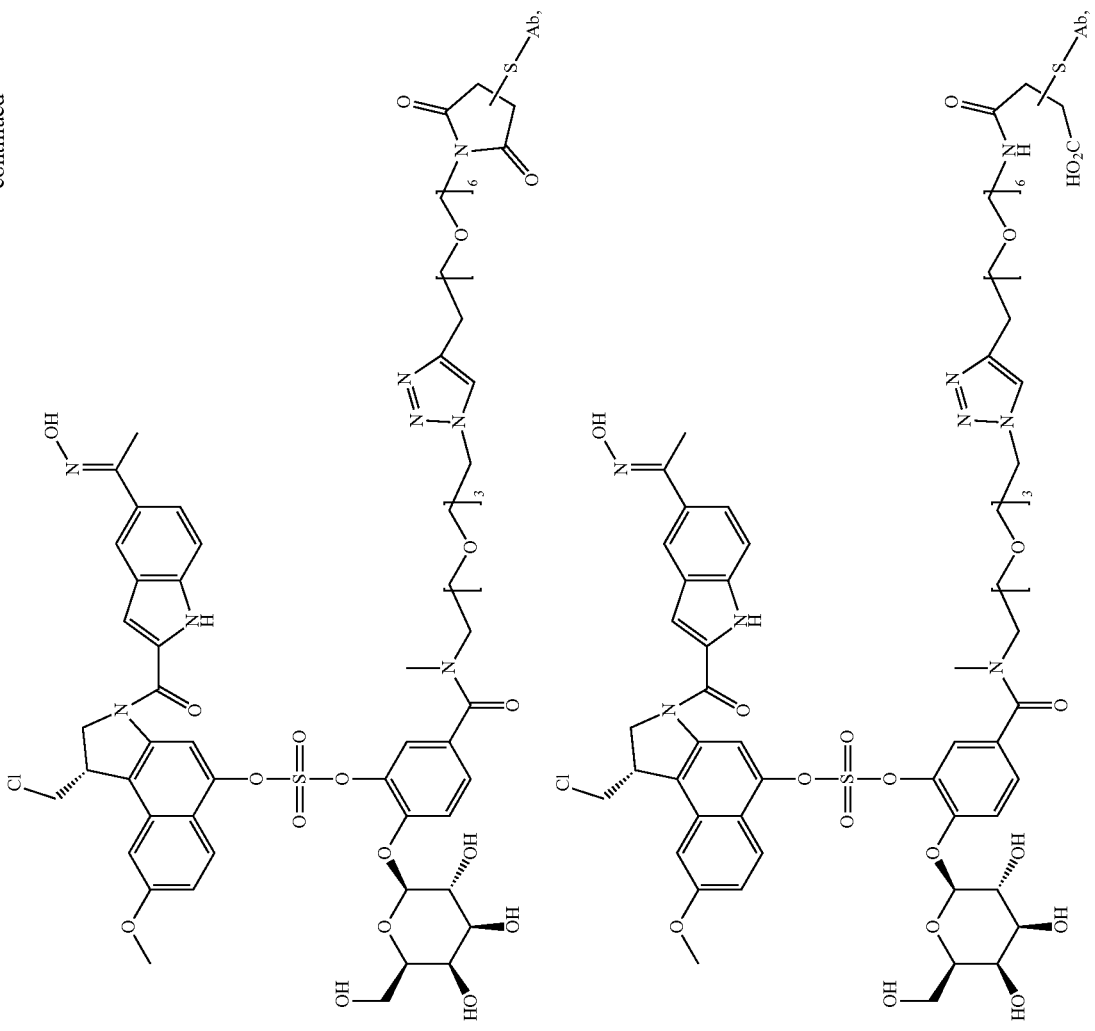

823 824
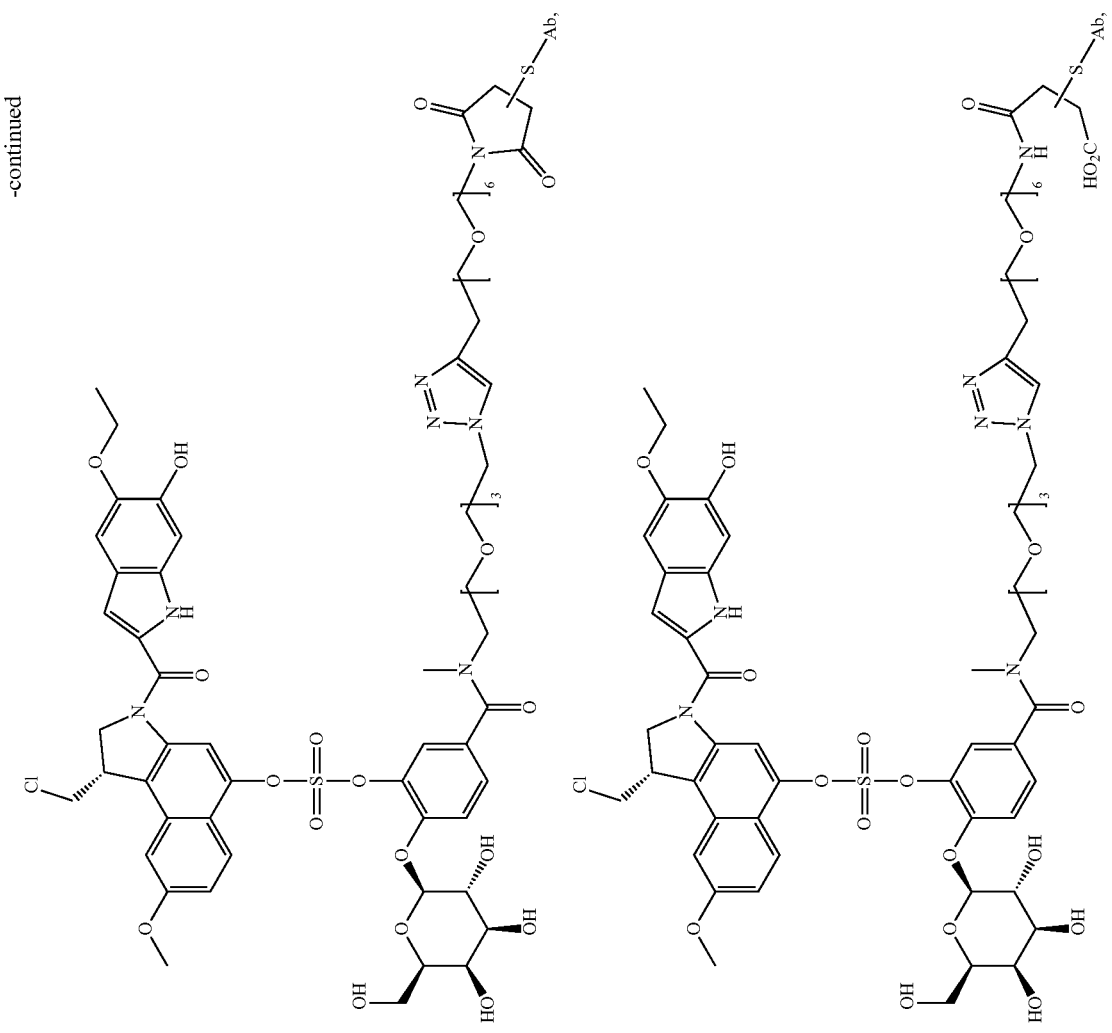

825 826
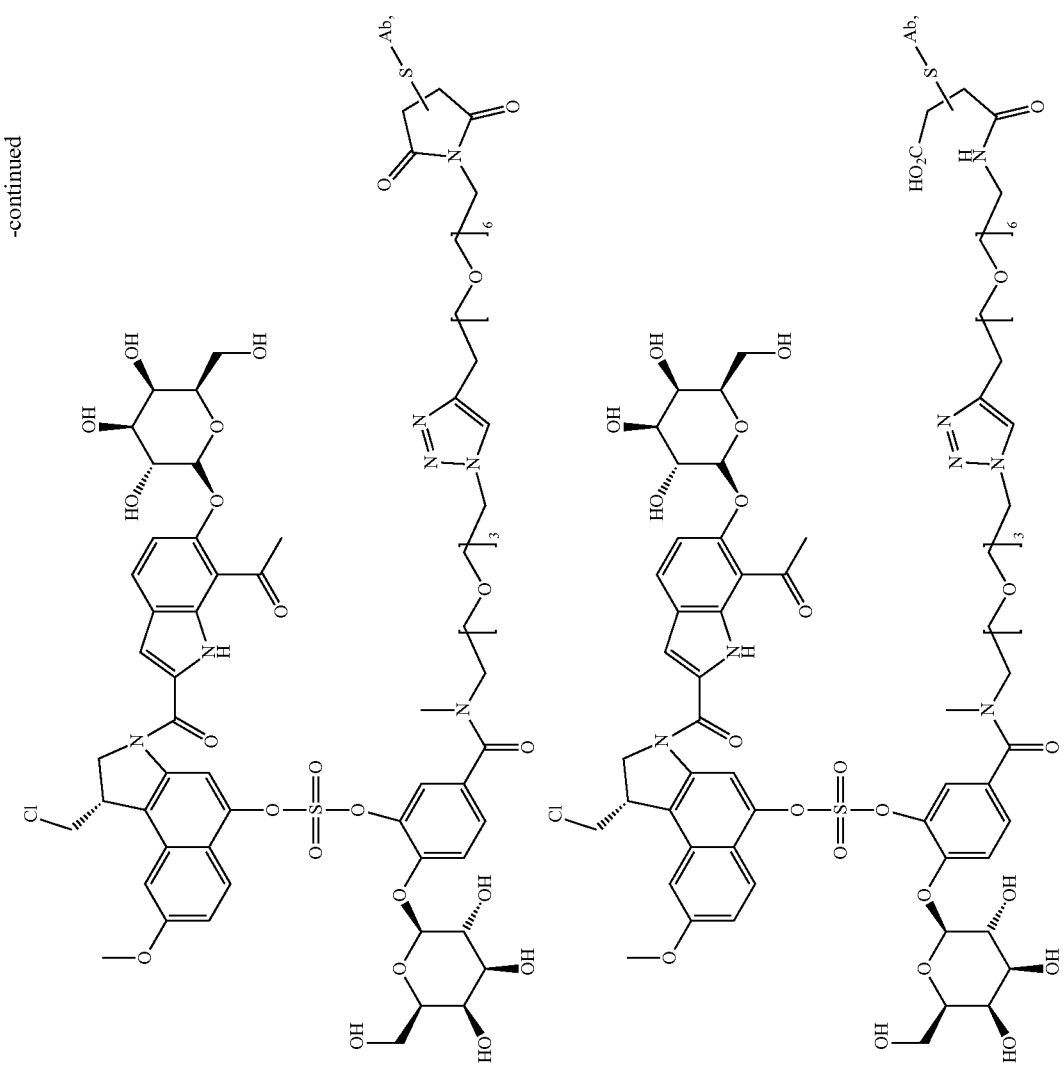

-continued
827 828
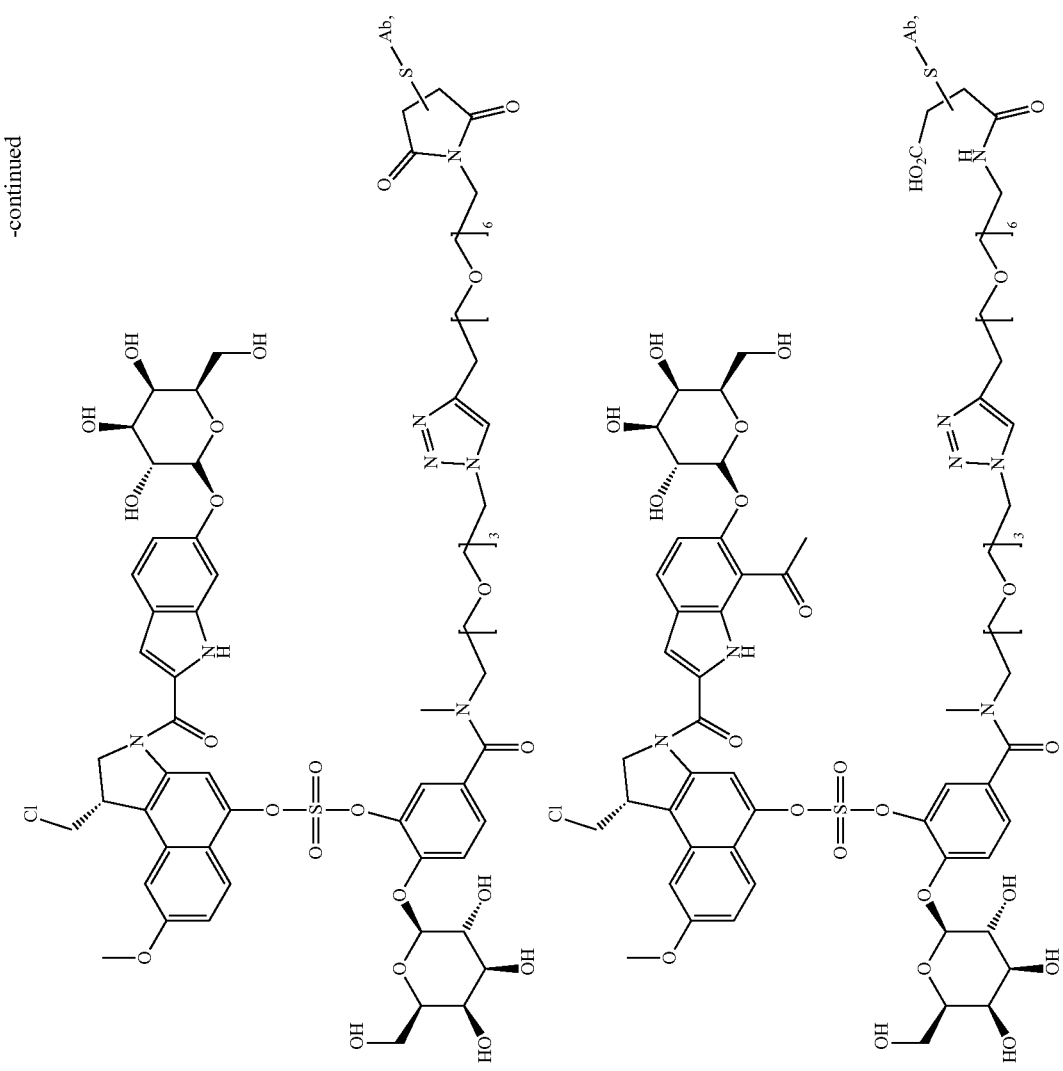

829 830
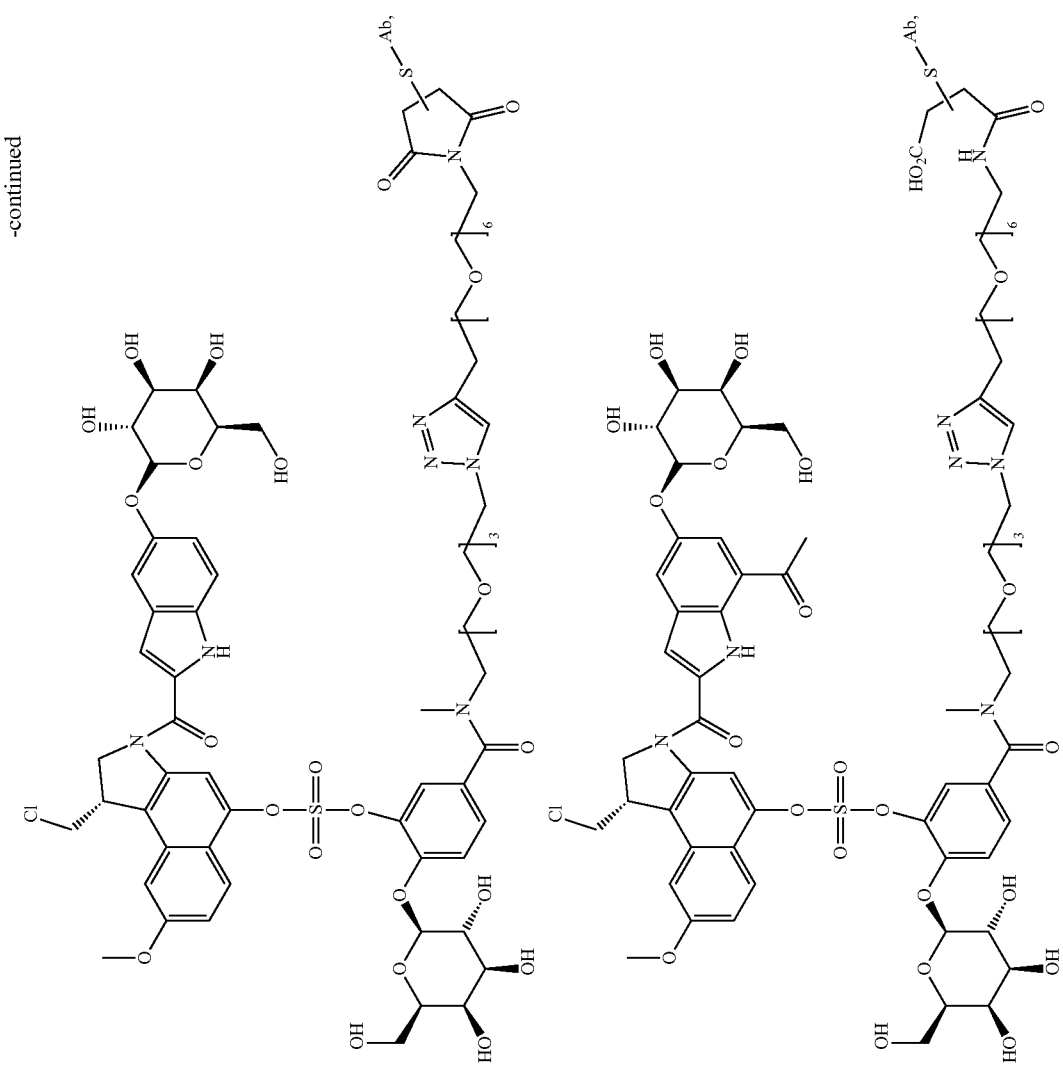

831
832
-continued
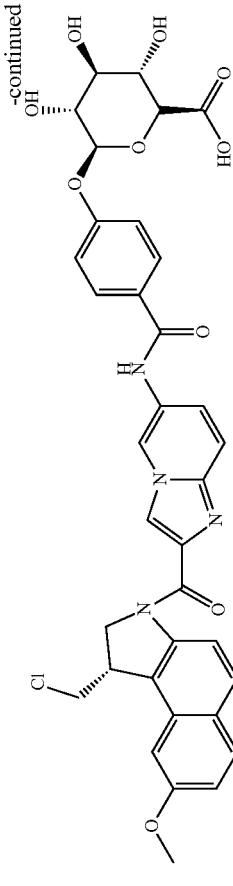
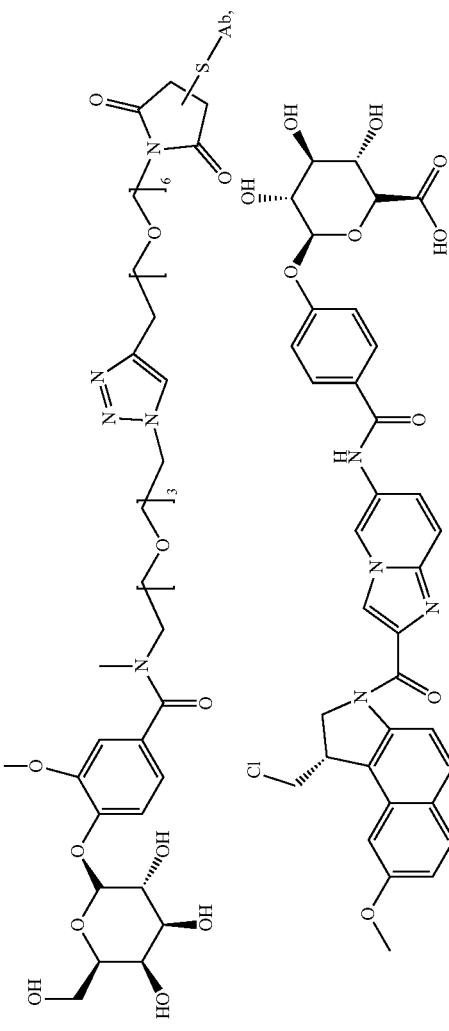
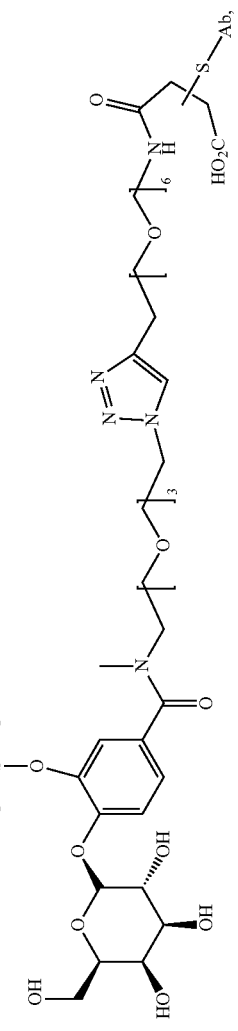

833
-continued
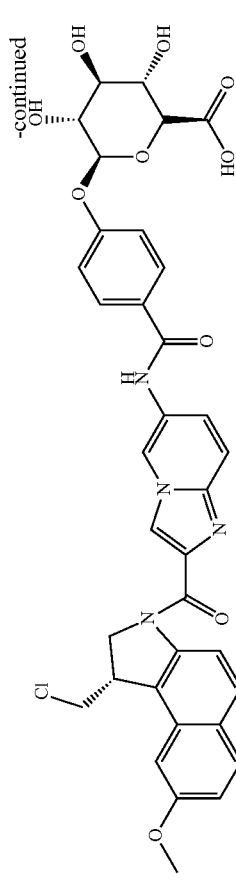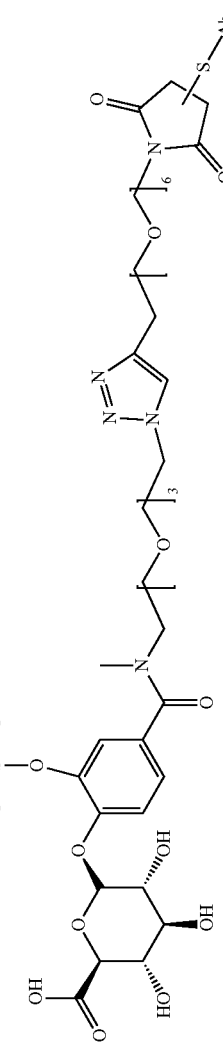
834
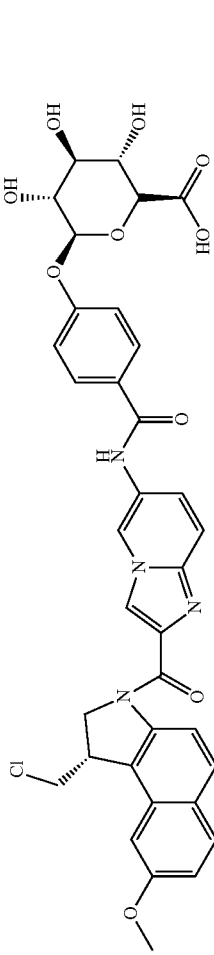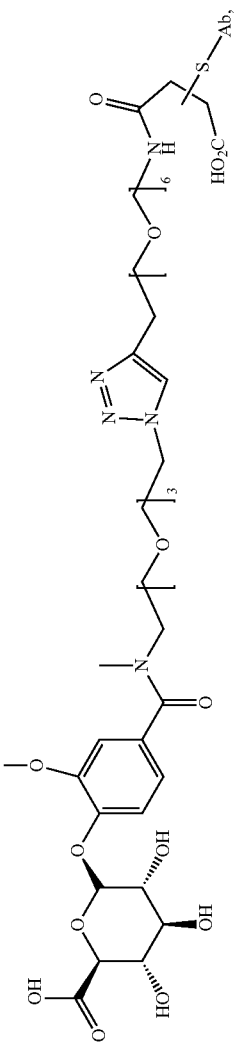

835 836
-continued
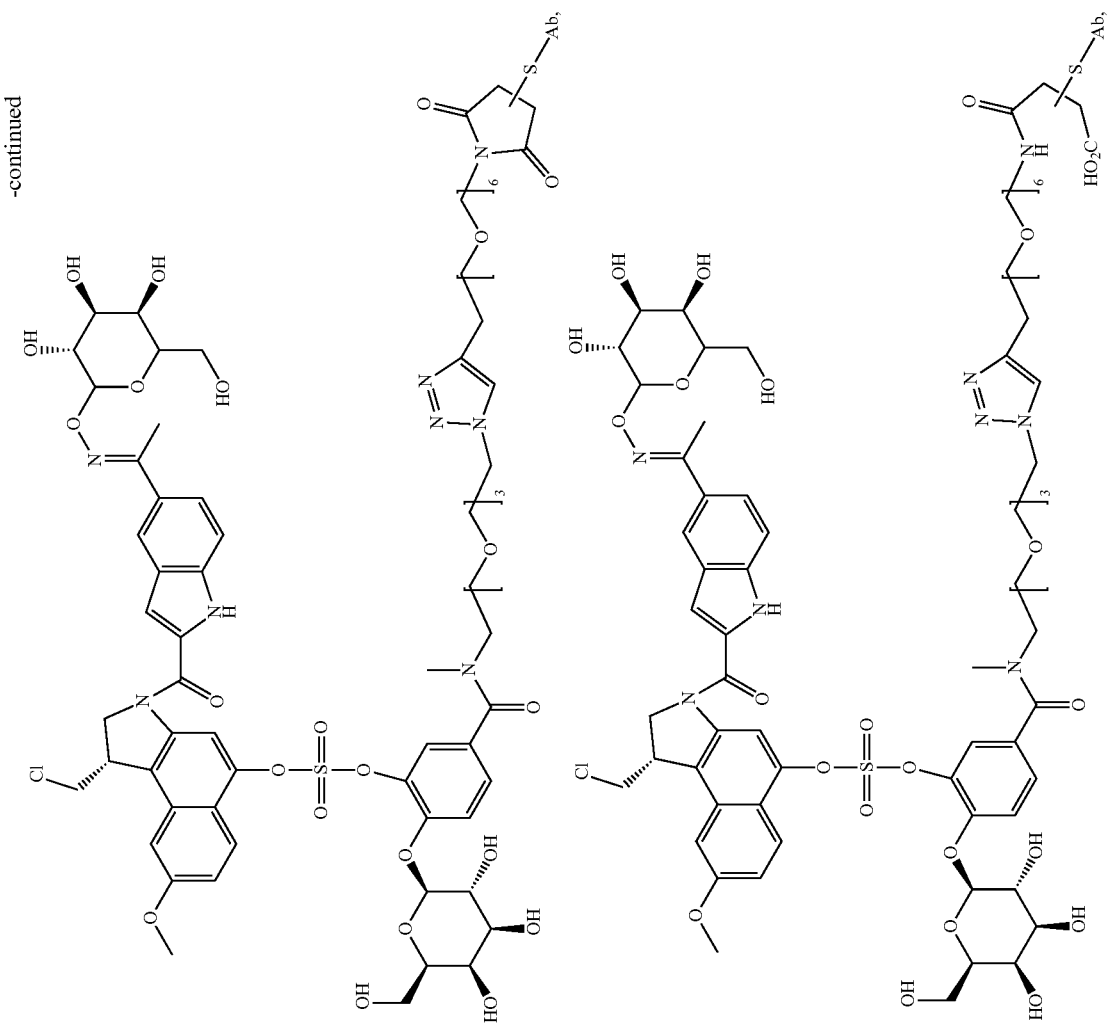

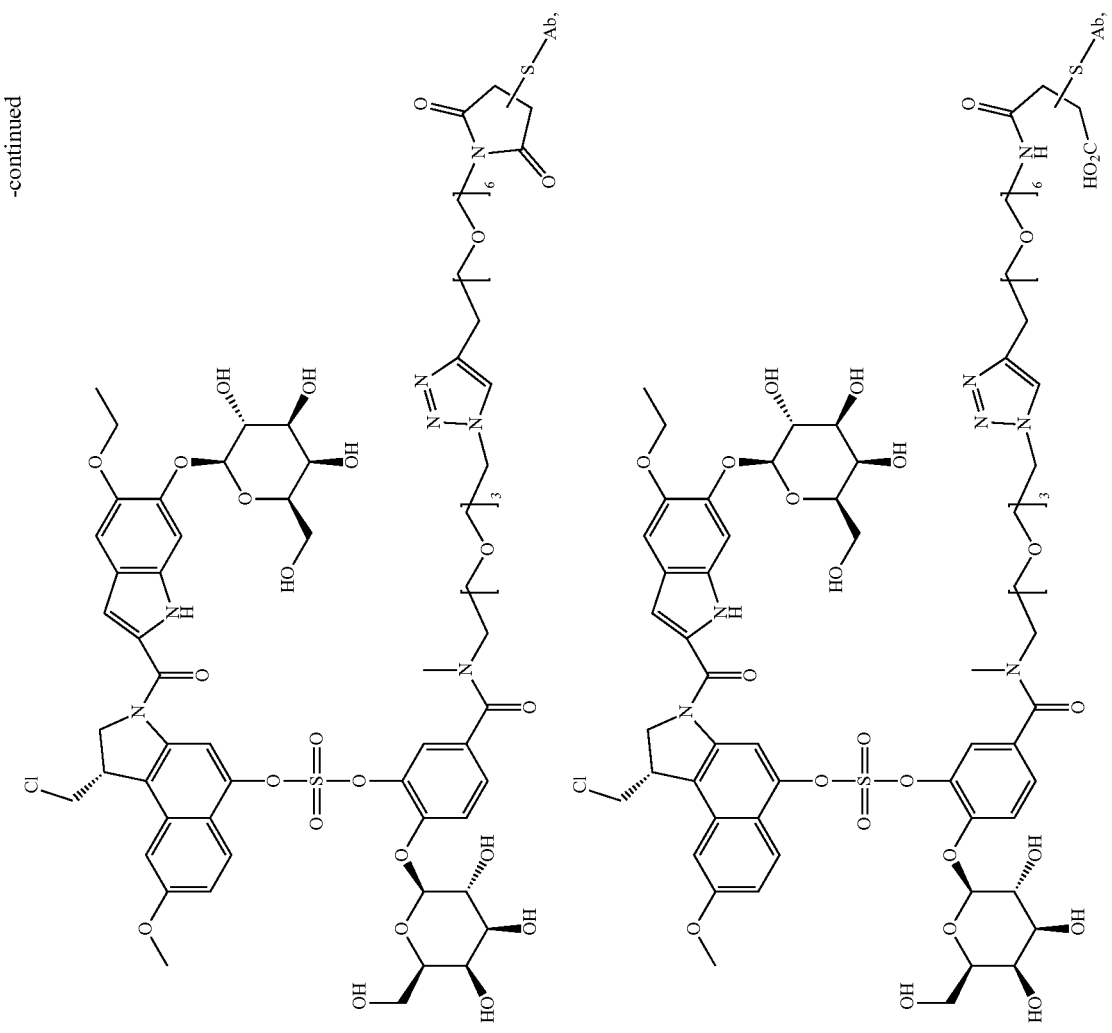

839 840
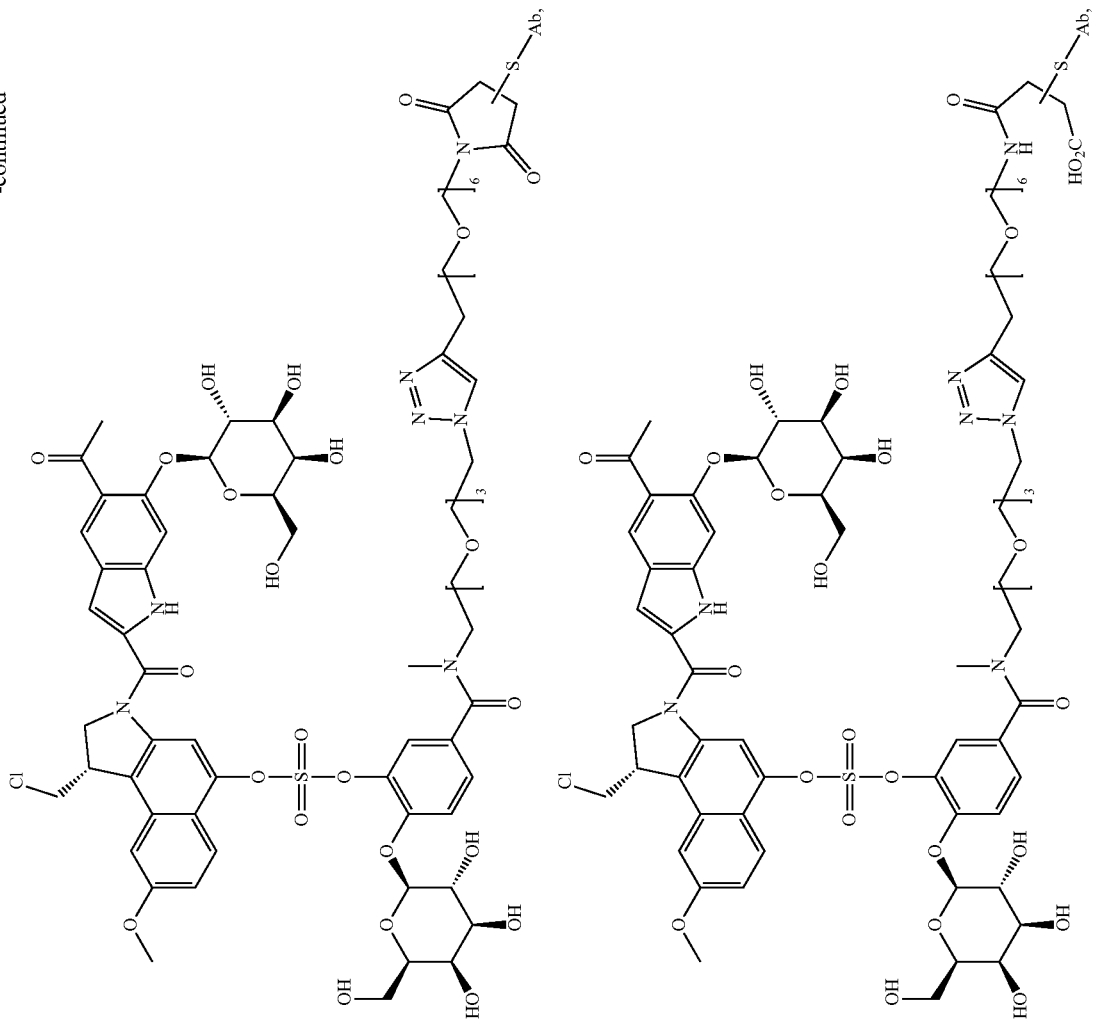

841 842
-continued
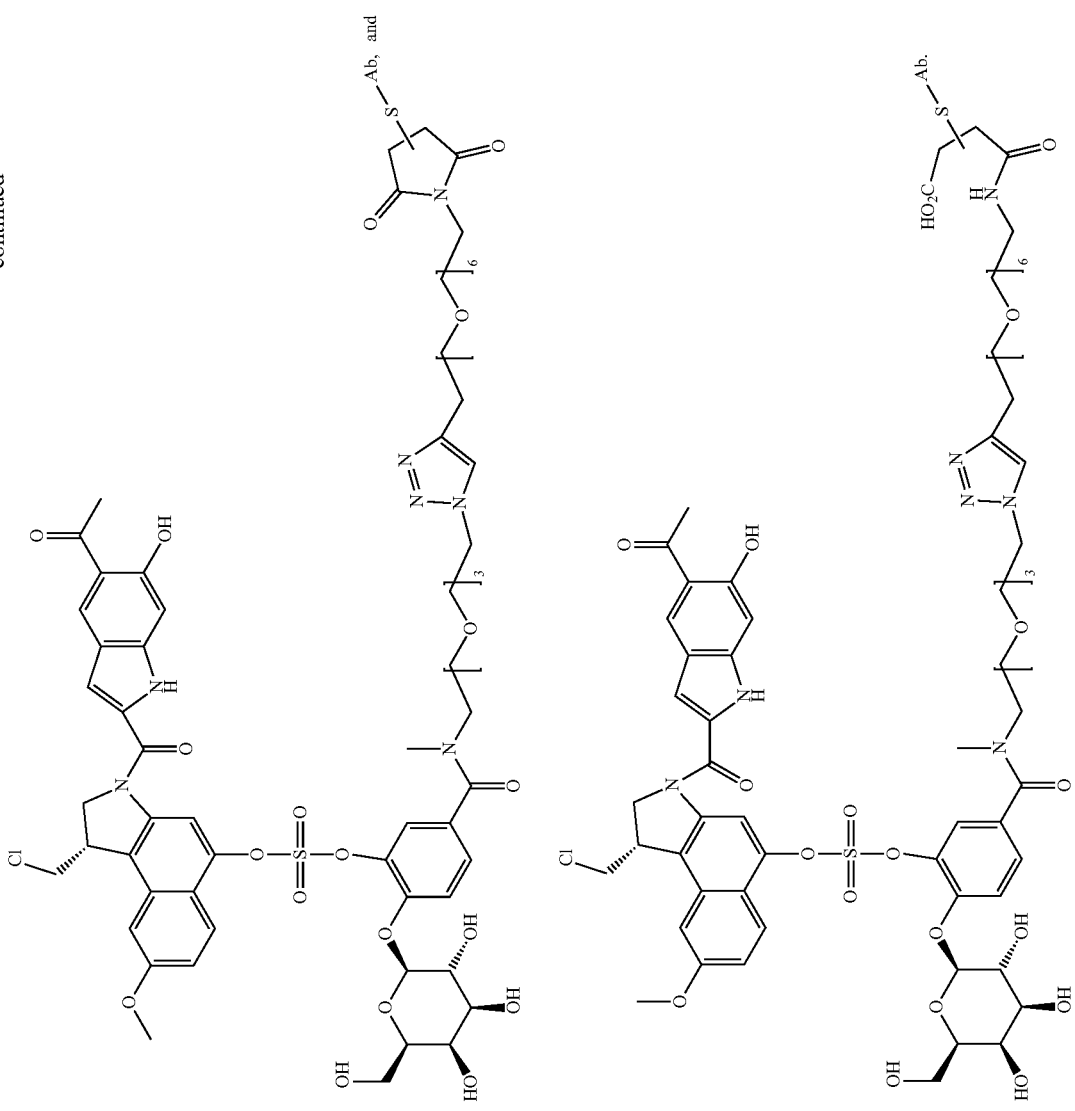

21. The antibody conjugate of claim 20, wherein the antibody conjugate
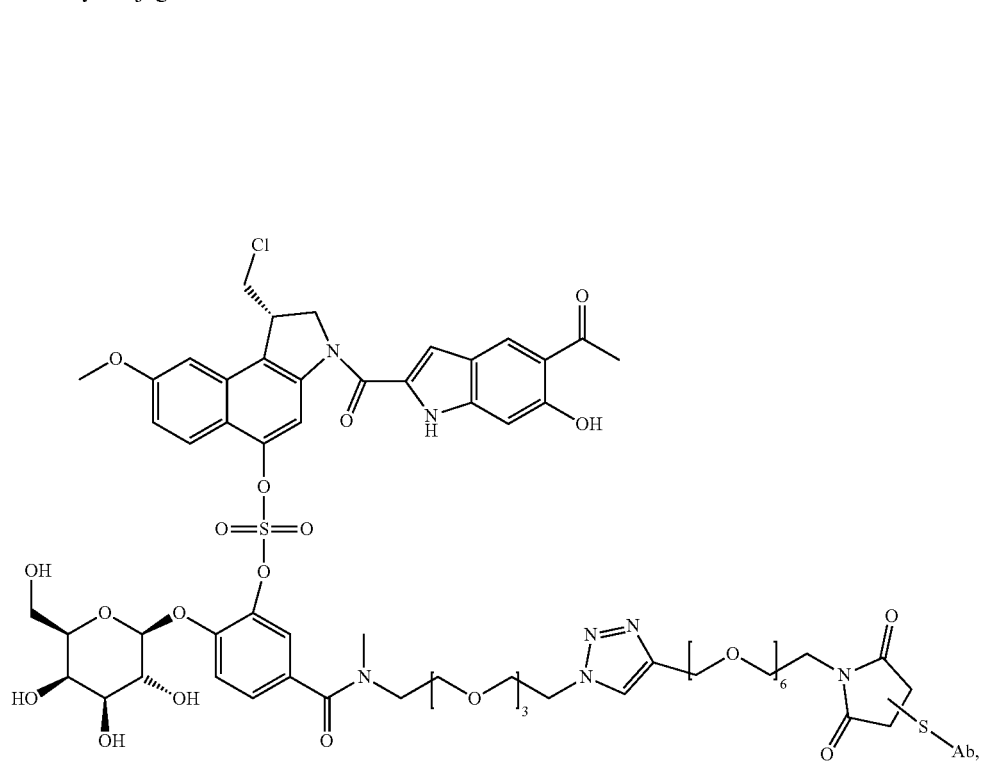
is selected from
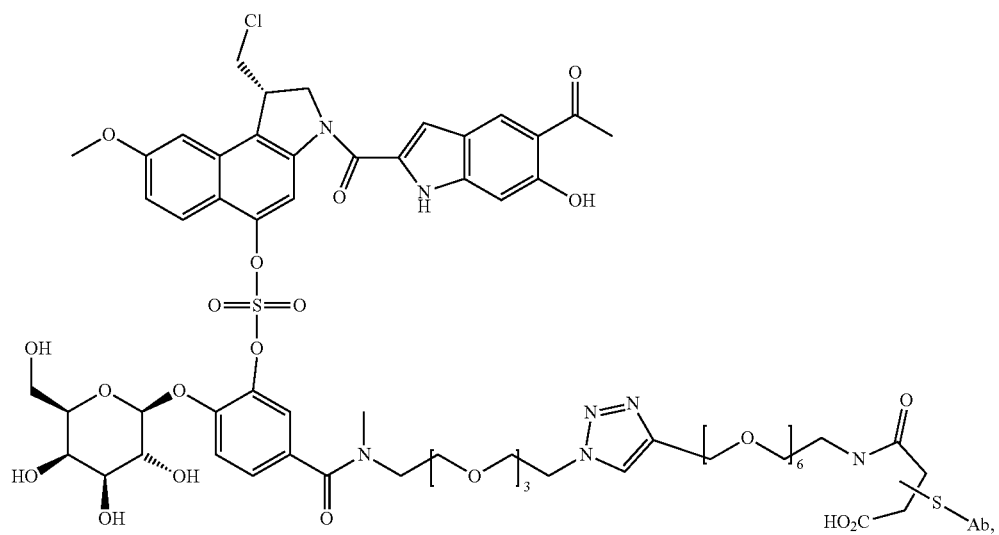

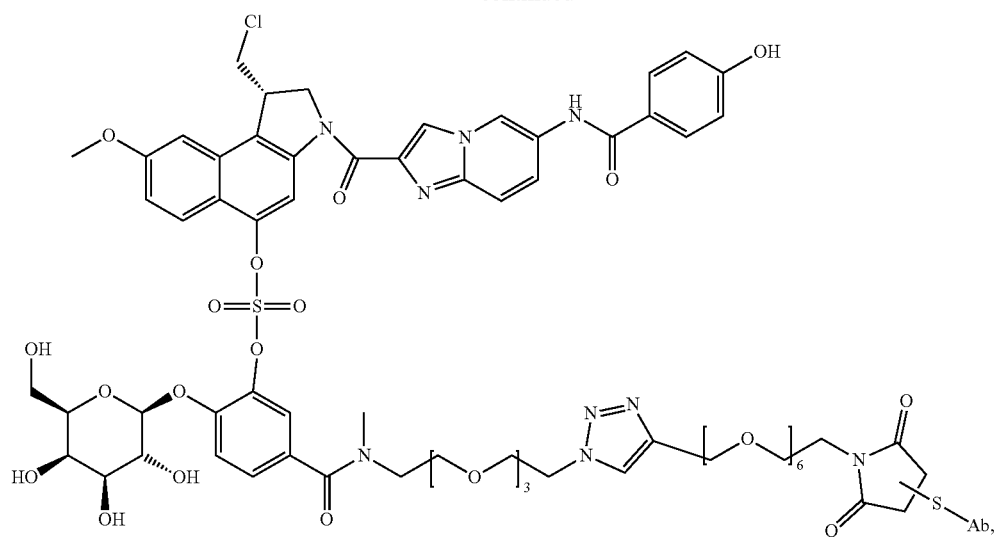
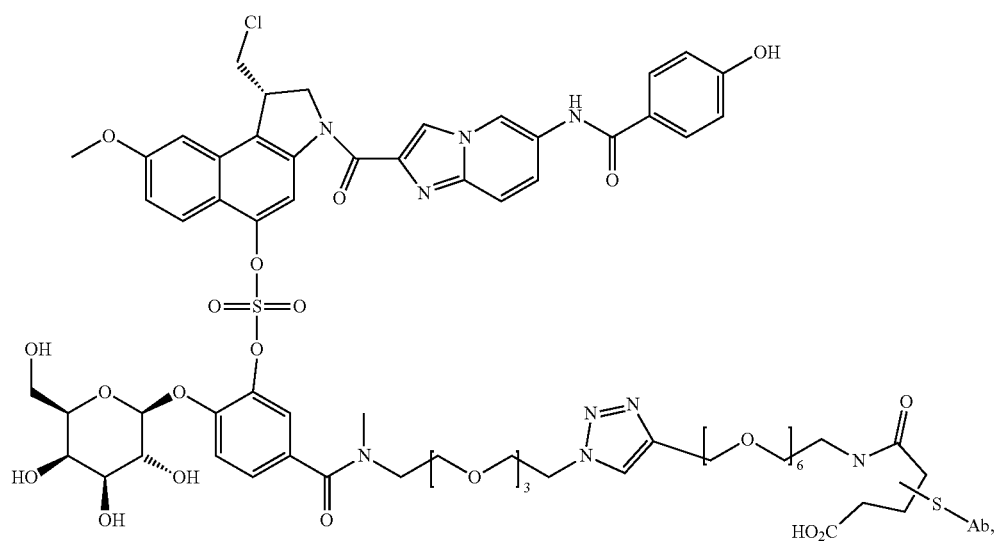
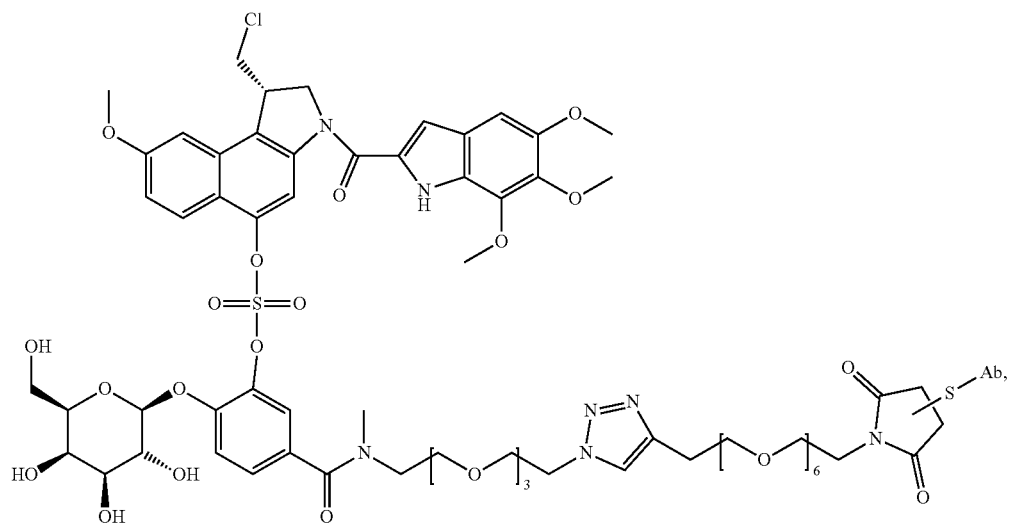

-continued
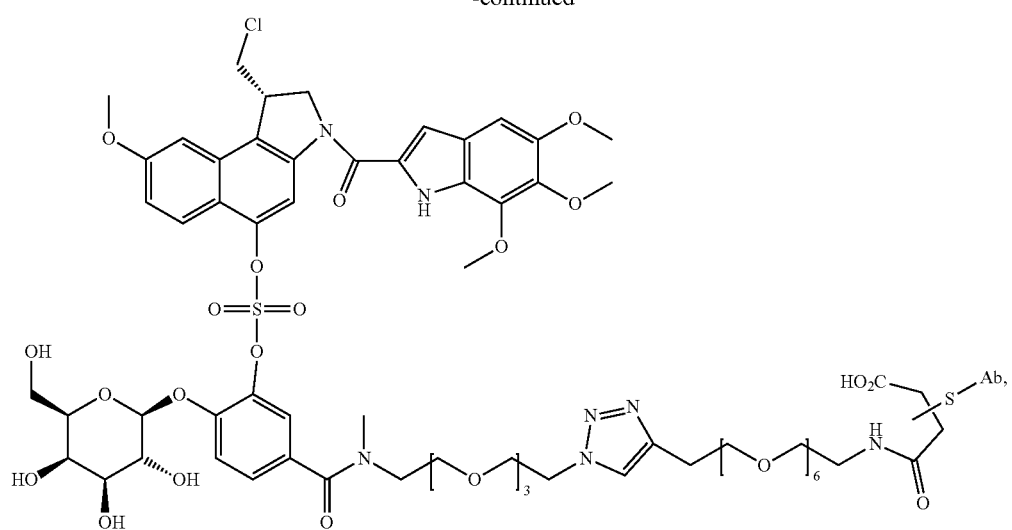
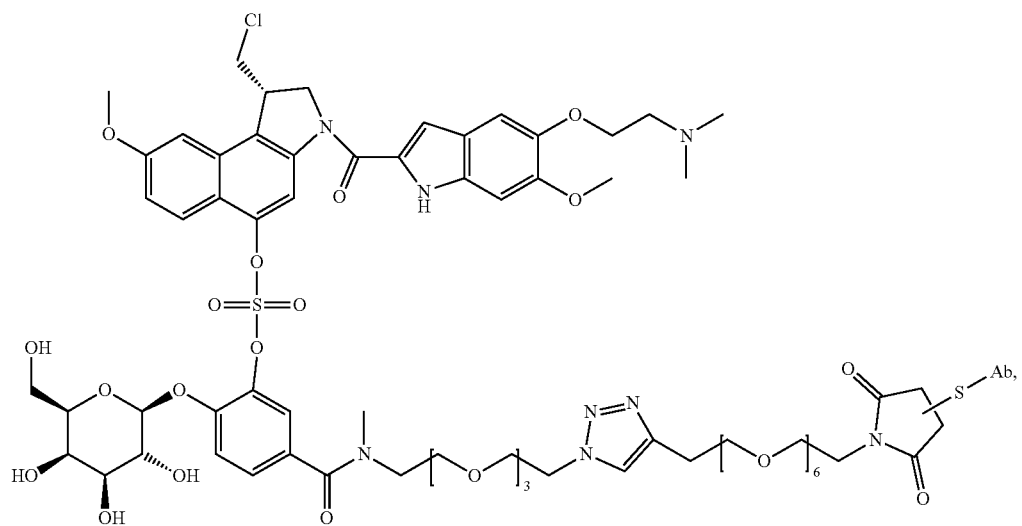
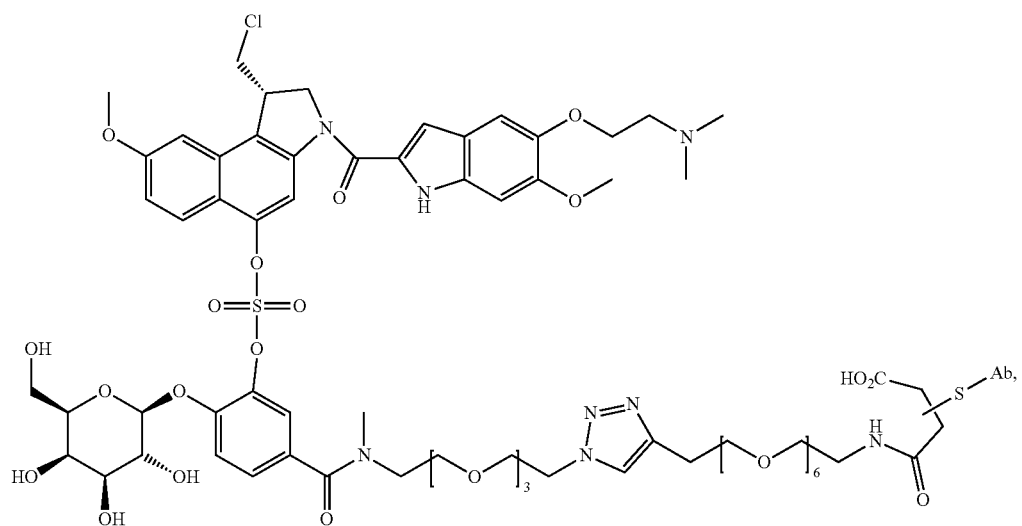

-continued
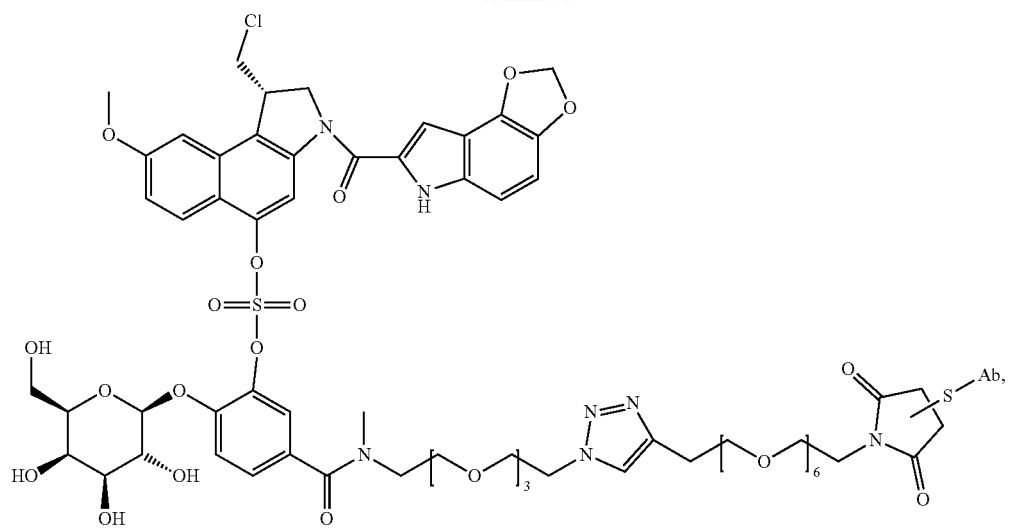
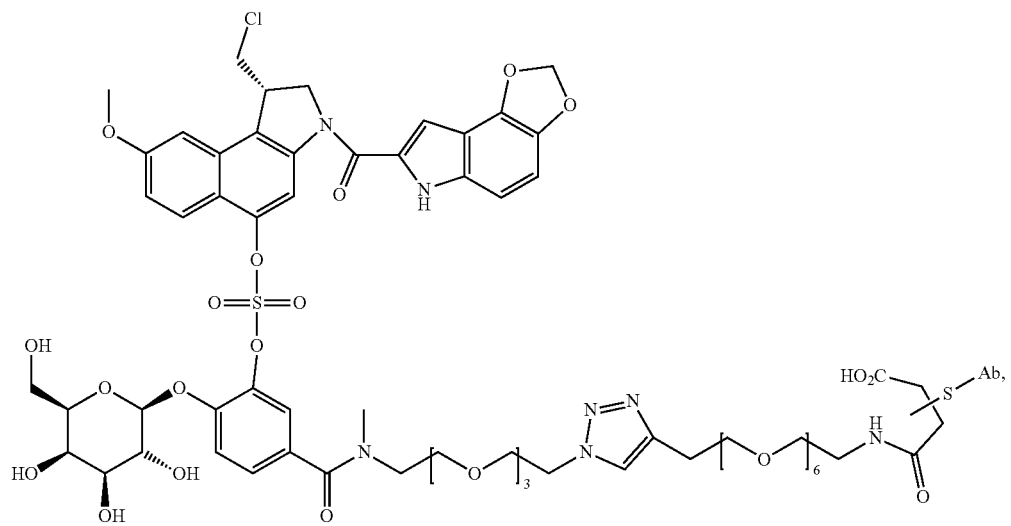
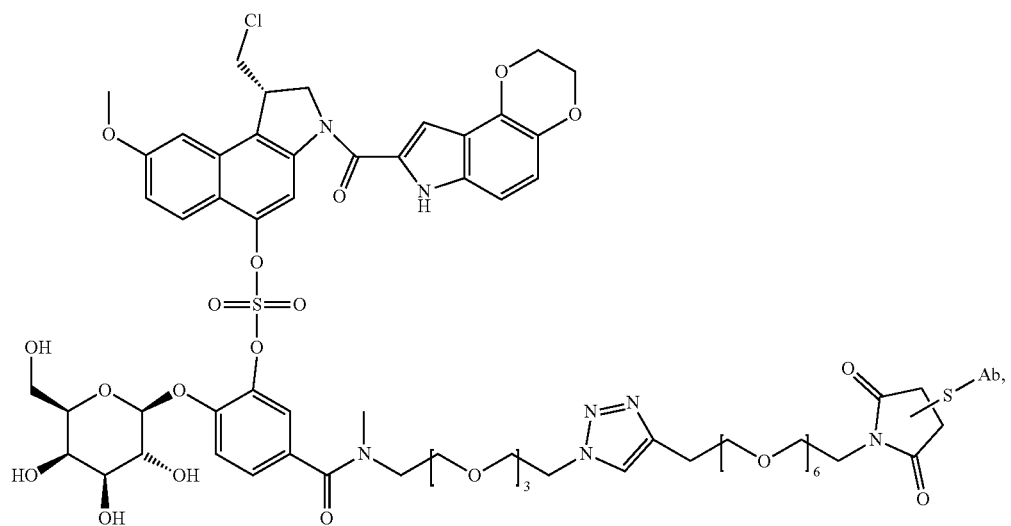

851
-continued
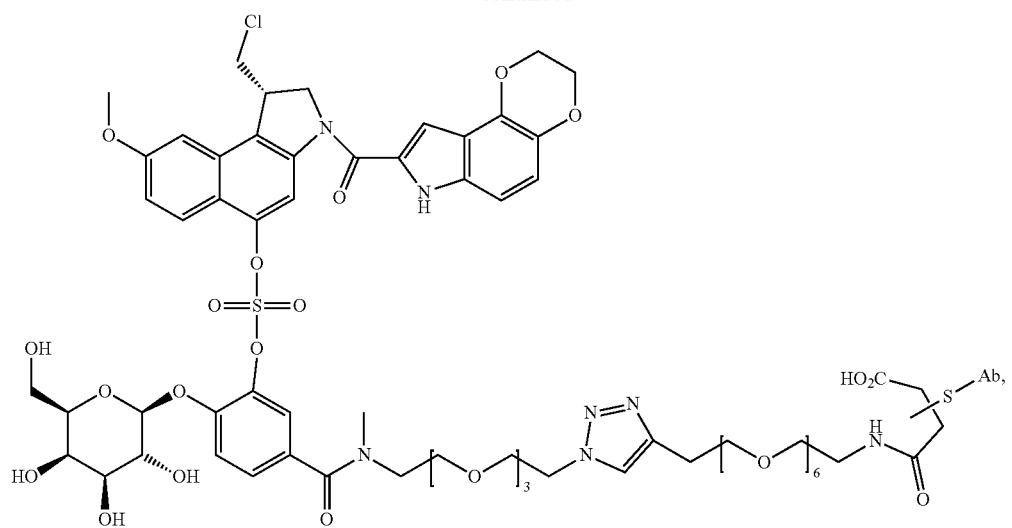
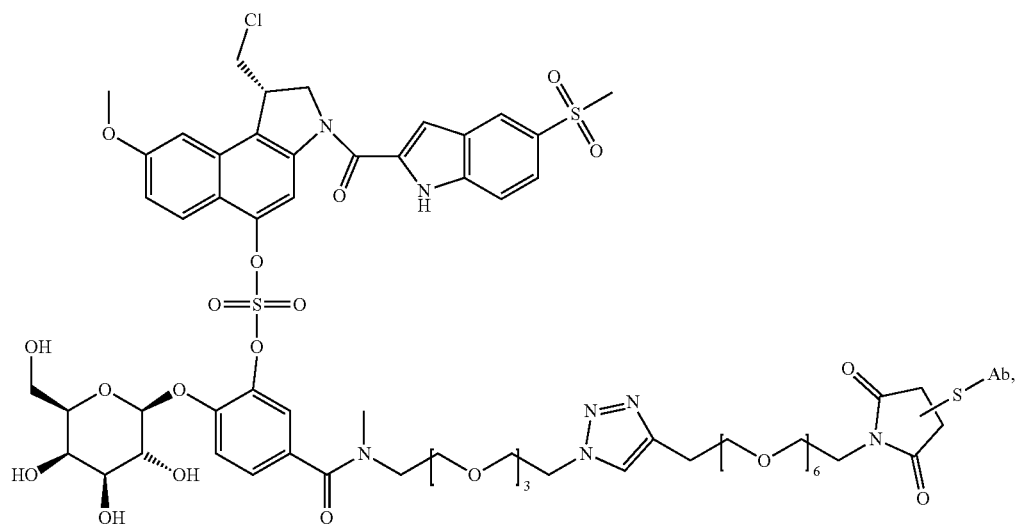
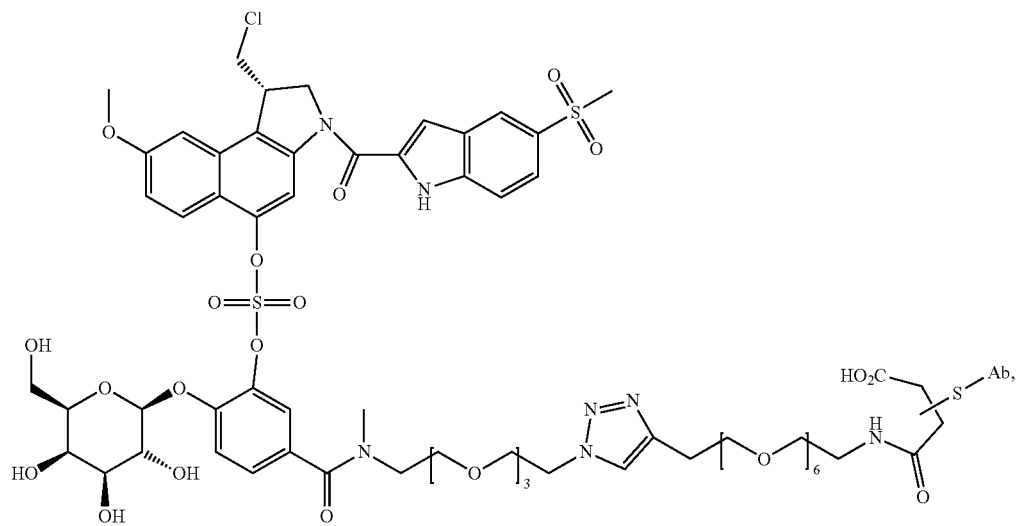

-continued
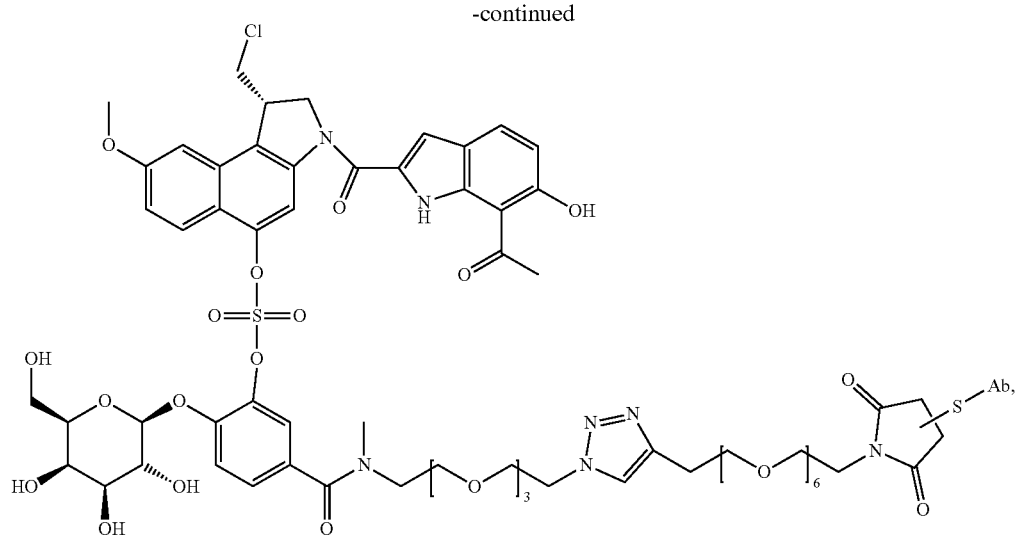
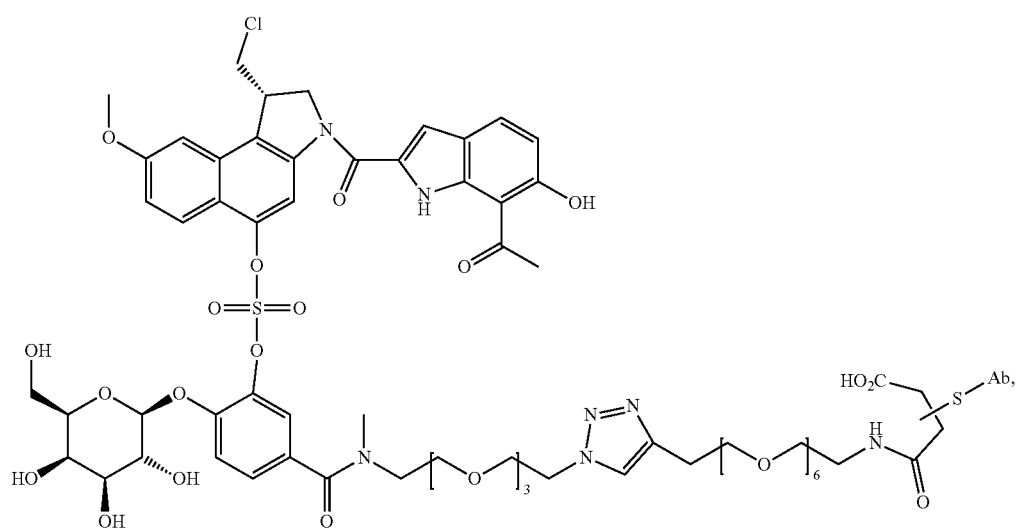
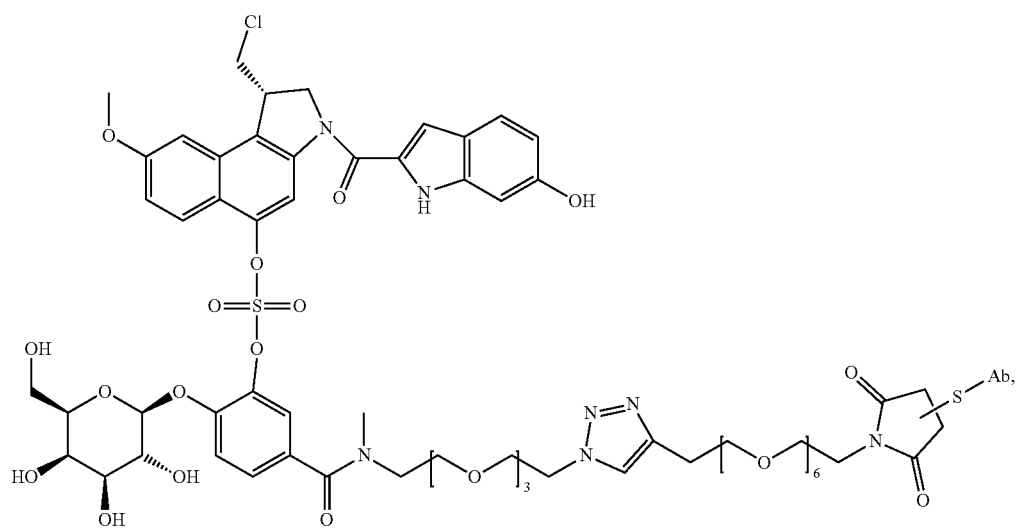

855
856
-continued
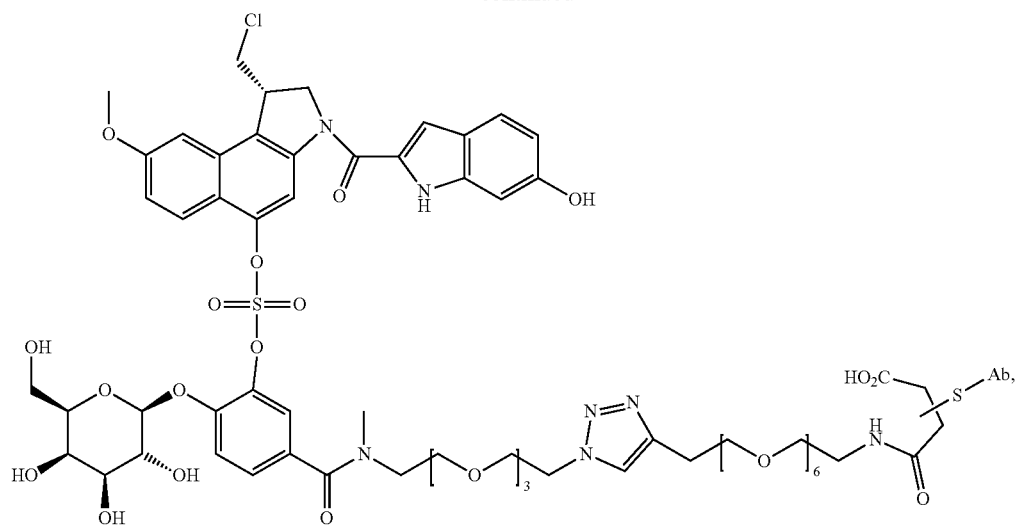
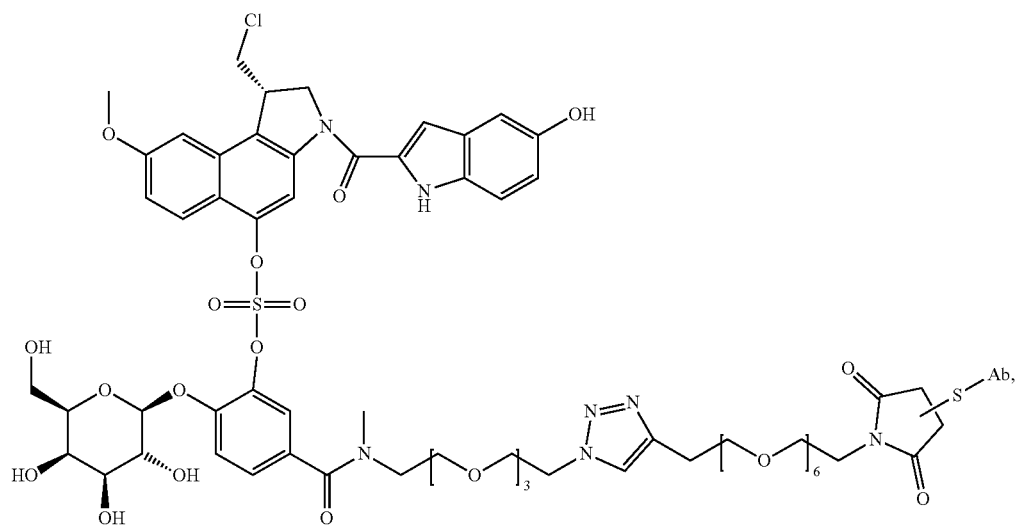
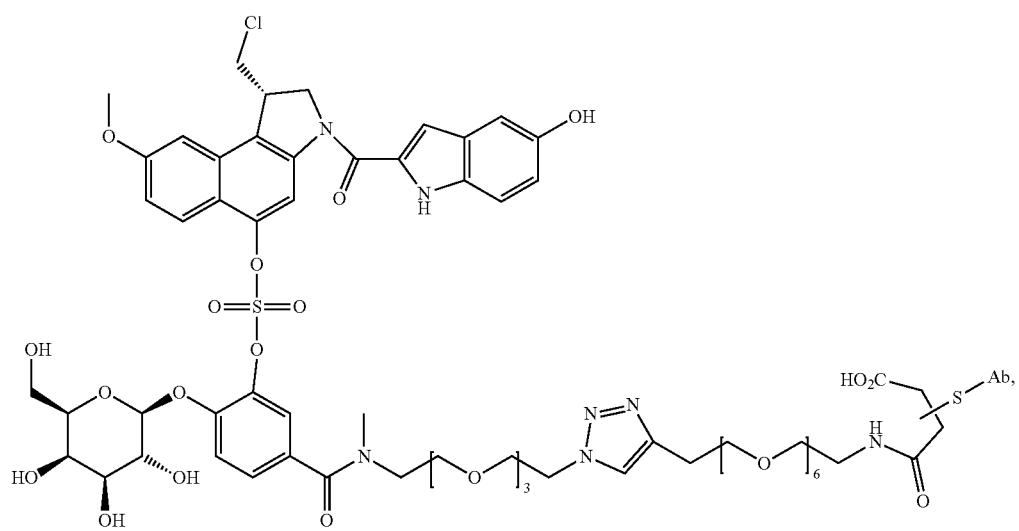

-continued
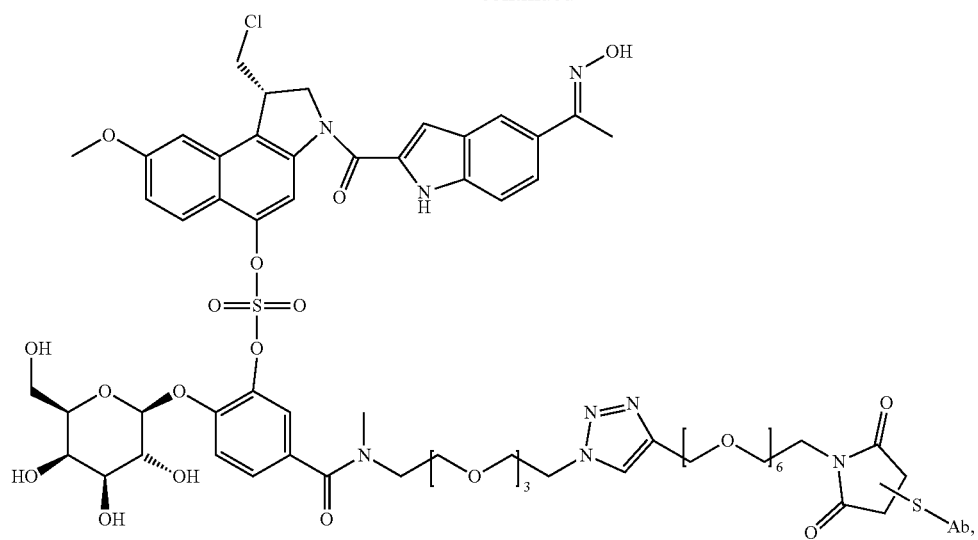
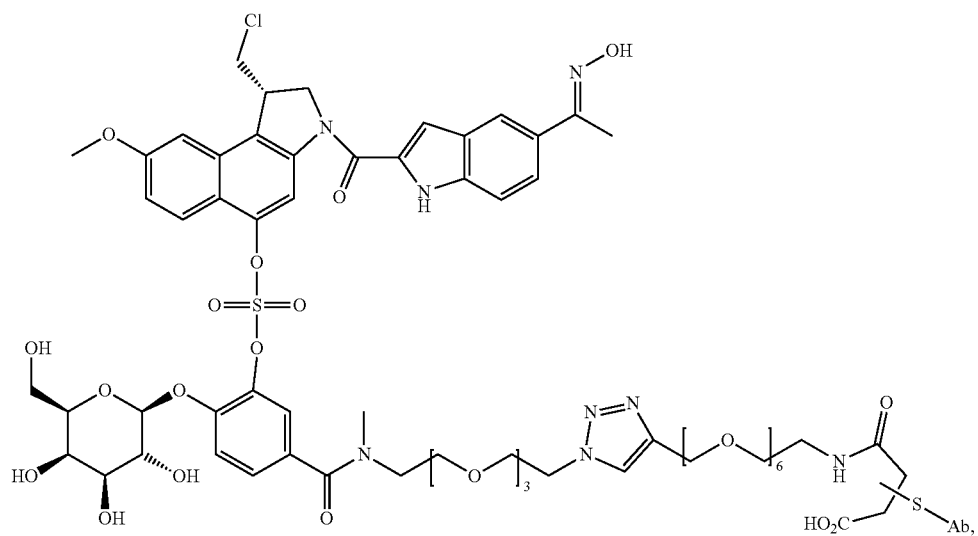
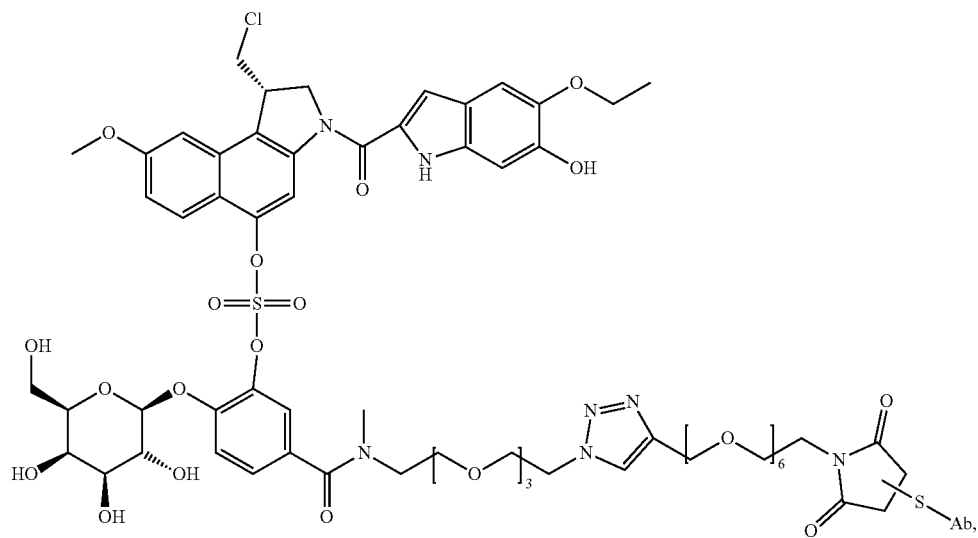

-continued
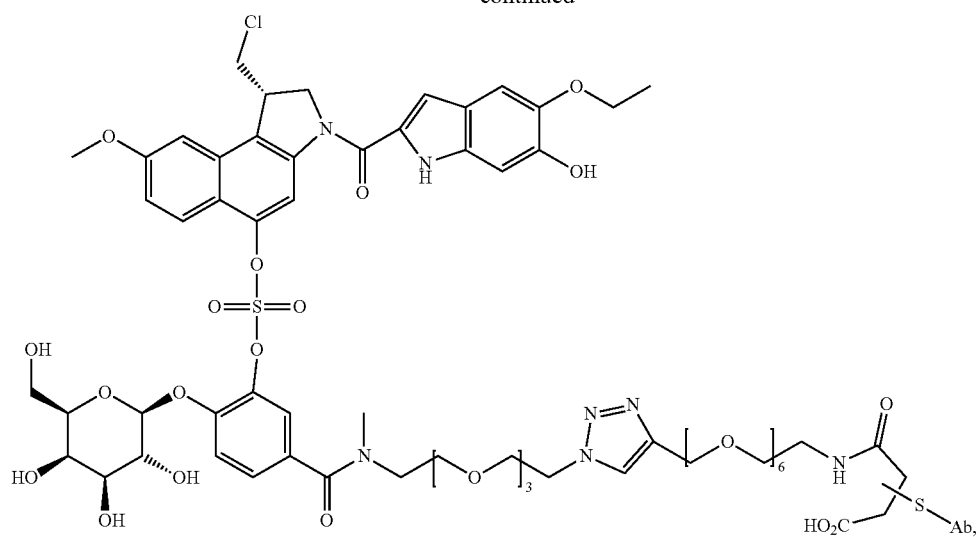
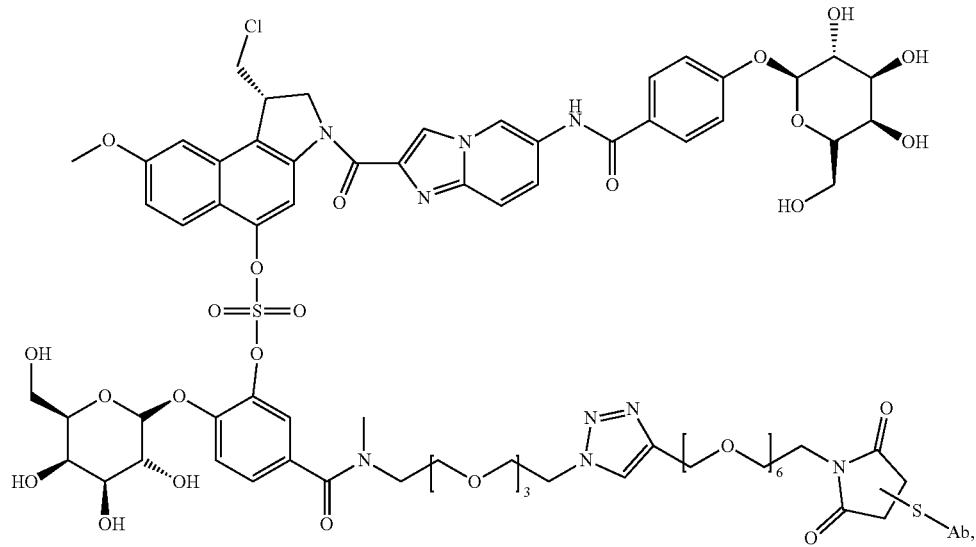
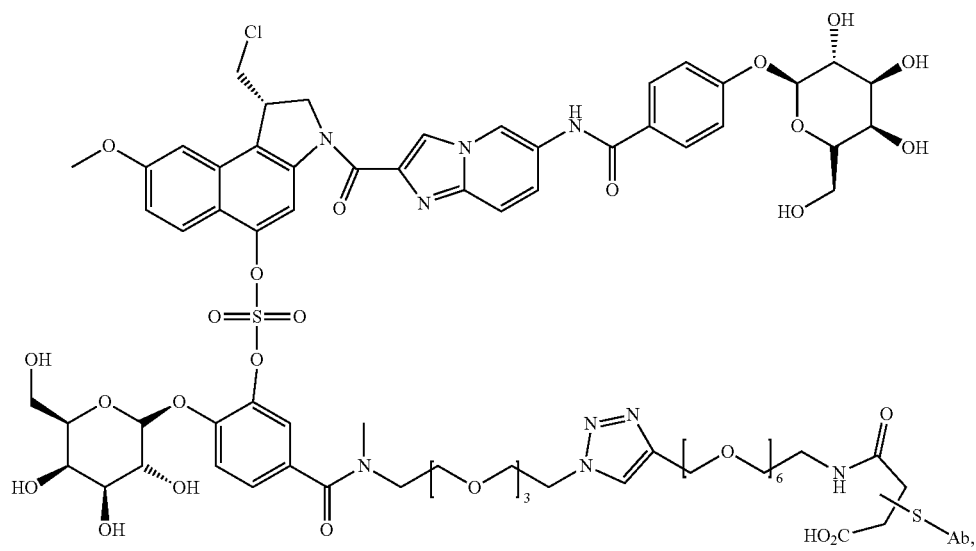

861
-continued
862
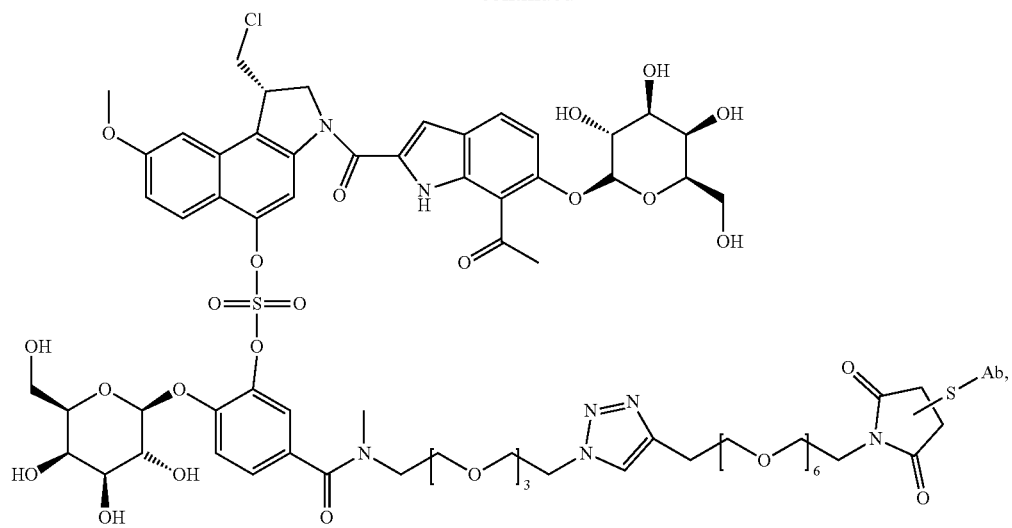
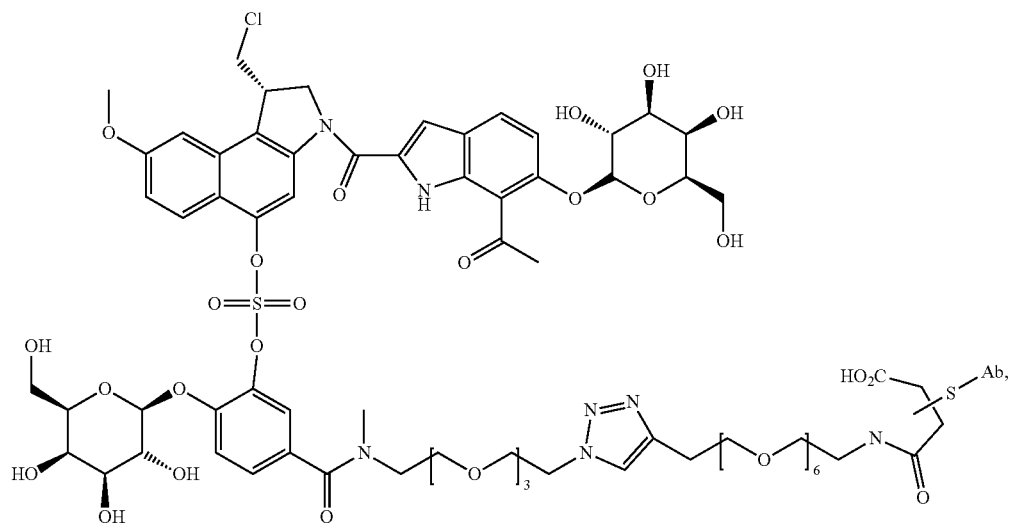
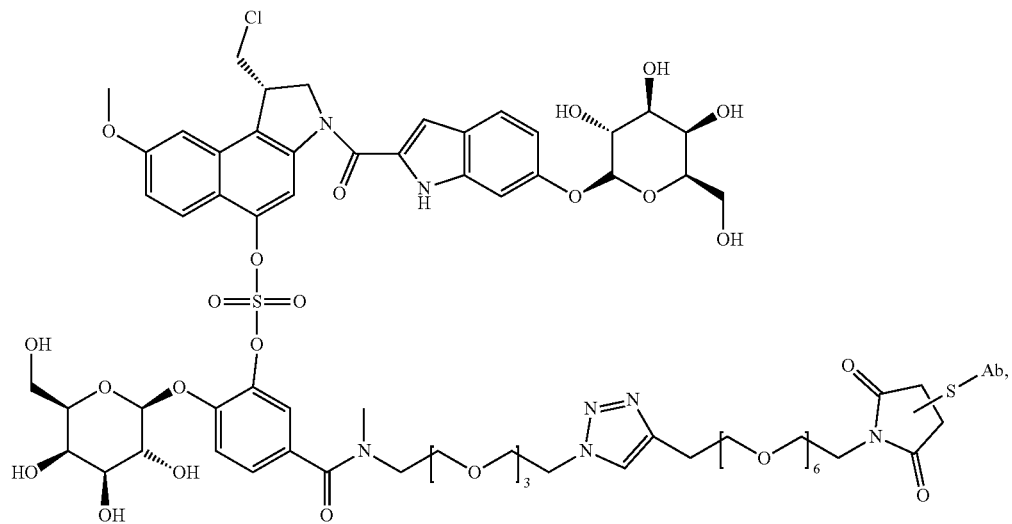

-continued
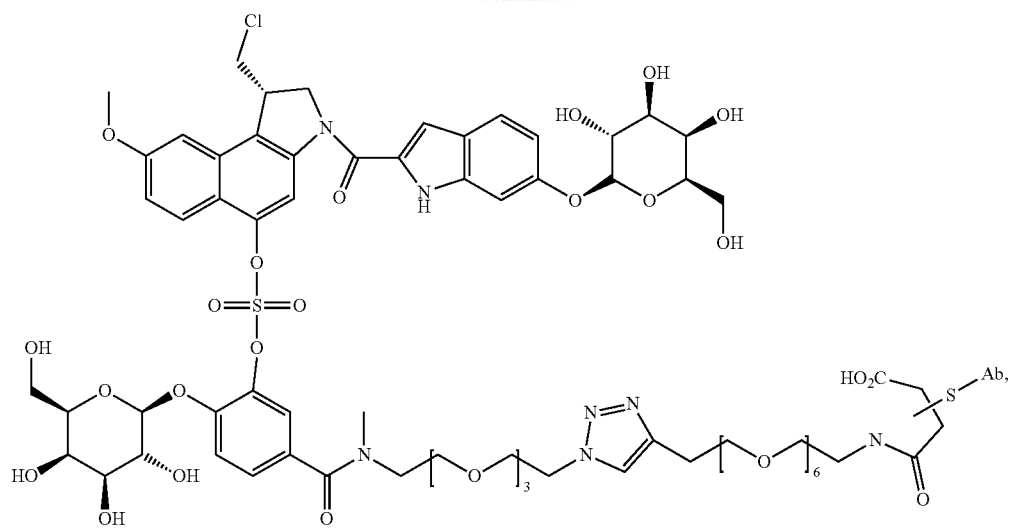
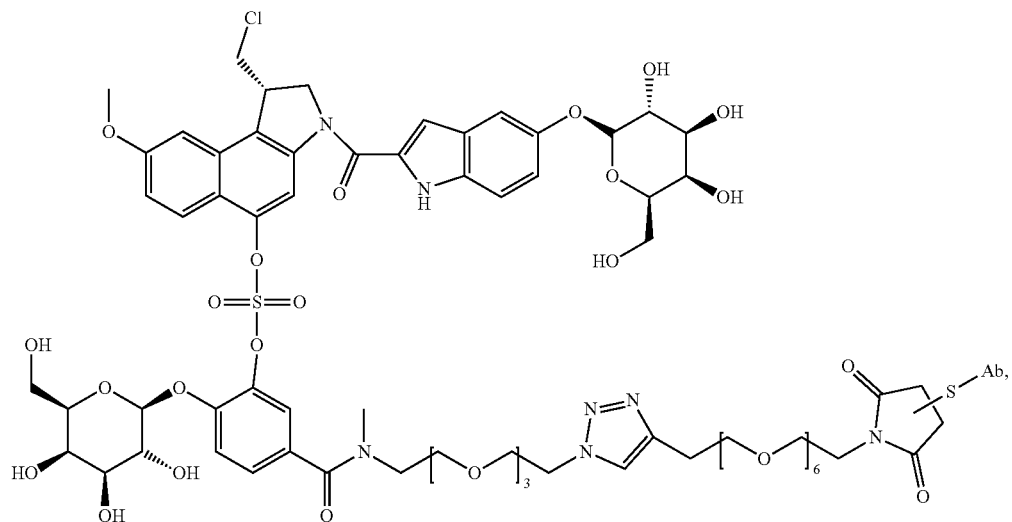
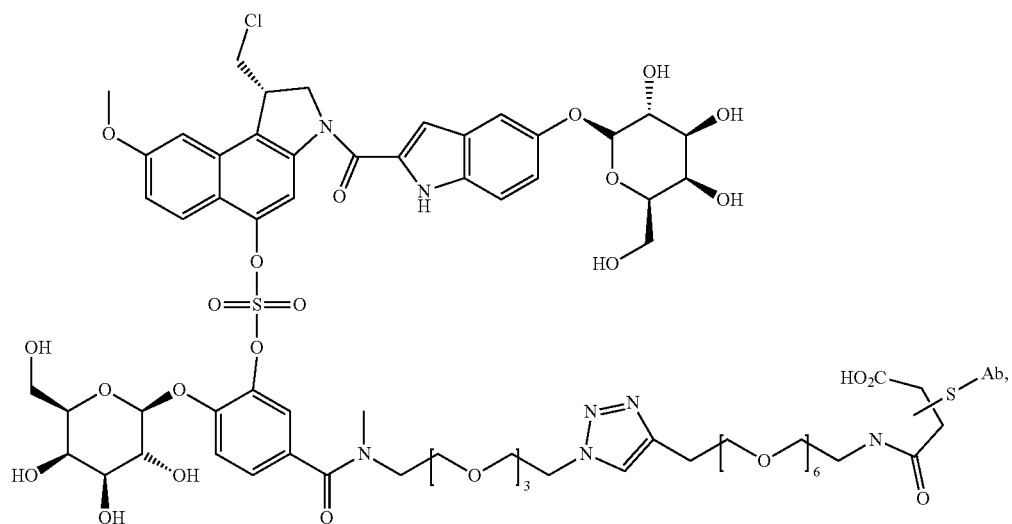

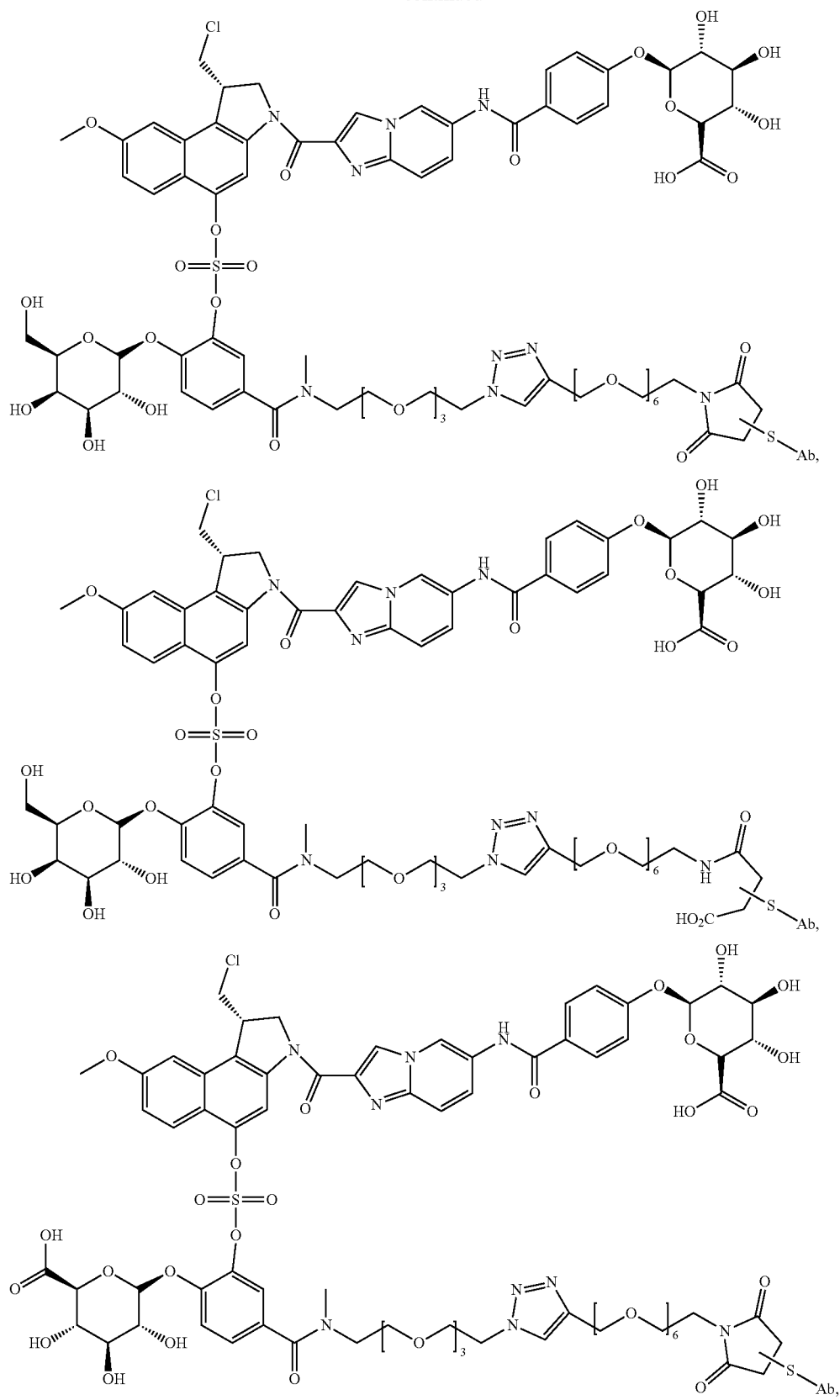

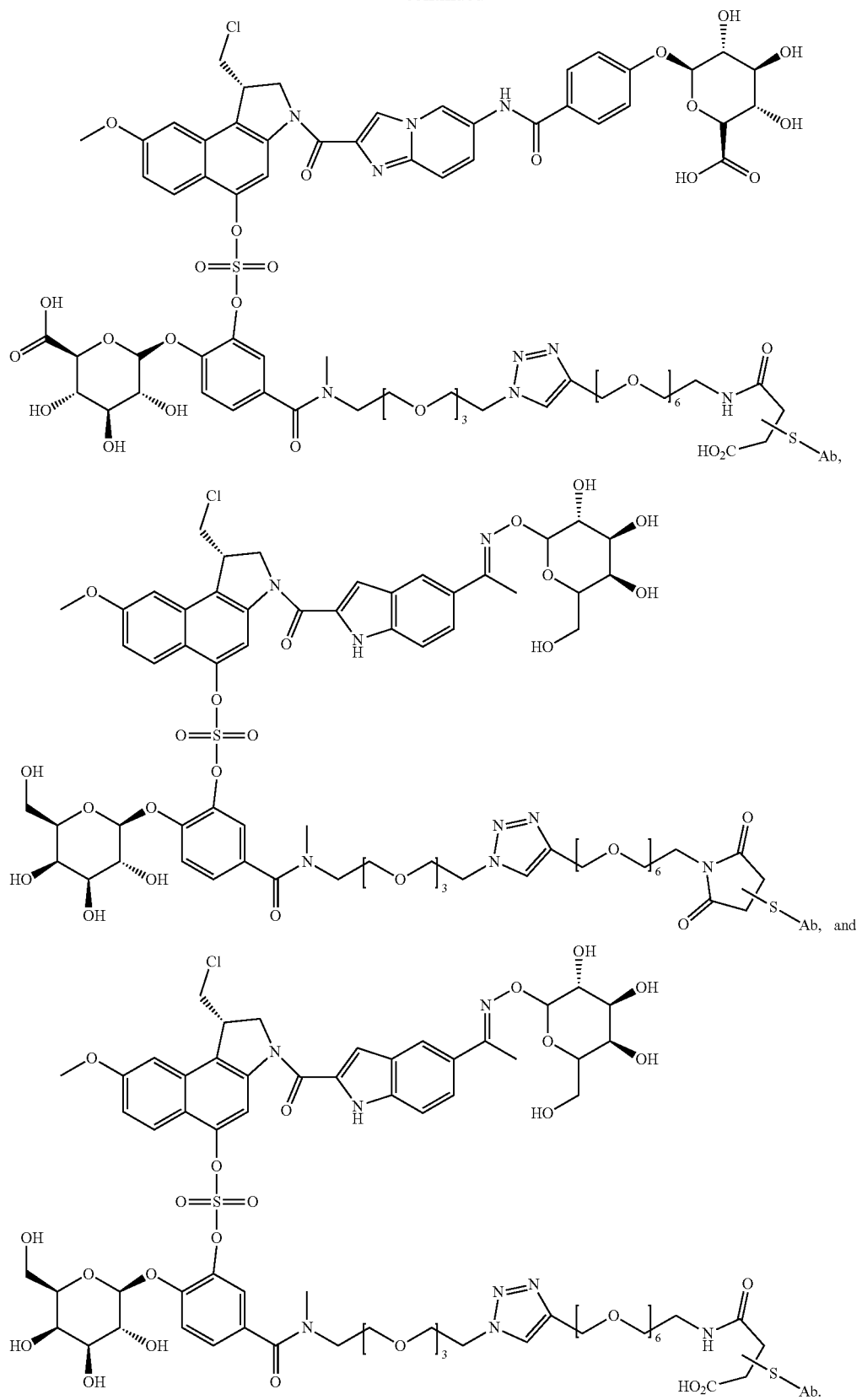

22. The antibody conjugate of claim 21, wherein the antibody conjugate
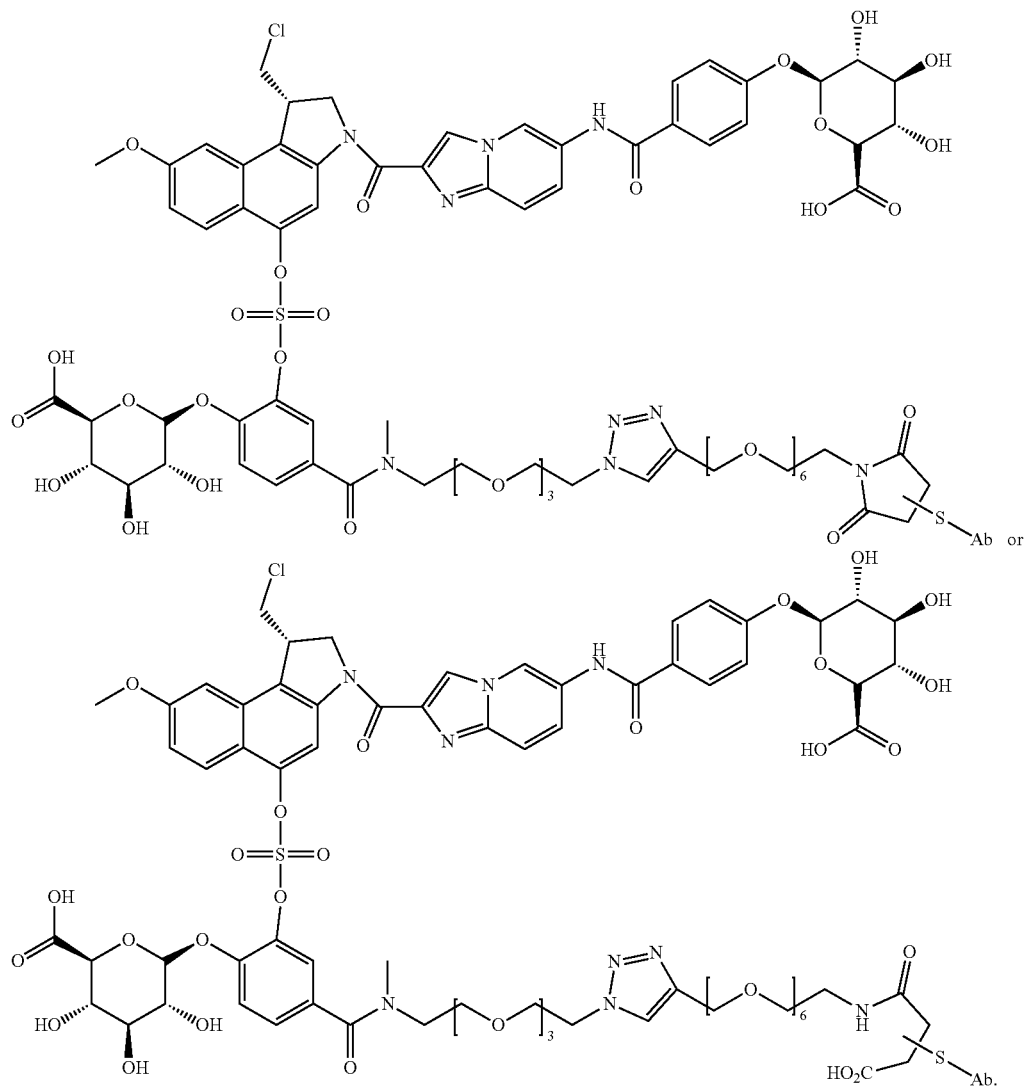
* * * * *

```
                         SEQUENCE LISTING

<160> NUMBER OF SEQ ID NOS: 109

<210> SEQ ID NO 1
   <211> LENGTH: 8
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 1

Gly Phe Thr Phe Ser Ser Tyr Ala
   1               5

<210> SEQ ID NO 2
   <211> LENGTH: 8
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 2

Ile Ser Gly Ser Gly Gly Ser Arg
   1               5

<210> SEQ ID NO 3
   <211> LENGTH: 11
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 3

Ala Ser His Thr Ile Pro Gly Ala Trp Asp Val
   1               5                   10

<210> SEQ ID NO 4
   <211> LENGTH: 9
   <212> TYPE: PRT
   <213> ORGANISM: Artificial Sequence
   <220> FEATURE:
   <223> OTHER INFORMATION: Description of Artificial Sequence: Synthetic
         peptide

<400> SEQUENCE: 4

Thr Arg Asp Val Gly Gly Tyr Asn Tyr
   1               5

<210> SEQ ID NO 5
   <211> LENGTH: 3
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Val Asn
1

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ser Tyr Thr Thr Ser Ser Arg Arg Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Thr Phe Ser Ser Tyr Trp
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Asn Pro Gly Asn Gly His Thr
1               5

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Ala Asp Pro Arg Arg Pro Lys Val Pro Thr Ala Leu Phe Val Tyr
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gly Ile Gly Thr Trp
```

-continued

```
1               5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Ala Ile Asn Phe Pro Ile Thr
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Thr Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ile Ile Pro Ile Leu Gly Ile Ala
1               5

<210> SEQ ID NO 15
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Asn Gly Gly Asp Ser Ser Ser Trp Tyr Thr Phe Asp Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
```

-continued peptide

<400> SEQUENCE: 16

Gln Ser Ile Ser Arg Trp
1               5

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Ala Ser
1

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gln Tyr Asn Thr Phe Pro Leu Thr
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Thr Phe Ser Ser Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Ile Pro Ile Leu Gly Ile Ala
1               5

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Asn Gly Gly Asp Ser Ser Trp Tyr Thr Phe Asp Tyr
1               5                   10

<210> SEQ ID NO 22

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Thr Ile Asn Ser Trp
1               5

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Lys Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Tyr Asn Ser Tyr Ser Leu Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Thr Phe Ser Ser Tyr Ala
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Ile Pro Ile Leu Gly Ile Ala
1               5

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

```
Ala Asn Gly Gly Asp Ser Ser Ser Trp Tyr Thr Phe Asp Tyr
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Asn Ile Asn Ser Trp
1               5

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gln Tyr Asp Ser Asn Pro Leu Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Thr Phe Ser Ser Tyr Ala
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ile Ile Pro Ile Leu Gly Ile Ala
1               5

<210> SEQ ID NO 33
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 33

Ala Asn Gly Gly Asp Ser Ser Trp Tyr Thr Phe Asp Tyr
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Gly Ile Ser Ser Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Ala Ser
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Tyr Tyr Ser Phe Pro Leu Thr
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Thr Phe Ser Ser Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ile Pro Ile Leu Gly Ile Ala
1               5
```

```
<210> SEQ ID NO 39
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Asn Gly Gly Asp Ser Ser Ser Trp Tyr Thr Phe Asp Tyr
1               5                   10

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Glu Thr Ile Ser Ser Trp
1               5

<210> SEQ ID NO 41
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Ala Ser
1

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gln Gln Tyr Tyr Ser Tyr Pro Ile Thr
1               5

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Gly Thr Phe Ser Ser Tyr Ala
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Ile Ile Pro Ile Leu Gly Ile Ala
1               5

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Asn Gly Gly Asp Ser Ser Ser Trp Tyr Thr Phe Asp Tyr
1               5                   10

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ser Ile Asp Asn Trp
1               5

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Ala Ser
1

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Tyr Asp Ser Asn Pro Leu Thr
1               5

<210> SEQ ID NO 49
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Val Ile Ser Gly Ser Gly Gly Ser Arg Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser His Thr Ile Pro Gly Ala Trp Asp Val Trp Gly Gln Gly Thr
                100                 105                 110

Leu Val Thr Val Ser Ser
            115

<210> SEQ ID NO 50
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Ser Ala Leu Thr Gln Pro Ala Ser Val Ser Gly Ser Pro Gly Gln
 1                   5                  10                  15

Ser Ile Thr Ile Ser Cys Thr Gly Thr Thr Arg Asp Val Gly Gly Tyr
                 20                  25                  30

Asn Tyr Val Ser Trp Tyr Gln Gln His Pro Gly Lys Ala Pro Lys Leu
             35                  40                  45

Met Ile Tyr Asp Val Asn Asn Arg Pro Ser Gly Val Ser Tyr Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Ser
                 85                  90                  95

Ser Arg Arg Val Phe Gly Thr Gly Thr Lys Val Thr Val Leu
                100                 105                 110

<210> SEQ ID NO 51
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Glu Ser Gly Ala Glu Val Lys Lys Pro Gly Ala
 1                   5                  10                  15

Ser Val Lys Leu Ser Cys Lys Ala Ser Gly Tyr Thr Phe Ser Ser Tyr
                 20                  25                  30

Trp Met His Trp Val Arg Gln Ala Pro Gly Gln Arg Leu Glu Trp Met
             35                  40                  45

Gly Glu Ile Asn Pro Gly Asn Gly His Thr Asn Tyr Asn Glu Lys Phe
 50                  55                  60

Lys Ser Arg Val Thr Ile Thr Val Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Val Ala Asp Pro Arg Arg Pro Lys Val Pro Thr Ala Leu Phe Val Tyr
                100                 105                 110
```

```
Trp Gly Gln Gly Thr Leu Val Thr Val Ser Ser
        115                 120
```

<210> SEQ ID NO 52
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Ile Gly Thr Trp
            20                  25                  30

Leu Ala Trp Tyr Gln Gln Lys Pro Gly Lys Ala Pro Arg Leu Leu Ile
        35                  40                  45

Tyr Ala Ala Ser Ser Leu Asp Ser Gly Val Pro Ser Arg Phe Ser Ala
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Asn Phe Pro Ile
                85                  90                  95

Thr Phe Gly Gln Gly Thr Arg Leu Glu Ile Lys
            100                 105
```

<210> SEQ ID NO 53
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
            100                 105                 110

Gln Gly Thr Leu Ile Thr Val Ser Ser
        115                 120
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Asp Ile Gln Met Thr Gln Ser Pro Ser Thr Leu Ser Ala Ser Val Gly
1               5                   10                  15

Asp Lys Leu Thr Leu Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Lys Ala Ser Tyr Leu Gln Thr Gly Val Pro Ser Arg Phe Ser Gly
50                  55                  60

Ser Gly Thr Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Phe Pro Leu
                85                  90                  95

Thr Phe Ala Gly Gly Thr Lys Val Glu Ile Lys
            100                 105

<210> SEQ ID NO 55
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
            100                 105                 110

Gln Gly Thr Leu Ile Thr Val Ser Ser
        115                 120

<210> SEQ ID NO 56
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Asp Ile Gln Met Thr Gln Ser Pro Ser Thr Leu Ser Ala Ser Val Gly
1               5                   10                  15

Asp Arg Val Asn Ile Thr Cys Arg Ala Ser Gln Thr Ile Asn Ser Trp
            20                  25                  30

Leu Ala Trp Tyr Gln Gln Lys Pro Gly Lys Ala Pro Lys Leu Leu Ile
        35                  40                  45

```
Tyr Lys Ala Ser Tyr Leu Gln Thr Gly Val Pro Ser Arg Phe Ser Gly
    50                  55                  60

Ser Gly Ala Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Leu
                85                  90                  95

Thr Phe Gly Gly Gly Thr Lys Val Glu Ile Lys
                100                 105

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
                100                 105                 110

Gln Gly Thr Leu Ile Thr Val Ser Ser
            115                 120

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Thr Leu Ser Ala Ser Val Gly
1               5                   10                  15

Asp Arg Leu Thr Ile Thr Cys Arg Ala Ser Gln Asn Ile Asn Ser Trp
                20                  25                  30

Leu Ala Trp Tyr Gln Gln Lys Pro Gly Lys Ala Pro Lys Leu Leu Ile
            35                  40                  45

Tyr Lys Ala Ser Tyr Leu Gln Thr Gly Val Pro Ser Arg Phe Ser Gly
    50                  55                  60

Ser Gly Ser Gly Thr Glu Phe Thr Leu Thr Ile Ser Leu Gln Pro
65                  70                  75                  80

Asp Asp Phe Ala Ser Tyr Tyr Cys Gln Gln Tyr Asp Ser Asn Pro Leu
                85                  90                  95

Thr Phe Gly Gly Gly Thr Lys Val Glu Ile Lys
                100                 105
```

<210> SEQ ID NO 59
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Trp Tyr Thr Phe Asp Tyr Trp Gly
                100                 105                 110

Gln Gly Thr Leu Ile Thr Val Ser Ser
            115                 120

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Phe Pro Leu
                85                  90                  95

Thr Phe Gly Gly Gly Thr Lys Val Glu Ile Lys
                100                 105

<210> SEQ ID NO 61
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Gln Val Gln Leu Val Glu Ser Gly Ala Glu Val Lys Lys Pro Gly Ser

```
                1               5                  10                 15
Ser Val Lys Val Ser Cys Lys Ala Ser Gly Gly Thr Phe Ser Ser Tyr
                20                 25                 30

Ala Ile Ser Trp Val Arg Gln Ala Pro Gly Gln Gly Leu Glu Trp Met
                35                 40                 45

Gly Arg Ile Ile Pro Ile Leu Gly Ile Ala Asn Tyr Ala Gln Lys Phe
                50                 55                 60

Gln Gly Arg Val Thr Ile Thr Ala Asp Lys Ser Thr Ser Thr Ala Tyr
65                  70                 75                  80

Met Glu Leu Ser Ser Leu Arg Ser Glu Asp Thr Ala Val Tyr Tyr Cys
                85                 90                 95

Ala Asn Gly Gly Asp Ser Ser Trp Tyr Thr Phe Asp Tyr Trp Gly
                100                105                110        Gly

Gln Gly Thr Leu Ile Thr Val Ser Ser
                115                120
```

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

```
Asp Ile Gln Met Thr Gln Ser Pro Ser Thr Leu Ser Ala Ser Val Gly
1               5                  10                 15

Asp Arg Val Thr Ile Thr Cys Arg Ala Ser Glu Thr Ile Ser Ser Trp
                20                 25                 30

Leu Ala Trp Tyr Gln Gln Lys Pro Gly Lys Ala Pro Lys Leu Leu Ile
                35                 40                 45

Tyr Lys Ala Ser Ser Leu Gln Ser Gly Val Pro Ser Arg Phe Ser Gly
                50                 55                 60

Ser Gly Ser Gly Thr Glu Phe Thr Leu Thr Ile Ser Ser Leu Gln Pro
65                  70                 75                  80

Asp Asp Phe Ala Thr Tyr Tyr Cys Gln Gln Tyr Tyr Ser Tyr Pro Ile
                85                 90                 95

Thr Phe Gly Gln Gly Thr Arg Leu Glu Ile Lys
                100                105
```

<210> SEQ ID NO 63
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

```
Gln Val Gln Leu Val Glu Ser Gly Ala Glu Val Lys Lys Pro Gly Ser
1               5                  10                 15

Ser Val Lys Val Ser Cys Lys Ala Ser Gly Gly Thr Phe Ser Ser Tyr
                20                 25                 30

Ala Ile Ser Trp Val Arg Gln Ala Pro Gly Gln Gly Leu Glu Trp Met
                35                 40                 45

Gly Arg Ile Ile Pro Ile Leu Gly Ile Ala Asn Tyr Ala Gln Lys Phe
                50                 55                 60

Gln Gly Arg Val Thr Ile Thr Ala Asp Lys Ser Thr Ser Thr Ala Tyr
```

```
                65                  70                  75                  80
Met Glu Leu Ser Ser Leu Arg Ser Glu Asp Thr Ala Val Tyr Tyr Cys
                    85                  90                  95

Ala Asn Gly Gly Asp Ser Ser Trp Tyr Thr Phe Asp Tyr Trp Gly
                100                 105                 110

Gln Gly Thr Leu Ile Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asp Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Asp Ser Asn Pro Leu
                85                  90                  95

Thr Phe Gly Gly Gly Thr Lys Val Glu Ile Lys
            100                 105

<210> SEQ ID NO 65
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Thr Ile Pro Gly Ala Trp Asp Val Trp Gly Gln Gly Thr
            100                 105                 110

Leu Val Thr Val Ser Ser
        115
```

```
<210> SEQ ID NO 66
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 67
<211> LENGTH: 118
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 67

Gln Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Gly Ser Gly Gly Ser Arg Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Thr Ile Pro Gly Ala Trp Asp Val Trp Gly Gln Gly Thr
            100                 105                 110

Leu Val Thr Val Ser Ser
            115

<210> SEQ ID NO 68
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Cys Leu Ser Pro Gly Lys
                325                 330

<210> SEQ ID NO 69
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Val Glu Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
                20                  25                  30

Trp Met His Trp Val Arg Gln Ala Pro Gly Gln Arg Leu Glu Trp Met
            35                  40                  45

Gly Glu Ile Asn Pro Gly Asn Gly His Thr Asn Tyr Asn Glu Lys Phe
        50                  55                  60

Lys Ser Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Ala Asp Pro Arg Arg Pro Lys Val Pro Thr Ala Leu Phe Val Tyr
            100                 105                 110

Trp Gly Gln Gly Thr Leu Val Thr Val Ser Ser
        115                 120

<210> SEQ ID NO 70
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 71
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Trp Tyr Thr Phe Asp Tyr Trp Gly
            100                 105                 110

Gln Gly Thr Leu Ile Thr Val Ser Ser
        115                 120

<210> SEQ ID NO 72
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr

```
305                 310                 315                 320
Gln Lys Ser Leu Ser Leu Ser Pro Gly Lys
                325                 330

<210> SEQ ID NO 73
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
                100                 105                 110

Gln Gly Thr Leu Ile Thr Val Ser Ser
            115                 120

<210> SEQ ID NO 74
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

```
            145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 75
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Glu Ser Gly Ala Glu Val Lys Lys Pro Gly Ser
1               5                   10                  15

Ser Val Lys Val Ser Cys Lys Ala Ser Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
                100                 105                 110

Gln Gly Thr Leu Ile Thr Val Ser Ser
            115                 120

<210> SEQ ID NO 76
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 76

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Gln Val Gln Leu Val Glu Ser Gly Ala Glu Val Lys Lys Pro Gly Ser
1               5                   10                  15

```
Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
            100                 105                 110

Gln Gly Thr Leu Ile Thr Val Ser Ser
            115                 120

<210> SEQ ID NO 78
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

-continued

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 79
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
            100                 105                 110

Gln Gly Thr Leu Ile Thr Val Ser Ser
        115                 120

<210> SEQ ID NO 80
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 81
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Asn Gly Gly Asp Ser Ser Ser Trp Tyr Thr Phe Asp Tyr Trp Gly
            100                 105                 110

Gln Gly Thr Leu Ile Thr Val Ser Ser
```

```
              115                 120
```

<210> SEQ ID NO 82
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

```
Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 83
<211> LENGTH: 110

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Gln Ser Ala Leu Thr Gln Pro Ala Ser Val Ser Gly Ser Pro Gly Gln
1               5                   10                  15

Ser Ile Thr Ile Ser Cys Thr Gly Thr Thr Arg Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Asn Asn Arg Pro Ser Gly Val Ser Tyr Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Arg Arg Val Phe Gly Thr Gly Thr Lys Val Thr Val Leu
            100                 105                 110

<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Arg Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Ile Gly Thr Trp
            20                  25                  30

Leu Ala Trp Tyr Gln Gln Lys Pro Gly Lys Ala Pro Arg Leu Leu Ile
```

```
              35                  40                  45

Tyr Ala Ala Ser Ser Leu Asp Ser Gly Val Pro Ser Arg Phe Ser Ala
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Ile Asn Phe Pro Ile
                 85                  90                  95

Thr Phe Gly Gln Gly Thr Arg Leu Glu Ile Lys
             100                 105
```

<210> SEQ ID NO 86
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Arg Ser Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
             100                 105
```

<210> SEQ ID NO 87
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

```
Asp Ile Gln Met Thr Gln Ser Pro Ser Thr Leu Ser Ala Ser Val Gly
 1               5                  10                  15

Asp Lys Leu Thr Leu Thr Cys Arg Ala Ser Gln Ser Ile Ser Arg Trp
             20                  25                  30

Leu Ala Trp Tyr Gln Gln Lys Pro Gly Lys Ala Pro Lys Leu Leu Ile
         35                  40                  45

Tyr Lys Ala Ser Tyr Leu Gln Thr Gly Val Pro Ser Arg Phe Ser Gly
     50                  55                  60

Ser Gly Thr Gly Thr Glu Phe Thr Leu Thr Ile Ser Ser Leu Gln Pro
 65                  70                  75                  80

Asp Asp Phe Ala Thr Tyr Tyr Cys Gln Gln Tyr Asn Thr Phe Pro Leu
                 85                  90                  95

Thr Phe Ala Gly Gly Thr Lys Val Glu Ile Lys
             100                 105
```

-continued

```
<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Arg Ser Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ile Gln Met Thr Gln Ser Pro Ser Thr Leu Ser Ala Ser Val Gly
1               5                   10                  15

Asp Arg Val Asn Ile Thr Cys Arg Ala Ser Gln Thr Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Tyr Leu Gln Thr Gly Val Pro Ser Arg Phe Ser Gly
    50                  55                  60

Ser Gly Ala Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Leu
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Arg Ser Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 91
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Asp Ile Gln Met Thr Gln Ser Pro Ser Thr Leu Ser Ala Ser Val Gly
 1               5                  10                  15

Asp Arg Leu Thr Ile Thr Cys Arg Ala Ser Gln Asn Ile Asn Ser Trp
                20                  25                  30

Leu Ala Trp Tyr Gln Gln Lys Pro Gly Lys Ala Pro Lys Leu Leu Ile
            35                  40                  45

Tyr Lys Ala Ser Tyr Leu Gln Thr Gly Val Pro Ser Arg Phe Ser Gly
     50                  55                  60

Ser Gly Ser Gly Thr Glu Phe Thr Leu Thr Ile Thr Ser Leu Gln Pro
 65                  70                  75                  80

Asp Asp Phe Ala Ser Tyr Tyr Cys Gln Gln Tyr Asp Ser Asn Pro Leu
                85                  90                  95

Thr Phe Gly Gly Gly Thr Lys Val Glu Ile Lys
            100                 105

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Arg Ser Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

-continued

<210> SEQ ID NO 93
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Phe Pro Leu
                85                  90                  95

Thr Phe Gly Gly Gly Thr Lys Val Glu Ile Lys
            100                 105

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Arg Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 95
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Asp Ile Gln Met Thr Gln Ser Pro Ser Thr Leu Ser Ala Ser Val Gly
1               5                   10                  15

```
Asp Arg Val Thr Ile Thr Cys Arg Ala Ser Glu Thr Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Tyr Ser Tyr Pro Ile
                85                  90                  95

Thr Phe Gly Gln Gly Thr Arg Leu Glu Ile Lys
                100                 105

<210> SEQ ID NO 96
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Arg Ser Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 97
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Asp Asn Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Ser Tyr Tyr Cys Gln Gln Tyr Asp Ser Asn Pro Leu
                85                  90                  95
```

```
Thr Phe Gly Gly Gly Thr Lys Val Glu Ile Lys
            100                 105

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Arg Ser Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 99
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Gly Ser Tyr His Met Asp Val Trp Gly Lys Gly
            100                 105                 110

Thr Thr Val Thr Val Ser Ser
        115

<210> SEQ ID NO 100
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 100

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 101
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Gln Ser Gly Ala Glu Val Lys Lys Pro Gly Ser
1               5                   10                  15

```
Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Gly Ser Tyr His Met Asp Val Trp Gly Lys Gly
            100                 105                 110

Thr Thr Val Thr Val Ser Ser
            115

<210> SEQ ID NO 102
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 103
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Gly Ser Tyr His Met Asp Val Trp Gly Lys Gly
            100                 105                 110

Thr Thr Val Thr Val Ser Ser
        115

<210> SEQ ID NO 104
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Cys Leu Ser Pro Gly Lys
                325                 330

<210> SEQ ID NO 105
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Arg Ile Thr Phe Gly Gln Gly Thr Arg Leu Glu Ile Lys
            100                 105
```

```
<210> SEQ ID NO 106
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Arg Ser Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 107
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Arg Ile Thr Phe Gly Gln Gly Thr Arg Leu Glu Ile Lys
            100                 105

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Arg Ser Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
             85                  90                  95

Pro Val Thr Lys Ser Phe Asn Arg Gly Glu Cys
            100                 105

<210> SEQ ID NO 109
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Gly Gly Pro Gly
1
```

UNITED STATES PATENT AND TRADEMARK OFFICE
CERTIFICATE OF CORRECTION

| | | |
|---|---|---|
| PATENT NO. | : 12,168,060 B2 | Page 1 of 1 |
| APPLICATION NO. | : 17/358306 | |
| DATED | : December 17, 2024 | |
| INVENTOR(S) | : Park et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 439 days.

Signed and Sealed this
Tenth Day of June, 2025

Coke Morgan Stewart
*Acting Director of the United States Patent and Trademark Office*